US012655188B2

(12) United States Patent
Mali et al.

(10) Patent No.: US 12,655,188 B2
(45) Date of Patent: Jun. 16, 2026

(54) COMPOUNDS CONTAINING ONE OR MORE DIBORONATES AND RELATED INSULIN ANALOGS

(71) Applicant: Protomer Technologies, Inc., Pasadena, CA (US)

(72) Inventors: Sachitanand Mali, Pasadena, CA (US); Diao Chen, Pasadena, CA (US); Ryan Kelly Spencer, Porter Ranch, CA (US); Jack Joseph Steele, La Cañada Flintridge, CA (US); Jingxin Liang, Covington, WA (US); Mirna Ekram Anwar Shaker, Cypress, CA (US); Alborz Mahdavi, Pasadena, CA (US)

(73) Assignee: Protomer Technologies, Inc., Indianapolis, IN (US)

( * ) Notice: Subject to any disclaimer, the term of this patent is extended or adjusted under 35 U.S.C. 154(b) by 13 days.

(21) Appl. No.: 18/632,799

(22) Filed: Apr. 11, 2024

(65) Prior Publication Data

US 2024/0400637 A1     Dec. 5, 2024

Related U.S. Application Data

(60) Provisional application No. 63/502,778, filed on May 17, 2023, provisional application No. 63/495,442, filed on Apr. 11, 2023.

(51) Int. Cl.
*C07K 14/62* (2006.01)
*A61K 38/00* (2006.01)

(52) U.S. Cl.
CPC .............. *C07K 14/62* (2013.01); *A61K 38/00* (2013.01)

(58) Field of Classification Search
CPC ........ C07K 14/62; A61K 38/00; A61K 47/54; A61K 47/545; A61P 3/10
See application file for complete search history.

(56) References Cited

U.S. PATENT DOCUMENTS

| | | | |
|---|---|---|---|
| 2019/0247468 A1* | 8/2019 | Mahdavi | ............... C07K 14/62 |
| 2020/0325160 A1* | 10/2020 | Kruse | .................. G01N 24/088 |
| 2023/0134116 A1* | 5/2023 | Mahdavi | ............... A61K 38/28 514/5.9 |
| 2023/0374045 A1* | 11/2023 | Mali | ..................... A61K 47/54 |

FOREIGN PATENT DOCUMENTS

| | | |
|---|---|---|
| WO | 2021/202802 A1 | 10/2021 |
| WO | 2022/109078 A1 | 5/2022 |
| WO | 2022/235691 A1 | 11/2022 |
| WO | 2023/225534 A1 | 11/2023 |

OTHER PUBLICATIONS

International Search Report mailed Oct. 15, 2024, in the International Application No. PCT/US2024/024054.

* cited by examiner

*Primary Examiner* — Sudhakar Katakam
(74) *Attorney, Agent, or Firm* — Thomas P. Weber

(57) ABSTRACT

The disclosure relates to novel compounds that include one or more aromatic boron-containing groups, including diboronates, and methods of making the disclosed compounds. The present disclosure further relates to pharmaceutical compositions comprising the disclosed compounds, and their use in prevention and treatment of diseases and disorders, such as hyperglycemia, type 2 diabetes, impaired glucose tolerance, type 1 diabetes, obesity, metabolic syndrome X, or dyslipidemia, diabetes during pregnancy, prediabetes. Alzheimer's disease, MODY 1, MODY 2 or MODY 3 diabetes, mood disorders, and psychiatric disorders.

29 Claims, 15 Drawing Sheets

Specification includes a Sequence Listing.

single chain insulin

DS-129A
DMSO/DIEA single chain insulin
intermdediate 1) 50 mM acetic acid (pH 4.5)
2) 100 mM NaCl and 30% ACN
3) 1 M Tris, pH 9
4) 500 mM CaCl₂
5) Trypsin + CBP Example 900

1

DSL-34B
DMSO/DIEA

2

1) 50 mM acetic acid (pH 4.5)
2) 100 mM NaCl and 30% ACN
3) 1 M Tris, pH 9
4) 500 mM CaCl₂
5) Trypsin Example 19A

COMPOUNDS CONTAINING ONE OR MORE DIBORONATES AND RELATED INSULIN ANALOGS

FIELD OF THE DISCLOSURE

The present disclosure relates to novel compounds that include one or more aromatic boron-containing groups, including diboronates. The disclosure relates to the use of the novel compounds to bind glucose. The present disclosure further relates to kits and the use of the compounds and/or pharmaceutical compositions comprising the disclosed compounds for the treatment of disorders characterized by elevated glucose levels, such as hyperglycemia, pre-diabetes and diabetes (e.g., type 1 diabetes, type 2 diabetes, diabetes during pregnancy, MODY 1, MODY 2 or MODY 3 diabetes), impaired glucose tolerance, obesity, metabolic syndromes, dyslipidemia, neurological diseases, mood disorders, and psychiatric disorders.

SEQUENCE LISTING

The present application is being filed along with a Sequence Listing in electronic format. The Sequence Listing is provided as a file titled "30583M_WO_SL.xml," created Apr. 10, 2024, and is 30,688,753 bytes in size. The information in the electronic format of the Sequence Listing is incorporated herein by reference in its entirety.

BACKGROUND OF THE DISCLOSURE

Boronic acids are generally considered Lewis acids that have a tendency to bind to hydroxyls, because, as Lewis acids, boronic acids can form complexes with Lewis bases such as, for example, hydroxide anions. Thus, molecules containing boronates including boronic acids have a general tendency to bind hydroxyl groups. This binding tendency can be used for detection of hydroxyl-containing groups by boronated labeling reagents wherein the boronate groups bind to the hydroxyls and, depending on the solvent and buffer conditions, the boronates can form hydrolysable boronate-ester bonds to the hydroxyl groups of hydroxyl containing molecules, such as the hydroxyl groups present in diols (e.g., glucose). Although boron-containing compounds can bind to diol containing molecules, achieving selectivity using boron-containing compounds has been challenging because of their ability to bind various diols, including cis diols, to varying degrees. While improved binding affinity of boron-containing compounds towards a specific vicinal diol of interest may be achieved, this may result in a loss of selectivity.

Glucose is the main fuel for the human body, and blood glucose values are tightly regulated in healthy individuals. For example, between meals, blood glucose is near 5 mmol/L (mM), and when blood glucose concentrations rise after a meal, the value is quickly adjusted back toward 5 mM by the action of insulin. The hormone insulin is secreted from pancreatic beta cells, and when insulin binds to insulin receptors on cells in the body (for example muscle and fat), the cells are stimulated to absorb glucose by translocation of glucose transporters from storage vesicles to the cell surface (GLUT4) (see, e.g., Huang, S. H. et al. *Cell Metabolism,* 5:237-252 (2007)).

People with diabetes may lose their ability to produce insulin due to autoimmunity against beta cells (type 1) or have low sensitivity to insulin in combination with impaired insulin secretion (type 2). For example, those with type 1 diabetes may rely on multiple daily insulin injections, both for basal coverage, typically once a day, and with meals (bolus) to control their glucose levels (see, e.g., Polonsky, K. S. et al. The Journal of Clinical Investigation 81: 442-448 (1988)). Because glucose values can fluctuate unpredictably, perfect insulin dosing day after day is extremely difficult. Indeed, despite many technological advances in diabetes treatment, researchers are currently observing, partly due to lifestyle problems, a worsening of long-term glucose control and/or overall metabolic health.

Glucose sensors and glucose sensing insulin analogs are known in the art. See, e.g., WO 2016/179568 A1 and WO 2021/202802 A1. However, there is a need in the art to develop glucose sensors and glucose sensing insulins that have improved properties, such as binding to the insulin receptor and being proportionately responsive to different glucose concentrations and providing a graded and reversible response to changes in glucose levels under physiological conditions.

Thus, there is an unmet medical need for novel compounds, such as compounds which bind glucose and may be utilized in glucose-responsive insulin analogues/conjugates, that can control blood glucose levels.

Here, according to certain embodiments, we disclose glucose sensors and glucose sensing insulin analogs that have improved properties, such as prolonged terminal half-life and/or a decrease in clearance, improved affinity for the insulin receptor, and/or improved activation of the insulin receptor.

SUMMARY OF THE DISCLOSURE

In a first aspect, a compound comprises one or more diboronates of the following formula, or a stereoisomer or a mixture of stereoisomers, or pharmaceutically acceptable salt thereof:

$$\left[ Z1c - \left( Z1b \right)_{n'} \right]_{q'} - X1.$$

Each Z1b is independently a linker moiety. Each n' is 0, 1, 2, 3, 4, or 5. At least one n' is 1, 2, 3, 4, or 5. X1 can comprise a drug substance or a polypeptide. Each Z1c is covalently conjugated directly or via one or more Z1b to an amine in X1. At least one Z1c is independently selected from a diboronate, wherein the diboronate is independently selected from Formulae FF12A, FF12B, FF12C, FF12D, FF116A, FF116B, FF116C, FF116D, FF225, and FF227. Each additional Z1c is optionally independently selected from a diboronate, a sugar moiety, a diol containing moiety, and a polyol containing moiety, wherein the diboronate is independently selected from Formulae FF12A, FF12B, FF12C, FF12D, FF116A, FF116B, FF116C, FF116D, FF225, and FF227 Each q' is 1, 2, 3, 4, or 5, wherein when q' is 2 or more, each corresponding Z1c and Z1b is independently selected and may be the same or different. Formulae FF12A, FF12B, FF12C, FF12D, FF116A, FF116B, FF116C, FF116D, FF225, and FF227 are:

FF12A

3

-continued

FF12B

FF12C

FF12D

FF116A

FF116B

FF116C

FF116D

4

-continued

FF225

FF227

X in the foregoing formulae represents a point of covalent attachment to an amine of Z1b or to an amine of X1 when n' is 0. Each i can be 1, 2, 3, 4, 5, 6, or 7. Groups $B_1$ and $B_2$ in the foregoing formulae may be identical or different, each independently represent an aromatic boron-containing group. When each Z1c is selected from Formulae FF225 and FF227, at least one of the $B_1$ and the $B_2$ is Formula F7, wherein Formula F7 is:

(F7)

One $R_1$ of F7 represents (C=O)—*, wherein —* represents the attachment point to the rest of Z1c. Each remaining $R_1$ can independently be selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_mCH_3$, and $OCF_3$, wherein m is 1, 2, 3, 4, 5, 6, or 7. Y8 can be O or NR, wherein R is a $C_1$-$C_6$ alkyl group or H. Each Y10 is independently selected from H, $CH_3$, F, and $CF_3$, wherein for at least one F7 at least one Y10 is not H.

In a second aspect, a compound is selected from the group consisting of a polypeptide comprising an A-chain and a B-chain, wherein the A-chain comprises a sequence selected from 1, 24051, and 24052. The B-chain can comprise a sequence selected from SEQ ID NOs 24063, 25228, 25229, 25232, 25305, 25308, 25312, 25236, 25095, and 25380-25397.

In a third aspect, a pharmaceutical composition comprises at least one compound or a pharmaceutically acceptable salt thereof according to any one of the embodiments according to the first and second aspects In a fourth aspect, the present disclosure includes a compound of the following formula, or a stereoisomer or a mixture of stereoisomers, or pharmaceutically acceptable salt thereof:

Z1c-Linker

The Z1c-Linker can be selected from:

FFL-1

FFL-2

FFL-3

-continued

FFL-4

FFL-5

FFL-6

FFL-7

-continued

FFL-8

FFL-9

FFL-10

FFL-11

-continued

FFL-12

FFL-13

FFL-14

FFL-15

-continued

FFL-16

FFL-17

FFL-18

-continued

FFL-19

FFL-20

FFL-21

FFL-22

-continued

FFL-23

FFL-24

FFL-25

FFL-26

-continued

FFL-27

FFL-28

FFL-29

21
22

FFL-30

FFL-31

FFL-32

-continued

FFL-33

FFL-34

FFL-35

FFL-36

-continued

FFL-37

FFL-38

FFL-39

FFL-40

-continued

FFL-41

FFL-42

FFL-43

FFL-44

-continued

FFL-45

FFL-46

FFL-47

FFL-48

-continued

FFL-49

FFL-50

FFL-51

-continued

FFL-52

FFL-53

FFL-54

-continued

FFL-55

FFL-56

FFL-57

FFL-58

-continued

FFL-59

FFL-60

FFL-61

FFL-62

-continued

FFL-63

FFL-64

FFL-65

-continued

FFL-66

FFL-67

FFL-68

The group X of the foregoing formulae can be selected from a leaving group, $NH_2$, and H. The groups $B_1$ and $B_2$, which may be identical or different, each independently represents an aromatic boron-containing group.

In a fifth aspect, the present disclosure includes a polypeptide comprising an A-chain and a B-chain, wherein the A-chain comprises a sequence selected from 1, 24051, and 24052. The B-chain can comprise a sequence selected from 25000-25397.

In a sixth aspect, the present disclosure includes a compound having agonist potency for an insulin receptor comprising at least one aromatic boron-containing group having agonist potency for an insulin receptor, or a pharmaceutically acceptable salt thereof. The compound can have a first EC50 potency for activating the insulin receptor at a first glucose concentration and a second EC50 potency for activating the insulin receptor at a second glucose concentration. When the first glucose concentration is 5.6 mM and the second glucose concentration is 16.7 mM, the compound has an insulin receptor agonist potency ratio of the first EC50 to the second EC50 of about 1.2 to about 20, such as about 1.5 to about 15, about 2 to about 14, about 2.5 to about 13, about 2.5 to about 12, about 2.5 to about 11, about 2.5 to about 10, about 2.5 to about 9, about 2.5 to about 8, about 2.5 to about 7, about 2.5 to about 6, about 2.5 to about 5, or about 2.5 to about 4.5.

In a seventh aspect, the present disclosure includes a compound having agonist potency for glucose comprising at least one aromatic boron-containing group having binding affinity for glucose, or a pharmaceutically acceptable salt thereof. When administered at a dose of 30 nmol/kg to a first group of rats with a first glucose infusion rate to provide a blood glucose concentration of 100 mg/dL and to a second group of rats with a second glucose infusion rate to provide a blood glucose concentration of 200 mg/dL, the compound provides a relative glucose infusion rate difference (mg/kg/min·min) of about 1 to about 2500, about 1 to about 2000, about 1 to about 1500, about 100 to about 1500, and about 1000 to about 1500, and a relative glucose infusion rate ratio of about 0.1 to about 5, about 0.2 to about 4.5, about 0.5 to about 4, about 0.5 to about 3.5, about 1 to about 3.5, about 1.5 to about 3.5, or about 2 to about 3.

In an eighth aspect, the present disclosure includes compound according to any one of the embodiments within the previous aspects or a pharmaceutically acceptable salt thereof, for use as a medicament.

In a ninth aspect, the present disclosure incudes a method of treatment or prevention of diabetes, impaired glucose tolerance, hyperglycemia or metabolic syndrome. The method comprises administering to a subject in need thereof a compound of any one embodiment of the foregoing first, second or fifth through eighth aspect, or a pharmaceutical composition according to the third aspect.

In a tenth aspect, the present disclosure incudes a compound, a use of the compound, a method of administering the compound, or a device or formulation comprising the compound according to any one embodiment of the foregoing first, second or fifth through eighth aspect, or a pharmaceutical composition according to the third aspect. The disclosure includes the use or the method in the treatment or prevention of diabetes, impaired glucose tolerance, hyperglycemia or metabolic syndrome. The disclosure includes the manufacture of a medicament comprising such compound. The disclosure includes the use of such compound as a therapeutic agent for the treatment of diabetes or obesity, for control of blood sugar levels, or for control of release of a drug. The disclosure includes the method comprises administering to the subject the compound as a therapeutic or prophylactic agent. The disclosure includes the use of a compound according to any one of the embodiments of the fourth aspect as an intermediate in the synthesis of a drug substance or a therapeutic of a prophylactic compound.

In an eleventh aspect, the present disclosure incudes a compound comprising at least one diboronate, wherein the diboronate comprises at least two aromatic boron-containing groups, wherein at least one aromatic boron-containing group is covalently attached to the compound and selected from F3-F11, and the other aromatic boron-containing group is covalently attached to the compound and optionally selected from F1-F11 or a boronic acid, (F1)

-continued (F2)

(F3)

(F4)

(F5)

(F6)

(F7)

(F8)

-continued (F9)

(F10)

and (F11)

At least one R1 in each of F1-F11 is covalently attached to the compound. Each remaining $R_1$ and $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_mCH_3$, and $OCF_3$, wherein m is 1, 2, 3, 4, 5, 6, or 7. For Formulae F3-F4, R, is O or S. For Formula F6, when Y8 is O, i is 1, 2, 3, 4, or 5; or i is 2, 3, 4, or 5; and none, one, or two R1 represents F, CI, $CF_2$, $CF_3$, $SF_5$, $OCF_3$, $SO_2CH_3$ and/or $SO_2CF_3$; or when Y8 is NR, R is an alkyl group or H, and i is 1, 2, 3, 4, or 5. For Formulae F5 and F7-F10, when Y8 is O, i is 1, 2, 3, 4, or 5; or when Y8 is NR, R is an alkyl group or H, and i is 1, 2, 3, 4, or 5; Y9 is $CH_3$, F, $CF_3$, $CHF_2$, or $OCH_3$; and each Y10 is independently selected from H, $CH_3$, $CH_2CH_3$, $CH_2CH_2OH$, F, $CF_3$, $CHF_2$, and $OCH_3$, with the proviso that at least one Y10 is not H.

In a twelfth aspect, the present disclosure incudes a tautomer, stereoisomer or a mixture of stereoisomers, or a pharmaceutically acceptable salt, or hydrate, or isotopic derivative thereof of the compound according to the eleventh aspect.

In a thirteenth aspect, the present disclosure incudes a compound comprising X1 and one or more Z1c, or a tautomer, stereoisomer or a mixture of stereoisomers, or a pharmaceutically acceptable salt, or hydrate, or isotopic derivative thereof. X1 comprises:

(i) $NH_2$ or OH;

(ii) a drug substance comprising an amine;

(iii) a drug substance that is covalently conjugated to an amine containing linker; or (iv) an amine configured to be covalently conjugated to a drug substance.

Each Z1c is covalently conjugated, directly or indirectly, to an amine in X1 or to OH when X1 is OH. Each Z1c is independently selected from:

a) Formulae FF1-FF48, wherein Formulae FF1-FF48 are:

(FF1)

(FF2)

(FF3)

(FF4)

(FF5)

(FF6)

(FF7)

47

-continued

48

-continued (FF8)

(FF9)

(FF10)

(FF11)

(FF12)

(FF13)

(FF14)

(FF15)

(FF16)

(FF17)

(FF18)

(FF19)

(FF20)

(FF21)

49

-continued (FF22)

(FF23)

(FF24)

(FF25)

(FF26)

(FF27)

(FF28)

50

-continued (FF29)

(FF30)

(FF31)

(FF32)

(FF33)

(FF34)

(FF35)

(FF36)

-continued (FF37)

(FF38)

(FF39)

(FF40)

(FF41)

(FF42)

(FF43)

(FF44)

-continued (FF45)

(FF46)

(FF47)

and (FF48)

;

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

j is 1, 2, 3, 4, 5, 6, or 7; and

B$_1$ and B$_2$, which may be identical or different, each independently represents an aromatic boron-containing group;

b) Formulae FF49-FF88, wherein Formulae FF49-FF88 are:

(FF49)

(FF50)

(FF51)

53

-continued (FF52)

(FF53)

(FF54)

(FF55)

(FF56)

(FF57)

(FF58)

(FF59)

(FF60)

54

-continued (FF61)

(FF62)

(FF63)

(FF64)

(FF65)

(FF66)

(FF67)

55

-continued (FF68)

(FF69)

(FF70)

(FF71)

(FF72)

(FF73)

56

-continued (FF74)

(FF75)

(FF76)

(FF77)

(FF78)

(FF79)

-continued

-continued (FF80)

(FF86)

(FF81)

(FF87)

and (FF82)

(FF88)

(FF83)

wherein X represents a point of covalent attachment either directly to an amine in X1 or to an amine that is covalently conjugated directly or indirectly to X11, or to OH when X1 is OH;

i is 1, 2, 3, 4, 5, 6, or 7;

j is 1, 2, 3, 4, 5, 6, or 7;

R1a is selected from COOH, CH$_3$, H, and OH;

(FF84)

R2, R3, R4 and R5 are each independently selected from CH$_3$, H, OH, and COOH, and at least one of R2, R3, R4 and R5 is CH$_3$ or OH; and B$_1$ and B$_2$, which may be identical or different, are each independently an aromatic boron-containing group;

c) Formulae FF89-FF112, wherein Formulae FF89-FF112 are:

(FF85)

(FF89)

-continued

-continued (FF90)

(FF95)

(FF91)

(FF96)

(FF92)

(FF97)

(FF93)

(FF98)

(FF94)

(FF99)

61
-continued (FF100)

(FF101)

(FF102)

(FF103)

(FF104)

62
-continued (FF105)

(FF106)

(FF107)

(FF108)

(FF109)

63
-continued

64
-continued (FF110)

(FF114)

(FF111)

and (FF115)

(FF112)

(FF116)

(FF117)

wherein X represents a point of covalent attachment either directly to an amine in X1 or to an amine that is covalently conjugated directly or indirectly to X1, or to OH when X1 is OH;

i is 1, 2, 3, 4, 5, 6, or 7; and $B_1$, $B_2$ and $B_3$, which may be identical or different, are each independently an aromatic boron-containing group, a carboxylic acid derivative, or a H, wherein in each FF89-FF112 structure containing $B_1$, $B_2$ and $B_3$ groups, at least two of the $B_1$, $B_2$ and $B_3$ groups are independently an aromatic boron-containing group;

d) Formulae FF113-FF136, wherein Formulae FF113-FF136 are:

(FF118)

(FF119)

(FF113)

(FF120)

65
-continued

66
-continued (FF121)

(FF128)

(FF122)

(FF129)

(FF123)

(FF130)

(FF124)

(FF131)

(FF125)

(FF132)

(FF126)

(FF127)

(FF133)

67

(FF134)

(FF135)

and

(FF136)

25 wherein X represents a point of covalent attachment either
directly to an amine in X1 or to an amine that is
covalently conjugated directly or indirectly to X1, or to
OH when X1 is OH;

i is 1, 2, 3, 4, 5, 6, or 7;

j is 1, 2, 3, 4, 5, 6, or 7;

k is 1, 2, 3, 4, 5, 6, or 7;

m is 1, 2, 3, 4, 5, 6, or 7;

each R1 is independently selected from H, an alkyl group,
an acyl group, a cycloalkyl group, a haloalkyl group, an
aryl group, and a heteroaryl group, each R1 optionally
comprises one or more alkyl-halide, halide, sulfhydryl,
aldehyde, amine, acid, hydroxyl, alkyl, or aryl groups;
and $B_1$ and $B_2$, which may be identical or different, each
independently represents an aromatic boron-containing
group;

e) Formulae FF137-FF160, wherein Formulae FF137-
FF160 are:

(FF137)

(FF138)

68

(FF139)

(FF140)

(FF141)

(FF142)

(FF143)

(FF144)

(FF145)

69

-continued (FF146)

(FF147)

(FF148)

(FF149)

(FF150)

(FF151)

(FF152)

70

-continued (FF153)

(FF154)

(FF155)

(FF156)

(FF157)

(FF158)

71

-continued (FF159)

and (FF160)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

j is 1, 2, 3, 4, 5, 6, or 7;

k is 1, 2, 3, 4, 5, 6, or 7;

m is 1, 2, 3, 4, 5, 6, or 7;

each R1 is independently selected from H, an alkyl group, an acyl group, a cycloalkyl group, a haloalkyl group, an aryl group, and a heteroaryl group, each R1 optionally comprises one or more alkyl-halide, halide, sulfhydryl, aldehyde, amine, acid, hydroxyl, alkyl, or aryl groups; and $B_1$ and $B_2$, which may be identical or different, each independently represents an aromatic boron-containing group;

f) Formulae FF61-FF164, wherein Formulae FF161-FF164 are:

(FF161)

(FF162)

(FF163)

72

-continued (FF164)

wherein X represents a point of covalent attachment either directly to an amine in X1 or to an amine that is covalently conjugated directly or indirectly to X1, or to OH when X1 is OH;

i is 1, 2, 3, 4, or 5;

j is 1, 2, 3, 4, or 5;

each R6, R7, R8, and R9 for different values of j is independently selected from H, $CF_3$, $CH_3$, $CHF_2$, and $(CH_2)_m CH_3$, wherein m is 1, 2, 3, 4, or 5;

Y3, Y4, Y5, Y6 and Y7 are each independently selected from H, $CH_2$—X4, and Formulae IV-1 to IV-135;

wherein X4 is selected from —COOH, —$(CH_2)_m$COOH, an alkyl group, an acyl group, a cycloalkyl group, a haloalkyl group, an aryl group, and a heteroaryl group, each X4 optionally comprises one or more alkyl-halide, halide, sulfhydryl, aldehyde, amine, acid, hydroxyl, alkyl or aryl groups; wherein m is 1, 2, 3, 4, or 5;

wherein at least one of Y5, Y6 and Y7 in Formulae FF162 and FF163 is not H and at least one of Y7, R8 and R9 in FF164 is not H; and wherein Formulae IV-1 to IV-135 are:

(IV-1)

(IV-2)

(IV-3)

(IV-4)

73
-continued (IV-5)

(IV-6)

(IV-7)

(IV-8)

(IV-9)

(IV-10)

(IV-11)

(IV-12)

(IV-13)

(IV-14)

74
-continued (IV-15)

(IV-16)

(IV-17)

(IV-18)

(IV-19)

(IV-20)

(IV-21)

(IV-22)

(IV-23)

(IV-24)

(IV-25)

75

-continued

76

-continued (IV-26)

(IV-27)

(IV-28)

(IV-29)

(IV-30)

(IV-31)

(IV-32)

(IV-33)

(IV-34)

(IV-35)

(IV-36)

(IV-37)

(IV-38)

(IV-39)

(IV-40)

(IV-41)

(IV-42)

(IV-43)

(IV-44)

(IV-45)

(IV-46)

(IV-47)

(IV-48)

77
-continued

78
-continued (IV-49)

(IV-50)

(IV-51)

(IV-52)

(IV-53)

(IV-54)

(IV-55)

(IV-56)

(IV-57)

(IV-58)

(IV-59)

(IV-60)

(IV-61)

(IV-62)

(IV-63)

79
-continued (IV-64)

(IV-65)

(IV-66)

(IV-67)

(IV-68)

(IV-69)

80
-continued (IV-70)

(IV-71)

(IV-72)

(IV-73)

(IV-74)

(IV-75)

(IV-76)

81
-continued

82
-continued (IV-77)

(IV-78)

(IV-79)

(IV-80)

(IV-81)

(IV-82)

(IV-83)

(IV-84)

(IV-85)

(IV-86)

(IV-87)

(IV-88)

(IV-89)

(IV-90)

(IV-91)

(IV-92)

(IV-93)

(IV-94)

83

-continued

84

-continued (IV-95)

(IV-96)

(IV-97)

(IV-98)

(IV-99)

(IV-100)

(IV-101)

(IV-102)

(IV-103)

(IV-104)

(IV-105)

(IV-106)

(IV-107)

(IV-108)

(IV-109)

85

-continued

86

-continued (IV-110)

(IV-120)

(IV-121)

(IV-111)

(IV-112)

(IV-122)

(IV-113)

(IV-123)

(IV-114)

(IV-115)

(IV-124)

(IV-116)

(IV-125)

(IV-117)

(IV-126)

(IV-118)

(IV-119)

(IV-127)

-continued (IV-128)

(IV-129)

(IV-130)

(IV-131)

(IV-132)

(IV-133)

(IV-134)

and (IV-135)

wherein Xa represents CH=O, CHF$_2$, CF$_3$, CH$_2$SH, COOH, CH$_2$OH, CH$_2$NO$_2$, CH$_2$NH$_2$, CH$_3$, C(CH$_3$)$_3$, CH(CH$_3$)$_2$, CH((CH$_2$)$_3$—CH$_3$)$_2$, or CH(CH$_2$—CH$_3$)$_2$;

Xb represents O, NH, CH$_2$, or S;

Xc represents CH or N;

each R$_{10}$ is independently selected from H, F, Cl, Br, CH$_3$, CF$_3$, CH=O, OH, COOH, and (CH$_2$)$_n$CH$_3$, m is 1, 2, 3, 4, or 5; and n is 1, 2, 3, 4, or 5;

B$_1$ and B$_2$, which may be identical or different, each independently represents an aromatic boron-containing group; and in Formulae IV-1 to IV-135 represents a point of attachment to corresponding Formulae FF161-164;

g) Formulae FF165-FF166, wherein Formulae FF165-FF166 are:

(FF165)

and (FF166)

wherein X represents a point of covalent attachment either directly to an amine in X1 or to an amine that is covalently conjugated directly or indirectly to X1, or to OH when X1 is OH;

m is 1, 2, 3, 4, 5, 6, or 7;

n is 1, 2, 3, 4, 5, 6, or 7;

X5 is S, O, or NH; and each R1 is independently selected from H, F, Cl, Br, OH, CH$_2$—NH$_2$, NH$_2$, (C=O)—NH$_2$, CH=O, SO$_2$CH$_3$, SO$_2$CF$_3$, CF$_3$, CHF$_2$, NO$_2$, CH$_3$, OCH$_3$, O(CH$_2$)$_m$CH$_3$, —(SO$_2$)NH—CH$_3$, —(SO$_2$)NH(CH$_2$)$_m$CH$_3$, and OCF$_3$, wherein m is 1, 2, 3, 4, 5, 6, or 7;

h) Formulae FF167-FF192, wherein Formulae FF167-FF192 are:

89

90

-continued (FF167)

(FF176)

(FF168)

(FF177)

(FF169)

(FF170)

(FF178)

(FF171)

(FF179)

(FF172)

(FF173)

(FF180)

(FF174)

(FF181)

(FF175)

| 91 | 92 |
|---|---|

(FF182)

(FF187)

(FF183)

(FF188)

(FF184)

(FF189)

(FF185)

(FF190)

(FF186)

(FF191)

and

-continued (FF192)

wherein X represents a point of covalent attachment either
directly to an amine in X1 or to an amine that is
covalently conjugated directly or indirectly to X1, or to
OH when X1 is OH;

$B_1$ and $B_2$, which may be identical or different, each
independently represents an aromatic boron-containing
group;

i) Formulae FF193-FF209, wherein Formulae FF193-
  FF209 are:

FF193

FF194

FF195

FF196

FF197

-continued

FF198

FF199

FF200

FF201

FF202

FF203

FF204

FF205

95

FF206

FF207

FF208

FF209 wherein R in FF208 and FF209 is an alkyl, aryl or halide
that is covalently conjugated through at least one CH$_2$
group to the amino group in the side chain of FF208 or
FF209, R1 and R2 are independently selected from H, CH$_3$, alkyl,
and formulae IV-1 to IV-135;

i is 1, 2, 3, 4, or 5;

j is 1, 2, 3, 4, or 5; and wherein X represents a point of covalent attachment either
directly to an amine in X1 or to an amine that is
covalently conjugated directly or indirectly to X1, or to
OH when X1 is OH; and B$_1$ and B$_2$, which may be identical or different, each
independently represents an aromatic boron-containing
group;

j) Formulae FF210-FF224, wherein Formulae FF210-
FF224 are:

FF210

FF211

96

FF212

FF213

FF214

FF215

FF216

FF217

FF218

FF219

FF220

-continued (FF221)

(FF222)

(FF223)

(FF224)

wherein R11 in FF210 to FF212 is selected from Formulae IV-1 to IV-135 and R12 is selected from an amine, a hydroxyl, an alkyl, and a halide group;

wherein each R13 is independently selected from H, $CH_3$, alkyl, aryl and Formulae IV-1 to IV-135; R14 is selected from H, $CH_3$, alkyl, aryl and heteroaryl;

wherein X represents a point of covalent attachment either directly to an amine in X1 or to an amine that is covalently conjugated directly or indirectly to X1, or to OH when X1 is OH;

X" represents a point of covalent attachment to an amine —N in the compound, wherein — represents a single covalent bond to a $CH_2$ or CH group in the compound;

i is 1, 2, 3, 4, or 5;

j is 1, 2, 3, 4, or 5; and $B_1$, $B_2$, $B_3$, $B_4$, $B_5$, and $B_6$ each independently represents an aromatic boron-containing group, wherein in each FF structure containing $B_1$, $B_2$ and $B_3$ groups, at least two of the $B_1$, $B_2$ and $B_3$ groups are independently an aromatic boron-containing group; and k) Formulae FF225-FF231, wherein Formulae FF225-FF231 are:

(FF225)

-continued (FF226)

(FF227)

(FF228)

(FF229)

(FF230)

(FF231)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

$B_1$ and $B_2$, which may be identical or different, each independently represents an aromatic boron-containing group, wherein $B_1$ and $B_2$ in Formulae FF225-FF231 are not a boronic acid or an F2 or F6 aromatic boron-containing group, wherein Formulae F2 and F6 are:

(F2)

and (F6)

$R_1$ at position 4' or position 5' represents (C=O)—*, wherein —* represents the attachment point to the rest of Z1c;

zero, one, or two $R_1$ represents F, CI, $CF_2$, $CF_3$, $SF_5$, $OCF_3$, $SO_2CH_3$, and/or $SO_2CF_3$, and each remaining $R_1$ represents H;

Y8 is O; and i is 1; and wherein at least one primary or secondary amine in FF1-FF223 and FF225-231 is optionally covalently conjugated to $B_6$.

In a fourteenth aspect, the present disclosure incudes a composition or a mixture comprising at least one compound of any one of the embodiments of the eleventh, twelfth, or the thirteenth aspect, for use as a medicament for the treatment of diabetes, for control of blood sugar levels, or to control. the release of a drug based on physiological levels of diol containing small molecules or sugars. The disclosure includes a method of administering such compound to a human subject as a therapeutic or prophylactic agent. The disclosure includes a method of making such a compound, wherein the method comprises at least one alkylation and/or amidation step. The disclosure includes a method of treating a subject by administering a device or formulation comprising such a compound. The disclosure includes a method of treatment or prevention of diabetes, impaired glucose toler-ance, hyperglycemia, or metabolic syndrome, wherein the method comprises administering to a subject in need thereof a therapeutically effective amount of such a compound.

In a fifteenth aspect, the present disclosure incudes a compound selected from Formulae FF1-FF231, wherein Formulae FF1-FF48 are:

(FF1)

(FF2)

(FF3)

(FF4)

(FF5)

(FF6)

(FF7)

101

-continued (FF8)

(FF9)

(FF10)

(FF11)

(FF12)

(FF13)

(FF14)

102

-continued (FF15)

(FF16)

(FF17)

(FF18)

(FF19)

(FF20)

(FF21)

103

-continued (FF22)

(FF23)

(FF24)

(FF25)

(FF26)

(FF27)

(FF28)

104

-continued (FF29)

(FF30)

(FF31)

(FF32)

(FF33)

(FF34)

(FF35)

(FF36)

105

-continued (FF37)

(FF38)

(FF39)

(FF40)

(FF41)

(FF42)

(FF43)

(FF44)

106

-continued (FF45)

(FF46)

(FF47)

and (FF48)

;

wherein X is selected from an maleimide, amine, OH, and halogen; and i is 1, 2, 3, 4, 5, 6, or 7;

j is 1, 2, 3, 4, 5, 6, or 7; and $B_1$ and $B_2$, which may be identical or different, each independently represents an aromatic boron-containing group;

wherein Formulae FF49-FF88 are:

(FF49)

(FF50)

(FF51)

107
-continued

108
-continued (FF52)

(FF53)

(FF54)

(FF55)

(FF56)

(FF57)

(FF58)

(FF59)

(FF60)

(FF61)

(FF62)

(FF63)

(FF64)

(FF65)

(FF66)

(FF67)

(FF68)

-continued (FF69)

(FF70)

(FF71)

(FF72)

(FF73)

(FF74)

(FF75)

-continued (FF76)

(FF77)

(FF78)

(FF79)

(FF80)

(FF81)

111

-continued (FF82)

(FF83)

(FF84)

(FF85)

(FF86)

(FF87)

and

112

-continued (FF88)

wherein X is selected from maleimide, an amine, OH, and halogen;

i is 1, 2, 3, 4, 5, 6, or 7;

j is 1, 2, 3, 4, 5, 6, or 7;

R1a is selected from COOH, CH$_3$, H, and OH;

R2, R3, R4 and R5 is each independently selected from CH$_3$, H, OH, and COOH, and at least one of R2, R3, R4 and R5 is CH$_3$ or OH; and B$_1$ and B$_2$, which may be identical or different, are each independently an aromatic boron-containing group;

wherein Formulae FF89-FF112 are:

(FF89)

(FF90)

113
-continued

114
-continued (FF91)

(FF97)

(FF92)

(FF98)

(FF93)

(FF99)

(FF94)

(FF100)

(FF95)

(FF96)

(FF101)

115
-continued (FF102)

(FF103)

(FF104)

(FF105)

(FF106)

116
-continued (FF107)

(FF108)

(FF109)

(FF110)

(FF111)

and

117

-continued (FF112)

wherein X is selected from maleimide, an amine, OH, and halogen;

i is 1, 2, 3, 4, 5, 6, or 7; and $B_1$, $B_2$ and $B_3$, which may be identical or different, each independently represents an aromatic boron-containing group, a carboxylic acid derivative, or a H, wherein at least two of B1, B2 and B3 in each FF structure are independently an aromatic boron-containing group;

wherein Formulae FF113-FF136 are:

(FF113)

(FF114)

(FF115)

(FF116)

118

-continued (FF117)

(FF118)

(FF119)

(FF120)

(FF121)

(FF122)

(FF123)

119

-continued (FF124)

(FF125)

(FF126)

(FF127)

(FF128)

(FF129)

(FF130)

120

-continued (FF131)

(FF132)

(FF133)

(FF134)

(FF135)

(FF136)

wherein X is selected from maleimide, an amine, OH, and halogen;

i is 1, 2, 3, 4, 5, 6, or 7;

j is 1, 2, 3, 4, 5, 6, or 7;

k is 1, 2, 3, 4, 5, 6, or 7;

m is 1, 2, 3, 4, 5, 6, or 7;

each R1 is independently selected from H, an alkyl group, an acyl group, a cycloalkyl group, a haloalkyl group, an aryl group, and a heteroaryl group, each R1 optionally comprises one or more alkyl-halide, halide, sulfhydryl, aldehyde, amine, acid, hydroxyl, alkyl or aryl groups; and $B_1$ and $B_2$, which may be identical or different, each independently represents an aromatic boron-containing group;

wherein Formulae FF137-FF160 are:

(FF137)

(FF138)

(FF139)

(FF140)

(FF141)

(FF142)

-continued (FF143)

(FF144)

(FF145)

(FF146)

(FF147)

(FF148)

(FF149)

-continued (FF150)

(FF151)

(FF152)

(FF153)

(FF154)

(FF155)

-continued (FF156)

(FF157)

(FF158)

(FF159)

and (FF160)

wherein X is selected from maleimide, an amine, OH, and halogen;

i is 1, 2, 3, 4, 5, 6, or 7;

j is 1, 2, 3, 4, 5, 6, or 7;

k is 1, 2, 3, 4, 5, 6, or 7;

m is 1, 2, 3, 4, 5, 6, or 7;

each R1 is independently selected from H, an alkyl group, an acyl group, a cycloalkyl group, a haloalkyl group, an aryl group, and a heteroaryl group, each R1 optionally comprises one or more alkyl-halide, halide, sulfhydryl, aldehyde, amine, acid, hydroxyl, alkyl or aryl groups; and $B_1$ and $B_2$, which may be identical or different, each independently represents an aromatic boron-containing group;

| 125 | 126 | wherein Formulae FF161-FF164 are:

(IV-2)

(FF161)

(FF162)

(FF163)

(FF164)

(IV-3)

(IV-4)

(IV-5)

(IV-6)

wherein X is selected from maleimide, an amine, OH, and halogen;

i is 1, 2, 3, 4, or 5;

j is 1, 2, 3, 4, or 5;

each R6, R7, R8, and R9 for different values of j is independently selected from H, CF$_3$, CH$_3$, CHF$_2$, and (CH$_2$)$_m$CH$_3$, wherein m is 1, 2, 3, 4, or 5;

Y3, Y4, Y5, Y6 and Y7 are each independently selected from H, CH$_2$—X4, and Formulae IV-1 to IV-135;

wherein X4 is selected from —COOH, —(CH$_2$)$_m$COOH, an alkyl group, an acyl group, a cycloalkyl group, a haloalkyl group, an aryl group, and a heteroaryl group, each optionally comprising one or more alkyl-halide, halide, sulfhydryl, aldehyde, amine, acid, hydroxyl, alkyl or aryl groups; wherein m is 1, 2, 3, 4, or 5;

wherein at least one of Y5, Y6, and Y7 in Formulae FF162 and FF163 is not H and at least one of Y7, R8 and R9 in FF164 is not H; and wherein Formulae IV-1 to IV-135 are:

(IV-7)

(IV-8)

(IV-9)

(IV-1)

(IV-10)

(IV-11)

127

-continued

128

-continued (IV-12)

(IV-23)

(IV-13)

(IV-24)

(IV-14)

(IV-25)

(IV-26)

(IV-15)

(IV-27)

(IV-16)

(IV-28)

(IV-17)

(IV-29)

(IV-18)

(IV-19)

(IV-30)

(IV-31)

(IV-20)

(IV-32)

(IV-33)

(IV-21)

(IV-34)

(IV-22)

(IV-35)

129

-continued (IV-36)

(IV-37)

(IV-38)

(IV-39)

(IV-40)

(IV-41)

(IV-42)

(IV-43)

(IV-44)

(IV-45)

(IV-46)

130

-continued (IV-47)

(IV-48)

(IV-49)

(IV-50)

(IV-51)

(IV-52)

(IV-53)

(IV-54)

131
-continued

132
-continued (IV-55)

(IV-56)

(IV-57)

(IV-58)

(IV-59)

(IV-60)

(IV-61)

(IV-62)

(IV-63)

(IV-64)

(IV-65)

(IV-66)

(IV-67)

(IV-68)

133
-continued

134
-continued (IV-69)

(IV-70)

(IV-71)

(IV-72)

(IV-73)

(IV-74)

(IV-75)

(IV-76)

(IV-77)

(IV-78)

(IV-79)

(IV-80)

(IV-81)

(IV-82)

(IV-83)

(IV-84)

(IV-85)

135

-continued (IV-86)

(IV-87)

(IV-88)

(IV-89)

(IV-90)

(IV-91)

(IV-92)

(IV-93)

(IV-94)

136

-continued (IV-95)

(IV-96)

(IV-97)

(IV-98)

(IV-99)

(IV-100)

(IV-101)

(IV-102)

(IV-103)

137
-continued (IV-104)

(IV-105)

(IV-106)

(IV-107)

(IV-108)

(IV-109)

138
-continued (IV-110)

(IV-111)

(IV-112)

(IV-113)

(IV-114)

(IV-115)

(IV-116)

(IV-117)

(IV-118)

(IV-119)

139

-continued (IV-120)

(IV-121)

(IV-122)

(IV-123)

(IV-124)

(IV-125)

(IV-126)

(IV-127)

140

-continued (IV-128)

(IV-129)

(IV-130)

(IV-131)

(IV-132)

(IV-133)

(IV-134)

and (IV-135)

65 wherein:

Xa represents CH=O, CHF$_2$, CF$_3$, CH$_2$SH, COOH, CH$_2$OH, CH$_2$NO$_2$, CH$_2$NH$_2$, CH$_3$, C(CH$_3$)$_3$, CH(CH$_3$)$_2$, CH((CH$_2$)$_3$ CH$_3$)$_2$, or CH(CH$_2$ CH$_3$)$_2$;

Xb represents O, NH, CH$_2$, or S;

Xc represents CH or N;

each R$_{10}$ is independently selected from H, F, Cl, Br, CH$_3$, CF$_3$, CH=O, OH, COOH, and (CH$_2$)$_n$CH$_3$, m is 1, 2, 3, 4, or 5; and n is 1, 2, 3, 4, or 5;

B$_1$ and B$_2$, which may be identical or different, each independently represents an aromatic boron-containing group; and

* in Formulae IV-1 to IV-135 represents the point of attachment to corresponding Formulae FF161-164;

wherein Formulae FF165-FF166 are:

(FF165)

and (FF166)

wherein X is selected from maleimide, an amine, OH, and halogen;

m is 1, 2, 3, 4, 5, 6, or 7;

n is 1, 2, 3, 4, 5, 6, or 7;

X5 is S, O, or NH; and each R$_1$ is independently selected from H, F, Cl, Br, OH, CH$_2$—NH$_2$, NH$_2$, (C=O)—NH$_2$, CH=O, SO$_2$CH$_3$, SO$_2$CF$_3$, CF$_3$, CHF$_2$, NO$_2$, CH$_3$, OCH$_3$, O(CH$_2$)$_m$CH$_3$, —(SO$_2$)NH CH$_3$, —(SO$_2$)NH(CH$_2$)$_m$CH$_3$, and OCF$_3$, wherein m is 1, 2, 3, 4, 5, 6, or 7;

wherein Formulae FF167-FF192 are:

(FF167)

(FF168)

(FF169)

(FF170)

(FF171)

(FF172)

(FF173)

(FF174)

(FF175)

143

-continued (FF176)

(FF177)

(FF178)

(FF179)

(FF180)

(FF181)

144

-continued (FF182)

(FF183)

(FF184)

(FF185)

(FF186)

145

-continued

146

-continued (FF187)

(FF192)

(FF188)

wherein X is selected from an maleimide, amine, OH, and halogen;

B₁ and B₂, which may be identical or different, each independently represents an aromatic boron-containing group, wherein Formulae FF193-FF209 are:

(FF189)

FF193

FF194

(FF190)

FF195

FF196

(FF191)

and

FF197

FF198

147

-continued

148

-continued

FF199

FF200

FF201

FF202

FF203

FF204

FF205

FF206

FF207

FF208

FF209 wherein R in FF208 and FF209 is an alkyl, aryl or halide that is covalently conjugated through at least one $CH_2$ group to the amino group in the side chain of FF208 or FF209;

R1 and R2 are independently selected from H, $CH_3$, alkyl, and formulae IV-1 to IV-135;

i is 1, 2, 3, 4, or 5;

j is 1, 2, 3, 4, or 5; and wherein X is selected from maleimide, an amine, OH, and halogen; and $B_1$ and $B_2$, which may be identical or different, each independently represents an aromatic boron-containing group;

wherein Formulae FF210-FF224 are:

FF210

FF211

FF212

149

-continued

FF213

FF214

FF215

FF216

FF217

FF218

FF219

FF220

FF221

150

-continued

FF222

FF223

FF224 wherein R11 in FF210 to FF212 is independently selected from Formulae IV-1 to IV-135 and R12 is selected from an amine, a hydroxyl, an alkyl, and a halide group;

wherein each R13 is independently selected from H, CH₃, alkyl, aryl, and formulae IV-1 to IV-135; R14 is selected from H, CH₃, alkyl, aryl, and heteroaryl;

wherein X is independently selected from maleimide, an amine, OH, and halogen;

X" is an amine;

i is 1, 2, 3, 4, or 5;

j is 1, 2, 3, 4, or 5;

and

B₁, B₂, B₃, B₄, B₅ and B₆ each independently represents an aromatic boron-containing group, wherein in each FF structure containing B1, B2 and B3 groups, at least two of the B1, B2 and B3 groups are independently an aromatic boron-containing group; and wherein Formulae FF225-FF231 are:

(FF225)

(FF226)

(FF227)

-continued (FF228)

(FF229)

(FF230)

(FF231)

wherein X is selected from an maleimide, amine, OH, and halogen;

i is 1, 2, 3, 4, 5, 6, or 7;

$B_1$ and $B_2$, which may be identical or different, each independently represents an aromatic boron-containing group, wherein $B_1$ and $B_2$ in Formulae FF225-FF231 are not a boronic acid or an F2 or F6 aromatic boron-containing group, wherein Formulae F2 and F6 are:

(F2)

and

-continued (F6)

$R_1$ at position 5' represents (C=O)—*, wherein —* represents the attachment point to the rest of FF225-FF231;

zero, one, or two $R_1$ represents F, Cl, $CF_2$, $CF_3$, $SF_5$, $OCF_3$, $SO_2CH_3$, and/or $SO_2CF_3$, and each remaining $R_1$ represents H;

Y8 is O; and i is 1; and each remaining $R_1$ is H;

Y8 is O; and i is 1; and wherein at least one primary or secondary amine in FF1-FF223 and FF225-FF231 is optionally covalently conjugated to $B_6$; and when X is an amine in any one of Formulae FF1 to FF223 and FF225-FF231, X is optionally acetylated or alkylated.

In a sixteenth aspect, the present disclosure incudes a human insulin analog, comprising an A-chain and a B-chain, wherein the sequence of the A-chain comprises:

$X_{aa'}X_{bb'}X_{cc'}X_{dd'}X_{ee'}X_{ff'}X_{gg'}$VEQCCX$_{hh'}X_{ii'}$ICSLYQLE-NYCNX$_{jj'}X_{kk'}X_{ll'}X_{mm'}X_{nn'}X_{oo'}X_{pp'}$ (SEQ ID NO:24015); and wherein the sequence of the B-chain comprises:

(i)

(SEQ ID NO: 24016)
$X_{aa}X_{bb'}X_{cc'}X_{dd'}$KX$_{ee'}X_{ff'}X_{gg'}X_{hh'}X_{ii'}X_{jj'}$KX$_{kk'}X_{ll'}X_{mm'}X_{nn'}$QHLCGSHLVEALYLVC $X_{oo'}X_{pp'}X_{qq'}$GFFYTX$_{rr'}X_{ss'}X_{tt'}X_{uu'}X_{vv'}X_{ww'}$, wherein $X_{aa'}$, $X_{bb'}$, $X_{cc'}$, $X_{dd'}$, $X_{ee'}$, $X_{ff'}$, $X_{gg'}$, $X_{hh'}$, $X_{ii'}$, $X_{jj'}$, $X_{kk'}$, $X_{ll'}$, $X_{mm'}$, $X_{nn'}$, $X_{oo'}$, $X_{pp'}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ii}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, (ii)

(SEQ ID NO: 24017)
$X_{aa}X_{bb}X_{cc}X_{dd}$KPX$_{ee}X_{ff}X_{gg}X_{hh}X_{ii}X_{jj}X_{kk}X_{ll}X_{mm}X_{nn}$QHLCGSHLVEALYLVC $X_{oo}X_{pp}X_{qq}$GFFYTX$_{rr}X_{ss}X_{tt}X_{uu}X_{vv}X_{ww}$, wherein $X_{aa'}$, $X_{bb'}$, $X_{cc'}$, $X_{dd'}$, $X_{ee'}$, $X_{ff'}$, $X_{gg'}$, $X_{hh'}$, $X_{ii'}$, $X_{jj'}$, $X_{kk'}$, $X_{ll'}$, $X_{mm'}$, $X_{nn'}$, $X_{oo'}$, $X_{pp'}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ii}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, E, F, G, H, I, K, L, N, P, Q, R, S, T, V, Y and W, FIG. 6 includes an insulin comprising an A-chain according to SEQ ID NO: 1 and B-chain according to DEQ ID NO: 24062.

FIG. 7 includes an insulin comprising an A-chain according to SEQ ID NO: 1 and B-chain according to DEQ ID NO: 24063.

FIG. 8 includes an insulin comprising an A-chain according to SEQ ID NO: 1 and B-chain according to DEQ ID NO: 25397.

FIGS. 9A and 9B illustrates a synthesis of a modified insulin according to Example 900.

FIGS. 10A and 10B illustrates a synthesis of a modified insulin according to Example 19A.

FIG. 11 includes a scheme of synthesis of diboronated sensors DS139 and DS139A.

FIG. 12 includes a scheme of synthesis of diboronated sensors DS149 and DS149A.

FIG. 13 includes a scheme of DSL Synthesis Method 1.

FIG. 14 includes a scheme of DSL Synthesis Method 2.

FIG. 15 includes a scheme of DSL Synthesis Method 3.

FIG. 16 includes a scheme of DSL Synthesis Method 4.

Figure 17:
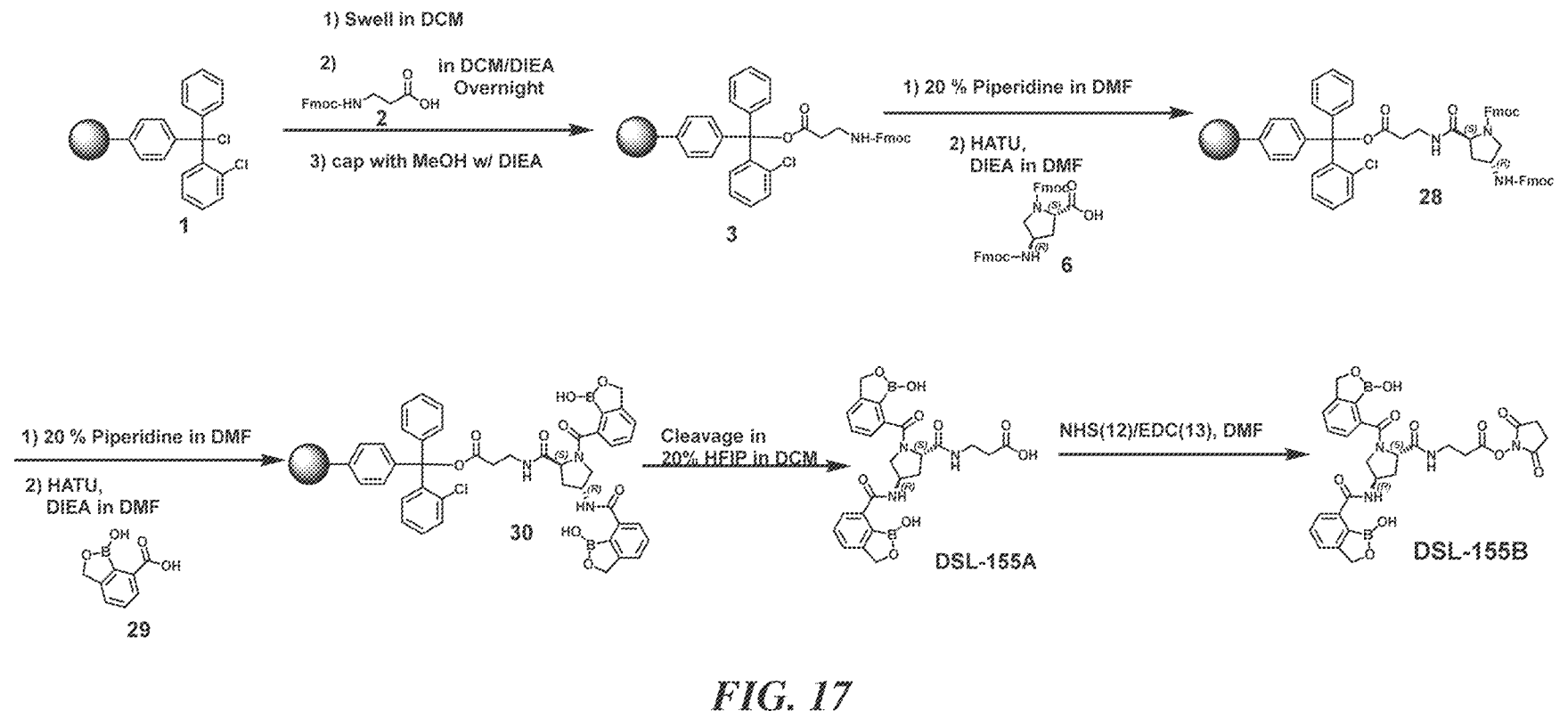

FIG. 17 includes a scheme of DSL Synthesis Method 5.

DETAILED DESCRIPTION OF THE DISCLOSURE

While aromatic boron-containing compounds (e.g., groups) can bind to diol containing molecules, achieving selectivity using aromatic boron-containing compounds (which can act as molecular sensors) is challenging because of their ability to bind various diols, including cis diols, to varying degrees. Improved binding affinity of aromatic boron-containing compounds (which can act as sensors) towards a specific vicinal diol of interest may result in a loss of selectivity.

Scaffolds that position the boron functionality (e.g., sensors) of the aromatic boron-containing compounds in a specific or particular ensemble of geometries can increase selectivity towards a specific vicinal diol while simultaneously maintaining affinity for the diol of interest. According to some embodiments, aromatic boron-containing compounds disclosed herein have different pendant groups on the aromatic boron-based scaffolds along with which specific scaffold geometries that impact binding to hydroxyl containing molecules.

According to some embodiments, the compounds of the present disclosure comprise aromatic boron-containing compounds that orient the boron functionalities in three dimensional space, so that the boron-containing compounds are spatially oriented to engage hexoses containing vicinal diols, such that the boron groups can appropriately engage the hydroxyls in the vicinal diol molecule and provide enhancement of selectivity. In some embodiments, the aromatic boron-containing compounds are modified with specific functional- groups on the aromatic ring that, together with an appropriate or suitable scaffold, may provide higher selectivity and/or affinity for binding towards a vicinal diol of interest and away from other diols in the body.

In some embodiments, the aromatic boron-containing compounds are conjugated to a drug substance (e.g., small-molecule, polypeptide) wherein the aromatic boron-containing compounds provide intramolecular and/or intermolecular interactions with the drug substance and/or with proteins in the body, such as circulating proteins in the blood and/or plasma including albumin and/or globulins. In some embodiments, aromatic boron-containing compounds exhibit reversible binding to glycated proteins in the body, (iii)

(SEQ ID NO: 24018)

$X_{aa'}X_{bb'}X_{cc'}X_{dd'}KX_{ee'}X_{ff'}X_{gg'}X_{hh'}X_{ii'}X_{jj'}KX_{kk'}X_{ll'}X_{mm'}X_{nn'}$QHLCGSHLVEALYLVC $X_{oo'}X_{pp'}X_{qq'}$GFFYTX$_{rr'}X_{ss'}X_{tt'}X_{uu'}X_{vv'}X_{ww'}$, wherein $X_{aa'}$, $X_{bb'}$, $X_{cc'}$, $X_{dd'}$, $X_{ee'}$, $X_{ff'}$, $X_{gg'}$, $X_{hh'}$, $X_{ii'}$, $X_{jj'}$, $X_{kk'}$, $X_{ll'}$, $X_{mm'}$, $X_{nn'}$, $X_{oo'}$, $X_{pp'}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ii}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, and at least one of $X_{cc}$, $X_{ff}$, $X_{gg}$, $X_{hh}$, $X_{ii}$, $X_{jj}$ is present and at least one of $X_{ee}$, $X_{ff}$, $X_{gg}$, $X_{hh}$, $X_{ii}$, $X_{jj}$ is G, (iv)

(SEQ ID NO: 24019)

$X_{aa'}X_{bb'}X_{cc'}X_{dd'}KX_{ee'}X_{ff'}X_{gg'}X_{hh'}X_{ii'}X_{jj'}KX_{kk'}X_{ll'}X_{mm'}X_{nn'}$QHLCGSHLVEALYLVC $X_{oo'}X_{pp'}X_{qq'}$GFFYTX$_{rr'}X_{ss'}X_{tt'}X_{uu'}X_{vv'}X_{ww'}$, wherein $X_{aa'}$, $X_{bb'}$, $X_{cc'}$, $X_{dd'}$, $X_{ee'}$, $X_{ff'}$, $X_{gg'}$, $X_{hh'}$, $X_{ii'}$, $X_{jj'}$, $X_{kk'}$, $X_{ll'}$, $X_{mm'}$, $X_{nn'}$, $X_{oo'}$, $X_{pp'}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ii}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, and at least one of $X_{cc}$, $X_{ff}$, $X_{gg}$, $X_{hh}$, $X_{ii}$, $X_{jj}$ is present and at least one of $X_{ee}$, $X_{ff}$, $X_{gg}$, $X_{hh}$, $X_{ii}$, $X_{jj}$ is S, or (v)

(SEQ ID NO: 24020)

$X_{aa'}X_{bb'}X_{cc'}X_{dd'}KX_{ee'}X_{ff'}X_{gg'}X_{hh'}X_{ii'}X_{jj'}KX_{kk'}X_{ll'}X_{mm'}X_{nn'}$QHLCGSHLVEALYLVC $X_{oo'}X_{pp'}X_{qq'}$GFFYTX$_{rr'}X_{ss'}X_{tt'}X_{uu'}X_{vv'}X_{ww'}$, wherein $X_{aa'}$, $X_{bb'}$, $X_{cc'}$, $X_{dd'}$, $X_{ee'}$, $X_{ff'}$, $X_{gg'}$, $X_{hh'}$, $X_{ii'}$, $X_{jj'}$, $X_{kk'}$, $X_{ll'}$, $X_{mm'}$, $X_{nn'}$, $X_{oo'}$, $X_{pp'}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ii}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, and at least one of $X_{cc}$, $X_{ff}$, $X_{gg}$, $X_{hh}$, $X_{ii}$, $X_{jj}$ are present and at least one of $X_{ee}$, $X_{ff}$, $X_{gg}$, $X_{hh}$, $X_{ii}$, $X_{jj}$ is S, and another is G.

BRIEF DESCRIPTION OF THE DRAWINGS

The present disclosure may be better understood, and its numerous features and advantages made apparent to those skilled in the art by referencing the accompanying drawings.

Figure 1:
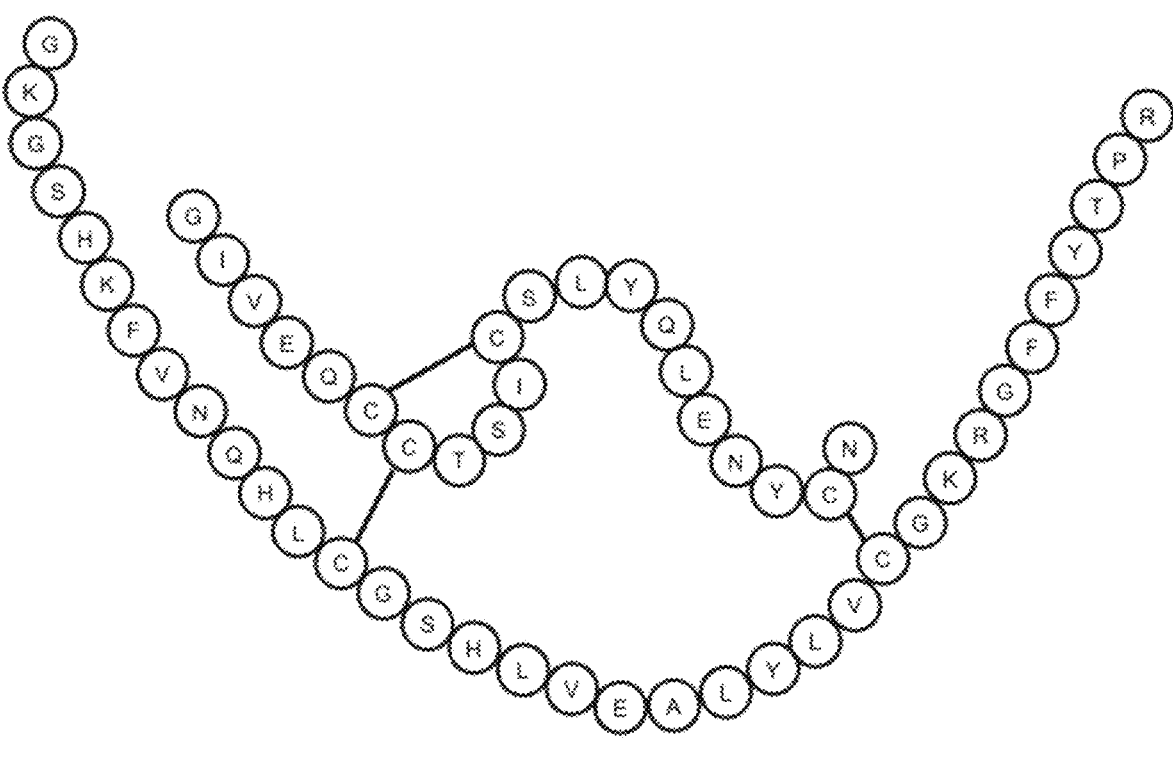
FIG. 1 includes an insulin comprising an A-chain according to SEQ ID NO: 1 and B-chain according to DEQ ID NO: 25228.

such as glycated albumin, and this binding is reversibly influenced by the levels of blood sugar or plasma sugar molecules. In some embodiments, the selective binding of the sensors to specific vicinal diols changes the extent of those intramolecular and/or intermolecular bindings and thereby modulates the pharmacokinetics and overall activity of the drug substance in the body; this effect can be controlled by the level of the vicinal diols present.

In some embodiments, the drug substance is a peptide hormone. In some embodiments, the peptide hormone is a human peptide hormone such as insulin or an insulin analogue, glucagon, or another incretin hormone. In some embodiments the sensors are selective towards the vicinal diols in glucose, and this selectivity is enhanced while maintaining affinity to glucose and simultaneously reducing affinity to other sugars in the blood. In some embodiments, the scaffolds as well as (e.g., in combination with) the pendant groups on the aromatic core of the boron-containing compounds enable controlling the overall activity and/or pharmacokinetics of the conjugated drug substances based on levels of glucose and/or other vicinal diols in the blood.

In some embodiments, the aromatic boron-containing compounds comprise specific scaffold molecules (e.g., FF structures, FFL-1 to FFL-68, DSL-1 to DSL-172) with conjugated boron functionalities (e.g., F1-F11), wherein the scaffolds have been used to orient the boron functionalities in three dimensional geometries so that the boron functionalities are oriented near each other and within a distance that helps engage specific hydroxyl orientations of select hexoses such as glucose. In some embodiments, the boron functionalities are selected from F1-F11. In some embodiments, the boron functionalities are selected from F2, F6, and F7. In some embodiments, the boron functionalities are selected from F2 and F7. In some embodiments, the boron functionality/group is F2. In some embodiments, the boron functionality/group is F7.

Without wishing to be bound by theory, it is believed that the aromatic boron-containing compounds (e.g., molecules) disclosed herein enhance selectivity through at least one or more of the following three mechanisms: (1) the FF scaffold facilitates matching the orientation of the hydroxyl and/or alkoxy groups on boron groups in the aromatic boron-containing compounds and the hydroxyls in the vicinal diol molecule which enhances selectivity; (2) further selectivity gain is obtained by identifying specific functional groups attached to, or near, for example, the aromatic core of the boron-containing compound which impact the electronic structure of the aromatic boron-containing compound and thereby favor reversible binding to the vicinal diols at physiological pH; and (3) functional groups attached to the aromatic boron-containing compound (e.g., the sensor scaffold) help to provide steric hindrance to reduce binding to unwanted hexoses while maintaining binding to the sugar of interest such as glucose. In some embodiments, the FF scaffolds provide glucose binding. In some embodiments, the combination of the FF scaffold and the indirect linker and/or direct linker provides affinity to plasma proteins, such as but not limited to glycated proteins, and the combination of the FF scaffold and the indirect linker and/or direct linker (e.g. Z1b) provides a reversible interaction with plasma proteins that is controlled through the binding of sugar molecules to the FF scaffolds under physiological conditions. These effects as combined together (e.g., compounds of Formulae I, III) in the present disclosure provide desired or suitable selectivity of binding towards a vicinal diol-containing molecule of interest and away from other diols in the body.

In some embodiments, the aromatic boron-containing compounds are conjugated to a drug substance wherein the aromatic boron-containing compounds provide intramolecular and/or intermolecular interactions with proteins in the body. Such proteins may include circulating proteins in the blood and/or human plasma such as albumin, glycosylated proteins and/or immunoglobulins, glycated proteins including glycated plasma proteins such as glycated albumin. In some embodiments the selective binding of the sensors to specific vicinal diols in a molecule of interest changes the extent of intramolecular and intermolecular bindings and thereby modulates the pharmacokinetics and overall activity of the drug substance in the body. In some embodiments, the drug substance is a peptide hormone and in certain embodiments thereof the peptide hormone is an incretin hormone such as insulin and the vicinal diol containing molecule is glucose, but the present disclosure is not limited thereto.

Definitions

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

Unless specifically described herein, functional groups, functional moieties, and reactions referred to herein are understood to have meanings consistent with standard descriptions in and/or general principles of organic chemistry, for example, as described in Organic Chemistry, Thomas Sorrell, University Science Books, Sausalito, 1999; Larock, Comprehensive Organic Transformations, VCH Publishers, Inc., New York, 1989; Carruthers, Some Modern Methods of Organic Synthesis, $3^{rd}$ Edition, Cambridge University Press, Cambridge, 1987; Smith and March, March's Advanced Organic Chemistry, $5^{th}$ Edition, John Wiley & Sons, Inc., New York, 2001. Generic functional groups (such as alkyl, aryl, acetyl, etc.) encompass specific examples or species falling within those functional group categories as generally defined in the field of organic chemistry, and those having ordinary skill in the art are capable of identifying specific example embodiments of functional groups.

Unless specifically described herein, chemical terms, functional groups, and general terms used throughout the specification are identified in accordance with the Periodic Table of the Elements, CAS version, Handbook of Chemistry and Physics, $75^{th}$ Ed., inside cover. In certain embodiments, the terms "a," "an," and "the" and similar referents used herein are to be construed to cover both the singular and the plural unless their usage in context indicates otherwise. The term "CAS #" as used herein is also referred to as CASRN or CAS Number, is a unique numerical identifier assigned by Chemical Abstracts Service (CAS) to every chemical substance described in the open scientific literature.

As used herein, nomenclature for compounds including organic compounds, can be given using common names, IUPAC, IUBMB, or CAS recommendations for nomenclature. One of skill in the art can readily ascertain the structure of a compound if given a name, either by systemic reduction of compound structure using naming conventions, or by commercially available software, such as CHEMDRAW™ (Cambridgesoft Corporation, U.S.A.).

The terminology used herein is for the purpose of describing embodiments and is not intended to be limiting of the present disclosure. It will be further understood that the terms "comprises," "comprising," "includes," and "including," when used in this specification, specify the presence of the stated features, integers, acts, operations, elements, and/or components, but do not preclude the presence or addition of one or more other features, integers, acts, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. The term "about" used throughout is used to describe and account for small variations. For instance, "about" may mean the numeric value may be modified by ±5%, ±4%, ±3%, ±2%, ±1% ±0.5%, ±0.4%, ±0.3%, ±0.2%, ±0.1% or ±0.05%. Numeric values modified by the term "about" include the specific identified value. For example, "about 5.0" includes 5.0.

Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all sub-ranges of the same numerical precision subsumed within the recited range. For example, a range of "1 to 10" is intended to include all subranges between (and including) the recited minimum value of 1 and the recited maximum value of 10, that is, having a minimum value equal to or greater than 1 and a maximum value equal to or less than 10, such as, for example, 2 to 7. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

As used herein, "aromatic boron-containing group" refers to a compound having at least one boron atom covalently bonded to an aromatic group and/or a compound having at least one boron atom covalently incorporated within an aromatic group. The term "aromatic" asused herein may include "heterocycle," "heterocyclyl," or "heterocyclic." As used herein the terms "heterocycle," "heterocyclyl," or "heterocyclic" each refer to an unsaturated 3- to 18-membered ring containing one, two, three, or four heteroatoms independently selected from nitrogen, oxygen, phosphorus, and sulfur. In some embodiments, the term "aromatic" may include an "aryl." The term "aryl" as used herein refers to a mono-, bi-, or other multi carbocyclic, aromatic ring system with 5 to 14 ring atoms. The aryl group can optionally be fused to one or more rings selected from aryls, cycloalkyls, heteroaryls, and heterocyclyls. Exemplary aryl groups also include but are not limited to a monocyclic aromatic ring system, wherein the ring comprises 6 carbon atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents. Heteroaryls can also be fused to non-aromatic rings. Exemplary heteroaryl groups include, but are not limited to, a monocyclic aromatic ring, wherein the ring comprises 2-5 carbon atoms and 1-3 heteroatoms. In some embodiments, the aromatic boron-containing group may include but is not limited to aryl- and heteroaryl boronic acids, aryl and heteroaryl boronate esters, and/or boroxoles. Exemplary aromatic boron-containing groups useful according to certain embodiments, include, e.g., those described herein as FF1-FF231, F1-F11, and FFL-1 to FFL-68, and further include, e.g., those as disclosed in patent application PCT/US2021/025261 (filed Mar. 31, 2021) as compounds F1-F9, F12-F43, F500-F520 and PCT/US2021/059802 (filed Nov. 18, 2021) as compounds FF1-FF224 and F1-F10; the disclosures of which are herein expressly incorporated by reference in their entirety.

The term "small-molecule linker" as used herein refers to a chemical group (e.g., scaffold, moiety) comprising a first attachment point toward X1 and a second attachment point toward Z1b, Z1a, or Z1c. In some embodiments, the first attachment point is toward X1 and the second attachment point is toward Z1c. In some embodiments, the first attachment point is toward X1 and the second attachment point is toward Z1a. In some embodiments, the small molecule linker is a moiety/chemical group selected from Formulae IIa-IIai and Formulae IIIa-IIIai. In some embodiments, the small molecule linker is a moiety/chemical group selected from Formulae FL1-FL19, FL5A, FL5B, FL65A, FL65B, FL69, FL69A, FL69B, FL70, FL70A, and FL70B, and an L- or D-amino acid comprising at least one amine group directly conjugated to Z1c, wherein an acid functional group of the amino acid is conjugated toward X1 in Formula I or Formula IB.

The term "indirect linker" as used herein refers to a chemical group (e.g., scaffold, moiety) comprising a first attachment point toward X1 and a second attachment point toward Z1b, Z1a, or Z1c. In some embodiments, the first attachment point is toward X1 and the second attachment point is toward Z1c. In some embodiments, the first attachment point is toward Z1a and the second attachment point is toward Z1c. In some embodiments, the indirect linker is a moiety/chemical group selected from Formulae FL1-FL19, FL5A, FL5B, FL65A, FL65B, FL69, FL69A, FL69B, FL70, FL70A, and FL70B, and an L- or D-amino acid comprising at least one amine group directly conjugated to Z1c, wherein an acid functional group of the amino acid is conjugated toward Z1a or X1, independently, in Formula I or Formula IB.

The term "moiety" as used herein refers to a chemical group (e.g., Z1c) comprising at least one attachment point to another group, such as a scaffold (e.g., X1, Z1b1, Z1b2). For example, a linker moiety is a chemical group having two points of attachment. As an example, in Formula IE Z1b is a linker moiety having a first point of attachment to an amine in X1 and a second point of attachment to a Z1c. In some embodiments, the first attachment point (i.e., covalent conjugation) is toward X1 and the second attachment point (i.e., covalent conjugation) is toward Z1c. In some embodiments, each Z1b is independently a linker moiety. In some embodiments, Z1b is selected from Formulae FL3, FL5, FL5A, FL5B, FL65A, FL65B, FL69, FL69A, FL69B, FL70, FL70A, and FL70B. In some embodiments, at least one Z1c is covalently conjugated via one or more Z1b to an amine in X1, wherein each Z1b is independently selected from Formulae FL(IA), FL(IB), FL3, FL5, FL5A, FL5B, FL65A, FL65B, FL69, FL69A, FL69B, FL70, FL70A, and FL70B.

As used herein, a "diol containing moiety" is a diol containing group comprising at least two hydroxyl groups. In some embodiments, the diol is not a saccharide. In some embodiments, the diol containing moiety may be 3-26 carbons long. In addition, or in the alternative, the molecular weight of the diol containing moiety may be between 90 and 570. Examples of such non-saccharide diol containing moieties may be provided by organic acids (such as gluconic acid, threonic acid, glyceric acid, galactonic acid, and dihydroxycinnamic acid), thiol-containing compounds (such as 1-thioglycerol, and 1, 2, 3-butanetriol-4-mercapto), and amino compounds (such as (±)-3-amino-1,2-propanediol, (±)-3-amino-1,2-propanediol, and glucosamine).

As used herein, a "polyol containing moiety" is an alcohol with more than one hydroxyl group. In some embodiments, the polyol may be, for example, sorbitol (produced from glucose), xylitol (from xylose), erythritol (from erythrose), lactitol (from lactose), maltitol (from maltose), mannitol (from mannose), polyglycitol (from starch hydrolysate), isomalt, glycerol, propylene glycol, polyethylene glycol (PEG), polypropylene glycol, polyoxyethylated polyols (e.g., POG), polyoxyethylated sorbitol, or polyoxyethylated glucose.

As used herein, "near the C-terminus of the B-chain" includes 10 or less amino acids (e.g., 9 amino acids, 8 amino acids, 7 amino acids, 6 amino acids, 5 amino acids) from the C-terminus of the B chain. In some embodiments, an amine to which a diboronate is covalently conjugated is at or near the C-terminus of the B-chain, preferably to an amine of a B29 lysine or a B21 lysine. The numbering used herein (e.g., B29, B21) refers to the wild-type sequence numbering used in chain-B of human insulin where the B-chain has an amino acid sequence FVNQHLCGSHLVEALYL-VCGERGFFYTPKT (SEQ ID NO: 2). For example, $B_{29}$ is K in the wild type sequence and B21 is E in the wild type sequence.

As used herein, "near the N-terminus" of the A-chain or B chain includes 10 or less amino acids (e.g., 9 amino acids, 8 amino acids, 7 amino acids, 6 amino acids, 5 amino acids) from the N-terminus of the A-chain or B chain.

As used herein, "amino acid" includes proteinogenic (or natural) amino acids (amongst those the 20 standard amino acids), as well as non-proteinogenic (or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification). In general, amino acid residues (peptide/protein sequences) may be identified by their full name, their one-letter code, and/or their three-letter code. These three ways are fully equivalent. In what follows, each amino acid of the compounds of the disclosure for which the optical isomer is not stated is to be understood to mean the L-isomer (unless otherwise specified). Amino acids, are molecules containing an amino group and a carboxylic acid group, and, optionally, one or more additional groups, often referred to as a side chain.

As used herein, the term "amino acid residue" is an amino acid from which, formally, a hydroxy group has been removed from a carboxy group and/or from which, formally, a hydrogen atom has been removed from an amino group. As is apparent from the below examples, amino acid residues may be identified by their full name, their one-letter code, and/or their three-letter code. These three ways are fully equivalent and interchangeable.

The term "alkyl" as used herein refers to a saturated straight or branched hydrocarbon, such as a straight or branched group of 1-30 carbon atoms, referred to herein as $C_{1-30}$ alkyl. In some embodiments, the alkyl group is a $C_1$-$C_{22}$ alkyl group. In some embodiments, the alkyl group is a $C_1$-$C_{20}$ alkyl group. In some embodiments, the alkyl group is a $C_1$-$C_{18}$ alkyl group. In some embodiments, the alkyl group is a $C_1$-$C_{16}$ alkyl group. In some embodiments, the alkyl group is a $C_1$-$C_{14}$ alkyl group. In some embodiments, the alkyl group is a $C_1$-$C_{12}$ alkyl group. In some embodiments, the alkyl group is a $C_1$-$C_{10}$ alkyl group. In some embodiments, the alkyl group is a $C_1$-$C_8$ alkyl group. In some embodiments, the alkyl group is a $C_1$-$C_6$ alkyl group. In some embodiments, the alkyl group is a $C_1$-$C_4$ alkyl group. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

The term "cycloalkyl" as used herein refers to a saturated or unsaturated cyclic, bicyclic, or bridged bicyclic hydrocarbon group of 3-16 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl (saturated or partially unsaturated), aryl, or heterocyclyl groups, to form a bicycle, tetracycle, etc. The term "cycloalkyl" also includes bridged and spiro-fused cyclic structures which may or may not contain heteroatoms. In some embodiments, the cycloalkyl group is a ($C_3$-$C_6$)cycloalkyl.

The term "acyl" as used herein refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, and (heterocyclyl)-C(O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cycloalkyl, or heteroaryl, portion plus the carbonyl carbon of acyl. For example, a $C_4$-acyl has three other ring or chain atoms plus carbonyl. In some embodiments, it is a $C_1$-$C_{22}$acyl group. In some embodiments, it is a $C_1$-$C_{20}$acyl group. In some embodiments, it is a $C_1$-$C_{18}$acyl group. In some embodiments, it is a $C_1$-$C_{16}$acyl group. In some embodiments, it is a $C_1$-$C_{14}$acyl group. In some embodiments, it is a $C_1$-$C_{12}$acyl group. In some embodiments, it is a $C_1$-$C_{10}$acyl group. In some embodiments, it is a $C_1$-$C_8$acyl group.

The term "haloalkyl" as used herein refers to an alkyl group substituted with one or more halogens. Examples of haloalkyl groups include, but are not limited to, trifluorom-ethyl, difluoromethyl, pentafluoroethyl, trichloromethyl, etc. In some embodiments, it is a $C_1$-$C_{22}$ haloalkyl group. In some embodiments, it is a $C_1$-$C_{20}$ haloalkyl group. In some embodiments, it is a $C_1$-$C_{18}$ haloalkyl group. In some embodiments, it is a $C_1$-$C_{16}$ haloalkyl group. In some embodiments, it is a $C_1$-$C_{14}$ haloalkyl group. In some embodiments, it is a $C_1$-$C_{12}$ haloalkyl group. In some embodiments, it is a $C_1$-$C_{10}$ haloalkyl group. In some embodiments, it is a $C_1$-$C_8$ haloalkyl group. In some embodiments, it is a $C_1$-$C_6$ haloalkyl group.

The term "aryl" as used herein refers to a mono-, bi-, or other multi-carbocyclic, aromatic ring system with 5 to 14 ring atoms. The aryl group can optionally be fused to one or more rings selected from aryls, cycloalkyls, heteroaryls, and heterocyclyls. The aryl groups of this present disclosure can be substituted with groups selected from alkoxy, aryloxy, alkyl, alkenyl, alkynyl, amide, amino, aryl, arylalkyl, car-bamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaph-thyl. Exemplary aryl groups also include but are not limited to a monocyclic aromatic ring system, wherein the ring comprises 6 carbon atoms.

As used herein, a "leaving group" is an atom (or a group of atoms) that can be displaced as stable species taking with it the bonding electrons. For example, leaving groups can be anions (e.g. Cl⁻) or neutral molecules (e.g. $H_2O$). In some embodiments, a leaving group is a halogen, a N-hydrox-ysuccinimide (NHS) group, a 2,3,5,6-tetrafluorophenol (TFP) group, a pentafluorophenol (Pfp) group, or a sulfonate ester.

"Isomers" means compounds having the same number and kind of atoms, and hence the same molecular weight, but differing with respect to the arrangement or configuration of the atoms in space.

"Stereoisomer" or "optical isomer" means a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure which may give rise to stereoisomerism, the disclosure contemplates stereoisomers and mixtures thereof. The com-pounds of the disclosure and their salts include asymmetric carbon atoms and may therefore exist as single stereoiso-mers, racemates, and as mixtures of enantiomers and diaste-reomers. In some embodiments, such compounds will be prepared as a racemic mixture. In some embodiments, such compounds can be prepared or isolated as pure stereoiso-mers, e.g., as individual enantiomers or diastereomers, or as stereoisomer-enriched mixtures. As discussed in more detail below, individual stereoisomers of compounds may be pre-pared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separa-tion of the enantiomers on chiral chromatographic columns. Starting compounds of particular stereochemistry are either commercially available or are made by the methods described below and resolved by techniques well-known in the art.

As used herein, a "fatty acid" is a carboxylic acid with an aliphatic chain. A saturated fatty acid has a saturated ali-phatic chain whereas an unsaturated fatty acid has an unsaturated aliphatic chain. In some embodiments, the fatty acid is a $C_3$-$C_{26}$ fatty acid. In some embodiments, the fatty acid is a $C_4$-$C_{20}$ fatty acid. In some embodiments, the fatty acid is a saturated fatty acid selected from $CH_3CH_2COOH$, $CH_3(CH_2)_2COOH$, $CH_3(CH_2)_3COOH$, $CH_3(CH_2)_4COOH$, $CH_3(CH_2)_5COOH$, $CH_3(CH_2)_6COOH$, $CH_3(CH_2)_7COOH$, $CH_3(CH_2)_8COOH$, $CH_3(CH_2)_9COOH$, $CH_3(CH_2)_{10}COOH$, $CH_3(CH_2)_{11}COOH$, and $CH_3(CH_2)_{12}COOH$, $CH_3(CH_2)_{13}COOH$, $CH_3(CH_2)_{14}COOH$, $CH_3(CH_2)_{15}COOH$, $CH_3(CH_2)_{16}COOH$, $CH_3(CH_2)_{17}COOH$, and $CH_3(CH_2)_{18}COOH$. In some embodiments, the fatty acid is an unsaturated fatty acid selected from α-linoleic acid, steari-donic acid, eicosapentaenoic acid, cervonic acid, linoleic acid, linolelaidic acid, γ-Linolenic acid, oleic acid, elaidic acid, and gondoic acid.

The term "pharmaceutically acceptable salt(s)" refers to salts of acidic or basic groups that may be present in compounds used in the present compositions.

As used herein, "drug substance" refers to small-molecule compounds and/or polypeptide containing compounds. According to some embodiments, a drug substance suitable for use in the compounds and methods described herein is a therapeutically, prophylactically and/or diagnostically active drug substance.

It will be understood that, although terms such as "first," "second," "third," etc., may be used herein to describe various elements (such as molecules, components, groups, and/or moieties, etc.), those elements should not be limited by these terms. These terms are merely used to distinguish one element from another element. Thus, a first element described below could be termed a second element without departing from the spirit and scope of the present disclosure. It will be understood that when an element or group is referred to as being "connected to," "conjugated with," "linked," or "coupled to" another element or group, the two elements may be directly connected, or one or more inter-vening elements may be present. It will be understood that conjugations and linkages described herein have the option of being direct conjugations or direct linkages, unless expressly excluded or precluded by the context.

As used herein, the terms "directly" or "directly cova-lently conjugated" or "covalently conjugated directly" may be interchangeably used to indicate that a first group is "directly" or "directly covalently conjugated" or "covalently conjugated directly" to a second group, which means the first and second groups are covalently bonded together without additional intervening groups.

As used herein, the terms "indirectly" or "indirectly covalently conjugated" or "covalently conjugated indi-rectly" may be interchangeably used to indicate that a first group is "indirectly" or "indirectly covalently conjugated" or "covalently conjugated indirectly" to a second group, which means the first and second groups are covalently bonded together with at least one additional intervening group (e.g., a small-molecule, a linker moiety, a spacer, a linear sequence of amino acids and/or nonlinear sequence of amino acids).

In some embodiments, one or more groups (e.g., X1a, Z1a, Z1b, Z1c) are covalently conjugated directly or indi-rectly (e.g., via one or more linker(s), such as Z1b, Z1b1, Z1b2) to each other. For example, according to certain embodiments Z1c is covalently conjugated, directly or indirectly (e.g., via one or more Z1b linkers) to an amine in X1 or to OH when X1 is OH. As one example, according to certain embodiments one or more drug substances or polypetides (X1) are covalently conjugated to one or more Z1b. As another example, according to certain embodiments one or more drug substances (X1) are covalently conjugated to one or more amine containing linkers. In some embodiments, X represents a point of covalent attachment either directly to an amine in X1 or to an amine that is covalently conjugated directly or via one or more Z1b to X1. In some embodiments, X represents a point of covalent attachment either directly to an amine in X1 or to an amine that is covalently conjugated directly or indirectly to X1, or to OH when X1 is OH. In some embodiment, each Z1c is independently covalently conjugated, directly or indirectly, to an amine of Z1a, to an amine of Z1b, or to X1. In some embodiments, each Z1c is independently covalently conjugated, directly or via one or more Z1b to an amine of X1. In some embodiments, at least one Z1c is covalently conjugated via one or more Z1b to an amine in X1.

The terms "insulin receptor agonist," "compound having agonist potency" in the context of having potency against an insulin receptor, and "agonist potency" in the context of a compound having agonist potency against an insulin receptor-refer to a compound (e.g., a compound of Formula I or Formula IB, a protein, a fusion proteinas described in, e.g., US 2016/0324932) that binds to and/or activates an insulin receptor.

The term "short-acting insulin receptor agonist" and "short-acting insulin" refer to an insulin receptor agonist having an onset of activity equal to or faster than insulin isophane human and insulin human, sold under the tradename Humulin®. For example, a short-acting of insulin may have an onset of action that occurs within 10 minutes of injection. As another example, a short-acting of insulin may have an onset of action that occurs within 20 minutes of injection. In some embodiments, a short-acting insulin may have a maximum effectiveness (peak) within 1-4 hours post injection. In some embodiments, short-acting insulin can be administered before or during and/or shortly after a meal.

The term "long-acting insulin receptor agonist" and "long-acting insulin" refer to an insulin receptor agonist having an onset of action slower than Humulin®. For example, a long-acting insulin may have an onset of action between 1-2 hours, or longer. In certain embodiments, a long-acting insulin may have a maximum effectiveness (peak) within between 6-20 hours and or have prolonged action. In some embodiments, a long-acting insulin can be administered at a frequency of once daily or, for example, once weekly.

When used herein in connection with an insulin receptor agonist, the term "suitable for meal dosing" refers to a short acting insulin receptor agonist suitable for controlling blood glucose levels during and/or shortly after a meal.

When used herein in connection with an insulin receptor agonist, the term "suitable for once-weekly dosing" refers to an insulin receptor agonist with a pharmacokinetic and pharmacodynamic profile that is sufficiently prolonged to control blood glucose levels throughout the day when administered no more frequently than once weekly. Examples of such molecules include fusion proteins as described in US2016/0324932, including BIF. BIF, also known as insulin efsitora alfa, comprises a dimer of an insulin receptor agonist fused to a human IgG Fc region, wherein the insulin receptor agonist comprises an insulin B-chain analogue fused to an insulin A-chain analogue through the use of a first peptide linker and wherein the C-terminal residue of the insulin A-chain analogue is directly fused to the N-terminal residue of a second peptide linker, and the C-terminal residue of the second peptide linker is directly fused to the N-terminal residue of the human IgG Fc region. BIF is identified by CAS registry number 2131038-11-2, which provides the following chemical names: (1) Insulin [16-glutamic acid, 25-histidine, 27-glycine, 28-glycine, 29-glycine, 30-glycine](human B-chain) fusion protein with peptide (synthetic 7-amino acid linker) fusion protein with insulin [47-threonine, 51-aspartic acid, 58-glycine](human A-chain) fusion protein with peptide (synthetic 20-amino acid linker) fusion protein with immunoglobulin G2 (human Fc fragment), dimer; and (2) *Homo sapiens* Insulin B-chain [Y16>Y(16), F25>H(25), TPKT27-30>GGGG(27-30)](1-30) fusion protein with di glycyl seryltetraglycyl (31-37) Insulin A-chain [I10>T(47), Y14>D(51), N21>G(58)](38-58) fusion protein with tris (tetraglycylglutaminyl)pentaglycyl (59-78) *Homo sapiens* Immunoglobulin heavy constant gamma 2 {del-CH1, hinge-(7-12), CH2, CH3[K$^{107}$>del(300)]}(79-299), dimer (80-80': 83-83')-bisdisulfide, expressed in CHO cells, alfa glycosylated.

As used herein, "glucose sensing insulin" refers to an insulin receptor agonist having an onset of activity and/or level of activity that depends on blood sugar level. Examples of such molecules include compounds of Formula I or Formula IB disclosed herein, such as Examples 1A-82A.

The term "incretin-based therapy" includes any treatment which comprises administration of, or promotes, enables, enhances and/or simulates the effects of, a group of metabolic hormones known as incretins, which group includes, but is not limited to, GLP-1, gastric inhibitory peptide (GIP), and glucagon. Incretin-based therapies which are currently available include GLP-1R agonists.

A "DPP-4 inhibitor" is a compound that blocks the DPP-4 enzyme, which is responsible for the degradation of incretins. Currently available DPP-4 inhibitors include sitagliptin (Januvia®) and linagliptin (Tradjenta®).

A "GLP-1R agonist" and "Glucagon receptor agonist" is defined as a compound comprising the amino acid sequence of native human GLP-1 (SEQ ID NO:25) or human glucagon, as well as a compound that maintains full or partial activity at the GLP-1 receptor that is a GLP-1 analogue, GLP-1 derivative or GLP-1 fusion protein. GLP-1R activity may be measured by methods known in the art, including using in vivo experiments and in vitro assays that measure GLP-1 receptor binding activity or receptor activation, e.g., assays employing pancreatic islet cells or insulinoma cells, as described in EP 619,322 and U.S. Pat. No. 5,120,712, respectively. A GLP-1 analogue is a molecule having a modification including one or more amino acid substitutions, deletions, inversions, or additions when compared with the amino acid sequence of native human GLP-1 (SEQ ID NO:25). A GLP-1 derivative is a molecule having the amino acid sequence of native human GLP-1 (SEQ ID NO:25) or of a GLP-1 analogue, but additionally having at least one chemical modification of one or more of its amino acid side groups, α-carbon atoms, terminal amino group, or terminal carboxylic acid group. A GLP-1 fusion protein is a heterologous protein comprising GLP-1, a GLP-1 analogue or a GLP-1 derivative portion and a second polypeptide. Currently available GLP-1R agonists include exenatide (Byetta® and Bydureon®), liraglutide (Victoza®), albiglutide (Tanzeum®) and dulaglutide (Trulicity®), the structures of which are known in the art. See, e.g., U.S. Pat. No. 5,424, 286 (exenatide); U.S. Pat. No. 6,268,343 (liraglutide); US20140447 I 7 (albiglutide); and U.S. Pat. No. 7,452,966 (dulaglutide).

The term "excipient" means any substance added to the composition other than the fusion protein or any other additional active ingredient(s). Examples of such excipients that may be used in the compositions of the present disclosure include buffering agents, surfactants, isotonicity agents and preservatives. A "pharmaceutically acceptable excipient" refers to an excipient that is compatible with the other ingredients in the composition and that is suitable for contact with any tissue, organ, or portion of the body that it may encounter, meaning that it must not carry a risk of toxicity, irritation, allergic response, immunogenicity, or any other complication that excessively outweighs its therapeutic benefits. In some embodiments the excipients may be used to stabilize the agonist while in solution or to increase the onset and maximum effectiveness. Such excipients may include mannitol, sorbitol, m-cresol, EDTA, and citrate.

A "buffering agent" is a substance which resists changes in pH by the action of its acid-base conjugate components. In certain embodiments, the composition of the present disclosure has a pH from about 5.5 to about 9.0, preferably, between about 7.0 and about 8.0, more preferably between about 7.2 and 7.8. Buffering agents suitable for controlling the pH of the compositions of the present disclosure in the desired range include, but are not limited to agents such as phosphate, acetate, citrate, or acids thereof, arginine, TRIS, HEPES, and histidine buffers, as well as combinations thereof. "TRIS" refers to 2-amino-2-hydroxymethyl-1,3,-propanediol, and to any pharmacologically acceptable salt thereof. The free base and the hydrochloride form (i.e., TRIS-HCl) are two common forms of TRIS. TRIS is also known in the art as trimethylol aminomethane, tromethamine, and tris(hydroxymethyl) aminomethane. Preferred buffering agents in the composition of the present disclosure are citrate, or citric acid, phosphate, and TRIS.

The compounds disclosed herein may comprise one or more protein components (e.g., where X1 comprises one or more protein components). In some embodiments, the compounds disclosed herein comprise two or more fused protein components or two or more conjugated protein components. The term "fusion protein" as used herein refers to the combination of two or more distinct proteins that are linked together directly via a peptide bond between the C-terminus of one protein and the N-terminus of another protein or indirectly via a linker (i.e., through chemical linkers such as biofunctionalized PEG linkers) or through a continuous amino acid chain) joining the C-terminus or the N-terminus or a side chain of one protein and the C-terminus or the N-terminus or a side chain of another protein. The term "conjugate protein" as used herein refers to the combination of two or more distinct proteins that are linked together chemically either directly via a chemical bond or indirectly via a chemical linker. In some instances, the two or more proteins may act on the same or similar receptors (i.e., a fusion of two insulin agonist peptides) or may act upon separate and distinct receptors (i.e., one protein is an insulin receptor agonist, and another protein is a glucagon receptor agonist). In some instances, the fusion protein may contain only one agonist protein while the other protein is a human IgG Fc region or a single domain antibody (nanobody) or a variable-heavy chain sequence ($V_HH$).

The phrase "composition comprising a fusion protein" encompasses compositions comprising a monomer, homodimer, heterodimer, or multimer of a fusion protein. In certain embodiments, a pharmaceutical composition of the present disclosure is a composition comprising a fusion protein in a concentration of at least 1 mg/mL, at least 2 mg/mL, at least 5 mg/mL, at least 10 mg/mL, at least 20 mg/mL, at least 25 mg/mL, at least 30 mg/mL, at least 35 mg/mL, at least 50 mg/mL, at least 55 mg/mL, at least 50 mg/mL, at least 65 mg/mL, at least 75 mg/mL, at least 100 mg/mL or greater. In some embodiments, the fusion protein is present in a concentration of 10-100 mg/mL. In some embodiments, the fusion protein is present in a concentration of 15-75 mg/mL, and in some embodiments, the fusion protein is present in a concentration of 20-65 mg/mL.

The pharmaceutical compositions of the present disclosure may also contain a "surfactant," meaning a substance that lowers the surface tension of a liquid. Examples of surfactants used in pharmaceutical compositions and which may be used in certain compositions of the present disclosure include polysorbate 20, polysorbate 80, polyethylene glycols (e.g., PEG 400, PEG 3000, TRITON X-100), polyethylene glycol alkyl ethers (e.g., BRIJ), polypropylene glycols, block copolymers (e.g., poloxamer, PLURONIC F68; poloxamer 407, PLURONIC F127; TETRONICS), sorbitan alkyl esters (e.g., SPAN), polyethoxylated castor oil (e.g., KOLLIPHOR, CREMOPHOR), and trehalose.

The pharmaceutical compositions of the present disclosure may also contain a preservative. The term "preservative" refers to a compound added to a pharmaceutical formulation to act as an anti-microbial agent. Among preservatives known in the art as being effective and acceptable in parenteral formulations are benzalkonium chloride, benzethonium, chlorohexidine, phenol, m-cresol, benzyl alcohol, methyl- or propyl-paraben, chlorobutanol, o-cresol, p-cresol, chlorocresol, phenylmercuric nitrate, thimerosal, benzoic acid, and various mixtures thereof. Phenolic preservative includes the compounds phenol, m-cresol, o-cresol, p-cresol, chlorocresol, methylparaben, benzyl alcohol, and mixtures thereof. If a preservative is necessary, the preservative used in compositions of the present disclosure is preferably a phenolic preservative, preferably either m-cresol, phenol, and/or benzyl alcohol. Certain phenolic preservatives, such as phenol and m-cresol, are known to bind to insulin and insulin hexamers and thereby stabilize a conformational change that increases either physical or chemical stability, or both. In compositions comprising other proteins, however, such preservatives may contribute to the formation of protein aggregates, or high molecular weight polymers (HMWP). See, e.g., Maa Y F and Hsu C C, Int J Pharm 140: 155-168 (1996); Fransson J, et al., Pharm. Res., 14: 606-612 (1997); Lam X M, et al., Pharm. Res., 14: 725-729 (1997); Remmele R L Jr, et al., Pharm Res 15: 200-208. (1998); Thirumangalathu R, et al., J Pharm Sci 95: 1480-1497 (2006). In some instances, protein aggregates in therapeutic formulations can be undesirable due to their tendency to induce an immune response.

As used herein, the term "lipophilic" means the ability to dissolve in lipids and/or the ability to penetrate, interact with and/or traverse biological membranes, and the term, "lipophilic moiety" or "lipophile" means a moiety which is lipophilic and/or which, when attached to another chemical moiety, increases the lipophilicity of such chemical moiety. Examples of lipophilic moieties include, but are not limited to, alkyls, fatty acids, esters of fatty acids, cholesteryl, adamantyl and the like. In some embodiments, the lipophilic moiety has at least 1, 2, 3, 4, 5, or 6 carbon atoms. In some embodiments, the lipophilic moiety has, between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. In some embodiments, the lipophilic moiety has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22 carbon atoms. In some embodiments, the lipophilic moiety has between a lower limit of 3, 4, 5, 6, 7, 8, or 9 and an upper limit of 4, 5, 6, 7, 8, 9, 10, 11, 12, 13, or 14 carbon atoms. In some embodiments, the lipophilic moiety has between a lower limit of 3, 4, 5, 6, or 7 and an upper limit of 6, 7, 8, 9, or 10 carbon atoms. In some embodiments, the lipophilic moiety is selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, myristate, palmitate, stearate, arachidate, behenate, lignocerate, and cerotate.

As used herein, "combination therapy" or administration "in combination with" one or more further therapeutic agents involves administration of two or more active agents (e.g., two or more pharmacological agents) intended to treat a predetermined indication and/or conditions associated therewith. The administration can be simultaneous (concurrent) or consecutive (sequential) in any order. The two or more agents of the "combination therapy" may be formulated as separate compositions (e.g., formulations) or may be formulated as a single composition (formulation). "Combination therapy" encompasses administration of agents having different mechanisms of action or targeting different indications and/or conditions as well as agents having similar mechanisms of actions or targeting similar indications and/or conditions. For example, because Type 1 diabetes patients produce little or no insulin, effective insulin therapy for Type 1 diabetics can involve the use of two types of exogenously administered insulin: a rapid-acting, mealtime insulin provided by bolus injections, and a long-acting, basal insulin, administered once or twice daily to control blood glucose levels between meals. Treatment of patients With Type 2 diabetes typically begins with prescribed weight loss, exercise, and a diabetic diet; but when these measures fail to control elevated blood sugars, then oral medications and incretin-based therapy, such as administration of glucagon-like peptide-1 (GLP-1) receptor agonists and/or dipeptidyl peptidase 4 (DPP-4) inhibitors that enable increased incretin levels, may be necessary. When these medications are still insufficient, treatment with insulin may be considered. Type 2 diabetes patients whose disease has progressed to the point that insulin therapy is required are may also be started on a single daily injection of a long-acting, basal insulin, although mealtime injections of rapid-acting insulins may be included, as necessary, in some cases. In some embodiments, the present disclosure provides a combination therapy comprising administering a rapid acting insulin and a basal insulin, and/or a fusion protein comprising, for example, one or more diboronate sensors disclosed herein.

The terms "administer," "administering," or "administration" include any method or act of delivery of a pharmacological agent (e.g., a medicament) to an intended subject (e.g., a patient). The pharmacological agent may be any suitable therapeutic agent, such as a biologic agent, such as an antibody or an antigen-binding fragment thereof (e.g., a pharmaceutical composition comprising such an antibody or antigen-binding fragment), a peptide agent (e.g., a hormone or a modified analogue thereof), or a low molecular weight agent (e.g., a structurally-defined small molecule or chemical entity). The administration of a pharmacological agent can be systemic or by local administration. In some embodiments, administration may involve one or more pharmacological agents that can be administered concurrently, simultaneously, or sequentially.

The terms "simultaneous" and "concurrently" are used interchangeably and are used herein to refer to administration of two or more therapeutic agents, where at least part of the administration overlaps in time or where the administration of second therapeutic agent falls within a short period of time, no longer than necessary to start the subsequent administration, after administration of a first therapeutic agent. For example, concurrent administration would include administering a second agent after a first agent without added delay beyond the time necessary to complete the first administration and start the second administration.

The terms "sequentially" and "consecutively" are used interchangeably and are used herein to refer to administration of two or more therapeutic agents where there is a period of delay between administering one therapeutic agent and administering another agent(s). For example, sequential administration would include administration of the two or more therapeutic agents are administered with a time separation of more than about 15 minutes, such as about any of 20, 30, 40, 50, or 60 minutes, 1 day, 2 days, 3 days, 1 week, 2 weeks, 3 weeks, or 1 month, or longer.

As used herein, the terms "basal insulin" and "basal insulins" may refer to several types of basal insulins (e.g., long-acting insulin). For example, insulin glargine, sold under the tradename LANTUS®, comprises a modified insulin structure in which the asparagine at position 21 in the insulin A-chain is replaced with glycine, and two arginines are added to the C-terminus of the B-chain. Another example, insulin glargine-algr, sold under the tradename Rezvoglar™, similarly comprises a modified insulin structure in which the asparagine at position 21 in the insulin A-chain is replaced with glycine, and two arginines are added to the C-terminus of the B-chain. As yet another example, insulin detemir, sold under the tradename LEVEMIR®, comprises a modified insulin structure in which the threonine at position 30 of the B-chain has been deleted and the lysine at position 29 of the B-chain has been derivatized through the covalent linkage of a 14-carbon, myristoyl fatty acid to the E-amine group of lysine at B29. Insulin degludec, available in Europe and Japan under the tradename TRESIBA®, comprises a modified insulin structure in which the threonine at position 30 of the B-chain has been deleted, and the ε-amino group of the lysine at position 29 of the B-chain is covalently derivatized with hexadecandioic acid via a γ-L-glutamic acid linker. All of these insulins are indicated for once-daily administration. In some embodiments, the present disclosure provides the use of one or more compounds (e.g., Formula I or Formula IB, fusion proteins) in the manufacture of a medicament for the treatment of a disease (e.g., diabetes mellitus, obesity, dyslipidemia or metabolic syndrome), wherein the medicament is to be administered simultaneously, separately or sequentially in combination with another active ingredient. The compounds and combinations disclosed herein (e.g., compounds of Formula I or Formula IB, fusion proteins) are effective in treating a disease and/or condition in a subject in need thereof by administering to a patient in need thereof a therapeutically effective amount of a compound and/or composition of the present disclosure.

As used herein, the phrase "therapeutically effective amount" and "prophylactically effective amount" refer to an amount that provides a therapeutic benefit in the treatment, prevention, or management of a disease or an overt symptom of the disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The set or specific amount that is therapeutically effective can be readily determined by an ordinary medical practitioner, and may vary depending on factors known in the art, such as, e.g. the type of disease, the patient's history and age, the stage of disease, and the administration of other therapeutic agents. In some embodiments, the phrase "therapeutically effective amount" refers to that amount of a compound and/or pharmaceutical composition and/or combination of actives disclosed herein that is sufficient to regulate blood glucose in a patient without causing unacceptable side effects. A therapeutically effective amount of the compound and/or pharmaceutical composition and/or combination of actives disclosed herein administered to a subject will depend on the type and severity of the disease and on the characteristics of the subject, such as general health, age, sex, body weight, and tolerance to drugs. The skilled artisan will be able to determine appropriate dosages depending on these and other factors. For example, a therapeutically effective amount of a fusion protein of the present disclosure when administered once weekly ranges from about 0.01 nmol/kg to about 100 nmol/kg. In some embodiments, a therapeutically effective amount of a fusion protein of the present disclosure when administered once weekly ranges from about 1 nmol/kg to about 50 nmol/kg. In some embodiments, a therapeutically effective amount of a fusion protein of the present disclosure when administered once weekly ranges from about 16 nmol/kg to about 25 nmol/kg. In some embodiments, a therapeutically effective amount of a fusion protein of the present disclosure when administered once weekly ranges from about 1 mg to about 200 mg. In some embodiments, a therapeutically effective amount of a fusion protein of the present disclosure when administered once weekly ranges from about 25 mg to about 175 mg. In some embodiments, a therapeutically effective amount of a fusion protein of the disclosure when administered once weekly ranges from about 100 mg to about 160 mg.

The terms "subject" and "patient" are herein used interchangeably and refer to a party receiving a therapy or treatment. In some embodiments, the "subject" and "patient" is a human.

The terms "blood sugar level" and "glycemia" are herein used interchangeably and refer to the concentration of sugar present in the blood. A blood sugar meter or glucometer can be used to measure the amount of sugar in a sample of blood. Blood sugar levels are generally measured as mg of sugar per dL blood (mg/dL). The blood sugar level can refer to the level of any of the sugars disclosed herein. For example, the blood sugar level would include the concentration of glucose in the blood, otherwise known as the blood glucose level/concentration.

As used herein, the term "steady state" refers to a constant/fixed condition with no increases or decreases in a variable of interest or with minimal (i.e., less than 10% or lower) variation. By way of context, in some embodiments, an insulin receptor agonist is infused intravenously (IV) in a fixed dose bolus, and blood glucose levels are maintained at some predetermined "steady state" level (e.g. 100 mg/dL for euglycemic state; 200 mg/dL mg/dL for hyperglycemic) by continuous infusion of glucose at a variable rate (mg/kg/min). The amount of glucose infused to maintain a "steady state" blood sugar level is equal to whole-body glucose uptake and utilization.

The term "hyperglycemia" is used herein to refer to physiologically high blood glucose levels. Hyperglycemic refers to a state of physiologically high blood glucose levels. Blood glucose levels that are considered hyperglycemic will vary based on the species of the subject. For example, in rats, hyperglycemia refers to a blood glucose level $\geq 200$ mg/dL. In humans, hyperglycemia refers to a blood glucose level >180 mg/dL.

The term "euglycemia" is used herein to refer to physiologically normal blood glucose level. Euglycemic refers to a state of normal blood glucose levels. Blood glucose levels that are considered euglycemic will vary based on the species of the subject. For example, in rats, euglycemia refers to a blood glucose level <200 mg/dL. In humans, euglycemia refers to blood glucose levels of between 70-180 mg/dL.

The phrase "glucose infusion rate" is used herein to refer to the rate at which glucose is infused into a subject. The glucose infusion rate (GIR), in units of mg/kg/min, is calculated as follows: (Infusion rate (mL/hr)×Glucose concentration (g/dL)×1000 (mg/g))/Weight (kg)×60 (min/hr)×100 (mL/dL), wherein "infusion rate" refers to the rate at which glucose is infused into the subject, "glucose concentration" refers to the concentration of glucose that is being infused, and "weight" refers to the subject's weight. In some embodiments, the GIR corresponds to the rate of glucose infusion that is required to maintain a specified blood glucose level.

The phrase "relative glucose infusion rate difference" as used herein, refers to the difference in the amount of glucose infused between two different conditions, experiments, or measurements. In some embodiments, it may be measured by taking the difference between (a) the area under the curve (AUC) for one recorded GIR for maintaining a specified blood glucose concentration and (b) the AUC for another recorded GIR for maintaining a different blood glucose concentration. Generally, the AUC for a GIR for maintaining a lower blood glucose concentration is subtracted from the AUC for a GIR for maintaining a higher blood glucose concentration. For example, where the AUC for a first GIR (providing a blood glucose concentration of 100 mg/dL) is 600 mg/kg/min. min and the AUC for a second GIR (providing a blood glucose concentration of 200 mg/dL) is 800 mg/kg/min·min, subtracting the AUC for the first GIR from the AUC for the second GIR provides a relative glucose infusion rate difference of 200 mg/kg/min·min.

As used herein, the phrase "relative glucose infusion rate ratio" refers to a ratio of the amount of glucose infused between two different conditions, experiments, or measurements. In some embodiments, it may be measured by taking the ratio between (a) the area under the curve (AUC) for one recorded GIR for maintaining a blood glucose concentration and (b) the AUC for another recorded GIR for maintaining a different glucose sugar concentration. Generally, the AUC for a GIR for maintaining a higher blood glucose concentration is divided by an AUC for a GIR for maintaining a lower blood glucose concentration. For example, where the AUC for a first GIR (providing a blood glucose concentration of 100 mg/dL) is 600 mg/kg/min·min and the AUC for a second GIR (providing a blood glucose concentration of 200 mg/dL) is 800 mg/kg/min·min, dividing the AUC for the second GIR by the AUC for the first GIR provides a relative glucose infusion rate ratio of 1.33

As used herein, the phrase "area under the curve" refers to the area bounded by a curve, the axis, and two boundary points, whether plotted or mathematically represented. In some embodiments, the curve used to calculate the area under the curve (AUC) is a measure of GIR as a function of time where the X-axis would correspond to time and the Y-axis would correspond the GIR, with the origin is at 0 on the Y-axis (i.e., the X-axis and Y-axis intersect at 0 on the Y-axis). For example, a curve may be a recorded GIR over a period of time, and the boundary points are the GIR at the start and end of the infusion in the experiment. The AUC would then be calculated for the area between the plotted curve and the X-axis, between the starting and ending boundary points. Mathematically, AUC can be calculated according to methods known to those skilled in the art, for example, as in Tai M. M. (1994) Diabetes Care, 17(2):152-154, the contents of which, are hereby incorporated by reference in its entirety. In some embodiments, area under the curve (AUC) is calculated using the trapezoid rule and with baseline correction applied. In some embodiments, the AUC is calculated using GraphPad Prism v9. For the baseline correction, an averaged GIR value from 30 minutes prior to injections (x=−30 min) to the time of injections (x=O) can be subtracted from each GIR value from time 0 (x=0) to time the last timepoint measured (x=300). The trapezoidal calculation is as follows:

$$\int_a^b f(x)dx \approx (b-a)\cdot\frac{1}{2}(f(a)+f(b)).$$

Where a is the first time point (e.g., 0 min) and b is the last time point (e.g., 300 min). The area was calculated as a subdivision of small trapezoids as follows:

$$\int_a^b f(x)dx \approx$$
$$\frac{\Delta x}{2}(f(x_0)+2f(x_1)+2f(x_2)+2f(x_3)+2f(x_4)+\cdots+2f(x_{N-1})+x(f_N)).$$

Such that $\Delta x$ is the difference between each time point (5-minute intervals).

As used herein, the term "EC50" refers to the half maximal effective concentration of a compound in a dose-response assay. The EC50 is a measure of the concentration of a compound that is required to produce half of the maximum possible effect as a result of exposure to the compound. The EC50 can be calculated using known methods in the art. In some embodiments, the EC50 can be calculated using a four-parameter logistic regression curve using the following equation: Y=Bottom+(X^Hillslope)*(Top−Bottom)/(X^HillSlope+EC50^HillSlope), wherein hillslope refers to the slope of the sigmoidal curve between the top and bottom plateaus of the dose-response curve. In some embodiments, the EC50 may be calculated using GraphPad Prism v7, 8, or 9. When a compound has its EC50 measured at two or more concentrations of a sugar (e.g., glucose), (a) the term "a first sugar concentration" refers to the first, lower, concentration of the sugar, for example where the concentration is about 3 mM or about 5.6 mM, and (b) "a second sugar concentration" refers to the second, higher, concentration of the sugar, for example where the concentration is about 10 mM, about 16.7 mM, about 20 mM, or about 30 mM. In some embodiments, for example, the EC50 of dose-response curves were compared to assess fold change in insulin receptor phosphorylation (IR Phosphorylation) activity of the exemplary compounds of Formula I or Formula IB from low (e.g., about 5.6 mM) to high glucose concentration (e.g., about 16.7 mM). This fold activity change was determined by dividing the EC50 of a compound (e.g., a compound of Formula I or Formula IB) at "low" glucose concentration (e.g., about 5.6 mM) by the EC50 of that compound at "high" glucose concentration (e.g., about 16.7 mM), with all other conditions held constant. See Example titled "In Vitro Demonstration of Activity for Compounds of Formula IB."

As used herein, the term "Kd" refers to the dissociation constant, and is reflective of the binding affinity between a ligand (e.g., a diboronate sensor as described herein) and its target (e.g., a sugar, for example, glucose). For example, "glucose Kd" and "average glucose Kd" in the context of diboronate sensors described herein refer to the affinity of the diboronate sensor for glucose where the Kd is measured before the diboronate sensor is conjugated to the insulin molecule to generate the compounds described herein. The binding of a diboronate sensor described herein to glucose may be measured through an Alizarin red S (ARS) displacement assay and is recorded prior to the diboronate sensor being conjugated (e.g., covalently bound) to the insulin molecule (e.g., compounds of Formula I or Formula IB). ARS displacement assays are known in the art, for example, in Springsteen and Wang (2001) Chem. Comm., 1608-1609, the content of which is incorporated by reference herein in its entirety. In the ARS displacement assay, a diboronate sensor as disclosed herein is incubated with ARS and a fluorescence emission is recorded. A composition of the diboronate sensor as described herein and ARS is then titrated against serial dilutions of a sugar (e.g., glucose), and fluorescence emission is then measured after incubation to determine displacement of ARS when the diboronate sensor binds to the sugar. The changes of intensity (fluorescence emission with and without the sugar) can be plotted against concentration of sugar to generate an associate constant for the binding of sugar. When a diboronate sensor has a higher association constant for the sugar, there is an increased Kd. Additionally, diboronate sensors as described herein include those with selective affinity/binding to sugars. For example, a diboronate sensor as described herein can include sensors having increased affinity for (binding to) glucose but not for other sugars, such as lactate and/or fructose. See Example titled "Procedure for determination of the glucose, fructose, and lactate binding (Kd) using ARS displacement assay."

As used herein the terms "clamp," "clamp assay," and "clamped" refer to hyperglycemic/euglycemic clamp (glucose clamp), which has been recognized as the "gold standard" method for detecting insulin activity via glucose utilization in experimental animals and in humans. In a hyperglycemic/euglycemic clamp, the plasma (blood) insulin concentration is acutely raised and, in certain embodiments, maintained by a continuous infusion of insulin while the plasma glucose concentration is held constant at predetermined hyperglycemic or euglycemic levels by a variable glucose infusion rate (GIR). When the steady-state blood glucose level is achieved, the glucose infusion rate equals insulin receptor-stimulated glucose uptake by all the tissues in the body and is therefore a measure of insulin activity at a specific blood glucose level. For example, in some embodiments, glucose is continuously infused to a subject over the course of a study and the glucose infusion rate is adjusted to maintain a constant blood glucose level in response to administration of a compound (e.g., a compound of Formula I or Formula IB). Changes in the sugar infusion rate in response to administration of a compound at a specific dose level or concentration are recorded and used to determine the sugar infusion rate. In some embodiments, the sugar is glucose. See, e.g., Lautt W. W., et al. (1998) Canadian Journal of Physiology and Pharmacology. 76(12): 1080-1086, the content of which is hereby incorporated by reference in its entirety. The clamp technique/assay referred to and used herein is a modified version of the technique known and disclosed in the art. See Example titled "In Vivo Demonstration of Activity for Compounds of Formula IB."

As used herein, terms such as "attachment point toward [group]," "attachment to," and "covalent linkage toward [group]" express that the indicated atom, attachment, or linkage is closer to the indicated group than the other attachment point or covalent linkage variables within the structure formula. In some embodiments, an attachment point or covalent linkage may be directly adjacent to the indicated group, and in some embodiments other atoms or groups may be present therebetween.

As used herein, the term "percentage homology" refers to the percentage of sequence identity between two sequences after optimal alignment. Identical sequences have a percentage homology of 100%. Optimal alignment may be performed by homology alignment algorithms described by the search for similarity method of Pearson and Lipman, *Proc. Natl. Acad. Sci. USA* 85:2444 (1988), by general methods described for search for similarities by Neddleman and Wunsch, *J. Mol. Biol.* 48:443 (1970), including implementation of these algorithms or visual comparison. As used herein, "insulin A-chain" is the chain of insulin that has the highest percentage homology to the A-chain of wild-type human insulin. As used herein, "insulin B-chain" is the chain of insulin that has the highest percentage homology to the B-chain of wild-type human insulin.

In some embodiments, the terms "covalently connected," "covalently conjugated," or "through a covalent conjugation" may be interchangeably used to indicate that two or more atoms, groups, or chemical moieties are bonded or connected via a chemical linkage. In some embodiments, the chemical linkage (which in some embodiments may be referred to as a covalent linkage) may be (e.g., consist of) one or more shared electron pairs (e.g., in a single bond, a double bond, or a triple bond) between two atoms, groups, or chemical moieties." In some embodiments, the chemical (covalent) linkage may further include one or more atoms or functional groups, and may be referred to using the corresponding name of that functional group in the art. For example, a covalent linkage including a —S—S— group may be referred to as a disulfide linkage; a covalent linkage including a —(C=O)— group may be referred to as a carbonyl linkage; a covalent linkage including a —(CF₂)— group may be referred to as a difluoromethylene linkage, etc. The type of linkage or functional group within the covalent bond is not limited unless expressly stated, for example when it is described as including or being selected from certain groups. The types or kinds of suitable covalent linkages will be understood from the description and/or context.

In some embodiments, the insulin receptor agonist may be bound or associated with human serum albumin (HSA) before binding to the insulin receptor. For example, insulin receptor agonists that contain any one of DSL-1 to DSL-172 may associate or bind either through hydrogen bonds, ionic associations, or hydrolysable boron ester bonds to HSA. These interactions may occur along the surface of HSA such as salt bridges to lysine residues, cleavable boron ester bonds formed with serine, threonine, and/or tyrosine hydroxyl groups, and/or to specific locations on HSA such as the Site I or Site II small molecule drug binding sites or one or more of the seven fatty acid binding sites (Yamasaki, K. et. al. (2013) Biochimica et Biophysica Acta 12:5435-5443).

In some embodiments, side chains of amino acids may be covalently connected (e.g., linked or cross-linked) through any number of chemical bonds (e.g., bonding moieties) as generally described in Bioconjugate Techniques (Third edition), edited by Greg T. Hermanson, Academic Press, Boston, 2013. For example, the side chains may be covalently connected through an amide, ester, ether, thioether, isourea, imine, triazole, or any suitable covalent conjugation chemistry available in the art for covalently connecting one peptide, protein, or synthetic polymer to a second peptide, protein, or synthetic polymer. The term polymer includes polypeptide. The term "covalent conjugation chemistry" may refer to one or more functional groups included in the bonding moiety, and/or the chemical reactions used to form the bonding moiety.

The term "vicinal diol" refers to a group of molecules in which two hydroxyl groups occupy vicinal positions, that is, they are attached to adjacent atoms. Such molecules may include, but are not limited to, sugars such as hexoses, glucose, mannose and fructose.

In some embodiments, the term "albumin" means human serum albumin or a protein with at least 60% percentage homology to human serum albumin protein. It is to be understood that in some embodiments the albumin may be further chemically modified for the purposes of conjugation. In some embodiments, modifications may include one or more covalently connected linkers. In some embodiments, the term "albumin" means human serum albumin or a protein with at least 80%, 85%, 90%, 95%, 96%, 97%, 98%, 99%, or 100% percentage homology to human serum albumin protein. In some embodiments, the term "albumin" means human serum albumin or a protein with at least 90% percentage homology to human serum albumin protein. In some embodiments, the term "albumin" means human serum albumin or a protein with at least 95% percentage homology to human serum albumin protein. In some embodiments, the term "albumin" means human serum albumin or a protein with at least 99% percentage homology to human serum albumin protein. In some embodiments, albumin is unmodified human serum albumin.

The term "treatment" is meant to include both the prevention and minimization of the referenced disease, disorder, or condition (i.e., "treatment" refers to both prophylactic and therapeutic administration of a compound of the present disclosure or a composition comprising a compound of the present disclosure unless otherwise indicated or clearly contradicted by context). The route of administration may be any route which effectively transports a compound of this disclosure to the desired or appropriate place in the body, such as parenterally, for example, subcutaneously, intramuscularly, orally, or intravenously. For parenterally adminis-
tration, a compound of the disclosure is formulated analo-
gously with the formulation of known insulins. Furthermore,
for parenteral administration, a compound of this disclosure
is administered analogously with the administration of
known insulins and the physicians are familiar with this
procedure. The amount of a compound of this disclosure to
be administered, the determination of how frequently to
administer a compound of this disclosure, and the election of
which compound or compounds of this disclosure to admin-
ister, optionally together with another antidiabetic com-
pound, is decided in consultation with a practitioner who is
familiar with the treatment of the condition (e.g. diabetes) to
be treated.

In some embodiments, "therapeutic composition" and
"pharmaceutical composition" as used herein means a com-
position that is intended to have a therapeutic effect such as
pharmaceutical compositions, genetic materials, biologics,
and other substances. Pharmaceutical compositions may be
configured to function in the body with therapeutic qualities;
concentration may be altered to reduce the frequency of
replenishment, and the like. In some embodiments, "thera-
peutically effective amount" and "prophylactically effective
amount" refer to an amount that provides a therapeutic
benefit in the treatment, prevention, or management of a
disease or an overt symptom of the disease. The therapeu-
tically effective amount may treat a disease or condition, a
symptom of disease, or a predisposition toward a disease,
with the purpose to cure, heal, alleviate, relieve, alter,
remedy, ameliorate, improve, or affect the disease, the
symptoms of disease, or the predisposition toward disease.
The set or specific amount that is therapeutically effective
can be readily determined by an ordinary medical practitio-
ner, and may vary depending on factors known in the art,
such as, e.g. the type of disease, the patient's history and age,
the stage of disease, and the administration of other thera-
peutic agents. In some embodiments, modified insulins
described herein are delivered to the body by injection or
inhalation, or by other routes, and can reversibly bind to
soluble glucose in a non-depot form. In some embodiments,
modified insulins described herein are released over an
extended period of time from a local depot in the body or
from bound forms to proteins in the serum such as albumin.
In some embodiments, the release of modified insulin is
accelerated at elevated glucose levels, and in some embodi-
ments such release rate may be dependent on blood sugar
levels or levels of other small molecules in the blood
including diol containing molecules. In some embodiments
the release, bioavailability, and/or solubility of modified
insulins described herein is controlled as a function of blood
or serum glucose concentrations or concentrations of other
small molecules in the body.

Additionally, unless otherwise stated, structures described
herein are also meant to include compounds that differ only
in the presence of one or more isotopically enriched atoms.
For example, compounds having the present structures
except for the replacement of hydrogen by deuterium ($^2$H) or
tritium ($^3$H), or the replacement of a carbon by a $^{13}$C- or
$^{14}$C-carbon atom are within the scope of this disclosure.
Such compounds may be useful as, for example, analytical
tools, probes in biological assays, or therapeutic agents.

In some embodiments, functional groups can be cova-
lently conjugated or linked via any suitable covalent con-
jugation chemistry (linker) that can be used to covalently
conjugate one functional group or amino acid side chain to
another functional group, non-limiting examples include an
amide, an ester, an ether, a thioether, an isourea, an imine, and a triazole linker. In some embodiments, functional
groups are covalently conjugated through click chemistry
reactions as defined in the art. These include, for example,
cycloaddition reactions including but not limited to 3+2
cycloadditions, strain-promoted alkyne-nitrone cycloaddi-
tion, reactions of strained alkenes, alkene and tetrazine
inverse-demand Diels-Alder, Copper(I)-Catalyzed Azide-
Alkyne Cycloaddition (CuAAC), thiol-maleimide addition,
Strain-promoted azide-alkyne cycloaddition, Staudinger
ligation, nucleophilic ring-opening reactions, and additions
to carbon-carbon multiple bonds. Some of these reactions
are described for example by H. C. Kolb, M. G. Finn and K.
B. Sharpless (2001); Click Chemistry: Diverse Chemical
Function from a Few Good Reactions, *Angewandte Chemie
International Edition* 40 (11): 2004-2021; Kolb and Sharp-
less, *Drug Discovery Today* 8:1128-1137, 2003; Huisgen, R.
*Angew. Chem. Int. Ed. Engl.* 1963, 2, 565; Agard, N. J.;
Baskin, J. M.; Prescher, J. A.; Lo, A.; Bertozzi, C. R. *ACS
Chem. Biol.* 2006, 1, 644. One skilled in the art will be
capable of selecting suitable buffers, pH and reaction con-
ditions for such click reactions. In some embodiments,
covalent conjugation is the result of a "bioorthogonal reac-
tion" as defined in the art. Such reactions are, for example,
described by Sletten, Ellen M.; Bertozzi, Carolyn R. (2009).
Bioorthogonal Chemistry: Fishing for Selectivity in a Sea of
Functionality, *Angewandte Chemie International Edition* 48
(38): 6974-98.; Prescher, Jennifer A; Bertozzi, Carolyn R
(2005). Chemistry in living systems, *Nature Chemical Biol-
ogy* 1 (1): 13-21.

In some embodiments, functional groups may be linked
using native chemical ligation as described for example by
Dawson, P. E.; Muir, T. W.; Clark-Lewis, I.; Kent, S. B.
(1994) Synthesis of proteins by native chemical ligation,
*Science* 266 (5186): 776-778. As used herein, terms such as
"linkage," "covalent conjugation," etc. may refer to any of
the chemistries described above in some embodiments. The
terms "amine," "amino group," and/or "amine group," when
used to describe part of a covalent bond or connectivity, may
be interchangeably used to indicate an amino group or an
amine group to which the described element is covalently
linked. In some embodiments, the amino group or amine
group may be a primary amine, a secondary amine, or a
fragment such as NH—⊕ to which a conjugation is made
and described.

In some embodiments, the amino group or amine group
may be the $NH_2$ group at the N-terminus of a peptide or
peptide chain, or the $NH_2$ group of a lysine side chain, but
embodiments of the present disclosure are not limited
thereto. In some embodiments, the connectivity of a first
group to a second group is described by reference to an
amine or amino group, originating from the second group,
that is part of a covalent linkage between the first group and
the second group. For example, an amine of a lysine side
chain on X1 may be referred to as an amine, and furthermore
may be described as being conjugated through an amide
bond in order to specify the structure and connectivity of the
functional groups that constitute the covalent bond. If a
covalent linkage is via an amine bond or amine linkage, then
it is referred to as an amine linkage. It is to be understood
that a carbonyl connected to an amine (e.g., a (C=O)—NH
moiety) constitutes an amide bond, and thus by definition, an
amine linkage is not directly connected to a carbonyl group.
Stated another way, the terms "amide bond" and/or "amide
linkage," when used to describe a covalent bond or connec-
tivity, may be interchangeably used to indicate a carbonyl
connected to an amine (e.g., a (C=O)—NH moiety).

In some embodiments, further modifications include attachment of a chemical entity (e.g., moiety or functional group) such as a carbohydrate group, one or more cis-diol containing groups, one or more phosphate groups, one or more catechol groups, a farnesyl group, an isofarnesyl group, a fatty acid group, or a linker for conjugation, functionalization, or other modifications meant to impact the pharmacokinetics, pharmacodynamics, and/or biophysical solution characteristics of insulin.

In some embodiments, a compound includes a human peptide hormone (e.g., as X1). In some embodiments, the peptide hormone is a polypeptide hormone of the human pancreas. In some embodiments, X1 in Formula I is $NH_2$. In some embodiments, a compound, such as a compound of Formula I or Formula IB, includes a human insulin or a human insulin analogue. In some embodiments, two different amine groups in insulin are covalently conjugated to as described by Formula I or Formula IB.

It will be understood that "human peptide hormone," "polypeptide hormone of the human pancreas," "insulin," "human insulin,"-"modified insulin," and "human insulin analogue" may be used interchangeably in some of the described embodiments; that is, for example, in certain embodiments "human insulin analogue" may instead be used in embodiments described as using human insulin. In some embodiments, a compound, such as a compound of Formula I or Formula IB, includes a human insulin or a human insulin analogue. In some embodiments, a compound includes a human insulin or a human insulin analogue as described by Formula I or Formula IB for p'=1 wherein a single amino group in insulin is conjugated to as described by Formula I or Formula IB. In some embodiments, the amino group is the N-terminus of the B-chain of insulin or an amino group of the side chain of a lysine. In some embodiments, two or more different amine groups in insulin are each independently covalently conjugated to as described by Formula I or Formula IB. In some embodiments, at least one amine group is the N-terminus of the B-chain of insulin. In some embodiments, amino groups comprise amino groups of side chains of lysine residues in insulin.

Various suitable modifications of the peptide hormone (e.g., human polypeptide hormone, for example, Insulin), known to those having ordinary skill in the art, are included in the scope of the disclosure. In some embodiments, an optionally extended polypeptide at the N-terminus of B-chain or C-terminus of A-chain of insulin is present and may contain sequences with up to 70%, 80%, 85%, 90%, 95%, 96%, 97%, 98%, 99%, or 100% sequence homology to a human polypeptide sequence. In some embodiments, the polypeptide of Z1a or the optionally extended polypeptide at the N-terminus of B-chain or C-terminus of A-chain of insulin contain sequences with up to 70% sequence homology to a human polypeptide sequence. In some embodiments, the polypeptide of Z1a or the optionally extended polypeptide at the N-terminus of B-chain or C-terminus of A-chain of insulin contain one or more lysine residues that are optionally next to a proline residue, such that the proline is C-terminal to lysine. In some embodiments, the amino group of lysine residues is each independently conjugated as described by Formula I or Formula IB.

In some embodiments, insulin is further modified through conjugation to a sugar, diol containing moiety, and/or polyol containing moiety. In some embodiments, the human polypeptide hormone is a dual or triple hybrid peptide comprising sequences of two or more human peptide hormones and which can act through multiple receptors; for example, a glucose-dependent insulinotropic polypeptide (GIP) and GLP-1 receptor agonist or GLP-1/GIP/glucagon triple agonist. In some embodiments, the human polypeptide hormone is a gut hormone. In some embodiments, the human polypeptide hormone is chosen from c-peptide, adrenocorticotropic hormone (ACTH), amylin, angiotensin, atrial natriuretic peptide (ANP), calcitonin, cholecystokinin (CCK), gastrin, ghrelin, glucagon, growth hormone, follicle-stimulating hormone (FSH), insulin, leptin, melanocyte-stimulating hormone (MSH), oxytocin, parathyroid hormone (PTH), prolactin, renin, somatostatin, thyroid-stimulating hormone (TSH), thyrotropin-releasing hormone (TRH), vasopressin, vasoactive intestinal peptide, a neuropeptide, a peptide hormone that impacts cardiovascular health or appetite, a hybrid of one or more of these peptides, and an analogue of one of these peptides. In some embodiments, compounds comprise a human polypeptide hormone further modified, for example, through the covalent conjugation to polymers, XTEN protein sequences or aliphatic chains. In some embodiments, polymer modified compounds have a longer circulation time in the blood. In some embodiments, polymer modified compounds have a circulation time in the blood such that they are suitable for injection once a day injection, once a week injection, or once a month injection. In some embodiments, polymer modified compounds, such long-acting variants require once a day injection, or one a week injection or once a month injection. In some embodiments, a human polypeptide hormone or the analogue thereof includes one or more L- or D- natural or unnatural amino acids that are each independently one of the twenty canonical amino acids or a non-canonical amino acid.

In some embodiments, the insulin receptor agonist is an insulin analogue comprising an A-chain and a B-chain, wherein optionally the A-chain comprises a sequence selected from SEQ ID NOs 1, 25, 24051, and 24052, and optionally the B-chain comprises a sequence selected from SEQ ID NOs 24060, 24061, 24062, 24063, 24064, and 25000-25397. In some embodiments, an insulin analogue comprises an A-chain comprising a sequence selected from SEQ ID NOs 1, 24051, and 24052, and a B-chain comprising a sequence selected from SEQ ID NOs 24063, 25095, 25228, 25229, 25232, 25236, 25305, 25308, 25312, and 25380-25397. In some embodiments, an insulin analogue comprises a human insulin with an A-chain and a B-chain wherein up to six residues have been mutated, deleted or additionally inserted into each of the A-chain and/or the B-chain. In some embodiments thereof, the insulin analogue includes insulins containing A- and B-chains with a connecting peptide connecting the C-terminus for the B-chain to the N-terminus for the A-chain, and the connecting peptide includes the natural proinsulin C-peptide as well as shorter version of the C-peptide as is known in the art, wherein shorter versions of the C-peptide allow the single chain insulin to retain biological activity and/or potency.

The words analog and analogue are alternative spellings of the same word, are interchangeably used herein and have the same meaning. In the context of a human hormone, an endocrine hormone, insulin, human insulin, glucagon, amylin, relaxin, GLP-1, oxyntomodulin, somatostatin, gastric inhibitory polypeptide, glucose-dependent insulinotropic polypeptide, a hybrid peptide comprising sequences from two or more human polypeptide hormones, an analogue means any related sequences resulting from the parent sequence that includes up to 8 mutations, deletions or insertions of amino acids and/or additional chemical modifications. In some embodiments, as is known in the art such analogs may enhance biological activity, pharmacokinetics, pharmacodynamics, potency, stability and or chemical, and physical characteristics.

In some embodiments, a human hormone analog includes one or more residues that are 2-aminoisobutyric acid and/or other artificial (i.e., unnatural) amino acids.

In some embodiments, in an insulin analog the C-terminus of the B-chain of insulin is covalently conjugated to the N-terminus of the A-chain. In some embodiments, the C-terminus of the B-chain of insulin is covalently conjugated to the N-terminus of the A-chain and the connecting peptide is a C-peptide. In some embodiments, the C-terminus of the B-chain of insulin is covalently conjugated to the N-terminus of the A-chain and the connecting peptide is a C-peptide and further includes any intermediate compounds that comprise a conjugate of Formula I or Formula IB.

In some embodiments, the insulin analog includes insulin lispro, or a glargine-type of modification, or any suitable modification to human insulin that impacts the pharmacokinetics or half-life of insulin in the body (e.g., blood). In some embodiments, the insulin lispro used to prepare the PEGylated insulin lispro compounds of the present disclosure may be prepared by any of a variety of recognized peptide synthesis techniques including solution-phase methods, solid-phase methods, semi-synthetic methods, and recombinant DNA methods. For example, U.S. Pat. No. 5,700,662 (Chance, et al.) and European Patent No. 214 826 (Brange, et al.), disclose the preparation of various insulin analogs. The A- and B-chains of insulin lispro may also be prepared via a proinsulin-like precursor molecule using recombinant DNA techniques. In some embodiments, a proinsulin-like precursor is used to make the insulin lispro used to make the PEGylated insulin lispro of the present disclosure.

In some embodiments, the insulin portion of the present compounds may be prepared via production of a precursor protein molecule using recombinant DNA techniques. The DNA, including cDNA and synthetic DNA, may be double-stranded or single-stranded. The coding sequences that encode the precursor protein molecule described herein may vary as a result of the redundancy or degeneracy of the genetic code. The DNA may be introduced into a host cell in order to produce the precursor protein of the present disclosure. An appropriate host cell is either transiently or stably transfected or transformed with an expression system for producing the precursor protein. The host cells may be bacterial cells such as K12 or B strains of *Escherichia coli*, fungal cells such as yeast cells, or mammalian cells such as Chinese hamster ovary ("CHO") cells. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit selection of those cells transformed with the desired DNA sequences.

In some embodiments, the polypeptide hormone is glucagon. In some embodiments, glucagon has additional mutations and modifications that are known to impact solubility and solution stability of glucagon. In some embodiments, a compound, such as a compound of Formula I or Formula IB, comprises a conjugation of a diboronate, a diol containing moiety, or a polyol to the N-terminus of the B-chain of insulin through a peptide bond, and at least one additional conjugation described by Formula I or Formula IB to insulin. In some embodiments, a compound comprises a conjugation of a Z1a to the N-terminus of the B-chain of insulin through a peptide bond, and at least one additional conjugation described by Formula I to insulin. In some embodiments, the additional conjugation is to a lysine residue in insulin. In some embodiments, at least one such lysine is a residue between position 15 and the C-terminus of the B-chain of insulin. In some embodiments, the lysine residue is optionally next to a proline, glycine, arginine, threonine or serine. In some embodiments, one or more amino acids in Formula I or Formula IB is a D-amino acid. In some embodiments, any secondary or primary amine in a compound, such as a compound represented by Formula I or Formula IB, is each independently optionally acetylated. In some embodiments, a compound of Formula I or Formula IB has a polypeptide hormone X1 further conjugated to a drug molecule, an imaging agent, a chelator, a contrast agent, a radioactive isotope or a molecule that engages immune cells.

In some embodiments, X1 is a polypeptide hormone comprising a peptide ligand that binds to an extracellular protein receptor. In some embodiments, X1 comprises a polypeptide analogue of a human polypeptide hormone that has at least 50% homology to a natural human polypeptide hormone. In some embodiments, X1 comprises a polypeptide analogue of a human polypeptide hormone that has at least 80%, 85%, 90%, 95%, 96%, 97%, 98%, 99%, or 100% homology to a natural human polypeptide hormone. In some embodiments, X1 comprises a polypeptide analogue of a human polypeptide hormone that has at least 90% homology to a natural human polypeptide hormone. In some embodiments, X1 comprises a polypeptide analogue of a human polypeptide hormone that has at least 95% homology to a natural human polypeptide hormone. In some embodiments, X1 comprises a polypeptide analogue of a human polypeptide hormone that has at least 99% homology to a natural human polypeptide hormone. In some embodiments, X1 is an analogue of human insulin with up to 10 additional residues added to the A-chain or the B-chain of insulin.

In some embodiments, the term "glucose responsiveness" refers to the change in activity in the presence and absence of glucose or in a difference of lower levels and higher levels of glucose (e.g., 5.6 mM glucose vs 16.7 mM glucose, 3 mM glucose vs 20 mM glucose). In some embodiments the activity of a conjugated insulin is assessed by the concentration of insulin (in nanomolar units (nM) of insulin) required to induce the half maximum response (EC50) in a cell-based assay. Lower EC50 concentrations of conjugated insulins have a higher activity than insulins with higher EC50 concentrations (e.g., an insulin with an EC50 of 3 nM is more active than an insulin with an EC50 of 50 nM). A "glucose response" is observed when the insulin changes from a less active EC50 (higher nM) to a more active EC50 (lower nM) in the absence and presence of glucose or in lower and higher levels of glucose, respectively.

In some embodiments, the compound of Formula I or Formula IB comprises one or more L- or D-artificial amino acids which are not one of the twenty naturally occurring amino acids. In some embodiments, the side chains of such artificial amino acids can be covalently conjugated through a number of reactions, including bio-orthogonal reactions such as, for example, described by: Rostovtsev, V. V., Green, L. G., Fokin, V. V. & Sharpless, K. B. A stepwise huisgen cycloaddition process: copper(I)-catalyzed regioselective "ligation" of azides and terminal alkynes. *Angew. Chem. Int. Ed.* 41, 2596-2599 (2002), or by: Liang, Y., Mackey, J. L., Lopez, S. A., Liu, F. & Houk, K. N. Control and design of mutual orthogonality in bioorthogonal cycloadditions. *J. Am. Chem. Soc.* 134, 17904-17907 (2012). In some embodiments, the compound of Formula I or Formula IB may contain one or more L- or D-artificial amino acids that are not one of the twenty naturally occurring amino acids. In some embodiments, Z1a contains one or more L- or D-artificial amino acids that are not one of the twenty naturally occurring amino acids. In some embodiments, the side chains of two amino acids in Formula I or Formula IB may be covalently conjugated together through a triazole bond.

Insulin hormone is an important regulator of blood glucose (sugar) levels. In a normal individual, insulin is present and, when released by the pancreas, it acts to reduce blood sugar levels, for example, by binding to and activating the insulin receptor, triggering glucose absorption by liver, fat, and skeletal muscle cells. Diabetes mellitus (DM), commonly referred to as diabetes, is a group of metabolic diseases characterized by the persistence of high blood sugar levels over a prolonged period.

As used herein, "insulin" encompasses both wild-type and altered forms of insulin capable of binding to and activating the insulin receptor, or capable of causing a measurable reduction in blood glucose when administered in vivo and encompasses both wild-type and altered forms of human insulin capable of binding to and activating the human insulin receptor, or capable of causing a measurable reduction in blood glucose when administered in vivo to a human.

In some embodiments, insulin includes insulin from any species whether in purified, synthetic, or recombinant form and includes human insulin, porcine insulin, bovine insulin, sheep insulin and rabbit insulin. In some embodiments, insulin has two chains: a B- and an A-chain. In some embodiments, the chains are connected together through peptides such as, for example, c-peptide as is known in the art, or a shortened version of the c-peptide, and in other embodiments the insulin may be provided as a proinsulin (insulin precursor) that can be further processed into mature insulin. A variety of altered forms of insulin are known in the art and may be chemically altered such as by addition of a chemical moiety such as a PEG group or a fatty acyl chain. Altered insulins may be mutated including additions, deletions or substitutions of amino acids. In some embodiments the term "desB30" refers to an insulin lacking the B30 amino acid residue.

As used herein, the term "insulin analogue" means a modified human insulin having insulin receptor agonist activity wherein from one to 10 amino acid residues of the insulin have been modified (e.g., substituted, deleted, added (i.e. extended), inserted, and any combination thereof) relative to human insulin. In this context, an insertion or addition of one or more amino acids is considered a single modification. For example, an insulin analogue may have from one to 9 modified amino acid residues. As yet another example, an insulin analogue may have from one to 8 modified amino acid residues. As yet another example, an insulin analogue may have from one to 7 modified amino acid residues. As yet another example, an insulin analogue may have from one to 6 modified amino acid residues. As yet another example, an insulin analogue may have from one to 5 modified amino acid residues. As yet another example, an insulin analogue may have from one to 4 modified amino acid residues. As yet another example, an insulin analogue may have from one to 3 modified amino acid residues. As yet another example, an insulin analogue may have from one to 2 modified amino acid residues. In some embodiments, an insulin analogue may have 2, 3, 4, 5, 6, 7, 8, or 9 modified amino acid residues.

Modifications in the insulin molecule are denoted stating the chain (A or B), the position, and the one or three letter code for the amino acid residue substituting the native amino acid residue. Herein terms like "A1", "A2" and "A3" etc.

indicates the amino acid in position 1, 2 and 3 etc., respectively, in the A chain of insulin (counted from the N-terminal end). Similarly, terms like B1, B2 and B3 etc. indicates the amino acid in position 1, 2 and 3 etc., respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are A21Ala, A21 Gly, and A21 Gln, respectively.

Thus, for example, an insulin analogue having 4 modifications comprises an A-chain and a B-chain, wherein the A-chain comprises sequence GIVEQCCTSICSLYQLE-NYCN (SEQ ID NO: 1); and wherein the B-chain comprises sequence GKGSHKFVNQHLCGSHLVEALYL-VCGKRGFFYTPR (SEQ ID NO: 25228), where the A chain has the wild-type sequence of chain A of human insulin (e.g. no mutations, deletions, additions) and the B chain has been extended at the N-terminal with GKGSHK (i.e. 6 amino acids have been added/appended to the N-terminus), and where the amino acid in position 21 (i.e. E) in the B chain is substituted with K, and the amino acid in position 29 (i.e. K) in the B chain is substituted with R, and the amino acid in position 30 (i.e, Thr) in the B chain is deleted (as illustrated in FIG. 1).

Figure 2:
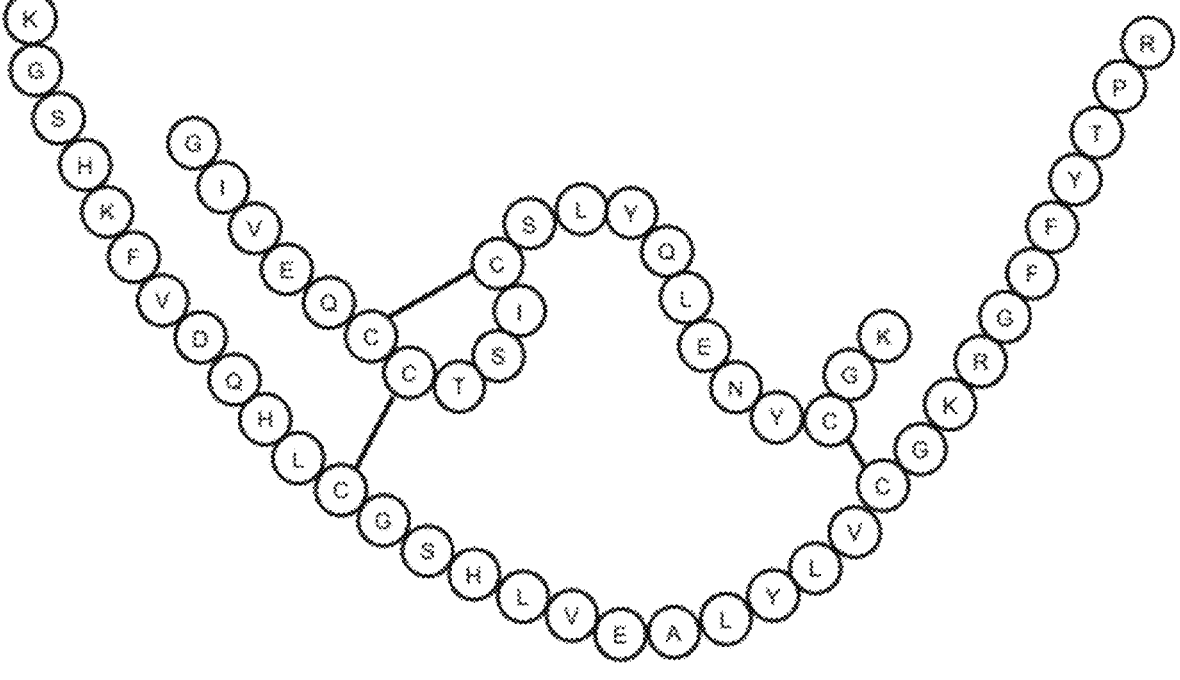
FIG. 2 includes an insulin comprising an A-chain according to SEQ ID NO: 25 and B-chain according to DEQ ID NO: 25393.

As yet another example, an insulin analogue having 7 modifications comprises an A-chain and a B-chain, wherein the A-chain comprises sequence GIVEQCCTSICSLYQLE-NYCGK (SEQ ID NO: 25); and wherein the B-chain comprises sequence KGSHKFVDQHLCGSHLVEALYL-VCGKRGFFYTPR (SEQ ID NO: 25393), where in the A chain the amino acid in position 21 (i.e. N) is substituted with G, and the A chain is extended at the C-terminal with K (i.e. 1 amino acid has been added/appended to the C-terminus), and the B chain has been extended at the N-terminal with KGSHK (i.e. 5 amino acids have been added/appended to the N-terminus), and where the amino acid in position 3 (i.e. N) in the B chain is substituted with D, and where the amino acid in position 21 (i.e. E) in the B chain is substituted with K, and the amino acid in position 29 (i.e. K) in the B chain is substituted with R, and the amino acid in position 30 (i.e. T) in the B chain is deleted (as illustrated in FIG. 2).

Figure 3:
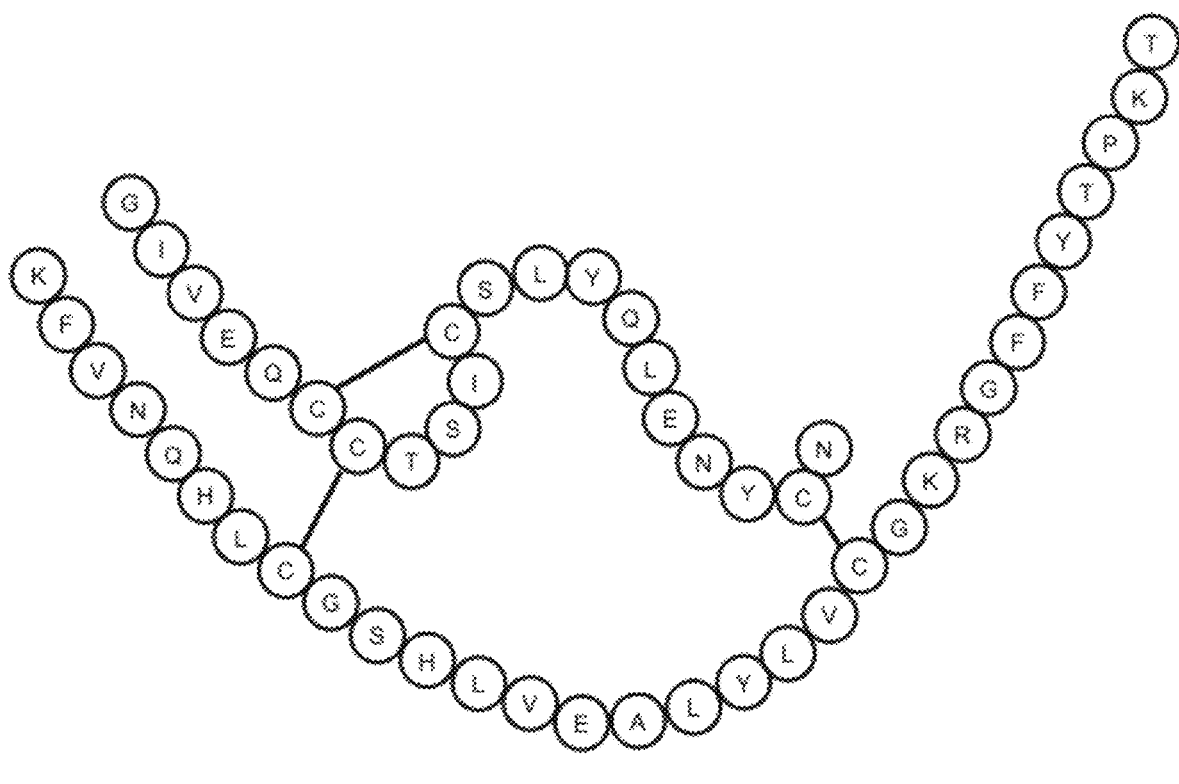
FIG. 3 includes an insulin comprising an A-chain according to SEQ ID NO: 1 and B-chain according to DEQ ID NO: 24060.

As yet another example, an insulin analogue, having 2 modifications comprises an A-chain and a B-chain, wherein the A-chain comprises sequence GIVEQCCTSICSLYQLE-NYCN (SEQ ID NO: 1); and wherein the B-chain comprises sequence KFVNQHLCGSHLVEALYL-VCGKRGFFYTPKT (SEQ ID NO: 24060), where the A chain has the wild-type sequence of chain A of human insulin (e.g. no mutations, deletions, additions) and the B chain has been extended at the N-terminal with K (i.e. 1 amino acid has been added/appended to the N-terminus), and where the amino acid in position 21 (i.e. E) in the B chain is substituted with K (as illustrated in FIG. 3).

Figure 4:
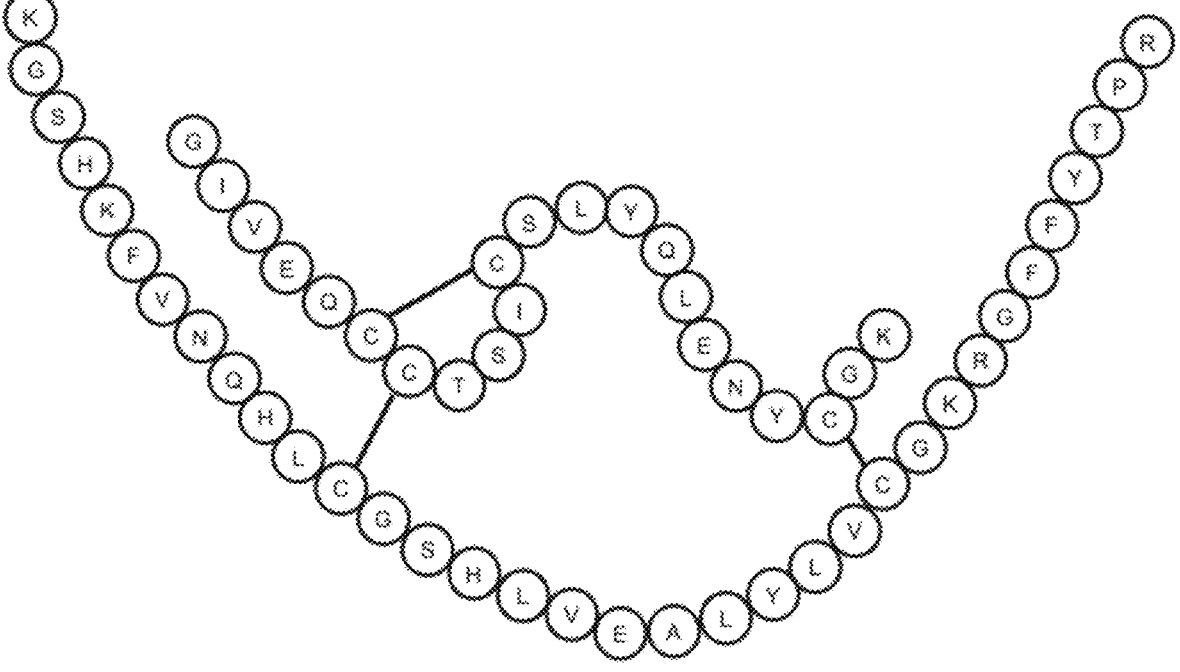
FIG. 4 includes an insulin comprising an A-chain according to SEQ ID NO: 25 and B-chain according to DEQ ID NO: 25313.

As yet another example, an insulin analogue having 6 modifications comprises an A-chain and a B-chain, wherein the A-chain comprises sequence GIVEQCCTSICSLYQLE-NYCGK (SEQ ID NO: 25); and wherein the B-chain comprises sequence KGSHKFVNQHLCGSHLVEALYL-VCGKRGFFYTPR (SEQ ID NO: 25313), where in the A chain the amino acid in position 21 (i.e. N) is substituted with G, and the A chain is extended at the C-terminal with K (i.e. 1 amino acid has been added/appended to the C-terminus), and the B chain has been extended at the N-terminal with KGSHK (i.e. 5 amino acids have been added/appended to the N-terminus), and where the amino acid in position 21 (i.e. E) in the B chain is substituted with K, and the amino acid in position 29 (i.e. K) in the B chain is substituted with R, and the amino acid in position 30 (i.e. T) in the B chain is deleted (as illustrated in FIG. 4).

Figure 5:
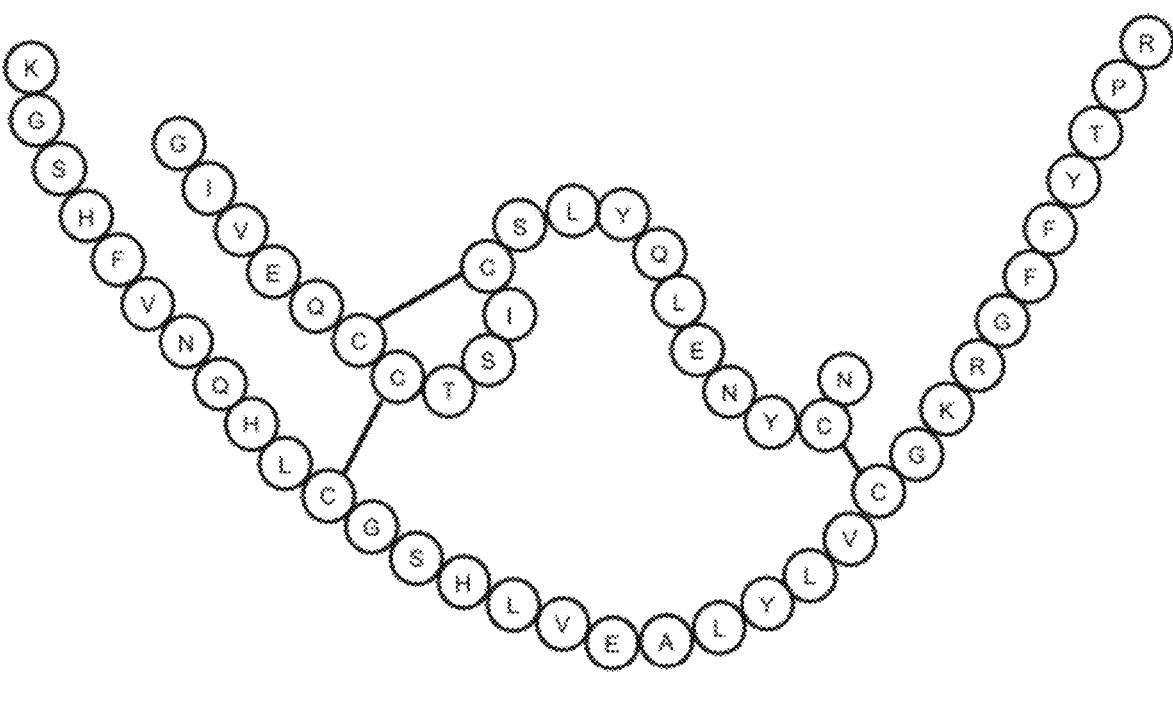
FIG. 5 includes an insulin comprising an A-chain according to SEQ ID NO: 1 and B-chain according to DEQ ID NO: 24061.

As yet another example, an insulin analogue having 4 modifications comprises an A-chain and a B-chain, wherein the A-chain comprises sequence GIVEQCCTSICSLYQLENYCN (SEQ ID NO: 1); and wherein the B-chain comprises sequence KGSHFVNQHLCGSHLVEALYLVCGKRGFFYTPR (SEQ ID NO: 24061); where the A chain has the wild-type sequence of chain A of human insulin (e.g. no mutations, deletions, additions) and the B chain has been extended at the N-terminal with KGSH (i.e. 4 amino acids have been added/appended to the N-terminus), and where the amino acid in position 21 (i.e. E) in the B chain is substituted with K, and the amino acid in position 29 (i.e. K) in the B chain is substituted with R, and the amino acid in position 30 (i.e., Thr) in the B chain is deleted (as illustrated in FIG. 5).

Figure 6:
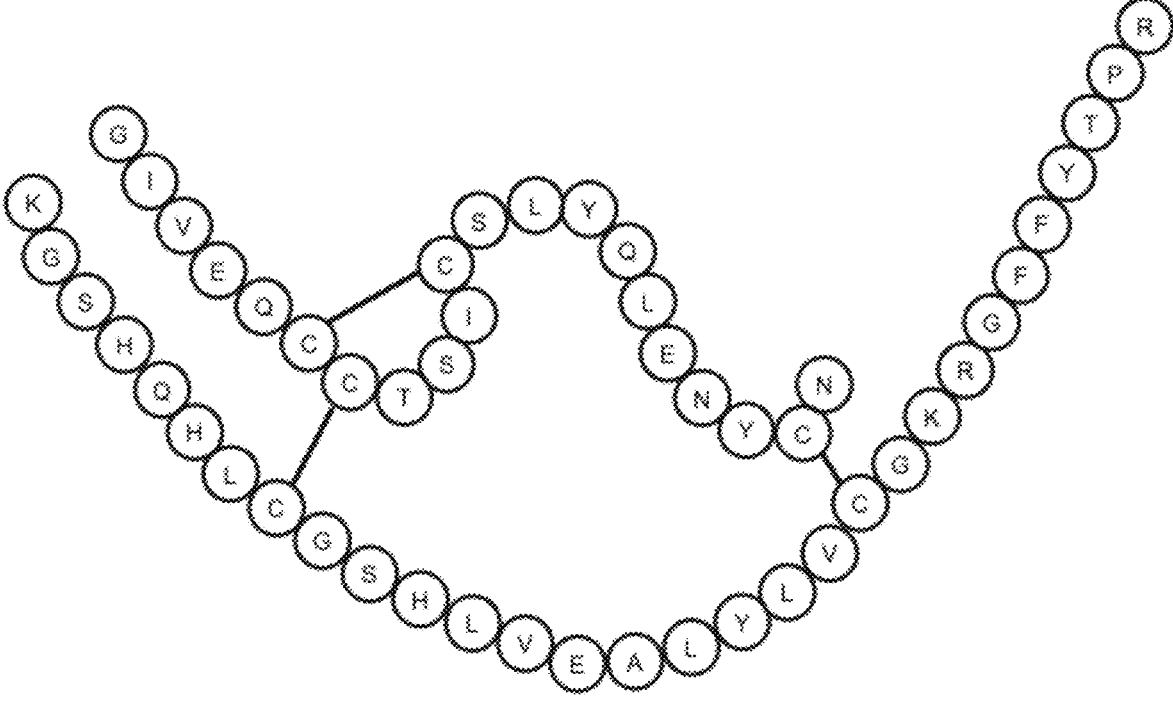

As yet another example, an insulin analogue having 5 modifications comprises an A-chain and a B-chain, wherein the A-chain comprises sequence GIVEQCCTSICSLYQLENYCN (SEQ ID NO:1); and wherein the B-chain comprises sequence KGSHQHLCGSHLVEALYLVCGKRGFFYTPR (SEQ ID NO: 24062); where the A chain has the wild-type sequence of chain A of human insulin (e.g. no mutations, deletions, additions) and the B chain has been extended at the N-terminal with KGSH (i.e. 4 amino acids have been added/appended to the N-terminus), and the first 3 residue (FVN) has been deleted, and where the amino acid in position 21 (i.e. E) in the B chain is substituted with K, and the amino acid in position 29 (i.e. K) in the B chain is substituted with R, and the amino acid in position 30 (i.e., Thr) in the B chain is deleted (as illustrated in FIG. 6).

Figure 7:
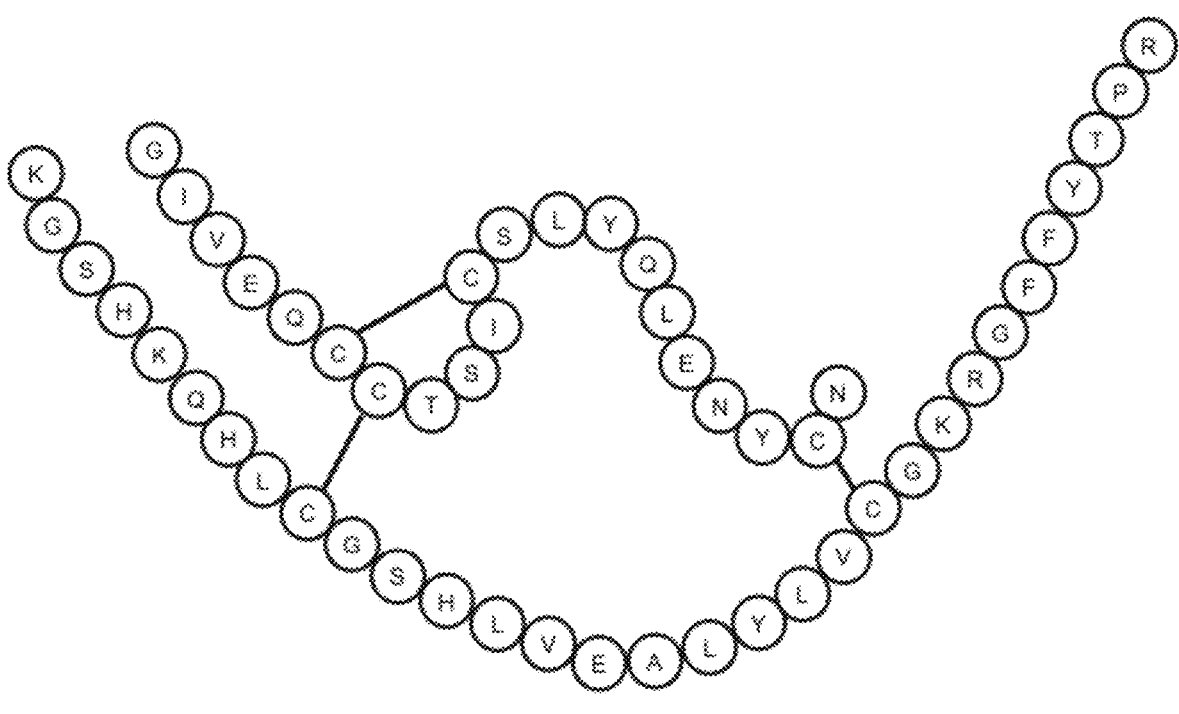

As yet another example, an insulin analogue having 5 modifications comprises an A-chain and a B-chain, wherein the A-chain comprises sequence GIVEQCCTSICSLYQLENYCN (SEQ ID NO:1); and wherein the B-chain comprises sequence KGSHKQHLCGSHLVEALYLVCGKRGFFYTPR (SEQ ID NO: 24063); where the A chain has the wild-type sequence of chain A of human insulin (e.g. no mutations, deletions, additions) and the B chain has been extended at the N-terminal with KGSHK (i.e. 5 amino acids have been added/appended to the N-terminus), and the first 3 residue (FVN) has been deleted, and where the amino acid in position 21 (i.e. E) in the B chain is substituted with K, and the amino acid in position 29 (i.e. K) in the B chain is substituted with R, and the amino acid in position 30 (i.e., Thr) in the B chain is deleted (as illustrated in FIG. 7).

Figure 8:
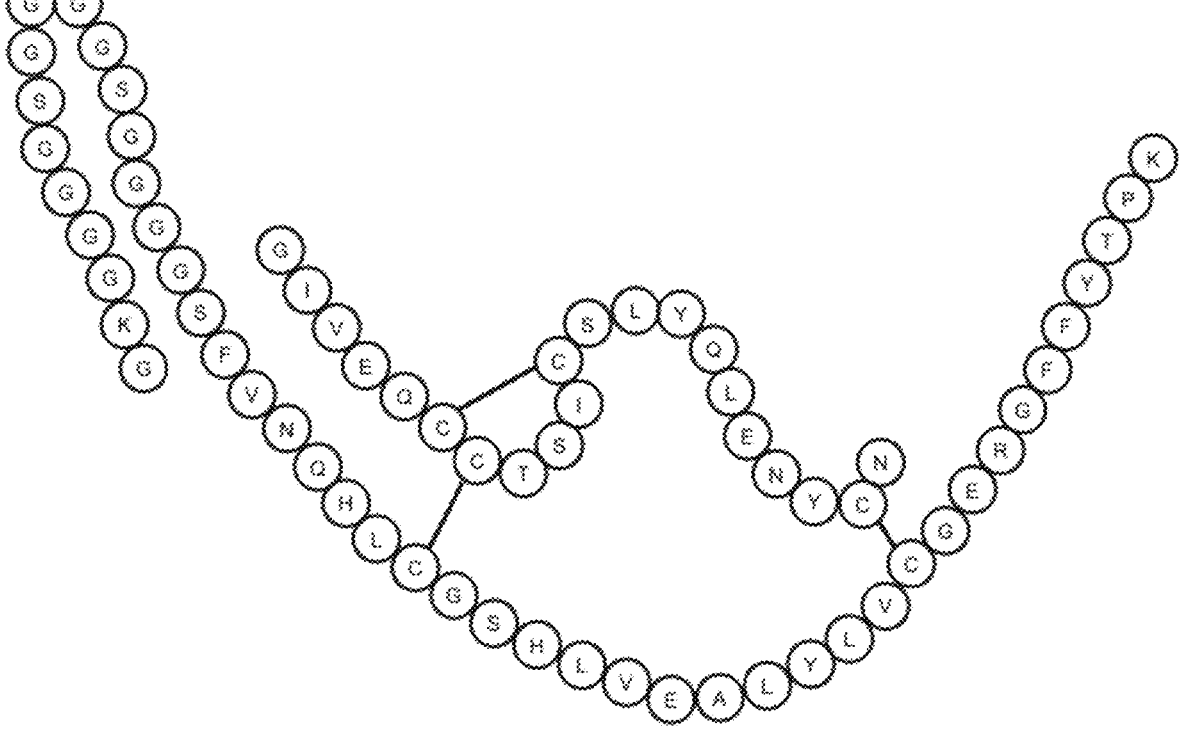

As yet another example, an insulin analogue having 2 modifications comprises an A-chain and a B-chain, wherein the A-chain comprises sequence GIVEQCCTSICSLYQLENYCN (SEQ ID NO: 1); and wherein the B-chain comprises sequence GKGGGGSGGGGSGGGGSFVNQHLCGSHLVEALYLVCGERGFFYTPK (SEQ ID NO: 25397), where the A chain has the wild-type sequence of chain A of human insulin (e.g. no mutations, deletions, additions) and the B chain has been extended at the N-terminal with GKGGGGSGGGGSGGGGS (i.e. 17 amino acids have been added/appended to the N-terminus), and the amino acid in position 30 (i.e. Thr) in the B chain is deleted (as illustrated in FIG. 8).

In some embodiments, insulin analogues include insulin that is chemically altered as compared to wild type human insulin, such as, but not limited to, by addition of a chemical moiety such as a PEG group or a fatty acyl chain. In some embodiments, altered insulins/insulin analogues/analogs, which are used herein interchangeably, may be mutated including additions, deletions or substitutions of amino acids. Different protomers of insulin may result from these changes and be incorporated into some embodiments. In some embodiments, active forms of insulins have fewer than 11 such modifications (e.g., 1-4, 1-3, 1-9, 1-8, 1-7, 1-6, 2-6, 2-5, 2-4, 1-5, 1-2, 2-9, 2-8, 2-7, 2-3, 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7-8, 8-9, 9, 8, 7, 6, 5, 4, 3, 2 or 1). As used herein, the wild-type sequence of human insulin (A-chain and B-chain), has an A-chain with the amino acid sequence GIVEQCCTSICSLYQLENYCN (SEQ ID NO: 1), and a B-chain having the amino acid sequence FVNQHLCGSHLVEALYLVCGERGFFYTPKT (SEQ ID NO: 2). In some embodiments, an insulin analogue has at least 70% sequence homology to a wild-type human insulin. In some embodiments, an insulin analogue has at least 80% sequence homology to a wild-type human insulin. In some embodiments, an insulin analogue has at least 90% sequence homology to a wild-type human insulin. In some embodiments, an insulin analogue has at least 95%, 96%, 97%, or 95% sequence homology to a wild-type human insulin. In some embodiments, an insulin analogue has at least 99% sequence homology to a wild-type human insulin.

Human insulin differs from rabbit, porcine, bovine, and sheep insulin in amino acids A8, A9, A10, and B30, which are in order the following: Thr, Ser, Ile, Thr for human; Thr, Ser, Ile, Ser for rabbit; Thr, Ser, Ile, Ala for porcine; Ala, Gly, Val, Ala for sheep; and Ala, Ser, Val, Ala for bovine. In some embodiments, a modified insulin may be mutated at position B1, B2, B28 or B29, or at positions B28 and B29 of the B-chain. In some embodiments, a modified insulin may be mutated at A1, A2, A21 or other positions of the A-chain. For example, insulin lispro is a fast-acting modified insulin in which the lysine and proline residues on the C-terminal end of the B-chain have been reversed. Insulin aspart is a fast-acting modified insulin in which proline has been substituted with aspartic acid at position B28. It is contemplated in some embodiments of the present disclosure that insulins mutated at B28 and B29 may further include additional mutations. For example, insulin glulisine is a fast-acting modified insulin in which aspartic acid has been replaced by a lysine residue at position B3, and lysine has been replaced by a glutamic acid residue at position B29. In some embodiments, longer acting and higher stability insulin analogs are covalently modified as described by Formula I or Formula IB, and may contain mutations such as tyrosine at A14 replaced with glutamic acid, the tyrosine at B16 replaced with histidine, and the phenylalanine at B25 replaced with a histidine.

In some embodiments, the isoelectric point of insulins herein may be shifted relative to wild-type human insulin using any suitable method, for example by addition or substitution of suitable amino acids. In some embodiments, the isoelectric point of the modified insulins may be modulated by glucose (e.g., by interaction with glucose). For example, insulin glargine is a basal insulin in which two arginine residues have been added to the C-terminus of the B-peptide, and A21 has been replaced by glycine. In some embodiments, the insulin may not have one or more of the residues B1, B2, B3, B26, B27, B28, B29, and B30 (e.g., the insulin may be a deletion mutant at one or more of the listed residues). In some embodiments, the insulin molecule contains up to five additional amino acid residues on the N- or C-terminus of the A-chain or B-chain. In some embodiments, one or more amino acid residues are located at positions A1, A21, B1, B29, B30 and/or B31 or are missing. In some embodiments, an insulin molecule of the present disclosure is mutated such that one or more amino acids are replaced (substituted) with their acidic forms. In some embodiments, an asparagine is replaced with aspartic acid or glutamic acid. In some embodiments, glutamine is replaced with aspartic acid or glutamic acid. In some embodiments, A21 may be an aspartic acid, B3 may be an aspartic acid, or both positions may contain an aspartic acid. One skilled in the art will recognize that it is possible to make any previously reported, or widely accepted mutations or modifications to insulin that retains biological activity, and that such an insulin analogue can be used in embodiments of the present disclosure. In some embodiments, an insulin may be linked at any position to a fatty acid, or acylated with a fatty acid at any amino group, including those on lysine side chains and the alpha-amino group on the N-terminus of insulin, and the fatty acid may include a C8, C9, C10, C11, C12, C14, C15, C16, C17, or C18 chain. In some embodiments, the fatty acid chain is 8-20 carbons long. In some embodiments, is an insulin detemir, in which a myristic acid is covalently conjugated to lysine at B29, and B30 is deleted or absent. In some embodiments, position B28 of the insulin molecule is lysine and the epsilon(s)-amino group of this lysine is conjugated to a fatty acid.

In some embodiments, the N- or C-terminal end of the A- or B-chain of the modified insulin is ligated using a peptide ligase. In some embodiments, a polypeptide is added to the C-terminus of the insulin A- and/or B-chain or to the N-terminus of insulin A- and/or B-chain using a protein ligase, and in some embodiments thereof the ligase is chosen from sortases, butelases, Trypsiligases, Subtilisins, Peptiligases or enzymes having at least 75% homology to these ligases. In some embodiments, ligation is achieved through expressed protein ligation as described in: Muir T W, Sondhi D, Cole P A. "Expressed protein ligation: a general method for protein engineering." *Proc Natl Acad Sci USA*. 1998; 95(12):6705-6710. In some embodiments, the polypeptide is linked to the modified insulin using Staudinger ligation, utilizing the Staudinger reaction and as described for example in Nilsson, B. L.; Kiessling, L. L.; Raines, R. T. (2000). "Staudinger ligation: A peptide from a thioester and azide". *Org. Lett.* 2 (13): 1939-1941. In some embodiments, a polypeptide is conjugated to the modified insulin using Ser/Thr ligation as, for example, described in: Zhang Y, Xu C, Kam H Y, Lee C L, Li X. 2013, "Protein chemical synthesis by serine/threonine ligation." *Proc. Natl. Acad. Sci. USA*. 17:6657-6662. In some embodiments, the B-chain itself has less than 32 amino acids or 34 amino acids, and in some embodiments the insulin has 4 disulfide bonds instead of 3. There are disulfide bonds present in the A and B chains of insulin. For example, a disulfide bond exists between the cysteine at position 6 of SEQ ID NO:1 and the cysteine at position 11 of SEQ ID NO:1, a disulfide bond exists between the cysteine at position 7 of SEQ ID NO:1 and the cysteine at position 7 of SEQ ID NO:2, and a disulfide bond exists between the cysteine at position 20 of SEQ ID NO:1 and the cysteine at position 19 of SEQ ID NO:2.

In some embodiments, a modified insulin of the present disclosure comprises one or more mutations and/or chemical modifications including, but not limited to one of the following insulin molecules: $N^{\varepsilon B29}$-octanoyl-$Arg^{B0}Gly^{A21}Asp^{B3}Arg^{B31}Arg^{B32}$-HI, $N^{\varepsilon B29}$-octanoyl-$Arg^{B31}Arg^{B32}$-HI, $N^{\varepsilon B29}$-octanoyl-$Arg^{40}Arg^{B31}Arg^{B32}$-HI, $N^{\varepsilon B28}$-myristoyl-$Gly^{A21}Lys^{B28}Pro^{B29}Arg^{B31}Ar^{B32}$-HI, $N^{\theta B28}$-myristoyl-$Gly^{A21}Gln^{B3}LyS^{B28}Pro^{B30}Arg^{B31}Arg^{B32}$-

HI, $N^{\varepsilon B28}$-myristoyl-$Arg^{40}Gly^{A21}Lys^{B28}Pro^{B29}Arg^{B31}Arg^{B32}$-HI, $N^{\geq B28}$-myristoyl-$Arg^{40}Gly^{A21}Gln^{B3}Lys^{B28}Pro^{B29}Arg^{B31}Arg^{B32}$-HI, $N^{\varepsilon B28}$-myristoyl-$Arg^{40}Gly^{A21}Asp^{B3}Lys^{B28}Pro^{B29}Arg^{B31}Arg^{B32}$-HI, $N^{\varepsilon B28}$-myristoyl-$Lys^{B28}Pro^{B29}Arg^{B31}Arg^{B32}$-HI, $N^{\varepsilon B28}$-myristoyl-$Arg^{40}Lys^{B28}Pro^{B29}Arg^{B31}Arg^{B32}$-HI, $N^{\varepsilon B28}$-octanoyl-$Gly^{A21}Lys^{B28}Pro^{B29}Arg^{B31}Arg^{B32}$-HI, $N^{\varepsilon B28}$-octanoyl-$Gly^{A21}Gln^{B3}Lys^{B28}Pro^{B29}Arg^{B31}Arg^{B32}$-HI, $N^{\varepsilon B28}$-octanoyl-$Arg^{40}Gly^{A21}Lys^{B28}Pro^{B29}Arg^{B31}Arg^{B32}$-HI, $N^{\varepsilon B29}$-palmitoyl-HI, $N^{\varepsilon B29}$-myrisotyl-HI, $N^{\varepsilon B28}$-palmitoyl-$Lys^{B28}Pro^{B29}$-HI, $N^{\varepsilon B28}$-myristoyl-$Lys^{B28}Pro^{B29}$-HI, $N^{\varepsilon B29}$-palmitoyl-des(B30)-HI, $NE^{B30}$-myristoyl-$Thr^{B29}Lys^{B30}$-HI, $NE^{B30}$-palmitoyl-$Thr^{B29}Lys^{B30}$-HI, $N^{\varepsilon B29}$—(N-palmitoyl-γ-glutamyl)-des(B30)-HI, $N^{\varepsilon B29}$—(N-lithocolyl-γ-glutamyl)-des(B30)-HI, $N^{\varepsilon B29}$-(ω-carboxyheptadecanoyl)-des(B30)-HI, $N^{\varepsilon B29}$-(ω-carboxyheptadecanoyl)-HI, $N^{\varepsilon B29}$-octanoyl-HI, $N^{\varepsilon B29}$-myristoyl-$Gly^{A21}Arg^{B31}Arg^{B31}$-HI, $N^{\varepsilon B29}$-myristoyl-$Gly^{A21}Gln^{B3}Arg^{B31}Arg^{B32}$-HI, $N^{\varepsilon B29}$-myristoyl-$Arg^{40}Gly^{A21}Arg^{B31}Arg^{B32}$-HI, $N^{\varepsilon B29}$-myristoyl-$Arg^{40}Gly^{A21}Gln^{B3}Arg^{B31}Arg^{B32}$-HI, $N^{\varepsilon B29}$-myristoyl-$Arg^{40}Gly^{A21}Asp^{B3}Arg^{B31}Arg^{B32}$-HI, $N^{\varepsilon B29}$-myristoyl-$Arg^{B31}Arg^{B32}$-HI, $N^{\varepsilon B29}$-myristoyl-$Arg^{40}Arg^{B31}Arg^{B32}$-HI, $N^{\varepsilon B29}$-octanoyl-$Gly^{A21}Arg^{B31}Arg^{B32}$-HI, $N^{\varepsilon B29}$-octanoyl-$Gly^{A21}Gln^{B3}Arg^{B31}Arg^{B32}$-HI, $N^{\varepsilon B29}$-octanoyl-$Arg^{40}Gly^{A21}Arg^{B31}Arg^{B32}$-HI, $N^{\varepsilon B29}$-octanoyl-$Arg^{40}Gly^{A21}Gln^{B3}Arg^{B31}Arg^{B32}$-HI, $N^{\varepsilon B28}$-octanoyl-$Arg^{40}Gly^{A21}Gln^{B3}Lys^{B28}Pro^{B29}Arg^{B31}Arg^{B32}$-HI, $N^{\varepsilon B28}$-octanoyl-$Arg^{40}Gly^{A21}Asp^{B3}Lys^{B28}Pro^{B29}Arg^{B31}Arg^{B32}$-HI, $N^{\varepsilon B28}$-octanoyl-$Lys^{B28}Pro^{B29}Arg^{B31}Arg^{B32}$-HI, $N^{\varepsilon B28}$-octanoyl-$Arg^{40}Lys^{B28}Pro^{B29}Arg^{B31}Arg^{B32}$-HI. $N^{\varepsilon B29}$-pentanoyl-$Gly^{A21}Arg^{B31}Arg^{B32}$-HI, $N^{\alpha B1}$-hexanoyl-$Gly^{A21}Arg^{B31}Arg^{B32}$-HI, $N^{\alpha A1}$-heptanoyl-$Gly^{A21}Arg^{B31}Arg^{B32}$-HI, $N^{\varepsilon B29}$-octanoyl-$N^{\alpha B1}$-octanoyl-$Gly^{A21}Arg^{B31}Arg^{B32}$-HI, $N^{\varepsilon B29}$-propionyl-$N^{\alpha A1}$-propionyl-$Gly^{A21}Arg^{B31}Arg^{B32}$-HI, $N^{\alpha A1}$-acetyl-$N^{\alpha B1}$-acetyl-$Gly^{A21}Arg^{B31}Arg^{B32}$-HI, $N^{\varepsilon B29}$-formyl-$N^{\alpha A1}$-formyl-$N^{\alpha B1}$-formyl-$Gly^{A21}Arg^{B31}Arg^{B32}$-HI, $N^{B29}$-formyl-des(B26)-HI, $N^{\alpha B1}$-acetyl-$Asp^{B28}$-HI, $N^{\varepsilon B29}$-propionyl-$N^{\alpha A1}$-propionyl-$N^{\alpha B1}$-propionyl-$Asp^{B1}Asp^{B3}Asp^{B21}$-HI, $N^{\varepsilon B29}$-pentanoyl-$Gly^{A21}$-HI, $N^{\alpha B1}$-hexanoyl-$Gly^{A21}$-HI, $N^{\alpha A1}$-heptanoyl-$Gly^{A21}$-HI, $N^{\varepsilon B29}$-octanoyl-$N^{\alpha B1}$-octanoyl-$Gly^{A21}$-HI, $N^{\varepsilon B29}$-propionyl-$N^{\alpha A1}$-propionyl-$Gly^{A21}$-HI, $N^{\alpha B1}$-acetyl-$N^{\alpha A1}$-acetyl-$Gly^{A21}$-HI, $N^{\varepsilon B29}$-formyl-$N^{\alpha A1}$-formyl-$N^{\alpha B1}$-formyl-$Gly^{A21}$-HI, $N^{B29}$-butyryl-des(B30)-HI, $N^{\alpha B31}$-butyryl-des(B30)-HI, $N^{\alpha A1}$-butyryl-des(B30)-HI, $N^{\varepsilon B29}$-butyryl-$N^{\alpha B3}$-butyryl-des(B30)-HI, $N^{\varepsilon B29}$-butyryl-$N^{\alpha A1}$-butyryl-des(B30)-HI, $N^{\alpha A1}$-butyryl-$N^{\alpha B31}$-butyryl-des(B30)-HI, $N^{\varepsilon B29}$-butyryl-$N^{\alpha A1}$-butyryl-$N^{\alpha B3}$-butyryl-des(B30)-HI, $Lys^{B28}Pro^{B29}$-HI (insulin lispro), $Asp^{B28}$-HI (insulin aspart), $Lys^{B3}Glu^{B29}$-HI (insulin glulisine), $Arg^{B31}Arg^{B32}$-HI (insulin glargine), $N^{\varepsilon B29}$-myristoyl-des(B30)-HI (insulin detemir), $Ala^{B26}$-HI, $Asp^{B1}$-HI, $Arg^{40}$-HI, $Asp^{B1}Glu^{B13}$-HI, $Gly^{A21}$-HI, $Gly^{A21}Arg^{B31}Arg^{B32}$-HI, $Arg^{40}Arg^{B3}$ $Ar^{B32}$-HI, $Arg^{40}Gly^{A21}$ $Arg^{B31}Arg^{B32}$-HI, des(B30)-HI, des(B27)-HI, des(B28-B30)-HI, des(B1)-HI, des(B1-B3)-HI $N^{\varepsilon B29}$-tridecanoyl-des(B30)-HI, $N^{\varepsilon B29}$-tetradecanoyl-des(B30)-HI, $N^{\varepsilon B29}$-decanoyl-des(B30)-HI, $N^{\varepsilon B29}$-dodecanoyl-des(B30)-HI, $N^{\varepsilon B29}$-tridecanoyl-$Gly^{A21}$-des(B30)-HI, $N^{\varepsilon B29}$-tetradecanoyl-$Gly^{A21}$-des(B30)-HI, $N^{\varepsilon B29}$-decanoyl-$Gly^{A21}$-des(B30)-HI, $N^{\varepsilon B29}$-dodecanoyl-$Gly^{A21}$-des(B30)-HI, $N^{\varepsilon B29}$-tridecanoyl-$Gly^{A21}Gln^{B3}$-des(B30)-HI, $N^{\varepsilon B29}$-tetradecanoyl-$Gly^{A21}Gln^{B3}$-des(B30)-HI, $N^{\varepsilon B29}$-decanoyl-$Gly^{A21}Gln^{B3}$-des(B30)-HI, $N^{\varepsilon B29}$-dodecanoyl-$Gly^{A21}Gln^{B3}$-des(B30)-HI, $N^{\varepsilon B29}$-tridecanoyl-$Ala^{A21}$-des(B30)-HI, $N^{\varepsilon B29}$-tetradecanoyl-$Ala^{A21}$-des(B30)-HI, $N^{\varepsilon B29}$-decanoyl-$Ala^{A21}$-des(B30)-HI, $N^{\varepsilon B29}$-dodecanoyl-$Ala^{A21}$- des(B30)-HI, $N^{\varepsilon B29}$-tridecanoyl-Ala$^{A21}$-Gln$^{B3}$-des(B30)-HI, $N^{\varepsilon B29}$-tetradecanoyl-Ala$^{A21}$Gln$^{B3}$-des(B30)-HI, $N^{\varepsilon B29}$-decanoyl-Ala$^{A21}$Gln$^{B3}$-des(B30)-HI, $N^{\varepsilon B29}$-dodecanoyl-Ala$^{A21}$Gln$^{B3}$-des(B30)-HI, $N^{\varepsilon B29}$-tridecanoyl-Gln$^{B3}$-des(B30)-HI, $N^{\varepsilon B29}$-tetradecanoyl-Gln$^{B3}$-des(B30)-HI, $N^{\varepsilon B29}$-decanoyl-Gln$^{B3}$-des(B30)-HI, $N^{\varepsilon B29}$-dodecanoyl-Gln$^{B3}$-des(B30)-HI, $N^{\varepsilon B29}$-Z1-Gly$^{A21}$-HI, $N^{\varepsilon B29}$-Z2-Gly$^{A21}$-HI, $N^{\varepsilon B29}$-Z4-Gly$^{A21}$-HI, $N^{\varepsilon B29}$-Z3-Gly$^{A21}$-HI, $N^{\varepsilon B29}$-Z1-Ala$^{A21}$-HI, $N^{\varepsilon B29}$-Z2-Ala$^{A21}$-HI, $N^{\varepsilon B29}$-Z4-Ala$^{A21}$-HI, $N^{\varepsilon B29}$-Z3-Ala$^{A21}$-HI, $N^{\varepsilon B29}$-Z1-Gly$^{A21}$Gln$^{B3}$-HI, $N^{\varepsilon B29}$-Z2-Gly$^{A21}$Gln$^{B3}$-HI, $N^{\varepsilon B29}$-Z4-Gly$^{A21}$Gln$^{B3}$-HI, $N^{\varepsilon B29}$-Z3-Gly$^{A21}$Gln$^{B3}$-HI, $N^{\varepsilon B29}$-Z1-Ala$^{A21}$Gln$^{B3}$-HI, $N^{\varepsilon B29}$-Z2-Ala$^{A21}$Gln$^{B3}$-HI, $N^{\varepsilon B29}$-Z4-Ala$^{A21}$Gln$^{B3}$-HI, $N^{\varepsilon B29}$-Z3-Ala$^{A21}$Gln$^{B3}$-HI, $N^{\varepsilon B29}$-Z1-Gln$^{B3}$-HI, $N^{\varepsilon B29}$-Z2-Gln$^{B3}$-HI, $N^{\varepsilon B29}$-Z4-Gln$^{B3}$-HI, $N^{\varepsilon B29}$-Z3-Gln$^{B3}$-HI, $N^{\varepsilon B29}$-Z1-Glu$^{B30}$-HI, $N^{\varepsilon B29}$-Z2-Glu$^{B30}$-HI, $N^{\varepsilon B29}$-Z4-Glu$^{B30}$HI, $N^{\varepsilon B29}$-Z3-Glu$^{B30}$-HI, $N^{\varepsilon B29}$-Z1-Gly$^{A21}$Glu$^{B30}$-HI, $N^{\varepsilon B29}$-Z2-Gly$^{A21}$Glu$^{B30}$-HI, $N^{\varepsilon B29}$-Z4-Gly$^{A21}$Glu$^{B30}$-HI, $N^{\varepsilon B29}$-Z3-Gly$^{A21}$Glu$^{B30}$-HI, $N^{\varepsilon B29}$-Z1-Gly$^{A21}$Gln$^{B3}$Glu$^{B30}$-HI, $N^{\varepsilon B29}$-Z2-Gly$^{A21}$Gln$^{B3}$Glu$^{B30}$-HI, $N^{\varepsilon B29}$-Z4-Gly$^{A21}$Gln$^{B3}$Glu$^{B30}$-HI, $N^{\varepsilon B29}$-Z3-Gly$^{A21}$Gln$^{B3}$Glu$^{B30}$-HI, $N^{\varepsilon B29}$-Z1-Ala$^{A21}$Glu$^{B30}$-HI, $N^{\varepsilon B29}$-Z2-Ala$^{A21}$Glu$^{B30}$-HI, $N^{\varepsilon B29}$-Z4-Ala$^{A21}$Gln$^{B30}$-HI, $N^{\varepsilon B29}$-Z3-Ala$^{A21}$Glu$^{B30}$-HI, $N^{\varepsilon B29}$-Z1-Ala$^{A21}$Gln$^{B3}$Glu$^{B30}$-HI, $N^{\varepsilon B29}$-Z2-Ala$^{A21}$Gln$^{B3}$Glu$^{B30}$-HI, $N^{\varepsilon B29}$-Z4-Ala$^{A21}$Gln$^{B3}$Glu$^{B30}$-HI, $N^{\varepsilon B29}$-Z3_Ala$^{A21}$Gln$^{B3}$Glu$^{B30}$-HI, $N^{\varepsilon B29}$-Z1-Gln$^{B3}$Glu$^{B30}$-HI, $N^{\varepsilon B29}$—Z2-Gln$^{B3}$Glu$^{B30}$-HI, $N^{\varepsilon B29}$-Z4-Gln$^{B3}$Glu$^{B30}$-HI, $N^{\varepsilon B29}$-Z3-Gln$^{B3}$Glu$^{B30}$-HI and where Z1 is tridecanoyl, Z2 is tetradecanoyl, Z3 is dodecanoyl, Z4 is decanoyl, and HI is human insulin.

In some embodiments, insulin includes one or more of the following mutations and/or chemical modifications: $N^{\varepsilon B28}$—XXXXX-Lys$^{B28}$Pro$^{B29}$-HI, $N^{\alpha B1}$—XXXXX-Lys$^{B28}$Pro$^{B29}$-HI, $N^{\alpha A1}$—XXXXX-Lys$^{B28}$Pro$^{B29}$-HI, $N^{\varepsilon B28}$—XXXXX—$N^{\alpha B1}$—XXXXX-Lys$^{B28}$Pro$^{B29}$-HI, $N^{\varepsilon B28}$—XXXXX—$N^{\alpha A1}$—XXXXX-Lys$^{B28}$Pro$^{B29}$-HI, $N^{\alpha A1}$—XXXXX—$N_{\alpha B1}$—XXXXX-Lys$^{B28}$Pro$^{B29}$-HI, $N^{\varepsilon B28}$—XXXXX—$N^{\alpha A1}$—XXXXX—$N^{\alpha B1}$—XXXXX-Lys$^{B28}$Pro$^{B29}$-HI, $N^{\varepsilon B29}$—XXXXX—HI, $N^{\alpha B1}$—XXXXX—HI, $N^{\alpha A1}$—XXXXX—HI, $N^{\varepsilon B29}$—XXXXX—$N^{\alpha B1}$—XXXXX—HI, $N^{\varepsilon B29}$—XXXXX—$N^{\alpha A1}$—XXXXX—HI, $N^{\alpha A1}$—XXXXX—$N^{\alpha B1}$—XXXXX—HI, $N^{\varepsilon B29}$—XXXXX—$N^{\alpha A1}$—XXXXX—$N^{\alpha B1}$—XXXXX—HI, $N^{\varepsilon B29}$—YYYYY—HI, $N^{\alpha B1}$—YYYYY—HI, $N^{\alpha A1}$—YYYYY—HI, $N^{\varepsilon B29}$—YYYYY—$N^{\alpha B1}$—YYYYY—HI, $N^{\varepsilon B29}$—YYYYY—$N^{\alpha A1}$—YYYYY—HI, $N^{\alpha A1}$—YYYYY—$N^{\alpha B1}$—YYYYY—HI, $N^{\varepsilon B29}$—YYYYY—$N^{\alpha A1}$—YYYYY—$N^{\alpha B1}$—YYYYY—HI, $N^{\varepsilon B28}$—YYYYY-Lys$^{B28}$Pro$^{B29}$-HI, $N^{\varepsilon B28}$—YYYYY-Lys$^{B28}$Pro$^{B29}$-HI, $N^{\alpha A1}$—YYYYY-Lys$^{B28}$Pro$^{B29}$-HI, $N^{\varepsilon B28}$—YYYYY—$N^{\alpha B1}$—YYYYY-Lys$^{B28}$Pro$^{B29}$-HI, $N^{\varepsilon B28}$—YYYYY—$N^{\alpha A1}$—YYYYY-Lys$^{B28}$Pro$^{B29}$-HI, $N^{\alpha A1}$—YYYYY—$N^{\alpha B1}$—YYYYY-Lys$^{B28}$Pro$^{B29}$-$N^{\varepsilon B28}$—YYYY—$N^{\alpha A1}$—YYYYY—$N^{\alpha B1}$—YYYYY-Lys$^{B28}$Pro$^{B29}$-HI, and where YYYYY is one of acetyl or formyl and where XXXXX is one of: propionyl, butyryl, pentanoyl, hexanoyl, heptanoyl, octanoyl, nonanoyl or decanoyl and HI is human insulin.

In some embodiments, insulin may be conjugated through a reactive moiety that is naturally present within the insulin structure or is added prior to conjugation, including, for example, carboxyl or reactive ester, amine, hydroxyl, aldehyde, sulfhydryl, maleimidyl, alkynyl, azido, etc. moieties. Insulin naturally includes reactive alpha-terminal amine and epsilon-amine lysine groups to which NHS-ester, isocyanates or isothiocyanates can be covalently conjugated. In some embodiments, a modified insulin may be employed in which a suitable amino acid (e.g., a lysine or a non-natural amino acid) has been added or substituted into the amino acid sequence in order to provide an alternative point of conjugation in addition to the modified amino acids of the embodiments described herein. In some embodiments, the conjugation process may be controlled by selectively blocking certain reactive moieties prior to conjugation. In some embodiments, insulin may include any combination of modifications and the present disclosure also encompasses modified forms of non-human insulins (e.g., porcine insulin, bovine insulin, rabbit insulin, sheep insulin, etc.) that comprise any one of the aforementioned modifications. It is understood that some embodiments include these and other previously described modified insulins such as those described in U.S. Pat. Nos. 5,474,978; 5,461,031; 4,421, 685; 7,387,996; 6,869,930; 6,174,856; 6,011,007; 5,866, 538; 5,750,4976; 906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; US 2015/0353619, including non-natural amino acids described or referenced herein and including such modifications to the non-human insulins described herein. It is also to be understood that in some embodiments the insulin may be covalently conjugated to polyethylene glycol polymers, such as polyethylene glycol polymers of no more than Mn 60,000, or covalently conjugated either through permanent or reversible bonds to albumin.

In some embodiments, a compound of the present disclosure (e.g., Formula I or Formula IB) is conjugated to a chelator, and in some embodiments the chelator can be used to capture a radioactive payload, such as gallium 68, copper 64, lutetium 177, or actinium 225. In some embodiments, the chelator is based on DOTA, NOTA, TETA, or 4-arm DOTA, and in some embodiments, the chelator can be linked to the peptide using a PEG linker through amide bonds to the chelator and to the peptide.

In some embodiments, the activity, bioavailability, solubility, isoelectric point, charge and/or hydrophobicity of the modified insulins can be controlled through chemical modifications and/or as result of interaction of a small molecule such as a sugar with the compounds, such as the compounds described herein which are either covalently linked or mixed with insulin.

In some embodiments one or more elements, functional groups, or atoms may be specifically omitted or excluded from a depicted structure (e.g., a terminal functional group may be replaced by a hydrogen atom, or a linking group may be replaced by a bond), for example in Formulae FF1-FF11, FF12, FF12A, FF12B, FF12C, FF12D, FF13-FF115, FF116, FF116A, FF116B, FF116C, FF116D, and FF117-FF231, and it will be understood that such omitted or excluded elements make these groups (structures) distinct and non-equivalent. For example, if an alternative version (variation) of a formula structure does not have a nitro group in R1 for B1 or B2, that variation is not equivalent (e.g., is structurally and chemically inequivalent) to a structure that includes the nitro group, at least because the nitro group changes the pKa of B1 and B2 in physiological conditions and hence the overall affinity of Z1c for glucose.

Rotationally Constrained Tethered Boron Conjugates.

In some embodiments, aromatic boron-containing compounds and/or aromatic boron-containing groups are rotationally constrained tether boron conjugates. In some embodiments, rotationally constrained tether boron conjugates presented in this disclosure contain scaffolds that are rotationally hindered by disfavored steric interactions (e.g. gauche vs anti interactions of substituents), hindered rotation due to bond hybridization (e.g., cis- vs trans-amide rotations), or through rigid covalent bonds (e.g., (E) vs (Z) configurations for alkene moieties). For example, formulae FF50-FF62, FF116, FF116A, FF116B, FF116C, FF116D, and FF121-134 contain alkyl functionalities geminal (e.g., attached to the same atom) to the amine groups that are covalently conjugated to the boronic acid functionalized moieties. Alkyl functionalities may limit the accessible dihedral angles and the rotation freedom around the C—C or C—X bond (commonly referred to as $\chi$ (chi) dihedral angles in amino acids). For example, the hydroxyl sidechain on a serine residue can access dihedral angles of 60°, 180°, or 240° (–60°) with near equal distribution while the hydroxyl sidechain of threonine may only adopt dihedral angles of 180° or 240° (–60°). The presence of a methyl group geminal to the hydroxy on threonine may provide steric bulk, creating unfavorable interactions when other bulky substituents are in a gauche conformation relative to the methyl. Formulae FF50-FF62, FF116, FF116A, FF116B, FF116C, and FF116D and FF121-134 contain geminal alkyl substituents which may limit the accessible dihedral angles that the boron conjugated amines adopt, influencing adopted dihedral angles and placing the boronic functionalized groups closer together and allowing for increased binding of the conjugates to target molecules such as proteins or sugars.

In some embodiments, an insulin receptor agonist disclosed herein may have an onset of action between 1-2 hours, or longer. In certain embodiments, the insulin receptor agonist may have a maximum effectiveness (peak) within between 6-20 hours and or have prolonged action. In some embodiments, the insulin receptor agonist can be administered at a frequency of once daily or, for example, once weekly.

In some embodiments, the insulin receptor agonists have an extended duration of bioavailability (e.g., prolonged in vivo plasma half-life). In some embodiments, the insulin receptor agonists disclosed herein comprise one or more linker moieties (e.g., one or more Z1b) and/or diboronates (e.g., F7) that results in increased terminal half-life and/or decreased clearance (CL) for the compounds disclosed herein in the blood. In some embodiments, compounds disclosed herein have a terminal half-life of at least 1 hour, at least 1.5 hours, at least 2 hours, at least 2.5 hours, at least 3 hours, at least 3.5 hours, at least 4 hours, at least 4.5 hours, or at least 5 hours. In some embodiments, compounds disclosed herein have a half-life of up to 1 hour, 2 hours, 3 hours, 4 hours, or 5 hours. In some embodiments, compounds disclosed herein have a CL value ranging from about 0.13 ml/min/kg to about 2.4 ml/min/kg.

In some embodiments, the linker comprises a $C_2$-$C_{20}$ acyl group optionally terminating in an acid group selected from A″ (e.g., AB-1-AB-39). In some embodiments, the linker comprises a lipophilic side chain selected from A″ (e.g., AB1-AB7, AB15-AB28, AB-32).

In some embodiments, the compound comprises one or more linkers comprising a $C_2$-$C_{20}$ acyl group optionally terminating in an acid group. In some embodiments, the compound comprises one or more Z1c comprising at least one F7. In further embodiments, the compounds have a prolonged terminal half-life and/or a decrease in clearance.

In some embodiments, the stereochemistry of isomeric structures (e.g., the stereochemistry of a compound (for example within the Z1c moiety)) may selectively increase the affinity of the conjugate (e.g., the Z1c moiety) for a specific target diol, such as glucose. For example, in some embodiments one or more stereoisomers (e.g., cis- or trans-, (R) or (S), and (E) or (Z)) of Z1c may be selected to increase or decreases the affinity of Z1c (and the molecular architecture or conjugate as a whole) for glucose. In some embodiments, the cis form of Formulae FF1-FF231 (e.g., FF12, FF12B, FF12C, FF12D, FF114, FF115, FF116, FF116A, FF116B, FF116C, FF116D, FF117, FF193, and FF203) is used when applicable (e.g., Z1c includes a structure having cis stereochemistry). In some embodiments, the trans form of Formulae FF1-FF231 (e.g., FF12, FF12B, FF12C, FF12D, FF115, FF116, FF116A, FF116B, FF116C, FF116D, FF117, FF193, and FF203) is used when applicable, e.g., when these Formulae include two stereocenters linked by a bond, (e.g., Z1c includes a structure having trans stereochemistry). In some embodiments, the R form of Formulae FF1-FF231 (e.g., FF12, FF114, FF115, FF116, FF117, FF193, and FF203) is used when applicable, e.g., when Formulae FF12, FF114, FF115, FF116, FF117, FF193, and FF203 include at least one stereocenter, (e.g., Z1c includes a structure having R stereochemistry). In some embodiments, the S form of Formulae FF1-FF231 (e.g., FF12, FF114, FF115, FF116, FF117, FF193, and FF203) is used when applicable, e.g., when Formulae FF12, FF114, FF115, FF116, FF117, FF193, and FF203 include at least one stereocenter, (e.g., Z1c includes a structure having S stereochemistry). In some embodiments, the S,S form of Formulae FF1-FF231 (e.g., FF12, FF114, FF115, FF116, FF117, FF193, and FF203) is used when applicable, e.g., when Formulae FF12, FF114, FF115, FF116, FF117, FF193, and FF203 include two stereocenters linked by a bond, (e.g., Z1c includes a structure having S,S stereochemistry). In some embodiments, the S,R form of Formulae FF1-FF231 (e.g., FF12, FF114, FF115, FF116, FF117, FF193, and FF203) is used when applicable, e.g., when Formulae FF12, FF114, FF115, FF116, FF117, FF193, and FF203 include two stereocenters linked by a bond, (e.g., Z1c includes a structure having S,R stereochemistry). In some embodiments, the R,R form of Formulae FF1-FF231 (e.g., FF12, FF114, FF115, FF116, FF117, FF193, and FF203) is used when applicable, e.g., when Formulae FF12, FF114, FF115, FF116, FF117, FF193, and FF203 include two stereocenters linked by a bond, (e.g., Z1c includes a structure having R,R stereochemistry). In some embodiments, the R,S form of Formulae FF1-FF231 (e.g., FF12, FF114, FF115, FF116, FF117, FF193, and FF203) is used when applicable, e.g., when Formulae FF12, FF114, FF115, FF116, FF117, FF193, and FF203 include two stereocenters linked by a bond, (e.g., Z1c includes a structure having R,S stereochemistry). In some embodiments, a compound includes one or more tautomers of a compound disclosed herein. In-some embodiments, a compound includes one or more stereoisomers or a mixture of stereoisomers of a compound disclosed herein.

In some embodiments, a compound is covalently conjugated to glucagon, GLP-1, GLP-2 or a variation of any of these (e.g., any variation with deletions, insertions and/or replacements of one or more amino acids). In some embodiments any suitable chemical modifications made to insulin discussed herein can be made to glucagon. In some embodiments the conjugate is mixed with a second or drug substance or one or more compounds chosen from: aminoethylglucose, aminoethylbimannose, aminoethyltrimannose, D-glucose, D-galactose, D-Allose, D-Mannose, D-Gulose, D-Idose, D-Talose, N-Azidomannosamine (ManNAz) or N-Azidogalactoseamine (GalNAz) or N-azidoglucoseamine (GlcNAz), 2'-fluororibose, 2'-deoxyribose, glucose, sucrose, maltose, mannose, derivatives of these (e.g., glucosamine, mannosamine, methylglucose, methylmannose, ethylglucose, ethylmannose, etc.), sorbitol, inositol, galactitol, dulcitol, xylitol, arabitol and/or higher order combinations of these (such as linear and/or branched bimannose, linear and/or branched trimannose), molecules containing cis-diols, catechols, tris, and DOPA molecules such as L-DOPA or L-3,4-dihydroxyphenylalanine.

Moreover, one skilled in the art will recognize that in some embodiments, one or more of suitable proteinogenic artificial amino acids can be used (included) in chain A or chain B. For example, in some embodiments one or more of the following artificial amino acids can be used based on the methods described in and referenced through, and the list of amino acids provided in: Liu, C. C.; Schultz, P. G. (2010). "Adding new chemistries to the genetic code." *Annual Review of Biochemistry* 79: 413-44. One skilled in the art will recognize that, in some embodiments, artificial amino acids can be incorporated in the drug or insulin (e.g., adding amino acids to chain A or chain B), and these include the amino acids referenced herein as well as previously reported non-proteinogenic amino acids. In some embodiments, artificial amino acids exist (e.g., may be included) in the insulin, and in some embodiments thereof, proteinogenic artificial amino acids can be incorporated through recombinant protein expression using suitable methods and approaches, including those described in United States patent and patent applications including: US 2008/0044854, U.S. Pat. Nos. 8,518,666, 8,980,581, US 2008/0044854, US 20140045261, US 2004/0053390, U.S. Pat. Nos. 7,229,634, 8,236,344, US 2005/0196427, US 2010/0247433, U.S. Pat. Nos. 7,198,915, 7,723,070, US 2002/0042097, US 2004/0058415, US 2008/0026422, US 2008/0160609, US 2010/0184193, US 2012/0077228, US 2014/025599, U.S. Pat. Nos. 7,198,915, 7,632,492, 7,723,070, and other proteinogenic artificial amino acids may be introduced recombinantly using methods and approaches described in: U.S. Pat. Nos. 7,736,872, 7,816,320, 7,829,310, 7,829,659, 7,883,866, 8,097,702, 8,946,148.

In some embodiments, cyclic amino acids such as 3-hydroxyproline, 4-hydroxyproline, aziridine-2-carboxylic acid, azetidine-2-carboxylic acid, piperidine-2-carboxylic acid, 3-carboxy-morpholine, 3-carboxy-thiamorpholine, 4-oxaproline, pyroglutamic acid, 1,3-oxazolidine-4-carboxylic acid, 1,3-thiazolidine-4-carboxylic acid, 3-thiaproline, 4-thiaproline, 3-selenoproline, 4-selenoproline, 4-ketoproline, 3,4-dehydroproline, 4-aminoproline, 4-fluoroproline, 4,4-difluoroproline, 4-chloroproline, 4,4-dichloroproline, 4-bromoproline, 4,4-dibromoproline, 4-methylproline, 4-ethylproline, 4-cyclohexyl-proline, 3-phenylproline, 4-phenylproline, 3,4-phenylproline, 4-azidoproline, 4-carboxyproline, a-methylproline, a-ethylproline, a-propylproline, a-allylproline, a-benzylproline, a-(4-fluorobenzyl)-proline, a-(2-chlorobenzyl)-proline, a-(3-chlorobenzyl)-proline, a-(2-bromobenzyl)-proline, a-(4-bromobenzyl)-proline, a-(4-methylbenzyl)-proline, a-(diphenylmethyl)-proline, a-(naphthylmethyl)-proline, D-proline, or S-homoproline, (2S, 4S)-4-fluoro-L-proline, (2S, 4R)-4-fluoro-L-proline, (2S)-3,4-dehydro-L-proline, (2S, 4S)-4-hydroxy-L-proline, (2S, 4R)-4-hydroxy-L-proline, (2S,4S)-4-azido-L-proline, (2S)-4,4-difluoro-L-proline, (2S)-azetidine-2-carboxylic acid, (2S)-piperidine-2-carboxylic acid, or (4R)-1,3-thiazolidine-4-carboxylic acid can be used in the molecular architecture that is conjugated to insulin.

It is to be understood that in some embodiments, a specific orientation of amino acids is achieved using, for example, methods of Albericio, F. (2000). *Solid-Phase Synthesis: A Practical Guide* (1 ed.). Boca Raton: CRC Press. p. 848. In some embodiments a compound of the present disclosure, such as a compound of Formula I, Formula IB, or Formula IF, can bind to a diol, a catechol, a hexose sugar, glucose, xylose, fucose, galactosamine, glucosamine, mannosamine, galactose, mannose, fructose, galacturonic acid, glucuronic acid, iduronic acid, mannuronic acid, acetyl galactosamine, acetyl glucosamine, acetyl mannosamine, acetyl muramic acid, 2-keto-3-deoxy-glycero-galacto-nononic acid, acetyl neuraminic acid, glycolyl neuraminic acid, a neurotransmitter, dopamine, or a disaccharide or polymer of saccharides or diols.

In some embodiments, modifications or intermediates may include the use of an N-methyliminodiacetic acid (MIDA) group to make a MIDA conjugated boronate or a MIDA boronate; such modifications can be used during preparation of boronates towards the final structures of use (e.g., in embodiments of methods for preparing the conjugates described herein). In some embodiments boronic acid pinacol esters are used towards the final structures wherein the pinacol group can be readily removed using standard techniques by one skilled in the art. The MIDA-protected boronate esters are easily handled, stable under air, compatible with chromatography, and unreactive under standard anhydrous cross-coupling conditions and easily deprotected at room temperature under mild aqueous basic conditions such as 1M NaOH, or even $NaHCO_3$, or as described by Lee, S. J. et al. (2008). *J. Am. Chem. Soc.* 130:466.

The biological mechanism by which wild type insulin binds to the insulin receptor is previously reported in Menting, J. G. et al. (2013). *Nature* 493, 241-245; and Menting, J. G. et al. (2014). "Protective hinge in insulin opens to enable its receptor engagement." *Proc. Natl. Acad. Sci. U.S.A.* 111, E3395-3404. The activity of such insulin can be measured using any suitable technique, for example, by using in vitro insulin receptor binding with TyrA14-$^{125}$I human insulin as tracer and utilizing antibody binding beads with an insulin receptor monoclonal antibody. In some embodiments, animal models can be used for in vivo assessment of insulin activity during glucose challenge using methods that are known to one skilled in the art. In some embodiments, a compound disclosed herein is partially or fully expressed along with a recombinant protein of interest such as insulin. The processes for expression of insulin in *E. coli* areknown and can be easily performed by one skilled in the art e.g., by using the procedures outlined in Jonasson (1996). *Eur. J. Biochem.* 236:656-661; Cowley (1997). *FEBS Lett.* 402:124-130; Cho (2001). *Biotechnol. Bioprocess Eng.* 6: 144-149; Tikhonov (2001). *Protein Exp. Pur.* 21: 176-182; Malik (2007). *Protein Exp. Pur.* 55: 100-111; and Min (2011). *J. Biotech.* 151:350-356. In the most common process, the protein is expressed as a single-chain proinsulin construct with a fission protein or affinity tag. The compound (e.g., a compound of Formula I or Formula IB) can be expressed as part of proinsulin, then modified chemically to conjugate, through amide linkages, to structures of interest. This approach provides good yield and reduces experimental complexity by decreasing the number of processing steps and allows refolding in a native-like insulin, see for example, Jonasson, *Eur. J. Biochem.* 236:656-661 (1996); Cho, *Biotechnol Bioprocess Eng.* 6: 144-149 (2001); Tikhonov, *Protein Exp. Pur.* 21: 176-182 (2001); Min, *J. Biotech.* 151:350-356 (2011)). When expressed in *E. coli*, proinsulin is usually found in inclusion bodies and can be easily purified by one skilled in the art.

In some embodiments, proinsulin can be expressed using standard IPTG (isopropylthio-β-galactoside) induction of IPTG inducible expression constructs and vectors in *E. coli* strains such as B21 strain. As an example, the expression construct consists of the B-chain, C-peptide, A-chain. For example, the c-peptide sequence of EAEDLQVGQVEL-GGGPGAGSLQPLALEGSLQR can be used for expression of the proinsulin. Proinsulin is expressed in inclusion bodies (IBs), IBs are captured, washed and further purified, for example via an existing his-tag before sensor conjugation. Expression of the desired proinsulin can be performed via known procedures in the art. See, e.g., U.S. Pat. Nos. 5,457,066, 5,700,662, 5,514,646, 9,050,371, and 10400021.

In some embodiments, a compound of the present disclosure (e.g. Formula I, Formula IB, Formula IF) may be formulated for injection. For example, it may be formulated for injection into a subject, such as a human. In some embodiments, the composition may be a pharmaceutical composition, such as a sterile, injectable pharmaceutical composition. In some embodiments, the composition may be formulated for subcutaneous injection. In some embodiments, the composition is formulated for transdermal, intradermal, transmucosal, nasal, inhalable or intramuscular administration. In some embodiments, the composition may be formulated in an oral dosage form or a pulmonary dosage form. Pharmaceutical compositions suitable for injection may include sterile aqueous solutions containing, for example, sugars, polyalcohols such as mannitol and sorbitol, phenol, meta-cresol, and sodium chloride and dispersions may be prepared in glycerol, liquid polyethylene glycols, and mixtures thereof and in oils and the carrier can, for example, be a solvent or dispersion medium containing, for example, water, saccharides, ethanol, polyol (for example, glycerol, propylene glycol, and liquid polyethylene glycol, and the like), and suitable mixtures thereof. One skilled in the art recognizes that specific formulations can be developed to best suit the application and method of use of the molecular architectures of the disclosure. General considerations in the formulation and manufacture of pharmaceutical compositions, routes of administrating and including suitable pharmaceutically acceptable carriers may be found, for example, in *Remington's Pharmaceutical Sciences,* 19th ed., Mack Publishing Co., Easton, Pa., 1995. In some embodiments, the pharmaceutical composition may include zinc, e.g., $Zn^{2+}$ along with insulin if the compound (e.g. a compound of Formula I or Formula IB) comprises insulin. Such zinc formulations are, for example, described in U.S. Pat. No. 9,034,818. For example, the pharmaceutical composition may comprise zinc at a molar ratio to the modified insulin of about M:N where M is 1-11 and N is 6-1. In some embodiments, such modified insulins may be stored in a pump, and that pump being either external or internal to the body releases the modified insulins. In some embodiments, a pump may be used to release a constant amount of modified insulin wherein the insulin is glucose responsive and can automatically adjust activity based on the levels of glucose in the blood and/or the release rate from the injection site. In some embodiments, the compositions may be formulated in dosage unit form for ease of administration and uniformity of dosage. In some embodiments, the pharmaceutical composition may further include a second insulin type to provide fast-acting or basal-insulin in addition to the effect afforded by the molecular architecture. In some embodiments, a compound of the present disclosure (e.g., a compound of Formula I or Formula IB) is injected separately from insulin but modulates the activity of insulin by binding to insulin, and in some embodiments this activity change is dependent on glucose.

In some embodiments, the pharmaceutical composition comprises one or more of the compounds disclosed herein and at least one additional component selected from pharmaceutically acceptable carriers, pharmaceutically acceptable vehicles, and pharmaceutically acceptable excipients. In some embodiments, the pharmaceutical composition comprises a compound of Formula I or Formula IB and at least one additional component selected from pharmaceutically acceptable carriers, pharmaceutically acceptable vehicles, and pharmaceutically acceptable excipients.

In some embodiments, the present disclosure includes compounds that can be part of a kit, wherein the kit includes a compound of Formula I or Formula IB comprising modified insulin, as well as a pharmaceutically acceptable carrier, and for injections may include a syringe or pen. In some embodiments, a kit may include a syringe or pen that is pre-filled with a pharmaceutical composition that includes the compound of Formula I or Formula IB with a liquid carrier. Alternatively, a kit may include a separate container such as a vial with a pharmaceutical composition that includes the compound of Formula I or Formula IB with a dry carrier and an empty syringe or pen. In some embodiments, such a kit may include a separate container that has a liquid carrier, which can be used to reconstitute a given composition that can then be taken up into the syringe or pen. In some embodiments, a kit may include instructions. In some embodiments, the kit may include blood glucose measuring devices that either locally or remotely calculate an appropriate dose of the modified insulin that is to be injected at a given point in time, or at regular intervals. Such a dosing regimen is unique to the patient and may, for example, be provided as instruction to program a pump either by a person or by a computer. The kit may include an electronic device which transfers blood glucose measurements to a second computer, either locally or elsewhere (for example, in the cloud) which then calculate the correct amount of compound of Formula I or Formula IB comprising, e.g., a modified insulin that needs to be used by the patient at a certain time.

In some embodiments, the disclosure relates to a method for treating a disease or condition in a subject, comprising administering to the subject a composition including a compound described herein. In some embodiments, the disease or condition may be hyperglycemia, type 2 diabetes, impaired glucose tolerance, type 1 diabetes, obesity, metabolic syndrome X, or dyslipidemia, diabetes during pregnancy, pre-diabetes, Alzheimer's disease, MODY 1, MODY 2 or MODY 3 diabetes, mood disorders and psychiatric disorders. It will be appreciated that this combination approach may also be used with insulin resistant patients who are receiving an insulin sensitizer or a secondary drug for diabetes (such as, for example, a biguanide such as metformin, a glitazone) or/and an insulin secretagogue (such as, for example, a sulfonylurea, GLP-1, exendin-4 etc.) or amylin.

In some embodiments, a compound of the present disclosure (e.g. a compound of Formula I or Formula IB) may be administered to a patient who is receiving at least one additional therapy or taking at least one additional drug or therapeutic protein. In some embodiments, the at least one additional therapy is intended to treat the same disease or disorder as the administered compound (e.g. a compound of Formula I or Formula IB). In some embodiments, the at least one additional therapy is intended to treat a side-effect of the compound (e.g. a compound of Formula I or Formula IB) or as an adjuvant. The timeframe of the two therapies may differ or be the same; they may be administered on the same or different schedules as long as there is a period when the patient is receiving a benefit from both therapies. The two or more therapies may be administered within the same or different formulations as long as there is a period when the patient is receiving a benefit from both therapies. Any of these approaches may be used to administer more than one anti-diabetic drug to a subject.

In some embodiments a therapeutically effective amount of the compound (e.g. a compound of Formula I or Formula IB) which is sufficient amount to treat (meaning for example to ameliorate the symptoms of, delay progression of, prevent recurrence of, or delay onset of) the disease or condition at a reasonable benefit to risk ratio will be used. In some embodiments, this may involve balancing of the efficacy and additional safety to toxicity. By additional safety, it is meant that, for example, the compound (e.g. a compound of Formula I or Formula IB) can be responsive to changes in blood glucose levels or level of other molecules, even when the patient is not actively monitoring the levels of that molecule, such as blood glucose levels at a given timeframe, for example during sleep. In some embodiments, therapeutic efficacy and toxicity may be determined by standard pharmacological procedures in cell cultures or in vivo with experimental animals, and for example measuring $ED_{50}$ and $LD_{50}$ for therapeutic index of the drug. In some embodiments, the average daily dose of insulin with the molecular architecture is in the range of 5 to 400 U, (for example 30-150 U where 1 Unit of insulin is about 0.04 mg). In some embodiments, an amount of compound (e.g. a compound of Formula I or Formula IB) with these insulin doses is administered on a daily basis or bi-daily basis or by every three days or by every 4 days.

In some embodiments, the basis is determined by an algorithm, which can be computed by a computer. In some embodiments, an amount of compound, such as a compound of Formula I or Formula IB, with 5 to 10 times the doses is administered on a weekly basis or at regular intervals. In some embodiments, an amount of conjugate with 10 to 20 times these doses is administered on a bi-weekly basis or at regular intervals. In some embodiments, an amount of compound (e.g. a compound of Formula I or Formula IB) with 20 to 40 times these doses is administered on a monthly basis or at regular intervals. In some embodiments, the C-terminus of the A-chain of insulin may be further extended with a peptide (amino acid sequence) including 1-20 amino acid residues. In some embodiments, the insulin analogue is a desB30 insulin.

In some embodiments, Z1a is an amino acid or a peptide. In at least some embodiments, the Z1a includes (is composed of) 1-50 amino acid residues, for example, 1 residue, 50 residues, or any intermediate number of residues (such as e.g., 10, 15, 25, 30, 42 residues, etc.). In some embodiments, the Z1a includes 1-15 amino acids. In at least some embodiments, the peptide Z1a includes 1-8 amino acids. In some embodiments, Z1a includes 5 to 6 amino acids. In some embodiments, Z1a comprises at least one amino acid independently selected from the: Alanine (A), Asparagine (N), Glutamine (Q), Threonine (T), Methionine (M), Histidine (H), Cysteine (C), Valine (V), Isoleucine (I), Lysine (K), and Leucine (L), and the rest of the amino acids each independent selected from any of the twenty naturally occurring amino acids. In some embodiments, Z1a may include diaminopropionic acid, diaminobutyric acid, or ornithine. In some embodiments, Z1a includes 1 to 5 lysines (K). In some embodiments, Z1a includes 1 to 3 K amino acids. In some embodiments Z1a includes 5 to 6 amino acids and at least one or more amino acids are K. In some embodiments, Z1a includes 5 to 6 amino acids and 1 to 3 amino acids are K. In some embodiments, Z1a is selected from any of KA, KD, KE, KF, KG, KH, KI, KL, KN, KP, KQ, KR, KS, KT, KY, KAA, KAD, KAE, KAF, KAG, KAH, KAI, KAL, KAN, KAQ, KAR, KAS, KAT, KAY, KDA, KDD, KDE, KDF, KDG, KDH, KDI, KDL, KDN, KDQ, KDR, KDS, KDT, KDY, KEA, KED, KEE, KEF, KEG, KEH, KEI, KEL, KEN, KEQ, KER, KES, KET, KEY, KFA, KFD, KFE, KFF, KFG, KFH, KFI, KFL, KFN, KFQ, KFR, KFS, KFT, KFY, KGA, KGD, KGE, KGF, KGG, KGH, KGI, KGL, KGN, KGQ, KGR, KGS, KGT, KGY, KHA, KHD, KHE, KHF, KHG, KHH, KHI, KHL, KHN, KHQ, KHR, KHS, KHT, KHY, KIA, KID, KIE, KIF, KIG, KIH, KII, KIL, KIN, KIQ, KIR, KIS, KIT, KIY, KLA, KLD, KLE, KLF, KLG, KLH, KLI, KLL, KLN, KLQ, KLR, KLS, KLT, KLY, KNA, KND, KNE, KNF, KNG, KNH, KNI, KNL, KNN, KNQ, KNR, KNS, KNT, KNY, KPA, KPD, KPE, KPF, KPG, KPH, KPI, KPL, KPN, KPQ, KPR, KPS, KPT, KPY, KQA, KQD, KQE, KQF, KQG, KQH, KQI, KQL, KQN, KQQ, KQR, KQS, KQT, KQY, KRA, KRD, KRE, KRF, KRG, KRH, KRI, KRL, KRN, KRQ, KRR, KRS, KRT, KRY, KSA, KSD, KSE, KSF, KSG, KSH, KSI, KSL, KSN, KSQ, KSR, KSS, KST, KSY, KTA, KTD, KTE, KTF, KTG, KTH, KTI, KTL, KTN, KTQ, KTR, KTS, KTT, KTY, KYA, KYD, KYE, KYF, KYG, KYH, KYI, KYL, KYN, KYQ, KYR, KYS, KYT, KYY, SEQ ID NOs 75-24014, 24037-24046. In some embodiments, Z1a is selected from KSNAPQK (SEQ ID NO:24037), KNASPQK (SEQ ID NO:24038), KLWAVK (SEQ ID NO:24039), KGARLK (SEQ ID NO:24040), ADKKTLN (SEQ ID NO:24041), KGSHK (SEQ ID NO:4238), KNSTK (SEQ ID NO:5085), GKNSTK (SEQ ID NO:13989), GKGSHK (SEQ ID NO:13198), GSHKGSHK (SEQ ID NO:24042), GKPSHKP (SEQ ID NO:24043), GKGPSK (SEQ ID NO:24044), GKGSKK (SEQ ID NO:24045), and GKKPGKK (SEQ ID NO:24046).

In some embodiments Z1a is appended to the N-terminus and/or C-terminus, and/or inserted into the sequence of the A-chain or B-chain of insulin.

Compounds

In some embodiments, the present disclosure provides a compound comprising at least two aromatic boron containing groups or a tautomer, stereoisomer or a mixture of stereoisomers, or a pharmaceutically acceptable salt, or hydrate, or isotopic derivative of the compound, wherein at least one aromatic boron-containing group is covalently attached to the compound and selected from F3-F111, and the other aromatic boron-containing group is covalently attached to the compound and optionally selected from F1-F11 or a boronic acid, (F1)

(F2)

-continued (F3)

(F4)

(F5)

(F6)

(F7)

(F8)

(F9)

-continued (F10)

(F11)

wherein at least one R1 in each of F1-F11 is covalently attached to the compound, and each remaining $R_1$ and $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_m$ $CH_3$, and $OCF_3$, wherein m is 1, 2, 3, 4, 5, 6, or 7, wherein, for Formulae F3-F4:

$R_w$ is O or S;

for Formulae F5-F10:

when Y8 is O, i is 2, 3, 4, or 5; or when Y8 is NR, R is an alkyl group or H, and i is 1, 2, 3, 4, or 5;

Y9 is H, $CH_3$, or an alkyl group, provided that when Y8 is O, Y9 is a $CH_3$ or an alkyl group; and each Y10 is independently selected from H, $CH_3$, F, $CF_3$, and $OCH_3$, with the proviso that at least one Y10 is not H.

In some embodiments, the present disclosure provides a compound comprising at least one diboronate, wherein the diboronate comprises at least two aromatic boron containing groups, wherein at least one aromatic boron-containing group is covalently attached to the compound and selected from F3-F11, and the other aromatic boron-containing group is covalently attached to the compound and optionally selected from F1-F11 or a boronic acid, (F1)

(F2)

-continued (F3)

(F4)

(F5)

(F6)

(F7)

(F8)

(F9)

-continued (F10)

(F11)

wherein at least one $R_1$ in each of F1-F11 is covalently attached to the compound, and each remaining $R_1$ and $R_2$ is independently selected from H, F, Cl, Br, OH, $CH_2$—$NH_2$, $NH_2$, (C$=$O)—$NH_2$, CH$=$O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_m$ $CH_3$, and $OCF_3$, wherein m is 1, 2, 3, 4, 5, 6, or 7, wherein, for Formulae F3-F4:

$R_w$ is O or S;

for Formula F6:

when Y8 is O, i is 1, 2, 3, 4, or 5; or i is 2, 3, 4, or 5; and none, one, or two $R_1$ represents F, Cl, $CF_2$, $CF_3$, $SF_5$, $OCF_3$, $SO_2CH_3$ and/or $SO_2CF_3$; or when Y8 is NR, R is an alkyl group or H, and i is 1, 2, 3, 4, or 5;

for Formulae F5 and F7-F10:

when Y8 is O, i is 1, 2, 3, 4, or 5; or when Y8 is NR; R is an alkyl group or H, and i is 1, 2, 3, 4, or 5;

Y9 is $CH_3$, F, $CF_3$, $CHF_2$, or $OCH_3$; and each Y10 is independently selected from H, $CH_3$, F, $CF_3$, $CHF_2$, and $OCH_3$, with the proviso that at least one Y10 is not H.

In some embodiments, the compound comprises at least two aromatic boron containing groups or a tautomer, stereoisomer or a mixture of stereoisomers, or a pharmaceutically acceptable salt, or hydrate, or isotopic derivative thereof.

In some embodiments, the compound is a diboron containing compound (e.g., has at least two aromatic boron containing groups as covalent conjugates). In some embodiments, at least one aromatic boron-containing group is F7. In some embodiments, at least one aromatic boron-containing group is F7, and when Y8 is O, each Y10 is $CH_3$. In some embodiments, the compound comprising at least two aromatic boron containing groups comprises X1 and one or more Z1c, or a tautomer, stereoisomer or a mixture of stereoisomers, or a pharmaceutically acceptable salt, or hydrate, or isotopic derivative thereof.

In some embodiments, the present disclosure provides a compound comprising X1 and one or more Z1c, or a tautomer, stereoisomer or a mixture of stereoisomers, or a pharmaceutically acceptable salt, or hydrate, or isotopic derivative thereof, wherein: X1 comprises:

(i) $NH_2$ or OH (for example, X1 is $NH_2$ or OH);

(ii) a drug substance comprising an amine;

201

202

(iii) a drug substance that is covalently conjugated to an amine containing linker; or (iv) an amine configured to be covalently conjugated to a drug substance;

wherein each Z1c is independently selected from Formulae FF1-FF231; and wherein each Z1c is covalently conjugated, directly or indirectly, to an amine in X1 or to OH when X1 is OH.

In some embodiments, Z1c is independently selected from Formulae FF1-FF48, Formulae FF49-FF88, FF89-FF112, FF113-FF136, FF137-FF160, FF161-FF164, FF165-FF166, FF167-FF192, FF193-FF209, and FF210-FF231, wherein each Z1c is independently selected from:

a) Formulae FF1-FF48, wherein Formulae FF1-FF48 are:

-continued (FF1)

(FF2)

(FF3)

(FF4)

(FF5)

(FF6)

(FF7)

(FF8)

(FF9)

(FF10)

(FF11)

(FF12)

(FF13)

203
-continued (FF14)

204
-continued (FF21)

(FF15)

(FF22)

(FF16)

(FF17)

(FF23)

(FF18)

(FF24)

(FF19)

(FF25)

(FF20)

(FF26)

(FF27)

205

-continued (FF28)

(FF29)

(FF30)

(FF31)

(FF32)

(FF33)

(FF34)

(FF35)

206

-continued (FF36)

(FF37)

(FF38)

(FF39)

(FF40)

(FF41)

(FF42)

(FF43)

207

-continued (FF44)

(FF45)

(FF46)

(FF47)

and (FF48)

;

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

j is 1, 2, 3, 4, 5, 6, or 7; and B1 and B2, which may be identical or different, each independently represents an aromatic boron-containing group;

b) Formulae FF49-FF88, wherein Formulae FF49-FF88 are:

(FF49)

(FF50)

208

-continued (FF51)

(FF52)

(FF53)

(FF54)

(FF55)

(FF56)

(FF57)

(FF58)

(FF59)

(FF60)

209

-continued (FF61)

(FF62)

(FF63)

(FF64)

(FF65)

(FF66)

(FF67)

(FF68)

210

-continued (FF69)

(FF70)

(FF71)

(FF72)

(FF73)

(FF74)

(FF75)

211
-continued

212
-continued (FF76)

(FF77)

(FF78)

(FF79)

(FF80)

(FF81)

(FF82)

(FF83)

(FF84)

(FF85)

(FF86)

(FF87)

and

-continued (FF88)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

j is 1, 2, 3, 4, 5, 6, or 7; R1a is selected from COOH, CH$_3$, H, and OH; R2, R3, R4 and R5 are each independently selected from CH$_3$, H, OH, and COOH, and at least one of R2, R3, R4 and R5 is CH$_3$ or OH; and B1 and B2, which may be identical or different, are each independently an aromatic boron-containing group.

c) Formulae FF89-FF112, wherein Formulae FF89-FF112 are:

(FF89)

(FF90)

-continued (FF91)

(FF92)

(FF93)

(FF94)

(FF95)

(FF96)

215

-continued (FF97)

(FF98)

(FF99)

(FF100)

(FF101)

(FF102)

216

-continued (FF103)

(FF104)

(FF105)

(FF106)

(FF107)

-continued (FF108)

(FF109)

(FF110)

(FF111)

and (FF112)

wherein X represents a point of covalent attachment either
directly to an amine in X1 or to an amine that is
covalently conjugated directly or indirectly to X1, or to
OH when X1 is OH;

i is 1, 2, 3, 4, 5, 6, or 7; and

B1, B2 and B3, which may be identical or different, are
each independently an aromatic boron-containing group, a carboxylic acid derivative, or a H, wherein in
each FF89-FF112 structure containing B1, B2 and B3
groups, at least two of the B1, B2 and B3 groups are
independently an aromatic boron-containing group;

d) Formulae FF113-FF136, wherein Formulae FF113-
FF136 are:

(FF113)

(FF114)

(FF115)

(FF116)

(FF117)

(FF118)

219

-continued (FF119)

(FF120)

(FF121)

(FF122)

(FF123)

(FF124)

(FF125)

220

-continued (FF126)

(FF127)

(FF128)

(FF129)

(FF130)

(FF131)

221
222

-continued (FF132)

(FF133)

(FF134)

(FF135)

and (FF136)

(FF137)

(FF138)

(FF139)

(FF140)

(FF141)

(FF142)

(FF143)

wherein X represents a point of covalent attachment either directly to an amine in X1 or to an amine that is covalently conjugated directly or indirectly to X1, or to OH when X1 is OH;

i is 0, 1, 2, 3, 4, 5, 6, or 7;

j is 0, 1, 2, 3, 4, 5, 6, or 7;

k is 0, 1, 2, 3, 4, 5, 6, or 7;

m is 0, 1, 2, 3, 4, 5, 6, or 7;

wherein i+j+k+m is greater than 0;

each R1 is independently selected from H, an alkyl group, an acyl group, a cycloalkyl group, a haloalkyl group, an aryl group, and a heteroaryl group, each R1 optionally comprises one or more alkyl-halide, halide, sulfhydryl, aldehyde, amine, acid, hydroxyl, alkyl or aryl groups; and B1 and B2, which may be identical or different, each independently represents an aromatic boron-containing group;

e) Formulae FF137-FF160, wherein Formulae FF137-FF160 are:

223

-continued (FF144)

(FF145)

(FF146)

(FF147)

(FF148)

(FF149)

(FF150)

224

-continued (FF151)

(FF152)

(FF153)

(FF154)

(FF155)

(FF156)

-continued (FF157)

(FF158)

(FF159)

and (FF160)

wherein X represents a point of covalent attachment either
directly to an amine in X1 or to an amine that is
covalently conjugated directly or indirectly to X1, or to
OH when X1 is OH;
i is 0, 1, 2, 3, 4, 5, 6, or 7;
j is 0, 1, 2, 3, 4, 5, 6, or 7;
k is 0, 1, 2, 3, 4, 5, 6, or 7;
m is 0, 1, 2, 3, 4, 5, 6, or 7;
wherein i+j+k+m is greater than 0;
each R1 is independently selected from H, an alkyl group,
an acyl group, a cycloalkyl group, a haloalkyl group, an
aryl group, and a heteroaryl group, each R1 optionally
comprises one or more alkyl-halide, halide, sulfhydryl,
aldehyde, amine, acid, hydroxyl, alkyl or aryl groups;
and
B1 and B2, which may be identical or different, each
independently represents an aromatic boron-containing
group. In one embodiment, B1 and B2 may be identical
or different;
f) Formulae FF161-FF164, wherein Formulae FF161-
FF164 are:

(FF161)

-continued (FF162)

(FF163)

(FF164)

wherein X represents a point of covalent attachment either
directly to an amine in X1 or to an amine that is
covalently conjugated directly or indirectly to X1, or to
OH when X1 is OH;
i is 1, 2, 3, 4, or 5 (e.g., 1, 2, 3, or 5);
j is 1, 2, 3, 4, or 5 (e.g., 1, 2, 3, or 5);
each R6, R7, R8, and R9 for different values of j is
independently selected from H, $CF_3$, $CH_3$, $CHF_2$, and
$(CH_2)_m CH_3$, wherein m is 1, 2, 3, 4, or 5;
Y3, Y4, Y5, Y6 and Y7 are each independently selected
from H, $CH_2$—X4, and Formulae IV-1 to IV-135;
wherein X4 is selected from —COOH, —$(CH_2)_m$COOH,
an alkyl group, an acyl group, a cycloalkyl group, a
haloalkyl group, an aryl group, and a heteroaryl group,
each X4 optionally comprises one or more alkyl-halide,
halide, sulfhydryl, aldehyde, amine, acid, hydroxyl,
alkyl or aryl groups; wherein m is 1, 2, 3, 4, or 5;
wherein at least one of Y5, Y6 and Y7 in Formulae FF162
and FF163 is not H and at least one of Y7, R8 and R9
in FF164 is not H; and
wherein Formulae IV-1 to IV-135 are:

(IV-1)

(IV-2)

227

-continued (IV-3)

(IV-4)

(IV-5)

(IV-6)

(IV-7)

(IV-8)

(IV-9)

(IV-10)

(IV-11)

(IV-12)

(IV-13)

228

-continued (IV-14)

(IV-15)

(IV-16)

(IV-17)

(IV-18)

(IV-19)

(IV-20)

(IV-21)

(IV-22)

(IV-23)

(IV-24)

229
-continued (IV-25)

(IV-26)

(IV-27)

(IV-28)

(IV-29)

(IV-30)

(IV-31)

(IV-32)

(IV-33)

(IV-34)

(IV-35)

(IV-36)

(IV-37)

230
-continued (IV-38)

(IV-39)

(IV-40)

(IV-41)

(IV-42)

(IV-43)

(IV-44)

(IV-45)

(IV-46)

(IV-47)

(IV-48)

231
-continued

232
-continued (IV-49)

(IV-50)

(IV-51)

(IV-52)

(IV-53)

(IV-54)

(IV-55)

(IV-56)

(IV-57)

(IV-58)

(IV-59)

(IV-60)

(IV-61)

(IV-62)

(IV-63)

233
-continued

234
-continued (IV-64)

(IV-65)

(IV-66)

(IV-67)

(IV-68)

(IV-69)

(IV-70)

(IV-71)

(IV-72)

(IV-73)

(IV-74)

(IV-75)

(IV-76)

235

-continued (IV-77)

(IV-78)

(IV-79)

(IV-80)

(IV-81)

(IV-82)

(IV-83)

(IV-84)

(IV-85)

236

-continued (IV-86)

(IV-87)

(IV-88)

(IV-89)

(IV-90)

(IV-91)

(IV-92)

(IV-93)

(IV-94)

237

-continued (IV-95)

(IV-96)

(IV-97)

(IV-98)

(IV-99)

(IV-100)

(IV-101)

(IV-102)

(IV-103)

238

-continued (IV-104)\

(IV-105)

(IV-106)

(IV-107)

(IV-108)

(IV-109)

239

-continued (IV-110)

(IV-111)

(IV-112)

20

(IV-113)

(IV-114)

(IV-115)

(IV-116)

(IV-117)

(IV-118)

(IV-119)

240

-continued (IV-120)

(IV-121)

(IV-122)

(IV-123)

(IV-124)

(IV-125)

(IV-126)

(IV-127)

-continued (IV-128)

(IV-129)

(IV-130)

(IV-131)

(IV-132)

(IV-133)\

(IV-134)

(IV-135)

wherein Xa represents CH=O, $CHF_2$, $CF_3$, $CH_2SH$, COOH, $CH_2OH$, $CH_2NO_2$, $CH_2NH_2$, $CH_3$, $C(CH_3)_3$, $CH(CH_3)_2$, $CH((CH_2)_3\ CH_3)_2$, or $CH(CH_2\ CH_3)_2$;

Xb represents O, NH, $CH_2$, or S;

Xc represents CH or N;

each $R_{10}$ is independently selected from H, F, Cl, Br, $CH_3$, $CF_3$, CH=O, OH, COOH, and $(CH_2)_nCH_3$, m is 1, 2, 3, 4, or 5; and n is 1, 2, 3, 4, or 5;

B1 and B2, which may be identical or different, each independently represents an aromatic boron-containing group; and \* in Formulae IV-1 to IV-135 represents the point of attachment to corresponding Formulae FF161-164;

g) Formulae FF165-FF166, wherein Formulae FF165-FF166 are:

(FF165)

and (FF166)

wherein X represents a point of covalent attachment either directly to an amine in X1 or to an amine that is covalently conjugated directly or indirectly to X1, or to OH when X1 is OH;

m is 1, 2, 3, 4, 5, 6, or 7;

n is 1, 2, 3, 4, 5, 6, or 7;

X5 is S, O, or NH; and each $R_1$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —($SO_2$)NH $CH_3$, —($SO_2$)NH$(CH_2)_mCH_3$, and $OCF_3$, wherein m is 1, 2, 3, 4, 5, 6, or 7;

h) Formulae FF167-FF192, wherein Formulae FF167-FF192 are:

243                           244

(FF167)

(FF168)

(FF169)

(FF170)

(FF171)

(FF172)

(FF173)

(FF174)

(FF175)

(FF176)

(FF177)

(FF178)

(FF179)

(FF180)

(FF181)

245
-continued

246
-continued (FF182)

(FF183)

(FF184)

(FF185)

(FF186)

(FF187)

(FF188)

(FF189)

(FF190)

(FF191)

and

-continued (FF192)

wherein X represents a point of covalent attachment either directly to an amine in X1 or to an amine that is covalently conjugated directly or indirectly to X1, or to OH when X1 is OH; and $B_1$ and $B_2$, which may be identical or different, each independently represents an aromatic boron-containing group;

i) Formulae FF193-FF209, wherein Formulae FF193-FF209 are:

FF193

FF194

FF195

FF196

FF197

-continued

FF198

FF199

FF200

FF201

FF202

FF203

FF204

FF205

249
-continued

250
-continued

FF206

FF212

FF207

FF213

FF208

FF214

FF209

FF215 wherein R in FF208 and FF209 is an alkyl, aryl or halide that is covalently conjugated through at least one $CH_2$ group to the amino group in the side chain of FF208 or FF209,

FF216

R1 and R2 are independently selected from H, CH3, alkyl, and formulae IV-1 to IV-135;

i is 1, 2, 3, 4, or 5;

j is 1, 2, 3, 4, or 5; and

FF217 wherein X represents a point of covalent attachment either directly to an amine in X1 or to an amine that is covalently conjugated directly or indirectly to X1, or to OH when X1 is OH; and $B_1$ and $B_2$, which may be identical or different, each independently represents an aromatic boron-containing group;

45 j) Formulae FF210-FF224, wherein Formulae FF210-FF224 are:

FF218

FF210

FF219

FF211

FF220

251
-continued

FF221

FF222

FF223

FF224 wherein R11 in FF210 to FF212 is selected from Formulae IV-1 to IV-135 and R12 is selected from an amine, a hydroxyl, an alkyl, and a halide group;

wherein each R13 is independently selected from H, CH₃, alkyl, aryl and Formulae IV-1 to IV-135; R14 is selected from H, CH₃, alkyl, aryl and heteroaryl;

wherein X represents a point of covalent attachment either directly to an amine in X1 or to an amine that is covalently conjugated directly or indirectly to X1, or to OH when X1 is OH;

X" represents a point of covalent attachment to an amine —N in the compound, wherein — represents a single covalent bond to a CH₂ or CH group in the compound;

i is 1, 2, 3, 4, or 5;

j is 1, 2, 3, 4, or 5; and

B₁, B₂, B₃, B₄, B₅, and B₆ each independently represents an aromatic boron-containing group, wherein in each FF structure containing B₁, B₂ and B₃ groups, at least two of the B1, B2 and B3 groups are independently an aromatic boron-containing group; and k) Formulae FF225-FF231, wherein Formulae FF225-FF231 are:

(FF225)

252
-continued (FF226)

(FF227)

(FF228)

(FF229)

(FF230)

(FF231)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

$B_1$ and $B_2$, which may be identical or different, each independently represents an aromatic boron-containing group; and wherein at least one primary or secondary amine in FF1-FF223 and FF225-231 is optionally covalently conjugated to $B_6$.

In some embodiments, $B_1$, $B_2$, $B_3$, $B_4$, $B_5$, and $B_6$ each independently represents the aromatic boron-containing groups, wherein in each FF structure containing $B_1$, $B_2$ and $B_3$ groups, at least two of the $B_1$, $B_2$ and $B_3$ groups are independently the aromatic boron-containing groups.

In some embodiments, at least one Z1c is (FF227)

In some embodiments, at least one Z1c is FF227 and i is 1.

In some embodiments, at least one Z1c is selected from FF12-FF35, FF104-FF117, FF180-FF193, and FF196-FF205. In some embodiments, Z1c is selected from FF12, FF116, FF193, and FF203.

In some embodiments, $B_1$ and $B_2$ in Formulae FF225-FF231 are not a boronic acid or an F2 or F6 aromatic boron-containing group, wherein Formulae F2 and F6 are:

(F2)

and (F6)

$R_1$ at position 5' represents (C=O)—*, wherein —* represents the attachment point to the rest of Z1c;

zero, one, or two $R_1$ represent F, Cl, $CF_2$, $CF_3$, $SF^5$, $OCF_3$, $SO_2CH_3$, and/or $SO_2CF_3$, and each remaining $R_1$ represents H;

Y8 is O; and i is 1.

In some embodiments, the aromatic boron-containing group is not an aromatic boron-containing group as disclosed in patent application PCT/US2020/058641 (filed Mar. 27, 2020) as Formula R1a, Formula R1b, Formula R1c, Formula R2a, Formula R2b, and Formula R2c; the disclosure of which is herein expressly incorporated by reference in its entirety.

In some embodiments, the present disclosure provides a compound of Formula (I) or a molecular conjugate represented by Formula I, or a stereoisomer or a mixture of stereoisomers, or pharmaceutically acceptable salt thereof:

(Formula I)

$$[[[Z1c]_{\overline{p'}}Z1a_{\overline{m'}}]_{o'}Z1b_{\overline{n'}}]_{q'}X1,$$

wherein X1 comprises:
  (i) $NH_2$ or OH (for example, X1 is $NH_2$ or OH),
  (ii) a polypeptide drug substance comprising an amine,
  (iii) a polypeptide drug substance that is covalently conjugated to an amine containing linker, or
  (iv) an amine configured to be covalently conjugated to a polypeptide drug substance;
each Z1c is independently selected from Formulae FF1-FF231; each Z1a independently comprises 1 to 50 amino acids connected together using amide or peptide bonds; each Z1b is independently a small-molecule linker; each m' is independently 0 or 1; each n' is independently 0 or a positive integer; each o' is independently an integer of 1 or greater; each p' is a positive integer; and q' is a positive integer of at least 1 and not more than two times the total number of amine groups in X1, wherein when any of n', o', p', or q' is 2 or more, the corresponding groups Z1a, Z1b, and Z1c are independently selected and may be the same or different; wherein each Z1c is independently covalently conjugated, directly or indirectly, to an amine of Z1a, to an amine of Z1b, or to X1; and wherein optionally the molecular conjugate may comprise one or more isotopes at any position of the molecular conjugate of Formula I.

In at least some embodiments, X1 comprises one of:
  (i) $NH_2$ or OH (for example, X1 is $NH_2$ or OH),
  (ii) a polypeptide drug substance comprising an amine,
  (iii) a polypeptide drug substance that is covalently conjugated to an amine containing linker, or
  (iv) an amine configured to be covalently conjugated to a polypeptide drug substance.

In some embodiments, the compound is a molecular conjugate represented by Formula I, or a stereoisomer or a mixture of stereoisomers, or pharmaceutically acceptable salts:

(Formula I)

$$[[[Z1c]_{\overline{p'}}Z1a_{\overline{m'}}]_{o'}Z1b_{\overline{n'}}]_{q'}X1,$$

wherein:
X1 is $NH_2$ or OH; or
X1 comprises:
  i. a polypeptide drug substance comprising an amine;
  ii. a polypeptide drug substance that is covalently conjugated to an amine containing linker; or
  iii. an amine configured to be covalently conjugated to a polypeptide drug substance;
each Z1c is independently selected from Formulae FF1-FF231;
each Z1a independently comprises 1 to 50 amino acids connected together using amide or peptide bonds; each Z1b is independently a small-molecule linker;
each m' is independently 0 or 1;
each n' is independently 0 or a positive integer;

each o' is independently an integer greater than or equal to 1;

each p' is a positive integer; and q' is a positive integer of at least 1 and not more than two times the total number of amine groups in X1, wherein when any of n', o', p', or q' is 2 or more, the corresponding groups Z1a, Z1b, and Z1c are independently selected and may be the same or different; wherein each Z1c is independently covalently conjugated, directly or indirectly, to an amine of Z1a, to an amine of Z1b, or to X1; and wherein optionally the molecular conjugate may comprise one or more isotopes at any position of the molecular conjugate of Formula I. In some embodiments, the compound is additionally covalently conjugated as described by Formula I, and/or wherein one or more amines are each independently acetylated and/or independently alkylated.

In some embodiments, the compound of Formula I is covalently conjugated to $B_1$ using a covalent linkage $X—B_1$, wherein X is an amino group in Formula I.

In some embodiments, X1 comprises a polypeptide drug substance and the covalent conjugation to X1 is to amino group(s) in one or more lysine residues and/or to the N-terminal amino groups in X1.

In some embodiments, the compound comprises at least one of $B_1$, $B_2$ and $B_3$ independently selected from Formulae F1-F11 or wherein the compound comprises at least one of $B_4$, $B_5$ and $B_6$ independently selected from Formulae F1-F11, wherein Formulae F1-F11 are:

(F1)

(F2)

(F3)

(F4)

-continued (F5)

(F6)

(F7)

(F8)

(F9)

(F10)

-continued (F11)

wherein for $B_1$, $B_2$, and $B_3$:

one $R_1$ represents (C=O)—*, S(=O)(=O)—*, $(CH_2)_m$ (C=O)—*, or $(CH_2)_m$—*, wherein —* represents an attachment point to the rest of Z1c or to the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$ $CH_3$, —$(SO_2)NH$ $(CH_2)_mCH_3$, and $OCF_3$, wherein m is 1, 2, 3, 4, 5, 6, or 7;

wherein for $B_4$ and $B_5$:

one $R_1$ for $B_4$ represents $(CH_2)_m$—ø, wherein —ø represents an attachment point to the rest of Z1c or to the compound and one $R_1$ for $B_5$ represents (C=O)—*, S(=O)(=O)—*, $(CH_2)_m(C=O)$—*, or $(CH_2)_m$—*, wherein —* represents an attachment point to the rest of Z1c or to the compound, and m is 1, 2, 3, 4, 5, 6, or 7; and each remaining $R_1$ or R2 is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$ $CH_3$, —$(SO_2)NH$ $(CH_2)_mCH_3$, and $OCF_3$, wherein m is 1, 2, 3, 4, 5, 6, or 7;

wherein for $B_6$:

one $R_1$ for $B_6$ represents $(CH_2)_m$—ø, wherein —ø represents an attachment point to the rest of the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$ $CH_3$, —$(SO_2)NH$ $(CH_2)_mCH_3$, and $OCF_3$, wherein m is 1, 2, 3, 4, 5, 6, or 7;

wherein, for Formulae F3-F4:

$R_w$ is O or S;

for Formulae F5-F10:

when Y8 is O, i is 1, 2, 3, 4, or 5; or when Y8 is NR, R is an alkyl group or H; and i is 1, 2, 3, 4, or 5;

Y9 is H, $CH_3$, or an alkyl group, provided that when Y8 is O, Y9 is a $CH_3$ or an alkyl group; and each Y10 is independently selected from H, $CH_3$, F, $CF_3$, and $OCH_3$, with the proviso that at least one Y10 is not H.

In some embodiments, for Formulae F5-F10:

when Y8 is O, i is 2, 3, 4, or 5; or when Y8 is NR, R is an alkyl group or H; and i is 1, 2, 3, 4, or 5;

Y9 is H, $CH_3$, or an alkyl group, provided that when Y8 is O, Y9 is a $CH_3$ or an alkyl group; and each Y10 is independently selected from H, $CH_3$, F, $CF_3$, and $OCH_3$, with the proviso that at least one Y10 is not H.

In at least some embodiments, $B_1$, $B_2$ and $B_3$ may be identical or different. If $B_1$, $B_2$ and $B_3$ are all present in a compound of the present disclosure, then each is independently an aromatic boron-containing group, a carboxylic acid derivative, or a H, wherein in each FF structure (i.e., FF1 to FF231) containing $B_1$, $B_2$ and $B_3$ groups, at least two of the B1, B2 and B3 are independently an aromatic boron-containing group.

In some embodiments, the compound comprises at least one group selected from $B_1$, $B_2$, $B_3$ $B_4$, $B_5$ and $B_6$, each independently selected from Formulae F2, F7, F8, and F11, wherein Formulae F2, F7, F8, and F11 are:

(F2)

(F7)

(F8)

(F11)

wherein for $B_1$, $B_2$, and $B_3$:

one $R_1$ represents (C=O)—* or $(CH_2)_m(C=O)$—*, wherein —* represents the attachment point to the rest of Z1c or to the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$— $CH_3$, —$(SO_2)NH(CH_2)_mCH_3$, and $OCF_3$, wherein m is 1, 2, 3, 4, 5, 6, or 7;

wherein for $B_4$ and $B_5$:

one $R_1$ for $B_4$ represents $(CH_2)_m$—ø, wherein —ø represents an attachment point to the rest of Z1c or to the compound and one R1 for $B_5$ represents (C=O)—*, S(=O)(=O)—*, $(CH_2)_m$(C=O)—*, or $(CH_2)_m$—*, wherein —* represents an attachment point to the rest of Z1c or to the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, $(SO_2)NH$ $(CH_2)_mCH_3$, and $OCF_3$, wherein m is 1, 2, 3, 4, 5, 6, or 7;

wherein for $B_6$:

one $R_1$ for $B_6$ represents $(CH_2)_m$—ø, wherein —ø represents an attachment point to the rest of the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7; and wherein for Formula F7:

Y8 is O or NR, wherein R is an alkyl group or H; and each Y10 is independently selected from $CH_3$, F, $CF_3$, and $OCH_3$;

wherein for Formula F8:

when Y8 is O, i is 1, 2, 3, 4, or 5; and when Y8 is NR, R is an alkyl group or H, and i is 1, 2, 3, 4, or 5;

each Y10 is independently selected from H, $CH_3$, F, $CF_3$, and $OCH_3$, with the proviso that at least one Y10 is not H; and — represents an attachment point to the rest of Z1c or to the compound.

In some embodiments, the compound comprises at least one group selected from $B_1$, $B_2$, $B_3$, $B_4$, $B_5$ and $B_6$, each independently selected from:

(F2)

(F7)

-continued (F8)

(F11)

wherein for $B_1$, $B_2$, and $B_3$:

one $R_1$ represents (C=O)—*, wherein —* represents the attachment point to the rest of Z1c or to the compound; and each remaining $R_1$ or R2 is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_m$, $CH_3$, —$(SO_2)NH$—$CH_3$, —$(SO_2)$ $NH(CH_2)_mCH_3$, and $OCF_3$, wherein m is 1, 2, 3, 4, 5, 6, or 7;

wherein for $B_4$ and $B_5$:

one $R_1$ for $B_4$ represents $(CH_2)_m$—ø, wherein —ø represents an attachment point to the rest of Z1c or to the compound and one $R_1$ for $B_5$ represents (C=O)—*, S(=O)(=O)—*, $(CH_2)_m$(C=O)—*, or $(CH_2)_m$—*, wherein —* represents an attachment point to the rest of Z1c or to the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7;

wherein for $B_6$:

one $R_1$ for $B_6$ represents $(CH_2)_m$—ø, wherein —ø represents an attachment point to the rest of the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7;

wherein for Formula F7:

Y8 is O; and each Y10 is independently selected from $CH_3$, F, and $CF_3$;

wherein for Formula F8:

Y8 is O;

i is 1, 2, 3, 4, or 5; and each Y10 is independently selected from H, $CH_3$, F, and $CF_3$, with the proviso that at least one Y10 is not H; and — represents an attachment point to the rest of Z1c or to the compound.

In some embodiments, the compound comprises at least one group selected from $B_1$, $B_2$, $B_3$, $B_4$, $B_5$ and $B_6$, each independently selected from:

(F7A)

(F8A)

and, (F11)

wherein for $B_1$, $B_2$, and $B_3$:

$R_1$ at position 5' represents (C=O)—*, wherein —* represents the attachment point to the rest of Z1c or to the compound; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_mCH_3$, and $OCF_3$, wherein m is 1, 2, 3, 4, 5, 6, or 7;

wherein for $B_4$ and $B_5$:

one $R_1$ for $B_4$ represents $(CH_2)_m$—ø, wherein —ø represents an attachment point to the rest of Z1c or to the compound and one $R_1$ for $B_5$ represents (C=O)—*, S(=O)(=O)—*, $(CH_2)_m(C=O)$—*, or $(CH_2)_m$—*, wherein —* represents an attachment point to the rest of Z1c or to the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_mCH_3$, and $OCF_3$, wherein m is 1, 2, 3, 4, 5, 6, or 7;

wherein for $B_6$: one $R_1$ for $B_6$ represents $(CH_2)_m$—ø, wherein —ø represents an attachment point to the rest of the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_mCH_3$, and $OCF_3$, wherein m is 1, 2, 3, 4, 5, 6, or 7;

wherein for Formulae F7A and F8A:

Y8 is O; and i is 1, 2, 3, 4, or 5; and

— represents an attachment point to the rest of Z1c or to the compound.

In some embodiments, for Formulae F7A and F8A:

Y8 is O; and i is 2, 3, 4, or 5.

In some embodiments, the compound comprises at least one group selected from $B_1$, $B_2$ $B_3$, $B_4$, $B_5$ and $B_6$, wherein each $B_1$, $B_2$ $B_3$, $B_4$, $B_5$ and $B_6$ is Formula F7A, (F7A)

wherein for $B_1$, $B_2$, and $B_3$:

$R_1$ at position 5' represents (C=O)—*, wherein —* represents the attachment point to the rest of Z1c or to the compound; and each remaining $R_1$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_mCH_3$, and $OCF_3$, wherein m is 1, 2, 3, 4, 5, 6, or 7;

wherein for $B_4$ and $B_5$:

one $R_1$ for $B_4$ represents $(CH_2)_m$—ø, wherein —ø represents an attachment point to the rest of Z1c or to the compound and one $R_1$ for $B_5$ represents (C=O)—*, S(=O)(=O)—*, $(CH_2)_m(C=O)$—*, or $(CH_2)_m$—*, wherein —* represents an attachment point to the rest of Z1c or to the compound, and m is 1, 2, 3, 4, 5, 6, or 7; and each remaining $R_1$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_mCH_3$, and $OCF_3$, wherein m is 1, 2, 3, 4, 5, 6, or 7;

wherein for $B_6$:

one $R_1$ for $B_6$ represents $(CH_2)_m$—ø, wherein —ø represents an attachment point to the rest of the compound, and m is 1, 2, 3, 4, 5, 6, or 7; and each remaining $R_1$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_mCH_3$, and $OCF_3$, wherein m is 1, 2, 3, 4, 5, 6, or 7;

Y8 is O; and

— represents an attachment point to the rest of Z1c or to the compound.

In some embodiments, at least one Z1c is covalently conjugated indirectly via a linker to an amine of X1 or to $NH_2$ when X1 is $NH_2$ or to OH when X1 is OH or to an amine of Z1a, wherein the linker is represented by Formula $(X'')_{n1}$, wherein each n1 is independently selected from 1, 2, 3, 4, and 5, and each X" is independently selected from:

i. an L- or D-amino acid, wherein an amine functional group of the L- or D-amino acid is covalently conjugated, directly or indirectly, to Z1c and an acid functional group of the L- or D-amino acid is conjugated, directly or indirectly, to X1 or to Z1a; and ii. Formulae FL(IA), FL(IB), FL69, and FL70;

wherein Formula FL(IA) and FL(IB) are:

FL(IA)

FL(IB)

and stereoisomers thereof;

wherein:

G is selected from a 3- to 6-membered cycloalkyl group, a 3- to 10-membered heterocyclyl group, a heteroaryl group, and an aryl group, wherein each group is optionally substituted with 1-3 groups independently selected from hydroxy, amino, halogen, cycloalkyl, alkoxy, and alkyl;

E is absent or is an alkylene group optionally substituted with 1-3 groups independently selected from halogen, hydroxy, and amino;

Q is absent or is selected from hydrogen, alkyl, halo, cyano, alkoxy, carboxylic acid, amino, hydroxy, amide, halo alkyl, cycloalkyl, heterocycle, heteroaryl, and aryl, wherein the alkyl, alkoxy, cycloalkyl, heterocycle, heteroaryl, and aryl is each optionally substituted with 1-5 groups independently selected from alkyl, amino, amide, halo, hydroxy, cyano, halo alkyl, and alkoxy;

Q' is selected from hydrogen, alkyl, and an acyl group;

Q and Q', together with the carbon and nitrogen atom to which they are attached, optionally form a 4-membered heterocyclyl, a 5-membered heterocyclyl, a 6-membered heterocyclyl, a 9-membered bicyclic heterocyclyl, or a 10-membered bicyclic heterocyclyl, wherein the 4-membered heterocyclyl, 5-membered heterocyclyl, 6-membered heterocyclyl, 9-membered bicyclic heterocyclyl, and 10-membered bicyclic heterocyclyl are each optionally substituted with 1-5 groups independently selected from alkyl, amino, halo, hydroxy, cyano, amide, halo alkyl, and alkoxy;

p is 0, 1, 2, 3, 4, or 5;

q is 0, 1, 2, 3, 4, or 5;

R" represents a covalent bond, directly or indirectly, to Z1c;

Z" represents a covalent bond, directly or indirectly, to X1 or to Z1a; and any primary amine is optionally acetylated or alkylated;

wherein Formulae FL69 and FL70 are:

FL69

FL70 and stereoisomers thereof;

wherein:

R" represents a covalent bond, directly or indirectly, to Z1c;

Z" represents a covalent bond, directly or indirectly, to X1 or to Z1a;

A' is selected from H, an alkyl, a saturated fatty acid, an unsaturated fatty acid, a cycloalkyl, a haloalkyl, an aryl, and a heteroaryl; and A" is (i) a bile acid conjugated, directly or indirectly, via its acid group to the amine in FL69 or FL70; or (ii) a $C_2$-$C_{20}$ acyl group optionally terminating in an acid group, wherein one or more carbon atoms of the $C_2$-$C_{20}$ acyl group are optionally and independently replaced by a group selected from C(=O), O, NH, $NH_2$, S, S(O), $SO_2$, phenyl, 5-membered heterocyclyl, 6-membered heterocyclyl, 5-membered heteroaryl, 6-membered heteroaryl, and wherein the one or more carbon atoms of the $C_2$-$C_{20}$ acyl group, NH, $NH_2$, $SO_2$, phenyl, 5-membered heterocyclyl, 6-membered heterocyclyl, 5-membered heteroaryl, and 6-membered heteroaryl is each independently substituted with 0, 1, 2, 3, or 4 $R_x$, wherein $R_x$ is selected from $C_1$-$C_5$ alkyl, halogen, $C_1$-$C_5$ haloalkyl, carboxylic acid, hydroxyl, —O—$C_1$-$C_5$ alkyl, $NH_2$, and a substituted or unsubstituted 5-membered heterocyclyl, 6-membered heterocyclyl, 5-membered heteroaryl, and 6-membered heteroaryl;

p is 1, 2, 3, 4, or 5, q is 1, 2, 3, 4, or 5, and any primary amine is optionally acetylated or alkylated.

In some embodiments, each A" is independently selected from:

AB-1

AB-2

265

-continued

AB-3

AB-4

AB-5

AB-6

AB-7

AB-8

AB-9

AB-10

AB-11

AB-12

AB-13

266

-continued

AB-14

AB-15

AB-16

AB-17

AB-18

AB-19

AB-20

AB-21

AB-22

AB-23

267
-continued

268
-continued

AB-24

AB-25

AB-26

AB-27

AB-28

AB-29

AB-30

AB-31

AB-32

AB-33

AB-34

AB-35

AB-36

AB-37

AB-37A

AB-38

-continued

AB-39

In some embodiments, the compound comprises at least one Z1b selected from Formulae IIa-IIai or Formulae IIIa-IIIai, wherein Formulae IIa-IIai are:

Formula IIa

Formula IIb

Formula IIc

Formula IId

Formula IIe

Formula IIf

Formula IIg

Formula IIh

Formula IIi

Formula IIj

Formula IIk

-continued

Formula IIl

Formula IIm

Formula IIn

Formula IIo

Formula IIp

Formula IIq

Formula IIr

Formula IIs

Formula IIt

Formula IIu

Formula IIv

Formula IIw

Formula IIx

Formula IIy

271

-continued

Formula IIz

Formula IIaa

Formula IIab

Formula IIac

Formula IIad

Formula IIae

Formula IIaf

Formula IIag

Formula IIah and

Formula IIai wherein:

r is 0, 1, 2, 3, 4, or 5;

s is 0, 1, 2, 3, 4, or 5;

W represents $CH_2$—~ or (C=O)—~, wherein —~ is a covalent linkage to X1; and each $V_1$ is independently selected from NH—†, $CH_2$—†, and (C=O)—† and each $V_2$ is N—†, wherein —† is a covalent linkage towards successive Z1b, Z1a or Z1c, provided that $V_1$ is NH—† when connected to Z1c; and the covalent linkages between Z1a and Z1b units each independently comprise an amine linkage or an amide

272 linkage; and when n'=0 and m'=1, Z1a is directly conjugated to X1 by an amine linkage or amide linkage, and wherein Formulae IIIa-IIIai are:

Formula IIIa

Formula IIIb

Formula IIIc

Formula IIId

Formula IIIe

Formula IIIf

Formula IIIg

Formula IIIh

Formula IIIi

Formula IIIj

Formula IIIk

Formula IIIl

273

-continued

274

-continued

Formula IIIm

Formula IIIaa

Formula IIIab

Formula IIIn

Formula IIIac

Formula IIIo

Formula IIIad

Formula IIIp

Formula IIIac

Formula IIIq

Formula IIIr

Formula IIIs

Formula IIIaf

Formula IIIt

Formula IIIag

Formula IIIu

Formula IIIah    and

Formula IIIv

Formula IIIai

Formula IIIw wherein:

r is 1, 2, 3, 4, or 5;

s is 1, 2, 3, 4, or 5; and each V₁ is independently selected from NH—†, CH₂—†, and (C═O)—† and each V₂ is N—†, wherein —† is a covalent linkage towards successive Z1b, Z1a or Z1c, provided that V₁ is NH—† when connected to Z1c; and the covalent linkages between Z1a and Z1b units each independently comprise an amine linkage or an amide linkage; and when n'=0 and m'=1, Z1a is directly conjugated to X1 by an amine linkage or amide linkage.

Formula IIIx

In some embodiments, at least one Z1c is covalently conjugated indirectly via a linker (indirect linker) to the compound (e.g., the compound of Formula I). In some embodiments, the linker is selected from (i) Formulae FL1-FL19, FL5A, FL5B, FL65A, FL65B, FL69, FL69A, FL69B, FL70, FL70A, and FL70B:

Formula IIIy

Formula IIIZ (FL1)

(FL2)

(FL3)

(FL4)

(FL4A)

(FL5)

(FL6)

(FL7)

(FL7A)

(FL8)

(FL9)

(FL8A)

(FL9A)

(FL10)

(FL11)

(FL12)

(FL13)

277

278

(FL14)

(FL15)

(FL16)

(FL17)

(FL18)

(FL19)

FL5B

FL65A

FL65B

FL69

FL69A

FL69B

FL70

FL70A

FL70B wherein, in Formulae FL1-FL19, FL5A, FL5B, FL65A, FL65B, FL69, FL69A, FL69B, FL70, FL70A, and FL70B:

Z" represents an attachment point toward X1;

R" represents an attachment point toward Z1c;

p is 1, 2, 3, 4, or 5, q is 1, 2, 3, 4, or 5, r is 1, 2, 3, 4, or 5; and any primary amine is optionally acetylated or alkylated; and (ii) an L- or D-amino acid comprising at least one amine group directly conjugated to Z1c, wherein an acid functional group of the amino acid is conjugated toward X1 in Formula I.

In some embodiments, n' is 1 and each of the Z1b is independently selected from (i) Formulae FL1-FL19, FL5A, FL5B, FL65A, FL65B, FL69, FL69A, FL69B, FL70, FL70A, and FL70, and;

wherein, in Formulae FL1-FL19, FL5A, FL5B, FL65A, FL65B, FL69, FL69A, FL69B, FL70, FL70A, and FL70B:

Z" represents an attachment point toward X1;

R" represents an attachment point toward Z1c;

p is 1, 2, 3, 4, or 5, q is 1, 2, 3, 4, or 5, r is 1, 2, 3, 4, or 5; and any primary amine is optionally acetylated or alkylated; and (ii) an L- or D-amino acid comprising at least one amine group directly conjugated to Z1c, wherein an acid functional group of the amino acid is conjugated toward X1 in Formula I.

In some embodiments, in Formula I, Z1c is directly connected to X1 through an optional covalent-spacer, and the optional covalent-spacer is independently selected from gamma-glutamic acid, beta-alanine, and (FL3)

$$Z'' - \left[ \phantom{x} \right]_p - \overset{\overset{\displaystyle O}{\|}}{\phantom{C}} - \overset{H}{N} - R''$$

Formula FL3, wherein p is 1 or 2; and (FL5)

$$R'' - \overset{H}{N} - \left[ \phantom{x} \right]_p - Z''$$

Formula FL5, wherein p is 2, 3, or 4;

In some embodiments, X1 is OH or $NH_2$, and X1 further comprises a drug substance covalently conjugated directly or indirectly to the compound.

In at least some embodiments, the compound of the present disclosure comprises a drug substance comprising a polypeptide hormone, a human polypeptide hormone and/or insulin, or an analogue thereof, or a hybrid polypeptide comprising one or more combinations thereof.

In at least some embodiments, the compound of the present disclosure comprises an amine in the compound that is conjugated via an amide linkage to an aromatic boron-containing compound (e.g., group). In some embodiments, the aromatic boron-containing group is selected from a phenylboronic acid, boroxole, and phenylboronate.

In at least some embodiments, the compound of the present disclosure is dehydrated (loses) by 1, 2, 3, 4, 5, 6, 7, 8, or more water molecules.

In at least some embodiments, the compound of the present disclosure is formulated in a solution comprising one or more of a buffer, stabilizer, vasodilator, preservative, surfactant, salt, sugar, or compounds containing one or more hydroxyls, alcohols, diols, or phenols. For example, the solution could comprise one or more of citrate, zinc, and/or cresol.

In at least some embodiments, X1 comprises a human polypeptide hormone of the human pancreas, insulin, glucagon, GLP-1, a somatostatin, a gastric inhibitory polypeptide, a glucose-dependent insulinotropic polypeptide, a hybrid peptide comprising sequences from two or more human polypeptide hormones, or an analogue thereof.

In some embodiments, X1 comprises human insulin or a human insulin analogue comprising an A-chain and a B-chain, wherein the A-chain comprises a sequence selected from SEQ ID NOs 1 and 3 to 33, and the B-chain comprises a sequence selected from SEQ ID NOs 2 and 34 to 74, 24047, and 24048;

each Z1c is independently selected from FF1, FF10, FF12, FF14, FF15, FF114, FF115, FF116, FF163, FF193, FF194, FF203, and FF221-FF231 and covalently conjugated either directly, or indirectly via the linker, to Z1a and/or Z1b, or to X1;

each Z1a is independently absent or independently comprises a sequence selected from K, GK, KGSH (SEQ ID NO:24049), KGSHK (SEQ ID NO:4238), KNSTK (SEQ ID NO:5085), GKASHK (SEQ ID NO:12414), GKEEEK (SEQ ID NO:12677), GKEEHK (SEQ ID NO:12680), GKGHSK (SEQ ID NO:13120), GKGSH (SEQ ID NO:24050), GKGSHK (SEQ ID NO:13198), GKGSTK (SEQ ID NO:13205), GKHENK (SEQ ID NO:13271), GKNSHK (SEQ ID NO:13982), GKNSTK (SEQ ID NO:13989), GKQSSK (SEQ ID NO:14380), GKYQFK (SEQ ID NO:15128), GKGSKK (SEQ ID NO:24045), GKKPGKK (SEQ ID NO:24046), GKGPSK (SEQ ID NO:24044), GKPSHKP (SEQ ID NO:24043), and GSHKGSHK (SEQ ID NO:24042);

each linker is selected from FL1, FL3, FL4, and FL5;

each m' is independently 0 or 1;

each n' is independently 0, 1, 2, or 3;

each o' is independently 1, 2, 3, 4, or 5;

each p' is 1, 2, 3, 4, or 5; and q' is 1, 2, 3, or 4, wherein when any of n', o', p', or q' is 2 or more, the corresponding groups Z1a, Z1b, and Z1c are independently selected and may be the same or different; and wherein each Z1c is independently covalently conjugated, directly or indirectly, to an amine of Z1a, to an amine of Z1b, or to X1.

In some embodiments, X1 comprises the human insulin or human insulin analogue comprising an A-chain and a B-chain, wherein the A-chain comprises SEQ ID NO:1; and the B-chain is selected from SEQ ID NOs 2, 36, 24047, and 24048;

each Z1c is independently selected from FF1, FF10, FF12, FF14, FF15, FF114, FF115, FF116, FF193, FF194, FF203, and FF221-FF224 and covalently conjugated either directly, or indirectly via the linker, to Z1a and/or Z1b, or to X1;

each Z1a independently comprises a sequence selected from K, GK, KGSH (SEQ ID NO:24049), KGSHK (SEQ ID NO:4238), KNSTK (SEQ ID NO:5085), GKASHK (SEQ ID NO:12414), GKEEEK (SEQ ID NO:12677), GKEEHK (SEQ ID NO:12680), GKGHSK (SEQ ID NO:13120), GKGSH (SEQ ID NO:24050), GKGSHK (SEQ ID NO:13198), GKG-STK (SEQ ID NO:13205), GKHENK (SEQ ID NO:13271), GKNSHK (SEQ ID NO:13982), GKN-STK (SEQ ID NO:13989), GKQSSK (SEQ ID NO:14380), GKYQFK (SEQ ID NO:15128), GKG-SKK (SEQ ID NO:24045), GKKPGKK (SEQ ID NO:24046), GKGPSK (SEQ ID NO:24044), GKP-SHKP (SEQ ID NO:24043), and GSHKGSHK (SEQ ID NO:24042);

each linker is independently absent or independently selected from FL3 and FL5;

each m' is independently 0 or 1;

each n' is independently 0 or 2;

each o' is independently 1, 2, or 3;

each p' is 1, 2, or 3; and q' is 1, 2, or 3, wherein when any of n', o', p', or q' is 2 or more, the corresponding groups Z1a, Z1b, and Z1c are independently selected and may be the same or different;

wherein each Z1c is independently covalently conjugated, directly or indirectly, to an amine of Z1a, to an amine of Z1b, or to X1.

In some embodiments, each of the Z1a is independently absent or independently comprises a sequence selected from K, GK, KGSH (SEQ ID NO:24049), GKGSH (SEQ ID NO:24050), KGSHK (SEQ ID NO:4238), and GKGSHK (SEQ ID NO:13198).

In some embodiments, each of the Z1c is independently selected from FF1, FF10, FF12, FF14, FF15, FF114, FF115, FF116, and FF221-FF231. In some embodiments, $B_1$ and $B_2$ are independently selected from Formulae F1 and F2. In some embodiments, the $B_1$ and the $B_2$ are independently selected from F2 and F7. In some embodiments, the $B_1$ and the $B_2$ are F2. In some embodiments, the $B_1$ and the $B_2$ are F7. In some embodiments, the $B_1$ is F2 and the $B_2$ is F7. In some embodiments, the $B_1$ is F7 and the $B_2$ is F2. In some embodiments, at least one R1 in $B_1$ or $B_2$ is F or $CF_3$. In some embodiments, Z1b is independently absent, FL3, or FL5. In some embodiments, each of the Z1c is independently selected from FF10, FF12, FF116, FF221, FF222, and FF224.

In some embodiments, each $B_1$ and $B_2$ is independently selected from F2 and F7 and is covalently conjugated to Z1c using an amide linkage, each Z1b is independently absent; FL3 wherein p is 1, 2, or 3; or FL5 wherein p is 2, 3, or 4;

each FF is independently selected from FF10, FF12, FF116, FF134, FF163, FF193, FF203, FF221, FF222 and FF224; wherein FF12 and FF222 has either (S,R) or (S,S) stereochemistry;

each Z1c is conjugated either directly or indirectly through FL3 or FL5 to the amine group in one or more lysine side chain in X1 or the N-terminus in X1; and X1 is a polypeptide drug substance and/or an insulin optionally having from 0 to 4 residues replaced, inserted, or mutated to lysines, and wherein the lysines are each conjugated directly or indirectly to a Z1c.

In some embodiments, each $B_1$ and $B_2$ is F2 and is covalently conjugated to Z1c using an amide linkage, each Z1b is independently absent; FL3 wherein p is 1, 2, or 3; or FL5 wherein p is 2, 3, or 4;

each FF is independently selected from FF10, FF12, FF116, FF134, FF163, FF193, FF203, FF221, FF222 and FF224; wherein FF12 and FF222 has either (S,R) or (S,S) stereochemistry;

each Z1c is conjugated either directly or indirectly through FL3 or FL5 to the amine group in one or more lysine side chain in X1 or the N-terminus in X1; and X1 is a polypeptide drug substance and/or an insulin optionally having from 0 to 4 residues replaced, inserted, or mutated to lysines, and wherein the lysines are each conjugated directly or indirectly to a Z1c.

In some embodiments, each $B_1$ and $B_2$ is F7 and is covalently conjugated to Z1c using an amide linkage, each Z1b is independently absent; FL3 wherein p is 1, 2, or 3; or FL5 wherein p is 2, 3, or 4;

each FF is independently selected from FF10, FF12, FF116, FF134, FF163, FF193, FF203, FF221, FF222 and FF224; wherein FF12 and FF222 has either (S,R) or (S,S) stereochemistry;

each Z1c is conjugated either directly or indirectly through FL3 or FL5 to the amine group in one or more lysine side chain in X1 or the N-terminus in X1; and X1 is a polypeptide drug substance and/or an insulin optionally having from 0 to 4 residues replaced, inserted, or mutated to lysines, and wherein the lysines are each conjugated directly or indirectly to a Z1c.

In some embodiments, Z1c is FF224, n' is 0, and Z1a is an amine containing amino acid.

In some embodiments, Z1c is covalently conjugated directly to X1 via a linker, and wherein the linker is independently selected from gamma-glutamic acid, beta-alanine, and Formula FL3

(FL3)

wherein p is 1, 2, or 3; and

Formula FL5

(FL5)

wherein p is 2, 3, or 4.

In some embodiments, the compound further comprises a drug substance covalently conjugated directly or indirectly to the compound.

In some embodiments, the compound of Formula I is selected from Examples 315, 318, 320, 605-608, 610-612, 589-595, 562-574, and 803-914.

In some embodiments, X1 is a polypeptide drug substance and/or an insulin optionally having from 0 to 4 residues replaced, inserted, or mutated to lysines, and wherein the lysines are each conjugated to a Z1c.

In some embodiments, one or more amines are each independently acetylated and/or independently alkylated.

In some embodiments, X1 comprises a polypeptide drug substance and the covalent conjugation to X1 is to amino group(s) in one or more lysine residues and/or to the N-terminal amino groups in X1.

In some embodiments, each R1 in FF1-FF231 is independently selected from a $C_1$-$C_{22}$ alkyl group, a $C_1$-$C_{22}$ acyl group, a ($C_3$-$C_8$)cycloalkyl group, a $C_1$-$C_{22}$ haloalkyl group, an aryl group, and a heteroaryl group, each R1 optionally comprises one or more $C_1$-$C_{22}$ alkyl-halide, halide, sulfhydryl, aldehyde, amine, acid, hydroxyl, $C_1$-$C_{22}$ alkyl, or aryl groups.

In some embodiments, X4 is selected from —COOH, —$(CH_2)_m$COOH, a $C_1$-$C_{22}$ alkyl group, a $C_1$-$C_{22}$acyl group, a ($C_3$-$C_8$)cycloalkyl group, a $C_1$-$C_{22}$ haloalkyl group, an aryl group, and a heteroaryl group, each X4 optionally comprises one or more $C_1$-$C_{22}$ alkyl-halide, halide, sulfhydryl, aldehyde, amine, acid, hydroxyl, $C_1$-$C_{22}$ alkyl, or aryl groups; wherein m is 1, 2, 3, 4, or 5.

In some embodiments, the alkyl group of Y9 is a $C_1$-$C_{22}$ alkyl. In some embodiments, Y9 is $CH_3$.

In some embodiments, at least one primary or secondary amine in FF1-FF223 and FF225-FF231 is covalently conjugated to $B_6$.

In some embodiments, an amine in the compound is conjugated via an amide linkage to an aromatic boron-containing group.

In some embodiments, the aromatic boron-containing group is selected from a phenylboronic acid, boroxole, and phenylboronate.

In some embodiments, the compound is formulated in a solution comprising one or more of a buffer, stabilizer, vasodilator, preservative, surfactant, salt, sugar, or compounds containing one or more hydroxyls, alcohols, diols, or phenols. In some embodiments, the solution comprises one or more of citrate, zinc, and/or cresol.

In some embodiments, Z1c is conjugated to a cysteine.

In some embodiments, the compound (e.g., the compound of Formula I) is covalently conjugated either directly or through a linker to a diol, sugar, carbohydrate or a diol containing molecule.

In some embodiments, the compound (e.g., the compound of Formula I) is covalently conjugated to an antibody, albumin or a fragment thereof, or covalently conjugated either directly or through a linker to a molecule that can bind to at least one protein present in human plasma. In at least one embodiment, the present disclosure provides a method to administer the compounds disclosed herein to a human subject as a therapeutic or prophylactic agent.

In some embodiments, the compounds disclosed herein are used as intermediate compounds for the manufacture of any compounds disclosed herein.

In some embodiments, the compounds disclosed herein comprise at least one Z1c. In at least some embodiments, the Z1c is a boron containing compound. In some embodiments, a subset of boron containing compounds is selected from a non-aromatic and/or an aromatic boron-containing group. In some embodiments, Z1c is an aromatic boron-containing group. In at least one embodiment, the compound of the present disclosure comprises at least one Z1c selected from FF1-FF18, FF35, FF56-FF62, FF65-FF67, FF70-FF72, FF75-FF77, FF80-FF81, FF84, FF88, FF92, FF101-FF102, FF107-FF136, FF193-194, FF203, and FF225-231. In at least some embodiments, the Z1c is selected from FF1-FF231. In some embodiments, the compound comprises at least one Z1c having at least one chiral center and selected from FF1, FF2, FF5, FF9, FF11-FF13, FF15-FF24, FF27, FF31, FF34-FF36, FF38, FF39, FF43-FF58, FF60-FF70, FF72-FF75, FF77-FF80, FF82-FF84, FF86-FF212, FF216-FF220, FF222, FF223, FF227, FF229, FF230, FF231, and combinations thereof.

In some embodiments, the compound comprises at least one FF12 and/or FF116. In some embodiments, the stereochemistry of FF12 and FF116 is independently selected from (S,S); (S,R); (R,R); and (R,S).

In some embodiments, X1 comprises human insulin or a human insulin analogue comprising an A-chain and a B-chain, wherein the C-terminus of the A-chain of the human insulin analogue is optionally extended with a polypeptide of up to 20 residues, and/or the N-terminus of the B-chain of the human insulin analogue is optionally extended with a polypeptide of up to 10 residues. In some embodiments, one to six residues of the insulin A-chain and/or the insulin B-chain are deleted or mutated.

In some embodiments, X1 comprises at least one lysine having an amine side chain, and Z1c is covalently conjugated directly to the amine side chain. In some embodiments, the compound of the present disclosure comprises at least one Z1a comprising one or more amino acids having an amine side chain, and wherein the one or more amino acids are selected from lysine, diaminopropionic acid, diaminobutyric acid, and ornithine; and wherein Z1c is covalently conjugated, directly or indirectly, to the amine side chain.

In some embodiments, the compound of the present disclosure may include one or more isotopes selected from deuterium, tritium, carbon-13, carbon-14, and iodine-124. In at least one embodiment, the compound comprises deuterium.

In some embodiments, X1 comprises a drug substance covalently conjugated to at least one Z1c through an acid containing linker. In some embodiments, a composition of the present disclosure comprises at least one compound as disclosed herein (e.g., a compound comprising X1 and one or more Z1c, Formula I), or a tautomer, stereoisomer or a mixture of stereoisomers, or a pharmaceutically acceptable salt, or hydrate, or isotopic derivative thereof formulated together with one or more pharmaceutically acceptable carriers.

In some embodiments, the present disclosure also provides a composition or a mixture comprising at least one compound as disclosed herein, for use as a medicament for the treatment of diabetes, for control of blood sugar levels, or to control the release of a drug based on physiological levels of diol containing small molecules or sugars.

In some disclosed embodiments are a method of administering a compound as disclosed herein to a human subject as a therapeutic or prophylactic agent.

In some embodiments, the disclosure provides a method of making a compound as disclosed herein comprising at least one alkylation and/or amidation step.

In some embodiments, the disclosure provides a method of treating a subject by administering a device or formulation comprising a compound as disclosed herein, such as Examples 1-915. For example, the device can be a fixed dose injector, microdosing injector, an internal or external patch.

In some embodiments, the disclosure provides a method of treating or preventing diabetes, impaired glucose tolerance, hyperglycemia, or metabolic syndrome (metabolic syndrome X, insulin resistance syndrome) comprising administering to a subject in need thereof a therapeutically effective amount of a compound disclosed herein.

In at least some embodiments, the present disclosure is directed to a compound of Formulae FF1-FF231, or a tautomer, stereoisomer or a mixture of stereoisomers, or a pharmaceutically acceptable salt, or hydrate, or isotopic derivative thereof. In at least some embodiments, the present disclosure is directed to a compound selected from Formulae FF1-FF48, Formulae FF49-FF88, FF89-FF112, FF113-FF136, FF137-FF160, FF161-FF164, FF165-FF166, FF167-FF192, FF193-FF209, and FF210-FF231.

In some embodiments, the present disclosure is directed to a compound selected from Formulae FF1-FF48, wherein X is selected from maleimide, an amine, OH, and halogen; and i is 1, 2, 3, 4, 5, 6, or 7;

j is 1, 2, 3, 4, 5, 6, or 7; and $B_1$ and $B_2$, which may be identical or different, each independently represents an aromatic boron-containing group.

In some embodiments, the present disclosure is directed to a compound selected from Formulae FF49-FF88, wherein X is selected from maleimide, an amine, OH, and halogen;

i is 1, 2, 3, 4, 5, 6, or 7;

j is 1, 2, 3, 4, 5, 6, or 7;

R1a is selected from COOH, $CH_3$, H, and OH;

R2, R3, R4 and R5 is each independently selected from $CH_3$, H, OH, and COOH, and at least one of R2, R3, R4 and R5 is $CH_3$ or OH; and $B_1$ and $B_2$, which may be identical or different, are each independently an aromatic boron-containing group.

In some embodiments, the present disclosure is directed to a compound selected from Formulae FF89-FF112, wherein X is selected from maleimide, an amine, OH, and halogen;

i is 1, 2, 3, 4, 5, 6, or 7; and $B_1$, $B_2$ and $B_3$, which may be identical or different, each independently represents an aromatic boron-containing group, a carboxylic acid derivative, or a H, wherein at least two of $B_1$, $B_2$ and $B_3$ in each FF structure are independently an aromatic boron-containing group.

In some embodiments, the present disclosure is directed to a compound selected from Formulae FF113-FF136, wherein X is selected from maleimide, an amine, OH, and halogen;

i is 0, 1, 2, 3, 4, 5, 6, or 7;

j is 0, 1, 2, 3, 4, 5, 6, or 7;

k is 0, 1, 2, 3, 4, 5, 6, or 7;

m is 0, 1, 2, 3, 4, 5, 6, or 7;

wherein i+j+k+m is greater than 0 each R1 is independently selected from H, an alkyl group, an acyl group, a cycloalkyl group, a haloalkyl group, an aryl group, and a heteroaryl group, each R1 optionally comprises one or more alkyl-halide, halide, sulfhydryl, aldehyde, amine, acid, hydroxyl, alkyl or aryl groups; and $B_1$ and $B_2$, which may be identical or different, each independently represents an aromatic boron-containing group.

In some embodiments, the present disclosure is directed to a compound selected from Formulae FF137-FF160, wherein X is selected from maleimide, an amine, OH, and halogen;

i is 0, 1, 2, 3, 4, 5, 6, or 7;

j is 0, 1, 2, 3, 4, 5, 6, or 7;

k is 0, 1, 2, 3, 4, 5, 6, or 7;

m is 0, 1, 2, 3, 4, 5, 6, or 7;

wherein i+j+k+m is greater than 0;

each R1 is independently selected from H, an alkyl group, an acyl group, a cycloalkyl group, a haloalkyl group, an aryl group, and a heteroaryl group, each R1 optionally comprises one or more alkyl-halide, halide, sulfhydryl, aldehyde, amine, acid, hydroxyl, alkyl or aryl groups; and $B_1$ and $B_2$, which may be identical or different, each independently represents an aromatic boron-containing group.

In some embodiments, the present disclosure is directed to a compound selected from Formulae FF161-FF164, wherein X is selected from maleimide, an amine, OH, and halogen;

i is 1, 2, 3, 4, or 5 (e.g., 1, 2, 3, or 5);

j is 1, 2, 3, 4, or 5 (e.g., 1, 2, 3, or 5);

each R6, R7, R8, and R9 for different values of j is independently selected from H, $CF_3$, $CH_3$, $CHF_2$, and $(CH_2)_m CH_3$, wherein m is 1, 2, 3, 4, or 5;

Y3, Y4, Y5, Y6 and Y7 are each independently selected from H, $CH_2$—X4, and Formulae IV-1 to IV-135 (as previously defined);

wherein X4 is selected from —COOH, —$(CH_2)_m$COOH, an alkyl group, an acyl group, a cycloalkyl group, a haloalkyl group, an aryl group, and a heteroaryl group, each optionally comprising one or more alkyl-halide, halide, sulfhydryl, aldehyde, amine, acid, hydroxyl, alkyl or aryl groups; wherein m is 1, 2, 3, 4, or 5;

wherein at least one of Y5, Y6, and Y7 in Formulae FF162 and FF163 is not H; and at least one of Y7, R8 and R9 in FF164 is not H; and Xa represents CH═O, $CHF_2$, $CF_3$, $CH_2SH$, COOH, $CH_2OH$, $CH_2NO_2$, $CH_2NH_2$, $CH_3$, $C(CH_3)_3$, $CH(CH_3)_2$, $CH((CH_2)_3 CH_3)_2$, or $CH(CH_2 CH_3)_2$;

Xb represents O, NH, $CH_2$, or S;

Xc represents CH or N;

each $R_{10}$ is independently selected from H, F, Cl, Br, $CH_3$, $CF_3$, CH═O, OH, COOH, and $(CH_2)$, $CH_3$, m is 1, 2, 3, 4, or 5; and n is 1, 2, 3, 4, or 5; and $B_1$ and $B_2$, which may be identical or different, each independently represents an aromatic boron-containing group. In some embodiments, when j is 4, X is not $NH_2$ for FF163.

In some embodiments, the present disclosure is directed to a compound selected from Formulae FF165-FF166, wherein X is selected from maleimide, an amine, OH, and halogen;

m is 1, 2, 3, 4, 5, 6, or 7;

n is 1, 2, 3, 4, 5, 6, or 7;

X5 is S, O, or NH; and each $R_1$ is independently selected from H, F, Cl, Br, OH, $CH_2$—$NH_2$, $NH_2$, (C═O)—$NH_2$, CH═O, $SO_2CH_3$, $SO_2CF_3$, $CF_3$, $CHF_2$, $NO_2$, $CH_3$, $OCH_3$, $O(CH_2)_m CH_3$, —$(SO_2)NH CH_3$, —$(SO_2)NH(CH_2)_m$, $CH_3$, and $OCF_3$, wherein m is 1, 2, 3, 4, 5, 6, or 7.

In some embodiments, the present disclosure is directed to a compound selected from Formulae FF167-FF192, wherein X is selected from maleimide, an amine, OH, and halogen; and $B_1$ and $B_2$, which may be identical or different, each independently represents an aromatic boron-containing group.

In some embodiments, the present disclosure is directed to a compound selected from Formulae FF193-FF209, wherein R in FF208 and FF209 is an alkyl, aryl or halide that is covalently conjugated through at least one $CH_2$ group to the amino group in the side chain of FF208 or FF209;

R1 and R2 are independently selected from H, $CH_3$, alkyl, and formulae IV-1 to IV-135;

i is 1, 2, 3, 4, or 5;

j is 1, 2, 3, 4, or 5; and wherein X is selected from maleimide, an amine, OH, and halogen; and $B_1$ and $B_2$, which may be identical or different, each independently represents an aromatic boron-containing group.

In some embodiments, the present disclosure is directed to a compound selected from Formulae FF210-FF224, wherein R11 in FF210 to FF212 is independently selected from Formulae IV-1 to IV-135 and R12 is selected from an amine, a hydroxyl, an alkyl, and a halide group;

wherein each R13 is independently selected from H, $CH_3$, alkyl, aryl, and formulae IV-1 to IV-135; R14 is selected from H, $CH_3$, alkyl, aryl, and heteroaryl; wherein X is independently selected from maleimide, an amine, OH, and halogen;

X" is an amine;

i is 1, 2, 3, 4, or 5;

j is 1, 2, 3, 4, or 5; and $B_1$, $B_2$, $B_3$, $B_4$, $B_5$, and $B_6$, each independently represents an aromatic boron-containing group, wherein in any compound containing $B_1$, $B_2$ and $B_3$ groups, at least two groups are independently an aromatic boron-containing group.

In some embodiments, the present disclosure is directed to a compound selected from Formulae FF225-FF231, (FF225)

(FF226)

(FF227)

(FF228)

-continued (FF229)

(FF230)

(FF231)

wherein X is selected from maleimide, an amine, OH, and halogen;

i is 1, 2, 3, 4, 5, 6, or 7;

$B_1$ and $B_2$, which may be identical or different, each independently represents an aromatic boron-containing group, wherein $B_1$ and $B_2$ in Formulae FF225-FF231 are not an F2 or F6 aromatic boron-containing group, wherein Formulae F2 and F6 are:

(F2)

and (F6)

R$_1$ at position 5' represents (C=O)—*, wherein —* represents the attachment point to the rest of FF225-FF231;

zero, one, or two R$_1$ represents F, Cl, CF$_2$, CF$_3$, SF$_5$, OCF$_3$, SO$_2$CH$_3$, and/or SO$_2$CF$_3$, and each remaining R$_1$ represents H;

Y8 is O; and i is 1; and each remaining R$_1$ is H;

Y8 is O; and i is 1.

In at least some embodiments, when X is an amine in any one of Formulae FF1 to FF223 and FF225-FF231, X is optionally acetylated or alkylated.

In some embodiments, the compound comprises at least one of B$_1$, B$_2$ and B$_3$ independently selected from Formulae F1-F11 or wherein the compound comprises at least one of B$_4$, B$_5$ and B$_6$ independently selected from Formulae F1-F11. In at least some embodiments, B$_1$, B$_2$ and B$_3$ may be identical or different. If B$_1$, B$_2$ and B$_3$ are all present in a compound of the present disclosure, then each is independently an aromatic boron-containing group, a carboxylic acid derivative, or a H, with the proviso that in each FF structure (i.e., FF1 to FF231) containing B$_1$, B$_2$ and B$_3$ groups, at least two groups are independently an aromatic boron-containing group.

In some embodiments, for B$_1$, B$_2$, B$_3$:

one R$_1$ represents (C=O)—*, S(=O)(=O)—*, (CH$_2$)$_m$ (C=O)—*, or (CH$_2$)$_m$—*, wherein —* represents an attachment point to the rest of Z1c or to the compound, and m is 1, 2, 3, 4, 5, 6, or 7;

each remaining R$_1$ or R$_2$ is independently selected from H, F, Cl, Br, OH, CH$_2$—NH$_2$, NH$_2$, (C=O)—NH$_2$, CH=O, SO$_2$CH$_3$, SO$_2$CF$_3$, CF$_3$, CHF$_2$, NO$_2$, CH$_3$, OCH$_3$, O(CH$_2$)$_m$CH$_3$, —(SO$_2$)NH CH$_3$, —(SO$_2$)NH (CH$_2$)$_m$CH$_3$, and OCF$_3$, wherein m is 1, 2, 3, 4, 5, 6, or 7;

In some embodiments, for B$_4$, B$_5$:

one R$_1$ for B$_4$ represents (CH$_2$)$_m$—ø, wherein —ø represents the attachment point (representing a covalent bond) to an amine in X1 and one R$_1$ for B$_5$ represents (C=O)—*, S(=O)(=O)—*, (CH$_2$)$_m$(C=O)—*, or (CH$_2$)$_m$—*, wherein —* represents the attachment point to the same amine in X1, and m is 1, 2, 3, 4, 5, 6, or 7;

each remaining R$_1$ or R$_2$ is independently selected from H, F, Cl, Br, OH, CH$_2$—NH$_2$, NH$_2$, (C=O)—NH$_2$, CH=O, SO$_2$CH$_3$, SO$_2$CF$_3$, CF$_3$, CHF$_2$, NO$_2$, CH$_3$, OCH$_3$, O(CH$_2$)$_m$CH$_3$, —(SO$_2$)NH CH$_3$, —(SO$_2$)NH (CH$_2$)$_m$CH$_3$, and OCF$_3$, wherein m is 1, 2, 3, 4, 5, 6, or 7.

In some embodiments, for B$_6$:

one R$_1$ for B$_6$ represents (CH$_2$)$_m$—ø, wherein —ø represents the attachment point (representing a covalent bond) to the rest of the compound, and m is 1, 2, 3, 4, 5, 6, or 7;

each remaining R$_1$ or R$_2$ is independently selected from H, F, Cl, Br, OH, CH$_2$—NH$_2$, NH$_2$, (C=O)—NH$_2$, CH=O, SO$_2$CH$_3$, SO$_2$CF$_3$, CF$_3$, CHF$_2$, NO$_2$, CH$_3$, OCH$_3$, O(CH$_2$)$_m$, CH$_3$, —(SO$_2$)NH CH$_3$, —(SO$_2$)NH (CH$_2$)$_m$CH$_3$, and OCF$_3$, wherein m is 1, 2, 3, 4, 5, 6, or 7.

In some embodiments, for Formulae F3-F4:

R$_w$ is O or S;

for Formulae F5-F10:

when Y8 is O, i is 1, 2, 3, 4, or 5; or when Y8 is NR, R is an alkyl group or H, and i is 1, 2, 3, 4, or 5;

Y9 is H, CH$_3$, or an alkyl group, provided that when Y8 is O, Y9 is a CH$_3$ or an alkyl group; and each Y10 is independently selected from H, CH$_3$, F, CF$_3$, and OCH$_3$, with the proviso that at least one Y10 is not H.

In some embodiments, for Formulae F5-F10:

when Y8 is O, i is 2, 3, 4, or 5;

Y9 is H, CH$_3$, or an alkyl group, provided that when Y8 is O, Y9 is a CH$_3$ or an alkyl group; and each Y10 is CH$_3$.In some embodiments, the compound is selected from:

N-(3-(3-borono-5-nitrobenzamido)propyl)-N-(3-borono-5-nitrobenzoyl)glycine (DS01);

N-(4-((4-(3-borono-5-nitrobenzamido)cyclohexyl)methyl) cyclohexyl)-N-(3-borono-5-nitrobenzoyl)glycine (DS02);

N-(4-((3-borono-5-nitrobenzamido)methyl)benzyl)-N-(3-borono-5-nitrobenzoyl)glycine (DS03);

N-(3-((3-borono-5-nitrobenzamido)methyl)benzyl)-N-(3-borono-5-nitrobenzoyl)glycine (DS04);

N-(4-(3-borono-5-nitrobenzamido)butyl)-N-(3-borono-5-nitrobenzoyl)glycine (DS05);

N-(3-(3-borono-5-fluorobenzamido)propyl)-N-(3-borono-5-fluorobenzoyl)glycine (DS06);

N-(3-(3-borono-5-fluorobenzamido)-2,2-dimethylpropyl)-N-(3-borono-5-fluorobenzoyl)glycine (DS07);

bis(3-(3-borono-5-fluorobenzamido)propyl)glycine (DS08);

N-(4-((3-borono-5-fluorobenzamido)methyl)benzyl)-N-(3-borono-5-fluorobenzoyl)glycine (DS09);

N-(3-((3-borono-5-fluorobenzamido)methyl)benzyl)-N-(3-borono-5-fluorobenzoyl)glycine (DS10);

N-(2-(3-borono-5-fluorobenzamido)cyclohexyl)-N-(3-borono-5-fluorobenzoyl)glycine (DS11);

N-(3-(3-borono-4-fluorobenzamido)propyl)-N-(3-borono-4-fluorobenzoyl)glycine (DS12);

N-(4-((4-(3-borono-4-fluorobenzamido)cyclohexyl)methyl) cyclohexyl)-N-(3-borono-4-fluorobenzoyl)glycine (DS13);

N-(3-(3-borono-4-fluorobenzamido)-2,2-dimethylpropyl)-N-(3-borono-4-fluorobenzoyl)glycine (DS14);

N-(4-((3-borono-4-fluorobenzamido)methyl)benzyl)-N-(3-borono-4-fluorobenzoyl)glycine (DS15);

N-(3-((3-borono-4-fluorobenzamido)methyl)benzyl)-N-(3-borono-4-fluorobenzoyl)glycine (DS16);

N-((1S,2R)-2-(3-borono-4-fluorobenzamido)cyclohexyl)-N-(3-borono-4-fluorobenzoyl)glycine (DS17);

N-((1S,2S)-2-(3-borono-4-fluorobenzamido)cyclohexyl)-N-(3-borono-4-fluorobenzoyl)glycine (DS18);

N-(3-(3-borono-5-bromobenzamido)propyl)-N-(3-borono-5-bromobenzoyl)glycine (DS19);

N-(4-((4-(3-borono-5-bromobenzamido)cyclohexyl) methyl)cyclohexyl)-N-(3-borono-5-bromobenzoyl)glycine (DS20);

bis(3-(3-borono-5-bromobenzamido)propyl)glycine (DS21);

N-(4-((3-borono-5-bromobenzamido)methyl)benzyl)-N-(3-borono-5-bromobenzoyl)glycine (DS22);

N-(3-((3-borono-5-bromobenzamido)methyl)benzyl)-N-(3-borono-5-bromobenzoyl)glycine (DS23);

N-(2-(3-borono-5-bromobenzamido)cyclohexyl)-N-(3-borono-5-bromobenzoyl)glycine (DS24);

N-(3-(4-borono-3-fluorobenzamido)propyl)-N-(4-borono-3-fluorobenzoyl)glycine (DS25);

N-(4-((4-(4-borono-3-fluorobenzamido)cyclohexyl)methyl)cyclohexyl)-N-(4-borono-3-fluorobenzoyl)glycine (DS26);

N-(3-(4-borono-3-fluorobenzamido)-2,2-dimethylpropyl)-N-(4-borono-3-fluorobenzoyl)glycine (DS27);

bis(3-(4-borono-3-fluorobenzamido)propyl)glycine (DS28);

N-(4-((4-borono-3-fluorobenzamido)methyl)benzyl)-N-(4-borono-3-fluorobenzoyl)glycine (DS29);

N-(3-((4-borono-3-fluorobenzamido)methyl)benzyl)-N-(4-borono-3-fluorobenzoyl)glycine (DS30);

N-((1S,2R)-2-(4-borono-3-fluorobenzamido)cyclohexyl)-N-(4-borono-3-fluorobenzoyl)glycine (DS31);

N-(1-hydroxy-1,3-dihydrobenzo[c][1,2]oxaborole-6-carbonyl)-N-(3-(1-hydroxy-1,3-dihydrobenzo[c][1,2]oxaborole-6-carboxamido)propyl)glycine (DS32);

N-(1-hydroxy-1,3-dihydrobenzo[c][1,2]oxaborole-6-carbonyl)-N-(5-(1-hydroxy-1,3-dihydrobenzo[c][1,2]oxaborole-6-carboxamido)pentyl)glycine (DS33);

N-(1-hydroxy-1,3-dihydrobenzo[c][1,2]oxaborole-6-carbonyl)-N-(3-(1-hydroxy-1,3-dihydrobenzo[c][1,2]oxaborole-6-carboxamido)-2,2-dimethylpropyl)glycine (DS34);

bis(3-(1-hydroxy-1,3-dihydrobenzo[c][1,2]oxaborole-6-carboxamido)propyl)glycine (DS35);

N-(1-hydroxy-1,3-dihydrobenzo[c][1,2]oxaborole-6-carbonyl)-N-(3-((1-hydroxy-1,3-dihydrobenzo[c][1,2]oxaborole-6-carboxamido)methyl)benzyl)glycine (DS36);

N-(1-hydroxy-1,3-dihydrobenzo[c][1,2]oxaborole-6-carbonyl)-N-((1S,2R)-2-(1-hydroxy-1,3-dihydrobenzo[c][1,2]oxaborole-6-carboxamido)cyclohexyl)glycine (DS37);

N-(1-hydroxy-1,3-dihydrobenzo[c][1,2]oxaborole-6-carbonyl)-N-(4-(1-hydroxy-1,3-dihydrobenzo[c][1,2]oxaborole-6-carboxamido)butyl)glycine (DS38);

N-(1-hydroxy-1,3-dihydrobenzo[c][1,2]oxaborole-6-carbonyl)-N-((1S,2S)-2-(1-hydroxy-1,3-dihydrobenzo[c][1,2]oxaborole-6-carboxamido)cyclohexyl)glycine (DS39);

(R)—N-(1-hydroxy-1,3-dihydrobenzo[c][1,2]oxaborole-6-carbonyl)-N-(2-(1-hydroxy-1,3-dihydrobenzo[c][1,2]oxaborole-6-carboxamido)propyl)glycine (DS40);

(S)—N-(1-hydroxy-1,3-dihydrobenzo[c][1,2]oxaborole-6-carbonyl)-N-(2-(1-hydroxy-1,3-dihydrobenzo[c][1,2]oxaborole-6-carboxamido)propyl)glycine (DS41);

N-(1-hydroxy-1,3-dihydrobenzo[c][1,2]oxaborole-6-carbonyl)-N-(2-(1-hydroxy-1,3-dihydrobenzo[c][1,2]oxaborole-6-carboxamido)cyclohexyl)glycine (DS42);

N-(3-(4-borono-3,5-difluorobenzamido)propyl)-N-(4-borono-3,5-difluorobenzoyl)glycine (DS43);

N-(3-(4-borono-2-fluorobenzamido)propyl)-N-(4-borono-2-fluorobenzoyl)glycine (DS44);

N-(2-(N-ethyl-1-hydroxy-1,3-dihydrobenzo[c][1,2]oxaborole-6-carboxamido)ethyl)-N-(1-hydroxy-1,3-dihydrobenzo[c][1,2]oxaborole-6-carbonyl)glycine (DS45);

N-(1-hydroxy-1,3-dihydrobenzo[c][1,2]oxaborole-6-carbonyl)-N-(2-(1-hydroxy-N-(2-hydroxyethyl)-1,3-dihydrobenzo[c][1,2]oxaborole-6-carboxamido)ethyl)glycine (DS46);

N-(1-hydroxy-1,3-dihydrobenzo[c][1,2]oxaborole-6-carbonyl)-N-(5-(1-hydroxy-1,3-dihydrobenzo[c][1,2]oxaborole-6-carboxamido)hexyl)glycine (DS47);

N-(1-hydroxy-1,3-dihydrobenzo[c][1,2]oxaborole-6-carbonyl)-N-(4-((4-(1-hydroxy-1,3-dihydrobenzo[c][1,2]oxaborole-6-carboxamido)cyclohexyl)methyl)cyclohexyl)glycine (DS48);

((2S,4S)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carbonyl)glycine (DS49);

((2S,4S)-4-(3-borono-4-fluorobenzamido)-1-(3-borono-4-fluorobenzoyl)pyrrolidine-2-carbonyl)glycine (DS50);

((2S,4S)-4-(3-borono-5-nitrobenzamido)-1-(3-borono-5-nitrobenzoyl)pyrrolidine-2-carbonyl)glycine (DS51);

((2S,4S)-4-(5-borono-2-fluorobenzamido)-1-(5-borono-2-fluorobenzoyl)pyrrolidine-2-carbonyl)glycine (DS52);

(S)-(1,4-bis(1-hydroxy-1,3-dihydrobenzo[c][1,2]oxaborole-6-carbonyl)piperazine-2-carbonyl)glycine (DS53);

(S)—N-(3-amino-2-(1-hydroxy-1,3-dihydrobenzo[c][1,2]oxaborole-6-carboxamido-3-oxopropyl)-N-benzyl-1-hydroxy-1,3-dihydrobenzo[c][1,2]oxaborole-6-carboxamide (DS54);

(S)—N-(3-amino-2-(1-hydroxy-1,3-dihydrobenzo[c][1,2]oxaborole-6-carboxamido)-3-oxopropyl)-1-hydroxy-N-(4-(trifluoromethyl)benzyl)-1,3-dihydrobenzo[c][1,2]oxaborole-6-carboxamide (DS55);

(S)—N-(3-amino-2-(1-hydroxy-1,3-dihydrobenzo[c][1,2]oxaborole-6-carboxamido)-3-oxopropyl)-N-ethyl-1-hydroxy-1,3-dihydrobenzo[c][1,2]oxaborole-6-carboxamide (DS56);

(S)—N-(3-amino-2-(1-hydroxy-1,3-dihydrobenzo[c][1,2]oxaborole-6-carboxamido)-3-oxopropyl)-1-hydroxy-N-propyl-1,3-dihydrobenzo[c][1,2]oxaborole-6-carboxamide (DS57);

(S)—N-(3-amino-2-(1-hydroxy-1,3-dihydrobenzo[c][1,2]oxaborole-6-carboxamido)-3-oxopropyl)-1-hydroxy-N-isobutyl-1,3-dihydrobenzo[c][1,2]oxaborole-6-carboxamide (DS58);

(S)—N-(3-amino-2-(1-hydroxy-1,3-dihydrobenzo[c][1,2]oxaborole-6-carboxamido)-3-oxopropyl)-1-hydroxy-N-((5-(thiophen-2-yl)pyridin-2-yl)methyl)-1,3-dihydrobenzo[c][1,2]oxaborole-6-carboxamide (DS59);

(S)—N-(3-amino-2-(1-hydroxy-1,3-dihydrobenzo[c][1,2]oxaborole-6-carboxamido)-3-oxopropyl)-1-hydroxy-N-isopentyl-1,3-dihydrobenzo[c][1,2]oxaborole-6-carboxamide (DS60);

(S)—N-(3-amino-2-(1-hydroxy-1,3-dihydrobenzo[c][1,2]oxaborole-6-carboxamido)-3-oxopropyl)-1-hydroxy-N-(quinolin-5-ylmethyl)-1,3-dihydrobenzo[c][1,2]oxaborole-6-carboxamide (DS61);

(S)—N-(3-amino-2-(1-hydroxy-1,3-dihydrobenzo[c][1,2]oxaborole-6-carboxamido)-3-oxopropyl)-1-hydroxy-N-(2-(trifluoromethoxy)benzyl)-1,3-dihydrobenzo[c][1,2]oxaborole-6-carboxamide (DS62);

(S)—N-(3-amino-2-(1-hydroxy-1,3-dihydrobenzo[c][1,2]oxaborole-6-carboxamido)-3-oxopropyl)-1-hydroxy-N-(4-(methylsulfonyl)benzyl)-1,3-dihydrobenzo[c][1,2]oxaborole-6-carboxamide (DS63);

(3-((2S,4S)-4-(5-borono-2-(methylsulfonyl)benzamido)-2-carbamoylpyrrolidine-1-carbonyl)-4-(methylsulfonyl)phenyl)boronic acid (DS64);

(4-(((3S,5S)-1-(4-borono-2,6-difluorobenzoyl)-5-carbamoylpyrrolidin-3-yl)carbamoyl)-3,5-difluorophenyl)boronic acid (DS65);

(R,E)-4,5-bis(1-hydroxy-1,3-dihydrobenzo[c][1,2]oxaborole-6-carboxanido)pent-2-enoic acid (DS66);

(2S,4S)-1-(1-hydroxy-4-(trifluoromethyl)-1,3-dihydrobenzo[c][1,2]oxaborole-6-carbonyl)-4-(1-hydroxy-4-(trifluoromethyl)-1,3-dihydrobenzo[c][1,2]oxaborole-6-carboxamido)pyrrolidine-2-carboxamide (DS67);

N,N'-((2S,3S)-1-amino-1-oxobutane-2,3-diyl)bis(1-hydroxy-1,3-dihydrobenzo[c][1,2]oxaborole-6-carboxamide) (DS68);

(R)-3,4-bis(1-hydroxy-1,3-dihydrobenzo[c][1,2]oxaborole-6-carboxamido)butanoic acid (DS69);

3-((2S,4S)-1-(1-hydroxy-1,3-dihydrobenzo[c][1,2]oxa-
borole-6-carbonyl)-4-(1-hydroxy-1,3-dihydrobenzo[c][1,
2]oxaborole-6-carboxamido)pyrrolidine-2-carboxamido)
propanoic acid (DS70);

(S)-3-(1-hydroxy-1,3-dihydrobenzo[c][1,2]oxaborole-5-
carboxamido)-4-(1-hydroxy-1,3-dihydrobenzo[c][1,2]
oxaborole-6-carboxamido)butanoic acid (DS71);

(R)-4-(1-hydroxy-1,3-dihydrobenzo[c][1,2]oxaborole-5-
carboxamido)-5-(1-hydroxy-1,3-dihydrobenzo[c][1,2]
oxaborole-6-carboxamido)pentanoic acid (DS72);

(2S,4R)-1-(1-hydroxy-1,3-dihydrobenzo[c][1,2]oxaborole-
6-carbonyl)-4-(1-hydroxy-1,3-dihydrobenzo[c][1,2]oxa-
borole-6-carboxamido)pyrrolidine-2-carboxylic    acid
(DS73);

(2S,4R)-1-(1-hydroxy-4-(trifluoromethyl)-1,3-dihyd-
robenzo[c][1,2]oxaborole-6-carbonyl)-4-(1-hydroxy-4-
(trifluoromethyl)-1,3-dihydrobenzo[c][1,2]oxaborole-6-
carboxamido)pyrrolidine-2-carboxylic acid (DS74);

(2S,3S)-3-(1-hydroxy-4-(trifluoromethyl)-1,3-dihyd-
robenzo[c][1,2]oxaborole-6-carboxamido)-2-(1-hydroxy-
7-(trifluoromethyl)-1,3-dihydrobenzo[c][1,2]oxaborole-
5-carboxamido)butanoic acid (DS75);

(R)-5-(1-hydroxy-4-(trifluoromethyl)-1,3-dihydrobenzo[c]
[1,2]oxaborole-6-carboxamido)-4-(1-hydroxy-7-(trifluo-
romethyl)-1,3-dihydrobenzo[c][1,2]oxaborole-5-carbox-
amido)pentanoic acid (DS76);

((2S,4S)-1-(5-borono-2-nitrobenzoyl)-4-(1-hydroxy-1,3-di-
hydrobenzo[c][1,2]oxaborole-6-carboxamido)pyrroli-
dine-2-carbonyl)glycine (DS77);

((2S,4S)-1-(5-borono-2-(methylsulfonyl)benzoyl)-4-(1-hy-
droxy-1,3-dihydrobenzo[c][1,2]oxaborole-6-carbox-
amido)pyrrolidine-2-carbonyl)glycine (DS78);

((2S,4S)-1-(3-borono-2,6-difluorobenzoyl)-4-(1-hydroxy-1,
3-dihydrobenzo[c][1,2]oxaborole-6-carboxamido)pyrro-
lidine-2-carbonyl)glycine (DS79);

(S)-(3-(3-borono-4-fluorobenzyl)(5,6-diamino-6-oxo-
hexyl)carbamoyl)-5-nitrophenyl)boronic acid (DS80);

(S)-(3-((4-borono-3,5-difluorobenzyl)(5,6-diamino-6-oxo-
hexyl)carbamoyl)-5-nitrophenyl)boronic acid (DS81);

(S)-(3-((3-boronobenzyl)(5,6-diamino-6-oxohexyl)carbam-
oyl)-5-nitrophenyl)boronic acid (DS82);

(S)-(3-((4-borono-2-methoxybenzyl)(5,6-diamino-6-oxo-
hexyl)carbamoyl)-5-nitrophenyl)boronic acid (DS83);

(S)-(3-((4-borono-2-(trifluoromethyl)benzyl)(5,6-diamino-
6-oxohexyl)carbamoyl)-5-nitrophenyl)boronic    acid
(DS84);

(S)-(5-((3-borono-N-(5,6-diamino-6-oxohexyl)-4-fluo-
robenzamido)methyl)-2-fluorophenyl)boronic    acid
(DS85);

(S)-(5-((4-borono-3,5-difluorobenzyl)(5,6-diamino-6-oxo-
hexyl)carbamoyl)-2-fluorophenyl)boronic acid (DS86);

(S)-(3-((3-borono-N-(5,6-diamino-6-oxohexyl)-4-fluo-
robenzamido)methyl) phenyl)boronic acid (DS87);

(S)-(5-((4-borono-2-methoxybenzyl)(5,6-diamino-6-oxo-
hexyl)carbamoyl)-2-fluorophenyl)boronic acid (DS88);

(S)-(5-((4-borono-3-(trifluoromethyl)benzyl)(5,6-diamino-
6-oxohexyl)carbamoyl)-2-fluorophenyl)boronic    acid
(DS89);

(S)-(4-((3-borono-4-fluorobenzyl)(5,6-diamino-6-oxo-
hexyl)carbamoyl)-2-fluorophenyl)boronic acid (DS90);

(S)-(4-((4-borono-3,5-difluorobenzyl)(5,6-diamino-6-oxo-
hexyl)carbamoyl)-2-fluorophenyl)boronic acid (DS91);

(S)-(4-((3-boronobenzyl)(5,6-diamino-6-oxohexyl)carbam-
oyl)-2-fluorophenyl)boronic acid (DS92);

(S)-(4-((4-borono-2-methoxybenzyl)(5,6-diamino-6-oxo-
hexyl)carbamoyl)-2-fluorophenyl)boronic acid (DS93);

(S)-(4-((4-borono-2-(trifluoromethyl)benzyl)(5,6-diamino-
6-oxohexyl)carbamoyl)-2-fluorophenyl)boronic    acid
(DS94);

(S)-(5-((3-borono-5-bromo-N-(5,6-diamino-6-oxohexyl)
benzamido)methyl)-2-fluorophenyl)boronic acid (DS95);

(S)-(3-((4-borono-3,5-difluorobenzyl)(5,6-diamino-6-oxo-
hexyl)carbamoyl)-5-bromophenyl)boronic acid (DS96);

(S)-(3-((3-borono-5-bromo-N-(5,6-diamino-6-oxohexyl)
benzamido)methyl) phenyl)boronic acid (DS97);

(S)-(3-((3-borono-5-bromo-N-(5,6-diamino-6-oxohexyl)
benzamido)methyl)-5-methoxyphenyl)boronic    acid
(DS98);

(S)-(3-((4-borono-2-(trifluoromethyl)benzyl)(5,6-diamino-
6-oxohexyl)carbamoyl)-5-bromophenyl)boronic    acid
(DS99);

(S)-(3-((3-borono-4-fluorobenzyl)(5,6-diamino-6-oxo-
hexyl)carbamoyl)-5-fluorophenyl)boronic acid (DS100);

(S)-(3-((4-borono-3-methoxybenzyl)(5,6-diamino-6-oxo-
hexyl)carbamoyl)-5-fluorophenyl)boronic acid (DS101);

(S)-(3-((4-borono-2-(trifluoromethyl)benzyl)(5,6-diamino-
6-oxohexyl)carbamoyl)-5-fluorophenyl)boronic    acid
(DS102);

(S)-(4-((N-(5,6-diamino-6-oxohexyl)-1-hydroxy-1,3-dihyd-
robenzo[c][1,2]oxaborole-6-carboxamido)methyl)-2-
fluorophenyl)boronic acid (DS103);

(S)-(4-((N-(5,6-diamino-6-oxohexyl)-1-hydroxy-1,3-dihyd-
robenzo[c][1,2]oxaborole-6-carboxamido)methyl)-2,6-
difluorophenyl)boronic acid (DS104);

(S)-(3-((N-(5,6-diamino-6-oxohexyl)-1-hydroxy-1,3-dihyd-
robenzo[c][1,2]oxaborole-6-carboxamido)methyl)phe-
nyl)boronic acid (DS105);

(S)-(4-((N-(5,6-diamino-6-oxohexyl)-1-hydroxy-1,3-dihyd-
robenzo[c][1,2]oxaborole-6-carboxamido)methyl)-3-
methoxyphenyl)boronic acid (DS106);

(S)—N-(5,6-diamino-6-oxohexyl)-1-hydroxy-N-((1-hy-
droxy-1,3-dihydrobenzo[c][1,2]oxaborol-6-yl)methyl)-1,
3-dihydrobenzo[c][1,2]oxaborole-6-carboxamide
(DS107);

(S)—N-(4-amino-3-(1-hydroxy-1,3-dihydrobenzo[c][1,2]
oxaborole-6-carboxamido-4-oxobutyl)-1-hydroxy-N-
((1-hydroxy-1,3-dihydrobenzo[c][1,2]oxaborol-6-yl)
methyl)-1,3-dihydrobenzo[c][1,2]oxaborole-6-
carboxamide (DS108);

(S)—N-(6-amino-5-(1-hydroxy-1,3-dihydrobenzo[c][1,2]
oxaborole-6-carboxamido)-6-oxohexyl)-1-hydroxy-N-
((1-hydroxy-1,3-dihydrobenzo[c][1,2]oxaborol-6-yl)
methyl)-1,3-dihydrobenzo[c][1,2]oxaborole-6-
carboxamide (DS109);

(2S,4S)-1-(1-hydroxy-1,3-dihydrobenzo[c][1,2]oxaborole-
6-carbonyl)-4-(1-hydroxy-1,3-dihydrobenzo[c][1,2]oxa-
borole-6-carboxamido)pyrrolidine-2-carboxylic    acid
(DS110);

(2S,3S)-2-(1-hydroxy-1,3-dihydrobenzo[c][1,2]oxaborole-
5-carboxamido)-3-(1'-hydroxy-1,3-dihydrobenzo[c][1,2]
oxaborole-6-carboxamido)butanoic acid (DS111); and (2S,4R)-1-(1-hydroxy-1,3-dihydrobenzo[c][1,2]oxaborole-
6-carbonyl)-4-(1-hydroxy-1,3-dihydrobenzo[c][1,2]oxa-
borole-6-carboxamido)pyrrolidine-2-carboxylic    acid
(DS112);

N-(1-hydroxy-3,3-dimethyl-1,3-dihydrobenzo[c][1,2]oxa-
borole-6-carbonyl)-N-(2-(1-hydroxy-3,3-dimethyl-1,3-
dihydrobenzo[c][1,2]oxaborole-6-carboxanido)ethyl)gly-
cine (DS113);

N-(1-hydroxy-3,4-dihydro-1H-benzo[c][1,2]oxaborinine-7-
carbonyl)-N-(2-(1-hydroxy-3,4-dihydro-1H-benzo[c][1,
2]oxaborinine-7-carboxamido)ethyl)glycine (DS114);

N-(2-(2-(1-hydroxy-1,3-dihydrobenzo[c][1,2]oxaborol-7-yl)acetamido)ethyl)-N-(2-(1-hydroxy-1,3-dihydrobenzo[c][1,2]oxaborol-7-yl)acetyl)glycine (DS115);

N-(1-hydroxy-3,3-dimethyl-1,3-dihydrobenzo[c][1,2]oxaborole-7-carbonyl)-N-(2-(1-hydroxy-3,3-dimethyl-1,3-dihydrobenzo[c][1,2]oxaborole-7-carboxamido)ethyl) glycine (DS116);

N-(1-hydroxy-1,3-dihydrobenzo[c][1,2]oxaborole-3-carbonyl)-N-(2-(1-hydroxy-1,3-dihydrobenzo[c][1,2]oxaborole-3-carboxamido)ethyl)glycine (DS117);

3,5-bis((1-hydroxy-3,3-dimethyl-1,3-dihydrobenzo[c][1,2]oxaborole-6-carboxamido)methyl)benzoic acid (DS118);

3,5-bis((1-hydroxy-3,4-dihydro-1H-benzo[c][1,2]oxaborinine-7-carboxamido) methyl)benzoic acid (DS119);

3,5-bis((2-(1-hydroxy-1,3-dihydrobenzo[c][1,2]oxaborol-7-yl)acetamido)methyl) benzoic acid (DS120);

3,5-bis((1-hydroxy-3,3-dimethyl-1,3-dihydrobenzo[c][1,2]oxaborole-7-carboxamido)methyl) benzoic acid (DS121);

3,5-bis((1-hydroxy-1,3-dihydrobenzo[c][1,2]oxaborole-3-carboxamido)methyl)benzoic acid (DS122);

(S)-3-(2,3-bis(1-hydroxy-3,3-dimethyl-1,3-dihydrobenzo[c][1,2]oxaborole-6-carboxamido) propanamido)propanoic acid (DS123);

(S)-3-(2,3-bis(1-hydroxy-3,4-dihydro-1H-benzo[c][1,2]oxaborinine-7-carboxamido) propanamido)propanoic acid (DS124);

(S)-3-(2,3-bis(2-(1-hydroxy-1,3-dihydrobenzo[c][1,2]oxaborol-7-yl)acetamido) propanamido)propanoic acid (DS125);

(S)-3-(2,3-bis(1-hydroxy-3,3-dimethyl-1,3-dihydrobenzo[c][1,2]oxaborole-7-carboxamido) propanamido)propanoic acid (DS126);

3-((2S)-2,3-bis(1-hydroxy-1,3-dihydrobenzo[c][1,2]oxaborole-3-carboxamido) propanamido)propanoic acid (DS127);

(3,5-bis((1-hydroxy-3,3-dimethyl-1,3-dihydrobenzo[c][1,2]oxaborole-6-carboxamido) methyl)benzoyl)glutamic acid (DS128);

(3,5-bis((1-hydroxy-3,4-dihydro-1H-benzo[c][1,2]oxaborinine-7-carboxamido) methyl)benzoyl)glutamic acid (DS129);

(3,5-bis((2-(1-hydroxy-1,3-dihydrobenzo[c][1,2]oxaborol-7-yl)acetamido)methyl)benzoyl) glutamic acid (DS130);

(3,5-bis((1-hydroxy-3,3-dimethyl-1,3-dihydrobenzo[c][1,2]oxaborole-7-carboxamido)methyl) benzoyl)glutamic acid (DS131);

(3,5-bis((1-hydroxy-1,3-dihydrobenzo[c][1,2]oxaborole-3-carboxamido)methyl)benzoyl) glutamic acid (DS132);

4-(3,4-bis(1-hydroxy-3,3-dimethyl-1,3-dihydrobenzo[c][1,2]oxaborole-6-carboxamido) pyrrolidin-1-yl)-4-oxobutanoic acid (DS133);

4-(3,4-bis(1-hydroxy-3,4-dihydro-1H-benzo[c][1,2]oxaborinine-7-carboxamido)pyrrolidin-1-yl)-4-oxobutanoic acid (DS134);

4-(3,4-bis(2-(1-hydroxy-1,3-dihydrobenzo[c][1,2]oxaborol-7-yl)acetamido)pyrrolidin-1-yl)-4-oxobutanoic acid (DS135);

4-(3,4-bis(1-hydroxy-3,3-dimethyl-1,3-dihydrobenzo[c][1,2]oxaborole-7-carboxamido)pyrrolidin-1-yl)-4-oxobutanoic acid (DS136);

4-(3,4-bis(1-hydroxy-1,3-dihydrobenzo[c][1,2]oxaborole-3-carboxamido)pyrrolidin-1-yl)-4-oxobutanoic acid (DS137);

((S)-2,3-bis(1-hydroxy-3,3-dimethyl-1,3-dihydrobenzo[c][1,2]oxaborole-6-carboxamido)propanoyl)-L-glutamic acid (DS138);

((S)-2,3-bis(1-hydroxy-3,4-dihydro-1H-benzo[c][1,2]oxaborinine-7-carboxamido) propanoyl)-L-glutamic acid (DS139);

((S)-2,3-bis(2-(1-hydroxy-1,3-dihydrobenzo[c][1,2]oxaborol-7-yl)acetamido)propanoyl)-L-glutamic acid (DS140);

((S)-2,3-bis(1-hydroxy-3,3-dimethyl-1,3-dihydrobenzo[c][1,2]oxaborole-7-carboxamido) propanoyl)-L-glutamic acid (DS141);

((2S)-2,3-bis(1-hydroxy-1,3-dihydrobenzo[c][1,2]oxaborole-3-carboxamido) propanoyl)-L-glutamic acid (DS142);

(4-(3,4-bis(1-hydroxy-3,3-dimethyl-1,3-dihydrobenzo[c][1,2]oxaborole-6-carboxamido)pyrrolidin-1-yl)-4-oxobutanoyl)-L-glutamic acid (DS143);

(4-(3,4-bis(1-hydroxy-3,4-dihydro-1H-benzo[c][1,2]oxaborinine-7-carboxamido) pyrrolidin-1-yl)-4-oxobutanoyl)-L-glutamic acid (DS144);

(4-(3,4-bis(2-(1-hydroxy-1,3-dihydrobenzo[c][1,2]oxaborol-7-yl)acetamido)pyrrolidin-1-yl)-4-oxobutanoyl)-L-glutamic acid (DS145);

(4-(3,4-bis(1-hydroxy-3,3-dimethyl-1,3-dihydrobenzo[c][1,2]oxaborole-7-carboxamido) pyrrolidin-1-yl)-4-oxobutanoyl)-L-glutamic acid (DS146);

(4-(3,4-bis(1-hydroxy-1,3-dihydrobenzo[c][1,2]oxaborole-3-carboxamido)pyrrolidin-1-yl)-4-oxobutanoyl)-L-glutamic acid (DS147);

(S)-2,3-bis(1-hydroxy-3,3-dimethyl-1,3-dihydrobenzo[c][1,2]oxaborole-6-carboxamido)propanoic acid (DS148);

(S)-2,3-bis(1-hydroxy-3,4-dihydro-1H-benzo[c][1,2]oxaborinine-7-carboxamido)propanoic acid (DS149);

(S)-2,3-bis(2-(1-hydroxy-1,3-dihydrobenzo[c][1,2]oxaborol-7-yl)acetamido)propanoic acid (DS150);

(S)-2,3-bis(1-hydroxy-3,3-dimethyl-1,3-dihydrobenzo[c][1,2]oxaborole-7-carboxamido)propanoic acid (DS151); and (2S)-2,3-bis(1-hydroxy-1,3-dihydrobenzo[c][1,2]oxaborole-3-carboxamido)propanoic acid (DS152). In some embodiments, the compound of Formula (I) is selected from:

$$\left( (Z1c)_{\overline{p'}}(Z1a)_{\overline{m'}} \right)_{q'} X1; \qquad \text{(Formula IA)}$$

$$\left[ Z1c{-}(Z1b)_{\overline{n'}} \right]_{q'} X1; \qquad \text{(Formula IB)}$$

$$\left( (Z1c)_{\overline{p'}}(Z1b)_{\overline{n'}} \right)_{q'} X1; \quad \text{and} \qquad \text{(Formula IC)}$$

$$\left( (Z1c)_{\overline{p'}} \right)_{q'} X1. \qquad \text{(Formula ID)}$$

In some embodiments, the compound of Formula I is selected from:

$$\left[ [Z1c]_1 \right]_1 X1; \quad \left[ [Z1c]_1 \right]_2 X1; \quad \left[ [Z1c]_1 \right]_3 X1; \quad \left[ [Z1c]_1 \right]_4 X1;$$

$$\left[ [Z1c]_1 \right]_5 X1; \quad \left[ [Z1c]_2{-}[Z1a]_1 \right]_2 X1;$$

$$\left[ [Z1c]_2{-}[Z1a]_1 \right]_2 X1{-}[Z1c]_1 \right]_1;$$

$$\left[ [Z1c]_2{-}[Z1a]_1 \right]_2 X1{-}[Z1c]_1 \right]_2;$$

-continued $$\left[[Z1c]_2 {-\!\!-\!} [Z1a]_1\!\!\mid\!\!_1\!\!\mid\!\!_1\!\!+\!\![Z1b]_1\!\mid\!\!_1\!\!\mid\!\!_1 {-\!} X1;\right.$$

$$\left[[Z1c]_2 {-\!\!-\!} [Z1a]_1 {-\!} [Z1b]_1\!\!\mid\!\!_1 {-\!} X1 {-\!}[Z1c]_1\right]_1;$$

$$\left[[Z1c]_1 {-\!\!-\!} [Z1b]_1\!\!\mid\!\!_1 {-\!} X1;\right. \quad \left[[Z1c]_2 {-\!\!-\!} [Z1a]_1\!\!\mid\!\!_1 {-\!} X1 {-\!}[Z1c]_1\right];$$

$$\left[[Z1c]_2 {-\!\!-\!} [Z1a]_1\!\!\mid\!\!_1 {-\!} X1 {-\!}[Z1c]_1\right]_2; \quad \text{and}$$

$$\left[[Z1c]_2 {-\!\!-\!} [Z1a]_1\!\!\mid\!\!_1 {-\!} X1 {-\!}[Z1c]_1\right]_2$$

In some embodiments, the compound is selected from $$\left[[Z1c]_2 {-\!\!-\!} [Z1a]_1\!\!\mid\!\!_1 {-\!} X1 {-\!}[Z1c]_1\right]_1 \quad \text{and} \quad \left[[Z1c]_1\!\!\mid\!\!_1 {-\!} X1.\right.$$

In some embodiments, the compound of Formula I is selected from:

$$\left[[Z1c]_1 {-\!}\boxed{\begin{matrix}\text{indirect}\\\text{linker}\end{matrix}}\!\mid\!\!_1 {-\!} X1;\right. \quad \left[\left[[Z1c]_1 {-\!}\boxed{\begin{matrix}\text{indirect}\\\text{linker}\end{matrix}}\!\mid\!\!_1 {-\!} Z1a {-\!} X1;\right.\right.$$

$$\left[\left[[Z1c]_1 {-\!}\boxed{\begin{matrix}\text{indirect}\\\text{linker}\end{matrix}}\!\mid\!\!_1 {-\!} Z1a {-\!} X1;\right]_2\right.$$

$$\left[\left[[Z1c]_1 {-\!}\boxed{\begin{matrix}\text{indirect}\\\text{linker}\end{matrix}}\!\mid\!\!_1 {-\!} Z1a\right]_2 {-\!} X1 {-\!}\boxed{\begin{matrix}\text{indirect}\\\text{linker}\end{matrix}} {-\![Z1c]_1}\right]_1; \quad \text{and}$$

$$\left[\left[[Z1c]_1 {-\!}\boxed{\begin{matrix}\text{indirect}\\\text{linker}\end{matrix}}\!\mid\!\!_1 {-\!} Z1a\right]_2 {-\!} X1 {-\!}\boxed{\begin{matrix}\text{indirect}\\\text{linker}\end{matrix}} {-\![Z1c]_1}\right]_2.$$

In some embodiments, the compound is $$\left[[Z1c]_1\!\!\mid\!\!_1 {-\!} X1,\right.$$

when p'=1, m'=0, o'=1, n'=0, and q'=1.

In some embodiments, the compound is $$\left[[Z1c]_2 {-\!\!-\!} [Z1a]_1\!\!\mid\!\!_2 {-\!} X1 {-\!}[Z1c]_1\right]_1,$$

when p'=1 and 2, m'=0 and 1, o'=1 and 1, n'=0, and q'=2 and 1.

In some embodiments, the present disclosure is directed to a compound comprising one or more diboronates, wherein the compound is represented by Formula IB, or a stereoisomer or a mixture of stereoisomers, or pharmaceutically acceptable salt thereof:

(Formula IB)

$$\left[Z1c {-\!}(Z1b)_{n'}\!\!\mid\!\!\right]_{q'} {-\!} X1\right.\!_{c,}$$

wherein:

each Z1b is independently a linker moiety, and each n' is 0, 1, 2, 3, 4, or 5;

X1 comprises a drug substance or a polypeptide;

each Z1c is covalently conjugated directly or via one or more Z1b to an amine in X1;

wherein a) at least one Z1c is independently selected from a diboronate, wherein the diboronate is independently selected from Formulae FF12A, FF12B, FF12C, FF12D, FF116A, FF116B, FF116C, FF116D, FF225, and FF227; and b) each additional Z1c is optionally independently selected from a diboronate, a sugar moiety, a diol containing moiety, and a polyol containing moiety, wherein the diboronate is independently selected from Formulae FF12A, FF12B, FF12C, FF12D, FF116A, FF116B, FF116C, FF116D, FF225, and FF227; and each q' is 1, 2, 3, 4, or 5, wherein when q' is 2 or more, each corresponding Z1c and Z1b is independently selected and may be the same or different; and wherein Formulae FF12A, FF12B, FF12C, FF12D, FF116A, FF116B, FF116C, FF116D, FF225, and FF227 are:

FF12A

FF12B

FF12C

FF12D

FF116A

FF116B

-continued

FF116C

FF116D

FF225

FF227 wherein X represents a point of covalent attachment to an amine of Z1b or to an amine of X1 when n' is 0;

i is 1, 2, 3, 4, 5, 6, or 7; and wherein $B_1$ and $B_2$, which may be identical or different, each independently represent an aromatic boron-containing group; and wherein when each Z1c is selected from Formulae FF225 and FF227, at least one of the $B_1$ and the $B_2$ is Formula F7, wherein Formula F7 is:

(F7)

wherein:

one $R_1$ represents (C=O)—*, wherein —* represents the attachment point to the rest of Z1c;

each remaining $R_1$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)$ $NH(CH_2)_mCH_3$, and $OCF_3$, wherein m is 1, 2, 3, 4, 5, 6, or 7;

Y8 is O or NR, wherein R is an alkyl group (e.g., $C_1$-$C_6$alkyl group) or H; and each Y10 is independently selected from H, $CH_3$, F, and $CF_3$, wherein for at least one F7 at least one Y10 is not H.

In some embodiments, each Z1b is independently a linker moiety, and each n' is 0, 1, 2, 3, 4, or 5, wherein at least one n' is 1, 2, 3, 4, or 5. In some embodiments, each n' is 1, 2, 3, 4, or 5. In some embodiments, each n' is 2, 3, or 4.

In some embodiments, the compound is selected from a compound represented by Formula IB, a stereoisomer thereof, a mixture of stereoisomers thereof, and pharmaceutically acceptable salt thereof, with the proviso that the compound is not any of Examples 1-880 disclosed in PCT/US2021/059802.

In some embodiments, the compound is represented by Formula IB, or a stereoisomer or a mixture of stereoisomers, or pharmaceutically acceptable salt thereof:

(Formula IB)

$$\left[ Z1c\text{—}(Z1b)_{n'} \right]_{q'}\text{—}X1,$$

wherein:

each n' is 0, 1, 2, or 3, wherein at least one n' is 1, 2, or 3;

each q' is 1, 2, 3, or 4;

each Z1b is independently a linker moiety, wherein each Z1c is covalently conjugated directly or via one or more of the Z1b to an amine of X1, with the proviso that the Z1b is not a diol containing moiety, and wherein one or more positions of the compound may comprise an isotope.

In some embodiments, each Z1c is covalently conjugated via one or more of the Z1b to an amine of X1, wherein each Z1b is independently selected from Formulae FL3, FL5, FL5A, FL5B, FL65A, FL65B, FL69, FL69A, FL69B, FL70, FL70A, and FL70B;

wherein FL3, FL5, FL5A, FL5B, FL65A, FL65B, FL69, FL69A, FL69B, FL70, FL70A, and FL70B are:

FL3

FL5

FL5A

FL5B

FL65A

-continued

FL65B

FL69

FL69A

FL69B

FL70

FL70A

FL70B wherein:

R″ represents a covalent bond, directly or indirectly, to Z1c;

Z″ represents a covalent bond, directly or indirectly, to X1;

A' is selected from H and a $C_1$- to $C_2$0 alkyl; and

A″ is a $C_2$-$C_{20}$ acyl group optionally terminating in an acid group, wherein one or more carbon atoms of the $C_2$-$C_{20}$ acyl group are optionally and independently replaced by a group selected from C(=O), O, NH, $NH_2$, S, S(O), $SO_2$, phenyl, 5-membered heterocyclyl, 6-membered heterocyclyl, 5-membered heteroaryl, 6-membered heteroaryl, and wherein the $C_2$-$C_{20}$ acyl group, NH, $NH_2$, $SO_2$, phenyl, 5-membered heterocyclyl, 6-membered heterocyclyl, 5-membered heteroaryl, and 6-membered heteroaryl is each independently substituted with 0, 1, 2, 3, or 4 $R_x$, wherein $R_x$ is selected from $C_1$-$C_5$ alkyl, halogen (e.g., F, Cl, Br, I), $C_1$-$C_5$ haloalkyl, carboxylic acid, hydroxyl, —O—$C_1$-$C_5$ alkyl, —S(=O)$_2$NH$_2$, $NH_2$, 5-membered heterocyclyl, 6-membered heterocyclyl, 5-membered heteroaryl, phenyl, and 6-membered heteroaryl;

p is 1, 2, 3, 4, or 5, q is 1, 2, 3, 4, or 5, and any primary amine is optionally acetylated or alkylated.

In some embodiments, A' is H. In some embodiments, A' is a $C_1$- to $C_{20}$ alkyl. In some embodiments, the alkyl group is a CI-Cis alkyl group. In some embodiments, the alkyl group is a $C_1$-$C_{16}$ alkyl group. In some embodiments, the alkyl group is a $C_1$-$C_{14}$ alkyl group. In some embodiments, the alkyl group is a $C_1$-$C_{12}$ alkyl group. In some embodiments, the alkyl group is a $C_1$-$C_{10}$ alkyl group. In some embodiments, the alkyl group is a $C_1$-$C_8$ alkyl group. In some embodiments, the alkyl group is a $C_1$-$C_6$ alkyl group. In some embodiments, the alkyl group is a $C_1$-$C_4$ alkyl group. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

In some embodiments, each Z1b is independently selected from:

FL3

FL5B

FL65A

-continued

FL65B

In some embodiments, each A" is independently selected from:

-continued

FL69A

wherein:

p is 1, 2, 3, 4, or 5.

In some embodiments, each Z1b is independently selected from:

AB-1

AB-2

AB-3

AB-4

AB-5

AB-6

AB-7

AB-8

305
-continued

306
-continued

AB-9

AB-10

AB-11

AB-12

AB-13

AB-14

AB-15

AB-16

AB-17

AB-18

AB-19

AB-20

AB-21

AB-22

AB-23

AB-24

AB-25

AB-26

AB-27

AB-28

-continued

AB-29

AB-30

AB-31

AB-32

AB-33

AB-34

AB-35

AB-36

-continued

AB-37

AB-37A

AB-38

, and

AB-39

In some embodiments, each A″ is independently selected from AB-1, AB-2, AB-3, AB-4, AB-5, AB-7, AB-8, AB-9, AB-10, AB-li, AB-12, AB-13, AB-14, AB-15, AB-16, AB-17, AB-18, AB-19, AB-20, AB-21, AB-22, AB-23, AB-24, AB-25, AB-26, AB-27, AB-28, AB-29, AB-30, AB-31, AB-32, AB-33, AB-34, AB-35, AB-36, AB-37, AB-38, and AB-39. In some embodiments, each A″ is independently selected from AB-1, AB-2, AB-3, AB-4, AB-5, AB-7, AB-8, AB-9, AB-10, AB-11, AB-12, AB-13, and AB-14. In some embodiments, each A″ is independently selected from AB-15, AB-16, AB-17, AB-18, AB-19, AB-20, AB-21, AB-22, AB-23, AB-24, AB-25, AB-26, AB-27, and AB-28.

In some embodiments, $B_1$ and $B_2$ are independently selected from Formulae F2 and F7, wherein Formulae F2 and F7 are:

(F2)

-continued (F7)

wherein:

one $R_1$ represents (C=O)—*, wherein —* represents the attachment point to the rest of Z1c;

each remaining $R_1$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_m$, $CH_3$, —$(SO_2)NH$—$CH_3$, —$(SO_2)$ $NH(CH_2)_mCH_3$, and $OCF_3$, wherein m is 1, 2, 3, 4, 5, 6, or 7;

Y8 is O, or Y8 is NR, wherein R is an alkyl group (e.g., $C_1$-$C_6$alkyl group) or H; and each Y10 is independently selected from H, $CH_3$, F, and $CF_3$, wherein for at least one F7 at least one Y10 is not H. In some embodiments, the $R_1$ at position 5' represents (C=O)—*, wherein —* represents the attachment point to the rest of Z1c.

In some embodiments, $B_1$ and the $B_2$ are independently represented by Formula F2, wherein Formula F2 is:

(F2)

wherein:

$R_1$ at position 5' represents (C=O)—*, wherein —* represents the attachment point to the rest of Z1c; and each remaining $R_1$ is independently selected from H, F, Cl, Br, OH, $CF_3$, $CHF_2$, $NO_2$, $CH_3$, $OCH_3$, and $OCF_3$.

In some embodiments, $B_1$ and $B_2$ are independently Formula F7, (F7)

wherein:

$R_1$ at position 5' represents (C=O)—*, wherein —* represents the attachment point to the rest of Z1c;

each remaining $R_1$ is independently selected from H, F, Cl, Br, OH, $CF_3$, $CHF_2$, $NO_2$, $CH_3$, $OCH_3$, and $OCF_3$;

Y8 is O or NR, wherein R is an alkyl group (e.g., $C_1$-$C_6$alkyl group) or H; and each Y10 is independently selected from H, $CH_3$, F, and $CF_3$, wherein for at least one F7 at least one Y10 is not H.

In some embodiments, $B_1$ and $B_2$ are independently Formula F7A, (F7A)

wherein:

$R_1$ at position 5' represents (C=O)—*, wherein —* represents the attachment point to the rest of Z1c; and each remaining $R_1$ is independently selected from H, F, Cl, Br, OH, $CF_3$, $CHF_2$, $NO_2$, $CH_3$, $OCH_3$, and $OCF_3$.

In some embodiments, at least one diboronate is F7 and wherein Y8 is 0 and each Y10 is CH3. In some embodiments, each remaining $R_1$ is independently selected from (a) H, $CF_3$, and F; or (b) two remaining $R_1$ are H and one remaining $R_1$ is $CF_3$ or F. In some embodiments, at least one $R_1$ in the $B_1$ or the $B_2$ is F or $CF_3$. In some embodiments, each remaining $R_1$ is H.

In some embodiments, the compound is represented by Formula IE, or a stereoisomer or a mixture of stereoisomers, or pharmaceutically acceptable salt thereof:

(Formula IE)

$$[Z1c\!-\!Z1b1\!-\!Z1b2\!\overset{}{]}_{q'}\!-\!X_1$$

wherein:

q' is 2, 3, or 4;

each corresponding Z1c and Z1b1 is independently selected and may be the same or different;

each Z1b1 is a bond or is selected from FL70, FL70A, and FL70B;

each Z1b2 is FL3;

each Z1c is covalently conjugated to Z1b1 via an amine in beta or gamma position of a backbone of the Z1b1, and wherein at least one Z1c is covalently conjugated to at least one Z1b1 selected from FL70, FL70A, and FL70B.

In some embodiments, the compound is represented by Formula IE, or a stereoisomer or a mixture of stereoisomers, or pharmaceutically acceptable salt thereof:

(Formula IE)

$$[Z1c\!-\!Z1b1\!-\!Z1b2\!\overset{}{]}_{q'}\!-\!X_1$$

wherein:

q' is 2, 3, or 4;

each corresponding Z1c and Z1b1 is independently selected and may be the same or different;

each Z1b1 is a bond or is selected from FL70, FL70A, and FL70B;

each Z1b2 is selected from FL5, FL5A, and FL5B;

each Z1c is covalently conjugated to Z1b1 via beta or gamma position of a backbone of the Z1b1, and wherein at least one Z1c is covalently conjugated to at least one Z1b1 selected from FL70, FL70A, and FL70B.

In some embodiments, at least one Z1c is conjugated to an amine in the beta position of the backbone of the Z1b.

In some embodiments, the compound is represented by Formula IE, or a stereoisomer or a mixture of stereoisomers, or pharmaceutically acceptable salt thereof:

$$[\text{Z1c} \text{---} \text{Z1b1} \text{---} \text{Z1b2}]_{q'} \text{---} \text{X1} \quad \text{(Formula IE)}$$

wherein:

q' is 2, 3, or 4;

each corresponding Z1c and Z1b1 is independently selected and may be the same or different;

each Z1b1 is a bond or is selected from FL69, FL69A, and FL69B;

each Z1b2 is FL3 or FL5B;

each Z1c is covalently conjugated to Z1b1 via an amine in an alpha position of a backbone of the Z1b1, and wherein, at least one Z1c is covalently conjugated to at least one Z1b1 selected from FL69, FL69A, and FL69B.

In some embodiments, the compound is represented by Formula IE, or a stereoisomer or a mixture of stereoisomers, or pharmaceutically acceptable salt thereof:

$$[\text{Z1c} \text{---} \text{Z1b1} \text{---} \text{Z1b2}]_{q'} \text{---} \text{X1} \quad \text{(Formula IE)}$$

wherein:

q' is 2, 3, or 4;

each corresponding Z1c is independently selected and may be the same or different;

each Z1b1 is a bond;

each Z1b2 is FL3; and each Z1c is covalently conjugated to Z1b2 via an amine in a beta position of a backbone of the Z1b2.

In some embodiments, the polypeptide comprises an insulin receptor agonist having an A-chain and a B-chain. In some embodiments, In some embodiments, each Z1c is selected from Formulae FFL-1 to FFL-68, wherein Formulae FFL-1 to FFL-68 are:

FFL-1

FFL-2

FFL-3

FFL-4

313 314

-continued

FFL-5

FFL-6

FFL-7

FFL-8

FFL-9

FFL-10

FFL-11

-continued

FFL-12

FFl-13

FFL-14

FFL-15

FFL-16

317                                                                    318

-continued

FFL-17                                                              FFL-18

FFL-19                                                              FFL-20

FFL-21                                                              FFL-22

-continued

FFL-23

FFL-24

FFL-25

FFL-26

FFL-27

FFL-28

321

322

FFL-29

FFL-30

FFL-31

FFL-32

FFL-33

FFL-34

323                                                                                                         324

FFL-35

FFL-36

FFL-37

FFL-38

FFL-39

FFL-40

FFL-41

-continued

FFL-42

FFL-43

FFL-44

FFL-45

FFL-46

FFL-47

-continued

FFL-48

FFL-49

FFL-50

FFL-51

-continued

FFL-52

FFL-53

FFL-54

FFL-55

FFL-56

FFL-57

331

332

FFL-58

FFL-59

FFL-60

FFL-61

FFL-62

FFL-63

-continued

FFL-64

FFL-65

FFL-66

FFL-67

FFL-68 or stereoisomers thereof;

wherein X represents a point of covalent attachment to the amine of X1.

In some embodiments, $B_1$ and $B_2$ are each independently selected from Formulae F2 and F7; wherein each remaining $R_1$ is independently selected from H, $CF_3$, and F, wherein each Z1c is covalently conjugated via one or more of the Z1b to an amine of X1 and each of the Z1c and the one or more Z1b in combination is selected from Formulae FFL 2-5, 9-12, 16, 20, 21, 27, 32, 34, 35, 37-40, 44-47, 51, 55, 56, 62, 66, and 67, or stereoisomers thereof; wherein X represents a point of covalent attachment to the amine of X1.

In some embodiments, $B_1$ and $B_2$ are each independently Formula F2, wherein each remaining $R_1$ is independently selected from H, $CF_3$, and F; wherein each Z1c is covalently conjugated via one or more of the Z1b to an amine of X1 and each of the Z1c and the one or more Z1b in combination is selected from Formulae FFL 2-5, 9-12, 16, 20, 21, 27, 32, 34, 35, 37-40, 44-47, 51, 55, 56, 62, 66, and 67, or stereoisomers thereof; wherein X represents a point of covalent attachment to the amine of X1.

In some embodiments, $B_1$ and $B_2$ are each independently Formula F7A, wherein each remaining $R_1$ is independently selected from H, $CF_3$, and F; wherein each Z1c is covalently conjugated via one or more of the Z1b to an amine of X1 and each of the Z1c and the one or more Z1b in combination is selected from Formulae FFL 2-5, 9-12, 16, 20, 21, 27, 32, 34, 35, 37-40, 44-47, 51, 55, 56, 62, 66, and 67, or stereoisomers thereof; wherein X represents a point of covalent attachment to the amine of XL.

In some embodiments, the compound (e.g., Formula I or Formula IB) has affinity to bind to one or more glycated proteins or glycosylated proteins and/or sugar moieties or saccharides or polysaccharides on surface of cells.

In some embodiments, q' is at least 2 and at least one of the Z1c is a sugar moiety, a diol containing moiety, and a polyol containing moiety. In some embodiments, the sugar moiety is selected from Formulae STR1, STR2, STR3, STR4, and STR5:

STR1

STR2

STR3

STR4

STR5 wherein:

one $R_1$''' represents the attachment point to a Z1b;

each remaining $R_1$''' is independently selected from —H, —$OR^3$, —$N(R^3)_2$, —$SR^3$, —OH, —$OCH_3$, —$OR^5$, $NHC(O)CH_3$, —$CH_2R^3$, —$C(O)NHOH$, —$NHC(O)CH_3$, —$CH_2OH$, —$CH_2OR^5$, —$NH_2$, —$CH_2R^4$, —$R^6$, and —$R^7$, wherein in STR1, STR2, and STR4 at least one of the remaining $R_1$''' is OH, each $R^3$ is independently selected from —H, acetyl, phosphate, —$R^2$, —$SO_2R^2$, —$S(O)R^2$, —$P(O)(OR^2)_2$, —$C(O)R^2$, —$CO_2R^2$, and —$C(O)N(R^2)_2$, each $R^2$ is independently selected from —H, $C_{1-6}$ aliphatic ring, phenyl ring, substituted 5-6 membered monocyclic heteroaryl ring having 1-4 heteroatoms selected from nitrogen, oxygen, and sulfur, a 4-7 membered heterocyclic ring having 1-2 heteroatoms selected from nitrogen, oxygen, and sulfur, and an alkyl (e.g., $C_1$-$C_6$alkyl), each $R^4$ is independently selected from —H, —OH, —$OR^3$, —$N(R^3)_2$, —$OR^5$ and —$SR^3$;

each $R^5$ is independently selected from a mono-saccharide, a di-saccharide, a tri-saccharide, a pentose, and a hexose, each $R^6$ is independently selected from —$NCOCH_2$—, —$(OCH_2CH_2)_n$—, a —O—$C_{1-9}$ alkylene group, and a substituted $C_{1-9}$ alkylene group in which one or more methylene groups are optionally replaced by —O—, —$(CH_2)_n$—, —$OCH_2$—, —$N(R^2)C(O)$—, —$N(R^2)C(O)N(R^2)$—, —$SO_2$—, —$SO_2N(R^2)$—, —$N(R^2)SO_2$—, —S—, —$N(R^2)$—, —$C(O)$—, —$OC(O)$—, —$C(O)O$—, —$C(O)N(R^2)$—, or —$N(R^2)SO_2N(R^2)$—, wherein index n is 1, 2, 3, 4, 5, 6, 7, or 8, each $R^7$ is independently selected from —$N(R^2)_2$, —F, —Cl, —Br, —I, —SH, —$OR^2$, —$SR^2$, —$NH_2$, —$N_3$, —$C\equiv CR^2$, —$CH_2C\equiv CH$, —$C\equiv CH$, —$CO_2R^2$, —$C(O)R^2$, —$OSO_2R^2$—$N(R^2)_2$, —$OR^2$, —$SR^2$, and —$CH_3$, —$CH_2NH_2$, and structures STR1, STR2, STR3, STR4, and STR5 optionally include one or more acetyl, acetylene, acetonide, and/or pinacol protecting groups.

In some embodiments, X1 comprises a polypeptide human hormone, an insulin receptor agonist, an endocrine hormone, insulin, human insulin, glucagon, amylin, relaxin, GLP-1, GIP, oxyntomodulin, somatostatin, gastric inhibitory polypeptide, glucose-dependent insulinotropic polypeptide, a hybrid peptide comprising sequences from two or more human polypeptide hormones, or an analogue of any thereof.

In some embodiments, X1 comprises an insulin having an A-chain and a B-chain, wherein optionally the A-chain comprises a sequence selected from SEQ ID NOs 1, 25, 24051, and 24052, and optionally the B-chain comprises a sequence selected from SEQ ID NOs 24060, 24061, 24062, 24063, 24064, and 25000-25397.

In some embodiments, X1 comprises an insulin having an A-chain and a B-chain, wherein the A-chain comprises a sequence selected from SEQ ID NOs 1, 24051, and 24052, and wherein the B-chain comprises a sequence selected from SEQ ID NOs 24063, 25095, 25228, 25229, 25232, 25236, 25305, 25308, 25312, and 25380-25397;

each Z1b is independently selected from FL3, FL5, FL5A, FL5B, FL65A, FL65B, FL69A, and FL69B;

each Z1c is independently selected from FF12A, FF12B, FF12C, FF12D, FF116A, FF116B, FF116C, FF116D, and FF227, wherein each Z1c is covalently conjugated via one or more of the Z1b to a lysine residue in X1; and $B_1$ and $B_2$ are each independently Formula F2 or Formula F7.

In some embodiments, each $B_1$ and $B_2$ is independently selected from F2 and F7 and is covalently conjugated to Z1c using an amide linkage, each Z1b is independently selected from (i) FL3, wherein p is 1, 2, or 3; (ii) FL5B, wherein p is 2, 3, or 4; (iii) FL65A; and (iv) FL69A, wherein p is 2, 3, or 4;

each Z1c is independently selected from FF12A, FF116A, and FF227, wherein each Z1c is covalently conjugated via one or more of the Z1b to a lysine residue in X1; and X1 is a polypeptide comprising an insulin receptor agonist having an A-chain and a B-chain, wherein the A-chain comprises a sequence selected from SEQ ID NOs 1, 24051, and 24052, and wherein the B-chain comprises a sequence selected from SEQ ID NOs 24063, 25095, 25228, 25229, 25232, 25236, 25305, 25308, 25312, and 25380-25397, and wherein at least two lysine in X1 are each independently conjugated to Z1b.

In some embodiments, at least one Z1c is FF227 and i is 1.

In some embodiments, provided herein are compounds selected from the group consisting of a polypeptide comprising an A-chain and a B-chain, wherein the A-chain comprises a sequence selected from 1, 24051, and 24052; and wherein the B-chain comprises a sequence selected from SEQ ID NOs 24063, 25228, 25229, 25232, 25305, 25308, 25312, 25236, 25095, and 25380-25397.

In some embodiments, X1 is an insulin further comprising from 1 to 5 residues replaced, inserted, appended, or mutated to an amino acid that has a free amine conjugated via one or more of the Z1b to a Z1c.

In some embodiments, at least one Z1c is conjugated via one or more of the Z1b to a free amine side chain of an amino acid in X1 that has been replaced, inserted, or mutated on an insulin.

In some embodiments, a compound is represented by Formula IF, or a stereoisomer or a mixture of stereoisomers, or pharmaceutically acceptable salt thereof:

Z1c-Linker          (Formula IF)

wherein the Z1c-Linker is selected from:

FFL-1

FFL-2

FFL-3

FFL-4

-continued

FFL-5

FFL-6

FFL-7

FFL-8

FFL-9

341

342

FFL-10

FFL-11

FFL-12

FFL-13

FFL-14

343      344

-continued

FFL-15

FFL-16

FFL-17

FFL-18

FFL-19

FFL-20

345

346

FFL-21

FFL-22

FFL-23

FFL-24

FFL-25

FFL-26

FFL-27

FFL-28

347                                                              348

FFL-29                                                           FFL-30

FFL-31                                                           FFL-32

FFL-33                                                           FFL-34

349             350

FFL-35

FFL-36

FFL-37

FFL-38

FFL-39

FFL-40

-continued

FFL-41

FFL-42

FFL-43   FFL-44

FFL-45   FFL-46

-continued

FFL-47

FFL-48

FFL-49

FFL-50

FFL-51

-continued

FFL-52

FFL-53

FFL-54

FFL-55

FFL-56

FFL-57

357 358

FFL-58

FFL-59

FFL-60

FFL-61

FFL-62

FFL-63

-continued

FFL-64                                                                                                              FFL-65

FFL-66                                                                                                              FFL-67

FFL-68 wherein X is selected from a leaving group, NH$_2$, and H; and B$_1$ and B$_2$, which may be identical or different, each independently represents an aromatic boron-containing group.

In some embodiments, the compound represented by Formula IF comprises at least one B$_1$ or B$_2$ independently selected from Formulae F2 and F7,

361 wherein Formulae F2 and F7 are:

(F2)

(F7)

362 wherein:

$R_1$ at position 5' represents (C=O)—*, wherein —* represents the attachment point to the rest of Z1c;

each remaining $R_1$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_mCH_3$, and $OCF_3$, wherein m is 1, 2, 3, 4, 5, 6, or 7;

Y8 is O, or Y8 is NR, wherein R is an alkyl group (e.g., C—$C_6$alkyl group) or H; and each Y10 is independently selected from H, $CH_3$, F, and $CF_3$, wherein for at least one F7 at least one Y10 is not H.

In some embodiments, the Z1c-Linker (i.e., Formula IF) is selected from:

DSL-1

DSL-2

363

364

DSL-3

DSL-4

DSL-5

-continued

DSL-6

DSL-7

367 368

-continued

DSL-8

DSL-9

DSL-10

DSL-11

DSL-12

-continued

DSL-13

DSL-14

371                                                                              372

DSL-15                                                                          DSL-16

DSL-17                                                                          DSL-18

-continued

DSL-19

DSL-20

-continued

DSL-21

DSL-22

DSL-23

377

378

-continued

DSL-24

DSL-25

DSL-26

-continued

DSL-27

DSL-28

381

382

DSL-29

DSL-30

DSL-31

DSL-32

383                                            384

-continued

DSL-33                                          DSL-34

DSL-35                                          DSL-36

385

386

DSL-37

DSL-38

DSL-39

DSL-40

387                                                                388

DSL-41                                                              DSL-42

DSL-43                                                              DSL-44

389                                                                                                    390

DSL-45                                                                                                  DSL-46

DSL-47                                                                                                  DSL-48

391    392

-continued

DSL-49    DSL-50

DSL-51    DSL-52

-continued

DSL-53

DSL-54

DSL-55

DSL-56

-continued

DSL-57

DSL-58

DSL-59

DSL-60

-continued

DSL-61

DSL-62

DSL-63

DSL-64

-continued

DSL-65

DSL-66

DSL-67

DSL-68

401 402

DSL-69

DSL-70

DSL-71

DSL-72

403

404

DSL-73

DSL-74

DSL-75

-continued

DSL-76

DSL-77

407      408

-continued

DSL-78      DSL-79

DSL-80      DSL-81

DSL-82

-continued

DSL-83

DSL-84

411

412

-continued

DSL-85

DSL-86

DSL-87

DSL-88

-continued

DSL-89

DSL-90

-continued

DSL-91

DSL-92

DSL-93

-continued

DSL-94

DSL-95

420

-continued

DSL-96

DSL-97

-continued

DSL-98

DSL-99

DSL-100

423 424

DSL-101

DSL-102

DSL-103

DSL-104

425 426

-continued

DSL-105

DSL-106

DSL-107

DSL-108

DSL-109

DSL-110

427                                                                 428

DSL-111                                                             DSL-112

DSL-113                                                             DSL-114

429
430

DSL-115

DSL-116

DSL-117

DSL-118

431

432

DSL-119

DSL-120

DSL-121

DSL-122

433    434

DSL-123    DSL-124

DSL-125    DSL-126

435

436

DSL-127

DSL-128

DSL-129

DSL-130

437 438

-continued

DSL-131                                    DSL-132

DSL-133                                    DSL-134

439 440

DSL-135

DSL-136

DSL-137

DSL-138

-continued

DSL-139                                                                                    DSL-140

DSL-141                                                                                    DSL-142

DSL-143                                                                                    DSL-144

443

444

DSL-145

DSL-146

DSL-147

DSL-148

DSL-149

DSL-150

445
446

DSL-151

DSL-152

DSL-153

DSL-154

DSL-155

DSL-156

447 448

-continued

DSL-157

DSL-158

DSL-159

DSL-160

DSL-161

DSL-162

449

450

DSL-163

DSL-164

DSL-165

DSL-166

451            452

DSL-167

DSL-168

DSL-169

DSL-170

DSL-171

DSL-172

-continued

DSL-173

DSL-174

-continued

DSL-175 or a stereoisomer or a mixture of stereoisomers, a pharmaceutically acceptable salt thereof, and combinations thereof, wherein X is a leaving group or represents a point of covalent attachment directly to X1 of Formula I or Formula IB.

In some embodiments, when X is a leaving group, X is selected from N-oxysuccinimide, 2,3,5,6-tetrafluorophenoxy (TFP), pentafluorophenoxy (Pfp), OH, halogen, maleimide alkyl amino, maleimide amido polyethylene glycol amino, and maleimide polyethylene glycol amino. In some embodiments, X is selected from N-oxysuccinimide and OH. In some embodiments, X is OH. In some embodiments, X is N-oxysuccinimide. In some embodiments, the maleimide polyethylene glycol amino is selected from Mal-PEG2-amine, Mal-PEG4-amine, and Mal-PEG5-amine, or a pharmaceutically acceptable salt thereof. In some embodiments, the maleimide alkyl amino is selected from Mal-C6-amine and N-(2-Aminoethyl)maleimide, or a pharmaceutically acceptable salt thereof. In some embodiments, the maleimide amido polyethylene glycol amino is selected from Mal-amido-PEG9-amine, Mal-amido-PEG11-amine, Mal-amido-PEG23-amine, 4-Mal-methyl-cyclohexanecarboxamide-methyl-[1,2,3]triazole-PEG8-amine, or a pharmaceutically acceptable salt thereof. In some embodiments, the Z1c-Linker is selected from:

DSL-1A

DSL-2A 457 458

DSL-3A

DSL-4A

DSL-5A

DSL-6A

-continued

DSL-7A

DSL-8A

DSL-9A

DSL-10A

DSL-11A

-continued

DSL-12A

DSL-13A

-continued

DSL-14A

DSL-15A

DSL-16A

465

466

-continued

DSL-17A

DSL-18A

DSL-19A

-continued

DSL-20A

DSL-21A 469 470

DSL-22A

DSL-23A

DSL-24A

DSL-25A

-continued

DSL-26A

DSL-27A

-continued

DSL-28A

DSL-29A

DSL-30A

475

476

DSL-31A

DSL-32A

DSL-33A

DSL-34A 477 478

DSL-35A

DSL-36A

DSL-37A

DSL-38A

479

480

-continued

DSL-39A

DSL-40A

DSL-41A

DSL-42A 481 482

DSL-43A DSL-44A

DSL-45A DSL-46A 483 484

-continued

DSL-47A

DSL-48A

DSL-49A

DSL-50A

-continued

DSL-51A

DSL-52A

DSL-53A

DSL-54A

487

488

DSL-55A

DSL-56A

DSL-57A

DSL-58A 489                                                              490

DSL-59A                                                          DSL-60A

DSL-61A                                                          DSL-62A

-continued

DSL-63A

DSL-64A

DSL-65A

DSL-66A 493 494

-continued

DSL-67A

DSL-68A

DSL-69A

DSL-70A 495 496

DSL-71A

DSL-72A

DSL-73A

DSL-74A

DSL-75A

-continued

DSL-76A

DSL-77A 499 500

DSL-78A

DSL-79A

DSL-80A

-continued

DSL-81A

DSL-82A

-continued

DSL-83A

DSL-84A

-continued

DSL-85A

DSL-86A

DSL-87A

DSL-88A

-continued

DSL-89A

DSL-90A

-continued

DSL-91A

DSL-92A

DSL-93A

511

512

DSL-94A

DSL-95A

-continued

DSL-96A

DSL-97A 515 516

DSL-101A

DSL-102A

DSL-103A

DSL-104A 517 518

DSL-105A

DSL-106A

DSL-107A

DSL-108A

-continued

DSL-109A

DSL-110A

DSL-111A

DSL-112A 521                                    522

DSL-113A                                DSL-114A

DSL-115A                                DSL-116A 523 524

-continued

DSL-117A

DSL-118A

DSL-119A

DSL-120A

525

526

-continued

DSL-121A

DSL-122A

DSL-123A

DSL-124A

-continued

DSL-125A

DSL-126A

DSL-127A

DSL-128A 529 530

-continued

DSL-129A

DSL-130A

DSL-131A

DSL-132A

DSL-133A

DSL-134A 531                                                 532

-continued

DSL-135A

DSL-136A

DSL-143A

DSL-144A

DSL-145A

DSL-146A 533 534

-continued

DSL-147A

DSL-148A

DSL-149A

DSL-150A

DSL-151A

DSL-152A

535

536

-continued

DSL-153A

DSL-154A

DSL-155A

DSL-156A

DSL-157A

DSL-158A

537

538

DSL-159A

DSL-160A

DSL-161A

DSL-162A

-continued

DSL-163A

DSL-164A

DSL-165A

DSL-166A

-continued

DSL-167A

DSL-168A

DSL-169A

DSL-170A

DSL-171A

DSL-172A

543

544

-continued

DSL-173A

DSL-174A

DSL-175A a stereoisomer or a mixture of stereoisomers, a pharmaceutically acceptable salt thereof, and combinations thereof. In some embodiments, the Z1c-Linker is selected from:

DSL-1B

DSL-2B

DSL-3B

DSL-4B

DSL-5B

-continued

DSL-6B

DSL-7B

DSL-8B

DSL-9B

-continued

DSL-10B

DSL-11B

DSL-12B

-continued

DSL-13B

DSL-14B

-continued

DSL-15B

DSL-16B

DSL-17B

DSL-18B

-continued

DSL-19B

DSL-20B

DSL-21B

DSL-22B

DSL-23B

DSL-24B

-continued

DSL-25B

DSL-26B

-continued

DSL-27B

DSL-28B

-continued

DSL-29B

DSL-30B

DSL-31B

DSL-32B

DSL-33B

DSL-34B 565 566

-continued

DSL-35B

DSL-36B

DSL-37B

DSL-38B

DSL-39B

DSL-40B

-continued

DSL-41B

DSL-42B

DSL-43B

DSL-44B 569　　　　　　　　　　　　　　　　　　570

-continued

DSL-45B　　　　　　　　　　　　　　　　DSL-46B

DSL-47B　　　　　　　　　　　　　　　　DSL-48B

-continued

DSL-49B                                                    DSL-50B

DSL-51B                                                    DSL-52B

DSL-53B                                                    DSL-54B

-continued

DSL-55B

DSL-56B

DSL-57B

DSL-58B

DSL-59B

DSL-60B

-continued

DSL-61B

DSL-62B

DSL-63B

DSL-64B 577 578

-continued

DSL-65B DSL-66B

DSL-67B DSL-68B

-continued

DSL-69B

DSL-70B

DSL-71B

DSL-72B

DSL-73B

-continued

DSL-74B

DSL-75B

-continued

DSL-76B

DSL-77B

DSL-78B  DSL-79B

-continued

DSL-80B

DSL-81B

-continued

DSL-82B

DSL-83B

-continued

DSL-84B

DSL-85B

DSL-86B

DSL-87B

-continued

DSL-88B

DSL-89B

-continued

DSL-90B

DSL-91B

-continued

DSL-92B

DSL-93B

DSL-94B

DSL-95B

-continued

DSL-96B

DSL-97B

-continued

DSL-98B

DSL-99B

DSL-100B

DSL-101B

DSL-102B 601 602

-continued

DSL-103B

DSL-104B

DSL-105B

DSL-106B

DSL-107B

DSL-108B 603 604

-continued

DSL-109B

DSL-110B

DSL-111B

DSL-112B

DSL-113B

DSL-114B

-continued

DSL-115B

DSL-116B

DSL-117B

DSL-118B

-continued

DSL-119B

DSL-120B

DSL-121B

DSL-122B

DSL-123B

DSL-124B

-continued

DSL-125B

DSL-126B

DSL-127B

DSL-128B

DSL-129B

DSL-130B 611 612

-continued

DSL-131B

DSL-132B

DSL-133B

DSL-134B

DSL-135B

DSL-136B 613 614

-continued

DSL-137B DSL-138B

DSL-139B DSL-140B

615

616

-continued

DSL-141B

DSL-142B

DSL-143B

DSL-144B

DSL-145B

DSL-146B 617                                                                                    618

-continued

DSL-147B                                                                         DSL-148B

DSL-149B                                                                         DSL-150B

DSL-151B                                                                         DSL-152B 619 620

-continued

DSL-153B

DSL-154B

DSL-155B

DSL-156B

DSL-157B

DSL-158B

621

622

DSL-159B

DSL-160B

DSL-161B

DSL-162B

623

624

-continued

DSL-163B

DSL-164B

DSL-165B

DSL-166B

DSL-167B

DSL-168B 625 626

DSL-169B

DSL-170B

DSL-171B

DSL-172B

-continued

DSL-173B

DSL-174B

DSL-175B a stereoisomer or a mixture of stereoisomers, a pharmaceutically acceptable salt thereof, and combinations thereof.

In at least one embodiment, the compound of the present disclosure may be used, as an intermediate in the manufacture of a drug substance or a therapeutic of a prophylactic compound.

In another aspect, the disclosure provides a human insulin analog, comprising an A-chain and a B-chain, wherein the sequence of the A-chain comprises:

$X_{aa}X_{bb}X_{cc}X_{dd}$, $X_{ee}X_{ff}X_{gg}$VEQCCX$_{hh}X_{ii}$ICS-LYQLENYCNX$_{jj}X_{kk}X_{ll}X_{mm}X_{nn}X_{oo}X_{pp}$, (SEQ ID NO:24015); and wherein the sequence of the B-chain comprises:

(i)

(SEQ ID NO: 24016)

$X_{aa}X_{bb}X_{cc}X_{dd}$KX$_{ee}X_{ff}X_{gg}X_{hh}X_{ii}X_{jj}$KX$_{kk}X_{ll}X_{mm}X_{nn}$QHLCGSHLVEALYLV CX$_{oo}X_{pp}X_{qq}$GFFYTX$_{rr}X_{ss}X_{tt}X_{uu}X_{vv}X_{ww}$, wherein $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, (ii)

(SEQ ID NO: 24017)

$X_{aa}X_{bb}X_{cc}X_{dd}$KPX$_{ee}X_{ff}X_{gg}X_{hh}X_{ii}X_{jj}X_{kk}X_{ll}X_{mm}X_{nn}$QHLCGSHLVEALYLV CX$_{oo}X_{pp}X_{qq}$GFFYTX$_{rr}X_{ss}X_{tt}X_{uu}X_{vv}X_{ww}$, wherein $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, (iii)

(SEQ ID NO: 24018)

$X_{aa}X_{bb}X_{cc}X_{dd}$KX$_{ee}X_{ff}X_{gg}X_{hh}X_{ii}X_{jj}$KX$_{kk}X_{ll}X_{mm}X_{nn}$QHLCGSHLVEALYLV CX$_{oo}X_{pp}X_{qq}$GFFYTX$_{rr}X_{ss}X_{tt}X_{uu}X_{vv}X_{ww}$, wherein $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, and at least one of $X_{ee}$, $X_{ff}$, $X_{gg}$, $X_{hh}$, $X_{ii}$, $X_{jj}$ is present and at least one of $X_{ee}$, $X_{ff}$, $X_{gg}$, $X_{hh}$, $X_{ii}$, $X_{jj}$ is G, (iv)

(SEQ ID NO: 24019)

$X_{aa}X_{bb}X_{cc}X_{dd}$KX$_{ee}X_{ff}X_{gg}X_{hh}X_{ii}X_{jj}$KX$_{kk}X_{ll}X_{mm}X_{nn}$QHLCGSHLVEALYLV CX$_{oo}X_{pp}X_{qq}$GFFYTX$_{rr}X_{ss}X_{tt}X_{uu}X_{vv}X_{ww}$, wherein $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, and at least one of $X_{ee}$, $X_{ff}$, $X_{gg}$, $X_{hh}$, $X_{ii}$, $X_{jj}$ is present and at least one of $X_{ee}$, $X_{ff}$, $X_{gg}$, $X_{hh}$, $X_{ii}$, $X_{jj}$ is S, or (v)

(SEQ ID NO: 24020)

$X_{aa}X_{bb}X_{cc}X_{dd}$KX$_{ee}X_{ff}X_{gg}X_{hh}X_{ii}X_{jj}$KX$_{kk}X_{ll}X_{mm}X_{nn}$QHLCGSHLVEALYLV CX$_{oo}X_{pp}X_{qq}$GFFYTX$_{rr}X_{ss}X_{tt}X_{uu}X_{vv}X_{ww}$, wherein $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, and at least one of $X_{ee}$, $X_{ff}$, $X_{gg}$, $X_{hh}$, $X_{ii}$, $X_{jj}$ are present and at least one of $X_{ee}$, $X_{ff}$, $X_{gg}$, $X_{hh}$, $X_{ii}$, $X_{jj}$ is S, and another is G.

In some embodiments, the A-chain comprises a sequence selected from SEQ ID NOs 1 and 3 to 33, and is optionally appended at the N-terminus and/or at the C-terminus by at least one selected from KA, KD, KE, KF, KG, KH, KI, KL, KN, KP, KQ, KR, KS, KT, KY, KAA, KAD, KAE, KAF, KAG, KAH, KAI, KAL, KAN, KAQ, KAR, KAS, KAT, KAY, KDA, KDD, KDE, KDF, KDG, KDH, KDI, KDL, KDN, KDQ, KDR, KDS, KDT, KDY, KEA, KED, KEE, KEF, KEG, KEH, KEI, KEL, KEN, KEQ, KER, KES, KET, KEY, KFA, KFD, KFE, KFF, KFG, KFH, KFI, KFL, KFN, KFQ, KFR, KFS, KFT, KFY, KGA, KGD, KGE, KGF, KGG, KGH, KGI, KGL, KGN, KGQ, KGR, KGS, KGT, KGY, KHA, KHD, KHE, KHF, KHG, KHH, KHI, KHL, KHN, KHQ, KHR, KHS, KHT, KHY, KIA, KID, KIE, KIF, KIG, KIH, KII, KIL, KIN, KIQ, KIR, KIS, KIT, KIY, KLA, KLD, KLE, KLF, KLG, KLH, KLI, KLL, KLN, KLQ, KLR, KLS, KLT, KLY, KNA, KND, KNE, KNF, KNG, KNH, KNI, KNL, KNN, KNQ, KNR, KNS, KNT, KNY, KPA, KPD, KPE, KPF, KPG, KPH, KPI, KPL, KPN, KPQ, KPR, KPS, KPT, KPY, KQA, KQD, KQE, KQF, KQG, KQH, KQI, KQL, KQN, KQQ, KQR, KQS, KQT, KQY, KRA, KRD, KRE, KRF, KRG, KRH, KRI, KRL, KRN, KRQ, KRR, KRS, KRT, KRY, KSA, KSD, KSE, KSF, KSG, KSH, KSI, KSL, KSN, KSQ, KSR, KSS, KST, KSY, KTA, KTD, KTE, KTF, KTG, KTH, KTI, KTL, KTN, KTQ, KTR, KTS, KTT, KTY, KYA, KYD, KYE, KYF, KYG, KYH, KYI, KYL, KYN, KYQ, KYR, KYS, KYT, KYY and SEQ ID NOs 75 to 24014, 24037-24046, and wherein the B-chain comprises at least one of SEQ ID NOs 2 and 34 to 74, 24047, and 24048, and is optionally appended at the N-terminus and/or at the C-terminus by at least one selected from KA, KD, KE, KF, KG, KH, KI, KL, KN, KP, KQ, KR, KS, KT, KY, KAA, KAD, KAE, KAF, KAG, KAH, KAI, KAL, KAN, KAQ, KAR, KAS, KAT, KAY, KDA, KDD, KDE, KDF, KDG, KDH, KDI, KDL, KDN, KDQ, KDR, KDS, KDT, KDY, KEA, KED, KEE, KEF, KEG, KEH, KEI, KEL, KEN, KEQ, KER, KES, KET, KEY, KFA, KFD, KFE, KFF, KFG, KFH, KFI, KFL, KFN, KFQ, KFR, KFS, KFT, KFY, KGA, KGD, KGE, KGF, KGG, KGH, KGI, KGL, KGN, KGQ, KGR, KGS, KGT, KGY, KHA, KHD, KHE, KHF, KHG, KHH, KHI, KHL, KHN, KHQ, KHR, KHS, KHT, KHY, KIA; KID, KIE, KIF, KIG, KIH, KII, KIL, KIN, KIQ, KIR, KIS, KIT, KIY, KLA, KLD, KLE, KLF, KLG, KLH, KLI, KLL, KLN, KLQ, KLR, KLS, KLT, KLY, KNA, KND, KNE, KNF, KNG, KNH, KNI, KNL, KNN, KNQ, KNR, KNS, KNT, KNY, KPA, KPD, KPE, KPF, KPG, KPH, KPI, KPL, KPN, KPQ, KPR, KPS, KPT, KPY, KQA, KQD, KQE, KQF, KQG, KQH, KQI, KQL, KQN, KQQ, KQR, KQS, KQT, KQY, KRA, KRD, KRE, KRF, KRG, KRH, KRI, KRL, KRN, KRQ, KRR, KRS, KRT, KRY, KSA, KSD, KSE, KSF, KSG, KSH, KSI, KSL, KSN, KSQ, KSR, KSS, KST, KSY, KTA, KTD, KTE, KTF, KTG, KTH, KTI, KTL, KTN, KTQ, KTR, KTS, KTT, KTY, KYA, KYD, KYE, KYF, KYG, KYH, KYI, KYL, KYN, KYQ, KYR, KYS, KYT, KYY and SEQ ID NOs 75 to 24014, 24037-24046.

In some embodiments, the A-chain comprises a sequence selected from SEQ ID NOs 1 and 3 to 33, the B-chain comprises at least one of SEQ ID NOs 2 and 34 to 74, 24047, and 24048, and (a)
the A-chain and the B-chain are each independently and optionally appended at the N-terminus and/or at the C-terminus by at least one selected from:
KA, KD, KE, KF, KG, KH, KI, KL, KN, KP, KQ, KR, KS, KT, KY, KAA, KAD, KAE, KAF, KAG, KAH, KAI, KAL, KAN, KAQ, KAR, KAS, KAT, KAY, KDA, KDD, KDE, KDF; KDG, KDH, KDI, KDL, KDN, KDQ, KDR, KDS, KDT, KDY, KEA, KED, KEE, KEF, KEG, KEH, KEI, KEL, KEN, KEQ, KER, KES, KET, KEY, KFA, KFD, KFE, KFF, KFG, KFH, KFI, KFL, KFN, KFQ, KFR, KFS, KFT, KFY, KGA, KGD, KGE, KGF, KGG, KGH, KGI, KGL, KGN, KGQ, KGR, KGS, KGT, KGY, KHA, KHD, KHE, KHF, KHG, KHH, KHI, KHL, KHN, KHQ, KHR, KHS, KHT, KHY, KIA, KID, KIE, KIF, KIG, KIH, KII, KIL, KIN, KIQ, KIR, KIS, KIT, KIY, KLA, KLD, KLE, KLF, KLG, KLH, KLI, KLL, KLN, KLQ, KLR, KLS, KLT, KLY, KNA, KND, KNE, KNF, KNG, KNH, KNI, KNL, KNN, KNQ, KNR, KNS, KNT, KNY, KPA, KPD, KPE, KPF, KPG, KPH, KPI, KPL, KPN, KPQ, KPR, KPS, KPT, KPY, KQA, KQD, KQE, KQF, KQG, KQH, KQI, KQL, KQN, KQQ, KQR, KQS, KQT, KQY, KRA, KRD, KRE, KRF, KRG, KRH, KRI, KRL, KRN, KRQ, KRR, KRS, KRT, KRY, KSA, KSD, KSE, KSF, KSG, KSH, KSI, KSL, KSN, KSQ, KSR, KSS, KST, KSY, KTA, KTD, KTE, KTF, KTG, KTH, KTI, KTL, KTN, KTQ, KTR, KTS, KTT, KTY, KYA, KYD, KYE, KYF, KYG, KYH, KYI, KYL, KYN, KYQ, KYR, KYS, KYT, KYY, SEQ ID NOs 75 to 24014, 24037-24046, KA, KD, KE, KF, KG, KH, KI, KL, KN, KP, KQ, KR, KS, KT, KY, KAA, KAD, KAE, KAF, KAG, KAH, KAI, KAL, KAN, KAQ, KAR, KAS, KAT, KAY, KDA, KDD, KDE, KDF, KDG, KDH, KDI, KDL, KDN, KDQ, KDR, KDS, KDT, KDY, KEA, KED, KEE, KEF, KEG, KEH, KEI, KEL, KEN, KEQ, KER, KES, KET, KEY, KFA, KFD, KFE, KFF, KFG, KFH, KFI, KFL, KFN, KFQ, KFR, KFS, KFT, KFY, KGA, KGD, KGE, KGF, KGG, KGH, KGI, KGL, KGN, KGQ, KGR, KGS, KGT, KGY, KHA, KHD, KHE, KHF, KHG, KHH, KHI, KHL, KHN, KHQ, KHR, KHS, KHT, KHY, KIA, KID, KIE, KIF, KIG, KIH, KII, KIL, KIN, KIQ, KIR, KIS, KIT, KIY, KLA, KLD, KLE, KLF, KLG, KLH, KLI, KLL, KLN, KLQ, KLR, KLS, KLT, KLY, KNA, KND, KNE, KNF, KNG, KNH, KNI, KNL, KNN, KNQ, KNR, KNS, KNT, KNY, KPA, KPD, KPE, KPF, KPG, KPH, KPI, KPL, KPN, KPQ, KPR, KPS, KPT, KPY, KQA, KQD, KQE, KQF, KQG, KQH, KQI, KQL, KQN, KQQ, KQR, KQS, KQT, KQY, KRA, KRD, KRE, KRF, KRG, KRH, KRI, KRL, KRN, KRQ, KRR, KRS, KRT, KRY, KSA, KSD, KSE, KSF, KSG, KSH, KSI, KSL, KSN, KSQ, KSR, KSS, KST, KSY, KTA, KTD, KTE, KTF, KTG, KTH, KTI, KTL, KTN, KTQ, KTR, KTS, KTT, KTY, KYA, KYD, KYE, KYF, KYG, KYH, KYI, KYL, KYN, KYQ, KYR, KYS, KYT, KYY and, KA, KD, KE, KF, KG, KH, KI, KL, KN, KP, KQ, KR, KS, KT, KY and SEQ ID NOs 75 to 3224, KA, KD, KE, KF, KG, KH, KI, KL, KN, KP, KQ, KR, KS, KT, KY and SEQ ID NOs 3225 to 6374, KA, KD, KE, KF, KG, KH, KI, KL, KN, KP, KQ, KR, KS, KT, KY and SEQ ID NOs 6375 to 15194, KA, KD, KE, KF, KG, KH, KI, KL, KN, KP, KQ, KR, KS, KT, KY and SEQ ID NOs 15195 to 18134, KA, KD, KE, KF, KG, KH, KI, KL, KN, KP, KQ, KR, KS, KT, KY and SEQ ID NOs 18135 to 21074, and KA, KD, KE, KF, KG, KH, KI, KL, KN, KP, KQ, KR, KS, KT, KY and SEQ ID NOs 21075 to 24014, 24037-24046, or (b)
both the N-terminus and the C-terminus of the B-chain are independently covalently conjugated, via a peptide bond, to one selected from:
KA, KD, KE, KF, KG, KH, KI, KL, KN, KP, KQ, KR, KS, KT, KY, KAA, KAD, KAE, KAF, KAG, KAH, KAI, KAL, KAN, KAQ, KAR, KAS, KAT, KAY, KDA, KDD, KDE, KDF, KDG, KDH, KDI, KDL, KDN, KDQ, KDR, KDS, KDT, KDY, KEA, KED, KEE, KEF, KEG, KEH, KEI, KEL, KEN, KEQ, KER, KES, KET, KEY, KFA, KFD, KFE, KFF, KFG, KFH, KFI, KFL, KFN, KFQ, KFR, KFS, KFT, KFY, KGA, KGD, KGE, KGF, KGG, KGH, KGI, KGL, KGN, KGQ, KGR, KGS, KGT, KGY, KHA, KHD, KHE, KHF, KHG, KHH, KHI, KHL, KHN, KHQ, KHR, KHS, KHT, KHY, KIA, KID, KIE, KIF, KIG, KIH, KII, KIL, KIN, KIQ, KIR, KIS, KIT, KIY, KLA, KLD, KLE, KLF, KLG, KLH, KLI, KLL, KLN, KLQ, KLR, KLS, KLT, KLY, KNA, KND, KNE, KNF, KNG, KNH, KNI, KNL, KNN, KNQ, KNR, KNS, KNT, KNY, KPA, KPD, KPE, KPF, KPG, KPH, KPI, KPL, KPN, KPQ, KPR, KPS, KPT, KPY, KQA, KQD, KQE, KQF, KQG, KQH, KQI, KQL, KQN, KQQ, KQR, KQS, KQT, KQY, KRA, KRD, KRE, KRF, KRG, KRH, KRI, KRL, KRN, KRQ, KRR, KRS, KRT, KRY, KSA, KSD, KSE, KSF, KSG, KSH, KSI, KSL, KSN, KSQ, KSR, KSS, KST, KSY, KTA, KTD, KTE, KTF, KTG, KTH, KTI, KTL, KTN, KTQ, KTR, KTS, KTT, KTY, KYA, KYD, KYE, KYF, KYG, KYH, KYI, KYL, KYN, KYQ, KYR, KYS, KYT, KYY, SEQ ID NOs 75 to 24014, 24037-24036, KA, KD, KE, KF, KG, KH, KI, KL, KN, KP, KQ, KR, KS, KT, KY, KAA, KAD, KAE, KAF, KAG, KAH, KAI, KAL, KAN, KAQ, KAR, KAS, KAT, KAY, KDA, KDD, KDE, KDF, KDG, KDH, KDI, KDL, KDN, KDQ, KDR, KDS, KDT, KDY, KEA, KED, KEE, KEF, KEG, KEH, KEI, KEL, KEN, KEQ, KER, KES, KET, KEY, KFA, KFD, KFE, KFF, KFG, KFH, KFI, KFL, KFN, KFQ, KFR, KFS, KFT, KFY, KGA, KGD, KGE, KGF, KGG, KGH, KGI, KGL, KGN, KGQ, KGR, KGS, KGT, KGY, KHA, KHD, KHE, KHF, KHG, KHH, KHI, KHL, KHN, KHQ, KHR, KHS, KHT, KHY, KIA, KID, KIE, KIF, KIG, KIH, KII, KIL, KIN, KIQ, KIR, KIS, KIT, KIY, KLA, KLD, KLE, KLF, KLG, KLH, KLI, KLL, KLN, KLQ, KLR, KLS, KLT, KLY, KNA, KND, KNE, KNF, KNG, KNH, KNI, KNL, KNN, KNQ, KNR, KNS, KNT, KNY, KPA, KPD, KPE, KPF, KPG, KPH, KPI, KPL, KPN, KPQ, KPR, KPS, KPT, KPY, KQA, KQD, KQE, KQF, KQG, KQH, KQI, KQL, KQN, KQQ, KQR, KQS, KQT, KQY, KRA, KRD, KRE, KRF, KRG, KRH, KRI, KRL, KRN, KRQ, KRR, KRS, KRT, KRY, KSA, KSD, KSE, KSF, KSG, KSH, KSI, KSL, KSN, KSQ, KSR, KSS, KST, KSY, KTA, KTD, KTE, KTF, KTG, KTH, KTI, KTL, KTN, KTQ, KTR, KTS, KTT, KTY, KYA, KYD, KYE, KYF, KYG, KYH, KYI, KYL, KYN, KYQ, KYR, KYS, KYT, KYY, KA, KD, KE, KF, KG, KH, KI, KL, KN, KP, KQ, KR, KS, KT, KY and SEQ ID NOs 75 to 3224, KA, KD, KE, KF, KG, KH, KI, KL, KN, KP, KQ, KR, KS, KT, KY and SEQ ID NOs 3225 to 6374, KA, KD, KE, KF, KG, KH, KI, KL, KN, KP, KQ, KR, KS, KT, KY and SEQ ID NOs 6375 to 15194, KA, KD, KE, KF, KG, KH, KI, KL, KN, KP, KQ, KR, KS, KT, KY and SEQ ID NOs 15195 to 18134, KA, KD, KE, KF, KG, KH, KI, KL, KN, KP, KQ, KR, KS, KT, KY and SEQ ID NOs 18135 to 21074, and KA, KD, KE, KF, KG, KH, KI, KL, KN, KP, KQ, KR, KS, KT, KY and SEQ ID NOs 21075 to 24014, 24037-24036.

In some embodiments, the A-chain comprises a sequence selected from SEQ ID NOs 1 and 3 to 33, and is optionally appended at the N-terminus and/or at the C-terminus by at least one selected from KA, KD, KE, KF, KG, KH, KI, KL, KN, KP, KQ, KR, KS, KT, KY, KAA, KAD, KAE, KAF, KAG, KAH, KAI, KAL, KAN, KAQ, KAR, KAS, KAT, KAY, KDA, KDD, KDE, KDF, KDG, KDH, KDI, KDL, KDN, KDQ, KDR, KDS, KDT, KDY, KEA, KED, KEE, KEF, KEG, KEH, KEI, KEL, KEN, KEQ, KER, KES, KET, KEY, KFA, KFD, KFE, KFF, KFG, KFH, KFI, KFL, KEN, KFQ, KFR, KFS, KFT, KFY, KGA, KGD, KGE, KGF, KGG, KGH, KGI, KGL, KGN, KGQ, KGR, KGS, KGT, KGY, KHA, KHD, KHE, KHF, KHG, KHH, KHI, KHL, KHN, KHQ, KHR, KHS, KHT, KHY, KIA, KID, KIE, KIF, KIG, KIH, KII, KIL, KIN, KIQ, KIR, KIS, KIT, KIY, KLA, KLD, KLE, KLF, KLG, KLH, KLI, KLL, KLN, KLQ, KLR, KLS, KLT, KLY, KNA, KND, KNE, KNF, KNG, KNH, KNI, KNL, KNN, KNQ, KNR, KNS, KNT, KNY, KPA, KPD, KPE, KPF, KPG, KPH, KPI, KPL, KPN, KPQ, KPR, KPS, KPT, KPY, KQA, KQD, KQE, KQF, KQG, KQH, KQI, KQL, KQN, KQQ, KQR, KQS, KQT, KQY, KRA, KRD, KRE, KRF, KRG, KRH, KRI, KRL, KRN, KRQ, KRR, KRS, KRT, KRY, KSA, KSD, KSE, KSF, KSG, KSH, KSI, KSL, KSN, KSQ, KSR, kSS, KST, KSY, KTA, KTD, KTE, KTF, KTG, KTH, KTI, KTL, KTN, KTQ, KTR, KTS, KTT, KTY, KYA, KYD, KYE, KYF, KYG, KYH, KYI, KYL, KYN, KYQ, KYR, KYS, KYT, KYY, SEQ ID NOs 75 to 24014, KGSH (SEQ ID NO:24049), GKGSH (SEQ ID NO:24050), GKGSKK-(SEQ ID NO:24045), GKKPGKK (SEQ ID NO:24046), GKGPSK (SEQ ID NO:24044), GKP-SHKP (SEQ ID NO:24043), and GSHKGSHK (SEQ ID NO:24042); and wherein the B-chain comprises a sequence selected from SEQ ID NOs 2 and 34 to 74, 24047, and 24048, and is optionally appended at the N-terminus and/or at the C-terminus by at least one selected from KA, KD, KE, KF, KG, KH, KI, KL, KN, KP, KQ, KR, KS, KT, KY, KAA, KAD, KAE, KAF, KAG, KAH, KAI, KAL, KAN, KAQ, KAR, KAS, KAT, KAY, KDA, KDD, KDE, KDF, KDG, KDH, KDI, KDL, KDN, KDQ, KDR, KDS, KDT, KDY, KEA, KED, KEE, KEF, KEG, KEH, KEI, KEL, KEN, KEQ, KER, KES, KET, KEY, KFA, KFD, KFE, KFF, KFG, KFH, KFI, KFL, KFN, KFQ, KFR, KFS, KFT, KFY, KGA, KGD, KGE, KGF, KGG, KGH, KGI, KGL, KGN, KGQ, KGR, KGS, KGT, KGY, KHA, KHD, KHE, KHF, KHG, KHH, KHI, KHL, KHN, KHQ, KHR, KHS, KHT, KHY, KIA, KID, KIE, KIF, KIG, KIH, KII, KIL, KIN, KIQ, KIR, KIS, KIT, KIY, KLA, KLD, KLE, KLF, KLG, KLH, KLI, KLL, KLN, KLQ, KLR, KLS, KLT, KLY, KNA, KND, KNE, KNF, KNG, KNH, KNI, KNL, KNN, KNQ, KNR, KNS, KNT, KNY, KPA, KPD, KPE, KPF, KPG, KPH, KPI, KPL, KPN, KPQ, KPR, KPS, KPT, KPY, KQA, KQD, KQE, KQF, KQG, KQH, KQI, KQL, KQN, KQQ, KQR, KQS, KQT, KQY, KRA, KRD, KRE, KRF, KRG, KRH, KRI, KRL, KRN, KRQ, KRR, KRS, KRT, KRY, KSA, KSD, KSE, KSF, KSG, KSH, KSI, KSL, KSN, KSQ, KSR, KSS, KST, KSY, KTA, KTD, KTE, KTF, KTG, KTH, KTI, KTL, KTN, KTQ, KTR, KTS, KTT, KTY, KYA, KYD, KYE, KYF, KYG, KYH, KYI, KYL, KYN, KYQ, KYR, KYS, KYT, KYY, SEQ ID NOs 75 to 24014, KGSH (SEQ ID NO:24049), GKGSH (SEQ ID NO:24050), GKGSKK (SEQ ID NO:24045), GKKPGKK (SEQ ID NO:24046), GKGPSK (SEQ ID NO:24044), GKPSHKP (SEQ ID NO:24043), and GSHKGSHK (SEQ ID NO:24042).

In some embodiments, no more than 4 residues are added or deleted from the A-chain and/or the B-chain of the insulin.

In some embodiments, a K residue is present at the N-terminus of the A-chain and/or the B-chain, and/or wherein no more than three K residues are present at the N-terminus of the A-chain and/or the B-chain, and/or wherein in (i) the tyrosine at A14 is replaced with glutamic acid, and/or (ii) the tyrosine at B16 is replaced with histidine, and/or (iii) the phenylalanine at B25 is replaced with a histidine, and/or wherein one to three residues selected from residues B20, B21, and B22-B29 of the B-chain, residues A4 or A8 of the A-chain, and residues of an optionally extended polypeptide, are lysine residues, and/or wherein only one K residue is present within 10 residues of the N-terminus of B-chain.

In some embodiments, X1 comprises an insulin and/or insulin analog as disclosed herein.

In some embodiments, X1 comprises an insulin and/or insulin analog as disclosed herein, and the insulin and/or insulin analog further comprises an optional covalent-spacer.

In some embodiments, an amino group of one or more side chain(s) of one to four lysine residues of insulin is each independently covalently conjugated as described by Formula I.

In some embodiments, the insulin comprises at least two amines that are covalently conjugated as described by Formula I, wherein one amine is the N-terminus amino group of the B-chain of insulin, and the other amine(s) are the side chain amine of a lysine that is 0 to 5 residues away from residue $B_{22}$ of the B-chain of insulin, and/or the side chain amine of a lysine that is 1 to 5 residues away from residue A21 of the A-chain of insulin.

In some embodiments, an amino group at the N-terminus of the B-chain of insulin is covalently conjugated as described by Formula I, and q' is optionally 2 or more, and the insulin includes at least one additional covalent conjugation to X1 as independently described by Formula I.

In some embodiments, the insulin is covalently conjugated as described by Formula I, such as in Examples 1-915, and wherein 1 to 4 residues are optionally added or deleted from the A-chain and/or B-chain of the insulins shown in Examples 1-915

In another aspect, the disclosure provides an insulin (e.g., a modified insulin) that may be used as an intermediate for the manufacture of a conjugate described by Formula I.

In some embodiments, each secondary amine in Formulae FF1-FF231 that is not conjugated to any of 1, $B_2$ or $B_3$, is optionally independently acetylated or alkylated.

In some embodiments, the N-terminus of the A-chain and/or the N-terminus of the B-chain of insulin are additionally each independently covalently conjugated to at least two aromatic boron-containing groups, and/or wherein the C-terminus of the B-chain is further extended with a polypeptide of up to 20 residues, or the C-terminus of the A-chain is further extended with a polypeptide of up to 40 residues, each polypeptide independently comprising, at least one lysine residue in which the amino group of the lysine side chain is covalently conjugated as described by Formula I.

In some embodiments, X1 is insulin having a sequence comprising one selected from: a lysine at residue B21 of the B-chain and an arginine at residue B29 of the B-chain; a lysine at residue B21 of the B-chain; and a lysine at residue B29 of the B-chain; wherein an amino group of at least one lysine of the sequence is covalently conjugated as described by Formula I.

In some embodiments, X1 is insulin having a sequence comprising: a lysine at residue B21 of the B-chain; and at least one lysine at the N-terminus of the B-chain; wherein an amino group of at least one lysine of the sequence is covalently-conjugated as described by Formula I.

In some embodiments, the C-terminus of Z1a is conjugated through an amide linkage to a Z1b, and the Z1b is conjugated to the N-terminus of the B-chain of insulin through an amine linkage, and wherein the insulin is optionally further conjugated as described by Formula I.

In some embodiments, the compound comprises at least one Z1a comprising at least three amino acid residues having a side chain; the side chain of two residues of Z1a are conjugated together through a covalent bond included in at least one selected from a triazole linkage, an amide linkage, a disulfide linkage, a thioether linkage, a thiolene linkage, and an amine linkage; and the two conjugated residues are at least one residue apart.

In some embodiments, the N-terminal amine of a Z1a is covalently conjugated to a Z1c.

In some embodiments, the compound comprises at least one Z1a comprising one or more amino acids selected from lysine, diaminopropionic acid, glycine, diaminobutyric acid, serine, histidine, and ornithine, and at least one or more of the side chains of the one or more amino acids, is covalently conjugated as described by Formula I.

In some embodiments, the compound comprises at least one Z1a comprising one or more glutamic or aspartic acid residues, and optionally other naturally occurring amino acids, and at least one lysine residue that is covalently conjugated as described by Formula I.

In some embodiments, the compound comprises at least one Z1a comprising at least one lysine residue that is covalently conjugated as described by Formula I, wherein the majority of the residues are negatively charged residues.

In some embodiments, the insulin is covalently conjugated as described by Formula I, and Z1b is absent and the C-terminus of Z1a is directly conjugated to the N-terminus of the B-chain of insulin through a peptide bond.

In some embodiments, the insulin is covalently conjugated as described by Formula I, n'=0 and the C-terminus of Z1a is directly conjugated to the N-terminus of the B-chain of insulin through a peptide bond; and Z1a comprises at least one amino acid from each of groups M1 and M2 such that no two adjacent residues are from the same group and Z1a contains at least one lysine that is covalently conjugated as described by Formula I, wherein: (i)group M1 comprises lysine and alanine and group M2 comprises glycine, glutamic acid, serine, threonine, alanine and proline; or (ii) group M1 consists of lysine and alanine; and group M2 consists of glycine, glutamic acid, serine, threonine, alanine and proline. 19. In some embodiments, the insulin is covalently conjugated as described by Formula I, n'=0 and the C-terminus of Z1a is directly conjugated to the N-terminus of the B-chain of insulin through a peptide bond;

Z1a comprises at least one amino acid selected from K, P, E, G, S, T, A, and R, such that the sequence comprises at least one lysine, at least one proline, and at least one amino acid selected from H, R, A and T; and the amino group of least one lysine side chain in Z1a is covalently conjugated as described by Formula I.

In some embodiments, the insulin is covalently conjugated as described by Formula I, n'=0 and the C-terminus of Z1a is directly conjugated to the N-terminus of the B-chain of Insulin through a peptide bond; and Z1a comprises at least one amino acid selected from the alanine, glycine, aspartic acid, threonine, histidine, methionine, cysteine, isoleucine, leucine, valine and glutamine; and at least one lysine having a side chain amino group that is covalently conjugated as described by Formula I; and the rest of the amino acids in Z1a are each independently selected from the twenty naturally occurring amino acids.

In some embodiments, the insulin is covalently conjugated as described by Formula I, n'=0 and the C-terminus of Z1a is directly conjugated to the N-terminus of the B-chain of Insulin through a peptide bond; Z1a has a sequence selected from: KPA, KPH, GKPA, GKPS, KP, GKPSG, and GKPGS; and Z1a comprises at least one lysine having a side chain amino group that is covalently conjugated as described by Formula I.

In some embodiments, the insulin is covalently conjugated as described by Formula I, n'=0 and the C-terminus of Z1a is directly conjugated to the N-terminus of the B-chain of Insulin through a peptide bond; Z1a comprises two or more copies of a sequence selected from: EGE, SGS, GSG, KP, GEG, E, GG, S, T, A, and R, such that no two adjacent copies are the same; Z1a optionally contains one or more of H, A, N and R; and the amino group of least one lysine side chain in Z1a is covalently conjugated as described by Formula I.

In some embodiments, the insulin is covalently conjugated as described by Formula I, n'=0 and the C-terminus of Z1a is directly conjugated to the N-terminus of the B-chain of Insulin through a peptide bond; Z1a comprises one or more amino acids selected from K, P, E, G, S, T, A, and R, such the sequence comprises at least one lysine, at least one proline, and at least one amino acid selected from H, R, A and T; and the amino group of least one lysine side chain in Z1a is covalently conjugated as described by Formula I.

In some embodiments, the insulin is covalently conjugated as described by Formula I, n'=0 and the C-terminus of Z1a is directly conjugated to the N-terminus of the B-chain of Insulin through a peptide bond; and at least one copy of KP is comprised in the polypeptide sequence of Z1a or insulin, wherein the amino group of the lysine side chain in KP is covalently conjugated as described by Formula I.

In some embodiments, the insulin is covalently conjugated as described by Formula I, n'=0 and the side chains of two residues of Z1a are conjugated via a covalent bond selected from a triazole, an amide bond, a disulfide bond, a thioether, a thiolene, and an amine; the two conjugated residues are separated by at least one amino acid; and the amino group of least one lysine side chain in Z1a is covalently conjugated as described by Formula I.

In some embodiments, the insulin is covalently conjugated as described by Formula I, n'=0 and the C-terminus of Z1a is directly conjugated to the N-terminus of the B-chain of insulin through a peptide bond; Z1a is a polypeptide selected from the a polypeptide from the sequence of human insulin, a polypeptide from the sequence of human glucagon, a polypeptide from the sequence of human C-peptide, a polypeptide from the sequence of human GLP-1, a polypeptide from the sequence of human GIP, a polypeptide from the sequence of human Extendin, and a human polypeptide hormone, and wherein the polypeptide comprises at least one lysine or Z1a contains at least one copy of dipeptide KP, and wherein the amino group of at least one lysine side chain in Z1a is covalently conjugated as described by Formula I.

In some embodiments, at least one lysine residue, an inserted cysteine residue, or a residue that has been mutated to cysteine is covalently conjugated to a structure independently selected from Formulae F411-F416:

(F411)

(F412)

(F413)

(F414)

(F415)

(F416)

and wherein in Formulae F411-F416, R represents an attachment point to the amine group of the lysine side chain, or the thiol group of the cysteine side chain; n is an integer in the range of 1 to 14, m is an integer between 1 and 12, o is an integer between 1 and 6, p is an integer between 1 and 12; and Z represents one of —(C═O)— OH, —NH$_2$, —CH$_3$, a cholesterol, 7-OH cholesterol, 7,25-dihydroxycholesterol, cholic acid, chenodeoxycholic acid, lithocholic acid, deoxycholic acid, glycocholic acid, glycodeoxycholic acid, glycolithocholic acid, glycochenodeoxycholic acid, α-tocopherol, β-tocopherol, γ-tocopherol, δ-tocopherol, αtocotrienol, β-tocotrienol, γ-tocotrienol, or δ-tocotrienol.

In some embodiments, the residue at position B29 of the B-chain of Insulin is a lysine covalently conjugated through an amide bond to the side chain of an L- or D-glutamic acid, and wherein the L- or D-glutamic acid is covalently conjugated through an amide bond to one of acid selected from hexanoic acid, myristic acid, octanoic acid, nonanoic acid, decanoic acid, lauric acid, stearic acid, and palmitic acid.

In some embodiments, the insulin is covalently conjugated as described by Formula I, Z1a comprises a polypeptide with the sequence (XA$_1$X)$_m$, wherein: A$_1$ is an L- or D-amino acid; m is an integer in the range of 1 to 4; and each X is K or KP; and the epsilon amine group of at least one lysine side chain in Z1a is further covalently conjugated as described by Formula I.

In some embodiments, the insulin is covalently conjugated as described by Formula I, Z1a comprises a polypeptide with the sequence (XA$_1$A$_2$X)$_m$ (SEQ ID NO:24021), wherein: A$_1$ and A$_2$ are each independently an L- or D-amino acid; m is an integer in the range of 1 to 4; each X is K or KP; and the epsilon amine group of at least one lysine side chain in Z1a is further covalently conjugated as described by Formula I.

In some embodiments, the insulin is covalently conjugated as described by Formula I, Z1a comprises a polypeptide with the sequence (XA$_1$A$_2$A$_3$X)$_m$(SEQ ID NO:24022), wherein: A$_1$, A$_2$, and A$_3$ are each independently an L- or D-amino acid; m is an integer in the range of 1 to 4; each X is K or KP; and the epsilon amine group of at least one lysine side chain in Z1a is covalently conjugated as described by Formula I.

In some embodiments, the insulin is covalently conjugated as described by Formula I, Z1a comprises a polypeptide with a sequence selected from (XA1X)m(GGGGS)n (SEQ ID NO:24023), (XA1A2X)m(GGGGS)n (SEQ ID NO:24024), (XA1A2A3X)$_m$(GGGGS)$_n$ (SEQ ID NO:24025), (XA1X)m (GGGGS)n (XA2X)o (SEQ ID NO:24026), and XA1A2X)m(GGGGS)n (XA3A4X)o (SEQ ID NO:24027), wherein: A$_1$, A$_2$, A$_3$, and A$_4$ are each independently an L- or D-amino acid; m is an integer in the range of 1 to 4; n is an integer in the range of 1 to 4; o is an integer in the range of 1 to 4; each X is K or KP; and the epsilon amine group of each lysine side chain of at least one lysine side chain in Z1a is further covalently conjugated as described by Formula I.

In some embodiments, the insulin is covalently conjugated as described by Formula I, Z1a comprises a polypeptide with the sequence (GX)$_m$, wherein: X is KV; m is an integer in the range of 1 to 4, and the epsilon amine group of at least one lysine side chain in Z1a is further covalently conjugated, as described by Formula I.

In some embodiments, the insulin is covalently conjugated as described by Formula I, Z1a comprises a polypeptide with a sequence selected from: GXA1KGEA2XT)m (GGSGSSS)n (GXGXA3GSSSGSSSXT)o (SEQ ID NO:24028), (GXA1ESA2LYL)m (SEQ ID NO:24029), (TXEX)m(GPGS)n (SEQ ID NO:24030), (GXESA1VA)m (KA2K)n (SEQ ID NO:24031), (GXEA1A2)m(GGS)n (TYA3XXT)o (SEQ ID NO:24032), and (TXAXYT)m (TSSS)n (SEQ ID NO:24033), wherein: each X is KV or KP; A$_1$, A$_2$, A$_3$ are each independently an L- or D-amino acid; m is an integer in the range of 1 to 4; n is an integer in the range of 1 to 4; and o is an integer in the range of 1 to 4; and the epsilon amine group of at least one lysine side chain in Z1a is further covalently conjugated as described by Formula I.

In some embodiments, the insulin is covalently conjugated as described by Formula I, Z1a comprises a polypeptide with a sequence selected from (TKPYA1KEVETA2GSGS)m (GGGGS)n (SEQ ID NO:24034), (YTPLEA1KPYSTSYKPYSEA1L)m (GKPTSLEA2FLVEA2LYTKP)n (SEQ ID NO:24035), and (GKEALYLTPLESALYKP)m(TKPLEALYLK-PEILSLKPESLA)n(GKPGSSSKPDTSSSGTP KTAAGS)o (SEQ ID NO:24036), wherein: A$_1$ and A$_2$ are each independently an L- or D-amino acid; m is an integer in the range of 1 to 4; n is an integer in the range of 1 to 4; and the epsilon amine group of at least one lysine side chain in Z1a is further covalently conjugated as described by Formula I.

In some embodiments, the compound is conjugated either directly, or via an optional covalent-spacer, to a drug molecule, an imaging agent, a contrast agent, a radioactive isotope, a radiotherapy agent, or a molecule that engages immune cells in the body.

In some embodiments, X1 is human glucagon or an analogue of human glucagon, and optionally covalently conjugated to one or more diol- or sugar-containing molecules, or X1 is an analogue of a human peptide hormone that is modified so that it binds to its cognate receptor but has diminished or null ability to activate the receptor in the body, or X1 is an analogue of a human peptide hormone that is modified so that it selectively binds or activates a subset of its cognate receptors or subsets of receptors of human polypeptide hormones.

In some embodiments, the aromatic boron-containing groups are modified to be MIDA protected, pinacol protected, or in an ester form. In some embodiments, the aromatic boron-containing group is MIDA protected or pinacol protected.

In some embodiments, the modified aromatic boron-containing groups are used as intermediates for the synthesis of a conjugate of Formula I.

In some embodiments, X1 comprises: (i) a human polypeptide hormone or an analogue of a human polypeptide hormone, wherein the covalent linkage to X1 is to an amine or via an optional covalent-spacer to an amine in X1; (ii) an amine configured to be covalently conjugated via an optional covalent-spacer to a human polypeptide hormone or an analogue of a human polypeptide hormone, or (iii) NH$_2$, and wherein the amine in X1 is covalently conjugated twice as described by Formula I, wherein the first covalent conjugation is through an amine bond and the second covalent conjugation is through an amide bond, and wherein each covalent conjugation is the same or different.

In some embodiments, residue B21 of the B-chain of Insulin is K, residue B22 of the B-chain of Insulin is P, and residue B29 of the B-chain of Insulin is R; and the N-terminus of the Insulin B-chain is covalently conjugated as described by Formula I to the C-terminus of Z1a, wherein: n'=0; Z1a has the sequence GKPGHKP; and one Z1c is attached to each lysine side chain in Z1a, wherein each Z1c is independently represented by Formula FF12, and each of B1 and B2 are represented by Formula F2, wherein one R1 at position 5' is the covalent amide bond to Formula FF12, and the amino group of the lysine at B21 (residue 21 of the B-chain of Insulin) is covalently conjugated as described by Formula I, wherein n'=0; m'=0; and Z1c is described by Formula FF12, wherein each of B1 and B2 are represented by formula F2, and wherein one R1 at position 5' is the covalent amide bond to Formula FF12.

In at least one embodiment, the present disclosure is directed to an insulin analog. In some embodiments, the insulin analog is desB30 human insulin; wherein the N-terminus of the Insulin B-chain is covalently conjugated as described by Formula I to the C-terminus of Z1a, wherein: n'=0; Z1a has the sequence KPGSEHESA, and one Z1c is attached to each lysine side chain in Z1a, wherein each Z1c is described byFormula FF1, and each of B1 and B2 are described by Formula F1, wherein one R1 at position 3' is the covalent amide bond to Formula FF1 and wherein one R1 at position 5' is F, and wherein the amino group of the lysine at B29 (residue 29 of the B-chain of Insulin) is covalently conjugated as described by Formula I, wherein n'=0; m'=0; and Z1c is described by Formula FF1, and each of B1 and B2 are described by Formula F1, wherein one R1 at position 3' is the covalent amide bond to Formula FF1 and one R1 at position 5' is F.

In some embodiments, the A- and/or B-chain sequence of the insulin is appended at the N-terminus or C-terminus by KX'K, KX', or X'K wherein X' represents a continuous sequence of 2, 3, 4, or 5 residues selected from within wild-type A-chain (SEQ ID NO:1) and wild-type B-chain (SEQ ID NO:2). In some embodiments, each K residue is optionally and independently covalently conjugated as described by Formula I. In some embodiments, X' is a polypeptide of up to 30 residues with amino acids independently selected from: K, G, S, E, H, E, N, Q, D, A, P, R and C and each K residue is optionally and independently covalently conjugated as described by Formula I.

In some embodiments, the N-terminus of the A-chain and/or B-chain are optionally and independently covalently conjugated as described by Formula I.

In some embodiments, each K residue when present in insulin (insulin analog) is optionally and independently covalently conjugated as described by Formula I, wherein Z1c is any one of formulae FF1-FF231 and the B1 and B2 are each independently selected from F1 and F2.

In some embodiments, each K residue when present in insulin is optionally and independently covalently conjugated as described by Formula I, wherein Z1c is any one of formulae:

Formulae FF1-F22 and the B1 and B2 are each independently selected from F1 and F2;

Formulae FF23-FF48 and the B1 and B2 are each independently selected from F1 and F2;

Formulae FF49-FF88 and the B1 and B2 are each independently selected from F1 and F2;

Formulae FF89-FF112 and the B1 and B2 are each independently selected from F1 and F2;

Formulae FF113-FF136 and the B1 and B2 are each independently selected from F1 and F2;

Formulae FF137-FF160 and the B1 and B2 are each independently selected from F1 and F2;

Formulae FF160-FF166 and the B1 and B2 are each independently selected from F1 and F2;

Formulae FF167-FF224 and the B1 and B2 are each independently selected from F1 and F2; or Formulae FF225-FF231 and the B1 and B2 are each independently selected from Formulae F3-F11.

In some embodiments, Z1b is optionally selected from Formula IIa-Formula IIi; and/or optionally selected from Formula IIIa-Formula IIIi.

In at least some embodiments, the insulin does not comprise Z1a and/or Z1b. In some embodiments, Z1a is not present. In some embodiments, Z1b is not present. In at least some embodiments, Z1a and/or Z1b are not present.

In some embodiments, each K residue when present in insulin is optionally and independently covalently conjugated as described by Formula I, and wherein Z1c is any one of formulae FF1-FF231 and the B1 and B2 are each independently selected from F3 and F4.

In some embodiments, each K residue when present in insulin is optionally and independently covalently conjugated as described by Formula I, wherein Z1c is any one of formulae:

Formulae FF1-F22 and the B1 and B2 are each independently selected from F3 and F4;

Formulae FF23-FF48 and the B1 and B2 are each independently selected from F3 and F4;

Formulae FF49-FF88 and the B1 and B2 are each independently selected from F3 and F4;

Formulae FF89-FF112 and the B1 and B2 are each independently selected from F3 and F4;

Formulae FF113-FF136 and the B1 and B2 are each independently selected from F3 and F4;

Formulae FF137-FF160 and the B1 and B2 are each independently selected from F3 and F4;

Formulae FF160-FF166 and the B1 and B2 are each independently selected from F3 and F4;

Formulae FF167-FF224 and the B1 and B2 are each independently selected from F3 and F4; or Formulae FF225-FF231 and the B1 and B2 are each independently selected from Formulae F3-F11.

In some embodiments, Z1b is optionally selected from Formula IIa-Formula IIi and Formula IIIa-Formula IIIi.

In some embodiments, Z1a and/or Z1b are not present.

In some embodiments, each K residue is optionally and independently covalently conjugated as described by Formula I, wherein Z1c is any one of Formulae FF1-F224 and the B1 and B2 are each independently selected from F5, F6, F7, and F8.

In some embodiments, each K residue when present in insulin is optionally and independently covalently conjugated as described by Formula I, wherein Z1c is any one of formulae:

Formulae FF1-F22 and the B1 and B2 are each independently selected from F5, F6, F7, and F8;

Formulae FF23-FF48 and the B1 and B2 are each independently selected from F5, F6, F7, and F8;

Formulae FF49-FF88 and the B1 and B2 are each independently selected from F5, F6, F7, and F8;

Formulae FF89-FF112 and the B1 and B2 are each independently selected from F5, F6, F7, and F8;

Formulae FF113-FF136 and the B1 and B2 are each independently selected from F5, F6, F7, and F8;

Formulae FF137-FF160 and the B1 and B2 are each independently selected from F5, F6, F7, and F8;

Formulae FF160-FF166 and the B1 and B2 are each independently selected from F5, F6, F7, and F8;

Formulae FF167-FF224 and the B1 and B2 are each independently selected from F5, F6, F7, and F8; or Formulae FF225-FF231 and the B1 and B2 are each independently selected from Formulae F3-F11.

In some embodiments, Z1b is optionally selected from Formula IIa-Formula IIi and Formula IIIa-Formula IIIi.

In some embodiments, Z1a and/or Z1b are not present.

In some embodiments, each K residue when present in insulin is optionally and independently covalently conjugated as described by Formula I, wherein Z1c is any one of 643 644 formulae FF1-F224and the B1 and B2 are each independently selected from F9 and F10.

In some embodiments, each K residue when present in insulin is optionally and independently covalently conjugated as described by Formula I, wherein Z1c is any one of formulae:

Formulae FF1-F22 and the B1 and B2 are each independently selected from F9 and F10;

Formulae FF23-FF48 and the B1 and B2 are each independently selected from F9 and F10;

Formulae FF49-FF88 and the B1 and B2 are each independently selected from F9 and F10;

Formulae FF89-FF112 and the B1 and B2 are each independently selected from F9 and F10;

Formulae FF113-FF136 and the B1 and B2 are each independently selected from F9 and F10;

Formulae FF137-FF166 and the B1 and B2 are each independently selected from F9 and F10;

Formulae FF167-FF224 and the B1 and B2 are each independently selected from F9 and F10; or Formulae FF225-FF231 and the B1 and B2 are each independently selected from Formulae F3-F11.

In some embodiments, $B_1$ and $B_2$ in Formulae FF225-FF231 are not a boronic acid, or an F2 or F6 aromatic boron-containing group, wherein Formulae F2 and F6 are:

(F2)

(F6)

$R_1$ at position 4' or position 5' represents (C=O)—*, wherein —* represents the attachment point to the rest of Z1c;

zero, one, or two $R_1$ represents F, Cl, $CF_2$, $CF_3$, $SF_5$, $OCF_3$, $SO_2CH_3$, and/or $SO_2CF_3$, and each remaining $R_1$ represents H;

Y8 is O; and i is 1.

In some embodiments, B1, B2, B3 are each independently Formula F7A, (F7A)

wherein:

$R_1$ at position 5' represents (C=O)—*, wherein —* represents the attachment point to the rest of Z1c or a compound; and each remaining $R_1$ is selected from H, F and $CF_3$. In some embodiments, each remaining $R_1$ is H.

In some embodiments, Z1b is not present in insulin (i.e., insulin analog) and wherein Z1a is a polypeptide that is covalently linked by a peptide bond to the N-terminus of the B-chain of insulin and/or Z1a is a polypeptide that is covalently linked by a peptide bond to the N-terminus of the B-chain of insulin C-terminus of A-chain of insulin.

In some embodiments, Z1b may be present in insulin. If present in insulin, Z1b is optionally selected from Formula IIa-Formula IIi and Formula IIIa-Formula IIIi.

In some embodiments, Z1b is not present in insulin. In some embodiments, Z1a is not present. In at least some embodiments, Z1b and/or Z1a are not present.

In some embodiments, a therapeutically-effective amount of a pharmaceutical composition of the present disclosure may be administered to a subject. In some embodiments, the pharmaceutical composition comprises at least one compound disclosed herein (e.g., Formula I, Formula IB, Formula IF) and a pharmaceutically acceptable carrier.

In some embodiments, a compound disclosed herein is used as a medicament.

In some embodiments, the disclosure provides a method of treatment or prevention of diabetes, impaired glucose tolerance, hyperglycemia or metabolic syndrome, comprises administering to a subject in need thereof a therapeutically effective amount of a compound disclosed herein or a pharmaceutical composition disclosed herein.

In some embodiments, the pharmaceutical composition comprises one or more polyalcohols. In some embodiments, the polyalcohols are selected from mannitol, sorbitol, erythritol, isomalt, lactitol, glucose, and maltitol.

In some embodiments, the pharmaceutical composition comprises at least one compound disclosed herein for use as a medicament for the treatment of diabetes or obesity, for control of blood sugar levels, or for control of release of a drug.

In some embodiments, the present disclosure provides a method of administering the compounds disclosed herein or a pharmaceutical composition disclosed herein to a subject as a therapeutic or prophylactic agent.

In some embodiments, the disclosure provides a method of making a compound as disclosed herein comprising at least one alkylation and/or amidation step.

In some embodiments, the disclosure provides a method of treating a subject by administering a device or formulation comprising a compound as disclosed herein, such as Examples 1A-82A. For example, the device can be a fixed dose injector, microdosing injector, an internal or external patch.

In some embodiments, the compound of the present disclosure may be used, as an intermediate in the manufacture/synthesis of a drug substance or a therapeutic of a prophylactic compound.

In another aspect, the disclosure provides a polypeptide comprising an A-chain and a B-chain, wherein the A-chain comprises a sequence selected from 1, 24051, and 24052; and wherein the B-chain comprises a sequence selected from 25000-25397. In some embodiments, the A-chain comprises a sequence selected from 1, 24051, and 24052, and the B-chain comprises a sequence selected from 24063, 25228, 25229, 25000, 25001, 25006-25009, 25076, 25077, 25082-25085, 25228, 25229, 25232, 25234-25237, 25304, 25305, 25308, and 25310-25313. In some embodiments, the A-chain comprises a sequence selected from 1 and 24051, and wherein the B-chain comprises a sequence selected from 24063, 25228, 25229, 25011, 25012, 25017-25020, 25087, 25088, 25093-25096, 25229, 25239, 25232, 25240, 25245-25248, 25305, 25308, 25315, 25316, and 25321-25324.

In some embodiments, the A-chain comprises a sequence selected from 1 and 24051, and the B-chain comprises a sequence selected from 24063, 25228, 25229, 25232, 25234-25237, 25304, 25305, 25308, and 25310-25313,.

In some embodiments, the agonist potency of a compound disclosed herein is determined by measuring the compound's potency for activation of a receptor (e.g., insulin receptor). In some embodiments, the present disclosure provides a compound having agonist potency for an insulin receptor comprising at least one aromatic boron-containing group, the compound having a first EC50 potency for activating the insulin receptor at a first glucose concentration and a second EC50 potency for activating the insulin receptor at a second glucose concentration, wherein when the first glucose concentration is 5.6 mM and the second glucose concentration is 16.7 mM the compound has an insulin receptor agonist potency ratio of the first EC50 to the second EC50 of about 1.2 to about 20, about 1.5 to about 15, about 2 to about 14, about 2.5 to about 13, about 2.5 to about 12, about 2.5 to about 11, about 2.5 to about 10, about 2.5 to about 9, about 2.5 to about 8, about 2.5 to about 7, about 2.5 to about 6, about 2.5 to about 5, or about 2:5 to about 4.5 In some embodiments, the present disclosure provides a compound comprising at least one aromatic boron-containing group having agonist potency for an insulin receptor, the compound having a first EC50 potency for activating the insulin receptor at a first glucose concentration and a second EC50 potency for activating the insulin receptor at a second glucose concentration, wherein when the first glucose concentration is 5.6 mM and the second glucose concentration is 16.7 mM the compound has an insulin receptor agonist potency ratio of the first EC50 to the second EC50 of about 1 to about 15, about 1 to about 10, about 2 to about 9, about 2 to about 8, about 3 to about 7, or about 3 to about 6. In some embodiments, when the first glucose concentration is 5.6 mM and the second glucose concentration is 16.7 mM the compound has an insulin receptor agonist potency ratio of the first EC50 to the second EC50 of at least or up to about 1, 2, 3, 4, 5, 6, 7, 8, 9, 10, 11, 12, 13, 14, or 15. In some embodiments, the compound has an insulin receptor agonist potency ratio of the first EC50 to the second EC50 of about 2, 3, 4, 5, 6, 7, 8, 9, 10, 11, 12, 13, or 14.

In some embodiments, the present disclosure provides a compound comprising at least one aromatic boron-containing group having agonist potency for an insulin receptor, the compound having a first EC50 potency for activating the insulin receptor at a first glucose concentration and a second EC50 potency for activating the insulin receptor at a second glucose concentration, wherein when the first glucose concentration is 5.6 mM and the second glucose concentration is 16.7 mM the compound has an insulin receptor agonist potency ratio of the first EC50 to the second EC50 of about 1.2 to about 14, about 1.3 to about 13, about 1.4 to about 12, about 1.5 to about 11, about 2 to about 10, about 3 to about 9, or about 3 to about 5. In some embodiments, when the first glucose concentration is 5.6 mM and the second glucose concentration is 16.7 mM the compound has an insulin receptor agonist potency ratio of the first EC50 to the second EC50 of at least or up to about 1.2, 1.3, 1.4, 1.5, 2, 3, 4, or 5.

In some embodiments, the present disclosure provides a compound comprising at least one diboronate sensor having binding affinity to glucose.

In some embodiments, the present disclosure provides a compound comprising at least one aromatic boron-containing group having binding affinity for glucose, wherein when administered at a dose of 30 nmol/kg to a first group of rats with a first glucose infusion rate to provide a blood glucose concentration of 100 mg/dL and to a second group of rats with a second glucose infusion rate to provide a blood glucose concentration of 200 mg/dL the compound provides a relative glucose infusion rate difference (mg/kg/min·min) of 1 to about 2500, about 1 to about 2000, about 1 to about 1500, about 100 to about 1500, and about 1000 to about 1500, and a relative glucose infusion rate ratio of about 0.1 to about 5, about 0.2 to about 4.5, about 0.5 to about 4, about 0.5 to about 3.5, about 1 to about 3.5, about 1.5 to about 3.5, or about 2 to about 3.

In some embodiments, the compound provides a relative glucose infusion rate difference (mg/kg/min·min) of at least about 50, 100, 200, 300, 400, 500, 1000, 1500, or 2000 and/or a relative glucose infusion rate ratio of at least about 1.5, 2, 2.5, 3, 3.5, 4, or 4.5.

In some embodiments, the present disclosure is directed to a compound comprising at least one aromatic boron-containing group having agonist potency for an insulin receptor, wherein when administered at a dose of 30 nmol/kg to a first group of rats with a first glucose infusion rate to provide a blood glucose concentration of 100 mg/dL and to a second group of rats with a second glucose infusion rate to provide a blood glucose concentration of 200 mg/dL, the compound has a relative glucose infusion rate difference (mg/kg/min·min) of about 700 to about 2500, about 750 to about 2500, about 800 to about 2500, about 850 to about 2500, about 900 to about 2500, and a relative glucose infusion rate ratio of about 2 to about 4, about 2 to about 3, or about 3 to about 4.

In some embodiments, the present disclosure provides a compound having agonist potency for glucose comprising at least one aromatic boron-containing group having binding affinity for glucose, wherein when administered at a dose of 30 nmol/kg to a first group of rats with a first glucose infusion rate to provide a blood glucose concentration of 100 mg/dL and to a second group of rats with a second glucose infusion rate to provide a blood glucose concentration of 200 mg/dL the compound provides a relative glucose infusion rate difference (mg/kg/min·min) of about 1 to about 2000, about 1 to about 1500, about 100 to about 1500, and about 1000 to about 1500, and a relative glucose infusion rate ratio of about 0.1 to about 5, about 0.2 to about 4.5, about 0.5 to about 4, about 0.5 to about 3.5, or about 1 to about 3. In some embodiments, the compound provides a relative glucose infusion rate difference (mg/kg/min·min) of at least about 50, 100, 200, 300, 400, 500, 600, 700, 800, 900, 1000, 1100, 1200, 1300, 1400, 1500, or 2000, and/or a relative glucose infusion rate ratio of at least or up to about 1.5, 2, 2.5, 3, 3.5, 4, or 4.5.

In some embodiments, at least one aromatic boron-containing group is attached to an FF scaffold, wherein the FF scaffold is selected from Formulae FF1-FF231 (e.g., FF1-FF12, FF12A, FF12B, FF12C, FF12D, FF13-FF116, FF116A, FF116B, FF116C, FF116D, and FF117-FF231).

In some embodiments, the present disclosure provides a compound comprising at least one aromatic boron-containing group having binding affinity for glucose, wherein when administered at a dose of 10 nmol/kg to a first group of rats with a first glucose infusion rate to provide a blood glucose concentration of 100 mg/dL and to a second group of rats with a second glucose infusion rate to provide a blood glucose concentration of 200 mg/dL the compound provides a relative glucose infusion rate difference (mg/kg/min·min) of 150 to 1500 and a relative glucose infusion rate ratio of about 1 to about 3. In some embodiments, the compound provides a relative glucose infusion rate difference (mg/kg/min·min) of at least about 150, 200, 250, 300, 450, 500, 600, 700, 800, 900, 1000, 1100, 1200, 1300, 1400, or 1500, and/or a relative glucose infusion rate ratio of at least or up to about 1, 1.5, 2, 2.5, 3, 3.5, or 4.

In some embodiments, the present disclosure provides a compound having agonist potency for glucose comprising at least one aromatic boron-containing group, wherein when administered at a dose of 60 nmol/kg to a first group of rats with a first glucose infusion rate to provide a blood glucose concentration of 100 mg/dL and to a second group of rats with a second glucose infusion rate to provide a blood glucose concentration of 200 mg/dL the compound provides a relative glucose infusion rate difference (mg/kg/min·min) of about 100 to about 2500, about 100 to about 2000, about 100 to about 1700, about 200 to about 1500, about 300 to about 1000, about 400 to about 800, and about 400 to about 700, and a relative glucose infusion rate ratio of about 1 to about 3.5, about 1 to about 3, about 1 to about 2.5, about 0.5 to about 2, or about 1 to about 1.5.

In some embodiments, the least one aromatic boron-containing group is attached to an FF scaffold, wherein the FF scaffold is selected from Formulae FF12A, FF12B, FF12C, FF12D, FF116A, FF116B, FF116C, FF116D, FF225, and FF227.

In some embodiments, at least one aromatic boron-containing group comprises at least one $B_1$ and $B_2$, which may be identical or different. In some embodiments, the at least one of the $B_1$ and the $B_2$ is Formula F2 or Formula F7.

In some embodiments, the present disclosure provides a compound (e.g., Formula I or Formula IB) comprising a diboronate covalently conjugated to an amine in X1, and a diol or polyol containing moiety conjugated to an amine in X1. In some embodiments, X1 is an insulin or analog thereof comprising an A-chain and a B-chain. In some embodiments, the amine to which the diboronate is covalently conjugated is at or near the C-terminus of the B-chain, preferably to an amine of a B29 lysine or a B21 lysine, and the amine to which the polyol is conjugated is at or near the N-terminus of the A-chain or B chain. In some embodiments, the amine to which the polyol is covalently conjugated is at or near the C-terminus of the B-chain, preferably to an amine of a B29 lysine or a B21 lysine, and the amine to which the diboronate is conjugated is at or near the N-terminus of the A-chain or B chain.

In some embodiments, the present disclosure provides a compound having binding affinity for glucose comprising at least one aromatic boron-containing group comprising at least one diboronate sensor having affinity to glucose.

In some embodiments, the present disclosure is directed to a compound having agonist potency for an insulin receptor comprising at least one aromatic boron-containing group comprising at least one diboronate sensor having affinity to glucose (e.g., diboronate sensor, such as DSL-1 to DSL-172). In some embodiments, the compound is selected from Examples 1A-82A. In some embodiments, at least one aromatic boron-containing group comprising at least one diboronate sensor has binding affinity to glucose. In some embodiments, a compound comprising two or more diboronate sensors has higher affinity to glucose. In some embodiments, a compound comprising three or more diboronate sensors has higher affinity to glucose.

In some embodiments, the binding constants of DSL compounds, such as DSL-1A to DSL-172A, to glucose, fructose, and/or lactate can be tested and calculated.

Methods of Preparation

In some embodiments, the present disclosure provides a method to prepare a compound comprising an aromatic boron-containing compound and/or an aromatic boron-containing group (e.g., Z1c, Z1c-Linker) or a pharmaceutical preparation comprising one or more compounds of the present disclosure.

In some embodiments, the disclosure provides a method for preparing rotationally constrained tether boron conjugates that contain scaffolds (Z1c, Z1c-Linker) that are rotationally hindered by disfavored steric interactions (e.g. gauche vs anti interactions of substituents), hindered rotation due to bond hybridization (e.g., cis- vs trans-amide rotations), or through rigid covalent bonds (e.g., (E) vs (Z) configurations for alkene moieties). For example, Formulae FF50-FF62, FF116, FF116, FF116A, FF116B, FF116C, FF116D, and FF121-FF134 contain alkyl functionalities geminal (e.g., attached to the same atom) to the amine groups that are covalently conjugated to the boronic acid functionalized moieties. As another example, one or more of Formulae FF50-FF62, FF116, FF116, FF116A, FF116B, FF116C, FF116D, and, and FF121-FF134 contain geminal alkyl substituents which may limit the accessible dihedral angles that the boron conjugated amines adopt, influencing adopted dihedral angles and placing the boronic functionalized groups closer together and allowing for increased binding of the conjugates to target molecules such as proteins or sugars.

In some embodiments, a compound as disclosed herein is further modified through connection (e.g., conjugation, fusion, etc.) to a second agent or therapy to form a fusion protein. In some embodiments, the second agent or therapy is a protein or peptide as herein described. In some embodiments, the second agent is a drug substance, wherein the drug substance is a polypeptide human hormone, an endocrine hormone, insulin, human insulin, glucagon or a glucagon analog, amylin, relaxin, GLP-1, oxyntomodulin, somatostatin, gastric inhibitory polypeptide, glucose-dependent insulinotropic polypeptide, a hybrid peptide comprising sequences from two or more human polypeptide hormones, or an analogue thereof. In some embodiments, the fusion protein comprises one or more diboronate sensor(s) as described herein. In some embodiments, two or more agents are connected (e.g., conjugation, fusion, etc.) to produce a fusion protein comprising one or more diboronate sensor(s). In some embodiments, the two or more agents are proteins or peptides as herein described. The biological activity (e.g., agonist potency, bioavailability, etc.) of the compounds and compositions or methods of treatment described herein may be evaluated according to methods known by those skilled in the art. In some embodiments, the biological activity of a compound is determined by evaluating the EC50 of a compound. In some embodiments, the biological activity of a compound is determined using an insulin receptor phosphorylation (IR Phosphorylation) assay disclosed herein. In some embodiments, the biological activity of a compound is determined by evaluating the binding affinity (Kd) of a compound for its target. In some embodiments, the biological activity of a compound is determined by assessing the relative glucose rate difference. In some embodiments, the biological activity of a compound is determined by assessing the relative glucose rate ratio.

Methods of Treatment

In some embodiments, the disclosure provides a method of treating a subject suffering from, or susceptible to, a disease that is beneficially treated by a compound disclosed herein or a pharmaceutical preparation comprising one or more of the compounds disclosed herein. In some embodiments, the method comprises the step of administering to a subject in need thereof an effective amount of a pharmaceutical preparation/composition of the present disclosure. In at least one embodiment, the compound(s) and/or pharmaceutical preparations of the present disclosure may be for use in (or in the manufacture of medicaments for) the treatment or prevention of disorders, including hyperglycemia, type 2 diabetes, impaired glucose tolerance, type 1 diabetes, obesity, metabolic syndrome X, or dyslipidemia, diabetes during pregnancy, pre-diabetes, Alzheimer's disease, MODY 1, MODY 2 or MODY 3 diabetes, neurological diseases, mood disorders, and psychiatric disorders. In at least one embodiment, a therapeutically-effective amount of a compound and/or pharmaceutical preparation of the present disclosure is administered to a subject suffering from diabetes. In some embodiments, the diabetes is type 1 diabetes or type 2 diabetes. In some embodiments, the diabetes is type 1 diabetes. In some embodiments, the diabetes is type 2 diabetes.

In some embodiments, when a first active agent is administered with a second (another) active agent the dose may be adjusted so that the activity of the two treatments combined is sufficient to regulate blood glucose levels in a patient. Thus, the amount of a first active agent or second active agent that can be administered to regulate blood glucose levels in such combinations may be less than would be required if the first active agent or second active agent were administered as a monotherapy.

Exemplary Compounds

The following are non-limiting Examples of compounds that can be prepared according to the methods described herein. In some embodiments, the compound of the present disclosure is selected from:

Example 1A 651 652

-continued

Example 2A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH

Example 3A

H—G—I—V—E—Q—C—C—T—S—I—C—S—L—Y—Q—L—E—N—Y—C—N—OH

653

654

-continued

H—G—K—G—S—H—K—F—V—N—Q—H—L—C—G—S—H—L—V—E—A—L—Y—L—V—C—G—K—R—G—F—F—Y—T—P—R—OH

Example 4A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH

-continued

Example 5A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH

Example 6A

H—G—I—V—E—Q—C—C—T—S—I—C—S—L—Y—Q—L—E—N—Y—C—N—OH

657                                                    658

-continued

H—G—K—G—S—H—K—F—V—N—Q—H—L—C—G—S—H—L—V—E—A—L—Y—L—V—C—K—R—G—F—F—Y—T—P—R—OH

Example 7A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—K—R—G—F—F—Y—T—P—R—OH

Example 8A

H—G—I—V—E—Q—C—C—T—S—I—C—S—L—Y—Q—L—E—N—Y—C—N—OH

659

660

-continued

H—G—K—G—S—H—K—F—V—N—Q—H—L—C—G—S—H—L—V—E—A—L—Y—L—V—C—G—K—R—G—F—F—Y—T—P—R—OH

Example 9A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH

-continued

Example 10A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH

Example 11A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH

-continued

Example 12A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH

Example 13A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

665                                                666

-continued

Example 14A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-R-G-F-F-Y-T-P-R—OH

667

668

-continued

Example 15A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

-continued

Example 16A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

-continued

Example 17A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

Example 18A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

673

674

-continued

Example 19A 675 676

-continued

Example 20A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

Example 21A

H–G–I–V–E–Q–C–C–T–S–I–C–S–L–Y–Q–L–E–N–Y–C–N–OH

H–G–K–G–S–H–K–F–V–N–Q–H–L–C–G–S–H–L–V–E–A–L–Y–L–V–C–G–K–R–G–F–F–Y–T–P–R–OH

-continued

Example 22A

-continued

Example 23A

-continued

Example 24A

-continued

Example 25A

-continued

Example 26A

-continued

Example 27A

-continued

Example 28A

-continued

Example 29A

-continued

Example 30A

697

698

Example 31A

-continued

Example 32A 701                                                                 702

Example 33A

H–G–I–V–E–Q–C–C–T–S–I–C–S–L–—–Y–Q–L–E–N–Y–C–N–OH

H–G–K–G–S–H–K–F–V–N–Q–H–L–C–G–S–H–L–V–E–A–—–L–Y–L–V–C–G–K–R–G–F–F–Y–T–P–R–OH

-continued

Example 34A

Example 35A

-continued

-continued

Example 36A

-continued

Example 37A

H-G-I-V-E-Q-C-C-T-S-I-C-S-L——Y-Q-L-E-N-Y-C-N-OH
|                                                      |
H-G-K-G-S-H-K-F-V-N-Q-H-L-C-G-S-H-L-V-E-A——L-Y-L-V-C-G-K-R-G-F-F-Y-T-P-R-OH

Example 38A

-continued

Example 39A 715 716

Example 40A

-continued

Example 41A

-continued

Example 42A

-continued

Example 43A

-continued

Example 44A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—R—G—F—F—Y—T—P—R—OH

Example 45A

-continued

H—G—I—V—E—Q—C—C—T—S—I—C—S—L—Y—Q—L—E—N—Y—C—N—OH

H—G—S—H—L—V—E—A—L—Y—L—V—C—G—K—R—G—F—F—Y—T—P—R—OH

H—G—K—G—S—H—K—F—V—N—Q—H—L—C—G—S—

-continued

Example 46A

-continued

Example 47A

-continued

Example 48A

-continued

Example 49A

H—G—I—V—E—Q—C—C—T—S—I—C—S—L—Y—Q—L—E—N—Y—C—N—OH

H—G—K—S—H—K—F—V—N—Q—H—L—C—G—S—H—L—V—E—A—L—Y—L—V—C—G—K—R—G—F—F—Y—T—P—R—OH

Example 50A

-continued

Example 51A

-continued

Example 52A

Example 53A

-continued

-continued

Example 54A 745            746

Example 55A

-continued

-continued

Example 56A

-continued

Example 57A

Example 58A

-continued

Example 59A

H—G—I—V—E—Q—C—C—T—S—I—C—S—L—Y—Q—L—E—N—Y—C—N—OH

H—G—S—H—K—F—V—N—Q—H—L—C—G—S—H—L—V—E—A—L—Y—L—V—C—G—K—R—G—F—F—Y—T—P—R—OH

Example 60A

-continued

US 12,655,188 B2

757 758

-continued

Example 61A

Example 62A

-continued

-continued

Example 63A 763 764

Example 64A

Example 65A

-continued

Example 66A

-continued

H—G—I—V—E—Q—C—C—T—S—I—C—S—L—Y—Q—L—E—N—Y—C—N—OH

H—G—S—H—K—F—V—N—Q—H—L—C—G—S—H—L—V—E—A—L—Y—L—V—C—G—K—R—G—F—F—Y—T—P—K—A

-continued

Example 67A

Example 68A

-continued

Example 69A

Example 70A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

Example 71A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

777                                                                 778

-continued

Example 72A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

-continued

Example 73A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

Example 74A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

781                                                                                                    782

Example 75A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

783

784

Example 76A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

-continued

Example 77A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH

787

788

-continued

Example 78A

H-G-I-V-E-Q-C-C-T-S-I——C-S-L-Y-Q-L-E-N-Y-C—N—OH

H-G-K-G-S-H-K-F-V-N-Q——H-L-C-G-S-H-L-V-E-A——L-Y-L-V-C-G-K-R-G-F—F-Y-T-P-R—OH

789

790

Example 79A

H-G-I-V-E-Q-C-C-T-S-I——C-S-L-Y-Q-L-E-N-Y-C—N—OH

H-G-K-G-S-H-K-F-V-N-Q——H-L-C-G-S-H-L-V-E-A——L-Y-L-V-C-G-K-R-G-F—F-Y-T-P-R—OH

-continued

Example 80A

H-G-I-V-E-Q-C-C-T-S-I——C-S-L-Y-Q-L-E-N-Y-C—N—OH

H-G-K-G-S-H-K-F-V-N-Q——H-L-C-G-S-H-L-V-E-A——L-Y-L-V-C-G-K-R-G-F—F-Y-T-P-R—OH

Example 81A

H-G-I-V-E-Q-C-C-T-S-I——C-S-L-Y-Q-L-E-N-Y-C—N—OH

793

794

-continued

H-G-K-G-S-H-K-F-V-N-Q——H-L-C-G-S-H-L-V-E-A——L-Y-L-V-C-G-K-R-G-F——F-Y-T-P-R—OH

H-G-K-G-S-H-K-F-V-N-Q——H-L-C-G-S-H-L-V-E-A——L-Y-L-V-C-G-K-R-G-F——F-Y-T-P-R—OH

Example 82A

H-G-I-V-E-Q-C-C-T-S-I——C-S-L-Y-Q-L-E-N-Y-C—N—OH

H-G-K-G-S-H-K-F-V-N-Q——H-L-C-G-S-H-L-V-E-A——L-Y-L-V-C-G-K-R-G-F——F-Y-T-P-R—OH

795

796

-continued

Example 83A

H-G-I-V-E-Q-C-C-T-S-I———————C-S-L-Y-Q-L-E-N-Y-C—N—OH

H-G-K-G-S-H-K-F-V-N-Q——H-L-C-G-S-H-L-V-E-A———L-Y-L-V-C-G-K-R-G-F—F-Y-T-P-R—OH

-continued

Example 84A

H-G-I-V-E-Q-C-C-T-S-I—C-S-L-Y-Q-L-E-N-Y-C—N—OH

H-G-K-G-S-H-K-F-V-N-Q—H-L-C-G-S-H-L-V-E-A—L-Y-L-V-C-G-K-R-G-F—F-Y-T-P-R—OH

-continued

Example 85A

H-G-I-V-E-Q-C-C-T-S-I——C-S-L-Y-Q-L-E-N-Y-C—N—OH

H-G-K-G-S-H-K-F-V-N-Q——H-L-C-G-S-H-L-V-E-A——L-Y-L-V-C-G-K-R-G-F—F-Y-T-P-R—OH

801                                                                                            802

Example 1

Example 2

-continued

Example 3

-continued

H—G—I—V—E—Q—C—C—T—S—I—C—S—L—Y—Q—L—E—N—Y—C—N—OH

H—G—K—P—G—S—H—K—P—F—V—N—Q—H—L—C—G—S—H—L—V—E—A—L—Y—L—V—C—G—K—R—G—F—F—Y—T—P—K—T—OH 807          808

-continued

Example 4

-continued

Example 5

811

812

Example 6

Example 7

-continued

813 814

Example 8

-continued

Example 9

-continued

817          818

Example 10

-continued

H-G-I-V-E-Q-C-C-T-S-I-C-S-L-Y-G-L-E-N-Y-C-N-OH

H-K-P-G-G-G-E-A-E-G-E-S-A-K-P-G-S-E-G-E-S-V-N-Q-H-L-C-G-S-H-L-V-E-A-L-Y-L-V-C-G-K-R-G-F-F-Y-T-P-K-T-OH

-continued

Example 11

821                                                                 822

Example 12:

H—K—G—R—E—D—E—A—Y—G—N—I—K—P—G—W—E—G—E—S—K—P—

H—G—I—V—E—Q—C—C—T—S—I—C—S—L—V—Q—L—E—N—Y—C—N—K—P—S—E—S—G—OH

—F—V—N—Q—H—L—C—G—S—H—L—V—E—A—L—Y—L—V—C—G—K—P—G—R—P—Y—T—P—K—T—OH

-continued

Example 13:

H—G—S—E—K—P—L—K—P—T—K—S—Q—E—T—A—Q—T—A—D—T—

—P—L—E—A—W—N—I—K—R—A—G—W—E—G—E—S—F—V—N—

H—G—I—V—E—C—C—C—T—S—I—C—S—L—V—G—L—E—N—Y—C—N—K—P—E—A—E—F—OH

—Q—H—L—C—G—S—H—L—V—E—A—L—Y—L—V—C—G—K—R—G—F—F—Y—T—P—K—T—OH 825 826

Example 14:

H—G—S—K—P—E—L—P—K—P—E—A—K—L—P—T—A—Q—W—N—I—K—P—A—G—W—E—G—E—

H—G—I—V—E—Q—C—C—T—S—I—C—S—L—Y—Q—L—G—N—Y—C—N—G—S—E—K—P—E—S—G—OH

—S—F—V—N—Q—H—L—C—G—S—H—L—V—E—A—L—Y—L—V—C—G—K—R—G—F—F—Y—T—P—K—T—OH

-continued

Example 15:

H—G—I—V—E—Q—C—C—T—S—I—G—

H—K—P—V—E—A—P—K—P—G—E—S—H—R—F—G—N—F—V—N—Q—H—L—C—G—S—H—L—

—S—L—Y—Q—L—E—N—Y—C—N—K—P—G—S—E—K—P—E—S—G—OH

—V—E—A—L—Y—L—V—C—G—R—G—F—F—Y—T—P—K—T—OH 829 830

-continued

Example 16:

H—G—I—V—E—Q—C—C—T—S—I—C—

H—G—V—E—A—A—I—P—A—G—K—P—E—G—K—S—A—G—E—T—F—G—E—S—F—V—N—Q—H—L—C—G—S—H—

—S—L—Y—Q—L—E—N—Y—C—N—G—S—K—G—E—K—E—S—G—OH

—L—V—E—A——L—Y—L—V—C—G—K—R—G—F—F—Y—T—P—K—T—OH

-continued

Example 17:

H—G—I—V—K—Q—C—C—T—S—I——C—

H—G—V—A—A—P—P—G—A—G—K—S—A—G—S—R—T—D—F—G—E—G—E—S—F—V—N—Q—H—L—C—G—S—H—

833                                                                                          834

-continued

Example 18:

835 836

-continued

—S—L—Y—Q—L—E—N—Y—C—N—OH

—L—V—E—A—L—Y—L—V—C—G—K—R—G—F—F—Y—T—P—K—T—OH

Example 19:

H—G—I—V—E—Q—C—C—T—S—I—C—

H—K—P—G—S—E—G—E—S—A—K—P—G—S—E—G—E—S—V—N—Q—H—L—C—G—S—H—L—

—S—L—Y—Q—L—E—N—Y—C—N—OH

—V—E—A—L—Y—L—V—C—G—K—R—G—F—F—Y—T—P—K—T—OH

Example 20:

H—G—I—V—E—Q—C—C—T—S—I—C—

H—K—P—G—S—E—V—G—E—S—A—I—K—P—G—S—E—G—E—S—V—N—Q—H—L—C—G—S—H—L—

-continued

—G—L—Y—O—L—E—N—Y—C—N—OH

—V—E—A—L—Y—L—V—C—G—K—R—G—F—F—Y—T—P—K—T—OH

Example 21:

H—K—P—S—G—E—R—S—E—G—A—I—K—P—G—S—E—G—E—S—K—

H—G—I—V—E—Q—C—C—T—S—I—C—S—L—Y—Q—L—E—N—Y—C—N—OH

—F—V—N—Q—H—L—C—G—S—H—L—V—E—A—L—Y—L—V—C—G—K—R—G—F—R—Y—T—R—K—T—OH

-continued

Example 22:

H—G—I—V—E—O—C—C—T—S—I—C—

H—K—P—S—G—R—S—E—G—A—N—I—K—P—G—W—E—G—E—S—K—P—F—V—N—Q—H—L—C—G—S—H—L—V—

—S—L—Y—Q—L—E—N—Y—C—N—OH

—E—A—L—Y—L—V—C—G—K—R—G—P—F—Y—T—R—K—T—OH

Example 23:

H—S—G—R—S—E—G—A—Q—W—N—I—K—P—G—W—E—G—E—S—K—P—F—V—N—Q—H—L—

-continued

H—G—I—V—E—Q—C—C—T—S—I—C—S—L—Y—Q—L—E—N—Y—C—N—OH

—C—Q—S—H—L—V—E—A—L—Y—L—V—C—G—K—R—G—F—F—Y—T—P—K—T—OH

Example 24:

H—G—I—V—E—Q—C—C—T—S—I—C—S—

H—S—G—R—E—T—A—O—W—N—I—K—P—A—G—W—E—G—E—S—P—V—N—Q—H—L—C—G—S—H—

—L—V—O—L—E—N—Y—C—N—OH

—L—V—E—A—L—Y—L—V—C—G—K—R—G—F—F—Y—T—P—K—T—OH 843                                                                                      844

-continued

Example 25:

H—G—S—E—K—P—S—E—L—K—P—T—K—S—G—R—E—T—A—Q—W—N—I—K—P—A—G—W—E—O—E—S—

H—G—I—V—E—Q—C—C—T—S—I—C—S—L—Y—Q—L—E—N—Y—C—N—OH

—F—V—N—Q—H—L—C—G—S—H——L—V—E—A—L—Y—L—V—C—G—K—R—G—F—F—Y—T—P—K—T—OH

Example 26:

H—G—I—V—E—Q—C—C—T—S—I—C—

H—S—G—R—S—E—G—A—Q—W—N—I—K—P—G—W—E—G—E—S—K—P—F—V—N—Q—H—L—C—G—S—H—L—V—

845                                                                                      846

-continued

847

848

Example 27

H-G-I-V-K-C-C-T-S-I-C-S-L-Y-Q-L-E-N-Y-C-N-G-S-E-K-P-E-S-G-OH

H-G-I-V-K-C-C-T-S-I-C-S-L-Y-Q-L-E-N-Y-C-N-G-S-E-K-P-E-S-G-OH

H-G-S-E-K-P-S-E-L-K-P-T-K-S-G-R-E-T-A-Q-W-N-I-K-P-A-G-W-E-G-G-S-F-V-N-Q-H-L-C-G-S-H-L-V-E-A-L-Y-L-V-C-G-K-R-G-F-F-Y-T-P-K-T-OH 849 850

-continued

Example 28

H-G-I-V-K-Q-C-C-T-S-I-C-S-L-Y-Q-L-E-N-Y-C-N-K-P-G-S-E-K-P-E-S-G-OH

H-D-G-S-H-L-V-E-A-L-Y-L-V-C-G-K-R-G-F-F-Y-T-P-K-T-OH

H-K-G-E-V-E-S-A-I-P-G-K-S-E-G-E-S-F-V-N-Q-H-L-C-G-S-H-L-V-E-A-L-Y-L-V-C-G-K-R-G-F-F-Y-T-P-K-T-OH 851                                                                                                        852

-continued

Example 29

H-G-I-V-E-Q-C-C-T-S-I-C-S-L-Y-Q-L-E-N-Y-C-N-K-P-G-S-E-K-P-E-S-G-OH

H-G-V-E-A-I-P-K-P-E-A-G-K-S-E-G-E-S-F-V-N-Q-H-L-C-G-S-H-L-V-E-A-L-Y-L-V-C-G-K-R-G-F-F-Y-T-P-K-T-OH

-continued

Example 30

H-G-I-V-E-Q-C-C-T-S-I-C-S-L-Y-Q-L-E-N-Y-C-N-K-P-A-S-G-E-K-P-E-S-G-OH

H-G-V-E-A-E-I-P-K-P-G-E-A-G-K-S-A-G-E-G-E-S-F-V-N-Q-H-L-C-G-S-H-L-V-E-A-L-Y-L-V-C-G-K-R-G-F-F-Y-T-P-K-T-OH

Example 31

-continued

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-K-R-G-F-F-Y-T-P-K-T-OH 857    858

-continued

Example 32

H-G-I-V-E-Q-C-C-T-S-I-C-S-L-Y-Q-L-E-N-Y-C-N-OH

H-G-K-P-G-H-K-P-F-V-N-Q-H-L-C-G-S-H-L-V-E-A-L-Y-L-V-C-G-K-R-G-F-F-Y-T-P-K-T-OH

Example 33

H-G-I-V-E-Q-C-C-T-S-I-C-S-L-Y-Q-L-E-N-Y-C-N-K-OH

H-G-K-P-G-S-H-K-P-F-V-N-Q-H-L-C-G-S-H-L-V-E-A-L-Y-L-V-C-G-K-R-G-F-F-Y-T-P-K-T-OH

Example 34

-continued

H-G-I-V-K-Q-C-C-T-S-I-C-S-L-Y-Q-L-E-N-Y — C-N-K-OH

H-G-K-G-E-H-K-F-V-N-Q-H-L-C-G-S-H-L-V-E-A-L-Y-L-V-C-G-K-R-G-F-F-Y-T-P-K-T-OH

861

862

Example 35

G—I—V—E—Q—C—C—T—S—I—C

F—V—N—C—H—L—C—G—S—H——L—V—

Dap—A—G—K—K

—S—L—Y—O—L—E—N—Y—C—N—OH

—E—A—L—Y—L—V—C—G——E—R—G—F—F—Y—T—P—K—T—OH

-continued

Example 36

865                                                                866

Example 37

-continued

Example 38

-continued

Example 39

871 872

-continued

Example 40

-continued

Example 41

875                                                                                             876

Example 42

H—G—I—V—E—Q—C—C—T—S—I—C—

HN—F—V—N—Q—H—L—C—G—S—H—

—S—L—Y—Q—L—E—N—Y—C—N—OH

—L—V—E—A—L—Y—L—V—C—G—K—P—G—F—F—Y—T—P—R—T—OH

-continued

Example 43

H—G—I—V—E—Q—C—C—T—S—I—C

H—G—K—P—G—H—K—P—F—V—N—Q—H—L—C—G—S—H—

—S—L—Y—Q—L—E—N—Y—C—N—OH

—L—V—E—A—L—Y—L—V—C—G—K—P—G—F—F—Y—T—P—R—T—OH

-continued

Example 44

H—G—I—V—K—Q—C—C—T—S—I————C—

H—G—K—G—E—H—K—F—V—N—Q—H—L—C—G—S—H—L—

881                                                                                    882

-continued

Example 45

883 884

-continued

Example 46

889                                                                 890

Example 47

H—G-I-V-K-Q-C-C-T-S-I———C-S-L-Y-Q-L-E-N-Y-C—N-K—OH

H—G-K-S-A-E-K-F-V-N-Q—H-L-C-G-S-H-L-V-E-A—L-Y-L-V-C-G-K-P-G-F—F-Y-T-P-R-T—OH

Example 48

891                                                                                    892

H—G-I-V-E-Q-C-C-T-S-I⎯C-S-L-Y-Q-L-E-N-Y-C⎯N-K⎯OH

H⎯G-K-P-A-S-E-K-P-F-V⎯N-Q-H-L-C-G-S-H-L-V⎯⎯E-A-L-Y-L-V-C-G-K-P⎯G-F-F-Y-T-P-R-T⎯OH

Example 49

H⎯G-I-V-E-Q-C-C-T-S-I⎯C-S-L-Y-Q-L-E-N-Y-C⎯N⎯OH

H⎯K-P-G-S-E-H-E-S-A-F⎯V-N-Q-H-L-C-G-S-H-L⎯V-E-A-L-Y-L-V-C-G-E⎯R-G-F-F-Y-T-P-K⎯OH

-continued

Example 50

H—G-I-V-E-Q-C-C-T-S-I—C-S-L-Y-Q-L-E-N-Y-C—N-A-E-G-S-K—OH

H—K-P-G-S-E-H-E-S-A-F—V-N-Q-H-L-C-G-S-H-L—V-E-A-L-Y-L-V-C-G-E—R-G-F-F-Y-T-P-K—OH

Example 51

H—K-P-G-I-V-E-Q-C-C-T—S-I-C-S-L-Y-Q-L-E-N—Y-C-N—OH

H—K-P-G-S-E-H-E-S-A-F—V-N-Q-H-L-C-G-S-H-L—V-E-A-L-Y-L-V-C-G-E—R-G-F-F-Y-T-P-K—OH

895

896

-continued

Example 52

H—G-I-V-E-Q-C-C-T-S-I—C-S-L-Y-Q-L-E-N-Y-C—N-A-E-G-S-K—OH

H—K-P-G-S-E-H-E-S-A-F—V-N-Q-H-L-C-G-S-H-L—V-E-A-L-Y-L-V-C-G-E—R-G-F-F-Y-T-P-K—OH 897 898

-continued

Example 53

H—G-I-V-K-P-Q-C-C-T-S—I-C-S-L-Y-Q-L-E-N-Y—C-N—OH

H—K-P-G-S-E-H-E-S-A-F—V-N-Q-H-L-C-G-S-H-L—V-E-A-L-Y-L-V-C-G-E—R-G-F-F-Y-T-P-K—OH

Example 54

H—G-I-V-E-Q-C-C-T-S-I—C-S-L-Y-Q-L-E-N-Y-C—N—OH

H—K-P-G-S-E-H-E-S-A-F—V-N-Q-H-L-C-G-S-H-L—V-E-A-L-Y-L-V-C-G-E—R-G-F-F-Y-T-P-K—OH

899

900

901

902

Example 55

H—G-I-V-E-Q-C- C-T-S-I-C-S-L-Y-Q-L-E-N-Y-C-N-A-E-G-S-K—OH

H—K-P-G-S-E-H-E-S-A-F-V-N-Q-H-L-C-G-S-H-L-V-E-A-L-Y-L-V-C-G-E-R-G-F-F-Y-T-P-R-T—OH

903

904

Example 56

-continued

H—K-P-G-I-V-E-Q-C-C-T-S-I-C-S-L-Y-Q-L-E-N-Y-C-N—OH

H—K-P-G-S-E-H-E-S-A-F-V-N-Q-H-L-C-G-S-H-L-V-E-A-L-Y-L-V-C-G-E-R-G-F-F-Y-T-P-K—OH 905          906

Example 57

-continued

H—G-I-V-E-Q-C-C-T-S-I-C-S-L-Y-Q-L-E-N-Y-C-N-A-E-G-S-K—OH

H—K-P-G-S-E-H-E-S-A-F-V-N-Q-H-L-C-G-S-H-L-V-E-A-L-Y-L-V-C-G-E-R-G-F-F-Y-T-P-K—OH

-continued

Example 58

H—G-I-V-K-P-Q-C- C-T-S-I-C-S-L-Y-Q-L-E-N-Y-C-N—OH

H—K-P-G-S-E-H-E-S-A-F-V-N-Q-H-L-C-G-S-H-L-V-E-A-L-Y-L-V-C-G-E-R-G-F-F-Y-T-P-K—OH

Example 59

-continued

H—G-I-V-E-Q-C-C-T-S-I-C-S-L-Y-Q-L-E-N-Y-C-N—OH

H—K-P-G-S-E-H-E-S-A-F-V-N-Q-H-L-C-G-S-H-L-V-E-A-L-Y-L-V-C-G-E-R-G-F-F-Y-T-P-K—OH

-continued

Example 60

913                                          914

Example 61

Example 62

-continued

H—G-I-V-E-Q-C-C-T-S-I-C-S-L-Y-Q-L-E-N-Y-C-N-A-E-G-S-K—OH

H—K-P-G-S-E-H-E-S-A-F-V-N-Q-H-L-C-G-S-H-L-V-E-A-L-Y-L-V-C-G-E-R-G-F-F-Y-T-P-K—OH

-continued

Example 63

H—K-P-G-S-E-H-E-S-A-F-V-N-Q-H-L-C-G-S-H-L-V-E-A-L-Y-L-V-C-G-E-R-G-F-F-Y-T-P-K—OH

H—G-I-V-K-P-Q-C-C-T-S-I-C-S-L-Y-Q-L-E-N-Y-C-N—OH

Example 64
-continued
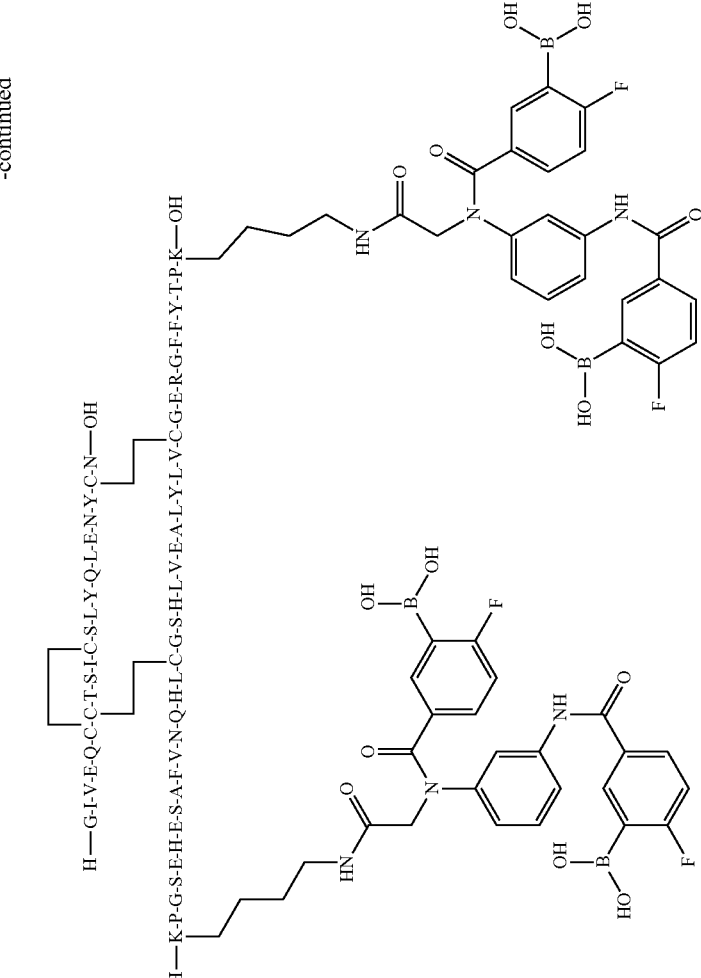

921                                                                 922

Example 65

H—G-I-V-E-Q-C-C-T-S-I-C-S-L-Y-Q-L-E-N-Y-C-N-A-E-G-S-K—OH

H—K-P-G-S-E-H-E-S-A-F-V-N-Q-H-L-C-G-S-H-L-V-E-A-L-Y-L-V-C-G-E-R-G-F-F-Y-T-P-R-T—OH 923 924

Example 66:

H—K—P—G—I—V—E—Q—C—C—T—S—I—C—

H—K—P—G—S—E—H—E—S—A—F—V—N—Q—H—L—C—G—S—H—L—V—

—S—L—Y—Q—L—E—N—Y—C—N—OH

—E—A—L—Y—L—V—C—G—E—R—G—F—F—Y—T—P—K—OH

-continued

Example 67:

H—K—P—G—I—V—E—Q—C—C—T—S—I—C—

H—K—P—G—S—E—H—E—S—A—F—V—N—Q—H—L—C—G—S—H—L—V—

—S—L—Y—Q—L—E—N—Y—C—N—OH

—E—A—L—Y—L—V—C—G—E—R—G—F—F—Y—T—P—K—OH

-continued

Example 68:

H—K—P—G—I—V—E—Q—C—C—T—S—I—C

H—K—P—G—S—E—H—E—S—A—F—V—N—Q—H—L—C—G—S—H—L—V

—S—L—Y—Q—L—E—N—Y—C—N—OH

—E—A—L—Y—L—V—C—G—E—R—G—F—F—Y—T—P—K—OH

929

930

Example 69:

-continued

Example 70:

-continued

Example 71:

-continued

Example 72:

H—G—I—V—E—Q—C—C—T—S—I—C—

H—K—P—G—S—E—H—E—S—A—F—V—N—Q—H—L—C—G—S—H

S—L—Y—Q—L—E—N—Y—C—N—A—E—G—S—K—OH

L—V—E—A—L—Y—L—V—C—G—E—R—G—F—F—Y—T—P—R—T—OH 937                                                             938

Example 73:

939

940

-continued

—S—L—Y—Q—L—E—N——V—C—N——OH

—E—A—L—Y—L—V—C—G—E——R—G—F—F—Y—T—P—K—OH 941                                                                                    942

Example 74

H-G-I-V-E-Q-C-C-T-S-I-C-S-L-Y-Q-L-E-N-Y-C-N-A-E-G-S-K-OH

H-K-P-G-S-E-H-E-S-A-F-V-N-Q-H-L-C-G-S-H-L-V-E-A-L-Y-L-V-C-G-E-R-G-F-F-Y-T-P-K-OH 943 944

Example 75

-continued

H-G-I-V-K-P-Q-C-C-T-S-I-C-S-L-Y-Q-L-E-N-Y-C-N-OH

H-G-I-V-K-P-Q-C-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH

H-K-P-G-S-E-H-E-S-A-F-V-N-Q-H-L-C-G-S-H-L-V-E-A-L-Y-L-V-C-G-E-R-G-F-F-Y-T-P-K-OH

Example 76

-continued

H-K-P-G-S-E-H-E-S-A-F-V-N-Q-H-L-C-G-S-H-L-V-E-A-L-Y-L-V-C-G-E-R-G-F-F-Y-T-P-K-OH

H-G-I-V-E-Q-C-C-T-S-I-C-S-L-Y-Q-L-E-N-Y-C-N-OH

Example 77

-continued

H-G-I-V-E-Q-C-C-T-S-I-C-S-L-Y-Q-L-E-N-Y-C-N-A-E-G-S-K-OH

H-K-P-G-S-E-H-E-S-A-F-V-N-Q-H-L-C-G-S-H-L-V-E-A-L-Y-L-V-C-G-E-R-G-F-F-Y-T-P-R-T-OH

-continued

Example 78

H-K-P-G-I-V-E-Q-C-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH

951

952

Example 79

H-G-I-V-E-Q-C-C-T-S-I-C-S-L-Y-Q-L-E-N-Y-C-N-A-E-G-S-K-OH

H-K-P-G-S-E-H-E-S-A-F-V-N-Q-H-L-C-G-S-H-L-V-E-A-L-Y-L-V-C-G-E-R-G-F-F-Y-T-P-K-OH

Example 80

-continued

Example 81

-continued

H-G-I-V-K-P-Q-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH

957 958

Example 82

-continued

H-G-I-V-K-P-Q-C-T-S-I-C-S-L-Y-Q-L-E-N-Y-C-N-A-E-G-S-K-OH

H-K-P-G-S-E-H-E-S-A-F-V-N-Q-H-L-C-G-S-H-L-V-E-A-L-Y-L-V-C-G-E-R-G-F-F-Y-T-P-R-T-OH

Example 83

-continued

H-K-P-G-S-E-H-E-S-A-F-V-N-Q-H-L-C-G-S-H-L-V-E-A-L-Y-L-V-C-G-E-R-G-F-F-Y-T-P-K-OH

H-K-P-G-I-V-E-Q-C-C-T-S-I-C-S-L-Y-Q-L-E-N-Y-C-N-A-E-G-S-K-OH

Example 84

-continued

H-G-I-V-E-Q-C-C-T-S-I-C-S-L-Y-Q-L-E-N-Y-C-N-A-E-G-S-K-OH

H-K-P-G-S-E-H-E-S-A-F-V-N-Q-H-L-C-G-S-H-L-V-E-A-L-Y-L-V-C-G-E-R-G-F-F-Y-T-P-K-OH

Example 85

-continued

Example 86

H-G-I-V-E-Q-C-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH

Example 87

H-G-I-V-E-Q-C-C-T-S-I-C-S-L-Y-Q-L-E-N-Y-C-N-A-E-G-S-K-OH

H-K-P-G-S-E-H-E-S-A-F-V-N-Q-H-L-C-G-S-H-L-V-E-A-L-Y-L-V-C-G-E-R-G-F-F-Y-T-P-R-T-OH

-continued

Example88

H-K-P-G-I-V-E-Q-C-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH

Example 89

H-G-I-V-E-Q-C-C-T-S-I-C-S-L-Y-Q-L-E-N-Y-C-N-A-E-G-S-K-OH

969

970

-continued

H-K-P-G-S-E-H-E-S-A-F-V-N-Q-H-L-C-G-S-H-L-V-E-A-L-Y-L-V-C-G-E-R-G-F-F-Y-T-P-K-OH

H-K-P-G-S-E-H-E-S-A-F-V-N-Q-H-L-C-G-S-H-L-V-E-A-L-Y-L-V-C-G-E-R-G-F-F-Y-T-P-K-OH

Example 90

H-G-I-V-K-P-Q-C-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH 971 972

-continued

Example 91

H-G-I-V-E-Q-C-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH

Example 92

H-G-I-V-E-Q-C-C-T-S-I-C-S-L-Y-Q-L-E-N-Y-C-N-A-E-G-S-K-OH

H-K-P-G-S-E-H-E-S-A-F-V-N-Q-H-L-C-G-S-H-L-V-E-A-L-Y-L-V-C-G-E-R-G-F-F-Y-T-P-R-T-OH
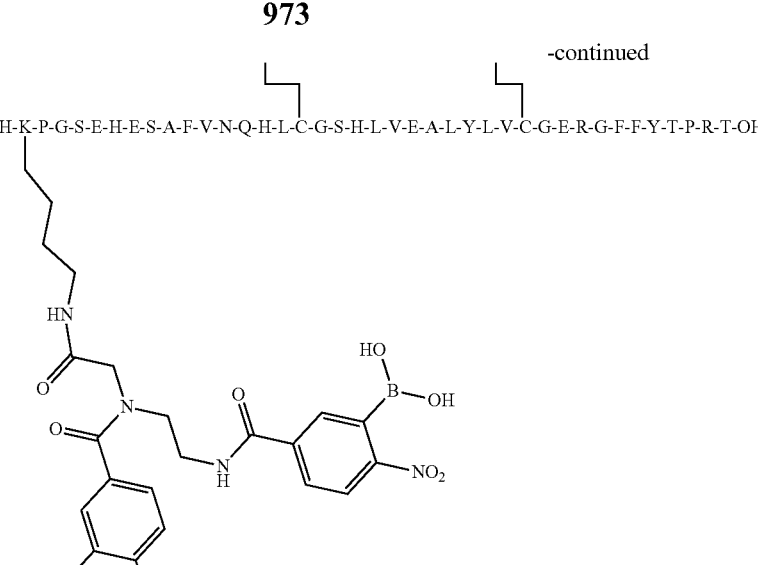

Example 93

Example 94

-continued

H-G-I-V-E-Q-C-C-T-S-I-C-S-L-Y-Q-L-E-N-Y-C-N-A-E-G-S-K-OH

H-K-P-G-S-E-H-E-S-A-F-V-N-Q-H-L-C-G-S-H-L-V-E-A-L-Y-L-V-C-G-E-R-G-F-F-Y-T-P-K-OH

Example 95

-continued

H-G-I-V-K-P-Q-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH

Example 96

-continued

H-G-I-V-E-Q-C-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH

-continued

Example 97

H-G-I-V-E-Q-C-C-T-S-I-C-S-L-Y-Q-L-E-N-Y-C-N-A-E-G-S-K-OH

H-K-P-G-S-E-H-E-S-A-F-V-N-Q-H-L-C-G-S-H-L-V-E-A-L-Y-L-V-C-G-E-R-G-F-F-Y-T-P-R-T-OH

985

986

Example 98

H-K-P-G-I-V-E-Q-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH

987

988

-continued

Example 99

H-G-I-V-E-Q-C-C-T-S-I-C-S-L-Y-Q-L-E-N-Y-C-N-A-E-G-S-K-OH

H-K-P-G-S-E-H-E-S-A-F-V-N-Q-H-L-C-G-S-H-L-V-E-A-L-Y-L-V-C-G-E-R-G-F-F-Y-T-P-K-OH

-continued

Example 100

H-G-I-V-K-P-E-Q-C-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH

991

992

Example 101

H-G-I-V-K-P-E-Q-C-T-S-I-C-S-L-Y-Q-L-E-N-Y-C-N-OH

H-K-P-G-S-E-H-E-S-A-F-V-N-Q-H-L-C-G-S-H-L-V-E-A-L-Y-L-V-C-G-E-R-G-F-F-Y-T-P-K-OH

Example 102

-continued

H-G-I-V-K-P-E-Q-C-C-T-S-I-C-S-L-Y-Q-L-E-N-Y-C-N-A-E-G-S-K-OH

H-K-P-G-S-E-H-E-S-A-F-V-N-Q-H-L-C-G-S-H-L-V-E-A-L-Y-L-V-C-G-E-R-G-F-F-Y-T-P-R-T-OH

Example 103

H–G–I–V–K–P–Q–C–C–T–S–I–C–S–L–Y–Q–L–E–N–Y–C–N–OH

H–K–P–G–S–E–H–E–S–A–F–V–N–Q–H–L–C–G–S–H–L–V–E–A–L–Y–L–V–C–G–E–R–G–F–F–Y–T–P–K–OH

-continued

Example 104

-continued

Example 105

1001

1002

Example 106

-continued

Example 107

-continued

-continued

Example 108

H—K—P—G—S—E—H—E—S—A—F—V—N—Q—H—L—C—G—S—H—L—V—E—A—L—Y—L—V—C—G—E—R—G—F—F—Y—T—P—K—OH
|
H—G—I—V—K—P—Q—C—C—T—S—I—C—S—L—Y—Q—L—E—N—Y—C—N—OH

1007　　　　　　　　　　　　　　　　1008

Example 109

-continued

-continued

Example 110

Example 111

-continued

Example 112

-continued

H–G–I–V–E–Q–C–C–T–S–I–C–S–L–Y–Q–L–E–N–Y–C–N–A–E–G–S–K–OH

H–K–P–G–S–E–H–E–S–A–F–V–N–Q–H–L–C–G–S–H–L–V–E–A–L–Y–L–V–C–G–E–R–G–F–F–Y–T–P–K–OH

Example 113

Exmaple 114

-continued

-continued

Exmaple 115

-continued

Example 116

Example 117

-continued

Exmaple 118

-continued

H—G—I—V—K—P—Q

H—K—P—G—S—E—H—E—S—A—F—V—N—Q—H—L—C—G—S—H—L—V—E—A—L—Y—L—C—G—E—R—G—F—F—V—T—P—K—OH

Q—C—C—T—S—I—C—S—L—Y—Q—L—E—N—Y—C—N—OH

Example 119

-continued

Exmaple 120

-continued

Example121

-continued

-continued

Example 122

-continued

Example 123

-continued

Example 124

Example 125

-continued

Example 126

Example 127

-continued

Example 128

-continued

-continued

Example 129

Example 130

-continued

-continued

Example 131

Example 132

-continued

Example 133

-continued

Example 134

-continued

-continued

Example 135

-continued

Example 136

1065                                                                                     1066

Example 137

-continued

1067                                                                 1068

Example 138

-continued

-continued
Example 139
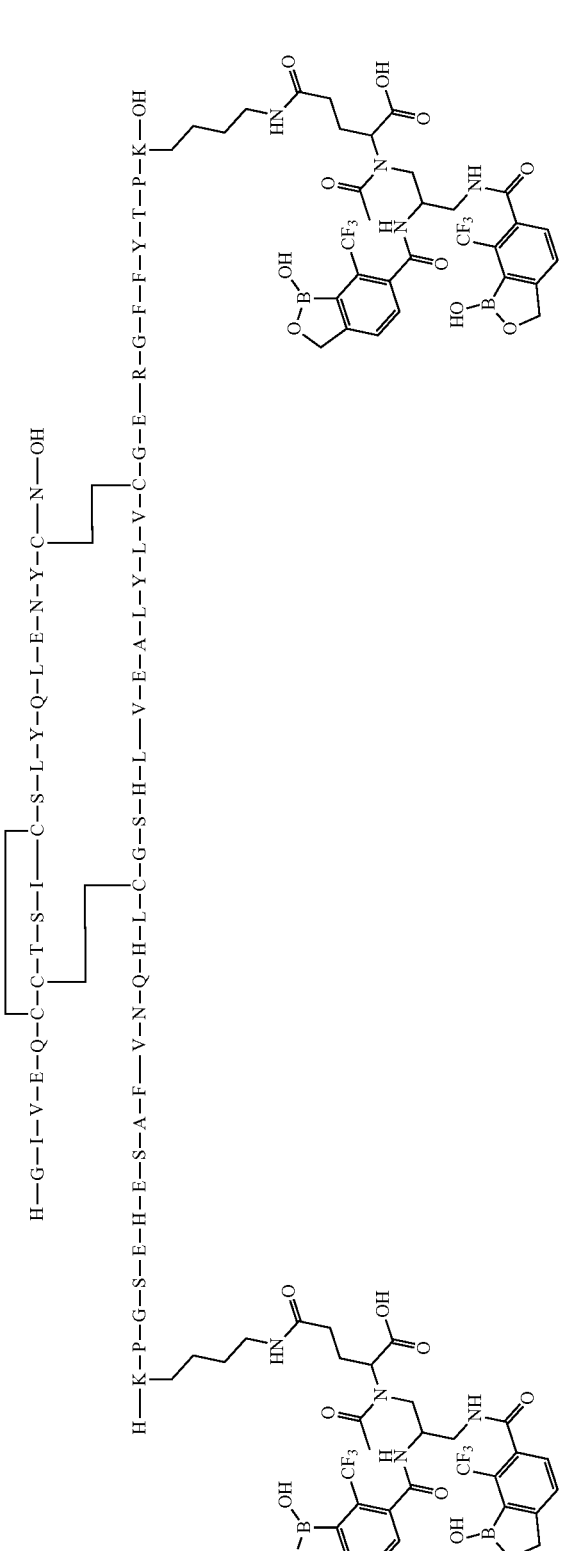

-continued

Example 140

H—G—I—V—E—Q—C—C—T—S—I—C—S—L—Y—Q—L—E—N—Y—C—N—A—E—G—S—K—OH

H—K—P—G—S—E—H—E—S—A—F—V—N—Q—H—L—C—G—S—H—L—V—E—A—L—Y—L—V—C—G—E—R—G—F—F—Y—T—P—R—T—OH

-continued

Example 141

-continued

Example 142

Example 143

-continued

-continued

Example 144

-continued

Example 145

Example 146

G—I-V-E-Q-C-C-T-S-I—C-S-L-Y-Q-

K—N—N—F-V-N-Q-H-L-C-G-S-H—

L-E-N-Y-C—N—OH

—L-V-E-A-L-Y-L-V-C-G—E-R-G-F-F-V-T-P-K-T—OH

Example 147

G—I-V-E-Q-C-C-T-S-I—C-S-L-Y-Q-L-E-N-Y-C—N—OH

—F-V-N-C-H-L-C-G-S-H—L-V-E-A-L-Y-L-V-C-G—E-R-G-F-F-Y-T-P-K-T—OH

-continued

Example 148

G—I-V-E-Q-C-C-T-S-I—C-S-L-Y-Q-L-E-N-Y-C—N—OH

—F-V-N-C-H-L-C-G-S-H—L-V-E-A-L-Y-L-V-C-G—E-R-G-F-F-Y-T-P-K-T—OH

Example 149

H—K-P-G-S-E-H-E-S-A-F—

G—I-V-E-Q-C-C-T-S-I—C-S-L-Y-Q-L-E-N-Y-C—N—OH

—V-N-Q-H-L-C-G-S-H-L—V-E-A-L-Y-L-V-C-G-E—R-G-F-F-Y-T-P-K—OH

1087

1088

-continued

Example 150

H—K-P-G-S-E-H-E-S-A-F——

H—G-I-V-E-Q-C-C-T-S-I—C-S-L-Y-Q-L-E-N-Y-C—N-A-E-G-S-K—OH

——V-N-Q-H-L-C-G-S-H-L—V-E-A-L-Y-L-V-C-G-E—R-G-F-F-Y-T-P-K—OH

-continued

Example 151

H—K-P-G-S-E-H-E-S-A-F——

H—K-P-G-I-V-E-Q-C-C-T—S-I-C-E-L-Y-Q-L-E-N—Y-C-N—OH

—V-N-Q-H-L-C-G-S-H-L—V-E-A-L-Y-L-V-C-G-E—R-G-F-F-Y-T-P-K—OH

1091                                                                1092

-continued

Example 152

H—K-P-G-S-E-H-E-S-A-F——

1093                                    1094

-continued

Example 153

H—K-P-G-S-E-H-E-S-A-F——

H—GI-V-K-P-Q-C-C-T-S—I-C—S-L-Y-Q-L-E-N-Y—C-N—OH

——V-N-Q-H-L-C-G-S-H-L—V-E-A-L-Y-L-V-C-G-E—R-G-F-F-Y-T-P-K—OH

1095

1096

-continued

Example 154

1097

1098

-continued

G—I-V-E-Q-C-C-T-S-I—C-S-L-Y-Q-L-E-N-Y-C—N—OH

—F-V-N-Q-H-L-C-G-S-H—L-V-E-A-L-Y-LV-C-G—E-R-G-F-F-Y-T-P-K-T—OH

Example 155

Dap—G-A-K—K

1099                                                    1100

-continued

G—I-V-E-Q-C-C-T-S-I—C-S-L-Y-Q-L-E-N-Y-C—N

—F-V-N-Q-H-L-C-G-S-H—L-V-E-A-L-Y-L-V-C-G—E-R-G-F-F-Y-T-P-K-T—OH

Example 156

Dap—K-A-G-K—K

1101

-continued

1102

G—I-V-E-Q-C-C-T-S-I—C-S-L-Y-C-L-E-N-Y-C—N—OH

—F-V-N-Q-H-L-C-G-S-H—L-V-E-A-L-Y-L-V-C-G—E-R-G-F-F-Y-T-P-K-T—OH

Example 157

Example 158

-continued

G—I—V—E—Q—C—C—T—G—I—C—S—L—Y—Q—L—E—N—Y—C—N—OH

H—F—V—N—Q—H—L—C—G—S—H—L—V—E—A—L—Y—L—V—C—G—E—R—G—F—F—Y—T—P—K—T—OH

NO₂

HN

AcHN

OH

H₂N—Dap—A—G—K—K

-continued

Example 159

Example 160

-continued

G—I—V—E—C—C—T—S—I—C—S—L—Y—Q—L—E—N—Y—C—N—OH

H—F—V—N—Q—H—L—C—G—S—H—L—V—E—A—L—Y—L—V—C—G—E—R—G—F—F—Y—T—P—K—T—OH

HN

Dap—A—G—K—K

HN

HN

OH

B—OH

HO—B

OH

F

B—OH

O

F

F

O

F

F

HO—B—OH

O

HN

NH

O

B—OH

O

OH

B

HN

HN

O

NH

B

O

HO

NH

O

B

HO

-continued

Example 161

-continued

Example 162

Example 163

-continued

Example 164

-continued

-continued

Example 165

1121                                          1122

Example 166

-continued

1123                                                                                    1124

Example 167

-continued

Example 168

Example 169

-continued

H-G-I-V-E-Q-C-C-T-S-I—C-S-L-Y-Q-L-E-N-Y-C—N-OH

HN-K-P-G-S-E-H-E-S-A-F-V-N-Q-H-L-C-G-S-H-L-V-E-A-L-Y-L-V-C-G-E-R-G-F-F-Y-T-P-K-OH

-continued

Example 170

Example 171

1133          1134

Example 172

1135                                                        1136

Example 173

-continued

-continued

Example 174

-continued

Example 175

-continued

Example 176

Example 177

-continued

-continued

Example 178

1147          1148

Example 179

-continued

—E—R—G—F—F—Y—T—P—K—OH

-continued

Example 180

Example 181

-continued

-continued

Example 182

1157 1158

Example 183

-continued

Example 184

-continued

Example 185

-continued

Example 186

Example 187

-continued

Example 188

-continued

-continued

Example 189

-continued

Example 190

1173 1174

-continued

Example 191

Example 192

Example 193

-continued

-continued

Example 194

-continued

Example 195

-continued

Example 196

-continued

Example 197

Example 198

-continued

Example 199

-continued

Example 200

H—G—I—V—E—Q—C—C—T—S—I—C—S—L—Y—Q—L—E—N—Y—C—N—A—E—G—S—K—OH

H—N—Q—L—C—G—S—H—L—V—E—A—L—Y—L—V—C—G—E—R—G—F—F—Y—T—P—R—T—OH

HN—K—P—G—S—E—H—E—S—A—F—V—N—Q—H—L—C—G—S—H—L—V—E—A—L—Y—L—V—C 1193                                                    1194

Example 201

-continued

Example 202

-continued

-continued

Example 203

-continued
Example 204
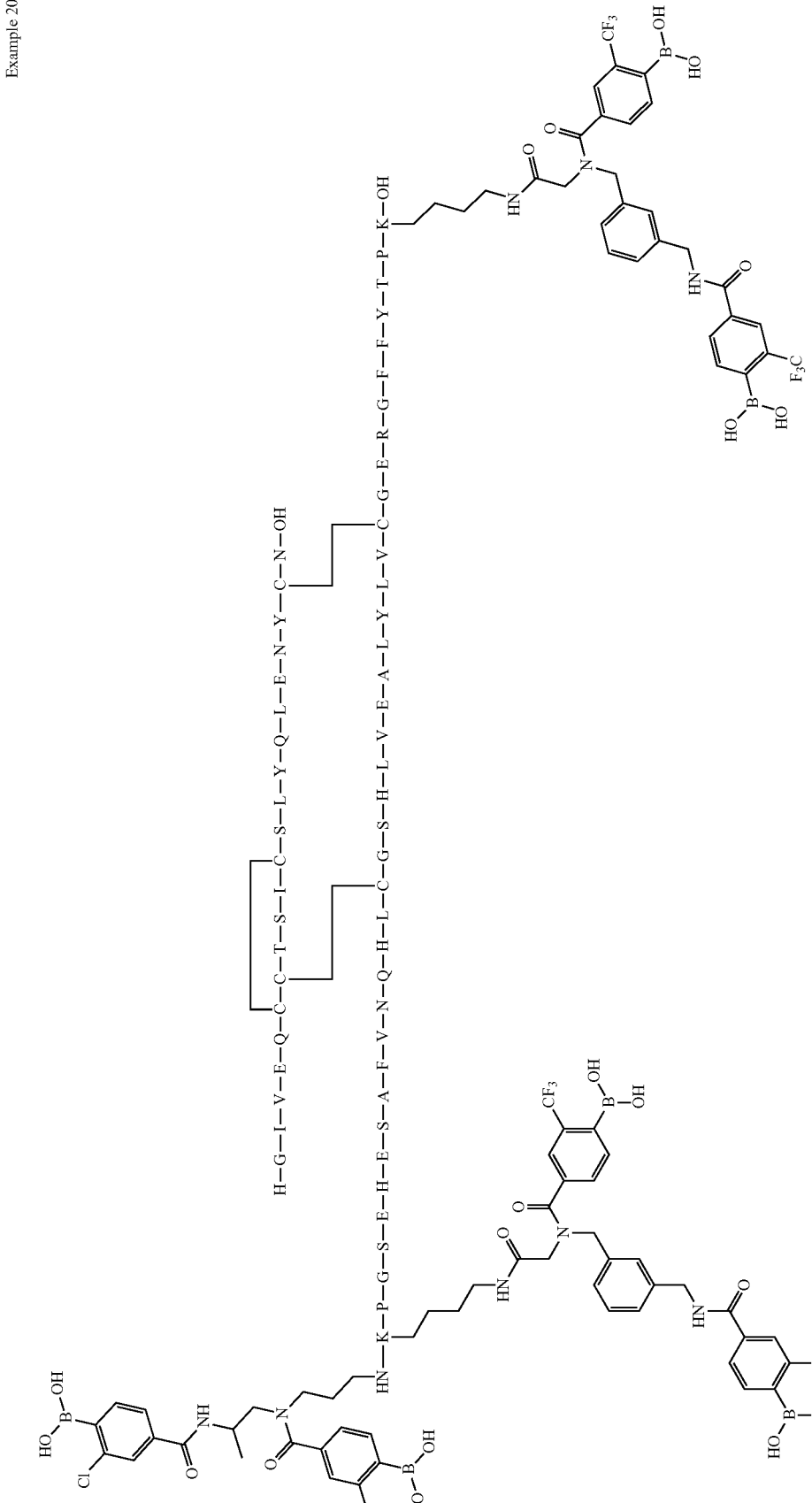

1201            1202

-continued

Example 205

1203

1204

Example 206

-continued

1205  1206

Example 207

-continued

1207

1208

Example 208

-continued

Example 209

-continued

H—G—I—V—E—Q—C—C—T—S—I—C—S—L—Y—Q—L—E—N—Y—C—N—OH

K—P—G—S—E—H—E—S—A—F—V—N—Q—H—L—C—G—S—H—L—V—E—A—L—Y—L—V—C—G—E—R—G—F—F—Y—T—P—K—OH

1211

1212

-continued

Example 210

1213　　　　　　　　　　　　　　　　1214

Example 211

-continued

1215  1216

Example 212

Example 213

-continued

Example 214

1221                                    1222

-continued

Example 215

-continued

Example 216

-continued

Example 217

-continued

Example 218

-continued

Example 219

-continued

Example 220

-continued

Example 221

-continued

Example 222

-continued

Example 223

1239          1240

-continued

Example 224

-continued

Example 225

1243                            1244

Example 226

Example 227

-continued

Example 228

-continued

H-G-I-V-K-P-Q-C-C-T-S-I-C-S-L-Y-Q-L-E-N-Y-C-N—OH

N—K-P-G-S-E-H-E-S-A-F-V-N-Q-H-L-C-G-S-H-L-V-E-A-L-Y-L-V-C-G-E-R-G-F-F-Y-T-P-K—OH
H

Example 229

-continued 1251                                                                    1252

-continued

Example 230

G-I-V-E-Q-C-C-T-S-I-C-S-L-Y-Q-L-E-N-Y-C-N—OH

H—F-V-N-Q-H-L-C-G-S-H-L-V-E-A-L-Y-L-V-C-G-E-R-G-F-F-Y-T-P-K-T—OH

Example 231

-continued

G-I-V-E-Q-C-C-T-S-I-C-S-L-Y-Q-L-E-N-Y-C-N—OH

HN—F-V-N-Q-H-L-C-G-S-H-L-V-E-A-L-Y-L-V-C-G-E-R-G-F-F-Y-T-P-K-T—OH

Example 232

Example 233

G-I-V-E-Q-C-C-T-S-I-C-S-L-Y-Q-L-E-N-Y-C-N-OH

N-F-V-N-Q-H-L-C-G-S-H-L-V-E-A-L-Y-L-V-C-G-E-R-G-F-F-Y-T-P-K-T-OH

G-I-V-E-Q-C-C-T-S-I-C-S-L-Y-Q-L-E-N-Y-C-N-OH

N-F-V-N-Q-H-L-C-S-G-H-L-V-E-A-L-Y-L-V-C-G-E-R-G-F-F-Y-T-P-K-T-OH

-continued

Example 234

-continued

Example 235

G-I-V-E-Q-C-C-T-S-I-C-S-L-Y-Q-L-E-N-Y-C-N-OH

N-F-V-N-Q-H-L-C-G-S-H-L-V-E-A-L-Y-L-V-C-G-E-R-G-F-F-Y-T-P-K-T-OH
H

Example 236

G-I-V-E-Q-C-C-T-S-I-C-S-L-Y-Q-L-E-N-Y-C-N-OH

N-F-V-N-Q-H-L-C-G-S-H-L-V-E-A-L-Y-L-V-C-G-E-R-G-F-F-Y-T-P-K-T-OH
H

-continued

Example 237

G-I-V-E-Q-C-C-T-S-I-C-S-L-Y-Q-L-E-N-Y-C-N-OH

N-F-V-N-Q-H-L-C-G-S-H-L-V-E-A-L-Y-L-V-C-G-E-R-G-F-F-Y-T-P-K-T-OH

Example 238

-continued

Example 239

-continued

Example 240

-continued

Example 241

-continued

Example 242

-continued

Example 243

1275                                  1276

Example 244

H·G-I-V-E-Q-C-C-T-S-I—C-S-L-Y-Q-L-E-N-Y-C-N—OH

HN-K-P-G-S-E-H-E-S-A-F—V-N-Q-H-L-C-G-S-H-L-·V-E-A-L-Y-L-·V-G-C-E·R-G-F-F-Y-T-P-K-OH

Example 245

H—G-I-V-E-Q-C-C-T-S-I—C-S-L-Y-Q-L-E-N-Y-C—N-A-E-G-S-K—OH

HN—K-P-G-S-E-H-E-S-A-F—V-N-Q-H-L-C-G-S-H-L—V-E-A-L-Y-L-V-C-G-E—R-G-F-F-Y-T-P-R-T—OH

1277                                                                      1278

Example 246

H—K-P-G-I-V-E-Q-C-C-T—S-I-C-S-L-V-Q-L-E-N—Y-C-N—OH

HN—K-P-G-S-E-H-E-S-A-F—V-N-Q-H-L-C-G-S-H-L—V-E-A-L-Y-L-V-C-G-E—R-G-F-F-Y-T-P-K—OH 1279 1280

Example 247

H—G-I-V-E-C-C-T-S-I—C-S-L-Y-Q-L-E-N-Y-C—N-A-E-G-S-K—OH

HN—K-P-G-S-E-H-E-S-A-F—V-N-Q-H-L-C-G-S-H-L—V-E-A-L-Y-L-V-C-G-E—R-G-F-F-Y-T-P-K—OH

1281

1282

Example 248

H—G-I-V-K-P-Q-C-C-T-S—I-C—S-L-Y-Q-L-E-N-Y—C-N—OH

NH—K-P-G-S-E-H-E-S-A-F—V-N-Q-H-L-C-G-S-H-L—V-E-A-L-Y-L-V-C-G-E—R-G-F-F-Y-T-P-K—OH

1283                                                    1284

-continued

Example 249

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

Example 250

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

-continued

Example 251

Example 252

1287

1288

Example 253

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH 1289            1290

Example 254

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

Example 255

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

1291                                                                 1292

Example 256

H–G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T-OH

Example 257

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

-continued

Example 258

Example 259

-continued

Example 260

Example 261

-continued

Example 262

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

Example 263

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

-continued

Example 264

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

Example 265

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

-continued

Example 266

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

Example 267

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

1303

1304

-continued

Example 268

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

Example 269

H—G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

-continued

Example 270

Example 271

-continued

Example 272

Example 273

1309  1310

Example 274

-continued

Example 275

H—G—I—V—E—Q—C—C—T—S—I—C—S—L—Y—Q—L—E—N—Y—C—N—OH

—C—G—S—H—L—V—E—A——L—Y—L—V—C—G—E—R—G—F—F—Y—T—P—K—T—OH

Example 276

-continued

H—G—I—V—E—Q—C—C—T—S—I—C—S—L—Y—Q—L—E—N—Y—C—N—OH

—C—G—S—H—L—V—E—A—L—Y—L—V—C—G—E—R—G—F—F—Y—T—P—K—T—OH

Example 277

—F—Y—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—E—R—G—F—F—Y—T—P—K—T—OH

-continued

Example 278

H—G—I—V—E—Q—C—C—T—S—I—C—S—L—Y—Q—L—E—N—Y—C—N—OH

—C—G—S—H—L—V—E—A—L—Y—L—V—C—G—E—R—G—F—F—Y—T—P—K—T—OH

-continued

Example 279

H—G—I—V—E—Q—C—C—T—S—I—C—S—L—Y—Q—L—E—N—Y—C—N—OH

—C—G—S—H—L—V—E—A——L—Y—L—V—C—G—E—R—G—F—F—Y—T—P—K—T—OH

Example 280

1319 1320

-continued

H—G—I—V—E—Q—C—C—T—S—I—C—S—L—Y—Q—L—E—N—Y—C—N—OH

—C—G—S—H—L—V—E—A——L—Y—L—V—C—G—E—R—G—F—F—Y—T—P—K—T—OH

Example 281

F—Y—N—Q—H—L—

-continued

H—G—I—V—E—Q—C—C—T—S—I—C—S—L—Y—Q—L—E—N—Y—C—N—OH

—C—G—S—H—L—V—E—A——L—Y—L—V—C—G—E—R—G—F—F—Y—T—P—K—T—OH

Example 282

H—G—I—V—E—Q—C—C—T—S—I—C—S—L—Y—

F—Y—N—Q—H—L—C—G—S—H—L—V—E—

-continued

Example 283

1325
1326
-continued
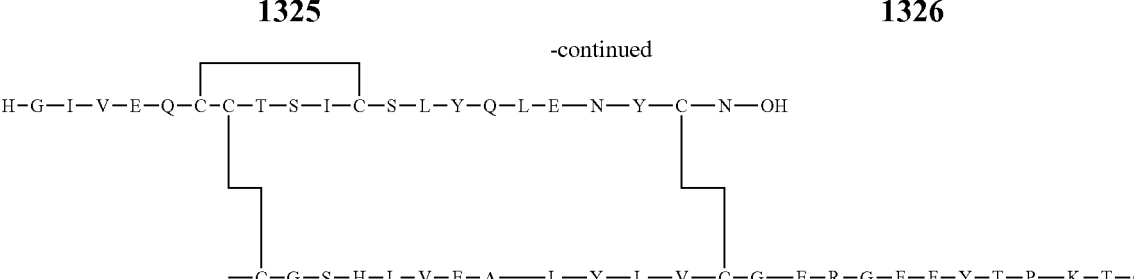

Example 284

1329                    1330
-continued
Example 285
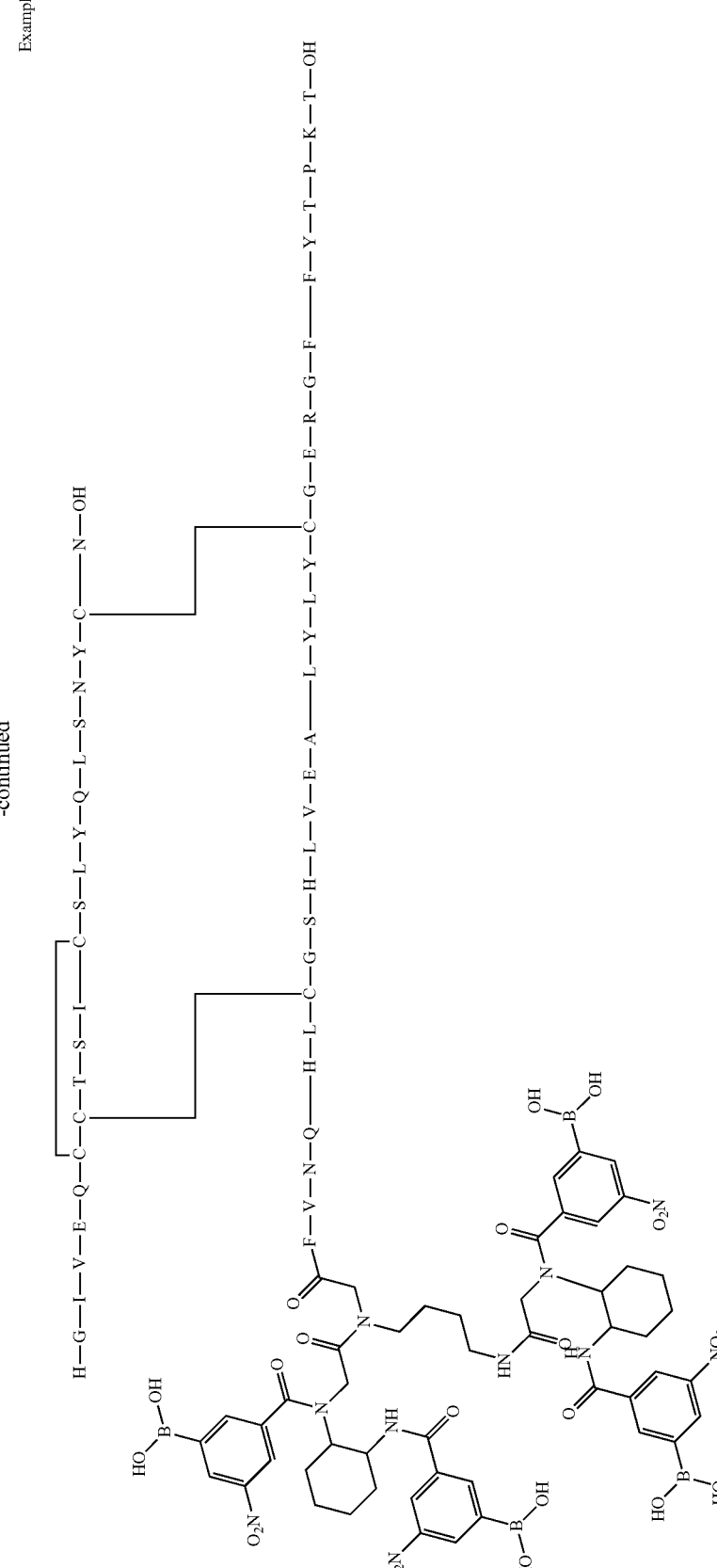

1331                                                                    1332
-continued
Example 286
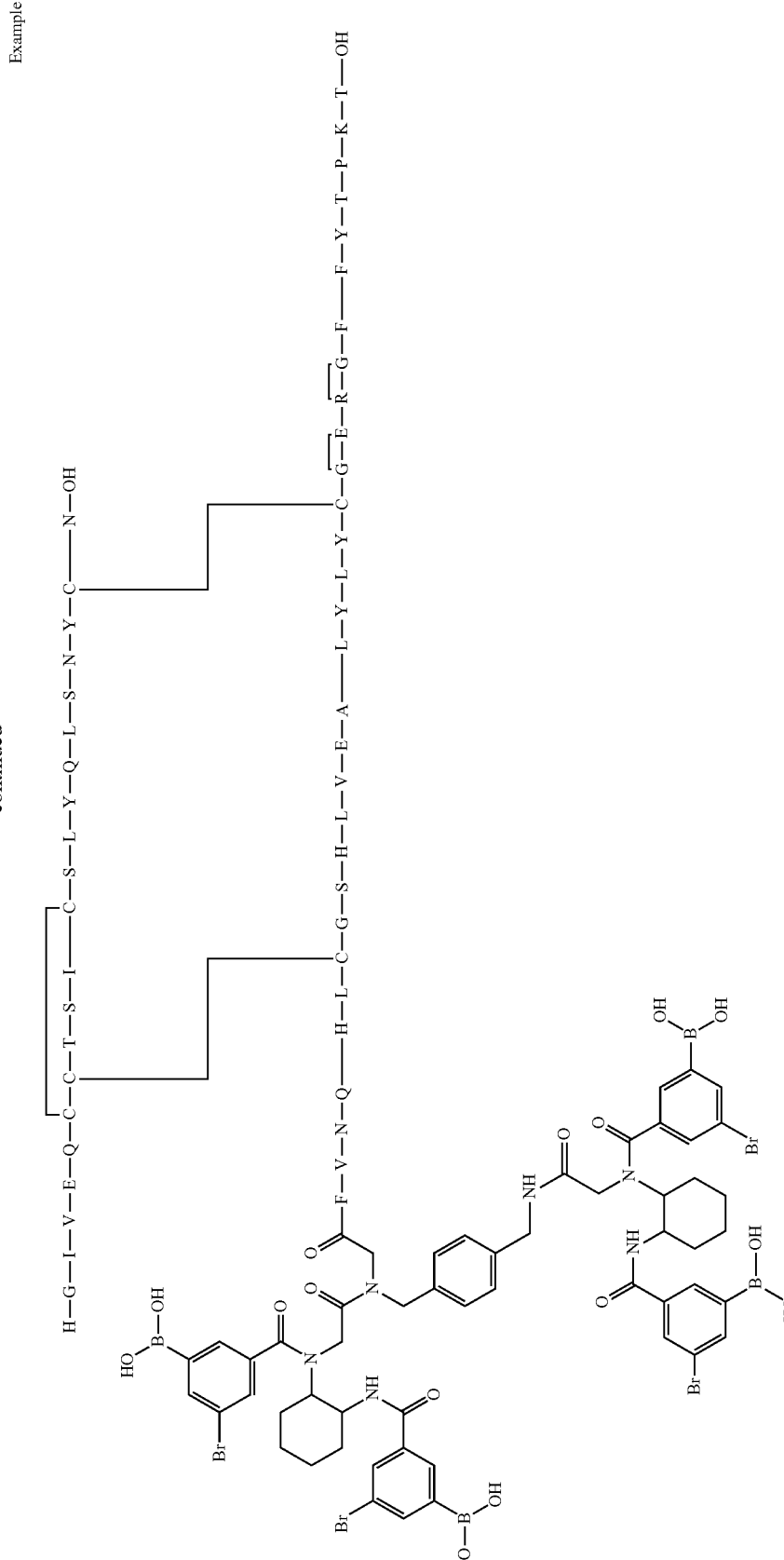

Example 287
-continued
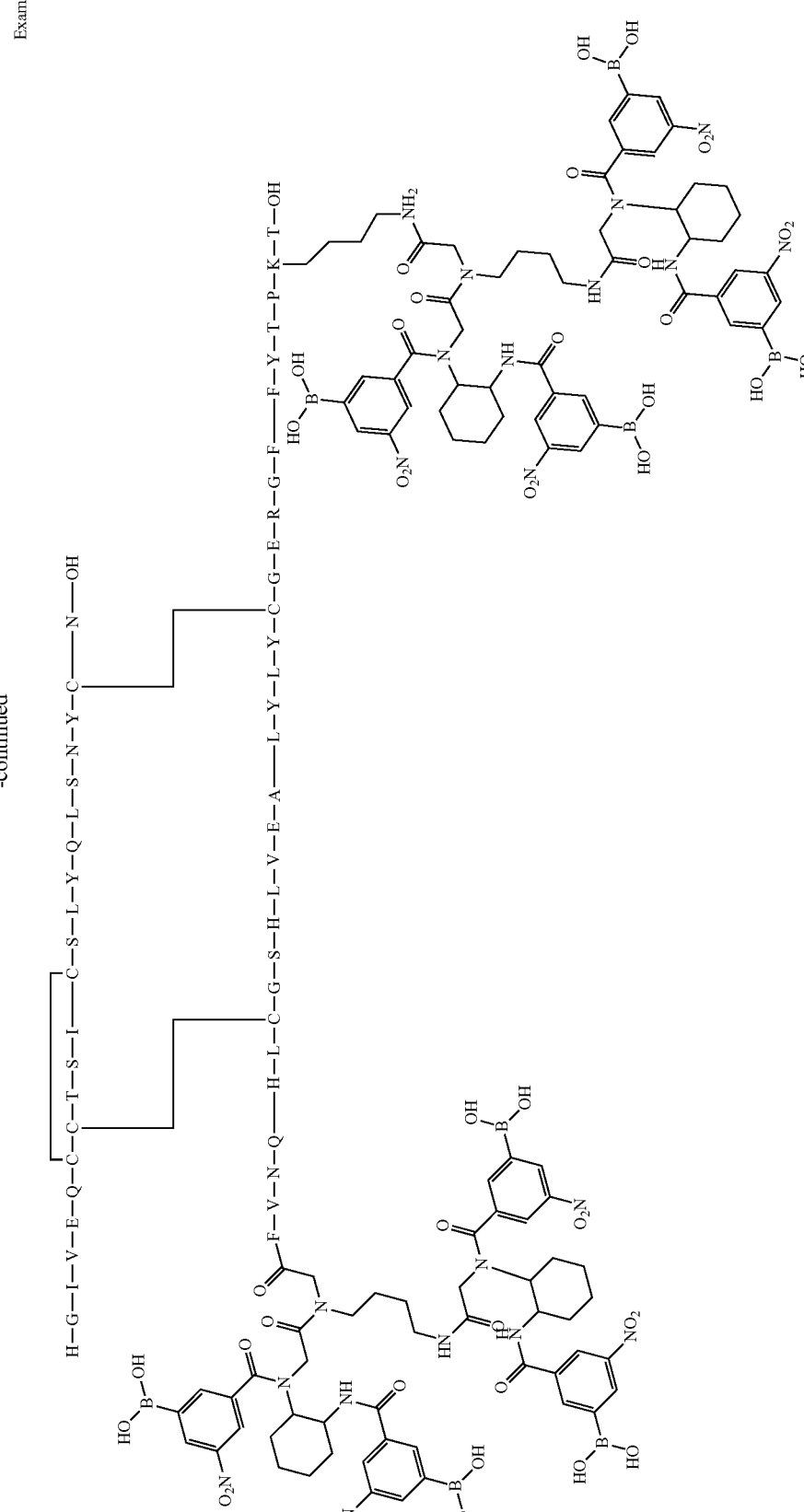

-continued

Example 288

1337                    1338
-continued
Example 289
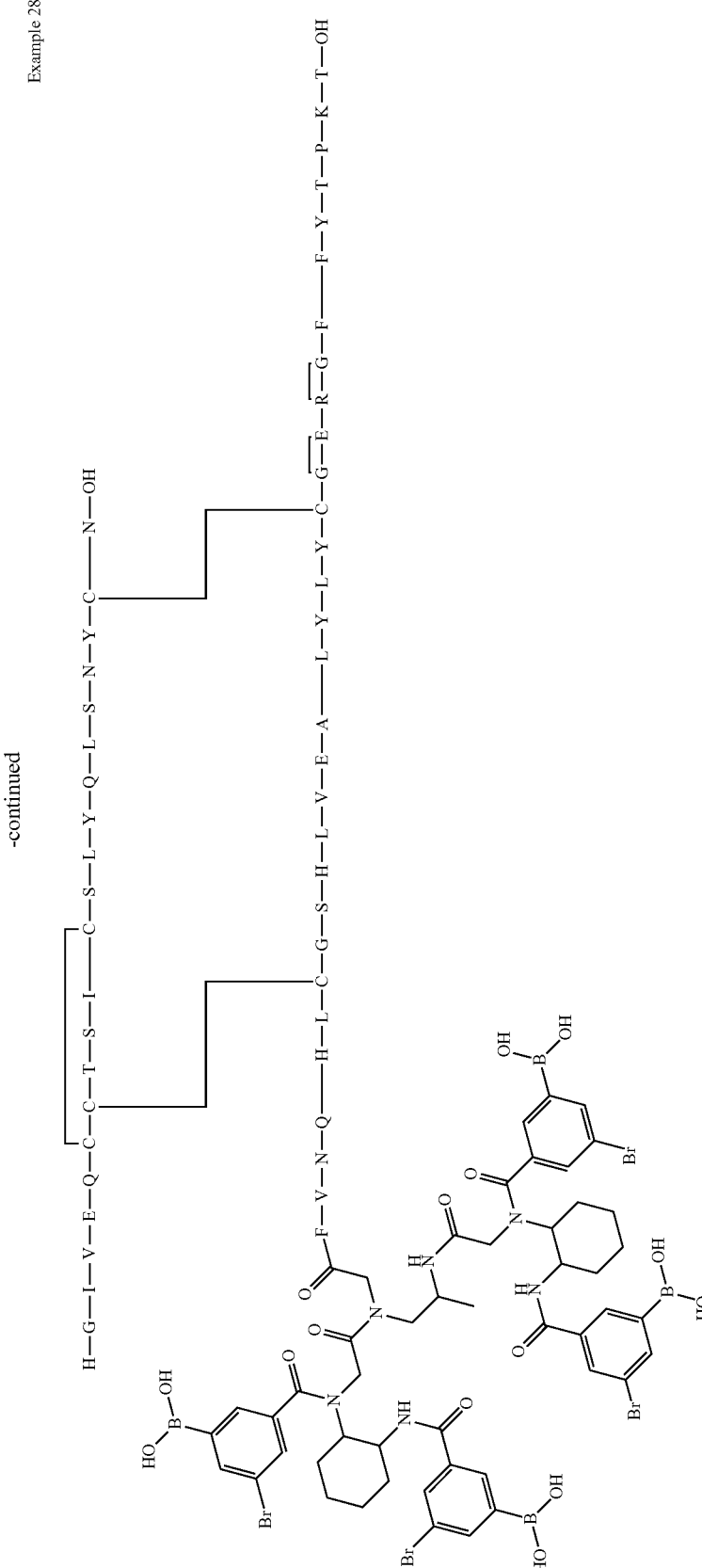

Example 290

-continued

H—G—I—V—E—Q—C—C—T—S—I—C—S—L—Y—Q—L—S—N—Y—C—N—OH

F—V—N—Q—H—L—C—G—S—H—L—V—E—A—L—Y—L—Y—C—G—E—R—G—F—F—Y—T—P—K—T—OH

1341                                                                                     1342
Example 291
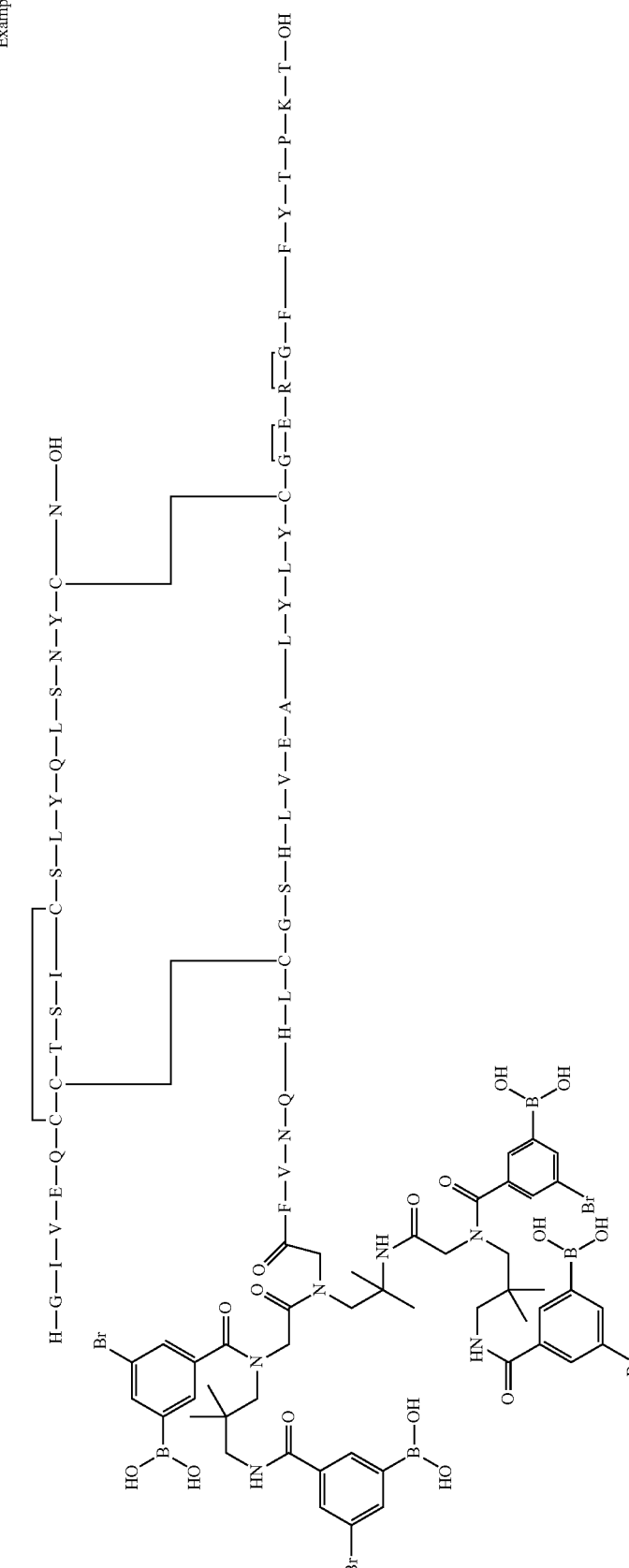

-continued

Example 292

Example 293
-continued
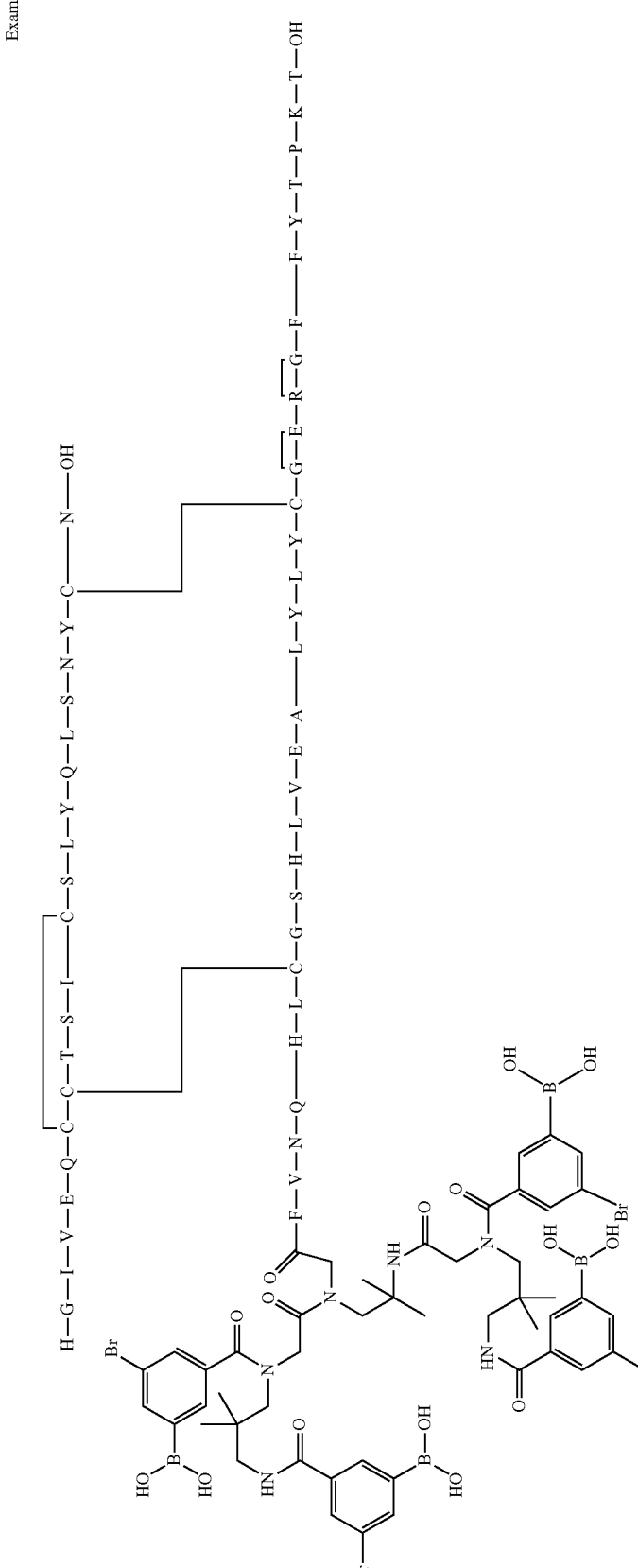

Example 294

-continued

-continued
Example 295
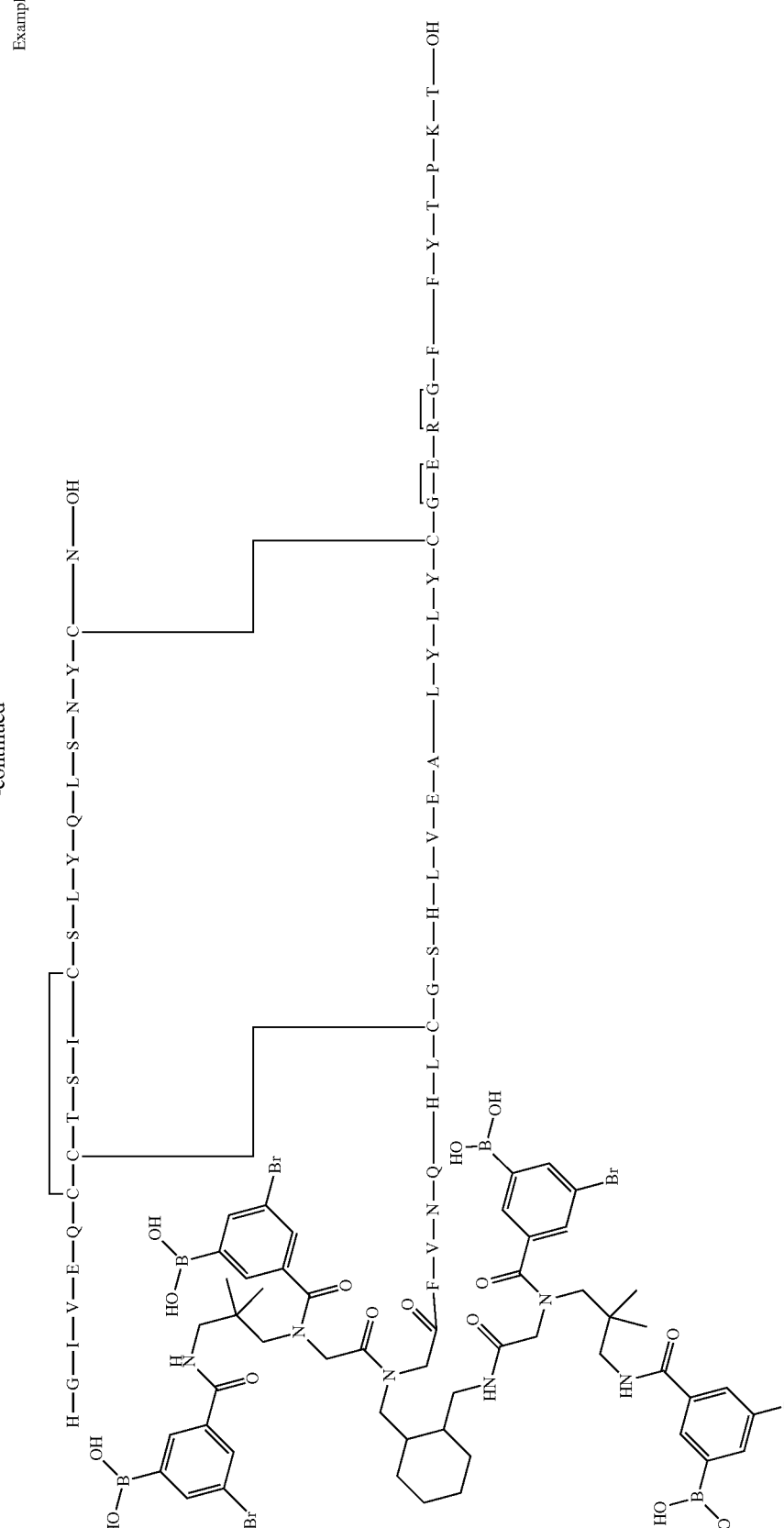

-continued

Example 296

-continued

Example 297

Example 298

-continued

1357

1358

Example 299

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-T—OH

-continued

Example 300

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-T—OH

-continued

Example 301

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-T—OH

-continued

Example 302

Example 303

-continued

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-T—OH

Example 304

-continued

Example 305

-continued

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-T—OH

-continued

Example 306

Example 307

-continued

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-T—OH

1375

1376

Example 308

-continued

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-T—OH 1377          1378

Example 309

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

Example 310

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

-continued

Example 311

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

Example 312

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

-continued

Example 313

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

Example 314

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

-continued

Example 315

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

Example 316

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

Example 317

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

-continued

Example 318

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

Example 319

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

-continued

Example 320

Example 321

Example 322

-continued

Example 323

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

Example 324

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

Example 325

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-K-T-OH

Example 326

H-G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-OH

Example 328

H-G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-OH

Example 328

H-G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-OH

-continued

Example 329

H-G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

Example 330

H-G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-OH

Example 331

H-G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

-continued

Example 332

H-G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-OH

Example 333

H-G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

-continued

Example 334

H-G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-OH

Example 335

H-G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-T—OH

Example 336

H—G—I—V—E—Q—C—C—T—S—I—C-S-L-Y-Q-L-E-N-Y-C—N-OH

F-V-N-Q-H-L-C-G-S-H-L-V-E-A—L-Y-L-V-C-G-E-R-G-F-F-Y-T-P-K-OH

-continued

Example 337

H-G-I-V-E-Q-C-C-T-S-I—C-S-L-Y-Q-L-E-N-Y-C—N—OH

F-V-N-Q—H-L-C-G-S-H-L-V-E-A—L-Y-L-V-C-G-E-R-G-F—F-Y-T-P-K-OH

Example 338

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

Example 339

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

1401

1402

-continued

Example 340

H—G-I-V-E-Q-C-C-T-S-I-C-S-L-Y-Q-L-E-N-Y-C-N—OH

F-V-N-Q-H-L-C-G-S-H-L-V-E-A-L-Y-L-V-C-G-E-R-G-F-F-Y-T-P-KOH

Example 341

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

-continued

Example 342

H—G-I-V-E-Q-C-C-T-S-I-C-S-L-Y-Q-L-E-N-Y-C N—OH

F-V-N-Q-H-L-C-G-S-H-L-V-E-A-L-Y-L-V-C-G-E-R-G-F-F-Y-T-P-K—OH

Example 343

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

-continued

Example 344

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

Example 345

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

-continued

Example 346

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-OH

Example 347

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

Example 348

1409                                                                                        1410

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

Example 349

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

-continued

Example 350

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

Example 351

H-G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

-continued

Example 352

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

Example 353

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-T—OH

1415　　　　　　　　　　　　　　　　　1416

-continued

Example 354

H—G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K—OH

1417                                                                 1418

Example 355

1419                                                                      1420

Example 356

1421                                                1422

Example 357

-continued

-continued

Example 358

G-I-V-E-Q-C-C-T-S-I-C-S-L-Y-Q-L-E-N-Y-C—N

F-V-N-Q-H-L-C-G-S-H-L-V-E-A-L-Y-L-V-C-G-E-R-G-F-F-Y-T-P-K-T—OH

K-G-A-K

-continued

Example 359

-continued

Example 360

Example 361

-continued

Example 362

-continued 1433      1434

Example 363

-continued

-continued

Example 364

-continued

Example 365

-continued

Example 366

-continued

Example 367

Example 368

-continued

Example 369

-continued

Example 370

-continued

Example 371

1451                                                                                          1452

-continued

Example 372

-continued

Example 373

-continued

Example 374

-continued

Example 375

-continued

Example 376

1461

1462

Example 377

Example 378

-continued

-continued

Example 379

-continued

Example 380

Example 381

-continued

-continued

Example 382

-continued

Example 383

-continued

Example 384

-continued

Example 385

Example 386

K-G-A-K-S

G—I-V-E-Q-C-C-T-S-I—C-S-L-Y-Q-L-E-N-Y-C—N—OH

—F-V-N-Q-H-L-C-G-S-H—L-V-E-A-L-Y-L-V-C-G—E-R-G-F-F-Y-T-P-K-T—OH

1481 1482

Example 387

K-G-A-K-S

G—I-V-E-Q-C-C-T-S-I—C-S-L-Y-Q-L-E-N-Y-C—N—OH

—F-V-N-Q-H-L-C-G-S-H—L-V-E-A-L-Y-L-V-C-G—E-R-G-F-F-Y-T-P-K-T—OH

-continued

Example 388

K-G-A-K-S

G—I-V-E-Q-C-C-T-S-I—C-S-L-Y-Q-L-E-N-Y-C—N—OH

—F-V-N-Q-H-L-C-G-S-H—L-V-E-A-L-Y-L-V-C-G—E-R-G-F-F-Y-T-P-K-T—OH

-continued

Example 389

G—I-V-E-Q-C-C-T-S-I—C-S-L-Y-Q-L-E-N-Y-C—N—OH

—F-V-N-Q-H-L-C-G-S-H—L-V-E-A-L-Y-L-V-C-G—E-R-G-F-F-Y-T-P-K-T—OH

-continued

Example 390

HO—S-K-A-G-K-K

AcHN

G—I-V-E-Q-C-C-T-S-I—C-S-L-Y-Q-L-E-N-Y-C—N—OH

—F-V-N-Q-H-L-C-G-S-H—L-V-E-A-L-Y-L-V-C-G—E-R-G-F-F-Y-T-P-K-T—OH

-continued

Example 391

1491                                                              1492

Example 392

-continued

Example 393

HO—S-K-A-G-K-K

AcHN

G—I-V-E-Q-C-C-T-S-I—C-S-L-Y-Q-L-E-N-Y-C—N—OH

—F-V-N-Q-H-L-C-G-S-H—L-V-E-A-L-Y-L-V-C-G—E-R-G-F-F-Y-T-P-K-T—OH

-continued

Example 394

1497                                                                 1498

Example 395

G—I-V-E-Q-C-C-T-S-I—C-S-L-Y-Q-L-E-N-Y-C—N—OH

—F-V-N-Q-H-L-C-G-S-H—L-V-E-A-L-Y-L-V-C-G—E-R-G-F-F-Y-T-P-K-T—OH

-continued

Example 396

1501                                                         1502

-continued

Example 397

Example 398

1503

1504

G—I-V-E-Q-C-C-T-S-I—C-S-L-Y-Q-L-E-N-Y-C—N—OH

—F-V-N-Q-H-L-C-G-S-H—L-V-E-A-L-Y-L-V-C-G—E-R-G-F-F-Y-T-P-K-T—OH

Example 399

G-I-V-E-Q-C-C-T-S-I-C-S-L-Y-Q-L-E-N-Y-C-N—OH

HN—F-V-N-Q-H-L-C-G-S-H-L-V-E-A-L-Y-L-V-C-G-E-R-G-F-F-Y-T-P-K-T—OH

-continued

Example 400

H—F-V-N-Q-H-L-C-G-S-H-L-V-E-A-L-Y-L-V-C-G-E-R-G-F-F-Y-T-P-K-T—OH

G-I-V-E-Q-C-T-S-I-C-S-L-Y-Q-L-E-N-Y-C-N—OH

HO—S-K-A-G-K-K

-continued

Example 401

-continued

Example 402

-continued

Example 403

-continued

Example 404

-continued

Example 405

1519                                                                                   1520

-continued

Example 406

1521                                                     1522

Example 407

-continued

Example 408

Example 409

-continued

1527

1528

-continued

Example 410

Example 411

-continued 1531 1532

-continued

Example 412

1533                                    1534

-continued

Example 413

-continued

Example 414

Example 415

-continued

G-I-V-E-Q-C-C-T-S-I-C-S-L-Y-Q-L-E-N-Y-C-N-OH

H₂N—F-V-N-Q-H-L-C-G-S-H-L-V-E-A-L-Y-L-V-C-G-E-R-G-F-F-Y-T-P-K-T-OH

H₂N—S-K-A-G-K-K

Example 416

-continued

-continued

Example 417

Example 418

-continued

Example 419

-continued

Example 420

G-I-V-E-Q-C-C-T-S-I—C-S-L-Y-Q-L-E-N-Y-C—N—OH

H | N—F—V-N-Q-H-L-C-G-S-H—L-V-E-A-L-Y-L-V-C-G—E-R-G-F-F-Y-T-P-K-T—OH

-continued

Example 421

-continued

G-I-V-E-Q-C-C-T-S-I—C-S-L-Y-Q-L-E-N-Y-C—N—OH

N—F—V-N-Q-H-L-C-G-S-H—L-V-E-A-L-Y-L-V-C-G—E-R-G-F-F-Y-T-P-K-T—OH

Example 422

1553                                                                1554

G-I-V-E-Q-C-C-T-S-I—C-S-L-Y-Q-L-E-N-Y-C—N—OH

N—F—V-N-Q-H-L-C-G-S-H—L-V-E-A-L-Y-L-V-C-G—E-R-G-F-F-Y-T-P-K-T—OH

Example 423

1555

1556

-continued

G-I-V-E-Q-C-C-T-S-I—C-S-L-Y-Q-L-E-N-Y-C—N—OH

N—F—V-N-Q-H-L-C-G-S-H—L-V-E-A-L-Y-L-V-C-G—E-R-G-F-F-Y-T-P-K-T—OH

Example 424

H₂N—S-K-A-G-K-K

1557 · 1558

G-I-V-E-Q-C-C-T-S-I—C-S-L-Y-Q-L-E-N-Y-C—N—OH

N—F—V-N-Q-H-L-C-G-S-H—L-V-E-A-L-Y-L-V-C-G—E-R-G-F-F-Y-T-P-K-T—OH

Example 425

H₂N—S-K-A-G-K-K

-continued

G-I-V-E-Q-C-C-T-S-I-C-S-L-Y-Q-L-E-N-Y-C—N—OH

H
N—F—V-N-Q-H-L-C-G-S-H—L-V-E-A-L-Y-L-V-C-G————E-R-G-F-F-Y-T-P-K-T—OH

Example 426

H₂N—S-K-A-G-K-K

1561　　　　　　　　　　　　　　　　　　　　　　　　1562

G-I-V-E-Q-C-C-T-S-I-C-S-L-Y-Q-L-E-N-Y-C—N—OH

N—F—V-N-Q-H-L-C-G-S-H—L-V-E-A-L-Y-L-V-C-G—E-R-G-F-F-Y-T-P-K-T—OH

H

Example 427

H₂N—S-K-A-G-K-K

-continued

G-I-V-E-Q-C-C-T-S-I—C-S-L-Y-Q-L-E-N-Y-C—N—OH

N
H—F—V-N-Q-H-L-C-G-S-H—L-V-E-A-L-Y-L-V-C-G—E-R-G-F-F-Y-T-P-K-T—OH

Example 428

H₂N—S-K-A-G-K-K

-continued

G-I-V-E-Q-C-C-T-S-I—C-S-L-Y-Q-L-E-N-Y-C—N—OH

N—F—V-N-Q-H-L-C-G-S-H—L-V-E-A-L-Y-L-V-C-G—E-R-G-F-F-Y-T-P-K-T—OH

Example 429

G-I-V-E-Q-C-C-T-S-I—C-S-L-Y-Q-L-E-N-Y-C—N—OH

N—F—V-N-Q-H-L-C-G-S-H—L-V-E-A-L-Y-L-V-C-G—E-R-G-F-F-Y-T-P-K-T—OH

1567

1568

Example 430

-continued

G-I-V-E-Q-C-C-T-S-I—C-S-L-Y-Q-L-E-N-Y-C—N—OH

N—F—V-N-Q-H-L-C-G-S-H—L-V-E-A-L-Y-L-V-C-G—E-R-G-F-F-Y-T-P-K-T—OH

Example 431

H₂N—S-K-A-G-K-K

-continued

G-I-V-E-Q-C-C-T-S-I—C-S-L-Y-Q-L-E-N-Y-C—N—OH

HN—F—V-N-Q-H-L-C-G-S-H—L-V-E-A-L-Y-L-V-C-G—E-R-G-F-F-Y-T-P-K-T—OH

Example 432

-continued

Example 433

-continued

Example 434

-continued

Example 435

-continued

Example 436

G-I-V-E-G-C-C-T-S-I—C-S-L-Y-Q-L-E-N-Y-C—N

N-F-V-N-Q-H-L-C-G-S-H-L—V-E-A-L-Y-V-C-G-E— R-G-F-F-Y-T-P-K-T—OH

-continued

Example 437

-continued

Example 438

-continued

Example 439

-continued

Example 440

-continued

Example 441

-continued

Example 442

G-I-V-E-G-C-C-T-S-I—C-S-L-Y-Q-L-E-N-Y-C—N—OH

N—F-V-N-Q-H-L-C-G-S-H—L-V-E-A-L-Y-V-C-G—E-R-G-F-F-Y-T-P-K-T—OH

-continued

Example 443

G-I-V-E-G-C-C-T-S-I——C-S-L-Y-Q-L-E-N-Y-C—N—OH

F-V-N-Q-H-L-C-G-S-H——L-V-E-A-L-Y-V-C-G——E-R-G-F-F-Y-T-P-K-T—OH

-continued

Example 444

-continued

Example 445

G-I-V-E-G-C-C-T-S-I—C-S-L-Y-Q-L-E-N-Y-C—N—OH

N—F-V-N-Q-H-L-C-G-S-H—L-V-E-A-L-Y-V-C-G—E-R-G-F-F-Y-T-P-K-T—OH
H 1601                                                                    1602

Example 446

G-I-V-E-G-C-C-T-S-I—C-S-L-Y-Q-L-E-N-Y-C—N—OH

N—F-V-N-Q-H-L-C-G-S-H—L-V-E-A-L-Y-V-C-G—E-R-G-F-F-Y-T-P-K-T-OH

-continued

Example 447

Example 448

-continued

Example 449

G-I-V-E-G-C-C-T-S-I—C-S-L-Y-Q-L-E-N-Y-C—N

N-F-V-N-Q-H-L-C-G-S-H—L-V-E-A-L-Y-V-C-G—E-R-G-F-F-Y-T-P-K-T—OH

-continued

Example 450

-continued
Example 451
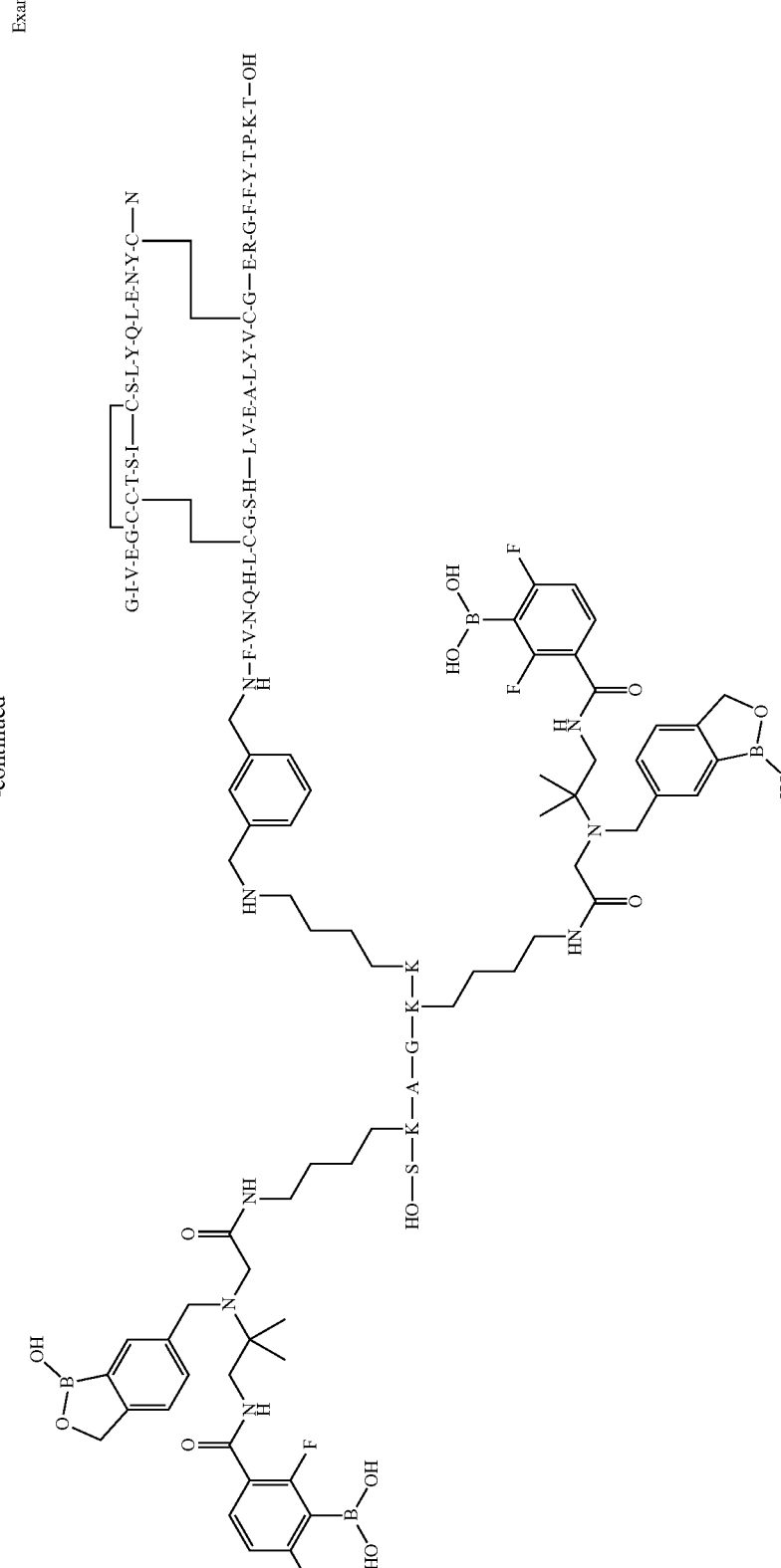

1611                                                                      1612

-continued

Example 452

-continued

Example 453

G-I-V-E-G-C-C-T-S-I—C-S-L-Y-Q-L-E-N-Y-C—N

H—F-V-N-Q-H-L-C-G-S-H—L-V-E-A-L-Y-V-C-G-E-R-G-F-F-Y-T-P-K-T-OH

1615

1616

Example 454

-continued

Example 455

G—I—V—E—Q—C—T—S—I—C—S—L—Y—Q—L—E—N—Y—C—N—OH

H—F—V—N—Q—H—L—C—G—S—H—L—V—E—A—L—Y—L—V—C—G—E—R—G—F—F—Y—T—P—K—T—OH

-continued
Example 456
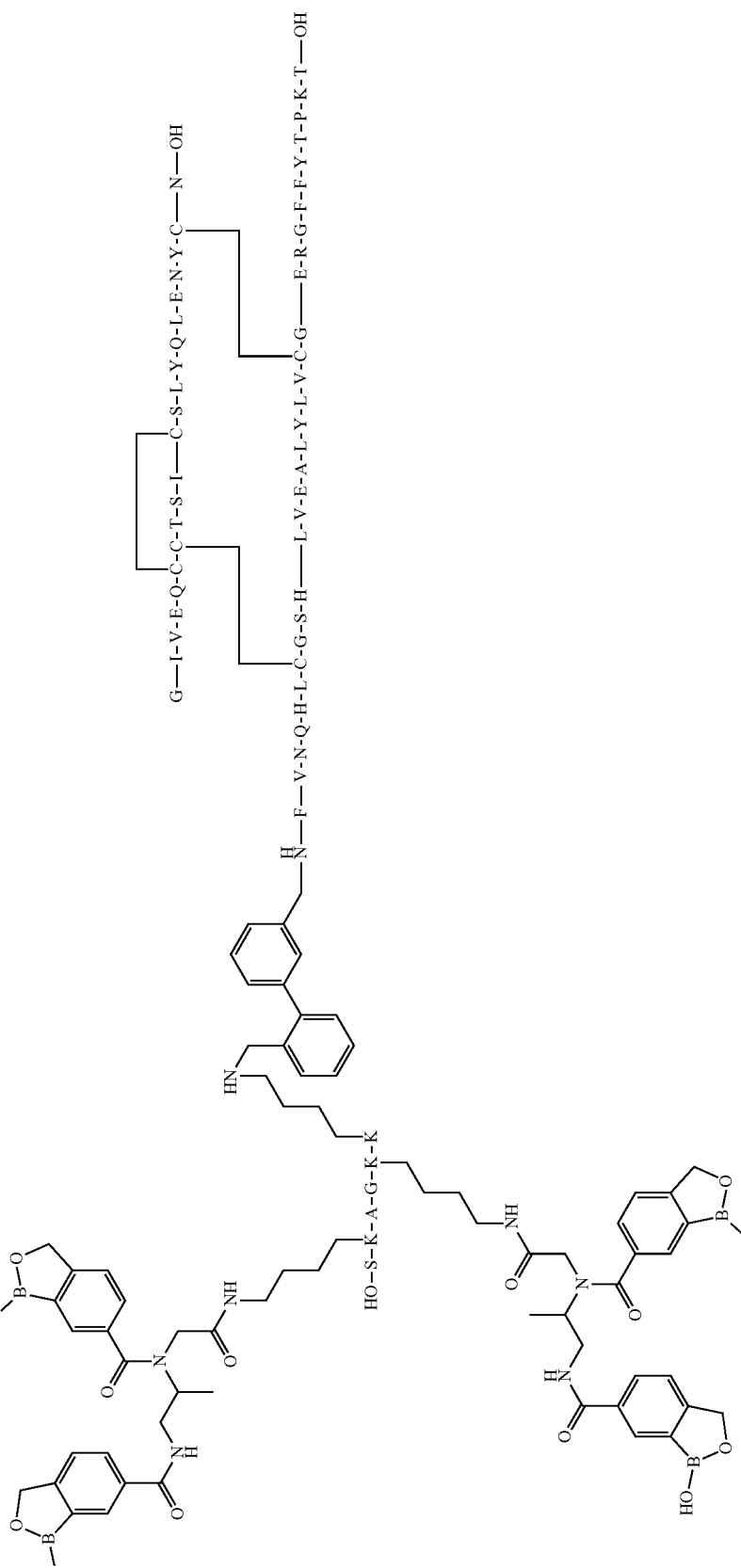

-continued

Example 457

Example 458

-continued

G—I—V—E—Q—C—C—T—S—I—C—S—L—Y—Q—L—E—N—Y—C—N—OH

H—F—V—N—Q—H—L—C—G—S—H—L—V—E—A—L—Y—L—V—C—G—E—R—G—F—F—Y—T—P—K—T—OH 1625                                                                                          1626

Example 459

-continued

Example 460

-continued

Example 461

-continued

Example 462

G-I-V-E-Q-C-C-T-S-I—C-S-L-Y-Q-L-E-N-Y-C—N—OH

H-F-V-N-Q-H-L-C-G-S-H—L-V-E-A-L-Y-L-V-C-G—E-R-G-F-F-Y-T-P-K-T—OH

-continued
Example 463
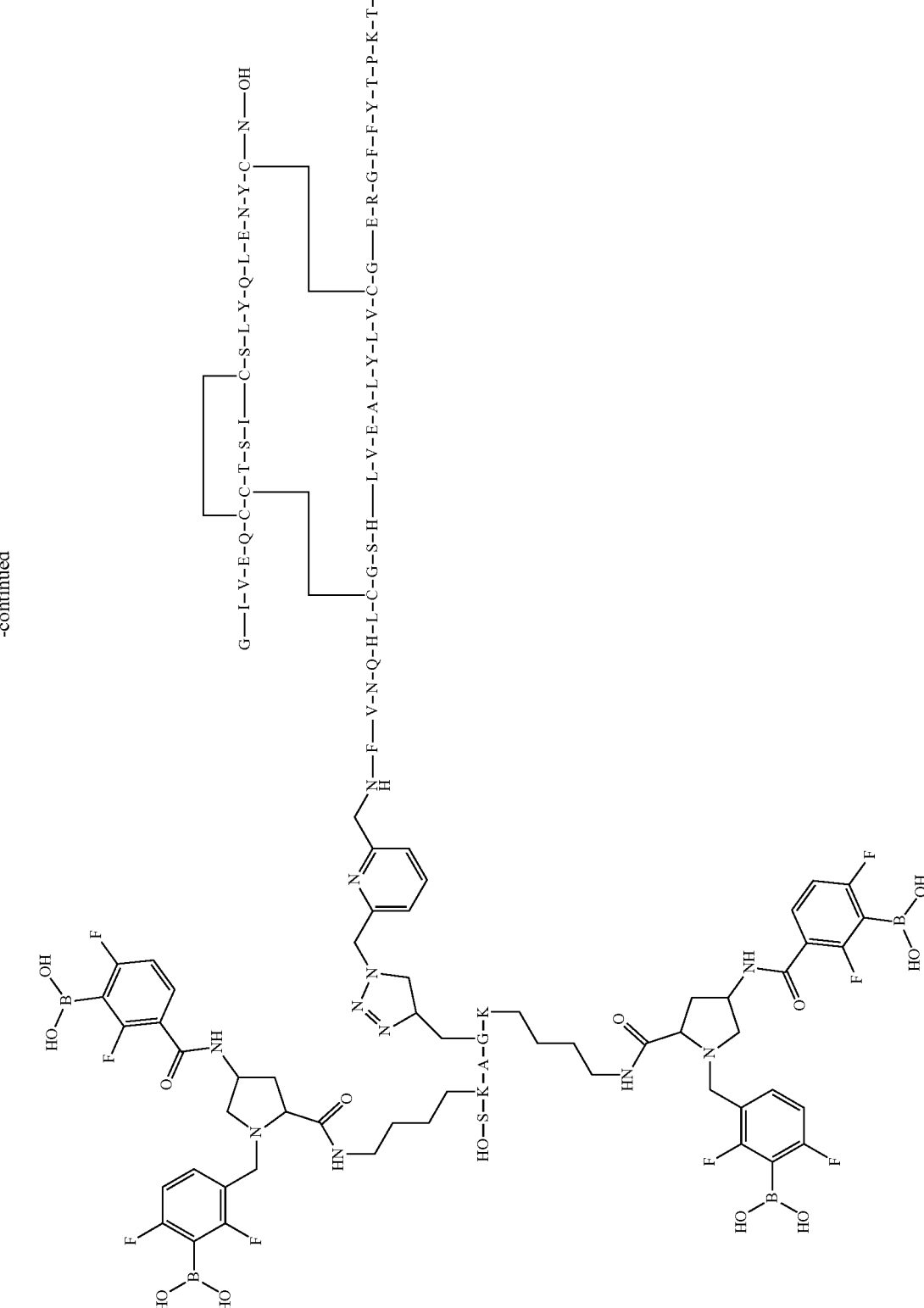

-continued

Example 464

-continued

Example 465

Example 466

-continued
Example 467
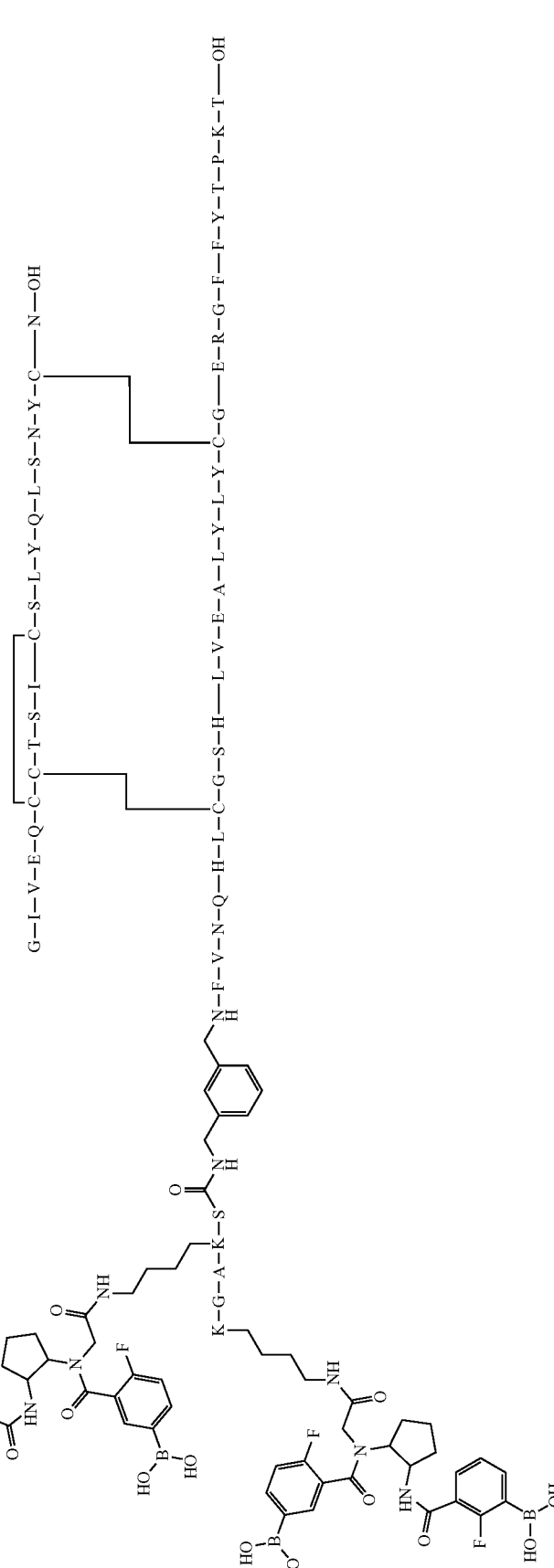

-continued
Example 468
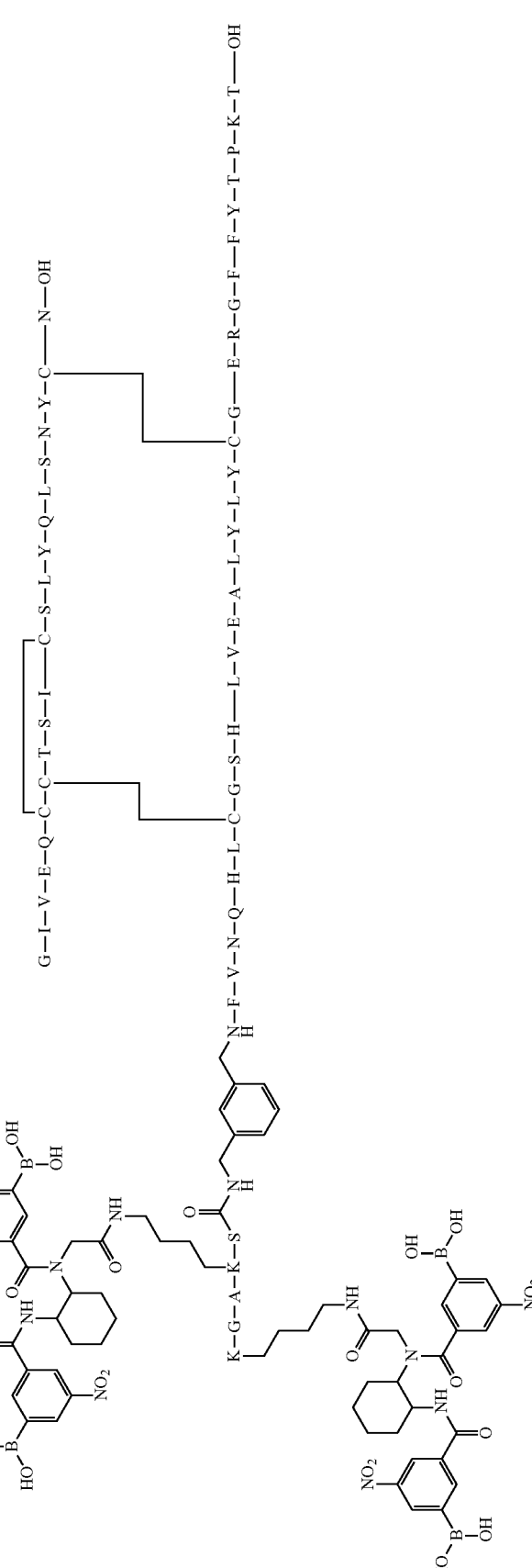

-continued
Example 469
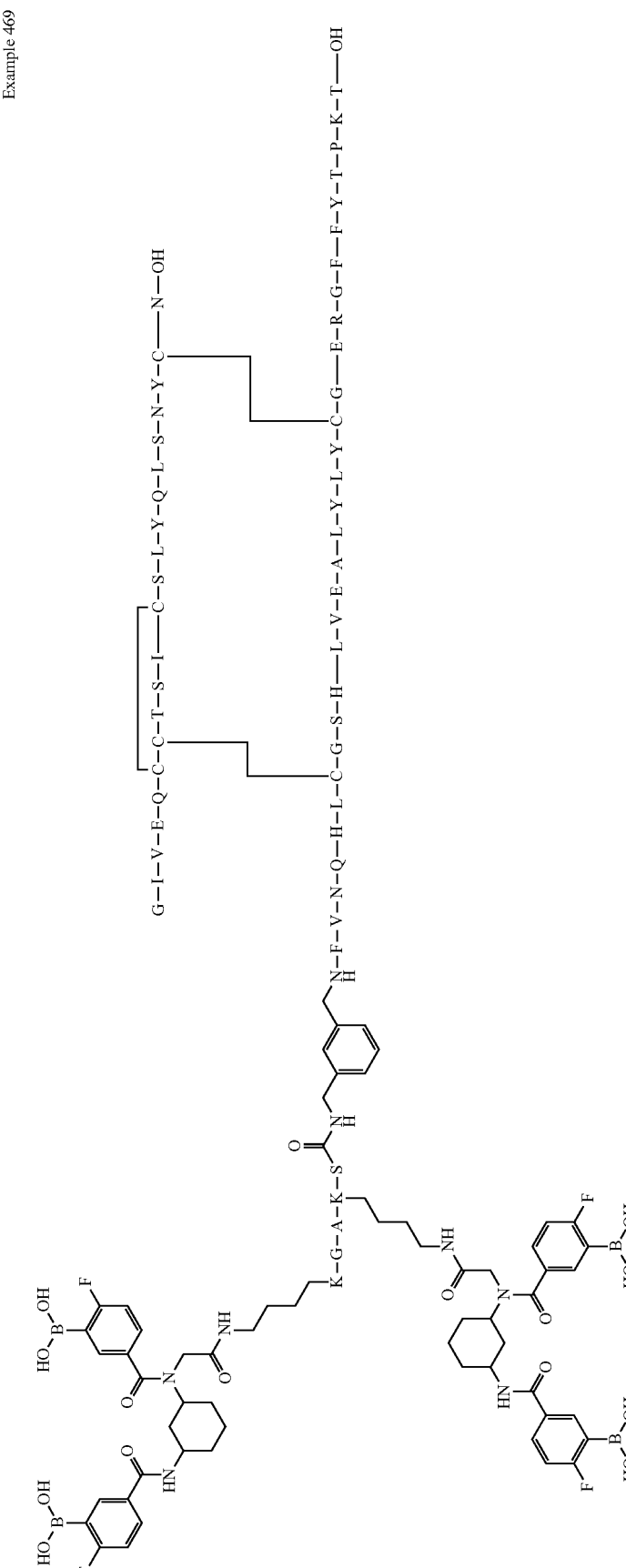

-continued

Example 470

G—I—V—E—Q—C—C—T—S—I—C—S—L—Y—Q—L—S—N—Y—C—N—OH

H—F—V—N—Q—H—L—C—G—S—H—L—V—E—A—L—Y—L—Y—C—G—E—R—G—F—F—Y—T—P—K—T—OH

HO—S—K—A—G—K—K

Example 471

-continued

-continued
Example 472
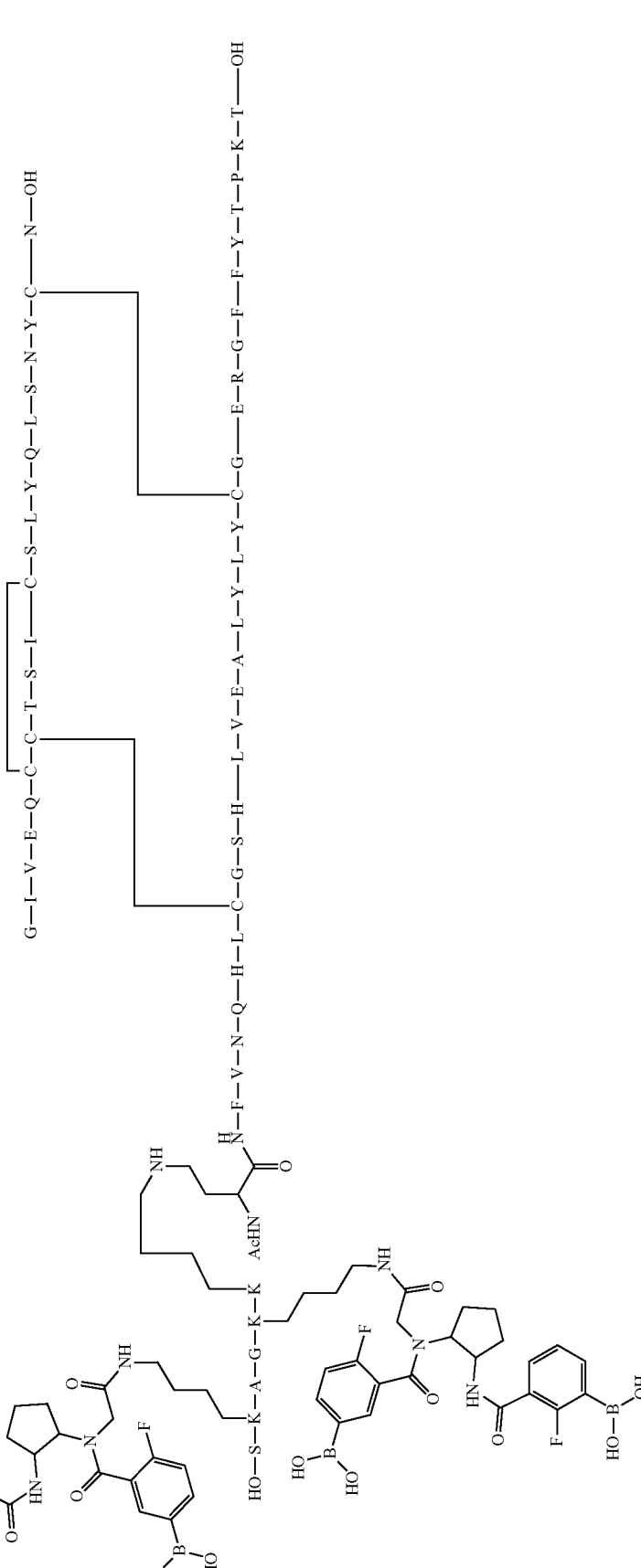

-continued
Example 473
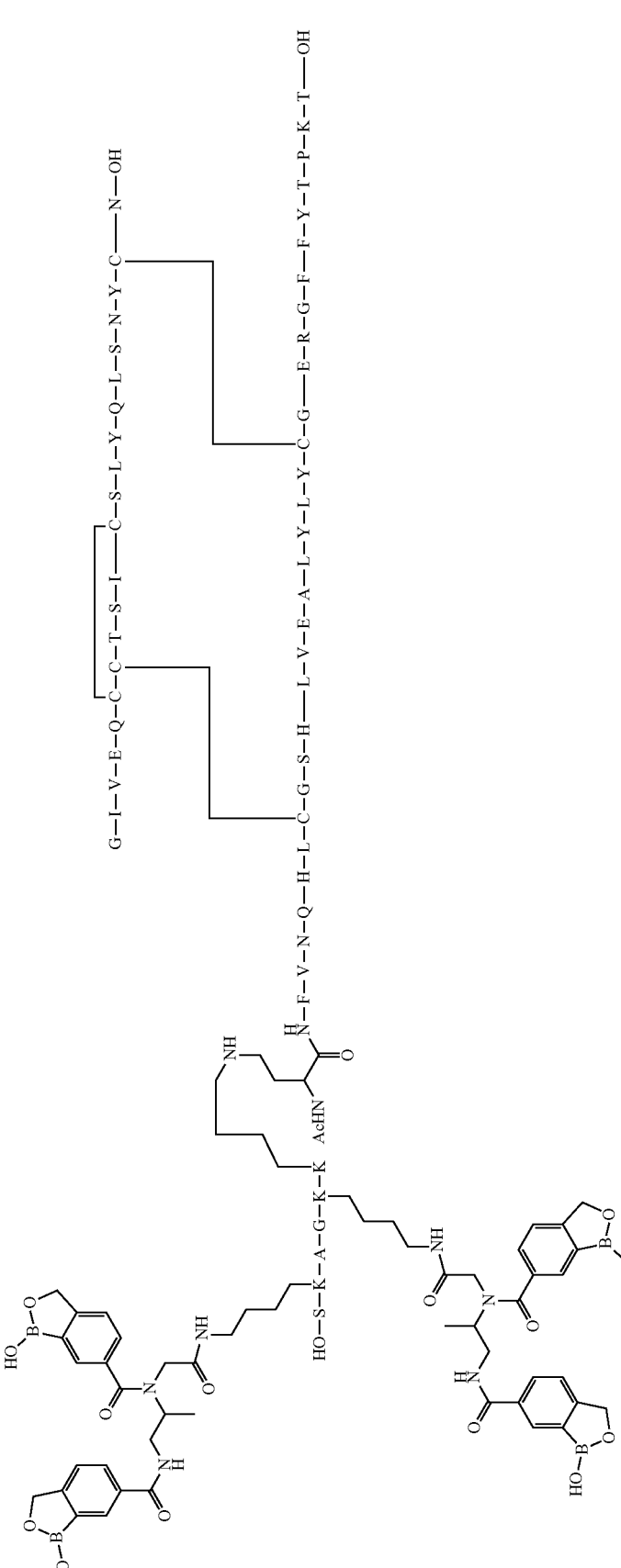

1655                                                                                     1656

-continued

Example 474

-continued
Example 475
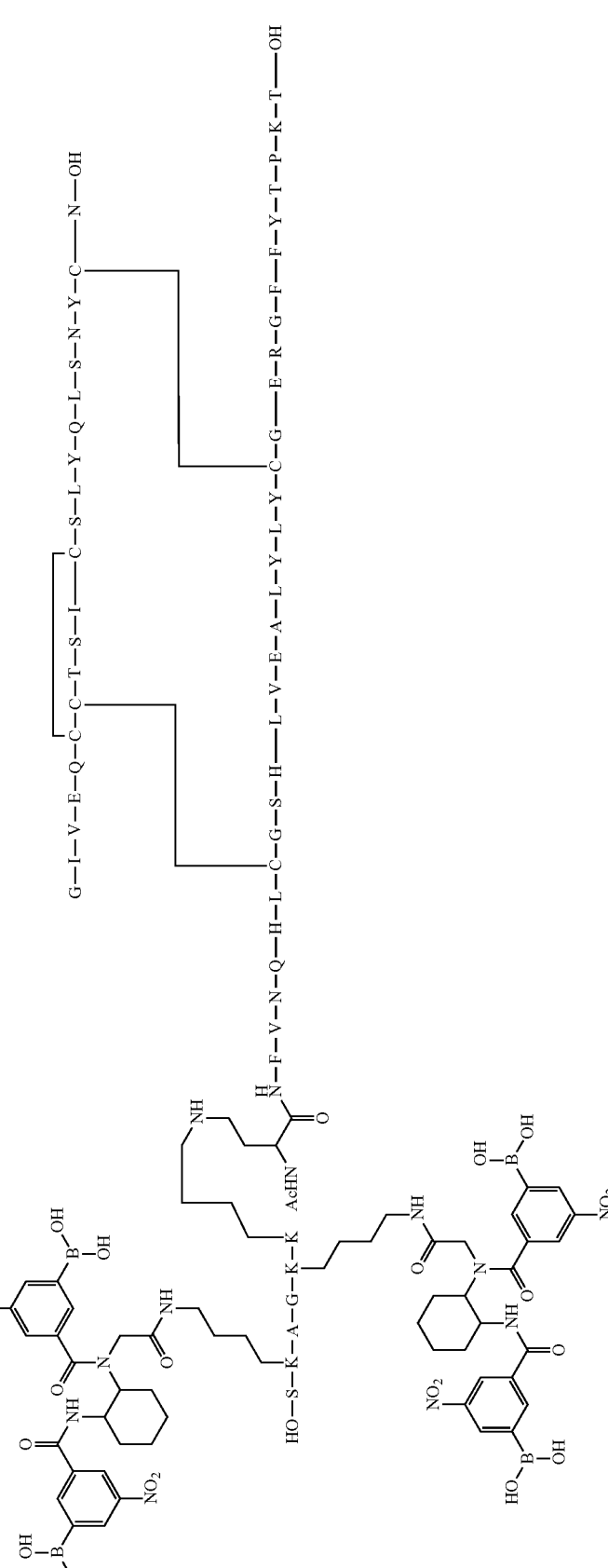

-continued
Example 476
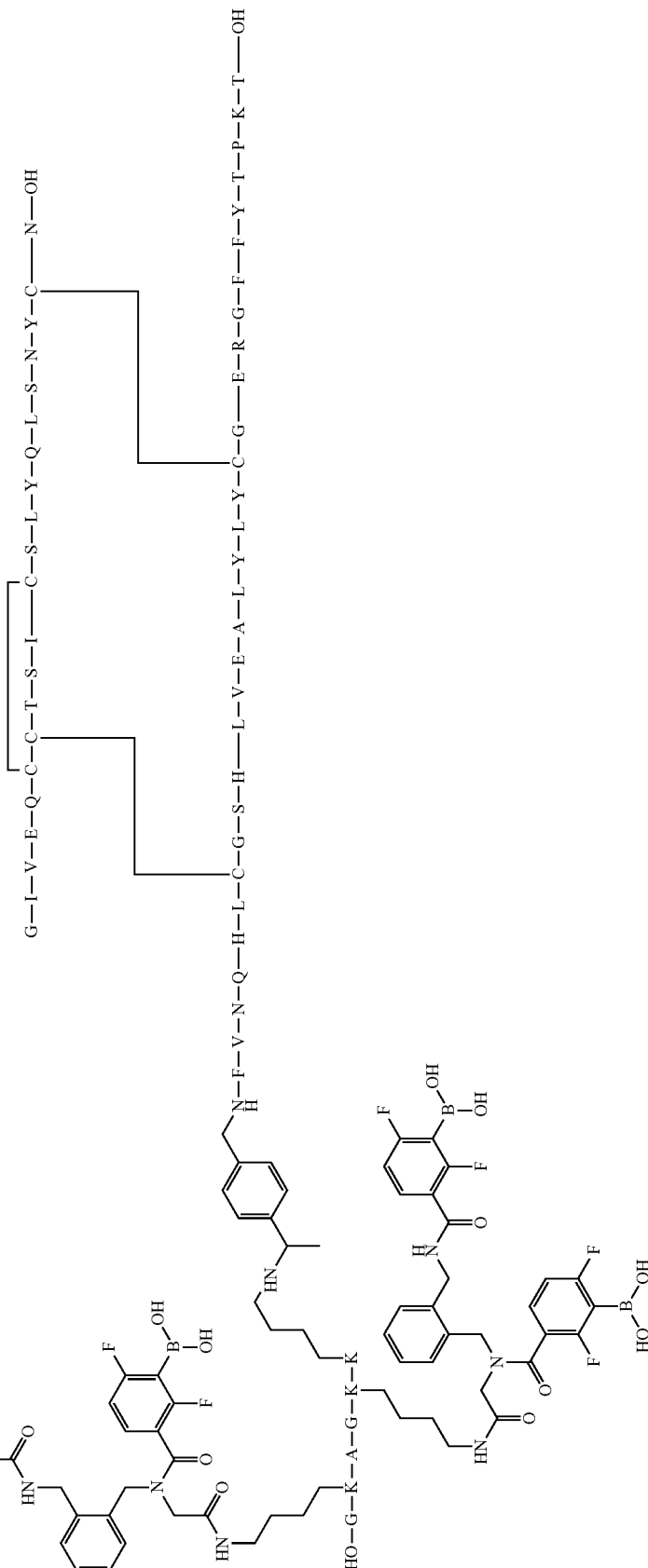

1661    1662
-continued
Example 477
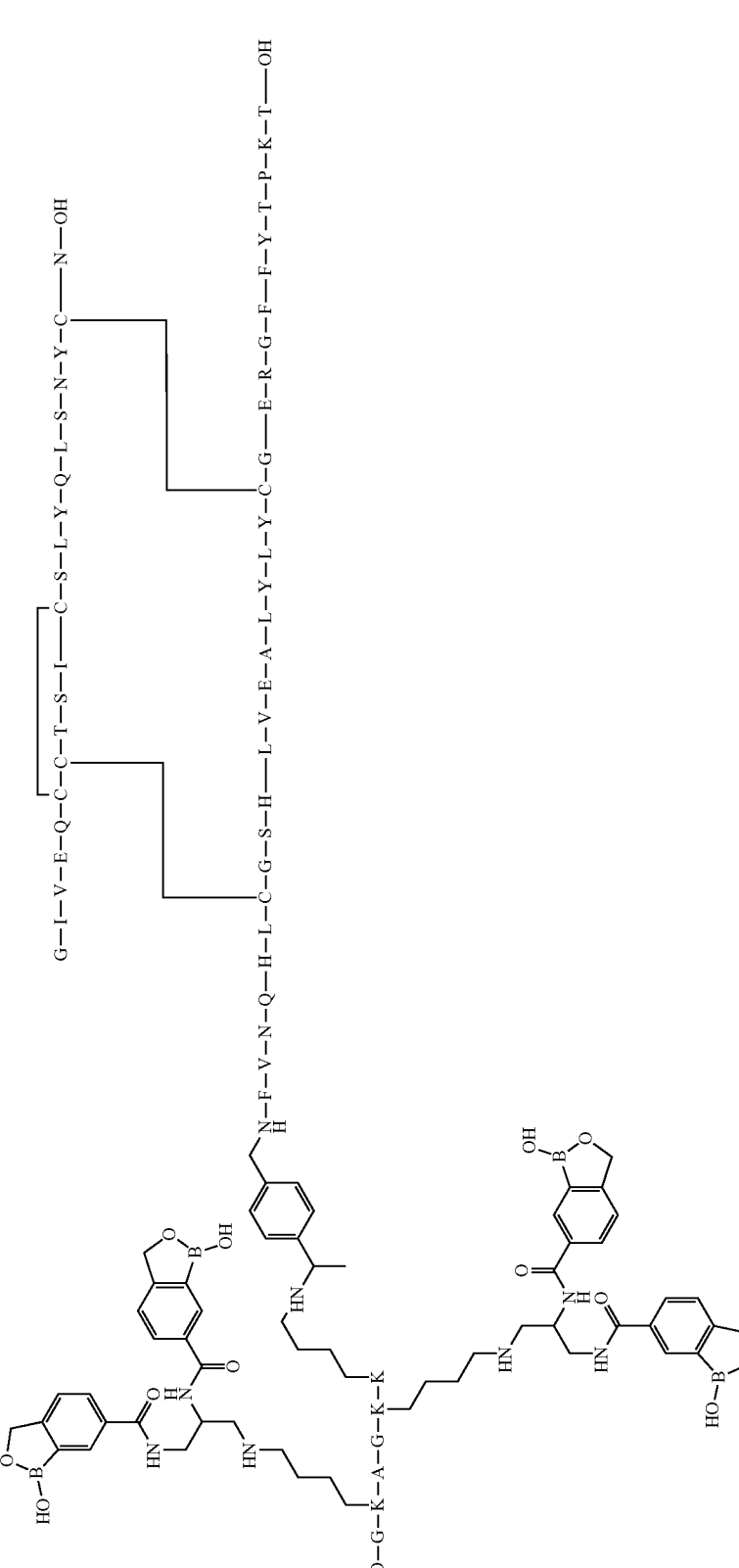

-continued

Example 478

-continued

Example 479

-continued

Example 480

-continued

Example 481

1671 1672

Example 482

-continued
Example 483
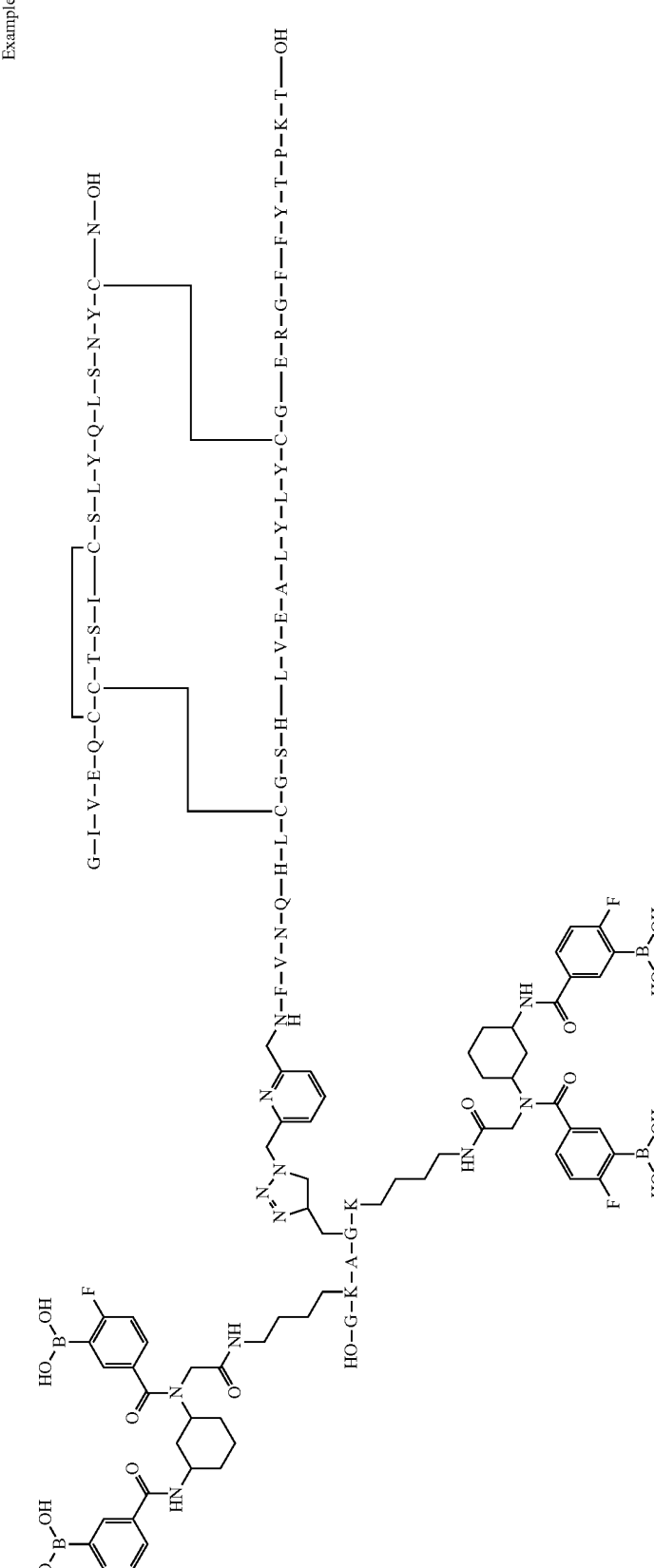

-continued

Example 484

Example 485

-continued

Example 486

G-I-V-E-Q-C-C-T-S-I-C-S-L-Y-Q-L-E-N-Y-C-N—OH

F-V-N-Q-H-L-C-G-S-H-L-V-E-A-L-Y-L-V-C-G-E-R-G-F-F-Y-T-P-K-T—OH

-continued

Example 487

-continued

Example 488

G-I-V-E-Q-C-C-T-S-I-C-S-L-Y-Q-L-E-N-Y-C-N—OH

H—F-V-N-Q-H-L-C-G-S-H-L-V-E-A-L-Y-L-V-C-G-E-R-G-F-F-Y-T-P-K-T—OH

Example 489
-continued
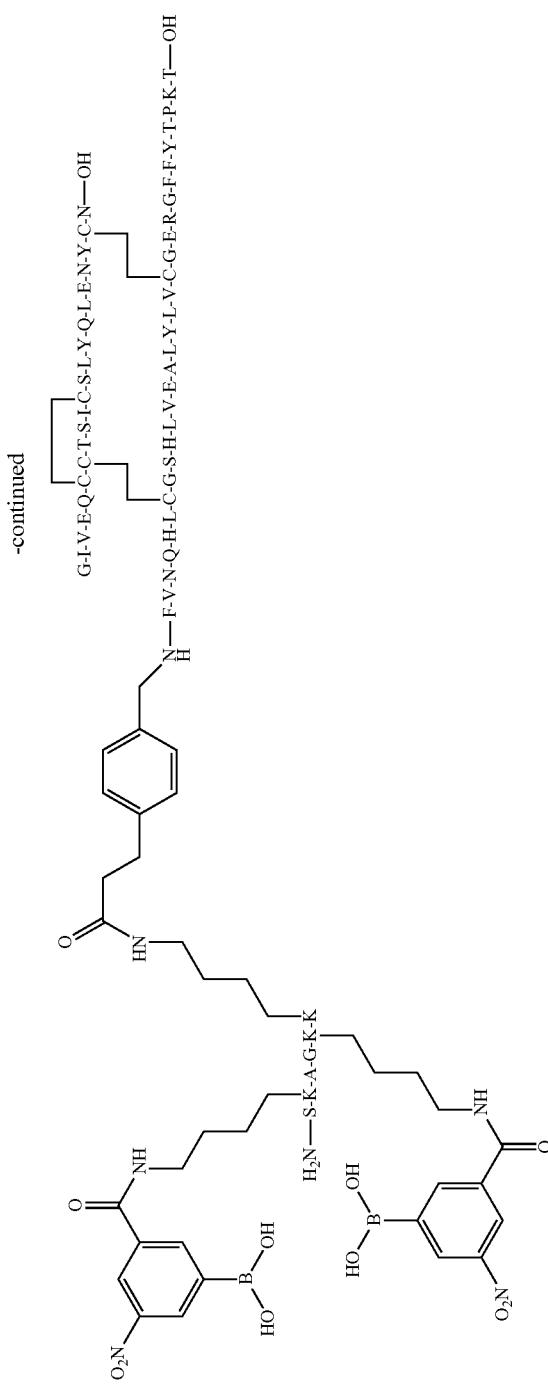

1687                                      1688

Example 490

1689

1690

Example 491

Example 492

-continued

G-I-V-E-Q-C-C-T-S-I-C-S-L-Y-Q-L-E-N-Y-C-N—OH

N—F-V-N-Q-H-L-C-G-S-H-L-V-E-A-L-Y-L-V-C-G-E-R-G-F-F-Y-T-P-K-T—OH

H₂N—S-K-A-G-K-K

HO—B, O, N, NH, HN, OH

Example 493

-continued

G-I-V-E-Q-C-C-T-S-I-C-S-L-Y-Q-L-E-N-Y-C-N—OH

F-V-N-Q-H-L-C-G-S-H-L-V-E-A-L-Y-L-V-C-G-E-R-G-F-F-Y-T-P-K-T—OH

H
N

H₂N—S-K-A-G-K-K

-continued

Example 494

G-I-V-E-Q-C-C-T-S-I-C-S-L-Y-Q-L-E-N-Y-C-N—OH

F-V-N-Q-H-L-C-G-S-H-L-V-E-A-L-Y-L-V-C-G-E-R-G-F-F-Y-T-P-K-T—OH

H₂N—S-K-A-G-K-K

Example 495

-continued

G-I-V-E-Q-C-C-T-S-I-C-S-L-Y-Q-L-E-N-Y-C-N—OH

F-V-N-Q-H-L-C-G-S-H-L-V-E-A-L-Y-L-V-C-G-E-R-G-F-F-Y-T-P-K-T—OH

Example 496

-continued

1701                    1702

Example 497

G-I-V-E-Q-C-C-T-S-I-C-S-L-Y-Q-L-E-N-Y-C—N—OH

N—F-V-N-Q-H-L-C-G-S-H-L-V-E-A-L-Y-L-V-C-G-E-R-G-F-F-Y-T-P-K-T—OH

K-G-A-K-S

-continued

Example 498

G-I-V-E-Q-C-C-T-S-I-C-S-L-Y-Q-L-E-N-Y-C-N—OH

H—F-V-N-Q-H-L-C-G-S-H-L-V-E-A-L-Y-L-V-C-G-E-R-G-F-F-Y-T-P-K-T—OH

Example 499

-continued

G-I-V-E-Q-C-C-T-S-I-C-S-L-Y-Q-L-E-N-Y-C—N—OH

H—F-V-N-Q-H-L-C-G-S-H-L-V-E-A-L-Y-L-V-C-G-E-R-G-F-F-Y-T-P-K-T—OH

1707                                                                 1708

Example 500

-continued

G-I-V-E-Q-C-C-T-S-I-C-S-L-Y-Q-L-E-N-Y-C—N—OH

H—F-V-N-Q-H-L-C-G-S-H-L-V-E-A-L-Y-L-V-C-G-E-R-G-F-F-Y-T-P-K-T—OH

-continued

Example 501

1711

1712

Example 502

-continued

G-I-V-E-Q-C-C-T-S-I-C-S-L-Y-Q-L-E-N-Y-C—N—OH

H—F-V-N-Q-H-L-C-G-S-H-L-V-E-A-L-Y-L-V-C-G-E-R-G-F-F-Y-T-P-K-T—OH $H_2N$—S-K-A-G-K-K

1713  1714

Example 503

-continued

G-I-V-E-Q-C-C-T-S-I-C-S-L-Y-Q-L-E-N-Y-C—N—OH

H—F-V-N-Q-H-L-C-G-S-H-L-V-E-A-L-Y-L-V-C-G-E-R-G-F-F-Y-T-P-K-T—OH

H₂N—S-K-A-G-K-K

Example 504

-continued

G-I-V-E-Q-C-C-T-S-I-C-S-L-Y-Q-L-E-N-Y-C-N—OH

N—F-V-N-Q-H-L-C-G-S-H-L-V-E-A-L-Y-L-V-C-G-E-R-G-F-F-Y-T-P-K-T—OH

HO-S-K-A-G-K-K

-continued

Example 505

G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-T—OH

Example 506

-continued

G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-T—OH

S-K-A-G-K-K 1721                                                                                    1722

Example 507

1723 1724
Example 508
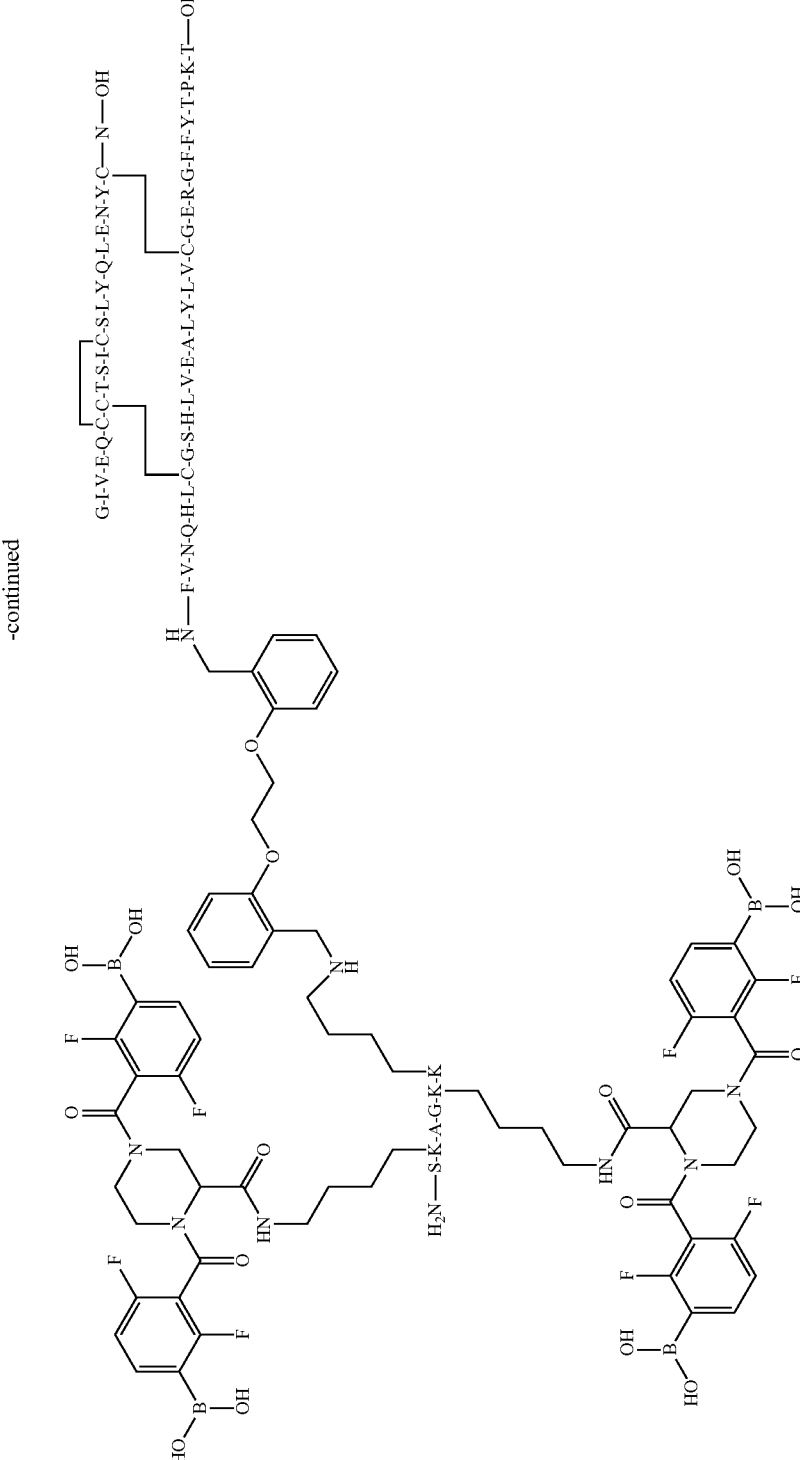

Example 509

-continued

G-I-V-E-Q-C-C-T-S-I-C-S-L-Y-Q-L-E-N-Y-C-N—OH
F-V-N-Q-H-L-C-G-S-H-L-V-E-A-L-Y-L-V-C-G-E-R-G-F-F-Y-T-P-K-T—OH

-continued
Example 510
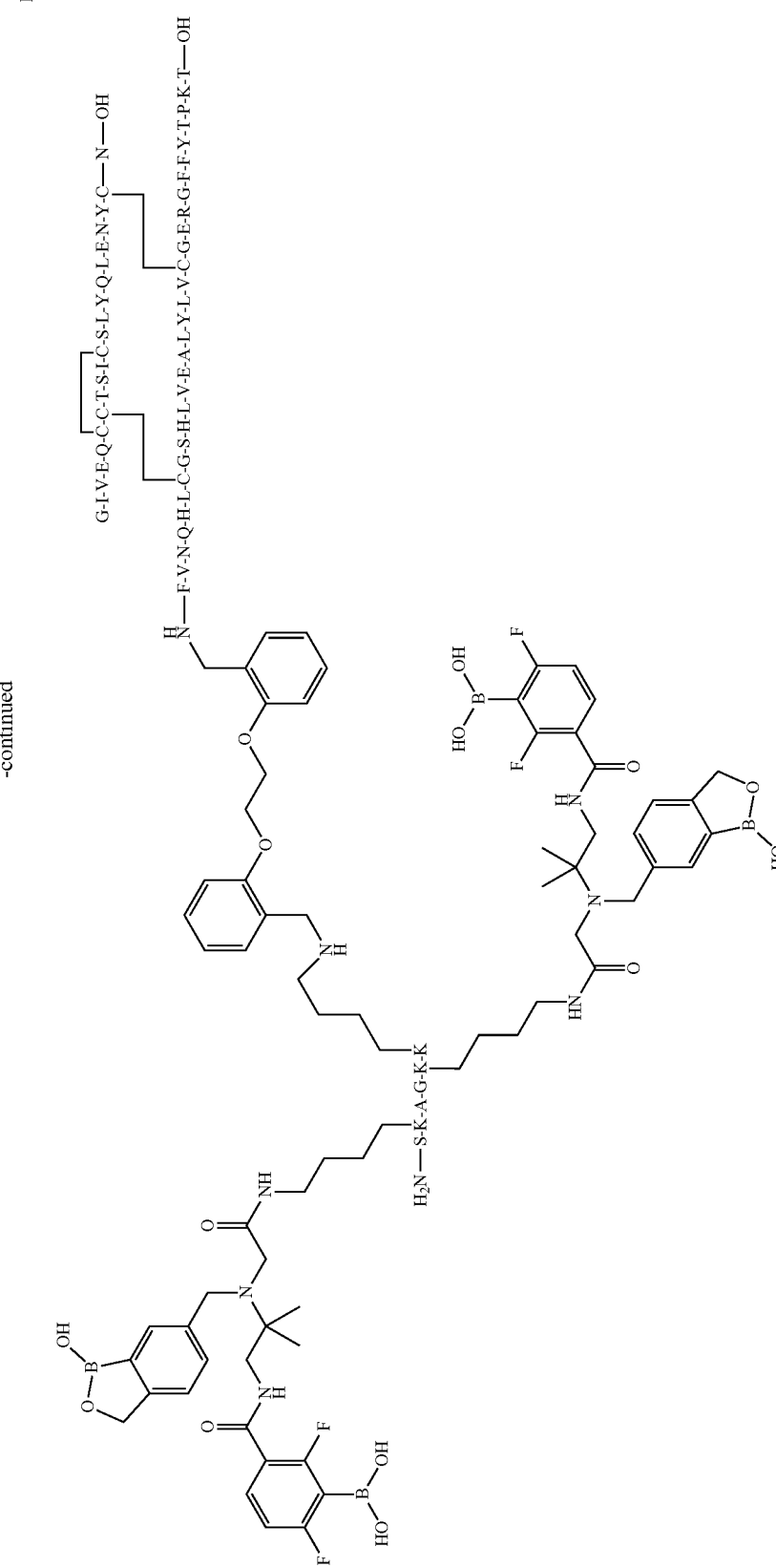

Example 511

-continued

G-I-V-E-Q-C-C-T-S-I-C-S-L-Y-Q-L-E-N-Y-C—N—OH

HN—F-V-N-Q-H-L-C-G-S-H-L-V-E-A-L-Y-L-V-C-G-E-R-G-F-F-Y-T-P-K-T—OH

1731    1732

-continued

Example 512

G-I-V-E-Q-C-C-T-S-I-C-S-L-Y-Q-L-E-N-Y-C—N—OH

N—F-V-N-Q-H-L-C-G-S-H-L-V-E-A-L-Y-L-V-C-G-E-R-G-F-F-Y-T-P-K-T—OH

-continued

Example 513

G-I-V-E-Q-C-C-T-S-I-C-S-L-Y-Q-L-E-N-Y-C—N—OH

H—F-V-N-Q-H-L-C-G-S-H-L-V-E-A-L-Y-L-V-C-G-E-R-G-F-F-Y-T-P-K-T—OH

Example 514

-continued

G-I-V-E-Q-C-C-T-S-I-C-S-L-Y-Q-L-E-N-Y-C—N—OH

F-V-N-Q-H-L-C-G-S-H-L-V-E-A-L-Y-L-V-C-G-E-R-G-F-F-Y-T-P-K-T—OH

K-G-A-K-S

1737

1738

1739

1740

Example 515

Example 516

1741

1742

-continued

Example 517

Example 518

1743

1744

Example 519

Example 520

-continued

-continued

Example 521

Example 522

-continued

Example 523

-continued

Example 524

-continued

Example 525

-continued

Example 526

-continued

Example 527

-continued

Example 528

1759

1760

Example 529

Example 530

-continued

G—I—V—E—Q—C—C—T—S—I—C—S—L—Y—Q—L—E—N—Y—C—N

N—F—V—N—Q—H—L—C—G—S—H—L—C—G—E—R—G—F—F—Y—T—P—K—T—OH

G—I—V—E—Q—C—C—T—S—I—C—S—L—Y—Q—L—E—N—Y—C—N

N—F—V—N—Q—H—L—C—G—S—H—L—V—E—A—L—Y—L—V—C—G—E—R—G—F—F—Y—T—P—K—T—OH

-continued

Example 531

Example 532

-continued

Example 533

-continued

Example 534

-continued

Example 535

-continued

Example 536

-continued

Example 537

G-I-V-E-Q-C-C-T-S-I-C-S-L-Y-C-L-E-N-Y-C-N—OH

N—F-V-N-Q-H-L-C-G-S-H-L-V-E-A-L-Y-L-V-C-G-E-R-G-F-F-Y-T-P-K-T—OH

1775

1776

Example 538

Example 539

1777

1778

-continued

Example 540

Example 541

-continued

Example 542

Example 543

-continued

-continued

Example 544

-continued

Example 545

-continued

Example 546

-continued

Example 547

-continued

Example 548

1793                                                                    1794

-continued

Example 549

-continued

Example 550

1797                                    1798

Example 551

-continued

Example 552

-continued

1801

1802

Example 553

1803            1804

Example 554

-continued

Example 555

Example 556

-continued

1809                                        1810

Example 557

-continued

Example 558

-continued

1813           1814

-continued

Example 559

-continued

Example 560

Example 561

-continued

Example 562

H—G—I—V—E—Q—C—C—T—S—I—C—S—

F—V—N—Q—H—L—C—G—S—

—L—Y—Q—L—E—N—Y—C—N—OH

—H—L—V—E—A—L—Y—L—V—C—G

R—G—F—F—Y—T—P—R—T—OH

1821                                                                    1822

-continued

Example 563

H—G—I—V—E—Q—C—C—T—S—I—C—S—

H—G—N—G—S—H—F—V—N—Q—H—L—C—G—S—

—L—Y—Q—L—E—N—Y—C—N—OH

—H—L—V—E—A—L—Y—L—V—C—G—R—G—F—F—Y—T—P—R—T—OH

-continued

Example 564

1825                                                                                     1826

Example 565

1827 1828

Example 566

-continued

Example 567

-continued

Example 568

-continued

Example 569

H–G–I–V–E–Q–C–C–T–S–I–C–S—

F–V–N–Q–H–L–C–G–S—

—L–Y–Q–L–E–N–Y–C–N–OH

—H–L–V–E–A–L–Y–L–V–C–G

R–G–F–F–Y–T–P–K–T–OH

-continued

Example 570

-continued

Example 571

-continued

Example 572

Example 573

1843
1844

-continued

Example 574

H—G-I-V-E-Q-C-C-T-S-I—C-S-L-Y-Q-L-E-N-Y-C—N—OH

F-V-N-Q-H-L—C-G-S-H-L-V-E-A-L-Y—L-V-C-G-E-R-G-F-F-Y—T-P—

H—G—

1845

1846

Example 575

-continued

Example 576

1849                                                    1850

Example 577

-continued

Example 578

-continued 1853                                    1854

-continued

Example 579

H—F-V-N-Q-H-L-C-G-S-H—L-V-E-A-L-Y-L-V-C-G—E-R-G-F-F-Y-T-P

G-I-V-E-Q-C-C-T-S-I—C-S-L-Y-Q-L-E-N-Y-C—N—OH

L-W-A-V

Example 580

-continued

G-I-V-E-Q-C-C-T-S-I-C-S-L-Y-Q-L-E-N-Y-C-N—OH

H—F-V-N-Q-H-L-C-G-S-H—L-V-E-A-L-Y-L-V-C-G—E-R-G-F-F-Y-T-P-

L-W-A-V-

1857                                          1858

Example 581

Example 582

1861

1862

Example 583

Example 584

-continued

-continued

Example 585

-continued

Example 586

-continued

Example 587

H—G-I-V-E-Q-C-C-T-S-I—C-S-L-Y-Q-L-E-N-Y-C—N—OH

F-V-N-Q-H-L-C-G-S-H—L-V-E-A-L-Y-L-V-C-G—E-R-G-F-F-Y-T-P—T-OH

G-A-R-L

-continued

Example 588

Example 589

-continued

Example 590

-continued

1877

1878

-continued

Example 591

Example 592

-continued

-continued

Example 593

1883

1884

Example 594

H—G-I-V-E-Q-C-C-T-S-I—C-S-L-Y-Q-L-E-N-Y-C-N—OH

F-V-N-Q-H-L-C-G-S-H-L-V-E-A-L-Y-L-V-C-G-E-R-G-F-F-Y-T-P 1885                                                1886

Example 595

-continued

1887          1888

Example 596

1889                                                                1890

Example 597

-continued

1891                                                1892

Example 598

-continued 1893                                                                1894

Example 599

-continued

1895                                                                                    1896

Example 600

-continued

1897

1898

Example 601

H—G—I—V—E—Q—C—C—T—S—I—C—S—L—Y—Q—L—E—N—Y—C—N—OH

H—F—V—N—Q—H—L—C—G—S—H—L—V—E—A—L—Y—L—V—C—G—E—R—G—F—F—Y—T—P

T—L—N—OH

1899

1900

Example 602

-continued

1901                                                        1902

Example 603

H—G-I-V-E-Q-C-C-T-S-I—C-S-L-Y-Q-L-E-N-Y-C—N—OH

H—A-D             T-L-N—F-V-N-Q-H-L-C-G-S-H—L-V-E-A-L-Y-L-V-C-G——

1903                     1904

-continued

Example 604

-continued

Example 605

-continued

Example 606

H—G-I-V-E-Q-C-C-T-S-I—C-S-L-Y-Q-L-E-N-Y-C—N—OH

—C-G-S-H-L-V-E-A-L-Y—L-V-C-G

R-G-F-F-Y—T-P-K-T—OH

-continued

Example 607

1911      1912

-continued

Example 608

Peptide sequences shown in structure 1911:

F-V-N-Q-H-L

N-S-T

Peptide sequences shown in structure 1912:

H—G-I-V-E-Q-C-C-T-S-I—C-S-L-Y-Q-L-E-N-Y-C—N—OH

—C-G-S-H-L-V-E-A-L-Y—L-V-C-G—N

R-G-F-F-Y—T-P-R-T—OH

-continued

Example 609

-continued

Example 610

1917

1918

Eample 611

-continued

Example 612

1921                                               1922

-continued

Example 613

1923                                          1924

Example 614

-continued

1927  1928

Example 615

1929  1930

Example 616

-continued 1931         1932

Example 617

-continued

T-L-N-OH

H—F-V-N-Q-H-L-C-G-S-H——L-V-E-A-L-Y-L-V-C-G—E-R-G-F-F-Y-T-P

H—G-I-V-E-Q-C-C-T-S-I——C-S-L-Y-Q-L-E-N-Y-C—N-A-D 1933                                                    1934

Example 618

1935

1936

Example 619

-continued

1937    1938

Example 620

-continued

H—G—I—V—E—Q—C—C—T—S—I—C—S—L—Y—Q—L—E—N—Y—C—N—OH

T—L—N—F—V—N—Q—H—L—C—G—S—H—L—V—E—A—L—Y—L—V—C—G—E—R—G—F—F—Y—T—P

1939                                         1940

Example 621

-continued

1941                                    1942

Example 622

1943                                                    1944

-continued

Example 623

-continued

Example 624

-continued

Example 625

1949                                                                                  1950

-continued

Example 626

H—G—I—V—E—Q—C—C—T—S—I—C—S—L—Y—Q—L—E—N—Y—C—N

F—V—N—Q—H—L—C—G—S—H—L—V—E—A—L—Y—L—V—C—G—E—R—G—F—F—Y—T—P—R—T—OH 1951                                                          1952

-continued

Example 627

1953

1954

1955 1956

Example 628

-continued

Example 629

-continued

Example 630

1961

1962

Example 631

-continued

Example 632

1965  1966

1967

1968

Example 633

-continued

Example 634

Example 635

-continued

1973
1974

Example 636

-continued

1975 1976

-continued

Example 637

Example 638

-continued

Example 639

1981 1982

Example 640

-continued

1983        1984

-continued

Example 641

Example 642

-continued

-continued

Example 643

1989                    1990

Example 644

Example 645

-continued

H-G-I-V-E-Q-C-C-T-S-I-C-S-L-Y-Q-L-E-N-Y-C-N

A-G-F-V-N-Q-H-L-C-G-S-H-L-V-E-A-L-Y-L-V-C-G-E-R-G-F-F-Y-T-P-R-T-OH

Example 646

-continued

-continued

Example 647

-continued

Example 648

-continued

Example 649

2001

2002

Example 650

2003                                    2004

Example 651

2005                                            2006

-continued

Example 652

-continued

2009                                                                 2010

-continued

2011                                                                                                 2012

-continued

Example 653

G—I—V—E—Q—C—C—T—S—I—C—S—L—Y—Q—L—E—N—Y—C—N—OH

2013                                        2014

-continued

Example 654

2017                                                        2018

-continued

2019

2020

Example 655

2021                                                                    2022

Example 656

-continued

Example 657

-continued

Example 658

H—G—I—V—E—Q—C—C—T—S—I—C—S—L—Y—Q—L—E—N—Y—C—N—OH

F—V—N—Q—H—L—C—G—S—H—L—V—E—A—L—Y—L—V—C—G—E—R—G—F—F—Y—T—P—R—T—OH

-continued

Example 659

H—F—V—N—Q—H—L—C—G—S—H—L—V—E—A—L—Y—L—V—C—G—E—R—G—F—F—Y—T—P—R—T—OH

G—I—V—E—Q—C—C—T—S—I—C—S—L—Y—Q—L—E—N—Y—C—N—OH 2029                                                      2030

Example 660

-continued

2031

2032

Example 661

-continued

Example 662

2035                                   2036

Example 663

Example 664

-continued

H-G-I-V-E-Q-C-C-T-S-I-C-S-L-Y-Q-L-E-N-Y-C-N

A-G-F-V-N-Q-H-L-C-G-S-H-L-V-E-L-Y-L-V-C-G-E-R-G-F-F-Y-T-P-R-OH

-continued

Example 665

2041

2042

Example 666

-continued

2043

2044

Example 667

2045

2046

-continued

Example 668

G-I-V-E-Q-C-C-Y-S-I-C-S-L-Y-Q-L-E-N-Y-C-N-OH

H-F-V-N-Q-H-L-C-G-S-H-L-V-E-A-L-Y-L-V-C-G-E-R-G-F-F-Y-T-P-R-T-OH

F-I-F

2047

2048

Example 669

-continued

H-G-I-V-E-Q-C-C-Y-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-R-T-OH

F-I-F

-continued

Example 670

H-G-I-V-E-Q-C-C-Y-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P

F-I-F

T-OH

2051                                        2052

Example 671

H-F-V-N-Q-H-L-C-Q-S-H-L-V-E-A-L-Y-L-V-C-G-E-R-G-F-F-Y-T-P-

G-I-V-E-Q-C-C-Y-S-I-C-S-L-Y-Q-L-E-N-Y-C-N-OH

T-OH

2053　　　　　　　　　　　　　　　2054

Example 672

-continued

H-G-I-V-E-Q-C-C-Y-S-I-C-S-L-Y-Q-L-E-N-Y-C-N-OH

H-F-V-N-Q-H-L-C-G-S-H-L-V-E-A-L-Y-L-V-C-G-E-R-G-F-F-Y-T-P

2055  2056

-continued

Example 673

Peptide sequence labels visible in structure:

F-I-F-T-OH

H-F-V-N-Q-H-L-C-G-S-H-L-V-E-A-L-Y-L-V-C-G-E-R-G-F-F-Y-T-P

G-I-V-E-Q-C-C-T-S-I-C-S-L-Y-Q-L-E-N-Y-C-N-OH

H₂N-

2057 2058

Example 674

2059 2060

Example 675

-continued

H-F-V-N-Q-H-L-C-G-S-H—L-V-E-A-L-Y-L-V-C-G—E-R-G-F-F-Y-T-P-

G-V-E-Q-C-C-T-S-I-C——S-L-Y-Q-L-E-N-Y-C-N-OH

Example 676

-continued

-continued

Example 677

2065

2066

-continued

Example 678

2067

2068

Example 679

-continued

2069

2070

Example 680

2071

2072

-continued

Example 681

-continued

Example 682

2075

2076

Example 683

-continued

Example 684

-continued

-continued

Example 685

Example 686

-continued

L-L-OH

Y-C-N-D

C-G-E-R-G-F-F-Y-T-P-R-T-OH

S-I-C-S-L-Y-Q-L-E-N

S-H-L-V-E-A-L-Y-L-V

L-L-V-E-Q-C-C-T

H-D-N

L-L-N-Q-H-L-C-G

H-D-N 2083           2084

Example 687

H—F-V-N-Q-H-L-C-G-S-H-L-V-E-A-L-Y-L-V-C-G-E-R-G-F-F-Y-T-P

H—D-N-I-G-I-V-E-Q-C-C-T-S-I-C-S-L-Y-Q-L-E-N-Y-C-N—OH

L-L-D

Example 688

H—G-I-V-E-Q-C-C-T-S-I-C-S-L-Y-Q-L-E-N-Y-C-N-D

H—F-V-N-Q-H-L-C-G-S-H-L-V-E-A-L-Y-L-V-C-G-E-R-G-F-F-Y-T-P

L-L-D

N-I—OH

2085

2086

-continued

Example 689

H—G-I-V-E-Q-C-C-T-S-I-C-S-L-Y-Q-L-E-N-Y-C-N—OH

—N-I-F-V-N-Q-H-L-C-G-S-H-L-V-E-A-L-Y-L-V-C-G-E-R-G-F-F-Y-T-P—NH

T—OH

2087                                                                                                  2088

Example 690

2089

2090

Example 691

2091

2092

Example 692

Example 693

2093                                                                 2094

-continued

Example 694

-continued

Example 695

H—G-I-V-E-Q-C-C-T-S-I-C-S-L-Y-Q-L-E-N-Y-C-N-D

H—D

L-L-N-Q-H-L-C-G-S-H-L-V-E-A-L-Y-L-V-C-G-E-R-G-F-F-Y-T-P

N-I—OH

T—OH

Example 696

2097

2098

-continued

H—G-I-V-E-Q-C-C-T-S-I-C-S-L-Y-Q-L-E-N-Y-C-N-D

L-L-F-V-N-Q-H-L-C-G-S-H-L-V-E-A-L-Y-L-V-C-G-E-R-G-F-F-Y-T-P

2099

2100

Example 697

2101

2102

Example 698

2103                                                    2104

Example 699

2105

2106

Example 700

-continued

2107

2108

Example 701

2109                                                                              2110

Example 702

Example 703

-continued

H-F-V-N-Q-H-L-C-G-S-H-L-V-E-A-L-Y-L-V-C-G-E-R-G-F-F-Y-T-P

H-D-H-L-L-G-I-V-E-Q-C-C-T-S-I-C-S-L-Y-Q-L-E-N-Y-C-N-OH 2113                                                                           2114

Example 704

H—G-I-V-E-Q-C-C-T-S-I-C-S-L-Y-Q-L-E-N-Y-C-N-D

L-L-F-V-N-Q-H-L-C-G-S-H-L-V-E-A-L-Y-L-V-C-G-E-R-G-F-F-Y-T-P-R-T—OH

L-L—OH

2115                    2116

Example 705

-continued

L-L-G-I-V-E-Q-C-C-T-S-I-C-S-L-Y-Q-L-E-N-Y-C-N-D

L-L-F-V-N-Q-H-L-C-G-S-H-L-V-E-A-L-Y-L-V-C-G-E-R-G-F-F-Y-T-P

T—OH

L-L—OH

H—D

H—D

2117

2118

Example 706

2119

2120

Example 707

2121          2122

Example 708

-continued 2123          2124

Example 709

2125                                           2126

Example 710

—G-I-V-E—Q-C-C-T-S-I-C-S-L-Y—Q-L-E-N-Y-C-N—OH

H—F-V-N-Q-H-L-C-G-S-H—L-V-E-A-L-Y-L-V-C-G—E-R-G-F-F-Y-T-P—N-H—T—OH

2127                                                                 2128

Example 711

2129                                                                                          2130

—G-I-V-E—Q-C-C-T-S-I-C-S-L-Y—Q-L-E-N-Y-C-N—OH

H—F-V-N-Q-H-L-C-G-S-H—L-V-E-A-L-Y-L-V-C-G—E-R-G-F-F-Y-T-P—N

Example 712

2131　　　　　　　　　　　　　　　　　　　　　　　　　2132

—I-V-E-Q—C-C-T-S-I-C-S-L-Y-Q—L-E-N-Y-C-N—OH

H—F-V-N-Q-H-L-C-G-S-H—L-V-E-A-L-Y-L-V-C-G—E-R-G-F-F-Y-T-P—N-H—T—OH 2133                                                          2134

-continued

Example 713

2135

2136

-continued

H—G-I-V-E—Q-C-C-T-S-I-C-S-L-Y—Q-L-E-N-Y-C-N—OH

—F-V-N-Q-H-L-C-G-S-H—L-V-E-A-L-Y-L-V-C-G—E-R-G-F-F-Y-T-P—T-OH

-continued

Example 714

—V-E-Q-C——C-T-S-I-C-S-L-Y-Q-L——E-N-Y-C-N——OH

H—F-V-N-Q-H-L-C-G-S-H——L-V-E-A-L-Y-L-V-C-G——E-R-G-F-F-Y-T-P——N——T—OH

2139

2140

-continued

Example 715

2141

2142

-continued

Example 716

H—G-I-V-E-Q-C-C-T-S-I-C-S-L-Y-Q-L-E-N-Y-C—N—OH

H—G—N—P-A-R—N—V-N-Q-H-L-C-G-S-H-L-V-E-A-L-Y-L-V-C-G-E-R-G-F-F-Y-T-P—N—T-OH

-continued

Example 717

Example 718

2145

2146

-continued

Example 719

-continued

Example 720

H—G-I-V-E-Q-C-C-T-S-I-C-S-L-Y-Q-L-E-N-Y-C—N—OH

H—G—N—...—P-A-R—N—F-V-N-Q-H-L-C-G-S-H-L-V-E-A-L-Y-L-V-C-G-E-R-G-F-F-Y-T-P-R-T—OH

Example 721

H₂N—G-E-G-I-V-E-Q-C-C-T-S-I-C-S-L-Y-Q-L-E-N-Y-C—N—OH

H—F-V-N-Q-H-L-C-G-S-H-L-V-E-A-L-Y-L-V-C-G-E-R-G-F-F-Y-T-P—N—...—T—OH

2149

2150

-continued

Example 722

2151                                                                    2152

Example 723

Example 724

2153  2154

-continued

Example 725

2155        2156

-continued

Example 726

2157

2158

-continued

Example 728

2161 2162

Example 729

-continued

Example 730

-continued 2165 2166

-continued

Example 731

-continued

Example 732

-continued

Example 733

2171      2172

Example 734

Example 735

-continued

-continued

Example 735

2177

2178

Example 737

2179                                                                                          2180

Example 738

H–F–V–N–Q–H–L–C–G–S–H–L–V–E–A–L–Y–L–V–C–G–E–R–G–F–F–Y–T–P–K–T–OH

2181

2182

-continued

Example 739

2183                                                                 2184

-continued

-continued

Example 740

-continued

-continued

Example 741

2191

2192

-continued

-continued
Example 742
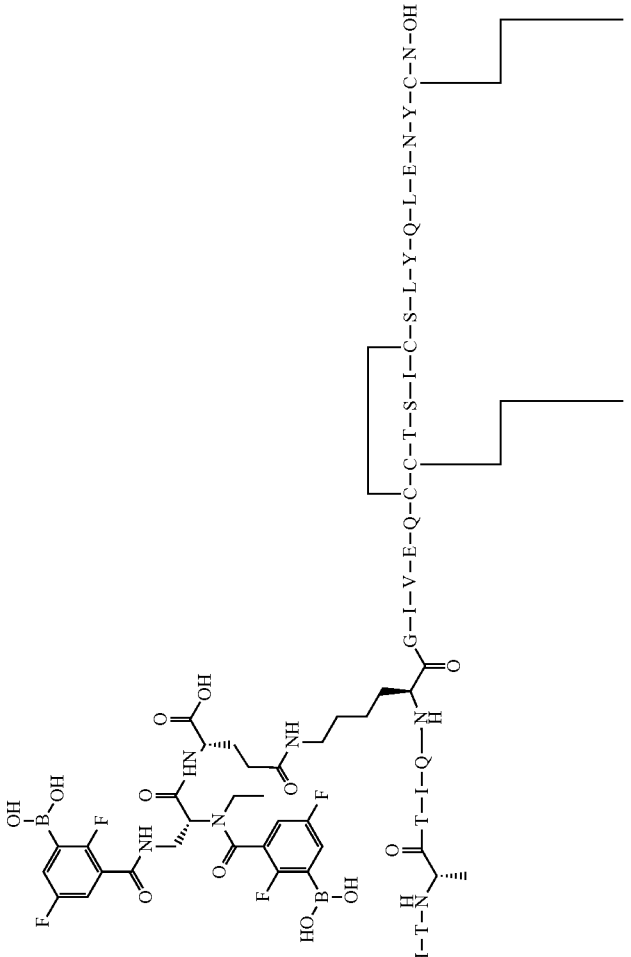

2195
2196
-continued
H—F—V—N—Q—H—L—C—G—S—H—L—V—E—A—L—Y—L—V—C—G—E—N
H—G—I—V—E—Q—C—C—T—S—I—C—S—L—Y—Q—L—E—N—Y—C—N—OH
G—F—F—Y—T—P—K—T—OH
Example 743
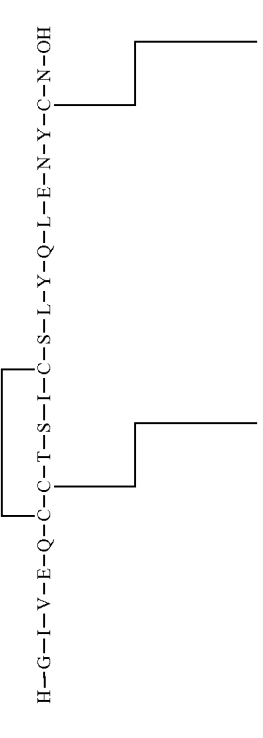

-continued

-continued

Example 744

2201　　　　　　　　　　　　　　　2202

-continued

Example 745

Example 746

-continued

Example 747

-continued

2209

2210

Example 748

2211

2212

Example 749

2213                                                                 2214

Example 750

2215

2216

Example 751

2217 2218

Example 752

2219

2220

2221

2222

-continued

Example 753

H—G-I-V-E-Q-C-C-T-S-I—C-S-L-Y-Q-L-E-N-Y-C—N—OH

F-V-N-Q-H-L-C-G-S-H—L-V-E-A-L-Y-L-V-C-G—E-R-G-F-F-Y-T-P-R-T—OH

P-A-E

H—G

2223

2224

2225                                                        2226

Example 754

2227

2228

-continued 2229                                            2230

Example 755

-continued

2231                                        2232

-continued

2233                                                2234

Example 756

2235
2236

Example 757

-continued 2237            2238

Example 758

-continued

2239

2240

Example 759

2241

2242

Example 760

-continued

-continued

Example 761

2245

2246

Example 762

2247 2248

Example 763

2249

2250

Example 764

2251 2252

-continued

Example 765

H—F-V-N-Q-H-L-C-G-S-H-L-V-E-A-L-Y-L-V-C-G-E-R-G-F-F-Y-T-P

A-E-G-I-V-E-Q-C-C-T-S-I-C-S-L-V-Q-L-E-N-Y-C—N—OH

2253                                                                 2254

-continued

Example 766

2255

2256

Example 767

-continued

2257

2258

Example 768

-continued

H—G-I-V-E-Q-C-C-T-S-I-C-S-L-V-Q-L-E-N-Y-C—N—OH

F-V-N-Q-H-L-C-G-S-H-L-V-E-A-L-Y-L-V-C-G-E-R-G-F-F-Y-T-P

E-E-S 2259 2260

Example 769

-continued

H—G-I-V-E-Q-C-C-T-S-I-C-S-L-V-Q-L-E-N-Y-C—N—OH

F-V-N-Q-H-L-C-G-S-H-L-V-E-A-L-Y-L-V-C-G-E-R-G-F-F-Y-T-P-R-T-OH

E-E-S

2261

2262

Example 770

H—F-V-N-Q-H-L-C-G-S-H-L-V-E-A-L-Y-L-V-C-G-E-R-G-F-F-Y-T-P-R-T—OH

G-I-V-E-Q-C-C-T-S-I-C-S-L-Y-Q-L-E-N-Y-C-N—OH

-continued

Example 771

2265                                          2266

Example 772

2267      2268

Example 773

H–F–V–N–Q–H–L–C–G–S–H–L–V–E–A–L–Y–L–V–C–G–E–R–G–F–F–Y–T–P

G–V–E–Q–C–C–T–S–I–C—S–L–Y–Q–L–E–N–Y–C–N–OH

2269

2270

Example 774

Example 775

-continued

E-E-G-I-V-E-Q-C-C-T—S-I-C-S-L-Y-Q-L-E-N-Y-C-N—OH

H—F-V-N-Q-H-L-C-G-S-H-L-V-E-A-L-Y-L-V-C-G-E-R-G-F-F-Y-T-P

2273

2274

Example 776

2275

2276

Example 777

-continued

E-E-E-I-V-E-Q-C—C-T-S-I-C-S-L-Y-Q-L—E-N-Y-C-N—OH

H-F-V-N-Q-H-L-C-G-S-H—L-V-E-A-L-Y-L-V-C-G-E-R-G-F-F-Y-T-P—

T—OH

E-E-N

E-E-N

H—G 2277                                                   2278

Example 778

2281

2282

Example 779

-continued

E-E-V-E-Q-C-C-T-S-I-C-S-L-V-Q-L-E-N-Y-C-N—OH

H—F-V-N-Q-H-L-C-G-S-H-L-V-E-A-L-Y-L-V-C-G-E-R-G-F-F-Y-T-P-

T—OH

H-G

E-E

2283

2284

Example 780

-continued

E-E-G-I-V-E-Q-C-C-T-S-I-C-S-L-Y-Q-L-E-N—Y-C—N—OH

E-E-F-V-N-Q-H-L-C-G-S-H-L-V-E-A-L-Y-L-V-C-G-E-R-G-F-F-Y-T-P—T-OH

2285

2286

Example 781

2287

2288

Example 782

-continued 2289  2290

Example 783

-continued

2291                                        2292

Example 784

H-G-I-V-E-Q-C-C-T-S-I-C-S-L-Y-Q-L-E-N-Y-C-N-

E-E-F-V-N-Q-H-L-C-G-S-H-L-V-E-A-L-Y-L-V-C-G-E-R-G-F-F-Y-T-P-

E-E-OH

T-OH

Example 785

-continued

H-F-V-N-Q-H-L-C-G-S-H-L-V-E-A-L-Y-L-V-C-G-E-R-G-F-F-Y-T-P

G-S-G-I-V-E-Q-C-C-T-S-I-C-S-L-Y-Q-L-E-N-Y-C-N—OH

H-G—NH

G-P-E-NH

T—OH

2295  2296

-continued

Example 786

N-I-G-I-V-E-Q-C-C-T-S-I-C-S-L-Y-Q-L-E-N-Y-C-N—OH

H-F-V-N-Q-H-L-C-G-S-H-L-V-E-A-L-Y-L-V-C-G-E-R-G-F-F-Y-T-P

H-E

T-OH 2297                                                         2298

Example 787

Example 788

-continued

H-F-V-N-Q-H-L-C-G-S-H-L-V-E-A-L-Y-L-V-C-G-E-R-G-F-F-Y-T-P

N-I-G-I-V-E-Q-C-C-T-S-I-C-S-L-Y-Q-L-E-N-Y-C-N-E

H-G 2301                                        2302

Example 789

-continued

N-I-G-I-V-E-Q-C-C-T-S-I-C-S-L-Y-Q-L-E-N-Y-C-N-OH

N-I-F-V-N-Q-H-L-C-G-S-H-L-V-E-A-L-Y-L-V-C-G-E-R-G-F-F-Y-T-P-

-continued

Example 790

2305      2306

-continued

Example 791

H-G-I-V-E-Q-C-C-T-S-I-C-S-L-Y-Q-L-E-N-Y-C-N-E

H-F-V-N-Q-H-L-C-G-S-H-L-V-E-A-L-Y-L-V-C-G-E-R-G-F-F-Y-T-P

2307

2308

Example 792

-continued

-continued

Example 793

2311 2312

Example 794

-continued

G-S—OH

H-F-V-N-Q-H-L-C-G-S-H-L-V-E-A-L-Y-L-V-C-G-E-R-G-F-F-Y-T-P

G-S-G-I-V-E-Q-C-C-T-S-I-C-S-L-Y-Q-L-E-N-Y-C-N-G-H

H-G—N

T—OH

Example 795

-continued

H-F-V-N-Q-H-L-C-G-S-H-L-V-E-A-L-Y-L-V-C-G-E-R-G-F-F-Y-T-P-H

H-E-H-N-I-E-H-N-I-G-I-V-E-Q-C-C-T-S-I-C-S-L-Y-Q-L-E-N-Y-C-N-OH

-continued

Example 796

2317

2318

-continued

Example 797

G-I-V-EQ-C-C-T-S-I-C-S-L-Y-Q-L-E-N-Y-C-N—OH

H-F-V-N-Q-H-L-C-G-S-H-L-V-E-A-L-Y-L-V-C-G-E-R-G-F-F-Y-T-P-R-T—OH

E-G-Y-D-A-Y

H-E

Example 798

G-I-V-E-Q-C-C-T-S-I-C-S-L-Y-Q-L-E-N-Y-C-N-OH

H-F-V-N-Q-H-L-C-G-S-H-L-V-E-A-L-Y-L-V-C-G-E-R-G-F-F-Y-T-P-R-T-OH

E-G-Y-D-A-Y

H-E

2321 2322

Example 799

-continued

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G-E-R-G-F-F-Y-T-P-R-T-OH

E-G-Y-D-A-Y

H-E 2323 2324

Example 800

Example 801

-continued

2327

2328

Example 802

-continued

G-I-V-E-Q-C-C-T-S-I-C-S-L-Y-Q-L-E-N-Y-C-N-OH

H-F-V-N-Q-H-L-C-G-S-H-L-V-E-A-L-Y-L-V-C-G-E-R-G-F-F-Y-T-P-R-T-OH

E-A-Y 2329                                                                                    2330

Example 803

-continued

2331                                                            2332

-continued

Example 804

H-G-F-F-Y-T-P-K-T-OH

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G

H-G-S-H

Example 805

-continued

H-G-I-V-E-Q-C-C-T-S-I-C-S-L-Y-Q-L-E-N-Y-C-N-OH

H—F-V-N-Q-H-L-C-G-S-H-L-V-E-A-L-Y-L-V-C-G-E-R-G-F-F-Y-T-P-

2335          2336

Example 806

-continued

H-G-I-V-E-Q-C-C-T-S-I-C-S-L-Y-Q-L-E-N-Y-C-N-OH

H-K-G-S-H-K-F-V-N-Q-H-L-C-G-S-H-L-V-E-A-L-Y-L-V-C-G-K-R-G-F-F-Y-T-P-K-T-OH 2337                                               2338

Example 807

-continued

2339

2340

Example 808

-continued

H-G-I-V-E-Q-C-C-T-S-I-C-S-L-Y-Q-L-E-N-Y-C-N-OH

F-V-N-Q-H-L-C-G-S-H-L-V-E-A-L-Y-L-V-C-G

R-G-F-F-Y-T-P

H-G

G-S-H

2341

2342

Example 809

-continued

GSI - 094135

H-G-I-V-E-Q-C-C-T-S-I-C-S-L-Y-Q-L-E-N-Y-C-N-OH

H-F-V-N-Q-H-L-C-G-S-H-L-V-E-A-L-Y-L-V-C-G-E-R-G-F-F-Y-T-P 2343 2344

Example 810

H—G-I-V-E-Q-C-C-T-S-I—C-S-L-Y-Q-L-E-N-Y-C—N—OH

H-L-C-G-S-H-L-V-E-A—L-Y-L-V-C-G-K-R-G-F—F-Y-T-P-K-T—OH

H—G-K-G-S-H-K-F-V-N-Q

2345 2346

Example 811

H—G-I-V-E-Q-C-C-T-S-I— C-S-L-Y-Q-L-E-N-Y-C-N—OH

H-L-C-G-S-H-L-V-E-A— L-Y-L-V-C-G-K-R-G-F— F-Y-T-P-K-T—OH

H—G-K-G-S-H-K-F-V-N-Q

-continued

Example 812

2349

2350

Example 813

Example 814

-continued

H—G-I-V-E-Q-C-C-T-S-I——C-S-L-Y-Q-L-E-N-Y-C—N—OH

H-L-C-G-S-H-L-V-E-A——L-Y-L-V-C-G-K-R-G-F——F-Y-T-P-K-T—H

H—G-K-G-S-H-K-F-V-N-Q

H—G-I-V-E-Q-C-C-T-S-I——C-S-L-Y-Q-L-E-N-Y-C—N—OH

H—G-I-V-E-Q-C-C-T-S-I——C-S-L-Y-Q-L-E-N-Y-C—N—OH

HN—F-V-N-Q-H-L-C-G-S-H——L-V-E-A-L-Y-L-V-C-G——E-R-G-F-F-Y-T-P-K-T—OH 2351                                                                 2352

Example 815

H—G-I-V-E-Q-C-C-T-S-I—C-S-L-Y-Q-L-E-N-Y-C—N—OH

H—F-V-N-Q-H-L-C-G-S-H—L-V-E-A-L-Y-L-V-C-G—E-R-G-F-F-Y-T-P-K-T—OH

2353

2354

Example 816

Example 817

-continued

H—G-I-V-E-Q-C-C-T-S-I—C-S-L-Y-Q-L-E-N-Y-C—N—OH

H-L-C-G-S-H-L-V-E-A—L-Y-L-V-C-G-K-R-G-F—F-Y-T-P-R-T—OH

H—G-K-G-S-H-K-F-V-N-O

2357

2358

Example 818

Example 819

-continued

Example 820

2361                  2362

-continued

Example 821

H—G-I-V-E-Q-C-C-T-S-I——C-S-L-Y-Q-L-E-N-Y-C—N—OH

H—L-C-G-S-B-L-V-E-A——L-Y-L-V-C-G-K-R-G-F——F-Y-T-P-K-T—OH

H—G-K-G-S-H-K-F-V-N-O

-continued

Example 822

-continued

Example 823

-continued

Example 824

2369          2370

Example 825

2371                                                                 2372

-continued

Example 826

2373           2374

Example 827

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH

Example 828

H-G-I-V-E-Q-C-C-T-S-I-C-S-L-Y-Q-L-E-N-Y-C-N-OH

H-G-K-F-V-N-Q-H-L-C-G-S-H-L-V-E-A-L-Y-L-V-C-G-K-R-G-F-F-Y-T-P-K-T-OH 2375 2376

Example 829

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH

Example 830

H-G-I-V-E-Q-C-C-T-S-I-C-S-L-Y-Q-L-E-N-Y-C-N-OH

HN-F-V-N-Q-H-L-C-G-S-H-L-V-E-A-L-Y-L-V-C-G-E-R-G-F-F-Y-T-P-K-T-OH

2377 2378

Example 831

H-G-I-V-E-Q-C-C-T-S-I-C-S-L-Y-Q-L-E-N-Y-C-N-OH

HN-F-V-N-Q-H-L-C-G-S-H-L-V-E-A-L-Y-L-V-C-G-E-R-G-F-F-Y-T-P

T-OH

Example 832

H-G-I-V-E-Q-C-C-T-S-I-C-S-L-Y-Q-L-E-N-Y-C-N-OH

H-G-K-F-V-N-Q-H-L-C-G-S-H-L-V-E-A-L-Y-L-V-C-G-K-R-G-F-F-Y-T-P-K-T-OH

Example 833

H-G-I-V-E-Q-C-C-T-S-I-C-S-L-Y-Q-L-E-N-Y-C-N-OH

H-G-K-H-E-N-K-F-V-N-Q-H-L-C-G-S-H-L-V-E-A-L-Y-L-V-C-G-K-R-G-F-F-Y-T-P-K-T-OH

-continued

Example 834

H-G-I-V-E-Q-C-C-T-S-I-C-S-L-Y-Q-L-E-N-Y-C-N-OH

H-G-K-F-V-N-Q-H-L-C-G-S-H-L-V-E-A-L-Y-L-V-C-G-K-R-G-F-F-Y-T-P-K-T-OH

Example 835

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH

Example 836

H-G-I-V-E-Q-C-C-T-S-I-C-S-L-Y-Q-L-E-N-Y-C-N-OH

H-G-K-F-V-N-Q-H-L-C-G-S-H-L-V-E-A-L-Y-L-V-C-G-K-R-G-F-F-Y-T-P-K-T-OH

2381          2382

Example 837

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH

Example 838

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-K-T—OH

-continued

Example 839

H-G-I-V-E-Q-C-C-T-S-I—C-S-L-Y-Q-L-E-N-Y-C—N—OH

HN—F-V-N-Q-H-L-C-G-S-H-L-V-E-A-L-Y-L-V-C-G-E-R-G-F-F-Y-T-P—N—T—OH

Example 840

H—G-I-V-E-Q-C-C-T-S-I-C-S-L-Y-Q-L-E-N-Y-C—N—OH

H—F-V-N-Q-H-L-C-G-S-H-L-V-E-A-L-Y-L-V-C-G-E-R-G-F-F-Y-T-P—N—T—OH

H—G-I-V-E-Q-C-C-T-S-I-C-S-L-Y-Q-L-E-N-Y-C—N—OH

V-N-Q-H-L-C-G-S-H-L-V-E-A-L-Y-L-V-C-G—R-G-F-F-Y-T-P-K-T—OH 2385                                                                     2386

Example 842

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-K-T—OH

Example 843

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-K-T—OH

Example 844

H—G-I-V-E-Q-C-C-T-S-I-C-S-L-Y-Q-L-E-N-Y-C—N—OH

H₂N   HN—F-V-N-Q-H-L-C-G-S-H-L-V-E-A-L-Y-L-V-C-G-E-R-G-F-F-Y-T-P—N—T—OH

-continued

Example 845

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-K-T—OH

Example 846

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-K-T—OH

Example 847

H—G-I-V-E-Q-C-C-T-S-I-C-S-L-Y-Q-L-E-N-Y-C—N—OH

HN—F-V-N-Q-H-L-C-G-S-H-L-V-E-A-L-Y-L-V-C-G-E-R-G-F-F-Y-T-P-K-T—OH

-continued

Example 848

H—G-I-V-E-Q-C-C-T-S-I-C-S-L-Y-Q-L-E-N-Y-C—N—OH

HN—F-V-N-Q-H-L-C-G-S-H-L-V-E-A-L-Y-L-V-C-G-E-R-G-F-F-Y-T-P-K-T—OH

Example 849

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-K-T—OH 2391                                                                                    2392

-continued

Example 850

H—G-I-V-E-Q-C-C-T-S-I-C-S-L-Y-Q-L-E-N-Y-C—N—OH

H-G-K-G-S-H-K-F-V-N-Q-H-L-C-G-S-H-L-V-E-A-L-Y-L-V-C-G-K-R-G-F-F-Y-T-P-K-T—OH

Example 851

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-K-T—OH

-continued

Example 852

H—G-I-V-E-Q-C-C-T-S-I-C-S-L-Y-Q-L-E-N-Y-C—N—OH

H—K-G-S-H-K-F-V-N-Q-H-L-C-G-S-H-L-V-E-A-L-Y-L-V-C-G-K-R-G-F-F-Y-T-P-K-T—OH

Example 853

H—G-I-V-E-Q-C-C-T-S-I-C-S-L-Y-Q-L-E-N-Y-C—N—OH

HN—F-V-N-Q-H-L-C-G-S-H-L-V-E-A-L-Y-L-V-C-G-E-R-G-F-F-Y-T-P

T—OH

-continued

Example 854

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-K-T—OH

Example 855

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-K-T—OH

-continued

Example 856

Example 857

-continued

Example 858

H-G-I-V-E-Q-C-C-T-S-I-C-S-L-Y-Q-L-E-N-Y-C-N-OH

H-G-K-Q-S-S-K-P-F-V-N-Q-H-L-C-G-S-H-L-V-E-A-L-Y-L-V-C-G-K-R-G-F-F-Y-T-P-K-T-OH

Example 859

H-G-I-V-E-Q-C-C-T-S-I-C-S-L-Y-Q-L-E-N-Y-C-N-OH

HN-F-V-N-Q-H-L-C-G-S-H-L-V-E-A-L-Y-L-V-C-G-K-R-G-F-F-Y-T-P-K-T-OH

Example 860

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH 2401                                                                                                                    2402

Example 861

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH

Example 862

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH

Example 863

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH

-continued

Example 864

H-G-I-V-E-Q-C-C-T-S-I-C-S-L-Y-Q-L-E-N-Y-C-N-OH

H-G-K-F-V-N-Q-H-L-C-G-S-H-L-V-E-A-L-Y-L-V-C-G-K-R-G-F-F-Y-T-P-K-T-OH

Example 865

H-G-I-V-E-Q-C-C-T-S-I-C-S-L-Y-Q-L-E-N-Y-C-N-OH

H-G ... G-S-K ... F-V-N-Q-H-L-C-G-S-H-L-V-E-A-L-Y-L-V-C-G ... R-G-F-F-Y-T-P ... T-OH

Example 866

H-G-I-V-E-Q-C-C-T-S-I-C-S-L-Y-Q-L-E-N-Y-C-N-OH

HN-F-V-N-Q-H-L-C-G-S-H-L-V-E-A-L-Y-L-V-C-G-E-R-G-F-F-Y-T-P

2405

2406

-continued

Example 867

H-G-I-V-E-Q-C-C-T-S-I-C-S-L-Y-Q-L-E-N-Y-C-N-OH

HN-F-V-N-Q-H-L-C-G-S-H-L-V-E-A-L-Y-L-V-C-G-E-R-G-F-F-Y-T-P 2407 2408

-continued

Example 868

Example 869

-continued

Example 870

-continued

Example 871

Example 872

-continued

—S—L—Y—Q—L—E—N—Y—C—N—OH

—A—L—Y—L—V—C—G—K—R—G—F—F—Y—T—P—K—T—OH

Example 873

H—G—I—V—E—Q—C—C—T—S—I—C—S—

H—G—K—N—S—T—K—F—V—N—Q—H—L—C—G—S—H—L—V—E—A—

-continued

Example 874

2417                                                    2418

Example 875

-continued

Example 876

H—G—I—V—E—Q—

H—G—I—V—E—Q— ... F—V—N—Q—H—

C—C—T—S—I—C—S—L—Y—Q—L—E—N—Y—C—N—OH

L—C—G—S—H—L—V—E—A—L—Y—L—V—C—G— ... R—G—F—F—Y—T—P—R—T—OH

2421

2422

Example 877

H—G—I—V—E—Q—C—C—T—S—I—C—

H—G—N

F—V—N—Q—H—L—C—G—S—H—L—

—S—L—Y—Q—L—E—N—Y—C—N—OH

—V—E—A——L—Y—L—V—C—G

R—G—F——F—Y—T—P—R—OH

2423                                                                 2424

Example 878

2425                                                2426

Example 879

Example 880

2429 2430

-continued

Example 881

H—G—I—V—E—Q—C—C—T—S—I—C—

H—G—K—P—G—G—G—S—G—G—G—S—G—G—G—S—F—V—N—O—H—L—C—G—S—H—L—V

—S—L—Y—Q—L—E—N—Y—C—N—OH

—E—A—L—Y—L—C—G—D—R—G—F—F—Y—T—P—K—OH

Example 882

H—G—I—V—E—Q—

H—G—K—P—G—G—G—S—G—G—G—G—S—G—G—G—S—F—V—N—Q—H—

2431                                                         2432

-continued

Example 883

2433                                                                                           2434

Example 884

H—G—I—V—E—Q—

H—G—K—P—G—G—G—S—G—G——G—G—S—G—G—G—S—F—V—N—Q—H—

—C—C—T—S—I—C—S—L—Y—Q—L—E—N—Y—C—N—OH

—L—C—G—S—H—L—V——E—A—L—Y—L—V—C—G—D—R—G—F—F—Y—T—P—K—OH

H-G-I-V-E-Q-C-C-T-S-I-C-S-L-Y-Q-L-E-N-Y-C-N-OH

H-G-K-F-G-G-G-S-G-G-G-S-G-G-G-S-F-V-N-Q-H-L-C-G-S-H-L-V-E-A-L-Y-L-V-C-G-D-R-G-F-F-Y-T-P-K-OH

-continued

Example 886

H-G-I-V-E-Q-C-C-T-S-I-C-S-L-Y-Q-L-E-N-Y-C-N-OH

H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 887

H-G-I-V-E-Q-C-C-T-S-I-C-S-L-Y-Q-L-E-N-Y-C-N-OH

H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 888

H-G-I-V-E-Q-C-C-T-S-I-C-S-L-Y-Q-L-E-N-Y-C-N-OH

H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH 2437             2438

-continued

Example 889

H-G-I-V-E-Q-C-C-T-S-I-C-S-L-Y-Q-L-E-N-Y-C-N-OH

H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

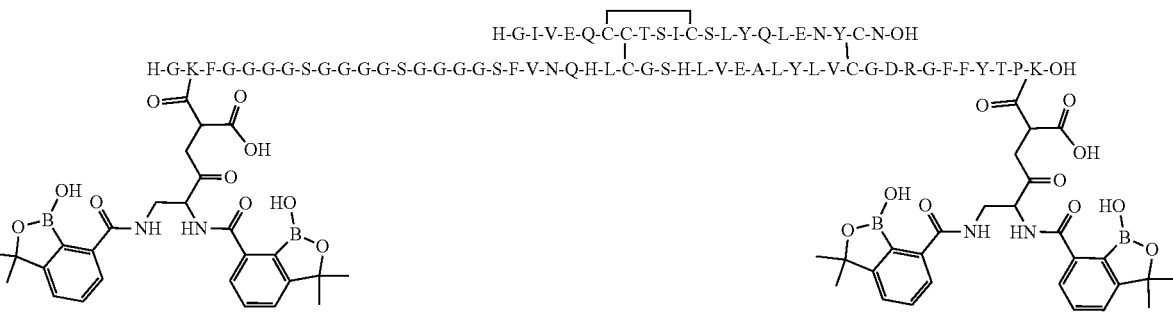

Example 890

H-G-I-V-E-Q-C-C-T-S-I-C-S-L-Y-Q-L-E-N-Y-C-N-OH

H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

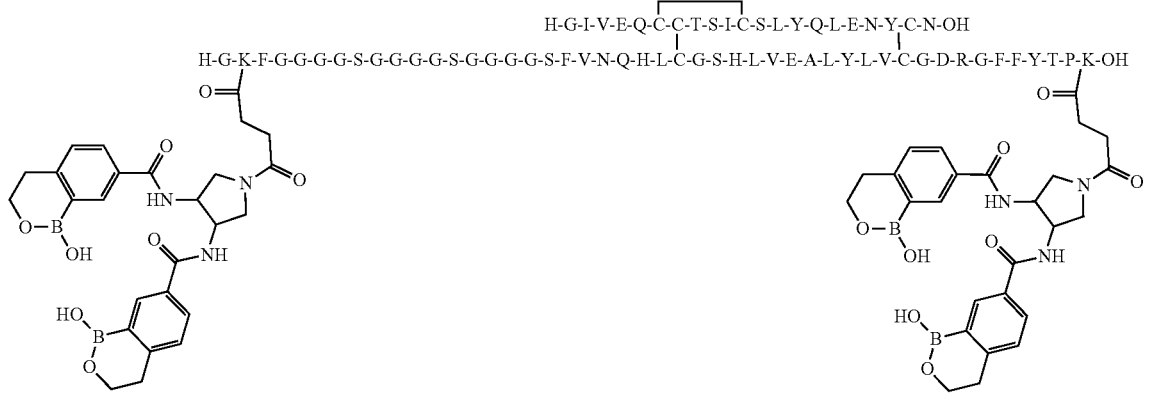

Example 891

H-G-I-V-E-Q-C-C-T-S-I-C-S-L-Y-Q-L-E-N-Y-C-N-OH

H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 892

H-G-I-V-E-Q-C-C-T-S-I-C-S-L-Y-Q-L-E-N-Y-C-N-OH

H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH 2439 2440

-continued

Example 893

H-G-I-V-E-Q-C-C-T-S-I-C-S-L-Y-Q-L-E-N-Y-C-N-OH
H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 894

H-G-I-V-E-Q-C-C-T-S-I-C-S-L-Y-Q-L-E-N-Y-C-N-OH
H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 895

H-G-I-V-E-Q-C-C-T-S-I-C-S-L-Y-Q-L-E-N-Y-C-N-OH
H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

-continued

Example 896

H-G-I-V-E-Q-C-C-T-S-I-C-S-L-Y-Q-L-E-N-Y-C-N-OH

H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 897

H-G-I-V-E-Q-C-C-T-S-I-C-S-L-Y-Q-L-E-N-Y-C-N-OH

H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 898

H-G-I-V-E-Q-C-C-T-S-I-C-S-L-Y-Q-L-E-N-Y-C-N-OH

H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH 2443        2444

-continued

Example 899

H-G-I-V-E-Q-C-C-T-S-I-C-S-L-Y-Q-L-E-N-Y-C-N-OH

H-G-K-F-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 900

H—G-K-P-G-G-G-G-S-G-G—G-G-S-G-G-G-G-S-F-V—

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH 2445      2446

-continued

Example 901

H—G-K-P-G-G-G-S-G-G—G-G-S-G-G-G-S-F-V——

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH 2447                                                    2448

-continued

Example 902

H—G-K-P-G-G-G-G-S-G-G—G-G-S-G-G-G-G-S-F-V——

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH

Example 903

H—G-K-P-G-G-G-G-S-G-G—G-G-S-G-G-G-G-S-F-V——

-continued

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH

Example 904

H—G-K-P-G-G-G-G-S-G-G—G-G-S-G-G-G-G-S-F-V—

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH

-continued

Example 905

H—G-K-P-G-G-G-G-S-G-G—G-G-S-G-G-G-G-S-F-V——

H-G-I-V-E-Q-C-C-T-S-I—C-S-L-Y-Q-L-E-N-Y-C—N—OH
—N-Q-H-L-C-G-S-H-L-V—E-A-L-V-L-V-C-G-D-R—G-F-F-Y—T—P-K—OH

Example 906

H—G-K-P-G-G-G-G-S-G-G—G-G-S-G-G-G-G-S-F-V——

-continued

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH

Example 907

H—G-K-P-G-G-G-G-S-G-G—G-G-S-G-G-G-S-F-V—

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH 2455 2456

-continued

Example 908

H—G-K-P-G-G-G-G-S-G-G—G-G-S-G-G-G-G-S-F-V——

Example 908

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH

Example 909

H—G-K-P-G-G-G-G-S-G-G—G-G-S-G-G-G-G-S-F-V——

-continued

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH

Example 910

H—G-K-P-G-G-G-G-S-G-G—G-G-S-G-G-G-G-S-F-V—

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH

-continued

Example 911

H—G-K-P-G-G-G-G-S-G-G—G-G-S-G-G-G-G-S-F-V—

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH

Example 912

H—G-K-P-G-G-G-G-S-G-G—G-G-S-G-G-G-G-S-F-V—

-continued

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH

Example 913

H—G-K-P-G-G-G-G-S-G-G—G-G-S-G-G-G-G-S-F-V—

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH

-continued

Example 914

H—G-K-P-G-G-G-G-S-G-G—G-G-S-G-G-G-G-S-F-V—

H-G-I-V-E-Q-C-C-T-S-I—C-S-L-Y-Q-L-E-N-Y-C—N—OH

—N-Q-H-L-C-G-S-H-L-V—E-A-L-V-L-V-C-G-D-R—G-F-F-Y—T—P-K—OH

Example 915

H—G-K-P-G-G-G-G-S-G-G—G-G-S-G-G-G-G-S-F-V—

-continued

H-G-I-V-E-Q-C-C-T-S-I——C-S-L-Y-Q-L-E-N-Y-C——N——OH

——N-Q-H-L-C-G-S-H-L-V——E-A-L-V-L-V-C-G-D-R——G-F-F-Y——T——P-K——OH

NUMBERED EMBODIMENTS

The present disclosure may also be defined according to any one of the following numbered embodiments:

1. A compound comprising one or more diboronates of the following formula, or a stereoisomer or a mixture of stereoisomers, or pharmaceutically acceptable salt thereof:

$$[Z1c-(Z_1b)_{\overline{n'}}]_{q'}-X1,$$

wherein:

each $Z_1b$ is independently a linker moiety, and each $n'$ is 0, 1, 2, 3, 4, or 5, wherein at least one $n'$ is 1, 2, 3, 4, or 5;

$X1$ comprises a drug substance or a polypeptide;

each $Z_1c$ is covalently conjugated directly or via one or more $Z_1b$ to an amine in $X1$; wherein a) at least one $Z_1c$ is independently selected from a diboronate, wherein the diboronate is independently selected from Formulae FF12A, FF12B, FF12C, FF12D, FF116A, FF116B, FF116C, FF116D, FF225, and FF227; and b) each additional $Z_1c$ is optionally independently selected from a diboronate, a sugar moiety, a diol containing moiety, and a polyol containing moiety, wherein the diboronate is independently selected from Formulae FF12A, FF12B, FF12C, FF12D, FF116A, FF116B, FF116C, FF116D, FF225, and FF227; and each $q'$ is 1, 2, 3, 4, or 5, wherein when $q'$ is 2 or more, each corresponding $Z_1c$ and $Z_1b$ is independently selected and may be the same or different; and wherein Formulae FF12A, FF12B, FF12C, FF12D, FF116A, FF116B, FF116C, FF116D, FF225, and FF227 are:

FF12A

-continued

FF12B

FF12C

FF12D

FF116A

FF116B

FF116C

2467

-continued

FF116D

FF225

FF227 wherein X represents a point of covalent attachment to an amine of Z1b or to an amine of X1 when n' is 0;

i is 1, 2, 3, 4, 5, 6, or 7; and wherein $B_1$ and $B_2$, which may be identical or different, each independently represent an aromatic boron-containing group; and wherein when each Z1c is selected from Formulae FF225 and FF227, at least one of the $B_1$ and the $B_2$ is Formula F7, wherein Formula F7 is:

(F7)

wherein:

one $R_1$ represents (C=O)—*, wherein —* represents the attachment point to the rest of Z1c;

each remaining $R_1$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)$ $NH(CH_2)_mCH_3$, and $OCF_3$, wherein m is 1, 2, 3, 4, 5, 6, or 7;

Y8 is 0 or NR, wherein R is a $C_1$-$C_6$alkyl group or H; and each Y10 is independently selected from H, $CH_3$, F, and $CF_3$, wherein for at least one F7 at least one Y10 is not H.

2. The compound of embodiment 1, or stereoisomer or a mixture of stereoisomers, or pharmaceutically acceptable salt thereof, wherein:

each n' is 0, 1, 2, or 3, wherein at least one n' is 1, 2, or 3;

each q' is 1, 2, 3, or 4;

each Z1b is independently a linker moiety, wherein each Z1c is covalently conjugated directly or via one or more of the Z1b to an amine of X1, with the proviso that the Z1b is not a diol containing moiety, and

2468 wherein one or more positions of the compound may comprise an isotope.

3. The compound of embodiment 1 or 2, or stereoisomer or a mixture of stereoisomers, or pharmaceutically acceptable salt thereof, wherein each Z1c is covalently conjugated via one or more of the Z1b to an amine of X1, wherein each Z1b is independently selected from Formulae FL3, FL5, FL5A, FL5B, FL65A, FL65B, FL69, FL69A, FL69B, FL70, FL70A, and FL70B;

wherein FL3, FL5, FL5A, FL5B, FL65A, FL65B, FL69, FL69A, FL69B, FL70, FL70A, and FL70B are:

FL3

FL5

FL5A

FL5B

FL65A

FL65B

FL69

2469

-continued

FL69A

FL69B

FL70

FL70A

FL70B

40 wherein:

R" represents a covalent bond, directly or indirectly, to Z1c;

Z" represents a covalent bond, directly or indirectly, to X1;

A' is selected from H and a $C_1$- to $C_{20}$ alkyl; and

A" is a $C_2$-$C_{20}$ acyl group optionally terminating in an acid group, wherein one or more carbon atoms of the $C_2$-$C_{20}$ acyl group are optionally and independently replaced by a group selected from C(=O), O, NH, $NH_2$, S, S(O), $SO_2$, phenyl, 5-membered heterocyclyl, 6-membered heterocyclyl, 5-membered heteroaryl, 6-membered heteroaryl, and wherein the $C_2$-$C_{20}$ acyl group, NH, $NH_2$, $SO_2$, phenyl, 5-membered heterocyclyl, 6-membered heterocyclyl, 5-membered heteroaryl, and 6-membered heteroaryl is each independently substituted with 0, 1, 2, 3, or 4 $R_x$, wherein $R_x$ is selected from $C_1$-$C_5$ alkyl, halogen, $C_1$-$C_5$ haloalkyl, carboxylic acid, hydroxyl, —O—$C_1$-$C_5$ alkyl, —S(=O)$_2$$NH_2$, $NH_2$, 5-membered heterocyclyl, 6-membered heterocyclyl, 5-membered heteroaryl, phenyl, and 6-membered heteroaryl;

p is 1, 2, 3, 4, or 5, q is 1, 2, 3, 4, or 5, and any primary amine is optionally acetylated or alkylated.

4. The compound of embodiment 3, wherein each Z1b is independently selected from:

2470

FL3

FL5B

FL65A

FL65B

FL69A wherein:

p is 1, 2, 3, 4, or 5.

5. The compound of embodiment 3 or 4, or pharmaceutically acceptable salt thereof, wherein each Z1b is independently selected from:

2471

-continued

6. The compound of any one of embodiments 3-5, or pharmaceutically acceptable salt thereof, wherein each A" is independently selected from:

AB-1

AB-2

AB-3

AB-4

AB-5

AB-6

2472

-continued

AB-7

AB-8

AB-9

AB-10

AB-11

AB-12

AB-13

AB-14

AB-15

AB-16

AB-17

2473

-continued

AB-18

AB-19

AB-20

AB-21

AB-22

AB-23

AB-24

AB-25

AB-26

AB-27

2474

-continued

AB-28

AB-30

AB-31

AB-31

AB-32

AB-33

AB-34

AB-35

| 2475 | 2476 |

-continued

-continued

AB-36

AB-37

AB-37A

AB-38

AB-39

7. The compound of any one of embodiments 1-5, or pharmaceutically acceptable salt thereof, wherein the $B_1$ and $B_2$ are independently selected from Formulae F2 and F7, wherein Formulae F2 and F7 are:

(F2)

(F7)

wherein:

one $R_1$ represents (C═O)—*, wherein —* represents the attachment point to the rest of Z1c;

each remaining $R_1$ is independently selected from H, F, Cl, Br, OH, $CH_2$—$NH_2$, $NH_2$, (C═O)—$NH_2$, CH═O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)$ $NH(CH_2)_mCH_3$, and $OCF_3$, wherein m is 1, 2, 3, 4, 5, 6, or 7;

Y8 is O, or Y8 is NR, wherein R is a $C_1$-$C_6$alkyl group or H; and each Y10 is independently selected from H, $CH_3$, F, and $CF_3$, wherein for at least one F7 at least one Y10 is not H.

8. The compound of embodiment 7, or pharmaceutically acceptable salt thereof, wherein the $R_1$ at position 5' represents (C═O)—*, wherein —* represents the attachment point to the rest of Z1c.

9. The compound of embodiment 7, or pharmaceutically acceptable salt thereof, wherein the $B_1$ and the $B_2$ are independently represented by Formula F2, wherein Formula F2 is:

(F2)

wherein:

$R_1$ at position 5' represents (C═O)—*, wherein —* represents the attachment point to the rest of Z1c; and each remaining $R_1$ is independently selected from H, F, Cl, Br, OH, $CF_3$, $CHF_2$, $NO_2$, $CH_3$, $OCH_3$, and $OCF_3$.

10. The compound of embodiment 7, or pharmaceutically acceptable salt thereof, wherein the $B_1$ and $B_2$ are independently Formula F7, (F7)

wherein:

$R_1$ at position 5' represents (C=O)—*, wherein —* represents the attachment point to the rest of Z1c;

each remaining $R_1$ is independently selected from H, F, Cl, Br, OH, $CF_3$, $CHF_2$, $NO_2$, $CH_3$, $OCH_3$, and $OCF_3$;

Y8 is O or NR, wherein R is a $C_1$-$C_6$alkyl group or H; and each Y10 is independently selected from H, $CH_3$, F, and $CF_3$, wherein for at least one F7 at least one Y10 is not H.

11. The compound of embodiment 7 or 10, or pharmaceutically acceptable salt thereof, wherein the $B_1$ and $B_2$ are independently Formula F7A, (F7A)

wherein:

$R_1$ at position 5' represents (C=O)—*, wherein —* represents the attachment point to the rest of Z1c; and each remaining $R_1$ is independently selected from H, F, Cl, Br, OH, $CF_3$, $CHF_2$, $NO_2$, $CH_3$, $OCH_3$, and $OCF_3$.

12. The compound of any one of embodiments 1-8, or pharmaceutically acceptable salt thereof, wherein at least one $B_1$ or $B_2$ is F7, and wherein Y8 is O and each Y10 is $CH_3$.

13. The compound of any one of embodiments 7-11, or pharmaceutically acceptable salt thereof, wherein each remaining $R_1$ is independently selected from H, $CF_3$, and F, optionally two remaining $R_1$ are H and one remaining $R_1$ is $CF_3$ or F.

14. The compound of any one of embodiments 7-11, or pharmaceutically acceptable salt thereof, wherein at least one $R_1$ in the $B_1$ or the $B_2$ is F or $CF_3$.

15. The compound of any one of embodiments 7-11, or pharmaceutically acceptable salt thereof, wherein each remaining $R_1$ is H.

16. The compound of embodiment 3 having the following formula, or a stereoisomer or a mixture of stereoisomers, or pharmaceutically acceptable salt thereof:

$$[Z1c\text{---}Z1b1\text{---}Z1b2]_{q'}\text{---}X1,$$

wherein:

q' is 2, 3, or 4;

each corresponding Z1c and Z1b1 is independently selected and may be the same or different;

each Z1b1 is a bond or is selected from FL70, FL70A, and FL70B, wherein FL70, FL70A, and FL70B are:

FL70

FL70A

FL70B and wherein R", Z", A', A", p and q are as defined in embodiment 3;

each Z1b2 is FL3, wherein FL3 is

FL3 and wherein R", Z", and p are as defined in embodiment 3;

each Z1c is covalently conjugated to Z1b1 via an amine in beta or gamma position of a backbone of the Z1b1, and wherein at least one Z1c is covalently conjugated to at least one Z1b1 selected from FL70, FL70A, and FL70B.

17. The compound of embodiment 3 having the following formula, or a stereoisomer or a mixture of stereoisomers, or pharmaceutically acceptable salt thereof:

$$[Z1c\text{---}Z1b1\text{---}Z1b2]_{q'}\text{---}X1$$

wherein:

q' is 2, 3, or 4;

each corresponding Z1c and Z1b1 is independently selected and may be the same or different;

each Z1b1 is a bond or is selected from FL70, FL70A, and FL70B wherein FL70, FL70A, and FL70B are:

FL70

FL70A

-continued

FL70B wherein R", Z", A', A", p and q are as defined in embodiment 3;

each Z1b2 is selected from FL5, FL5A, and FL5B, wherein FL5, FL5A, and FL5B are:

FL5

FL5A

FL5B wherein R", Z", and p are as defined in embodiment 3;

each Z1c is covalently conjugated to Z1b1 via an amine in an beta or gamma position of a backbone of the Z1b1, and wherein at least one Z1c is covalently conjugated to at least one Z1b1 selected from FL70, FL70A, and FL70B.

18. The compound of embodiment 16 or 17, or pharmaceutically acceptable salt thereof, wherein at least one Z1c is conjugated to an amine in the beta position of the backbone of the Z1b1 or Z1b2.

19. The compound of embodiment 3 having the following formula, or a stereoisomer or a mixture of stereoisomers, or pharmaceutically acceptable salt thereof:

$$[Z1c\!-\!Z1b1\!-\!Z1b2]_{q'}\!-\!X1$$

wherein:

q' is 2, 3, or 4;

each corresponding Z1c and Z1b1 is independently selected and may be the same or different;

each Z1b1 is a bond or is selected from FL69, FL69A, and FL69B, wherein FL69, FL69A, and FL69B are:

FL69

FL69A

FL69B and wherein R", Z", A', A", and p are as defined in embodiment 3;

each Z1b2 is FL3 or FL5B, wherein FL3 and FL5B are:

FL3 and

FL5B wherein R", Z", and p are as defined in embodiment 3;

each Z1c is covalently conjugated to Z1b1 via an amine in an alpha position of a backbone of the Z1b1, and wherein at least one Z1c is covalently conjugated to at least one Z1b1 selected from FL69, FL69A, and FL69B.

20. The compound of embodiment 3 having the following formula, or a stereoisomer or a mixture of stereoisomers, or pharmaceutically acceptable salt thereof:

$$[Z1c\!-\!Z1b1\!-\!Z1b2]_{q'}\!-\!X1$$

wherein:

q' is 2, 3, or 4;

each corresponding Z1c is independently selected and may be the same or different;

each Z1b1 is a bond;

each Z1b2 is FL3, wherein FL3 is

FL3 and wherein R″, Z″, and p are as defined in embodiment 3;

and each Z1c is covalently conjugated to Z1b2 via an amine in a beta position of a backbone of the Z1b2.

21. The compound of any one of embodiments 1-20, or pharmaceutically acceptable salt thereof, wherein X1 is a polypeptide and the polypeptide comprises an insulin receptor agonist having an A-chain and a B-chain.

22. The compound of embodiment 1, or pharmaceutically acceptable salt thereof, wherein each Z1c is selected from Formulae FFL-1 to FFL-68, wherein Formulae FFL-1 to FFL-68 are:

FFL-1

FFL-2

FFL-3

FFL-4

FFL-5

-continued

FFL-6

FFL-7

FFL-8

FFL-9

FFL-10

-continued

FFL-11

FFL-12

FFL-13

FFL-14

2487                                                        2488

FFL-15                                                      FFL-16

FFL-17                                                      FFL-18

FFL-19                                                      FFL-20

2489                                2490

-continued

FFL-21

FFL-22

FFL-23

FFL-24

FFL-25

FFL-26

FFL-27

FFL-28

2491 2492

FFL-29 FFL-30

FFL-31 FFL-32

FFL-33 FFL-34

2493　　　　　　　　　　　　　　　　　　　　　　2494

-continued

FFL-35

FFL-36

FFL-37

FFL-38

FFL-39

FFL-40

-continued

FFL-41

FFL-42

FFL-43

FFL-44

FFL-45

-continued

FFL-46

FFL-47

FFL-48

FFL-49

2499                             2500

-continued

FFL-50

FFL-51

FFL-52

FFL-53

FFL-54

FFL-55

FFL-56

FFL-57

2501                                                                                    2502

FFL-58

FFL-59

FFL-60

FFL-61

FFL-62

FFL-63

2503 2504

FFL-64

FFL-65

FFL-66

FFL-67

FFL-68 or stereoisomers thereof, wherein X represents a point of covalent attachment to the amine of X1.

23. The compound of embodiment 7, or pharmaceutically acceptable salt thereof, wherein the B₁ and the B₂ are each independently selected from Formulae F2 and F7; wherein each remaining $R_1$ is independently selected from H, $CF_3$, and F, wherein each Z1c is covalently conjugated via one or more of the Z1b to an amine of X1 and each of the Z1c and the one or more Z1b in combination is selected from Formulae FFL 2-5, 9-12, 16, 20, 21, 27, 32, 34, 35, 37-40, 44-47, 51, 55, 56, 62, 66, and 67:

2505

2506

FFL-2

FFL-3

FFL-4

FFL-5

FFL-9

FFL-10

FFL-11

2507                                                              2508

-continued

FFL-12

FFL-16

FFL-20

FFL-21

FFL-27

2509                                                           2510

FFL-32                                                            FFL-34

FFL-35                                                            FFL-37

FFL-38                                                            FFL-39

FFL-40

2511                  2512

-continued

FFL-44

FFL-45

FFL-46

FFL-47

FFL-51             FFL-55

2513

2514

FFL-56

FFL-62

FFL-66

FFL-67 or stereoisomers thereof;

wherein X represents a point of covalent attachment to the amine of X1.

24. The compound of embodiment 7, or pharmaceutically acceptable salt thereof, wherein the $B_1$ and the $B_2$ are each independently Formula F2, wherein each remaining $R_1$ is independently selected from H, $CF_3$, and F; wherein each Z1c is covalently conjugated via one or more of the Z1b to an amine of X1 and each of the Z1c and the one or more Z1b in combination is selected from Formulae FFL 2-5, 9-12, 16, 20, 21, 27, 32, 34, 35, 37-40, 44-47, 51, 55, 56, 62, 66, and 67:

FFL-2

FFL-3

2515 2516

-continued

FFL-4

FFL-5

FFL-9

FFL-10

FFL-11

FFL-12

-continued

FFL-16

FFL-20

FFL-21

FFL-27

FFL-32

FFL-34

-continued

FFL-35

FFL-37

FFL-38

FFL-39

FFL-40

FFL-44

FFL-45

2521                                                                          2522

FFL-46

FFL-47

FFL-51                                                    FFL-55

FFL-56

FFL-62

FFL-66 and

FFL-67 or stereoisomers thereof;

wherein X represents a point of covalent attachment to the amine of X1.

25. The compound of embodiment 11, or pharmaceutically acceptable salt thereof, wherein the $B_1$ and the $B_2$ are each independently Formula F7A, wherein each remaining $R_1$ is independently selected from H, $CF_3$, and F; wherein each Z1c is covalently conjugated via one or more of the Z1b to an amine of X1 and each of the Z1c and the one or more Z1b in combination is selected from Formulae FFL 2-5, 9-12, 16, 20, 21, 27, 32, 34, 35, 37-40, 44-47, 51, 55, 56, 62, 66, and 67:

FFL-2

FFL-3

2525                                                           2526

FFL-4

FFL-5

FFL-9

FFL-10

FFL-11

FFL-12

-continued

FFL-16

FFL-20

FFL-21

FFL-27

FFL-32

FFL-34

2529                                                                      2530

-continued

FFL-35

FFL-37

FFL-38

FFL-39

FFL-40

FFL-44

FFL-45

2531                                                                2532

FFL-46

FFL-47

FFL-51                                                            FFL-55

2533 2534

FFL-56

FFL-62

FFL-66

FFL-67 or stereoisomers thereof;

wherein X represents a point of covalent attachment to the amine of X1.

26. The compound of embodiment 1 or 2, or pharmaceutically acceptable salt thereof, wherein the compound has affinity to bind to one or more glycated proteins or glycosylated proteins and/or sugar moieties or saccharides or polysaccharides on surface of cells.

27. The compound of embodiment 1, or pharmaceutically acceptable salt thereof, wherein q' is at least 2, and wherein at least one of the Z1c is a sugar moiety, a diol containing moiety, and a polyol containing moiety.

28. The compound of embodiment 27, or pharmaceutically acceptable salt thereof, wherein the Z1c is selected from Formulae STR1, STR2, STR3, STR4, and STR5:

STR1

STR2

STR3

STR4

-continued

STR5 wherein:

one $R_1'''$ represents the attachment point to a Z1b;

each carbon atom attached to an $R_1'''$ independently has (R) or (S) stereochemistry;

each remaining $R_1'''$ is independently selected from —H, —OR$^3$, —N(R$^3$)$_2$, —SR$^3$, —OH, —OCH$_3$, —OR$^5$, NHC(O)CH$_3$, —CH$_2$R$_3$, —C(O)NHOH, —NHC(O) CH$_3$, —CH$_2$OH, —CH$_2$OR$^5$, —NH$_2$, —CH$_2$R$_4$, —R$^6$, and —R$^7$, wherein in STR1, STR2, and STR4 at least one of the remaining $R_1$ is OH, each R$^3$ is independently selected from —H, acetyl, phosphate, —R$_2$, —SO$_2$R$^2$, —S(O)R$^2$, —P(O)(OR$^2$)$_2$, —C(O)R$^2$, —CO$_2$R$^2$, and —C(O)N(R$^2$)$_2$, each R$^2$ is independently selected from —H, C$_{1-6}$ aliphatic ring, phenyl ring, 5-6 membered monocyclic heteroaryl ring having 1-4 heteroatoms selected from nitrogen, oxygen, and sulfur, a 4-7 membered heterocyclic ring having 1-2 heteroatoms selected from nitrogen, oxygen, and sulfur, and a C$_1$-C$_6$alkyl, each R$^4$ is independently selected from —H, —OH, —OR$^3$, —N(R$^3$)$_2$, —OR$^5$ and —SR$^3$;

each R$^5$ is independently selected from a mono-saccharide, a di-saccharide, a tri-saccharide, a pentose, and a hexose, each R$^6$ is independently selected from —NCOCH$_2$—, —(OCH$_2$CH$_2$)$_n$—, a —O—C$_{1-9}$ alkylene group, and a substituted C$_{1-9}$ alkylene group in which one or more methylene groups are optionally replaced by —O—, —(CH$_2$)$_n$—, —OCH$_2$—, —N(R$^2$)C(O)—, —N(R$^2$)C (O)N(R$^2$)—, —SO$_2$—, —SO$_2$N(R$^2$)—, —N(R$^2$) SO$_2$—, —S—, —N(R$^2$)—, —C(O)—, —OC(O)—, —C(O)O—, —C(O)N(R$^2$)—, or —N(R$^2$)SO$_2$N (R$^2$)—, wherein index n is 1, 2, 3, 4, 5, 6, 7, or 8, each R$^7$ is independently selected from —N(R$^2$)$_2$, —F, —Cl, —Br, —I, —SH, —OR$^2$, —SR$^2$, —NH$_2$, —N$_3$, —C≡CR$^2$, —CH$_2$C≡CH, —C≡CH, —CO$_2$R$^2$, —C(O) R$^2$, —OSO$_2$R$^2$—N(R$^2$)$_2$, —OR$^2$, —SR$^2$, and —CH$_3$, —CH$_2$NH$_2$, and structures STR1, STR2, STR3, STR4, and STR5 optionally include one or more acetyl, acetylene, acetonide, and/or pinacol protecting groups.

29. The compound of embodiment 1 or 2, or pharmaceutically acceptable salt thereof, wherein X1 comprises a polypeptide human hormone, an insulin receptor agonist, an endocrine hormone, insulin, human insulin, glucagon, amylin, relaxin, GLP-1, GIP, oxyntomodulin, somatostatin, gastric inhibitory polypeptide, glucose-dependent insulinotropic polypeptide, a hybrid peptide comprising sequences from two or more human polypeptide hormones, or an analogue of any thereof.

30. The compound of any one of embodiments 1-2 and 19-29, or pharmaceutically acceptable salt thereof, wherein:

X1 comprises an insulin having an A-chain and a B-chain, wherein optionally the A-chain comprises a sequence selected from SEQ ID NOs 1, 25, 24051, and 24052, and optionally the B-chain comprises a sequence selected from SEQ ID NOs 24060, 24061, 24062, 24063, 24064, and 25000-25397.

31. The compound of embodiment 30, or pharmaceutically acceptable salt thereof, wherein:

X1 comprises an insulin having an A-chain and a B-chain, wherein the A-chain comprises a sequence selected from SEQ ID NOs 1, 24051, and 24052, and wherein the B-chain comprises a sequence selected from SEQ ID NOs 24063, 25095, 25228, 25229, 25232, 25236, 25305, 25308, 25312, and 25380-25397;

each Z1b is independently selected from FL3, FL5, FLSA, FL5B, FL65A, FL65B, FL69A, and FL69B;

each Z1c is independently selected from FF12A, FF12B, FF12C, FF12D, FF116A, FF116B, FF116C, FF116D, and FF227, wherein each Z1c is covalently conjugated via one or more of the Z1b to a lysine residue in X1; and B$_1$ and B$_2$ are each independently Formula F2 or Formula F7.

32. The compound of embodiment 1 or 2, or pharmaceutically acceptable salt thereof, wherein:

each B$_1$ and B$_2$ is independently selected from F2 and F7 and is covalently conjugated to Z1c using an amide linkage, each Z1b is independently selected from (i) FL3, wherein p is 1, 2, or 3; (ii) FL5B, wherein p is 2, 3, or 4; (iii) FL65A; and (iv) FL69A, wherein p is 2, 3, or 4;

each Z1c is independently selected from FF12A, FF116A, and FF227, wherein each Z1c is covalently conjugated via one or more of the Z1b to a lysine residue in X1; and X1 is a polypeptide comprising an insulin receptor agonist having an A-chain and a B-chain, wherein the A-chain comprises a sequence selected from SEQ ID NOs 1, 24051, and 24052, and wherein the B-chain comprises a sequence selected from SEQ ID NOs 24063, 25095, 25228, 25229, 25232, 25236, 25305, 25308, 25312, and 25380-25397, and wherein at least two lysine in X1 are each independently conjugated to Z1b.

33. The compound of embodiment 1 or 2, or pharmaceutically acceptable salt thereof, wherein at least one Z1c is FF227 and i is 1.

34. The compound of embodiment 1 or 2, wherein the compound is selected from:

2537

2538

Example 1A

-continued

Example 2A

-continued

Example 3A

-continued

Example 4A 2545                                                      2546

Example 5A

-continued

H—G—I—V—E—Q—C—C—T—S—I—C—S—L—Y—Q—L—E—N—Y—C—N—OH

L—Y—L—V—C—G—K—R—G—F—F—Y—T—P—R—OH

H—L—C—G—S—H—L—V—E—A

H—G—K—G—S—H—K—F—V—N—Q

-continued

Example 6A

H—G—I—V—E—Q—C—C—T—S—I—C—S—L—Y—Q—L—E—N—Y—C—N—OH

H—L—C—G—S—H—L—V—E—A——L—Y—L—V—C—G—K—R—G—F—F—Y—T—P—R—OH,

H—G—K—G—S—H—K—F—V—N—Q

Example 7A

-continued

H—G—I—V—E—Q—C—C—T—S—I—C—S—L—Y—Q—L—E—N—Y—C—N—OH

H—L—C—G—S—H—L—V—E—A—L—Y—L—V—C—G—K—R—G—F—F—Y—T—P—R—OH

H—G—K—G—S—H—K—F—V—N—Q

2551          2552

Example 8A

Example 9A

-continued

H—G—I—V—E—Q—C—C—T—S—I——C—S—L—Y—Q—L—E—N—Y—C—N—OH

H—L—C—G—S—H—L—V—E—A——M—L—V—C—G—K—R—G—F—F—Y—T—P—R—OH

Example 10A

-continued

H—G—I—V—E—Q—C—C—T—S—I—C—S—L—Y—Q—L—E—N—Y—C—N—OH

H—L—C—G—S—H—L—V—E—A—L—Y—L—V—C—G—K—R—G—F—F—Y—T—P—R—OH,

H—G—K—G—S—H—K—F—V—N—Q (S)

(R)

(R)

(S)

-continued

Example 11A

Example 12A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 13A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

-continued

Example 14A

Example 15A

-continued

Example 16A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH

Example 17A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH

-continued

Example 18A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH

Example 19A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH 2567                                                    2568

Example 20A

-continued

Example 21A

2571  2572

Example 22A

-continued

H—G—I—V—E—Q—C—C—T—S—I—C—S—L—Y—Q—L—E—N—Y—C—N—OH

H—L—C—G—S—H—L—V—E—A—L—Y—L—V—C—G—K—R—G—F—F—Y—T—P—R—OH,

H—G—K—S—H—K—F—V—N—Q

-continued

Example 23A

-continued

Example 24A

H—G—I—V—E—Q—C—C—T—S—I—C—S—L—Y—Q—L—E—N—Y—C—N—OH,

H—L—C—G—S—H—L—V—E—A—L—Y—L—V—C—G—K—R—G—F—F—Y—T—P—R—OH,

H—G—S—H—K—F—V—N—Q—

HOOC

COOH

2577

2578

-continued

Example 25A

-continued

Example 26A

Example 27A

-continued

2583  2584

-continued

Example 28A

H—G—I—V—E—Q—C—C—T—S—I—C—S—L—Y—Q—L—E—N—Y—C—N—OH,

H—G—S—H—K—F—V—N—Q—H—L—C—G—S—H—L—V—E—A—L—Y—L—V—C—G—K—G—F—F—Y—T—P—R—OH,

-continued

Example 29A

2587

2588

Example 30A

-continued

Example 31A

Example 32A

H-G-I-V-E-Q-C-C-T-S-I-C-S-L-Y-Q-L-E-N-Y-C-N-OH
H-G-K-G-S-H-K-P-V-N-Q-H-L-C-G-S-H-L-V-E-A-L-Y-L-V-C-G-K-R-G-P-P-Y-T-P-R-OH,

Example 33A

H-G-I-V-E-Q-C-C-T-S-I-C-S-L-Y-Q-L-E-N-Y-C-N-OH
H-G-K-G-S-H-K-P-V-N-Q-H-L-C-G-S-H-L-V-E-A-L-Y-L-V-C-G-K-R-G-P-P-Y-T-P-R-OH,

-continued

Example 34A

H-G-I-V-E-Q-C-C-T-S-I-C-S-L-Y-Q-L-E-N-Y-C-N-OH

H-G-K-G-S-H-K-P-V-N-Q-H-L-C-G-S-H-L-V-E-A-L-Y-L-V-C-G-K-R-G-P-P-Y-T-P-R-OH,

Example 35A

H-G-I-V-E-Q-C-C-T-S-I-C-S-L-Y-Q-L-E-N-Y-C-N-OH

H-G-K-G-S-H-K-P-V-N-Q-H-L-C-G-S-H-L-V-E-A-L-Y-L-V-C-G-K-R-G-P-P-Y-T-P-R-OH,

-continued

Example 36A

H-G-I-V-E-Q-C-C-T-S-I-C-S-L-Y-Q-L-E-N-Y-C-N-OH

H-G-K-G-S-H-K-P-V-N-Q-H-L-C-G-S-H-L-V-E-A-L-Y-L-V-C-G-K-R-G-P-P-Y-T-P-R-OH,

Example 37A

H-G-I-V-E-Q-C-C-T-S-I-C-S-L-Y-Q-L-E-N-Y-C-N-OH

H-G-K-G-S-H-K-P-V-N-Q-H-L-C-G-S-H-L-V-E-A-L-Y-L-V-C-G-K-R-G-P-P-Y-T-P-R-OH,

-continued

Example 38A

H-G-I-V-E-Q-C-C-T-S-I-C-S-L-Y-Q-L-E-N-Y-C-N-OH

H-G-K-G-S-H-K-P-V-N-Q-H-L-C-G-S-H-L-V-E-A-L-Y-L-V-C-G-K-R-G-P-P-Y-T-P-R-OH,

Example 39A

H-G-I-V-E-Q-C-C-T-S-I-C-S-L-Y-Q-L-E-N-Y-C-N-OH

H-G-K-G-S-H-K-P-V-N-Q-H-L-C-G-S-H-L-V-E-A-L-Y-L-V-C-G-K-R-G-P-P-Y-T-P-R-OH,

Example 40A

H—G-I-V-E-Q-C-C-T-S-I—C-S-L-Y-Q-L-E-N-Y-C—N—OH

H-G-K-S-H-K-F-V-N-Q—H-L-C-G-S-H-L-V-E-A———L-Y-L-V-C-G-K-R-G-F—F-Y-T-P-R—OH,

Example 41A

H—G-I-V-E-Q-C-C-T-S-I—C-S-L-Y-Q-L-E-N-Y-C—N—OH

H-G-K-S-H-K-F-V-N-Q—H-L-C-G-S-H-L-V-E-A———L-Y-L-V-C-G-K-R-G-F—F-Y-T-P-R—OH,

2601

2602

-continued

Example 42A

H—G-I-V-E-Q-C-C-T-S-I—C-S-L-Y-Q-L-E-N-Y-C—N—OH

H—G-K-S-H-K-F-V-N-Q—H-L-C-G-S-H-L-V-E-A————L-Y-L-V-C-G-K-R-G-F—F-Y-T-P-R—OH,

2603  2604

-continued

Example 43A

H—G-I-V-E-Q-C-C-T-S-I—C-S-L-Y-Q-L-E-N-Y-C—N—OH

H—G-K-S-H-K-F-V-N-Q—H-L-C-G-S-H-L-V-E-A————L-Y-L-V-C-G-K-R-G-F—F-Y-T-P-R—OH,

Example 44A

H—G-I-V-E-Q-C-C-T-S-I—C-S-L-Y-Q-L-E-N-Y-C—N—OH

H—G-K-S-H-K-F-V-N-Q—H-L-C-G-S-H-L-V-E-A————L-Y-L-V-C-G-K-R-G-F—F-Y-T-P-R—OH,

2605

2606

-continued

Example 45A

H—G-I-V-E-Q-C-C-T-S-I—C-S-L-Y-Q-L-E-N-Y-C—N—OH

H—G-K-S-H-K-F-V-N-Q—H-L-C-G-S-H-L-V-E-A———L-Y-L-V-C-G-K-R-G-F—F-Y-T-P-R—OH,

-continued

Example 46A

H—G-I-V-E-Q-C-C-T-S-I—C-S-L-Y-Q-L-E-N-Y-C—N—OH

H-G-K-S-H-K-F-V-N-Q—H-L-C-G-S-H-L-V-E-A————L-Y-L-V-C-G-K-R-G-F—F-Y-T-P-R—OH,

Example 47A

H—G-I-V-E-Q-C-C-T-S-I—C-S-L-Y-Q-L-E-N-Y-C—N—OH

H-G-K-S-H-K-F-V-N-Q—H-L-C-G-S-H-L-V-E-A————L-Y-L-V-C-G-K-R-G-F—F-Y-T-P-R—OH,

2609                                                    2610

-continued

Example 48A

H—G-I-V-E-Q-C-C-T-S-I—C-S-L-Y-Q-L-E-N-Y-C—N—OH

H—G-K-S-H-K-F-V-N-Q—H-L-C-G-S-H-L-V-E-A——L-Y-L-V-C-G-K-R-G-F—F-Y-T-P-R—OH,

-continued

Example 49A

H—G-I-V-E-Q-C-C-T-S-I—C-S-L-Y-Q-L-E-N-Y-C—N—OH

H—G-K-S-H-K-F-V-N-Q—H-L-C-G-S-H-L-V-E-A————L-Y-L-V-C-G-K-R-G-F—F-Y-T-P-R—OH,

Example 50A

H—G-I-V-E-Q-C-C-T-S-I—C-S-L-Y-Q-L-E-N-Y-C—N—OH

H-G-K-S-H-K-F-V-N-Q—H-L-C-G-S-H-L-V-E-A————L-Y-L-V-C-G-K-R-G-F—F-Y-T-P-R—OH,

2613                                                      2614

-continued

Example 51A

H—G-I-V-E-Q-C-C-T-S-I—C-S-L-Y-Q-L-E-N-Y-C—N—OH

H—G-K-S-H-K-F-V-N-Q—H-L-C-G-S-H-L-V-E-A————L-Y-L-V-C-G-K-R-G-F—F-Y-T-P-R—OH,

Example 52A

H-G-I-V-E-Q-C-C-T-S-I—C-S-L-Y-Q-L-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH,

Example 53A

H-G-I-V-E-Q-C-C-T-S-I—C-S-L-Y-Q-L-E-N-Y-C-N-OH

H-G-K-G-S-H-K-F-V-N-Q——H-L-C-G-S-H-L-V-E-A—L-Y-L-V-C-G-K-R-G-F-F-Y-T-P-R-OH,

2617  2618

-continued

Example 54A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH, 2619                                                                              2620

Example 55A

H-G-I-V-E-Q-C-C-T-S-I—C-S-L-Y-Q-L-E-N-Y-C-N-OH

H-G-K-G-S-H-K-F-V-N-Q——H-L-C-G-S-H-L-V-E-A——L-Y-L-V-C-G-K-R-G-F-F-Y-T-P-R-OH,

Example 56A

H-G-I-V-E-Q-C-C-T-S-I——C-S-L-Y-Q-L-E-N-Y-C-N-OH

H-G-K-G-S-H-K-F-V-N-Q——H-L-C-G-S-H-L-V-E-A——L-Y-L-V-C-G-K-R-G-F-F-Y-T-P-R-OH,

2621                                    2622

Example 57A

H-G-I-V-E-Q-C-C-T-S-I-C-S-L-Y-Q-L-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH,

Example 58A

H-G-I-V-E-Q-C-C-T-S-I—C-S-L-Y-Q-L-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH,

Example 59A

H-G-I-V-E-Q-C-C-T-S-I—C-S-L-Y-Q-L-E-N-Y-C-N-OH

H-G-K-G-S-H-K-F-V-N-Q——H-L-C-G-S-H-L-V-E-A—L-Y-L-V-C-G-K-R-G-F-F-Y-T-P-R-OH,

2625                                                                    2626

-continued

Example 60A:

-continued

-continued

Example 61A:

-continued 2633                                                                                2634

-continued

Example 62A:

H—G—I—V—E—Q—C—C—T—S—I—C—

H—G—K—G—S—H—K—F—V—N—Q—H—L—C—G—S—H—L—V—E—

-continued

-continued

Example 63A:

H—G—I—V—E—Q—C—C—T—S—I—C—

H—G—K—G—S—H—K—F—V—N—Q—H—L—C—G—S—H—L—V—E—

-continued

-continued

Example 64A:

-continued

-continued

Example 65A:

H—G—I—V—E—Q—C—C—T—S—I—C—

H—G—K—G—S—H—K—F—V—N—Q—H—L—C—G—S—H—L—V—E—

-continued

—S—L—Y—Q—L—E—N—Y—C—N—OH

—A————L—Y—L—V—C—G—K—R—G—F———F—Y—T—P—R—OH,

Example 66A:

-continued

Example 67A:

-continued

Example 68A:

H—G—I—V—E—Q—C—C—T—S—I—C—

H—G—K—G—S—H—K—F—V—N—Q—H—L—C—G—S—H—L—V—E—

-continued 2657 2658

-continued

Example 69A:

H—G—I—V—E—Q—C—C—T—S—I—C—

H—G—K—G—S—H—K—F—V—N—Q—H—L—C—G—S—H—L—V—E—

-continued

-continued

Example 70A:

H—G—I—V—E—Q—C—C—T—S—I—C—

H—G—K—G—S—H—K—F—V—N—Q—H—L—C—G—S—H—L—V—E—

-continued

-continued

Example 71A:

H—G—I—V—E—Q—C—C—T—S—I—C—

H—G—K—G—S—H—K—F—V—N—Q—H—L—C—G—S—H—L—V—E—

-continued

S—L—Y—Q—L—E—N—Y—C—N—OH

A——L—Y—L—V—C—G—K—R—G—F——F—Y—T—P—R—OH,

Example 72A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH,

-continued

Example 73A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH,

Example 74A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH

Example 75A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH,

Example 76A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH,

-continued

Example 77A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH,

Example 78A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH,

-continued

Example 79A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-K-T-OH,

Example 80A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH

2677

2678

Example 81A

2679

2680

-continued

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

Example 82A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH

2681

2682

-continued

Example 83A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH

,

-continued

Example 84A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH,

-continued

Example 85A

H—G-I-V-E-Q-C-C-T-S-I-C-S-L-Y-Q-L-E-N-Y-C-N—OH

H—G-K-G-S-H-K-F-V-N-Q-H-L-C-G-S-H-L-V-E-A-L-Y-L-V-C-G-K-R-G-F-F-Y-T-P-R—OH or a pharmaceutically acceptable salt thereof, an isotope thereof, and combinations thereof.

35. A compound selected from the group consisting of a polypeptide comprising an A-chain and a B-chain, wherein the A-chain comprises a sequence selected from 1, 24051, and 24052; and wherein the B-chain comprises a sequence selected from SEQ ID NOs 24063, 25228, 25229, 25232, 25305, 25308, 25312, 25236, 25095, and 25380-25397.

36. A pharmaceutical composition comprising at least one compound or a pharmaceutically acceptable salt thereof according to any one of embodiments 1-35 and a pharmaceutically acceptable carrier.

37. The compound of any one of embodiments 1-35, or a pharmaceutically acceptable salt thereof, wherein X1 is an insulin further comprising from 1 to 5 residues replaced, inserted, appended, or mutated to an amino acid that has a free amine conjugated via one or more of the Z1b to a Z1c.

38. The compound of any one of embodiments 1-35, or a pharmaceutically acceptable salt thereof, wherein at least one Z1c is conjugated via one or more of the Z1b to a free amine side chain of an amino acid in X1 that has been replaced, inserted, or mutated on an insulin.

39. A compound of the following formula, or a stereoisomer or a mixture of stereoisomers, or pharmaceutically acceptable salt thereof

2687                                 2688

Z1c-Linker wherein the Z1c-Linker is selected from:

FFL-1

FFL-2

FFL-3

FFL-4

FFL-5

-continued

FFL-6

FFL-7

FFL-8　　　　　　　　　　　　　　　　　　FFL-9

FFL-10　　　　　　　　　　　　　　　　　　FFL-11

-continued

FFL-12

FFL-13

FFL-14

2693                                                                                                  2694

FFL-15                                                                                              FFL-16

FFL-17                                                                                              FFL-18

FFL-19                                                                                              FFL-20

2695            2696

FFL-21

FFL-22

FFL-23

FFL-24

FFL-25

FFL-26

2697 2698

FFL-27

FFL-28

FFL-29

FFL-30

FFL-31

FFL-32

2699                                                    2700

FFL-33                                                 FFL-34

FFL-35                                                 FFL-36

FFL-37                                                 FFL-38

-continued

FFL-39

FFL-40

FFL-41

FFL-42

2703

2704

FFL-43

FFL-44

FFL-45

FFL-46

FFL-47

FFL-48

-continued

FFL-49

FFL-50

FFL-51

FFL-52

FFL-53

2707

2708

FFL-54

FFL-55

FFL-56

FFL-57

FFL-58

FFL-59

-continued

FFL-60

FFL-61

FFL-62

FFL-63

FFL-64

FFL-65

-continued

FFL-66

FFL-67

FFL-68 wherein X is selected from a leaving group, $NH_2$, and H; and

B$_1$ and B$_2$, which may be identical or different, each independently represents an aromatic boron-containing group.

40. The compound of embodiment 39, or a pharmaceutically acceptable salt thereof, comprising at least one B$_1$ or B$_2$ independently selected from Formulae F2 and F7, wherein Formulae F2 and F7 are:

(F2)

-continued (F7)

wherein:

R$_1$ at position 5' represents (C=O)—*, wherein —* represents the attachment point to the rest of Z1c;

each remaining R$_1$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_mCH_3$, and $OCF_3$, wherein m is 1, 2, 3, 4, 5, 6, or 7;

Y8 is O, or Y8 is NR, wherein R is a $C_1$-$C_6$alkyl group or H; and each Y10 is independently selected from H, $CH_3$, F, and $CF_3$, wherein for at least one F7 at least one Y10 is not H.

41. The compound of embodiment 39, wherein the Z1c-Linker is selected from:

2713

2714

DSL-1

DSL-2

DSL-3

DSL-4

-continued

DSL-5

DSL-6

2717                                                                                            2718

DSL-7

DSL-8                                                           DSL-9

2719                                                                                              2720

DSL-10                                                                                                DSL-11

DSL-12

-continued

DSL-13

DSL-14

2723

2724

-continued

DSL-15

DSL-16

DSL-17

DSL-18

2725

2726

DSL-19

DSL-20

2727                                                                    2728

DSL-21

DSL--22                                                                    DSL-23

2729

2730

DSL-24

DSL-25

DSL-26

-continued

DSL-27

DSL-28

2733 2734

DSL29 DSL-30

DSL-31 DSL-32

2735                                                                 2736

-continued

DSL-33                                                           DSL-34

DSL-35                                                           DSL-36

2737                                              2738

-continued

DSL-37                                          DSL-38

DSL-39                                          DSL-40

2739

2740

DSL-41

DSL-42

DSL-43

DSL-44

2741                                                                    2742

DSL-45

DSL-46

DSL-47

2743                                 2744

-continued

DSL-48

DSL-49

DSL-50

DSL-51

2745 2746

-continued

DSL-52

DSL-53

DSL-54

DSL-55

2747 2748

DSL56 DSL-57

DSL-58 DSL-59

2749      2750

-continued

DSL-60      DSL-61

DSL-62      DSL-63

2751

2752

DSL-64

DSL-65

DSL-66

DSL-67

2753           2754

DSL-68        DSL-69

DSL-70        DSL-71

2755                                    2756

DSL-72                                                      DSL-73

DSL-74

-continued

DSL-75

DSL-76

2759            2760

-continued

DSL-77

DSL-78

DSL-79

2761                                                              2762

-continued

DSL-80

DSL-81

-continued

DSL-82

DSL-83

2765 2766

DSL-84

DSL-85

DSL-86

2767

2768

DSL-87

DSL-88

DSL-89

-continued

DSL-90

DSL-91

2771

2772

DSL-92

DSL-93

DSL-94

-continued

DSL-95

DSL-96

-continued

DSL-97

DSL-98

2777                                                                      2778

DSL-99                                                                          DSL-100

DSL-101                                                                         DSL102

2779                                                                                2780

DSL-103                                                                             DSL-104

DSL-105                                                                             DSL-106

2781

2782

-continued

DSL-107

DSL-108

DSL-109

DSL-110

DSL-111

DSL-112

2783            2784

-continued

DSL-113            DSL-114

DSL-115            DSL-116

2785 2786

DSL-117

DSL-118

DSL-119

DSL-120

2787                                                                  2788

DSL-121                                                              DSL-122

DSL-123                                                              DSL-124

2789　　　　　　　　　　　　　　　　　　　　2790

DSL-125　　　　　　　　　　　　　　　　　　DSL-126

DSL-127　　　　　　　　　　　　　　　　　　DSL-128

2791 2792

DSL-129

DSL-130

DSL-131

DSL-132

2793                                                                                    2794

DSL-133

DSL-134

DSL-135

DSL-136

2795                                                              2796

DSL-137                                                          DSL-138

DSL-139                                                          DSL-140

DSL-141                                                          DSL-142

2797                                                                 2798

DSL-143                                                               DSL-144

DSL-145                                                               DSL-146

DSL-147                                                               DSL-148

2799

2800

DSL-149

DSL-150

DSL-151

DSL-152

2801

2802

-continued

DSL-153

DSL-154

DSL-155

DSL-156

DSL-157

DSL-158

2803                                                                 2804

DSL-159                                                                 DSL-160

DSL-161                                                                 DSL-162

2805

2806

-continued

DSL-163

DSL-164

DSL-165

DSL-166

-continued

DSL-167

DSL-168

DSL-169

DSL-170

DSL-171

DSL-172

-continued

DSL-173

DSL-174

O, and

-continued

DSL-175 or a stereoisomer or a mixture of stereoisomers, a pharmaceutically acceptable salt thereof, and combinations thereof; wherein X is a leaving group.

42. The compound of embodiment 41, or a pharmaceutically acceptable salt thereof, wherein X is selected from N-oxysuccinimide, 2,3,5,6-tetrafluorophenoxy (TFP), pentafluorophenoxy (Pfp), OH, halogen, maleimide alkyl amino, maleimide amido polyethylene glycol amino, and maleimide polyethylene glycol amino.

43. The compound of embodiment 42, wherein the compound is selected from:

DSL-1A

DSL-2A

2813                                                 2814

DSL-3A                                                    DSL-4A

DSL-5A

DSL-6A 2815            2816

-continued

DSL-7A

DSL-8A        DSL-9A

DSL-10A        DSL-11A

-continued

DSL-12A

DSL-13A 2819 2820

DSL-14A

DSL-15A

DSL-16A

2821

2822

DSL-17A

DSL-18A

DSL-19A

-continued

DSL-20A

DSL-21A 2825       2826

DSL-22A       DSL-23A

DSL-24A       DSL-25A

-continued

DSL-26A

DSL-27A

2829

2830

DSL-28A

DSL-29A

DSL-30A 2831                                                                                    2832

DSL-31A                                                                                    DSL-32A

DSL-33A                                                                                    DSL-34A

2833

2834

DSL-35A

DSL-36A

DSL-37A

DSL-38A

2835                                                              2836

DSL-39A                                                              DSL-40A

DSL-41A                                                              DSL-42A

2837                                             2838

-continued

DSL-43A                                          DSL-44A

DSL-45A                                          DSL-46A

-continued

DSL-47A

DSL-48A

DSL-49A

DSL-50A

2841

2842

DSL-51A

DSL-52A

DSL-53A

DSL-54A

2843

2844

-continued

DSL-55A

DSL-56A

DSL-57A

DSL-58A 2845                                            2846

-continued

DSL-59A

DSL-60A

DSL-61A

DSL-62A

2847

2848

DSL-63A

DSL-64A

DSL-65A

DSL-66A 2849 2850

DSL-67A

DSL-68A

DSL-69A

DSL-70A

2851                                                                                           2852

DSL-71A                                                                                           DSL-72A

DSL-73A                                                                                           DSL-74A

DSL-75A

-continued

DSL-76A

DSL-77A

2855 2856

DSL-78A

DSL-79A

DSL-80A 2857                                                                 2858

DSL-81A

DSL-82A

-continued

DSL-83A

DSL-84A

2861                                                                     2862

DSL-85A                                                                      DSL-86A

DSL-87A                                                                      DSL-88A

-continued

DSL-89A

DSL-90A

-continued

DSL-91A

DSL-92A

DSL-93A

-continued

DSL-94A

DSL-95A

-continued

DSL-96A

DSL-97A

2871                             2872

-continued

DSL-98A

DSL-99A

DSL-100A 2873 2874

DSL-101A

DSL-102A

DSL-103A

DSL-104A 2875 2876

DSL-105A DSL-106A

DSL-107A DSL-108A

2877
                 2878

-continued

DSL-109A
                 DSL-110A

DSL-111A
                 DSL-112A

2879

2880

DSL-113A

DSL-114A

DSL-115A

DSL-116A

2881

2882

DSL-117A

DSL-118A

DSL-119A

DSL-120A 2883 2884

-continued

DSL-121A

DSL-122A

DSL-123A

DSL-124A 2885                                                                 2886

DSL-125A                                                         DSL-126A

DSL-127A                                                         DSL-128A

-continued

DSL-129A

DSL-130A

DSL-131A

DSL-132A

DSL-133A

DSL-134A

2889            2890

-continued

DSL-135A

DSL-136A

DSL-137A

DSL-138A

2891

2892

DSL-139A

DSL-140A

DSL-141A

DSL-142A

DSL-143A

DSL-144A

2893                                                                        2894

DSL-145A

DSL-146A

DSL-147A

DSL-148A

DSL-149A

DSL-150A

2895

2896

-continued

DSL-151A

DSL-152A

DSL-153A

DSL-154A

DSL-155A

DSL-156A 2897 2898

DSL-157A

DSL-158A

DSL-159A

DSL-160A

DSL-161A

DSL-162A

2899

2900

DSL-163A

DSL-164A

DSL-165A

DSL-166A

2901

2902

DSL-167A

DSL-168A

DSL-169A

DSL-170A

DSL-171A

DSL-172A

-continued

DSL-173A

DSL-174A

-continued

DSL-175A

, or a stereoisomer or a mixture of stereoisomers, a pharmaceutically acceptable salt thereof, and combinations thereof.

44. A polypeptide comprising an A-chain and a B-chain, wherein the A-chain comprises a sequence selected from 1, 24051, and 24052; and wherein the B-chain comprises a sequence selected from 25000-25397.

45. The polypeptide of embodiment 44, wherein the A-chain comprises a sequence selected from 1, 24051, and 24052; and wherein the B-chain comprises a sequence selected from 24063, 25228, 25229, 25000, 25001, 25006-25009, 25076, 25077, 25082-25085, 25228, 25229, 25232, 25234-25237, 25304, 25305, 25308, and 25310-25313.

46. The polypeptide of embodiment 44, wherein the A-chain comprises a sequence selected from 1 and 24051; and wherein the B-chain comprises a sequence selected from 24063, 25228, 25229, 25011, 25012, 25017-25020, 25087, 25088, 25093-25096, 25229, 25239, 25232, 25240, 25245-25248, 25305, 25308, 25315, 25316, and 25321-25324.

47. The polypeptide of embodiment 44, wherein the A-chain comprises a sequence selected from 1 and 24051; and wherein the B-chain comprises a sequence selected from 24063, 25228, 25229, 25232, 25234-25237, 25304, 25305, 25308, and 25310-25313.

48. A compound having agonist potency for an insulin receptor comprising at least one aromatic boron-containing group having agonist potency for an insulin receptor, or a pharmaceutically acceptable salt thereof, the compound having a first EC50 potency for activating the insulin receptor at a first glucose concentration and a second EC50 potency for activating the insulin receptor at a second glucose concentration, wherein when the first glucose concentration is 5.6 mM and the second glucose concentration is 16.7 mM the compound has an insulin receptor agonist potency ratio of the first EC50 to the second EC50 of about 1.2 to about 20, about 1.5 to about 15, about 2 to about 14, about 2.5 to about 13, about 2.5 to about 12, about 2.5 to about 11, about 2.5 to about 10, about 2.5 to about 9, about 2.5 to about 8, about 2.5 to about 7, about 2.5 to about 6, about 2.5 to about 5, or about 2.5 to about 4.5.

49. A compound having agonist potency for glucose comprising at least one aromatic boron-containing group having binding affinity for glucose, or a pharmaceutically acceptable salt thereof, wherein when administered at a dose of 30 nmol/kg to a first group of rats with a first glucose infusion rate to provide a blood glucose concentration of 100 mg/dL and to a second group of rats with a second glucose infusion rate to provide a blood glucose concentration of 200 mg/dL the compound provides a relative glucose infusion rate difference (mg/kg/min·min) of about 1 to about 2500, about 1 to about 2000, about 1 to about 1500, about 100 to about 1500, and about 1000 to about 1500, and a relative glucose infusion rate ratio of about 0.1 to about 5, about 0.2 to about 4.5, about 0.5 to about 4, about 0.5 to about 3.5, about 1 to about 3.5, about 1.5 to about 3.5, or about 2 to about 3.

50. The compound of embodiment 48 or 49, or pharmaceutically acceptable salt thereof, wherein the at least one aromatic boron-containing group is attached to an FF scaffold, wherein the FF scaffold is selected from Formulae FF12A, FF12B, FF12C, FF12D, FF116A, FF116B, FF116C, FF116D, FF225, and FF227.

51. The compound of embodiment 48 or 49, or pharmaceutically acceptable salt thereof, wherein the at least one aromatic boron-containing group comprises at least one $B_1$ and $B_2$, which may be identical or different.

52. The compound of embodiment 51, or pharmaceutically acceptable salt thereof, wherein at least one of the $B_1$ and the $B_2$ is Formula F2 or Formula F7.

53. The compound of embodiment 1, or pharmaceutically acceptable salt thereof, wherein the compound comprises a diboronate covalently conjugated to an amine in X1, and a diol or polyol containing moiety conjugated to an amine in X1.

54. The compound of embodiment 53, or pharmaceutically acceptable salt thereof, wherein the X1 is an insulin or analog thereof comprising an A-chain and a B-chain.

55. The compound of embodiment 54, or pharmaceutically acceptable salt thereof, wherein the amine to which the diboronate is covalently conjugated is at or near the C-terminus of the B-chain, preferably to an amine of a B29 lysine or a B21 lysine, and the amine to which the polyol is conjugated is at or near the N-terminus of the A-chain or B chain.

56. The compound of embodiment 54, or pharmaceutically acceptable salt thereof, wherein the amine to which the polyol is covalently conjugated is at or near the C-terminus of the B-chain, preferably to an amine of a B29 lysine or a B21 lysine, and the amine to which the diboronate is conjugated is at or near the N-terminus of the A-chain or B chain.

57. A compound according to any one of embodiments 1-35 and 48-56, or pharmaceutically acceptable salt thereof, for use as a medicament.

58. A method of treatment or prevention of diabetes, impaired glucose tolerance, hyperglycemia or metabolic syndrome, wherein the method comprises administering to a subject in need thereof the compound of any one of embodiments 1-35, 37-43, and 48-56, or a pharmaceutical composition according to embodiment 36.

59. A compound according to any one of embodiments 1-35, 37-43, and 48-56, or the pharmaceutical composition according to embodiment 36, for use in the treatment or prevention of diabetes, impaired glucose tolerance, hyperglycemia or metabolic syndrome.

60. Use of the compound according to any one of embodiments 1-35, 37-43, and 48-56, or the pharmaceutical composition according to embodiment 36, in the manufacture of a medicament.

61. A compound according to any one of embodiments 1-35, 37-43, and 48-56, or the pharmaceutical composition according to embodiment 36, for use as a therapeutic agent for the treatment of diabetes or obesity, for control of blood sugar levels, or for control of release of a drug.

62. A method of administering the compound of any one of embodiments 1-35, 37-43, and 48-56, or a pharmaceutical composition according to embodiment 36 to a subject, wherein the method comprises administering to the subject the compound as a therapeutic or prophylactic agent.

63. A method of treating a subject by administering a device or formulation comprising a compound of any one of embodiments 1-35, 37-43, and 48-56.

64. Use of the compound according to any one of embodiments 1-35, 37-43, and 48-56 as an intermediate in the synthesis of a drug substance or a therapeutic of a prophylactic compound.

65. A device or formulation comprising the compound of any one of embodiments 1-35, 37-43, and 48-56, or a pharmaceutical composition according to embodiment 36.

66. A compound comprising at least one diboronate, wherein the diboronate comprises at least two aromatic boron-containing groups, wherein at least one aromatic boron-containing group is covalently attached to the compound and selected from F3-F11, and the other aromatic boron-containing group is covalently attached to the compound and optionally selected from F1-F11 or a boronic acid, (F1)

-continued (F2)

(F3)

(F4)

(F5)

(F6)

(F7)

(F8)

-continued (F9)

(F10)

(F11)

wherein at least one R1 in each of F1-F11 is covalently attached to the compound, and each remaining $R_1$ and $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH(CH_2)_mCH_3$, and $OCF_3$, wherein m is 1, 2, 3, 4, 5, 6, or 7, wherein, for Formulae F3-F4:

$R_w$ is O or S;

for Formula F6:

when Y8 is O, i is 1, 2, 3, 4, or 5; or i is 2, 3, 4, or 5; and none, one, or two $R_1$ represents F, Cl, $CF_2$, $CF_3$, $SF_5$, $OCF_3$, $SO_2CH_3$ and/or $SO_2CF_3$; or when Y8 is NR, R is an alkyl group or H, and i is 1, 2, 3, 4, or 5;

for Formulae F5 and F7-F10:

when Y8 is O, i is 1, 2, 3, 4, or 5; or when Y8 is NR, R is an alkyl group or H, and i is 1, 2, 3, 4, or 5;

Y9 is $CH_3$, F, $CF_3$, $CHF_2$, or $OCH_3$; and each Y10 is independently selected from H, $CH_3$, F, $CF_3$, $CHF_2$, and $OCH_3$, with the proviso that at least one Y10 is not H.

67. The compound of embodiment 66, wherein the compound is a diboron containing compound.

68. The compound of embodiment 66, wherein the compound is a diboron containing compound.

69. The compound of embodiment 66, wherein the at least one aromatic boron-containing group is F7.

70. The compound of embodiment 66, wherein the at least one aromatic boron-containing group is F7, and wherein Y8 is O and each Y10 is $CH_3$.

71. The compound of any one of embodiments 66-70 comprising X1 and one or more Z1c, or a tautomer, stereoisomer or a mixture of stereoisomers, or a pharmaceutically acceptable salt, or hydrate, or isotopic derivative thereof, wherein:

X1 comprises:

i. $NH_2$ or OH;

ii. a drug substance comprising an amine;

iii. a drug substance that is covalently conjugated to an amine containing linker; or iv. an amine configured to be covalently conjugated to a drug substance;

wherein each Z1c is covalently conjugated, directly or indirectly, to an amine in X1 or to OH when X1 is OH, and wherein each Z1c is independently selected from:

a) Formulae FF1-FF48, wherein Formulae FF1-FF48 are:

(FF1)

(FF2)

(FF3)

(FF4)

(FF5)

(FF6)

-continued (FF7)

(FF8)

(FF9)

(FF10)

(FF11)

(FF12)

(FF13)

-continued (FF14)

(FF15)

(FF16)

(FF17)

(FF18)

(FF19)

(FF20)

-continued (FF21)

(FF22)

(FF23)

(FF24)

(FF25)

(FF26)

(FF27)

-continued (FF28)

(FF29)

(FF30)

(FF31)

(FF32)

(FF33)

(FF34)

(FF35)

2915

-continued (FF36)

(FF37)

(FF38)

(FF39)

(FF40)

(FF41)

(FF42)

(FF43)

(FF44)

2916

-continued (FF45)

(FF46)

(FF47) and (FF48)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

j is 1, 2, 3, 4, 5, 6, or 7; and $B_1$ and $B_2$, which may be identical or different, each independently represents the aromatic boron-containing groups;

b) Formulae FF49-FF88, wherein Formulae FF49-FF88 are:

(FF49)

(FF50)

(FF51)

-continued

-continued (FF52)

(FF53)

(FF54)

(FF55)

(FF56)

(FF57)

(FF58)

(FF59)

(FF60)

(FF61)

(FF62)

(FF63)

(FF64)

(FF65)

(FF66)

(FF67)

(FF68)

2919

-continued (FF69)

(FF70)

(FF71)

(FF72)

(FF73)

(FF74)

(FF75)

2920

-continued (FF76)

(FF77)

(FF78)

(FF79)

(FF80)

(FF81)

-continued (FF82)

(FF83)

(FF84)

(FF85)

(FF86)

(FF87)

and

-continued (FF88)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

j is 1, 2, 3, 4, 5, 6, or 7;

R1a is selected from COOH, $CH_3$, H, and OH;

R2, R3, R4 and R5 are each independently selected from $CH_3$, H, OH, and COOH, and at least one of R2, R3, R4 and R5 is $CH_3$ or OH; and $B_1$ and $B_2$, which may be identical or different, are each independently the aromatic boron-containing groups;

c) Formulae FF89-FF112, wherein Formulae FF89-FF112 are:

(FF89)

(FF90)

2923

-continued (FF91)

(FF92)

(FF93)

(FF94)

(FF95)

(FF96)

2924

-continued (FF97)

(FF98)

(FF99)

(FF100)

(FF101)

(FF102)

2925

-continued (FF103)

2926

-continued (FF108)

(FF104)

(FF109)

(FF105)

(FF110)

(FF111)

(FF106)

and (FF112)

(FF107)

wherein X represents a point of covalent attachment either directly to an amine in X1 or to an amine that is covalently conjugated directly or indirectly to X1, or to OH when X1 is OH;

i is 1, 2, 3, 4, 5, 6, or 7; and $B_1$, $B_2$ and $B_3$, which may be identical or different, are each independently the aromatic boron-containing

2927 groups, a carboxylic acid derivative, or a H, wherein in each FF89-FF112 structure containing B1, B2 and B3 groups, at least two of the B1, B2 and B3 groups are independently the aromatic boron-containing groups;

d) Formulae FF113-FF136, wherein Formulae FF113-FF136 are:

(FF113)

(FF114)

(FF115)

(FF116)

(FF117)

(FF118)

2928

-continued (FF119)

(FF120)

(FF121)

(FF122)

(FF123)

(FF124)

(FF125)

(FF126)

(FF127)

(FF128)

(FF129)

(FF130)

(FF131)

(FF132)

(FF133)

(FF134)

(FF135)

and (FF136)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

j is 1, 2, 3, 4, 5, 6, or 7;

k is 1, 2, 3, 4, 5, 6, or 7;

m is 1, 2, 3, 4, 5, 6, or 7;

each R1 is independently selected from H, an alkyl group, an acyl group, a cycloalkyl group, a haloalkyl group, an aryl group, and a heteroaryl group, each R1 optionally comprises one or more alkyl-halide, halide, sulfhydryl, aldehyde, amine, acid, hydroxyl, alkyl, or aryl groups; and $B_1$ and $B_2$, which may be identical or different, each independently represents the aromatic boron-containing groups;

e) Formulae FF137-FF160, wherein Formulae FF137-FF160 are:

2931

2932

(FF137)

(FF144)

(FF138)

(FF145)

(FF139)

(FF146)

(FF140)

(FF147)

(FF141)

(FF148)

(FF142)

(FF149)

(FF143)

(FF150)

2933

-continued (FF151)

(FF152)

(FF153)

(FF154)

(FF155)

(FF156)

2934

-continued (FF157)

(FF158)

(FF159)

and (FF160)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

j is 1, 2, 3, 4, 5, 6, or 7;

k is 1, 2, 3, 4, 5, 6, or 7;

m is 1, 2, 3, 4, 5, 6, or 7;

each R1 is independently selected from H, an alkyl group, an acyl group, a cycloalkyl group, a haloalkyl group, an aryl group, and a heteroaryl group, each R1 optionally comprises one or more alkyl-halide, halide, sulfhydryl, aldehyde, amine, acid, hydroxyl, alkyl, or aryl groups; and $B_1$ and $B_2$, which may be identical or different, each independently represents the aromatic boron-containing groups;

f) Formulae FF161-FF164, wherein Formulae FF161-FF164 are:

(FF161)

2935

-continued (FF162)

(FF163)

(FF164)

wherein X represents a point of covalent attachment either directly to an amine in X1 or to an amine that is covalently conjugated directly or indirectly to X1, or to OH when X1 is OH;

i is 1, 2, 3, 4, or 5;

j is 1, 2, 3, 4, or 5;

each R6, R7, R8, and R9 for different values of j is independently selected from H, CF₃, CH₃, CHF₂, and (CH₂)ₘCH₃, wherein m is 1, 2, 3, 4, or 5;

Y3, Y4, Y5, Y6 and Y7 are each independently selected from H, CH₂—X4, and Formulae IV-1 to IV-135;

wherein X4 is selected from —COOH, —(CH₂)ₘCOOH, an alkyl group, an acyl group, a cycloalkyl group, a haloalkyl group, an aryl group, and a heteroaryl group, each X4 optionally comprises one or more alkyl-halide, halide, sulfhydryl, aldehyde, amine, acid, hydroxyl, alkyl or aryl groups; wherein m is 1, 2, 3, 4, or 5;

wherein at least one of Y5, Y6 and Y7 in Formulae FF162 and FF163 is not H and at least one of Y7, R8 and R9 in FF164 is not H; and wherein Formulae IV-1 to IV-135 are:

(IV-1)

(IV-2)

2936

-continued (IV-3)

(IV-4)

(IV-5)

(IV-6)

(IV-7)

(IV-8)

(IV-9)

(IV-10)

(IV-11)

(IV-12)

(IV-13)

2937

-continued (IV-14)

(IV-15)

(IV-16)

(IV-17)

(IV-18)

(IV-19)

(IV-20)

(IV-21)

(IV-22)

(IV-23)

(IV-24)

2938

-continued (IV-25)

(IV-26)

(IV-27)

(IV-28)

(IV-29)

(IV-30)

(IV-31)

(IV-32)

(IV-33)

(IV-34)

(IV-35)

(IV-36)

(IV-37)

2939

-continued (IV-38)

(IV-39)

(IV-40)

(IV-41)

(IV-42)

(IV-43)

(IV-44)

(IV-45)

(IV-46)

(IV-47)

(IV-48)

2940

-continued (IV-49)

(IV-50)

(IV-51)

(IV-52)

(IV-53)

(IV-54)

(IV-55)

(IV-56)

2941

-continued (IV-57)

(IV-58)

(IV-59)

(IV-60)

(IV-61)

(IV-62)

60 (IV-63)

2942

-continued (IV-64)

(IV-65)

(IV-66)

(IV-67)

(IV-68)

(IV-69)

2943

-continued (IV-70)

(IV-71)

(IV-72)

(IV-73)

(IV-74)

(IV-75)

(IV-76)

2944

-continued (IV-77)

(IV-78)

(IV-79)

(IV-80)

(IV-81)

(IV-82)

(IV-83)

(IV-84)

(IV-85)

2945

-continued (IV-86)

(IV-87)

(IV-88)

(IV-89)

(IV-90)

(IV-91)

(IV-92)

(IV-93)

(IV-94)

2946

-continued (IV-95)

(IV-96)

(IV-97)

(IV-98)

(IV-99)

(IV-100)

(IV-101)

(IV-102)

(IV-103)

2947

-continued (IV-104)

(IV-105)

(IV-106)

(IV-107)

(IV-108)

(IV-109)

2948

-continued (IV-110)

(IV-111)

(IV-112)

(IV-113)

(IV-114)

(IV-115)

(IV-116)

(IV-117)

(IV-118)

(IV-119)

2949

-continued (IV-120)

(IV-121)

(IV-122)

(IV-123)

(IV-124)

(IV-125)

(IV-126)

(IV-127)

2950

-continued (IV-128)

(IV-129)

(IV-130)

(IV-131)

(IV-132)

(IV-133)

(IV-134)

and (IV-135)

wherein Xa represents CH=O, CHF$_2$, CF$_3$, CH$_2$SH, COOH, CH$_2$OH, CH$_2$NO$_2$, CH$_2$NH$_2$, CH$_3$, C(CH$_3$)$_3$, CH(CH$_3$)$_2$, CH((CH$_2$)$_3$—CH$_3$)$_2$, or CH(CH$_2$—CH$_3$)$_2$;

Xb represents O, NH, $CH_2$, or S;

Xc represents CH or N;

each $R_{10}$ is independently selected from H, F, Cl, Br, $CH_3$, $CF_3$, CH=O, OH, COOH, and $(CH_2)_nCH_3$, m is 1, 2, 3, 4, or 5; and n is 1, 2, 3, 4, or 5;

$B_1$ and $B_2$, which may be identical or different, each independently represents the aromatic boron-containing groups; and

* in Formulae IV-1 to IV-135 represents a point of attachment to corresponding Formulae FF161-164;

g) Formulae FF165-FF166, wherein Formulae FF165-FF166 are:

(FF165)

and (FF166)

and;

wherein X represents a point of covalent attachment either directly to an amine in X1 or to an amine that is covalently conjugated directly or indirectly to X1, or to OH when X1 is OH;

m is 1, 2, 3, 4, 5, 6, or 7;

n is 1, 2, 3, 4, 5, 6, or 7;

X5 is S, O, or NH; and each $R_1$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)$NH—$CH_3$, —$(SO_2)$NH$(CH_2)_mCH_3$, and $OCF_3$, wherein m is 1, 2, 3, 4, 5, 6, or 7;

h) Formulae FF167-FF192, wherein Formulae FF167-FF192 are:

(FF167)

(FF168)

(FF169)

(FF170)

(FF171)

(FF172)

(FF173)

(FF174)

(FF175)

2953

-continued (FF176)

(FF177)

(FF178)

25

(FF179)

(FF180)

(FF181)

(FF182)

2954

-continued (FF183)

(FF184)

(FF185)

(FF186)

(FF187)

(FF188)

(FF189)

2955

-continued (FF190)

(FF191)

and (FF192)

wherein X represents a point of covalent attachment either directly to an amine in X1 or to an amine that is covalently conjugated directly or indirectly to X1, or to OH when X1 is OH;

$B_1$ and $B_2$, which may be identical or different, each independently represents the aromatic boron-containing groups;

i) Formulae FF193-FF209, wherein Formulae FF193-FF209 are:

FF193

FF194

FF195

2956

-continued

FF196

FF197

FF198

FF199

FF200

FF201

FF202

FF203

2957

-continued

FF204

FF205

FF206

FF207

FF208

FF209 wherein R in FF208 and FF209 is an alkyl, aryl or halide that is covalently conjugated through at least one $CH_2$ group to the amino group in the side chain of FF208 or FF209, R1 and R2 are independently selected from H, $CH_3$, alkyl, and formulae IV-1 to IV-135;

i is 1, 2, 3, 4, or 5;

j is 1, 2, 3, 4, or 5; and wherein X represents a point of covalent attachment either directly to an amine in X1 or to an amine that is covalently conjugated directly or indirectly to X1, or to OH when X1 is OH; and $B_1$ and $B_2$, which may be identical or different, each independently represents the aromatic boron-containing groups;

j) Formulae FF210-FF224, wherein Formulae FF210-FF224 are:

2958

FF210

FF211

FF212

FF213

FF214

FF215

FF216

FF217

FF218

-continued

FF219

FF220

FF221

FF222

FF223

FF224

(FF225)

(FF226)

(FF227)

(FF228)

(FF229)

(FF230)

(FF231)

wherein R11 in FF210 to FF212 is selected from Formulae IV-1 to IV-135 and R12 is selected from an amine, a hydroxyl, an alkyl, and a halide group;

wherein each R13 is independently selected from H, CH₃, alkyl, aryl and Formulae IV-1 to IV-135; R14 is selected from H, CH₃, alkyl, aryl and heteroaryl;

wherein X represents a point of covalent attachment either directly to an amine in X1 or to an amine that is covalently conjugated directly or indirectly to X1, or to OH when X1 is OH;

X" represents a point of covalent attachment to an amine —N in the compound, wherein — represents a single covalent bond to a CH₂ or CH group in the compound;

i is 1, 2, 3, 4, or 5;

j is 1, 2, 3, 4, or 5; and

B₁, B₂, B₃, B₄, B₅, and B₆ each independently represents the aromatic boron-containing groups, wherein in each FF structure containing B₁, B₂ and B₃ groups, at least two of the B₁, B₂ and B₃ groups are independently the aromatic boron-containing groups; and k) Formulae FF225-FF231, wherein Formulae FF225-FF231 are:

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

$B_1$ and $B_2$, which may be identical or different, each independently represents the aromatic boron-containing groups; and wherein at least one primary or secondary amine in FF1-FF223 and FF225-231 is optionally covalently conjugated to $B_6$.

72. The compound of embodiment 71, wherein the at least one Z1c is FF227.

73. The compound of embodiment 72, wherein the least one Z1c is FF227 and i is 1.

74. The compound of embodiment 71, wherein the least one Z1c is selected from FF12-FF35, FF104-FF117, FF180-FF193, and FF196-FF205.

75. The compound of embodiment 71, wherein the compound is a molecular conjugate represented by the following formula, or a stereoisomer or a mixture of stereoisomers, or pharmaceutically acceptable salt thereof:

$$[[[Z1c]_{\overline{p'}}+Z1a\,)_{\overline{m'}}]_{\overline{o'}}+Z1b\,)_{\overline{n'}}]_{\overline{q'}}-X1,$$

wherein

X1 comprises:

(i) $NH_2$ or OH, (ii) a polypeptide drug substance comprising an amine, (iii) a polypeptide drug substance that is covalently conjugated to an amine containing linker, or (iv) an amine configured to be covalently conjugated to a polypeptide drug substance;

each Z1c is independently selected from Formulae FF1-FF231;

each Z1a independently comprises 1 to 50 amino acids connected together using amide or peptide bonds;

each Z1b is independently a small-molecule linker;

each m' is independently 0 or 1;

each n' is independently 0 or a positive integer;

each o' is independently an integer greater than or equal to 1;

each p' is a positive integer; and q' is a positive integer of at least 1 and not more than two times the total number of amine groups in X1, wherein when any of n', o', p', or q' is 2 or more, the corresponding groups Z1a, Z1b, and Z1c are independently selected and may be the same or different;

wherein each Z1c is independently covalently conjugated, directly or indirectly, to an amine of Z1a, to an amine of Z1b, or to X1; and wherein optionally the molecular conjugate may comprise one or more isotopes at any position of the molecular conjugate.

76. The compound of embodiment 71, wherein the compound comprises at least one group selected from $B_1$, $B_2$, $B_3$, $B_4$, $B_5$ and $B_6$, each independently selected from:

(F2)

(F7)

(F8)

(F11)

wherein for $B_1$, $B_2$, and $B_3$:

one $R_1$ represents (C=O)—*, wherein —* represents the attachment point to the rest of Z1c; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —($SO_2$)NH—$CH_3$, —($SO_2$)NH $(CH_2)_mCH_3$, and $OCF_3$, wherein m is 1, 2, 3, 4, 5, 6, or 7;

wherein for $B_4$ and $B_5$:

one $R_1$ for $B_4$ represents $(CH_2)_m$—ø, wherein —ø represents an attachment point to the rest of Z1c and one R1 for $B_5$ represents (C=O)—*, S(=O)(=O)—*, ($CH_2$) nm(C=O)—*, or $(CH_2)_m$—*, wherein —* represents an attachment point to the rest of Z1c, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$; CH=O, $SO_2CH_3$, $SO_2CF_3$, $CF_3$, $CHF_2$, $NO_2$, $CH_3$, $OCH_3$, $O(CH_2)_mCH_3$, ($SO_2$)NH—$CH_3$, —($SO_2$)NH $(CH_2)_mCH_3$, and $OCF_3$, wherein m is 1, 2, 3, 4, 5, 6, or 7;

wherein for $B_6$:

one $R_1$ for $B_6$ represents $(CH_2)_m$—ø, wherein —ø represents an attachment point to the rest of the compound, and m is 1, 2, 3, 4, 5, 6, or 7; and each remaining $R_1$ or $R_2$ is independently selected from H, F, Cl, Br, OH, $CH_2$—$NH_2$, $NH_2$, $(C=O)$—$NH_2$, $CH=O$, $SO_2CH_3$, $SO_2CF_3$, $CF_3$, $CHF_2$, $NO_2$, $CH_3$, $OCH_3$, $O(CH_2)_m CH_3$, —$(SO_2)NH$—$CH_3$, —$(SO_2)NH$ $(CH_2)_m CH_3$, and $OCF_3$, wherein m is 1, 2, 3, 4, 5, 6, or 7;

wherein for Formula F7:

Y8 is O; and each Y10 is independently selected from $CH_3$, F, and $CF_3$;

wherein for Formula F8:

Y8 is O;

i is 2, 3, 4, or 5; and each Y10 is independently selected from H, $CH_3$, F, and $CF_3$, with the proviso that at least one Y10 is not H; and — represents an attachment point to the rest of Z1c.

77. The compound of embodiment 71, wherein the compound comprises at least one group selected from $B_1$, $B_2$, $B_3$, $B_4$, $B_5$ and $B_6$, each independently selected from:

(F7A)

(F8A)

(F11)

wherein for $B_1$, $B_2$, and $B_3$:

$R_1$ at position 5' represents $(C=O)$—*, wherein —* represents the attachment point to the rest of Z1c; and each remaining $R_1$ or $R_2$ is independently selected from H, F, Cl, Br, OH, $CH_2$—$NH_2$, $NH_2$, $(C=O)$—$NH_2$, $CH=O$, $SO_2CH_3$, $SO_2CF_3$, $CF_3$, $CHF_2$, $NO_2$, $CH_3$, $OCH_3$, $O(CH_2)_m CH_3$, —$(SO_2)NH$—$CH_3$, —$(SO_2)NH$ $(CH_2)_m CH_3$, and $OCF_3$, wherein m is 1, 2, 3, 4, 5, 6, or 7;

wherein for $B_4$ and $B_5$:

one $R_1$ for $B_4$ represents $(CH_2)_m$—ø, wherein —ø represents an attachment point to the rest of $Z1_c$ and one $R_1$ for $B_5$ represents $(C=O)$—*, $S(=O)(=O)$—*, $(CH_2)_m(C=O)$—*, or $(CH_2)_m$—*, wherein —* represents an attachment point to the rest of Z1c, and m is 1, 2, 3, 4, 5, 6, or 7; and each remaining $R_1$ or $R_2$ is independently selected from H, F, Cl, Br, OH, $CH_2$—$NH_2$, $NH_2$, $(C=O)$—$NH_2$, $CH=O$, $SO_2CH_3$, $SO_2CF_3$, $CF_3$, $CHF_2$, $NO_2$, $CH_3$, $OCH_3$, $O(CH_2)_m CH_3$, —$(SO_2)NH$—$CH_3$, —$(SO_2)NH$ $(CH_2)_m CH_3$, and $OCF_3$, wherein m is 1, 2, 3, 4, 5, 6, or 7;

wherein for $B_6$:

one $R_1$ for $B_6$ represents $(CH_2)_m$—ø, wherein —ø represents an attachment point to the rest of the compound, and m is 1, 2, 3, 4, 5, 6, or 7; and each remaining $R_1$ or $R_2$ is independently selected from H, F, Cl, Br, OH, $CH_2$—$NH_2$, $NH_2$, $(C=O)$—$NH_2$, $CH=O$, $SO_2CH_3$, $SO_2CF_3$, $CF_3$, $CHF_2$, $NO_2$, $CH_3$, $OCH_3$, $O(CH_2)_m CH_3$, —$(SO_2)NH$—$CH_3$, —$(SO_2)NH$ $(CH_2)_m CH_3$, and $OCF_3$, wherein m is 1, 2, 3, 4, 5, 6, or 7;

wherein for Formula F7A:

Y8 is O; and wherein for Formula F8A:

Y8 is O; and i is 2, 3, 4, or 5; and

— represents an attachment point to the rest of Z1c.

78. The compound of any one of embodiments 71-77, wherein the $B_1$, $B_2$, $B_3$, $B_4$, $B_5$ and $B_6$ are each independently Formula F7A, (F7A)

wherein for $B_1$, $B_2$, and $B_3$:

$R_1$ at position 5' represents $(C=O)$—*, wherein —* represents the attachment point to the rest of Z1c; and each remaining $R_1$ is independently selected from H, F, Cl, Br, OH, $CH_2$—$NH_2$, $NH_2$, $(C=O)$—$NH_2$, $CH=O$, $SO_2CH_3$, $SO_2CF_3$, $CF_3$, $CHF_2$, $NO_2$, $CH_3$, $OCH_3$, $O(CH_2)_m CH_3$, —$(SO_2)NH$—$CH_3$, —$(SO_2)$ $NH(CH_2)_m CH_3$, and $OCF_3$, wherein m is 1, 2, 3, 4, 5, 6, or 7;

wherein for $B_4$ and $B_5$:

one $R_1$ for $B_4$ represents $(CH_2)_m$—ø, wherein —ø represents an attachment point to the rest of Z1c and one $R_1$ for $B_5$ represents $(C=O)$—*, $S(=O)(=O)$—*, $(CH_2)_m(C=O)$—*, or $(CH_2)_m$—*, wherein —* represents an attachment point to the rest of Z1c, and m is 1, 2, 3, 4, 5, 6, or 7; and each remaining $R_1$ is independently selected from H, F, Cl, Br, OH, $CH_2$—$NH_2$, $NH_2$, $(C=O)$—$NH_2$, $CH=O$, $SO_2CH_3$, $SO_2CF_3$, $CF_3$, $CHF_2$, $NO_2$, $CH_3$, $OCH_3$, $O(CH_2)_m CH_3$, —$(SO_2)NH$—$CH_3$, —$(SO_2)$ $NH(CH_2)_m CH_3$, and $OCF_3$, wherein m is 1, 2, 3, 4, 5, 6, or 7;

wherein for $B_6$:

one $R_1$ for $B_6$ represents $(CH_2)_m$—ø, wherein —ø represents an attachment point to the rest of the compound, and m is 1, 2, 3, 4, 5, 6, or 7; and each remaining $R_1$ is independently selected from H, F, Cl, Br, OH, $CH_2$—$NH_2$, $NH_2$, $(C=O)$—$NH_2$, $CH=O$, $SO_2CH_3$, $SO_2CF_3$, $CF_3$, $CHF_2$, $NO_2$, $CH_3$, $OCH_3$, $O(CH_2)_mCH_3$,    —$(SO_2)NH$—$CH_3$,    —$(SO_2)$$NH(CH_2)_mCH_3$, and $OCF_3$, wherein m is 1, 2, 3, 4, 5, 6, or 7;

Y8 is O; and

— represents an attachment point to the rest of Z1c

79. The compound of any one of embodiments 71-75, wherein at least one Z1c is covalently conjugated indirectly via a linker to an amine of X1 or to $NH_2$ when X1 is $NH_2$ or to OH when X1 is OH or to an amine of Z1a, wherein the linker is represented by Formula $(X'')_{n1}$, wherein each n1 is independently selected from 1, 2, 3, 4, and 5, and each X" is independently selected from:

i. an L- or D-amino acid, wherein an amine functional group of the L- or D-amino acid is covalently conjugated, directly or indirectly, to Z1c and an acid functional group of the L- or D- amino acid is conjugated, directly or indirectly, to X1 or to Z1a; and ii. Formulae FL(IA), FL(IB), FL69, and FL70;

wherein Formula FL(IA) and FL(IB) are:

FL(IA)

FL(IB)

and stereoisomers thereof;

wherein:

G is selected from a 3- to 6-membered cycloalkyl group, a 3- to 10-membered heterocyclyl group, a heteroaryl group, and an aryl group, wherein each group is optionally substituted with 1-3 groups independently selected from hydroxy, amino, halogen, cycloalkyl, alkoxy, and alkyl;

E is absent or is an alkylene group optionally substituted with 1-3 groups independently selected from halogen, hydroxy, and amino;

Q is absent or is selected from hydrogen, alkyl, halo, cyano, alkoxy, carboxylic acid, amino, hydroxy, amide, halo alkyl, cycloalkyl, heterocycle, heteroaryl, and aryl, wherein the alkyl, alkoxy, cycloalkyl, heterocycle, heteroaryl, and aryl is each optionally substituted with 1-5 groups independently selected from alkyl, amino, amide, halo, hydroxy, cyano, halo alkyl, and alkoxy;

Q' is selected from hydrogen, alkyl, and an acyl group;

Q and Q', together with the carbon and nitrogen atom to which they are attached, optionally form a 4-membered heterocyclyl, a 5-membered heterocyclyl, a 6-membered heterocyclyl, a 9-membered bicyclic heterocyclyl, or a 10-membered bicyclic heterocyclyl, wherein the 4-membered heterocyclyl, 5-membered heterocyclyl, 6-membered heterocyclyl, 9-membered bicyclic heterocyclyl, and 10-membered bicyclic heterocyclyl are each optionally substituted with 1-5 groups independently selected from alkyl, amino, halo, hydroxy, cyano, amide, halo alkyl, and alkoxy;

p is 0, 1, 2, 3, 4, or 5;

q is 0, 1, 2, 3, 4, or 5;

R" represents a covalent bond, directly or indirectly, to Z1c;

Z" represents a covalent bond, directly or indirectly, to X1 or to Z1a; and any primary amine is optionally acetylated or alkylated; wherein Formulae FL69 and FL70 are:

FL69

FL70 and stereoisomers thereof;

wherein:

R" represents a covalent bond, directly or indirectly, to Z1c;

Z" represents a covalent bond, directly or indirectly, to X1 or to Z1a;

A' is selected from H, an alkyl, a saturated fatty acid, an unsaturated fatty acid, a cycloalkyl, a haloalkyl, an aryl, and a heteroaryl; and A" is (i) a bile acid conjugated, directly or indirectly, via its acid group to the amine in FL69 or FL70; or (ii) a $C_2$-$C_{20}$ acyl group optionally terminating in an acid group, wherein one or more carbon atoms of the $C_2$-$C_{20}$ acyl group are optionally and independently replaced by a group selected from C(=O), O, NH, $NH_2$, S, S(O), $SO_2$, phenyl, 5-membered heterocyclyl, 6-membered heterocyclyl, 5-membered heteroaryl, 6-membered heteroaryl, and wherein the one or more carbon atoms of the $C_2$-$C_{20}$ acyl group, NH, $NH_2$, $SO_2$, phenyl, 5-membered heterocyclyl, 6-membered heterocyclyl, 5-membered heteroaryl, and 6-membered heteroaryl is each independently substituted with 0, 1, 2, 3, or 4 $R_x$, wherein $R_x$ is selected from $C_1$-$C_5$ alkyl, halogen, $C_1$-$C_5$ haloalkyl, carboxylic acid, hydroxyl, —O—$C_1$-$C_5$ alkyl, $NH_2$, and a substituted or unsubstituted 5-membered heterocyclyl, 6-membered heterocyclyl, 5-membered heteroaryl, and 6-membered heteroaryl;

p is 1, 2, 3, 4, or 5, q is 1, 2, 3, 4, or 5, and any primary amine is optionally acetylated or alkylated.

80. The compound of embodiment 79, wherein each A" is independently selected from:

AB-1

2967

AB-2

AB-3

AB-4

AB-5

AB-6

AB-7

AB-8

AB-9

AB-10

AB-11    55

AB-12

2968

AB-13

AB-14

AB-15

AB-16

AB-17

AB-18

AB-19

AB-20

AB-21

AB-22

2969

-continued

AB-23

AB-24

AB-25

AB-26

AB-27

AB-28

AB-29

AB-30

2970

-continued

AB-31

AB-32

AB-33

AB-34

AB-35

81. The compound of embodiment 71 or 75, wherein the compound comprises at least one Z1b selected from Formulae IIa-IIai and Formulae IIIa-IIIai, wherein Formulae IIa-IIai are:

Formula IIa

Formula IIb

Formula IIc

Formula IId

2971

-continued

Formula IIe

Formula IIf

Formula IIg

Formula IIh

Formula IIi

Formula IIj

Formula IIk

Formula IIl

Formula IIm

Formula IIn

Formula IIo

Formula IIp

Formula IIq

2972

-continued

Formula IIr

Formula IIs

Formula IIt

Formula IIu

Formula IIv

Formula IIw

Formula IIx

Formula IIy

Formula IIz

Formula IIaa

Formula IIab

Formula IIac

Formula IIad

Formula IIae

2973

-continued

Formula IIaf

Formula IIag

Formula IIah and

Formula IIai

wherein:

r is 0, 1, 2, 3, 4, or 5;

25 s is 0, 1, 2, 3, 4, or 5;

W represents CH$_2$——~ or (C=O)——~, wherein ——~ is a covalent linkage to X1; and

30 each V$_1$ is independently selected from NH—†, CH$_2$—†, and (C=O)—† and each V$_2$ is N—†, wherein —† is a covalent linkage towards successive Z1b, Z1a or Z1c, provided that V$_1$ is NH—† when connected to Z1c; and the covalent linkages between Z1a and Z1b units each independently comprise an amine linkage or an amide linkage; and when n'=0 and m'=1, Z1a is directly conjugated to X1 by an amine linkage or amide linkage, and

35 wherein Formulae IIIa-IIIai are:

Formula IIIa

Formula IIIb

Formula IIIc

Formula IIId

Formula IIIe

Formula IIIf

2974

-continued

Formula IIIg

Formula IIIh

Formula IIIi

Formula IIIj

Formula IIIk

Formula IIIl

Formula IIIm

Formula IIIn

Formula IIIo

Formula IIIp

Formula IIIq

Formula IIIr

Formula IIIs

-continued

Formula IIIt

Formula IIIu

Formula IIIv

Formula IIIw

Formula IIIx

Formula IIIy

Formula IIIz

Formula IIIaa

Formula IIIab

Formula IIIac

-continued

Formula IIIad

Formula IIIae

Formula IIIaf

Formula IIIag

Formula IIIah and

Formula IIIai wherein
  r is 1, 2, 3, 4, or 5;
  s is 1, 2, 3, 4, or 5; and
  each $V_1$ is independently selected from NH—†, CH$_2$—†, and (C=O)—† and each $V_2$ is N—†, wherein —† is a covalent linkage towards successive Z1b, Z1a or Z1c, provided that $V_1$ is NH—† when connected to Z1c; and the covalent linkages between Z1a and Z1b units each independently comprise an amine linkage or an amide linkage; and when n'=0 and m'=1, Z1a is directly conjugated to X1 by an amine linkage or amide linkage.
  82. The compound of embodiment 75, wherein the at least one Z1c is covalently conjugated indirectly via a linker selected from (i) Formulae FL1-FL19:

(FL1)

(FL2)

(FL3)

(FL4)

(FL4A)

(FL5)

2977

2978

(FL6)

(FL7)

(FL7A)

(FL8)

(FL9)

(FL8A)

(FL9A)

(FL10)

(FL11)

(FL12)

(FL13)

(FL14)

(FL15)

(FL16)

(FL17)

(FL18)

(FL19)

wherein, in Formulae FL1 to FL19:

Z″ represents an attachment point toward X1;

R″ represents an attachment point toward Z1c;

p is 1, 2, 3, 4, or 5, q is 1, 2, 3, 4, or 5, r is 1, 2, 3, 4, or 5; and any primary amine is optionally acetylated or alkylated; and (ii) an L- or D-amino acid comprising at least one amine group directly conjugated to Z1c, wherein an acid functional group of the amino acid is conjugated toward X1.

83. The compound of embodiment 75 wherein n' is 1 and each of the Z1b is independently selected from (i) Formulae FL1-FL19:

(FL14)

-continued wherein, in Formulae FL1 to FL19:

Z″ represents an attachment point toward X1;

R″ represents an attachment point toward Z1c;

p is 1, 2, 3, 4, or 5, q is 1, 2, 3, 4, or 5, r is 1, 2, 3, 4, or 5; and any primary amine is optionally acetylated or alkylated; and (ii) an L- or D-amino acid comprising at least one amine group directly conjugated to Z1c, wherein an acid functional group of the amino acid is conjugated toward X1.

84. The compound of embodiment 71 or 75, wherein the compound comprises a drug substance comprising a human polypeptide hormone of the human pancreas, insulin, glucagon, GLP-1, a somatostatin, a gastric inhibitory polypeptide, a glucose-dependent insulinotropic polypeptide, a hybrid peptide comprising sequences from two or more human polypeptide hormones, or an analogue thereof.

85. The compound of embodiment 71 or 75, wherein:

X1 comprises human insulin or a human insulin analogue comprising an A-chain and a B-chain, wherein the A-chain comprises a sequence selected from SEQ ID NOs 1 and 3 to 33, and the B-chain comprises a sequence selected from SEQ ID NOs 2 and 34 to 74, 24047, and 24048;

each Z1c is independently selected from FF1, FF10, FF12, FF14, FF15, FF114, FF115, FF116, FF163, FF193, FF194, FF203, FF221-FF231 and covalently conjugated either directly, or indirectly via the linker, to Z1a and/or Z1b, or to X1;

each Z1a is independently absent or independently comprises a sequence selected from K, GK, KGSH (SEQ ID NO:24049), KGSHK (SEQ ID NO:4238), KNSTK (SEQ ID NO:5085), GKASHK (SEQ ID NO:12414), GKEEEK (SEQ ID NO:12677), GKEEHK (SEQ ID NO:12680), GKGHSK (SEQ ID NO:13120), GKGSH (SEQ ID NO:24050), GKGSHK (SEQ ID NO:13198), GKGSTK (SEQ ID NO:13205), GKHENK (SEQ ID NO:13271), GKNSHK (SEQ ID NO:13982), GKN-STK (SEQ ID NO:13989), GKQSSK (SEQ ID NO:14380), GKYQFK (SEQ ID NO:15128), GKG- SKK (SEQ ID NO:24045), GKKPGKK (SEQ ID NO:24046), GKGPSK (SEQ ID NO:24044), GKP-SHKP (SEQ ID NO:24043), and GSHKGSHK (SEQ ID NO:24042);

each said linker is selected from FL1, FL3, FL4, and FL5;

each m′ is independently 0 or 1;

each n′ is independently 0, 1, 2, or 3;

each o′ is independently 1, 2, 3, 4, or 5;

each p′ is 1, 2, 3, 4, or 5; and q′ is 1, 2, 3, or 4, wherein when any of n′, o′, p′, or q′ is 2 or more, the corresponding groups Z1a, Z1b, and Z1c are independently selected and may be the same or different; and wherein each Z1c is independently covalently conjugated, directly or indirectly, to an amine of Z1a, to an amine of Z1b, or to X1.

86. The compound of embodiment 71 or 75, wherein:

X1 comprises the human insulin or human insulin analogue comprising an A-chain and a B-chain, wherein the A-chain comprises SEQ ID NO:1; and the B-chain is selected from SEQ ID NOs 2, 36, 24047, and 24048;

each Z1c is independently selected from FF1, FF10, FF12, FF14, FF15, FF114, FF115, FF116, FF193, FF194, FF203, and FF221-FF231 and covalently conjugated either directly, or indirectly via the linker, to Z1a and/or Z1b, or to X1;

each Z1a independently comprises a sequence selected from K, GK, KGSH (SEQ ID NO:24049), KGSHK (SEQ ID NO:4238), KNSTK (SEQ ID NO:5085), GKASHK (SEQ ID NO:12414), GKEEEK (SEQ ID NO:12677), GKEEHK (SEQ ID NO:12680), GKGHSK (SEQ ID NO:13120), GKGSH (SEQ ID NO:24050), GKGSHK (SEQ ID NO:13198), GKG-STK (SEQ ID NO:13205), GKHENK (SEQ ID NO:13271), GKNSHK (SEQ ID NO:13982), GKN-STK (SEQ ID NO:13989), GKQSSK (SEQ ID NO:14380), GKYQFK (SEQ ID NO:15128), GKG-SKK (SEQ ID NO:24045), GKKPGKK (SEQ ID NO:24046), GKGPSK (SEQ ID NO:24044), GKP-SHKP (SEQ ID NO:24043), and GSHKGSHK (SEQ ID NO:24042);

each said linker is independently absent or independently selected from FL3 and FL5;

each m' is independently 0 or 1;

each n' is independently 0 or 2;

each o' is independently 1, 2, or 3;

each p' is 1, 2, or 3; and q' is 1, 2, or 3, wherein when any of n', o', p', or q' is 2 or more, the corresponding groups Z1a, Z1b, and Z1c are independently selected and may be the same or different;

wherein each Z1c is independently covalently conjugated, directly or indirectly, to an amine of Z1a, to an amine of Z1b, or to X1.

87. The compound of embodiment 71 or 75, wherein each of the Z1a is independently absent or independently comprises a sequence selected from K, GK, KGSH (SEQ ID NO:24049), GKGSH (SEQ ID NO:24050), KGSHK (SEQ ID NO:4238), and GKGSHK (SEQ ID NO:13198).

88. The compound of embodiment 71 or 75, wherein each of the Z1c is independently selected from FF1; FF10, FF12, FF14, FF15, FF114, FF115, FF116, and FF221-FF231, and wherein the $B_1$ and the $B_2$ are independently selected from Formulae F1 and F2.

89. The compound of any one of embodiments 71 and 75-76, wherein the $B_1$ and the $B_2$ are independently selected from F2 and F7.

90. The compound of any one of embodiments 76-78, wherein at least one $R_1$ in $B_1$ or $B_2$ is F or $CF_3$.

91. The compound of embodiment 71 or 75, wherein Z1b is independently absent, FL3, or FL5.

92. The compound of embodiment 71 or 75, wherein each of the Z1c is independently selected from FF10, FF12, FF116, FF221, FF222, and FF224-FF231.

93. The compound of embodiment 76, wherein:

each $B_1$ and $B_2$ is independently selected from F2 and F7 and is covalently conjugated to Z1c using an amide linkage, each Z1b is independently absent; FL3 wherein p is 1, 2, or 3; or FL5 wherein p is 2, 3, or 4;

each FF is independently selected from FF10, FF12, FF116, FF134, FF163, FF193, FF203, FF221, FF222 and FF224-FF231; wherein each FF12 and FF222 has either (S,R) or (S,S) stereochemistry;

each Z1c is conjugated either directly or indirectly through FL3 or FL5 to the amine group in one or more lysine side chain in X1 or the N-terminus in X1; and X1 is a polypeptide drug substance and/or an insulin optionally having from 0 to 4 residues replaced, inserted, or mutated to lysines, and wherein the lysines are each conjugated directly or indirectly to a Z1c.

94. The compound of embodiment 71 or 75, wherein Z1c is FF224, n' is 0, and Z1a is an amine containing amino acid.

95. The compound of any one of embodiments 71-94, wherein the compound is selected from:

$$((Z1c)\overline{\tfrac{}{p'}}(Z1a\overline{\tfrac{}{m'}})_{q'}\!-X1; \tag{IA}$$

$$((Z1c)\overline{\tfrac{}{p'}}(Z1b\overline{\tfrac{}{m'}})_{q'}\!-X1; \text{ and} \tag{IB}$$

$$((Z1c)\overline{\tfrac{}{p'}})_{q'}\!X1. \tag{IC}$$

96. The compound of any one of embodiments 71-94, wherein the compound is selected from:

$$\left[[Z1c]_1\right]_1\!\!-X1; \quad \left[[Z1c]_1\right]_2\!\!-X1; \quad \left[[Z1c]_1\right]_3\!\!-X1; \quad \left[[Z1c]_1\right]_4\!\!-X1;$$

$$\left[[Z1c]_1\right]_5\!\!-X1; \quad \left[[Z1c]_2\!-\![Z1a]_1\right]_2\!\!-X1;$$

$$\left[[Z1c]_2\!-\![Z1a]_1\right]_2\!\!-X1\!-\!\left[[Z1c]_1\right]_1;$$

$$\left[[Z1c]_2\!-\![Z1a]_1\right]_2\!\!-X1\!-\!\left[[Z1c]_1\right]_2;$$

$$\left[[Z1c]_2\!-\![Z1a]_1\!+\!Z1b]_1\right]_1\!\!-X1;$$

$$\left[[Z1c]_2\!-\![Z1a]_1\!-\![Z1b]_1\right]_1\!\!-X1\!-\!\left[[Z1c]_1\right]_1;$$

$$\left[[Z1c]_1\!-\![Z1b]_1\right]_1\!\!-X1; \quad \left[[Z1c]_2\!-\![Z1a]_1\right]_1\!\!-X1\!-\![Z1c]_1\right]_1;$$

$$\left[[Z1c]_2\!-\![Z1a]_1\right]_1\!\!-X1\!-\!\left[[Z1c]_1\right]_2; \text{ and}$$

$$\left[[Z1c]_2\!-\![Z1a]_1\right]_1\!\!-X1\!-\!\left[[Z1c]_1\right]_2.$$

97. The compound of embodiment 96, wherein the compound is selected from $$[[Z1c]\!-\!(Z1a)\overline{\tfrac{}{1}}\overline{\tfrac{}{1}}\!-X1\!-\![Z1c]_1]_1 \text{ and}$$

$$[[Z1a]\overline{\tfrac{}{1}}\overline{\tfrac{}{1}}\!-X1.$$

98. The compound of embodiment 71 or 75, wherein Z1c is covalently conjugated directly to X1 via a linker, and wherein the linker is independently selected from gamma-glutamic acid, beta-alanine, and Formula FL3

(FL3)

wherein p is 1, 2, or 3; and

Formula FL5

(FL5)

wherein p is 2, 3, or 4.

99. The compound of embodiment 71 or 75, wherein X1 is OH or $NH_2$, and the compound further comprises a drug substance covalently conjugated directly or indirectly to the compound.

100. A tautomer, stereoisomer or a mixture of stereoisomers, or a pharmaceutically acceptable salt, or hydrate, or isotopic derivative thereof of the compound of any one of embodiments 66-71.

101. A compound comprising X1 and one or more Z1c, or a tautomer, stereoisomer or a mixture of stereoisomers, or a pharmaceutically acceptable salt, or hydrate, or isotopic derivative thereof,

2985

2986 wherein:

X1 comprises:

(i) NH$_2$ or OH;

(ii) a drug substance comprising an amine;

(iii) a drug substance that is covalently conjugated to an amine containing linker; or (iv) an amine configured to be covalently conjugated to a drug substance;

wherein each Z1c is covalently conjugated, directly or indirectly, to an amine in X1 or to OH when X1 is OH, and wherein each Z1c is independently selected from:

a) Formulae FF1-FF48, wherein Formulae FF1-FF48 are:

(FF1)

(FF2)

(FF3)

(FF4)

(FF5)

(FF6)

(FF7)

(FF8)

(FF9)

(FF10)

(FF11)

(FF12)

(FF13)

2987

-continued (FF14)

(FF15)

(FF16)

(FF17)

(FF18)

(FF19)

(FF20)

2988

-continued (FF21)

(FF22)

(FF23)

(FF24)

(FF25)

(FF26)

(FF27)

2989

-continued (FF28)

(FF29)

(FF30)

(FF31)

(FF32)

(FF33)

(FF34)

(FF35)

2990

-continued (FF36)

(FF37)

(FF38)

(FF39)

(FF40)

(FF41)

(FF42)

(FF43)

(FF44)

2991

(FF45)

(FF46)

(FF47)

20 and

(FF48)

30 wherein X represents a point of covalent attachment either
directly to an amine in X1 or to an amine that is
covalently conjugated directly or indirectly to X1, or to
OH when X1 is OH;

i is 1, 2, 3, 4, 5, 6, or 7;

j is 1, 2, 3, 4, 5, 6, or 7; and

B₁ and B₂, which may be identical or different, each
independently represents an aromatic boron-containing
group;

b) Formulae FF49-FF88, wherein Formulae FF49-
    FF88 are:

(FF49)

(FF50)

60

(FF51)

2992

(FF52)

(FF53)

(FF54)

(FF55)

(FF56)

(FF57)

(FF58)

(FF59)

(FF60)

2993

-continued (FF61)

(FF62)

(FF63)

(FF64)

(FF65)

(FF66)

(FF67)

(FF68)

2994

-continued (FF69)

(FF70)

(FF71)

(FF72)

(FF73)

(FF74)

(FF75)

2995

-continued (FF76)

(FF77)

(FF78)

(FF79)

(FF80)

(FF81)

2996

-continued (FF82)

(FF83)

(FF84)

(FF85)

(FF86)

(FF87)

and

-continued (FF88)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

j is 1, 2, 3, 4, 5, 6, or 7;

R1a is selected from COOH, $CH_3$, H, and OH;

R2, R3, R4 and R5 are each independently selected from $CH_3$, H, OH, and COOH, and at least one of R2, R3, R4 and R5 is $CH_3$ or OH; and $B_1$ and $B_2$, which may be identical or different, are each independently an aromatic boron-containing group;

c) Formulae FF89-FF112, wherein Formulae FF89-FF112 are:

(FF89)

(FF90)

-continued (FF91)

(FF92)

(FF93)

(FF94)

(FF95)

(FF96)

-continued (FF97)

(FF98)

(FF99)

(FF100)

(FF101)

(FF102)

-continued (FF103)

(FF104)

(FF105)

(FF106)

(FF107)

3001

-continued (FF108)

(FF109)

(FF110)

(FF111)

and (FF112)

wherein X represents a point of covalent attachment either directly to an amine in X1 or to an amine that is covalently conjugated directly or indirectly to X1, or to OH when X1 is OH;

i is 1, 2, 3, 4, 5, 6, or 7; and $B_1$, $B_2$ and $B_3$, which may be identical or different, are each independently an aromatic boron-containing

3002 group, a carboxylic acid derivative, or a H, wherein in each FF89-FF112 structure containing B1, B2 and B3 groups, at least two of the B1, B2 and B3 groups are independently an aromatic boron-containing group;

d) Formulae FF113-FF136, wherein Formulae FF113-FF136 are:

(FF113)

(FF114)

(FF115)

(FF116)

(FF117)

(FF118)

3003

-continued (FF119)

(FF120)

(FF121)

(FF122)

(FF123)

(FF124)

(FF125)

3004

-continued (FF126)

(FF127)

(FF128)

(FF129)

(FF130)

(FF131)

3005

-continued (FF132)

(FF133)

(FF134)

(FF135)

(FF136)

3006

(FF137)

(FF138)

(FF139)

(FF140)

(FF141)

(FF142)

(FF143)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

j is 1, 2, 3, 4, 5, 6, or 7;

k is 1, 2, 3, 4, 5, 6, or 7;

mis 1, 2, 3, 4, 5, 6, or 7;

each R1 is independently selected from H, an alkyl group, an acyl group, a cycloalkyl group, a haloalkyl group, an aryl group, and a heteroaryl group, each R1 optionally comprises one or more alkyl-halide, halide, sulfhydryl, aldehyde, amine, acid, hydroxyl, alkyl, or aryl groups; and B₁ and B₂, which may be identical or different, each independently represents an aromatic boron-containing group;

e) Formulae FF137-FF160, wherein Formulae FF137-FF160 are:

3007

-continued (FF144)

(FF145)

(FF146)

(FF147)

(FF148)

(FF149)

(FF150)

3008

-continued (FF151)

(FF152)

(FF153)

(FF154)

(FF155)

(FF156)

3009

-continued (FF157)

(FF158)

(FF159)

(FF160)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

j is 1, 2, 3, 4, 5, 6, or 7;

k is 1, 2, 3, 4, 5, 6, or 7;

m is 1, 2, 3, 4, 5, 6, or 7;

each R1 is independently selected from H, an alkyl group, an acyl group, a cycloalkyl group, a haloalkyl group, an aryl group, and a heteroaryl group, each R1 optionally comprises one or more alkyl-halide, halide, sulfhydryl, aldehyde, amine, acid, hydroxyl, alkyl, or aryl groups; and B₁ and B₂, which may be identical or different, each independently represents an aromatic boron-containing group;

f) Formulae FF161-FF164, wherein Formulae FF161-FF164 are:

FF161

3010

-continued

FF162

FF163

FF164 wherein X represents a point of covalent attachment either directly to an amine in X1 or to an amine that is covalently conjugated directly or indirectly to X1, or to OH when X1 is OH;

i is 1, 2, 3, 4, or 5;

j is 1, 2, 3, 4, or 5;

each R6, R7, R8, and R9 for different values of j is independently selected from H, CF₃, CH₃, CHF₂, and (CH₂)ₘCH₃, wherein m is 1, 2, 3, 4, or 5;

Y3, Y4, Y5, Y6 and Y7 are each independently selected from H, CH₂—X4, and Formulae IV-1 to IV-135;

wherein X4 is selected from —COOH, —(CH₂)ₘCOOH, an alkyl group, an acyl group, a cycloalkyl group, a haloalkyl group, an aryl group, and a heteroaryl group, each X4 optionally comprises one or more alkyl-halide, halide, sulfhydryl, aldehyde, amine, acid, hydroxyl, alkyl or aryl groups; wherein m is 1, 2, 3, 4, or 5;

wherein at least one of Y5, Y6 and Y7 in Formulae FF162 and FF163 is not H and at least one of Y7, R8 and R9 in FF164 is not H; and wherein Formulae IV-1 to IV-135 are:

(IV-1)

(IV-2)

3011

-continued (Iv-3)

(IV-4)

(IV-5)

(IV-6)

(IV-7)

(IV-8)

(IV-9)

45 (IV-10)

(IV-11)

(IV-12)

(IV-13)

3012

-continued (IV-14)

(IV-15)

(IV-16)

(IV-17)

(IV-18)

(IV-19)

(IV-20)

(IV-21)

(IV-22)

(IV-23)

(IV-24)

3013

-continued (IV-25)

(IV-26)

(IV-27)

(IV-28)

(IV-29)

(IV-30)

(IV-31)

(IV-32)

(IV-33)

(IV-34)

(IV-35)

(IV-36)

(IV-37)

3014

-continued (IV-38)

(IV-39)

(IV-40)

(IV-41)

(IV-42)

(IV-43)

(IV-44)

(IV-45)

(IV-46)

(IV-47)

(IV-48)

3015

-continued (IV-49)

(IV-50)

(IV-51)

(IV-52)

(IV-53)

(IV-54)

(IV-55)

(IV-56)

3016

-continued (IV-57)

(IV-58)

(IV-59)

(IV-60)

(IV-61)

(IV-62)

(IV-63)

3017

-continued (IV-64)

(IV-65)

(IV-66)

(IV-67)

(IV-68)

(IV-69)

3018

-continued (IV-70)

(IV-71)

(IV-72)

(IV-73)

(IV-74)

(IV-75)

(IV-76)

3019
-continued

3020
-continued (IV-77)

(IV-86)

(IV-78)

(IV-87)

(IV-79)

(IV-88)

(IV-80)

(IV-89)

(IV-81)

(IV-90)

(IV-82)

(IV-91)

(IV-83)

(IV-92)

(IV-84)

(IV-93)

(IV-85)

(IV-94)

3021

-continued (IV-95)

(IV-96)

(IV-97)

(IV-98)

(IV-99)

(IV-100)

(IV-101)

(IV-102)

(IV-103)

3022

-continued (IV-104)

(IV-105)

(IV-106)

(IV-107)

(IV-108)

(IV-109)

3023

-continued

3024

-continued (IV-110)

(IV-111)

(IV-112)

(IV-113)

(IV-114)

(IV-115)

(IV-116)

(IV-117)

(IV-118)

(IV-119)

(IV-120)

(IV-121)

(IV-122)

(IV-123)

(IV-124)

(IV-125)

(IV-126)

(IV-127)

-continued (IV-128)

(IV-129)

(IV-130)

(IV-131)

(IV-132)

(IV-133)

(IV-134)

and (IV-135)

wherein Xa represents $CH=O$, $CHF_2$, $CF_3$, $CH_2SH$, $COOH$, $CH_2OH$, $CH_2NO_2$, $CH_2NH_2$, $CH_3$, $C(CH_3)_3$, $CH(CH_3)_2$, $CH((CH_2)_3-CH_3)_2$, or $CH(CH_2-CH_3)_2$;

Xb represents O, NH, $CH_2$, or S;

Xc represents CH or N;

each $R_{10}$ is independently selected from H, F, Cl, Br, $CH_3$, $CF_3$, $CH=O$, OH, COOH, and $(CH_2)_n CH_3$, m is 1, 2, 3, 4, or 5; and n is 1, 2, 3, 4, or 5;

$B_1$ and $B_2$, which may be identical or different, each independently represents an aromatic boron-containing group; and

* in Formulae IV-1 to IV-135 represents a point of attachment to corresponding Formulae FF161-164;

g) Formulae FF165-FF166, wherein Formulae FF165-FF166 are:

(FF165)

and (FF166)

wherein X represents a point of covalent attachment either directly to an amine in X1 or to an amine that is covalently conjugated directly or indirectly to X1, or to OH when X1 is OH;

m is 1, 2, 3, 4, 5, 6, or 7;

n is 1, 2, 3, 4, 5, 6, or 7;

X5 is S, O, or NH; and each $R_1$ is independently selected from H, F, Cl, Br, OH, $CH_2-NH_2$, $NH_2$, $(C=O)-NH_2$, $CH=O$, $SO_2CH_3$, $SO_2CF_3$, $CF_3$, $CHF_2$, $NO_2$, $CH_3$, $OCH_3$, $O(CH_2)_m CH_3$, $-(SO_2)NH-CH_3$, $-(SO_2)NH(CH_2)_m CH_3$, and $OCF_3$, wherein m is 1, 2, 3, 4, 5, 6, or 7;

h) Formulae FF167-FF192, wherein Formulae FF167-FF192 are:

3027

3028

-continued (FF167)

(FF168)

(FF169)

(FF170)

(FF171)

(FF172)

(FF173)

(FF174)

(FF175)

(FF176)

(FF177)

(FF178)

(FF179)

(FF180)

(FF181)

(FF182)

-continued (FF183)

(FF184)

(FF185)

(FF186)

(FF187)

(FF188)

(FF189)

-continued (FF190)

(FF191)

and (FF192)

wherein X represents a point of covalent attachment either directly to an amine in X1 or to an amine that is covalently conjugated directly or indirectly to X1, or to OH when X1 is OH;

$B_1$ and $B_2$, which may be identical or different, each independently represents an aromatic boron-containing group;

i) Formulae FF193-FF209, wherein Formulae FF193-FF209 are:

FF193

FF194

FF195

-continued

FF196

FF197

FF198

FF199

FF200

FF201

FF202

FF203

-continued

FF204

FF205

FF206

FF207

FF208

FF209 wherein R in FF208 and FF209 is an alkyl, aryl or halide that is covalently conjugated through at least one $CH_2$ group to the amino group in the side chain of FF208 or FF209, $R_1$ and $R_2$ are independently selected from H, $CH_3$, alkyl, and formulae IV-1 to IV-135;

i is 1, 2, 3, 4, or 5;

j is 1, 2, 3, 4, or 5; and wherein X represents a point of covalent attachment either directly to an amine in X1 or to an amine that is covalently conjugated directly or indirectly to X1, or to OH when X1 is OH; and $B_1$ and $B_2$, which may be identical or different, each independently represents an aromatic boron-containing group;

j) Formulae FF210-FF224, wherein Formulae FF210-FF224 are:

FF210

FF211

FF212

FF213

FF214

FF215

FF216

FF217

FF218

-continued

FF219

FF220

FF221

FF222

FF223 and

FF224 wherein R11 in FF210 to FF212 is selected from Formulae IV-1 to IV-135 and R12 is selected from an amine, a hydroxyl, an alkyl, and a halide group;

wherein each R13 is independently selected from H, CH$_3$, alkyl, aryl and Formulae IV-1 to IV-135; R14 is selected from H, CH$_3$, alkyl, aryl and heteroaryl;

wherein X represents a point of covalent attachment either directly to an amine in X1 or to an amine that is covalently conjugated directly or indirectly to X1, or to OH when X1 is OH;

X" represents a point of covalent attachment to an amine —N in the compound, wherein — represents a single covalent bond to a CH$_2$ or CH group in the compound;

i is 1, 2, 3, 4, or 5;

j is 1, 2, 3, 4, or 5; and

B$_1$, B$_2$, B$_3$, B$_4$, B$_5$, and B$_6$ each independently represents an aromatic boron-containing group, wherein in each FF structure containing B$_1$, B$_2$ and B$_3$ groups, at least two of the B$_1$, B$_2$ and B$_3$ groups are independently an aromatic boron-containing group; and k) Formulae FF225-FF231, wherein Formulae FF225-FF231 are:

(FF225)

(FF226)

(FF227)

(FF228)

(FF229)

(FF230)

(FF231)

wherein X represents a point of covalent attachment either directly to an amine in X1 or to an amine that is covalently conjugated directly or indirectly to X1, or to OH when X1 is OH;

i is 1, 2, 3, 4, 5, 6, or 7;

$B_1$ and $B_2$, which may be identical or different, each independently represents an aromatic boron-containing group, wherein $B_1$ and $B_2$ in Formulae FF225-FF231 are not a boronic acid or an F2 or F6 aromatic boron-containing group, wherein Formulae F2 and F6 are:

(F2)

(F6)

$R_1$ at position 4' or position 5' represents (C=O)—*, wherein —* represents the attachment point to the rest of Z1c;

zero, one, or two $R_1$ represents F, Cl, $CF_2$, $CF_3$, $SF_5$, $OCF_3$, $SO_2CH_3$, and/or $SO_2CF_3$, and each remaining $R_1$ represents H;

Y8 is O; and i is 1; and wherein at least one primary or secondary amine in FF1-FF223 and FF225-231 is optionally covalently conjugated to $B_6$.

102. The compound of embodiment 101, wherein the compound is a molecular conjugate represented by the following formula, or a stereoisomer or a mixture of stereoisomers, or pharmaceutically acceptable salt thereof:

$$\left[\left[\left[Z1c\right]_{p'}\!\!\left(Z1a\right)_{m'}\right]_{o'}\!\!\left(Z1b\right)_{n'}\right]_{q'}\!\!X1,$$

wherein

X1 comprises:
  (i) $NH_2$ or OH,
  (ii) a polypeptide drug substance comprising an amine,
  (iii) a polypeptide drug substance that is covalently conjugated to an, amine containing linker, or
  (iv) an amine configured to be covalently conjugated to a polypeptide drug substance;

each Z1c is independently selected from Formulae FF1-FF231;

each Z1a independently comprises 1 to 50 amino acids connected together using amide or peptide bonds;

each Z1b is independently a small-molecule linker;

each m' is independently 0 or 1;

each n' is independently 0 or a positive integer;

each o' is independently an integer greater than or equal to 1;

each p' is a positive integer; and q' is a positive integer of at least 1 and not more than two times the total number of amine groups in X1, wherein when any of n', o', p', or q' is 2 or more, the corresponding groups Z1a, Z1b, and Z care independently selected and may be the same or different;

wherein each Z1c is independently covalently conjugated, directly or indirectly, to an amine of Z1a, to an amine of Z1b, or to X1; and wherein optionally the molecular conjugate may comprise one or more isotopes at any position of the molecular conjugate.

103. The compound of embodiment 101 or 102, wherein the compound comprises at least one of $B_1$, $B_2$ and $B_3$ independently selected from Formulae F1-F11 or wherein the compound comprises at least one of $B_4$, $B_5$ and $B_6$ independently selected from Formulae F1-F11, wherein Formulae F1-F11 are:

(F1)

(F2)

(F3)

(F4)

-continued (F5)

(F6)

(F7)

(F8)

(F9)

(F10)

-continued (F11)

wherein for $B_1$, $B_2$, and $B_3$:

one $R_1$ represents (C=O)—*, S(=O)(=O)—*, $(CH_2)_m$ (C=O)—*, or $(CH_2)_m$—*, wherein —* represents the attachment point to the rest of Z1c, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7;

wherein for $B_4$ and $B_5$:

one $R_1$ for $B_4$ represents $(CH_2)_m$—ø, wherein —ø represents an attachment point to the rest of $Z1_c$ and one $R_1$ for $B_5$ represents (C=O)—*, S(=O)(=O)—*, $(CH_2)_m(C=O)$—*, or $(CH_2)_m$—*, wherein —* represents an attachment point to the rest of Z1c, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7;

wherein for $B_6$:

one $R_1$ for $B_6$ represents $(CH_2)_m$—ø, wherein —ø represents an attachment point to the rest of the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7;

wherein, for Formulae F3-F4:

$R_w$ is O or S;

for Formulae F5-F10:

when Y8 is O, i is 1, 2, 3, 4, or 5; or when Y8 is NR, R is an alkyl group or H, and i is 1, 2, 3, 4, or 5;

Y9 is H, $CH_3$, or an alkyl group, provided that when Y8 is O, Y9 is a $CH_3$ or an alkyl group; and each Y10 is independently selected from H, $CH_3$, F, $CF_3$, and $OCH_3$, with the proviso that at least one Y10 is not H.

104. The compound of any one of embodiments 101-103, wherein the compound comprises at least one group selected from $B_1$, $B_2$, $B_3$ $B_4$, $B_5$ and $B_6$, each independently selected from Formulae F2, F7, F8, and F11, wherein Formulae F2, F7, F8, and F11 are:

(F2)

(F7)

(F8)

and (F11)

wherein for $B_1$, $B_2$, and $B_3$:

one $R_1$ represents (C=O)—* or $(CH_2)_m(C=O)$—*, wherein —* represents the attachment point to the rest of Z1c, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7;

wherein for $B_4$ and $B_5$:

one $R_1$ for $B_4$ represents $(CH_2)_m$—ø, wherein —ø represents an attachment point to the rest of $Z1_c$ and one $R_1$ for $B_5$ represents (C=O)—*, S(=O)(=O)—*, $(CH_2)_m(C=O)$—*, or $(CH_2)_m$—*, wherein —* represents an attachment point to the rest of $Z1_c$, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7;

wherein for $B_6$:

one $R_1$ for $B_6$ represents $(CH_2)_m$—ø, wherein —ø represents an attachment point to the rest of the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7; and wherein for Formula F7:

Y8 is 0 or NR, wherein R is an alkyl group or H; and each Y10 is independently selected from $CH_3$, F, $CF_3$, and $OCH_3$;

wherein for Formula F8:

when Y8 is O, i is 1, 2, 3, 4, or 5; and when Y8 is NR, R is an alkyl group or H, and i is 1, 2, 3, 4, or 5;

each Y10 is independently selected from H, $CH_3$, F, $CF_3$, and $OCH_3$, with the proviso that at least one Y10 is not H; and — represents an attachment point to the rest of Z1c.

105. The compound of any one of embodiments 101-104, wherein the compound comprises at least one group selected from $B_1$, $B_2$, $B_3$, $B_4$, $B_5$ and $B_6$, each independently selected from:

(F2)

(F7)

(F8)

(F11)

wherein for $B_1$, $B_2$, and $B_3$:

one $R_1$ represents (C=O)—*, wherein —* represents the attachment point to the rest of Z1c; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7;

wherein for $B_4$ and $B_5$:

one $R_1$ for $B_4$ represents $(CH_2)_m$—ø, wherein —ø represents an attachment point to the rest of $Z1_c$ and one $R_1$ for $B_5$ represents (C=O)—*, S(=O)(=O)—*, $(CH_2)_m(C$=O)—*, or $(CH_2)_m$—*, wherein —* represents an attachment point to the rest of $Z1_c$, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7;

wherein for $B_6$:

one $R_1$ for $B_6$ represents $(CH_2)_m$—ø, wherein —ø represents an attachment point to the rest of the compound, and m is 1, 2, 3, 4, 5, 6, or 7; and each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$—$CH_3$, —$(SO_2)NH$ $(CH_2)_mCH_3$, and $OCF_3$, wherein m is 1, 2, 3, 4, 5, 6, or 7;

wherein for Formula F7:

Y8 is O; and each Y10 is independently selected from $CH_3$, F, and $CF_3$;

wherein for Formula F8:

Y8 is O;

i is 1, 2, 3, 4, or 5; and each Y10 is independently selected from H, $CH_3$, F, and $CF_3$, with the proviso that at least one Y10 is not H; and — represents an attachment point to the rest of Z1c.

106. The compound of any one of embodiments 101-105, wherein the compound comprises at least one group selected from $B_1$, $B_2$, $B_3$, $B_4$, $B_5$ and $B_6$, each independently selected from:

(F7A)

(F8A)

3043

-continued (F11)

wherein for B$_1$, B$_2$, and B$_3$:

R$_1$ at position 5' represents (C═O)—*, wherein —* represents the attachment point to the rest of Z1c; and each remaining R$_1$ or R$_2$ is independently selected from H, F, Cl, Br, OH, CH$_2$—NH$_2$, NH$_2$, (C═O)—NH$_2$, CH═O, SO$_2$CH$_3$, SO$_2$CF$_3$, CF$_3$, CHF$_2$, NO$_2$, CH$_3$, OCH$_3$, O(CH$_2$)$_m$CH$_3$, —(SO$_2$)NH—CH$_3$, —(SO$_2$)NH (CH$_2$)$_m$CH$_3$, and OCF$_3$, wherein m is 1, 2, 3, 4, 5, 6, or 7;

wherein for B$_4$ and B$_5$:

one R$_1$ for B$_4$ represents (CH$_2$)$_m$—ø, wherein —ø represents an attachment point to the rest of Z1$_c$ and one R$_1$ for B$_5$ represents (C═O)—*, S(═O)(═O)—*, (CH$_2$)$_m$(C═O)—*, or (CH$_2$)$_m$—*, wherein —* represents an attachment point to the rest of Z1$_c$, and m is 1, 2, 3, 4, 5, 6, or 7; and each remaining R$_1$ or R$_2$ is independently selected from H, F, Cl, Br, OH, CH$_2$—NH$_2$, NH$_2$, (C═O)—NH$_2$, CH═O, SO$_2$CH$_3$, SO$_2$CF$_3$, CF$_3$, CHF$_2$, NO$_2$, CH$_3$, OCH$_3$, O(CH$_2$)$_m$CH$_3$, —(SO$_2$)NH—CH$_3$, —(SO$_2$)NH (CH$_2$)$_m$CH$_3$, and OCF$_3$, wherein m is 1, 2, 3, 4, 5, 6, or 7;

wherein for B$_6$:

one R$_1$ for B$_6$ represents (CH$_2$)$_m$—ø, wherein —ø represents an attachment point to the rest of the compound, and m is 1, 2, 3, 4, 5, 6, or 7; and each remaining R$_1$ or R$_2$ is independently selected from H, F, Cl, Br, OH, CH$_2$—NH$_2$, NH$_2$, (C═O)—NH$_2$, CH═O, SO$_2$CH$_3$, SO$_2$CF$_3$, CF$_3$, CHF$_2$, NO$_2$, CH$_3$, OCH$_3$, O(CH$_2$)$_m$CH$_3$, —(SO$_2$)NH—CH$_3$, —(SO$_2$)NH (CH$_2$)$_m$CH$_3$, and OCF$_3$, wherein m is 1, 2, 3, 4, 5, 6, or 7;

wherein for Formula F7A:

Y8 is O; and wherein for Formula F8A:

Y8 is O; and i is 1, 2, 3, 4, or 5; and

— represents an attachment point to the rest of Z1c.

107. The compound of any one of embodiments 101-106, wherein the B$_1$, B$_2$ B$_3$, B$_4$, B$_5$ and B$_6$ are each independently Formula F7A, (F7A)

3044 wherein for B$_1$, B$_2$, and B$_3$:

R$_1$ at position 5' represents (C═O)—*, wherein —* represents the attachment point to the rest of Z1c; and each remaining R$_1$ is independently selected from H, F, Cl, Br, OH, CH$_2$—NH$_2$, NH$_2$, (C═O)—NH$_2$, CH═O, SO$_2$CH$_3$, SO$_2$CF$_3$, CF$_3$, CHF$_2$, NO$_2$, CH$_3$, OCH$_3$, O(CH$_2$)$_m$CH$_3$, —(SO$_2$)NH—CH$_3$, —(SO$_2$) NH(CH$_2$)$_m$CH$_3$, and OCF$_3$, wherein m is 1, 2, 3, 4, 5, 6, or 7;

wherein for B$_4$ and B$_5$:

one R$_1$ for B$_4$ represents (CH$_2$)$_m$—ø, wherein —ø represents an attachment point to the rest of Z1$_c$ and one R$_1$ for B$_5$ represents (C═O)—*, S(═O)(═O)—*, (CH$_2$)$_m$(C═O)—*, or (CH$_2$)$_m$—*, wherein —* represents an attachment point to the rest of Z1$_c$, and m is 1, 2, 3, 4, 5, 6, or 7; and each remaining R$_1$ is independently selected from H, F, Cl, Br, OH, CH$_2$—NH$_2$, NH$_2$, (C═O)—NH$_2$, CH═O, SO$_2$CH$_3$, SO$_2$CF$_3$, CF$_3$, CHF$_2$, NO$_2$, CH$_3$, OCH$_3$, O(CH$_2$)$_m$CH$_3$, —(SO$_2$)NH—CH$_3$, —(SO$_2$) NH(CH$_2$)$_m$CH$_3$, and OCF$_3$, wherein m is 1, 2, 3, 4, 5, 6, or 7;

wherein for B$_6$:

one R$_1$ for B$_6$ represents (CH$_2$)$_m$—ø, wherein —ø represents an attachment point to the rest of the compound, and m is 1, 2, 3, 4, 5, 6, or 7; and each remaining R$_1$ is independently selected from H, F, Cl, Br, OH, CH$_2$—NH$_2$, NH$_2$, (C═O)—NH$_2$, CH═O, SO$_2$CH$_3$, SO$_2$CF$_3$, CF$_3$, CHF$_2$, NO$_2$, CH$_3$, OCH$_3$, O(CH$_2$)$_m$CH$_3$, —(SO$_2$)NH—CH$_3$, —(SO$_2$) NH(CH$_2$)$_m$CH$_3$, and OCF$_3$, wherein m is 1, 2, 3, 4, 5, 6, or 7;

Y8 is O; and

— represents an attachment point to the rest of Z1c.

108. The compound of any one of embodiments 101-107, wherein at least one Z1c is covalently conjugated indirectly via a linker to an amine of X1 or to NH$_2$ when X1 is NH$_2$ or to OH when X1 is OH or to an amine of Z1a, wherein the linker is represented by Formula (X")$_{n1}$, wherein each n1 is independently selected from 1, 2, 3, 4, and 5, and each X" is independently selected from:

a) an L- or D-amino acid, wherein an amine functional group of the L- or D-amino acid is covalently conjugated, directly or indirectly, to Z1c and an acid functional group of the L- or D- amino acid is conjugated, directly or indirectly, to X1 or to Z1a; and b) Formulae FL(IA), FL(IB), FL69, and FL70; wherein Formula FL(IA) and FL(IB) are:

FL(IA)

FL(IB)

and stereoisomers thereof;

wherein:

G is selected from a 3- to 6-membered cycloalkyl group, a 3- to 10-membered heterocyclyl group, a heteroaryl group, and an aryl group, wherein each group is optionally substituted with 1-3 groups independently selected from hydroxy, amino, halogen, cycloalkyl, alkoxy, and alkyl;

E is absent or is an alkylene group optionally substituted with 1-3 groups independently selected from halogen, hydroxy, and amino;

Q is absent or is selected from hydrogen, alkyl, halo, cyano, alkoxy, carboxylic acid, amino, hydroxy, amide, halo alkyl, cycloalkyl, heterocycle, heteroaryl, and aryl, wherein the alkyl, alkoxy, cycloalkyl, heterocycle, heteroaryl, and aryl is each optionally substituted with 1-5 groups independently selected from alkyl, amino, amide, halo, hydroxy, cyano, halo alkyl, and alkoxy;

Q' is selected from hydrogen, alkyl, and an acyl group;

Q and Q', together with the carbon and nitrogen atom to which they are attached, optionally form a 4-membered heterocyclyl, a 5-membered heterocyclyl, a 6-membered heterocyclyl, a 9-membered bicyclic heterocyclyl, or a 10-membered bicyclic heterocyclyl, wherein the 4-membered heterocyclyl, 5-membered heterocyclyl, 6-membered heterocyclyl, 9-membered bicyclic heterocyclyl, and 10-membered bicyclic heterocyclyl are each optionally substituted with 1-5 groups independently selected from alkyl, amino, halo, hydroxy, cyano, amide, halo alkyl, and alkoxy;

p is 0, 1, 2, 3, 4, or 5;

q is 0, 1, 2, 3, 4, or 5;

R" represents a covalent bond, directly or indirectly, to Z1c;

Z" represents a covalent bond, directly or indirectly, to X1 or to Z1a; and any primary amine is optionally acetylated or alkylated; wherein Formulae FL69 and FL70 are:

FL69

FL70 and stereoisomers thereof;

wherein:

R" represents a covalent bond, directly or indirectly, to Z1c;

Z" represents a covalent bond, directly or indirectly, to X1 or to Z1a;

A' is selected from H, an alkyl, a saturated fatty acid, an unsaturated fatty acid, a cycloalkyl, a haloalkyl, an aryl, and a heteroaryl; and A" is (i) a bile acid conjugated, directly or indirectly, via its acid group to the amine in FL69 or FL70; or (ii) a $C_2$-$C_{20}$ acyl group optionally terminating in an acid group, wherein one or more carbon atoms of the $C_2$-$C_{20}$ acyl group are optionally and independently replaced by a group selected from C(=O), O, NH, $NH_2$, S, S(O), $SO_2$, phenyl, 5-membered heterocyclyl, 6-membered heterocyclyl, 5-membered heteroaryl, 6-membered heteroaryl, and wherein the one or more carbon atoms of the $C_2$-$C_{20}$ acyl group, NH, $NH_2$, $SO_2$, phenyl, 5-membered heterocyclyl, 6-membered heterocyclyl, 5-membered heteroaryl, and 6-membered heteroaryl is each independently substituted with 0, 1, 2, 3, or 4 $R_x$, wherein $R_x$ is selected from $C_1$-$C_5$ alkyl, halogen, $C_1$-$C_5$ haloalkyl, carboxylic acid, hydroxyl, —O—$C_1$-$C_5$ alkyl, $NH_2$, and a substituted or unsubstituted 5-membered heterocyclyl, 6-membered heterocyclyl, 5-membered heteroaryl, and 6-membered heteroaryl;

p is 1, 2, 3, 4, or 5, q is 1, 2, 3, 4, or 5, and any primary amine is optionally acetylated or alkylated.

109. The compound of embodiment 108, wherein each A" is independently selected from:

AB-1

AB-2

AB-3

AB-4

AB-5

AB-6

AB-7

AB-8

3047

-continued

AB-9

AB-10

AB-11

AB-12

AB-13

AB-14

AB-15

AB-16

AB-17

AB-18

3048

-continued

AB-19

AB-20

AB-21

AB-22

AB-23

AB-24

AB-25

AB-26

AB-27

3049

-continued

AB-28

AB-29

AB-30

AB-31

AB-32

AB-33

AB-34

COOH, and

3050

-continued

AB-35

110. The compound of embodiment 102, wherein the compound comprises at least one Z1b selected from Formulae IIa-IIai and Formulae IIIa-IIIai, wherein Formulae IIa-IIai are:

Formula IIa

Formula IIb

Formula IIc

Formula IId

Formula IIe

Formula IIf

Formula IIg

Formula IIh

Formula IIi

Formula IIj

Formula IIk

3051

-continued

Formula Ill

Formula IIm

Formula IIn

Formula IIo

Formula IIp

Formula IIq

Formula IIr

Formula IIs

Formula IIt

Formula IIu

Formula IIv

Formula IIw

Formula IIx

Formula IIy

3052

-continued

Formula IIz

Formula IIaa

Formula IIab

Formula IIac

Formula IIad

Formula IIae

Formula IIaf

Formula IIag

Formula IIah

Formula IIai wherein:

r is 0, 1, 2, 3, 4, or 5;

s is 0, 1, 2, 3, 4, or 5;

W represents $CH_2$——~ or (C=O)——~, wherein ——~ is a covalent linkage to X1; and each $V_1$ is independently selected from NH—†, $CH_2$—†, and (C=O)—† and each $V_2$ is N—†, wherein —† is a covalent linkage towards successive Z1b, Z1a or Z1c, provided that $V_1$ is NH—† when connected to Z1c; and the covalent linkages between Z1a and Z1b units each independently comprise an amine linkage

3053 or an amide linkage; and when n'=0 and m'=1, Z1a is directly conjugated to X1 by an amine linkage or amide linkage, and wherein Formulae IIIa-IIIai are:

Formula IIIa

Formula IIIb

Formula IIIc

Formula IIId

Formula IIIe

Formula IIIf

Formula IIIg

Formula IIIh

Formula IIIi

Formula IIIj

Formula IIIk

Formula IIIl

3054

-continued

Formula IIIm

Formula IIIn

Formula IIIo

Formula IIIp

Formula IIIq

Formula IIIr

Formula IIIs

Formula IIIt

Formula IIIu

Formula IIIv

Formula IIIw

Formula IIIx

Formula IIIy

Formula IIIz

-continued

Formula IIIaa

Formula IIIab

Formula IIIac

Formula IIIad

Formula IIIae

Formula IIIaf

-continued

Formula IIIag

Formula IIIah and

Formula IIIai wherein:

r is 1, 2, 3, 4, or 5;

s is 1, 2, 3, 4, or 5; and each $V_1$ is independently selected from NH—†, $CH_2$—†, and (C=O)—† and each $V_2$ is N—†, wherein —† is a covalent linkage towards successive Z1b, Z1a or Z1c, provided that $V_1$ is NH—† when connected to Z1c; and the covalent linkages between Z1a and Z1b units each independently comprise an amine linkage or an amide linkage; and when n'=0 and m'=1, Z1a is directly conjugated to X1 by an amine linkage or amide linkage.

111. The compound of embodiment 101 or 102, wherein the at least one Z1c is covalently conjugated indirectly via a linker selected from (i) Formulae FL1-FL19:

(FL1)

(FL2)

(FL3)

(FL4)

(FL4A)

(FL5)

(FL6)

(FL7)

(FL7A)

(FL8)

-continued (FL9)

(FL8A)

(FL9A)

(FL10)

(FL11)

(FL12)

(FL13)

(FL14)

(FL15)

(FL16)

(FL17)

(FL18) and (FL19)

wherein, in Formulae FL1 to FL19:

Z" represents an attachment point toward X1;

R" represents an attachment point toward Z1c;

p is 1, 2, 3, 4, or 5, q is 1, 2, 3, 4, or 5, r is 1, 2, 3, 4, or 5; and any primary amine is optionally acetylated or alkylated; and (ii) an L- or D-amino acid comprising at least one amine group directly conjugated to Z1c, wherein an acid functional group of the amino acid is conjugated toward X1.

112. The compound of embodiment 102, wherein n' is 1 and each of the Z1b is independently selected from (i) Formulae FL1-FL19:

(FL1)

(FL2)

(FL3)

(FL4)

(FL4A)

(FL5)

(FL6)

(FL7)

(FL7A)

(FL8)

(FL9)

(FL8A)

(FL9A)

(FL10)

(FL11)

(FL12)

(FL13)

(FL14)

(FL15)

-continued (FL16)

(FL17)

(FL18)

(FL19)

wherein, in Formulae FL1 to FL19:

Z" represents an attachment point toward X1;

R" represents an attachment point toward Z1c p is 1, 2, 3, 4, or 5, q is 1, 2, 3, 4, or 5, r is 1, 2, 3, 4, or 5; and any primary amine is optionally acetylated or alkylated; and (ii) an L- or D-amino acid comprising at least one amine group-directly conjugated to Z1c, wherein an acid functional group of the amino acid is conjugated toward X1.

113. The compound of embodiment 101 or 102, wherein the compound comprises a drug substance comprising a human polypeptide hormone of the human pancreas, insulin, glucagon, GLP-1, a somatostatin, a gastric inhibitory polypeptide, a glucose-dependent insulinotropic polypeptide, a hybrid peptide comprising sequences from two or more human polypeptide hormones, or an analogue thereof.

114. The compound of embodiment 101 or 102, wherein:

X1 comprises human insulin or a human insulin analogue comprising an A-chain and a B-chain, wherein the A-chain comprises a sequence selected from SEQ ID NOs 1 and 3 to 33, and the B-chain comprises a sequence selected from SEQ ID NOs 2 and 34 to 74, 24047, and 24048;

each Z1c is independently selected from FF1, FF10, FF12, FF14, FF15, FF114, FF115, FF116, FF163, FF193, FF194, FF203, FF221, FF231 and covalently conjugated either directly, or indirectly via the linker, to Z1a and/or Z1b, or to X1;

each Z1a is independently absent or independently comprises a sequence selected from K, GK, KGSH (SEQ ID NO:24049), KGSHK (SEQ ID NO:4238), KNSTK (SEQ ID NO:5085), GKASHK (SEQ ID NO:12414), GKEEEK (SEQ ID NO:12677), GKEEHK (SEQ ID NO:12680), GKGHSK (SEQ ID NO:13120), GKGSH (SEQ ID NO:24050), GKGSHK (SEQ ID NO:13198), GKGSTK (SEQ ID NO:13205), GKHENK (SEQ ID NO:13271), GKNSHK (SEQ ID NO:13982), GKNSTK (SEQ ID NO:13989), GKQSSK (SEQ ID NO:14380), GKYQFK (SEQ ID NO:15128), GKGSKK (SEQ ID NO:24045), GKKPGKK (SEQ ID NO:24046), GKGPSK (SEQ ID NO:24044), GKPSHKP (SEQ ID NO:24043), and GSHKGSHK (SEQ ID NO:24042);

each said linker is selected from FL1, FL3, FL4, and FL5;

each m' is independently 0 or 1;

each n' is independently 0, 1, 2, or 3;

each o' is independently 1, 2, 3, 4, or 5;

each p' is 1, 2, 3, 4, or 5; and q' is 1, 2, 3, or 4, wherein when any of n', o', p', or q' is 2 or more, the corresponding groups Z1a, Z1b, and Z1c are independently selected and may be the same or different; and wherein each Z1c is independently covalently conjugated, directly or indirectly, to an amine of Z1a, to an amine of Z1b, or to X1.

115. The compound of embodiment 113 or 114, wherein:

X1 comprises the human insulin or human insulin analogue comprising an A-chain and a B-chain, wherein the A-chain comprises SEQ ID NO:1; and the B-chain is selected from SEQ ID NOs 2, 36, 24047, and 24048;

each Z1c is independently selected from FF1, FF10, FF12, FF14, FF15, FF114, FF115, FF116, FF193, FF194, FF203, and FF221-FF231 and covalently conjugated either directly, or indirectly via the linker, to Z1a and/or Z1b, or to X1;

each Z1a independently comprises a sequence selected from K, GK, KGSH (SEQ ID NO:24049), KGSHK (SEQ ID NO:4238), KNSTK (SEQ ID NO:5085), GKASHK (SEQ ID NO:12414), GKEEEK (SEQ ID NO:12677), GKEEHK (SEQ ID NO:12680), GKGHSK (SEQ ID NO:13120), GKGSH (SEQ ID NO:24050), GKGSHK (SEQ ID NO:13198), GKGSTK (SEQ ID NO:13205), GKHENK (SEQ ID NO:13271), GKNSHK (SEQ ID NO:13982), GKNSTK (SEQ ID NO:13989), GKQSSK (SEQ ID NO:14380), GKYQFK (SEQ ID NO:15128), GKGSKK (SEQ ID NO:24045), GKKPGKK (SEQ ID NO:24046), GKGPSK (SEQ ID NO:24044), GKPSHKP (SEQ ID NO:24043), and GSHKGSHK (SEQ ID NO:24042);

each said linker is independently absent or independently selected from FL3 and FL5;

each m' is independently 0 or 1;

each n' is independently 0 or 2;

each o' is independently 1, 2, or 3;

each p' is 1, 2, or 3; and q' is 1, 2, or 3, wherein when any of n', o', p', or q' is 2 or more, the corresponding groups Z1a, Z1b, and Z1c are independently selected and may be the same or different;

wherein each Z1c is independently covalently conjugated, directly or indirectly, to an amine of Z1a, to an amine of Z1b, or to X1.

116. The compound of embodiment 101 or 102, wherein each of the Z1a is independently absent or independently comprises a sequence selected from K, GK, KGSH (SEQ ID NO:24049), GKGSH (SEQ ID NO:24050), KGSHK (SEQ ID NO:4238), and GKGSHK (SEQ ID NO:13198).

117. The compound of embodiment 101 or 102, wherein each of the Z1c is independently selected from FF1, FF10, FF12, FF14, FF15, FF114, FF115, FF116, and FF221-FF231, and wherein the $B_1$ and the $B_2$ are independently selected from Formulae F1 and F2.

118. The compound of embodiment 103, wherein the $B_1$ and the $B_2$ are independently selected from F2 and F7.

119. The compound of embodiment 103, wherein at least one $R_1$ in $B_1$ or $B_2$ is F or $CF_3$.

120. The compound of embodiment 111 or 112, wherein Z1b is independently absent, FL3, or FL5.

121. The compound of embodiment 101 or 102, wherein each of the Z1c is independently selected from FF10, FF12, FF116, FF221, FF222, and FF224-FF231.

122. The compound of embodiment 101 or 102, wherein:

each $B_1$ and $B_2$ is independently selected from F2 and F7 and is covalently conjugated to Z1c using an amide linkage, each Z1b is independently absent; FL3 wherein p is 1, 2, or 3; or FL5 wherein p is 2, 3, or 4;

each FF is independently selected from FF10, FF12, FF116, FF134, FF163, FF193, FF203, FF221, FF222 and FF224-FF231; wherein each FF12 and FF222 has either (S,R) or (S,S) stereochemistry;

each Z1c is conjugated either directly or indirectly through FL3 or FL5 to the amine group in one or more lysine side chain in X1 or the N-terminus in X1; and X1 is a polypeptide drug substance and/or an insulin optionally having from 0 to 4 residues replaced, inserted, or mutated to lysines, and wherein the lysines are each conjugated directly or indirectly to a Z1c.

123. The compound of embodiment 101 or 102, wherein Z1c is FF224, n' is 0, and Z1a is an amine containing amino acid.

124. The compound of any one of embodiments 101-123, wherein the compound is selected from:

$$\left[[Z1c]_{p'}\!-\!\!\left[Z1a\!\frac{}{}\!\right]_{m'}\!\right]_{q'}\!\!-\!X1; \tag{IA}$$

$$\left[[Z1c]_{p'}\!-\!\!\left[Z1b\!\frac{}{}\!\right]_{n'}\!\right]_{q'}\!\!-\!X1; \quad \text{and} \tag{IB}$$

$$\left[[Z1c]_{p'}\!\frac{}{}\!\right]_{q'}\!\!-\!X1. \tag{IC}$$

125. The compound of any one of embodiments 101-123, wherein the compound is selected from:

$$\left[[Z1c]_1\!\frac{}{}\!\right]_1\!\!-\!X1; \quad \left[[Z1c]_1\!\frac{}{}\!\right]_2\!\!-\!X1; \quad \left[[Z1c]_1\!\frac{}{}\!\right]_3\!\!-\!X1; \quad \left[[Z1c]_1\!\frac{}{}\!\right]_4\!\!-\!X1;$$

$$\left[[Z1c]_1\!\frac{}{}\!\right]_5\!\!-\!X1; \quad \left[[Z1c]_2\!-\!\![Z1a]_1\!\frac{}{}\!\right]_2\!\!-\!X1;$$

$$\left[[Z1c]_2\!-\!\![Z1a]_1\!\frac{}{}\!\right]_2\!\!-\!X1\!-\!\!\left[[Z1c]_1\right]_1;$$

$$\left[[Z1c]_2\!-\!\![Z1a]_1\!\frac{}{}\!\right]_2\!\!-\!X1\!-\!\!\left[[Z1c]_1\right]_2;$$

$$\left[[Z1c]_2\!-\!\![Z1a\!\frac{}{}\!\frac{}{}\!Z1b]_1\!\frac{}{}\!\right]_1\!\!-\!X1;$$

-continued $$\left[[Z1c]_2\!-\!\![Z1a]_1\!-\!\![Z1b]_1\!\frac{}{}\!\right]_1\!\!-\!X1\!-\!\!\left[[Z1c]_1\right]_1;$$

$$\left[[Z1c]_1\!-\!\![Z1b]_1\!\frac{}{}\!\right]_1\!\!-\!X1; \quad \left[[Z1c]_2\!-\!\![Z1a]_1\!\frac{}{}\!\right]_1\!\!-\!X1\!-\!\!\left[[Z1c]_1\right]_1;$$

$$\left[[Z1c]_2\!-\!\![Z1a]_1\!\frac{}{}\!\right]_1\!\!-\!X1\!-\!\!\left[[Z1c]_1\right]_2; \quad \text{and}$$

$$\left[[Z1c]_2\!-\!\![Z1a]_1\!\frac{}{}\!\right]_1\!\!-\!X1\!-\!\!\left[[Z1c]_1\right]_2.$$

126. The compound of embodiment 125, wherein the compound is selected from $$\left[\left[Z1c\!\frac{}{}\!\right]_2\!(Z1a\!\frac{}{}\!)_1\!\!-\!X1\!-\!\!\left[Z1c\right]_1\right]_1 \quad \text{and} \quad \left[\left[Z1c\!\frac{}{}\!\right]_1\!\!-\!X1.\right]_1$$

127. The compound of embodiment 111 or 112; wherein Z1c is covalently conjugated directly to X1 via a linker, and wherein the linker is independently selected from gamma-glutamic acid, beta-alanine, and Formula FL3

$$\tag{FL3}$$

[chemical structure diagram]

wherein p is 1, 2, or 3; and

Formula FL5

$$\tag{FL5}$$

[chemical structure diagram]

wherein p is 2, 3, or 4.

128. The compound of embodiment 101 or 102, wherein X1 is OH or $NH_2$, and the compound further comprises a drug substance covalently conjugated directly or indirectly to the compound.

129. The compound of embodiment 101 or 102, wherein the compound is selected from:

3065 3066

Example 881

H—G—K—P—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 882

H—G—K—P—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

-continued

Example 883

H—G—K—P—G—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 884

H—G—K—P—G—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

-continued

Example 885

H—G—K—P—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 886

H—G—K—P—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH 3071           3072

-continued

H—G—K—P—G—G—G—G—S—G—G—G—G—S—G—G—G—G—S—F—V—N—Q—H—L—

Example 887

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 888

H—G—K—P—G—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

-continued

Example 889

H—G—K—P—G—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

890

H—G—K—P—G—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

-continued

891

H—G—K—P—G—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 892

H—G—K—P—G—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

-continued

Example 893

H—G—K—P—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 894

H—G—K—P—G—G—G—S—G—G—G—G—S—G—G—G—G—S—F—V—N—Q—H—L—

-continued

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 895

H—G—K—P—G—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 896

H—G—K—P—G—G—G—G—S—G—G—G—G—S—G—G—G—G—S—F—V—N—Q—H—L—

-continued

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 897

H—G—K—P—G—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH,

Example 898

H—G—K—P—G—G—G—G—S—G—G—G—G—S—G—G—G—G—S—F—V—N—Q—H—L—

-continued

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 899

H—G—K—P—G—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 900

H—G—K—P—G—G—G—G—S—G—G—G—G—S—G—G—G—G—S—F—V—N—Q—H—L—

-continued

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 901

H—G—K—P—G—G—G—S—G—G—G—G—S—G—G—G—G—S—F—V—N—Q—H—L—

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 902

H—G—K—P—G—G—G—S—G—G—G—G—S—G—G—G—G—S—F—V—N—Q—H—L—

-continued

H—G—I—V—E—Q—C—C—T—S—I—C—S—L—Y—Q—L—E—N—Y—C—N—OH

—C—G—S—H—L—V—E—A—L—Y—L—V—C—G—D—R—G—F—F—Y—T—P—K—OH

Example 903

H-G-I-V-E-Q-C-C-T-S-I-C-S-L-Y-Q-L-E-N-Y-C-N-OH

H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 904

H-G-I-V-E-Q-C-C-T-S-I-C-S-L-Y-Q-L-E-N-Y-C-N-OH

H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 905

H-G-I-V-E-Q-C-C-T-S-I-C-S-L-Y-Q-L-E-N-Y-C-N-OH

H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

-continued

Example 906

H-G-I-V-E-Q-C-C-T-S-I-C-S-L-Y-Q-L-E-N-Y-C-N-OH

H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 907

H-G-I-V-E-Q-C-C-T-S-I-C-S-L-Y-Q-L-E-N-Y-C-N-OH

H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 908

H-G-I-V-E-Q-C-C-T-S-I-C-S-L-Y-Q-L-E-N-Y-C-N-OH

H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 909

H-G-I-V-E-Q-C-C-T-S-I-C-S-L-Y-Q-L-E-N-Y-C-N-OH

H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

3091  3092

-continued

Example 910

H-G-I-V-E-Q-C-C-T-S-I-C-S-L-Y-Q-L-E-N-Y-C-N-OH
H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

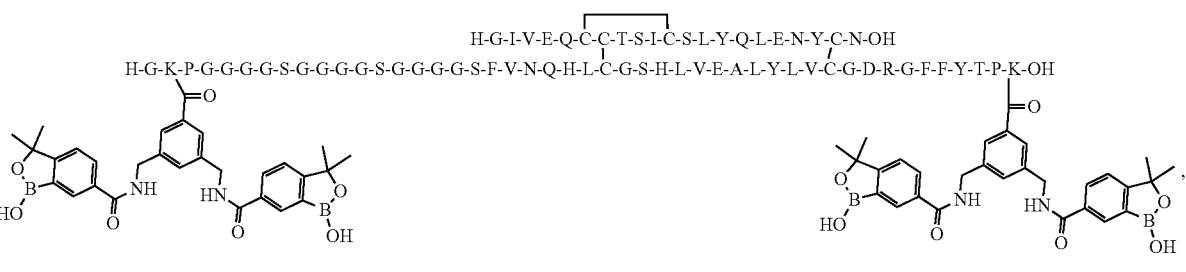

Example 911

H-G-I-V-E-Q-C-C-T-S-I-C-S-L-Y-Q-L-E-N-Y-C-N-OH
H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

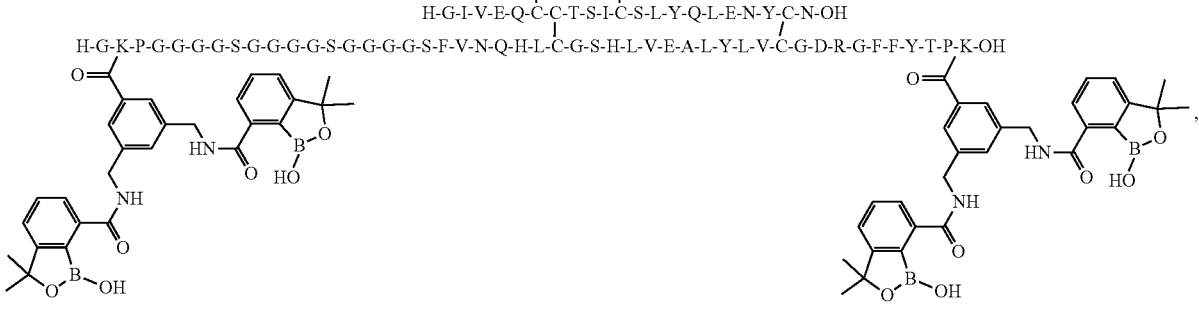

Example 912

H-G-I-V-E-Q-C-C-T-S-I-C-S-L-Y-Q-L-E-N-Y-C-N-OH
H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 913

H-G-I-V-E-Q-C-C-T-S-I-C-S-L-Y-Q-L-E-N-Y-C-N-OH
H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

Example 914

H-G-I-V-E-Q-C-C-T-S-I-C-S-L-Y-Q-L-E-N-Y-C-N-OH
H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

-continued

Example 915

H-G-I-V-E-Q-C-C-T-S-I-C-S-L-Y-Q-L-E-N-Y-C-N-OH

H-G-K-P-G-G-G-G-S-G-G-G-G-S-G-G-G-G-S-F-V-N-Q-H-L-C-G-S-H-L-V-E-A-L-Y-L-V-C-G-D-R-G-F-F-Y-T-P-K-OH

130. The compound of embodiment 101 or 102, wherein X1 is a polypeptide drug substance and/or an insulin optionally having from 0 to 4 residues replaced, inserted, or mutated to lysines, and wherein the lysines are each conjugated to a Z1c.

131. The compound of embodiment 101 or 102, wherein one or more amines are each independently acetylated and/or independently alkylated.

132. The compound of embodiment 101 or 102, wherein wherein X1 comprises a polypeptide drug substance and the covalent conjugation to X1 is to amino group(s) in one or more lysine residues and/or to the N-terminal amino groups in X1.

133. The compound of embodiment 101 or 102, wherein each $R_1$ is independently selected from a $C_1$-$C_{22}$ alkyl group, a $C_1$-$C_{22}$ acyl group, a $(C_3$-$C_8)$cycloalkyl group, a $C_1$-$C_{22}$ haloalkyl group, an aryl group, and a heteroaryl group, each $R_1$ optionally comprises one or more $C_1$-$C_{22}$ alkyl-halide, halide, sulfhydryl, aldehyde, amine, acid, hydroxyl, $C_1$-$C_{22}$ alkyl, or aryl groups.

134. The compound of embodiment 101 or 102, wherein X4 is selected from —COOH, —$(CH_2)_m$COOH, a $C_1$-$C_{22}$ alkyl group, a $C_1$-$C_{22}$acyl group, a $(C_3$-$C_8)$cycloalkyl group, a $C_1$-$C_{22}$ haloalkyl group, an aryl group, and a heteroaryl group, each X4 optionally comprises one or more $C_1$-$C_{22}$ alkyl-halide, halide, sulfhydryl, aldehyde, amine, acid, hydroxyl, $C_1$-$C_{22}$ alkyl, or aryl groups; wherein m is 1, 2, 3, 4, or 5.

135. The compound of embodiment 103, wherein the alkyl group of Y9 is a $C_1$-$C_{22}$ alkyl.

136. The compound of embodiment 135, wherein Y9 is $CH_3$.

137. The compound of embodiment 101, wherein the at least one primary or secondary amine in FF1-FF223 and FF225-FF231 is covalently conjugated to B6.

138. The compound of embodiment 101 or 102, wherein an amine in the compound is conjugated via an amide linkage to an aromatic boron-containing group.

139. The compound of embodiment 138, wherein the aromatic boron-containing group is selected from a phenylboronic acid, boroxole, and phenylboronate.

140. The compound of any one of embodiments 101-139, wherein the compound is formulated in a solution comprising one or more of a buffer, stabilizer, vasodilator, preservative, surfactant, salt, sugar, or compounds containing one or more hydroxyls, alcohols, diols, or phenols.

141. The compound of embodiment 140, wherein the solution comprises one or more of citrate, zinc, and/or cresol.

142. The compound of embodiment 101 or 102, wherein Z1c is conjugated to a cysteine.

143. The compound of embodiment 101 or 102, wherein the compound is covalently conjugated either directly or through a linker to a diol, sugar, carbohydrate or a diol containing molecule.

144. The compound of embodiment 101 or 102, wherein the compound is covalently conjugated to an antibody, albumin or a fragment thereof, or covalently conjugated either directly or through a linker to a molecule that can bind to at least one protein present in human plasma.

145. The compound of any one of embodiments 101-144, wherein the compound comprises at least one Z1c selected from:

(FF1)

(FF2)

(FF6)

(FF9)

(FF10)

3095

-continued (FF11)

(FF12)

(FF13)

(FF14)

(FF16)

(FF17)

(FF18)

(FF35)

3096

-continued (FF56)

(FF57)

(FF58)

(FF59)

(FF61)

(FF60)

(FF62)

(FF65)

(FF66)

3097

-continued (FF67)

(FF70)

(FF71)

(FF72)

(FF75)

(FF76)

(FF77)

3098

-continued (FF80)

(FF81)

(FF84)

(FF88)

(FF92)

(FF101)

3099

-continued (FF102)

(FF107)

(FF108)

(FF109)

(FF110)

3100

-continued (FF111)

(FF112)

(FF113)

(FF114)

(FF115)

(FF116)

3101

-continued (FF117)

(FF118)

(FF119)

(FF120)

(FF121)

(FF122)

(FF123)

3102

-continued (FF124)

(FF125)

(FF126)

(FF127)

(FF128)

(FF129)

(FF130)

-continued (FF131)

(FF132)

(FF133)

(FF134)

(FF135)

(FF136)

FF193

-continued

FF194

FF203

(FF225)

(FF226)

(FF227)

(FF228)

(FF229)

-continued (FF230)

(FF231)

146. The compound of embodiment 145, wherein the compound comprises at least one Z1c having at least one chiral center and selected from FF1, FF2, FF5, FF9, FF11-FF13, FF15-FF24, FF27, FF31, FF34-FF36, FF38, FF39, FF43-FF58, FF60-FF70, FF72-FF75, FF77-FF80, FF82-FF84, FF86-FF212, FF216-FF220, FF222, FF223, and combinations thereof.

147. The compound of embodiment 146, wherein the compound comprises at least one FF12 and/or FF116; and
  wherein the stereochemistry of FF12 and FF116 is independently selected from (S,S); (S,R); (R,R); and (R,S).

148. The compound of embodiment 101 or 102, wherein X1 comprises human insulin or a human insulin analogue comprising an A-chain and a B-chain, wherein the C-terminus of the A-chain of the human insulin analogue is optionally extended with a polypeptide of up to 20 residues, and/or the N-terminus of the B-chain of the human insulin analogue is optionally extended with a polypeptide of up to 10 residues.

149. The compound of embodiment 148, wherein X1 comprises at least one lysine having an amine side chain, and Z1c is covalently conjugated directly to the amine side chain.

150. The compound of embodiment 101 or 102, wherein X1 comprises a drug substance covalently conjugated to at least one Z1c through an acid containing linker.

151. A composition or a mixture comprising at least one compound of any one of embodiments 101-150, for use as a medicament for the treatment of diabetes, for control of blood sugar levels, or to control the release of a drug based on physiological levels of diol containing small molecules or sugars.

152. A method of administering the compound of any one of embodiments 101-150 to a human subject as a therapeutic or prophylactic agent.

153. A method of making a compound of any one of embodiments 101-150, wherein the method comprises at least one alkylation and/or amidation step.

154. A method of treating a subject by administering a device or formulation comprising a compound of any one of embodiments 101-150 and Examples 881-915.

155. A method of treatment or prevention of diabetes, impaired glucose tolerance, hyperglycemia, or metabolic syndrome, wherein the method comprises administering to a subject in need thereof a therapeutically effective amount of the compound of any one of embodiments 101-150 or the composition or the mixture of embodiment 151.

156. A compound selected from Formulae FF1-FF231:
  wherein Formulae FF1-FF48 are:

(FF1)

(FF2)

(FF3)

(FF4)

(FF5)

(FF6)

(FF7)

3107

-continued (FF8)

(FF9)

(FF10)

(FF11)

(FF12)

(FF13)

(FF14)

3108

-continued (FF15)

(FF16)

(FF17)

(FF18)

(FF19)

(FF20)

(FF21)

3109

-continued (FF22)

(FF23)

(FF24)

(FF25)

(FF26)

(FF27)

(FF28)

3110

-continued (FF29)

(FF30)

(FF31)

(FF32)

(FF33)

(FF34)

(FF35)

(FF36)

-continued (FF37)

(FF38)

(FF39)

(FF40)

(FF41)

(FF42)

(FF43)

(FF44)

(FF45)

-continued (FF46)

(FF47)

and (FF48)

wherein X is selected from an maleimide, amine, OH, and halogen; and i is 1, 2, 3, 4, 5, 6, or 7;

j is 1, 2, 3, 4, 5, 6, or 7; and $B_1$ and $B_2$, which may be identical or different, each independently represents an aromatic boron-containing group; and wherein Formulae FF49-FF88 are:

(FF49)

(FF50)

(FF51)

(FF52)

(FF53)

-continued (FF54)

(FF55)

(FF56)

(FF57)

(FF58)

(FF59)

(FF60)

(FF61)

(FF62)

-continued (FF63)

(FF64)

(FF65)

(FF66)

(FF67)

(FF68)

(FF69)

3115

-continued (FF70)

(FF71)

(FF72)

(FF73)

(FF74)

(FF75)

(FF76)

3116

-continued (FF77)

(FF78)

(FF79)

(FF80)

(FF81)

(FF82)

3117

-continued (FF83)

(FF84)

(FF85)

(FF86)

(FF87)

and (FF88)

wherein X is selected from maleimide, an amine, OH, and halogen;

i is 1, 2, 3, 4, 5, 6, or 7;

3118 j is 1, 2, 3, 4, 5, 6, or 7;

R₁a is selected from COOH, CH₃, H, and OH;

R₂, R₃, R₄ and R₅ is each independently selected from CH₃, H, OH, and COOH, and at least one of R₂, R₃, R₄ and R₅ is CH₃ or OH; and B₁ and B₂, which may be identical or different, are each independently an aromatic boron-containing group; and wherein Formulae FF89-FF112 are:

(FF89)

(FF90)

(FF91)

(FF92)

-continued (FF93)

(FF94)

(FF95)

(FF96)

(FF97)

(FF98)

-continued (FF99)

(FF100)

(FF101)

(FF102)

(FF103)

-continued (FF104)

(FF105)

(FF106)

(FF107)

(FF108)

-continued (FF109)

(FF110)

(FF111)

and (FF112)

wherein X is selected from maleimide, an amine, OH, and halogen;

i is 1, 2, 3, 4, 5, 6, or 7; and $B_1$, $B_2$ and $B_3$, which may be identical or different, each independently represents an aromatic boron-containing group, a carboxylic acid derivative, or a H, wherein at least two of B1, B2 and B3 in each FF structure are independently an aromatic boron-containing group; and

3123 wherein Formulae FF113-FF136 are:

(FF113)

(FF114)

(FF115)

(FF116)

(FF117)

(FF118)

(FF119)

3124

(FF120)

(FF121)

(FF122)

(FF123)

(FF124)

(FF125)

(FF126)

3125

-continued (FF127)

(FF128)

(FF129)

(FF130)

(FF131)

(FF132)

3126

-continued (FF133)

(FF134)

(FF135)

and (FF136)

wherein X is selected from maleimide, an amine, OH, and halogen;

i is 1, 2, 3, 4, 5, 6, or 7;

j is 1, 2, 3, 4, 5, 6, or 7 k is 1, 2, 3, 4, 5, 6, or 7;

m is 1, 2, 3, 4, 5, 6, or 7;

each $R_1$ is independently selected from H, an alkyl group, an acyl group, a cycloalkyl group, a haloalkyl group, an aryl group, and a heteroaryl group, each $R_1$ optionally comprises one or more alkyl-halide, halide, sulfhydryl, aldehyde, amine, acid, hydroxyl, alkyl or aryl groups; and $B_1$ and $B_2$, which may be identical or different, each independently represents an aromatic boron-containing group; and wherein Formulae FF137-FF160 are:

(FF137)

3127

-continued (FF138)

(FF139)

(FF140)

(FF141)

(FF142)

(FF143)

(FF144)

3128

-continued (FF145)

(FF146)

(FF147)

(FF148)

(FF149)

(FF150)

(FF151)

3129

-continued (FF152)

(FF153)

(FF154)

(FF155)

(FF156)

(FF157)

3130

-continued (FF158)

(FF159)

and (FF160)

wherein X is selected from maleimide, an amine, OH, and halogen;

i is 1, 2, 3, 4, 5, 6, or 7;

j is 1, 2, 3, 4, 5, 6, or 7;

k is 1, 2, 3, 4, 5, 6, or 7;

m is 1, 2, 3, 4, 5, 6, or 7;

each $R_1$ is independently selected from H, an alkyl group, an acyl group, a cycloalkyl group, a haloalkyl group, an aryl group, and a heteroaryl group, each, R optionally comprises one or more alkyl-halide, halide, sulfhydryl, aldehyde, amine, acid, hydroxyl, alkyl or aryl groups; and $B_1$ and $B_2$, which may be identical or different, each independently represents an aromatic boron-containing group; and wherein Formulae FF161-FF164 are:

(FF161)

(FF162)

-continued (FF163)

(FF164)

wherein X is selected from maleimide, an amine, OH, and halogen;

i is 1, 2, 3, 4, or 5;

j is 1, 2, 3, 4, or 5;

each $R_6$, $R_7$, $R_8$, and $R_9$ for different values of j is independently selected from H, $CF_3$, $CH_3$, $CHF_2$, and $(CH_2)_m CH_3$, wherein m is 1, 2, 3, 4, or 5;

Y3, Y4, Y5, Y6 and Y7 are each independently selected from H, $CH_2$—X4, and Formulae IV-1 to IV-135;

wherein X4 is selected from —COOH, —$(CH_2)_m$COOH, an alkyl group, an acyl group, a cycloalkyl group, a haloalkyl group, an aryl group, and a heteroaryl group, each optionally comprising one or more alkyl-halide, halide, sulfhydryl, aldehyde, amine, acid, hydroxyl, alkyl or aryl groups; wherein m is 1, 2, 3, 4, or 5;

wherein at least one of Y5, Y6, and Y7 in Formulae FF162 and FF163 is not H and at least one of Y7, $R_8$ and $R_9$ in FF164 is not H; and wherein Formulae IV-1 to IV-135 are:

(IV-1)

(IV-2)

(IV-3)

(IV-4)

-continued (IV-5)

(IV-6)

(IV-7)

(IV-8)

(IV-9)

(IV-10)

(IV-11)

(IV-12)

(IV-13)

(IV-14)

3133

-continued (IV-15)

(IV-16)

(IV-17)

(IV-18)

(IV-19)

(IV-20)

(IV-21)

(IV-22)

(IV-23)

(IV-24)

(IV-25)

3134

-continued (IV-26)

(IV-27)

(IV-28)

(IV-29)

(IV-30)

(IV-31)

(IV-32)

(IV-33)

(IV-34)

(IV-35)

(IV-36)

(IV-37)

(IV-38)

3135

-continued (IV-39)

(IV-40)

(IV-41)

(IV-42)

(IV-43)

(IV-44)

(IV-45)

(IV-46)

(IV-47)

(IV-48)

3136

-continued (IV-49)

(IV-50)

(IV-51)

(IV-52)

(IV-53)

(IV-54)

(IV-55)

(IV-56)

3137

-continued (IV-57)

(IV-58)

(IV-59)

(IV-60)

(IV-61)

(IV-62)

(IV-63)

3138

-continued (IV-64)

(IV-65)

(IV-66)

(IV-67)

(IV-68)

(IV-69)

3139

-continued (IV-70)

(IV-71)

(IV-72)

(IV-73)

(IV-74)

(IV-75)

(IV-76)

3140

-continued (IV-77)

(IV-78)

(IV-79)

(IV-80)

(IV-81)

(IV-82)

(IV-83)

(IV-84)

(IV-85)

3141

-continued (IV-86)

(IV-87)

(IV-88)

(IV-89)

(IV-90)

(IV-91)

(IV-92)

(IV-93)

(IV-94)

3142

-continued (IV-95)

(IV-96)

(IV-97)

(IV-98)

(IV-99)

(IV-100)

(IV-101)

(IV-102)

(IV-103)

3143

-continued (IV-104)

(IV-105)

(IV-106)

(IV-107)

(IV-108)

(IV-109)

3144

-continued (IV-110)

(IV-111)

(IV-112)

(IV-113)

(IV-114)

(IV-115)

(IV-116)

(IV-117)

(IV-118)

(IV-119)

3145

-continued (IV-120)

(IV-121)

(IV-122)

(IV-123)

(IV-124)

(IV-125)

(IV-126)

(IV-127)

3146

-continued (IV-128)

(IV-129)

(IV-130)

(IV-131)

(IV-132)

(IV-133)

(IV-134)

and (IV-135)

wherein:

Xa represents CH=O, CHF$_2$, CF$_3$, CH$_2$SH, COOH, CH$_2$OH, CH$_2$NO$_2$, CH$_2$NH$_2$, CH$_3$, C(CH$_3$)$_3$, CH(CH$_3$)$_2$, CH((CH$_2$)$_3$CH$_3$)$_2$, or CH(CH$_2$CH$_3$)$_2$;

Xb represents O, NH, CH$_2$, or S

Xc represents CH or N;

each R$_{10}$ is independently selected from H, F, Cl, Br, CH$_3$, CF$_3$, CH=O, OH, COOH, and (CH$_2$)$_n$CH$_3$, m is 1, 2, 3, 4, or 5; and n is 1, 2, 3, 4, or 5;

B$_1$ and B$_2$, which may be identical or different, each independently represents an aromatic boron-containing group; and

* in Formulae IV-1 to IV-135 represents the point of attachment to corresponding Formulae FF161-164; and wherein Formulae FF165-FF166 are:

(FF165)

and (FF166)

wherein X is selected from maleimide, an amine, OH, and halogen;

m is 1, 2, 3, 4, 5, 6, or 7;

n is 1, 2, 3, 4, 5, 6, or 7;

X5 is S, O, or NH; and each R$_1$ is independently selected from H, F, Cl, Br, OH, CH$_2$—NH$_2$, NH$_2$, (C=O)—NH$_2$, CH=O, SO$_2$CH$_3$, SO$_2$CF$_3$, CF$_3$, CHF$_2$, NO$_2$, CH$_3$, OCH$_3$, O(CH$_2$)$_m$CH$_3$, —(SO$_2$)NH CH$_3$, —(SO$_2$)NH(CH$_2$)$_m$CH$_3$, and OCF$_3$, wherein m is 1, 2, 3, 4, 5, 6, or 7; and wherein Formulae FF167-FF192 are:

(FF167)

(FF168)

(FF169)

(FF170)

(FF171)

(FF172)

(FF173)

(FF174)

(FF175)

3149

-continued (FF176)

(FF177)

(FF178)

(FF179)

(FF180)

(FF181)

(FF182)

3150

-continued (FF183)

(FF184)

(FF185)

(FF186)

(FF187)

(FF188)

(FF189)

-continued (FF190)

(FF191)

and (FF192)

wherein X is selected from an maleimide, amine, OH, and halogen;

B₁ and B₂, which may be identical or different, each independently represents an aromatic boron-containing group, and wherein Formulae FF193-FF209 are:

FF193

FF194

FF195

-continued

FF196

FF197

FF198

FF199

FF200

FF201

FF202

FF203

3153

-continued

FF204

FF205

FF206

FF207

FF208

FF209 wherein R in FF208 and FF209 is an alkyl, aryl or halide that is covalently conjugated through at least one $CH_2$ group to the amino group in the side chain of FF208 or FF209; $R_1$ and $R_2$ are independently selected from H, $CH_3$, alkyl, and formulae IV-1 to IV-135;

i is 1, 2, 3, 4, or 5;

j is 1, 2, 3, 4, or 5; and wherein X is selected from maleimide, an amine, OH, and halogen; and $B_1$ and $B_2$, which may be identical or different, each independently represents an aromatic boron-containing group;

3154 wherein Formulae FF210-FF224 are:

FF210

FF211

FF212

FF213

FF214

FF215

FF216

FF217

FF218

3155

-continued

FF219

FF220

FF221

FF222

FF223 and

FF224 wherein $R_{11}$ in FF210 to FF212 is independently selected from Formulae IV-1 to IV-135 and $R_{12}$ is selected from an amine, a hydroxyl, an alkyl, and a halide group;

wherein each $R_{13}$ is independently selected from H, $CH_3$, alkyl, aryl, and formulae IV-1 to IV-135; $R_{14}$ is selected from H, $CH_3$, alkyl, aryl, and heteroaryl;

wherein X is independently selected from maleimide, an amine, OH, and halogen;

X" is an amine;

i is 1, 2, 3, 4, or 5;

j is 1, 2, 3, 4, or 5;

and $B_1$, $B_2$, $B_3$, $B_4$, $B_5$ and $B_6$ each independently represents an aromatic boron-containing group, wherein in each FF structure containing B1, B2 and B3 groups, at least two of the B1, B2 and B3 groups are independently an aromatic boron-containing group; and

3156 wherein Formulae FF225-FF231 are:

(FF225)

(FF226)

(FF227)

(FF228)

(FF229)

(FF230)

3157

-continued (FF231)

wherein X is selected from an maleimide, amine, OH, and halogen;

i is 1, 2, 3, 4, 5, 6, or 7;

$B_1$ and $B_2$, which may be identical or different, each independently represents an aromatic boron-containing group, wherein $B_1$ and $B_2$ in Formulae FF225-FF231 are not a boronic acid or an F2 or F6 aromatic boron-containing group, wherein Formulae F2 and F6 are:

(F2)

and (F6)

$R_1$ at position 5' represents (C=O)—*, wherein —* represents the attachment point to the rest of FF225-FF231;

zero, one, or two $R_1$ represents F, Cl, $CF_2$, $CF_3$, $SF_5$, $OCF_3$, $SO_2CH_3$, and/or $SO_2CF_3$, and each remaining $R_1$ represents H;

Y8 is O; and i is 1; and each remaining $R_1$ is H;

Y8 is O; and i is 1; and wherein at least one primary or secondary amine in FF1-FF223 and FF225-FF231 is optionally covalently conjugated to $B_6$; and when X is an amine in any one of Formulae FF1 to FF223 and FF225-FF231, X is optionally acetylated or alkylated.

157. The compound of embodiment 156, wherein the compound comprises at least one of $B_1$, $B_2$ and $B_3$ independently selected from Formulae F1-F11 or wherein the compound comprises at least one of $B_4$, $B_5$ and $B_6$ independently selected from Formulae F1-F11,

3158 wherein Formulae F1-F11 are:

(F1)

(F2)

(F3)

(F4)

(F5)

(F6)

(F7)

-continued (F8)

(F9)

(F10)

and (F11)

wherein for $B_1$, $B_2$, $B_3$:

one $R_1$ represents (C=O)—*, S(=O)(=O)—*, $(CH_2)_m$(C=O)—*, or $(CH_2)_m$—*, wherein —* represents an attachment point to the rest of Z1c, and m is 1, 2, 3, 4, 5, 6, or 7;

each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$ $CH_3$, —$(SO_2)NH$ $(CH_2)_mCH_3$, and $OCF_3$, wherein m is 1, 2, 3, 4, 5, 6, or 7;

wherein for $B_4$, $B_5$:

one $R_1$ for $B_4$ represents $(CH_2)_m$—ø, wherein —ø represents the attachment point (representing a covalent bond) to an amine in X1 and one $R_1$ for $B_5$ represents (C=O)—*, S(=O)(=O)—*, $(CH_2)_m(C=O)$—*, or $(CH_2)_m$—*, wherein —* represents the attachment point to the same amine in X1, and m is 1, 2, 3, 4, 5, 6, or 7;

each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$ $CH_3$, —$(SO_2)NH$ $(CH_2)_mCH_3$, and $OCF_3$, wherein m is 1, 2, 3, 4, 5, 6, or 7;

wherein for $B_6$:

one $R_1$ for $B_6$ represents $(CH_2)_m$—ø, wherein —ø represents the attachment point (representing a covalent bond) to the rest of the compound, and m is 1, 2, 3, 4, 5, 6, or 7;

each remaining $R_1$ or $R_2$ is independently selected from H, F, Cl, Br, OH, $CH_2$—$NH_2$, $NH_2$, (C=O)—$NH_2$, CH=O, $SO_2CH_3$, $SO_2CF_3$, $CF_3$, $CHF_2$, $NO_2$, $CH_3$, $OCH_3$, $O(CH_2)_mCH_3$, —$(SO_2)NH$ $CH_3$, —$(SO_2)NH$ $(CH_2)_mCH_3$, and $OCF_3$, wherein m is 1, 2, 3, 4, 5, 6, or 7; for Formulae F3-F4:

$R_w$ is O or S;

for Formulae F5-F10:

when Y8 is O, i is 2, 3, 4, or 5; or when Y8 is NR, R is an alkyl group or H, and i is 1, 2, 3, 4, or 5;

Y9 is H, $CH_3$, or an alkyl group, provided that when Y8 is O, Y9 is a $CH_3$ or an alkyl group; and each Y10 is independently selected from H, $CH_3$, F, $CF_3$, and $OCH_3$, with the proviso that at least one Y10 is not H.

158. The compound of embodiment 156 or 157, wherein the compound is selected from:

N-(3-(3-borono-5-nitrobenzamido)propyl)-N-(3-borono-5-nitrobenzoyl)glycine (DS01);

N-(4-((4-(3-borono-5-nitrobenzamido)cyclohexyl)methyl) cyclohexyl)-N-(3-borono-5-nitrobenzoyl)glycine (DS02);

N-(4-((3-borono-5-nitrobenzamido)methyl)benzyl)-N-(3-borono-5-nitrobenzoyl)glycine (DS03);

N-(3-((3-borono-5-nitrobenzamido)methyl)benzyl)-N-(3-borono-5-nitrobenzoyl)glycine (DS04);

N-(4-(3-borono-5-nitrobenzamido)butyl)-N-(3-borono-5-nitrobenzoyl)glycine (DS05);

N-(3-(3-borono-5-fluorobenzamido)propyl)-N-(3-borono-5-fluorobenzoyl)glycine (DS06);

N-(3-(3-borono-5-fluorobenzamido)-2,2-dimethylpropyl)-N-(3-borono-5-fluorobenzoyl)glycine (DS07);

bis(3-(3-borono-5-fluorobenzamido)propyl)glycine (DS08);

N-(4-((3-borono-5-fluorobenzamido)methyl)benzyl)-N-(3-borono-5-fluorobenzoyl)glycine (DS09);

N-(3-((3-borono-5-fluorobenzamido)methyl)benzyl)-N-(3-borono-5-fluorobenzoyl)glycine (DS10);

N-(2-(3-borono-5-fluorobenzamido)cyclohexyl)-N-(3-borono-5-fluorobenzoyl)glycine (DS11);

N-(3-(3-borono-4-fluorobenzamido)propyl)-N-(3-borono-4-fluorobenzoyl)glycine (DS12);

N-(4-((4-(3-borono-4-fluorobenzamido)cyclohexyl)methyl) cyclohexyl)-N-(3-borono-4-fluorobenzoyl)glycine (DS13);

N-(3-(3-borono-4-fluorobenzamido)-2,2-dimethylpropyl)-N-(3-borono-4-fluorobenzoyl)glycine (DS14);

N-(4-((3-borono-4-fluorobenzamido)methyl)benzyl)-N-(3-borono-4-fluorobenzoyl)glycine (DS15);

N-(3-((3-borono-4-fluorobenzamido)methyl)benzyl)-N-(3-borono-4-fluorobenzoyl)glycine (DS16);

N-((1S,2R)-2-(3-borono-4-fluorobenzamido)cyclohexyl)-N-(3-borono-4-fluorobenzoyl)glycine (DS17);

N-((1S,2S)-2-(3-borono-4-fluorobenzamido)cyclohexyl)-N-(3-borono-4-fluorobenzoyl)glycine (DS18);

N-(3-(3-borono-5-bromobenzamido)propyl)-N-(3-borono-5-bromobenzoyl)glycine (DS19);

N-(4-((4-(3-borono-5-bromobenzamido)cyclohexyl) methyl)cyclohexyl)-N-(3-borono-5-bromobenzoyl)glycine (DS20);

bis(3-(3-borono-5-bromobenzamido)propyl)glycine (DS21);

N-(4-((3-borono-5-bromobenzamido)methyl)benzyl)-N-(3-borono-5-bromobenzoyl)glycine (DS22);

N-(3-((3-borono-5-bromobenzamido)methyl)benzyl)-N-(3-borono-5-bromobenzoyl)glycine (DS23);

N-(2-(3-borono-5-bromobenzamido)cyclohexyl)-N-(3-borono-5-bromobenzoyl)glycine (DS24);

N-(3-(4-borono-3-fluorobenzamido)propyl)-N-(4-borono-3-fluorobenzoyl)glycine (DS25);

N-(4-((4-(4-borono-3-fluorobenzamido)cyclohexyl)methyl)cyclohexyl)-N-(4-borono-3-fluorobenzoyl)glycine (DS26);

N-(3-(4-borono-3-fluorobenzamido)-2,2-dimethylpropyl)-N-(4-borono-3-fluorobenzoyl)glycine (DS27);

bis(3-(4-borono-3-fluorobenzamido)propyl)glycine (DS28);

N-(4-((4-borono-3-fluorobenzamido)methyl)benzyl)-N-(4-borono-3-fluorobenzoyl)glycine (DS29);

N-(3-((4-borono-3-fluorobenzamido)methyl)benzyl)-N-(4-borono-3-fluorobenzoyl)glycine (DS30);

N-((1S,2R)-2-(4-borono-3-fluorobenzamido)cyclohexyl)-N-(4-borono-3-fluorobenzoyl)glycine (DS31);

N-(1-hydroxy-1,3-dihydrobenzo[c][1,2]oxaborole-6-carbonyl)-N-(3-(1-hydroxy-1,3-dihydrobenzo[c][1,2]oxaborole-6-carboxamido)propyl)glycine (DS32);

N-(1-hydroxy-1,3-dihydrobenzo[c][1,2]oxaborole-6-carbonyl)-N-(5-(1-hydroxy-1,3-dihydrobenzo[c][1,2]oxaborole-6-carboxamido)pentyl)glycine (DS33);

N-(1-hydroxy-1,3-dihydrobenzo[c][1,2]oxaborole-6-carbonyl)-N-(3-(1-hydroxy-1,3-dihydrobenzo[c][1,2]oxaborole-6-carboxamido)-2,2-dimethylpropyl)glycine (DS34);

bis(3-(1-hydroxy-1,3-dihydrobenzo[c][1,2]oxaborole-6-carboxamido)propyl)glycine (DS35);

N-(1-hydroxy-1,3-dihydrobenzo[c][1,2]oxaborole-6-carbonyl)-N-(3-((1-hydroxy-1,3-dihydrobenzo[c][1,2]oxaborole-6-carboxamido)methyl)benzyl)glycine (DS36);

N-(1-hydroxy-1,3-dihydrobenzo[c][1,2]oxaborole-6-carbonyl)-N-((1S,2R)-2-(1-hydroxy-1,3-dihydrobenzo[c][1,2]oxaborole-6-carboxamido)cyclohexyl)glycine (DS37);

N-(1-hydroxy-1,3-dihydrobenzo[c][1,2]oxaborole-6-carbonyl)-N-(4-(1-hydroxy-1,3-dihydrobenzo[c][1,2]oxaborole-6-carboxamido)butyl)glycine (DS38);

N-(1-hydroxy-1,3-dihydrobenzo[c][1,2]oxaborole-6-carbonyl)-N-((1S,2S)-2-(1-hydroxy-1,3-dihydrobenzo[c][1,2]oxaborole-6-carboxanido)cyclohexyl)glycine (DS39);

(R)—N-(1-hydroxy-1,3-dihydrobenzo[c][1,2]oxaborole-6-carbonyl)-N-(2-(1-hydroxy-1,3-dihydrobenzo[c][1,2]oxaborole-6-carboxamido)propyl)glycine (DS40);

(S)—N-(1-hydroxy-1,3-dihydrobenzo[c][1,2]oxaborole-6-carbonyl)-N-(2-(1-hydroxy-1,3-dihydrobenzo[c][1,2]oxaborole-6-carboxamido)propyl)glycine (DS41);

N-(1-hydroxy-1,3-dihydrobenzo[c][1,2]oxaborole-6-carbonyl)-N-(2-(1-hydroxy-1,3-dihydrobenzo[c][1,2]oxaborole-6-carboxamido)cyclohexyl)glycine (DS42);

N-(3-(4-borono-3,5-difluorobenzamido)propyl)-N-(4-borono-3,5-difluorobenzoyl)glycine (DS43);

N-(3-(4-borono-2-fluorobenzanido)propyl)-N-(4-borono-2-fluorobenzoyl)glycine (DS44);

N-(2-(N-ethyl-1-hydroxy-1,3-dihydrobenzo[c][1,2]oxaborole-6-carboxamido)ethyl)-N-(1-hydroxy-1,3-dihydrobenzo[c][1,2]oxaborole-6-carbonyl)glycine (DS45);

N-(1-hydroxy-1,3-dihydrobenzo[c][1,2]oxaborole-6-carbonyl)-N-(2-(1-hydroxy-N-(2-hydroxyethyl)-1,3-dihydrobenzo[c][1,2]oxaborole-6-carboxamido)ethyl)glycine (DS46);

N-(1-hydroxy-1,3-dihydrobenzo[c][1,2]oxaborole-6-carbonyl)-N-(5-(1-hydroxy-1,3-dihydrobenzo[c][1,2]oxaborole-6-carboxamido)hexyl)glycine (DS47);

N-(1-hydroxy-1,3-dihydrobenzo[c][1,2]oxaborole-6-carbonyl)-N-(4-((4-(1-hydroxy-1,3-dihydrobenzo[c][1,2]oxaborole-6-carboxamido)cyclohexyl)methyl)cyclohexyl)glycine (DS48);

((2S,4S)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carbonyl)glycine (DS49);

((2S,4S)-4-(3-borono-4-fluorobenzamido)-1-(3-borono-4-fluorobenzoyl)pyrrolidine-2-carbonyl)glycine (DS50);

((2S,4S)-4-(3-borono-5-nitrobenzamido)-1-(3-borono-5-nitrobenzoyl)pyrrolidine-2-carbonyl)glycine (DS51);

((2S,4S)-4-(5-borono-2-fluorobenzamido)-1-(5-borono-2-fluorobenzoyl)pyrrolidine-2-carbonyl)glycine (DS52);

(S)-(1,4-bis(1-hydroxy-1,3-dihydrobenzo[c][1,2]oxaborole-6-carbonyl)piperazine-2-carbonyl)glycine (DS53);

(S)—N-(3-amino-2-(1-hydroxy-1,3-dihydrobenzo[c][1,2]oxaborole-6-carboxamido)-3-oxopropyl)-N-benzyl-1-hydroxy-1,3-dihydrobenzo[c][1,2]oxaborole-6-carboxamide (DS54);

(S)—N-(3-amino-2-(1-hydroxy-1,3-dihydrobenzo[c][1,2]oxaborole-6-carboxamido)-3-oxopropyl)-1-hydroxy-N-(4-(trifluoromethyl)benzyl)-1,3-dihydrobenzo[c][1,2]oxaborole-6-carboxamide (DS55);

(S)—N-(3-amino-2-(1-hydroxy-1,3-dihydrobenzo[c][1,2]oxaborole-6-carboxamido)-3-oxopropyl)-N-ethyl-1-hydroxy-1,3-dihydrobenzo[c][1,2]oxaborole-6-carboxamide (DS56);

(S)—N-(3-amino-2-(1-hydroxy-1,3-dihydrobenzo[c][1,2]oxaborole-6-carboxamido)-3-oxopropyl)-1-hydroxy-N-propyl-1,3-dihydrobenzo[c][1,2]oxaborole-6-carboxamide (DS57);

(S)—N-(3-amino-2-(1-hydroxy-1,3-dihydrobenzo[c][1,2]oxaborole-6-carboxamido)-3-oxopropyl)-1-hydroxy-N-isobutyl-1,3-dihydrobenzo[c][1,2]oxaborole-6-carboxamide (DS58);

(S)—N-(3-amino-2-(1-hydroxy-1,3-dihydrobenzo[c][1,2]oxaborole-6-carboxamido)-3-oxopropyl)-1-hydroxy-N-((5-(thiophen-2-yl)pyridin-2-yl)methyl)-1,3-dihydrobenzo[c][1,2]oxaborole-6-carboxamide (DS59);

(S)—N-(3-amino-2-(1-hydroxy-1,3-dihydrobenzo[c][1,2]oxaborole-6-carboxamido)-3-oxopropyl)-1-hydroxy-N-isopentyl-1,3-dihydrobenzo[c][1,2]oxaborole-6-carboxamide (DS60);

(S)—N-(3-amino-2-(1-hydroxy-1,3-dihydrobenzo[c][1,2]oxaborole-6-carboxamido)-3-oxopropyl)-1-hydroxy-N-(quinolin-5-ylmethyl)-1,3-dihydrobenzo[c][1,2]oxaborole-6-carboxamide (DS61);

(S)—N-(3-amino-2-(1-hydroxy-1,3-dihydrobenzo[c][1,2]oxaborole-6-carboxamido)-3-oxopropyl)-1-hydroxy-N-(2-(trifluoromethoxy)benzyl)-1,3-dihydrobenzo[c][1,2]oxaborole-6-carboxamide (DS62);

(S)—N-(3-amino-2-(1-hydroxy-1,3-dihydrobenzo[c][1,2]oxaborole-6-carboxamido)-3-oxopropyl)-1-hydroxy-N-(4-(methylsulfonyl)benzyl)-1,3-dihydrobenzo[c][1,2]oxaborole-6-carboxamide (DS63);

(3-((2S,4S)-4-(5-borono-2-(methylsulfonyl)benzamido)-2-carbamoylpyrrolidine-1-carbonyl)-4-(methylsulfonyl)phenyl)boronic acid (DS64);

(4-(((3S,5S)-1-(4-borono-2,6-difluorobenzoyl)-5-carbamoylpyrrolidin-3-yl)carbamoyl)-3,5-difluorophenyl)boronic acid (DS65);

(R,E)-4,5-bis(1-hydroxy-1,3-dihydrobenzo[c][1,2]oxaborole-6-carboxamido)pent-2-enoic acid (DS66);

(2S,4S)-1-(1-hydroxy-4-(trifluoromethyl)-1,3-dihydrobenzo[c][1,2]oxaborole-6-carbonyl)-4-(1-hydroxy-4-

(trifluoromethyl)-1,3-dihydrobenzo[c][1,2]oxaborole-6-carboxamido)pyrrolidine-2-carboxamide (DS67);

N,N'-((2S,3S)-1-amino-1-oxobutane-2,3-diyl)bis(1-hydroxy-1,3-dihydrobenzo[c][1,2]oxaborole-6-carboxamide) (DS68);

(R)-3,4-bis(1-hydroxy-1,3-dihydrobenzo[c][1,2]oxaborole-6-carboxamido)butanoic acid (DS69);

3-((2S,4S)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxamido)propanoic acid (DS70);

(S)-3-(1-hydroxy-1,3-dihydrobenzo[c][1,2]oxaborole-5-carboxamido)-4-(1-hydroxy-1,3-dihydrobenzo[c][1,2]oxaborole-6-carboxamido)butanoic acid (DS71);

(R)-4-(1-hydroxy-1,3-dihydrobenzo[c][1,2]oxaborole-5-carboxamido)-5-(1-hydroxy-1,3-dihydrobenzo[c][1,2]oxaborole-6-carboxamido)pentanoic acid (DS72);

(2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxylic acid (DS73);

(2S,4R)-1-(1-hydroxy-4-(trifluoromethyl)-1,3-dihydrobenzo[c][1,2]oxaborole-6-carbonyl)-4-(1-hydroxy-4-(trifluoromethyl)-1,3-dihydrobenzo[c][1,2]oxaborole-6-carboxamido)pyrrolidine-2-carboxylic acid (DS74);

(2S,3S)-3-(1-hydroxy-4-(trifluoromethyl)-1,3-dihydrobenzo[c][1,2]oxaborole-6-carboxamido)-2-(1-hydroxy-7-(trifluoromethyl)-1,3-dihydrobenzo[c][1,2]oxaborole-5-carboxamido)butanoic acid (DS75);

(R)-5-(1-hydroxy-4-(trifluoromethyl)-1,3-dihydrobenzo[c][1,2]oxaborole-6-carboxamido)-4-(1-hydroxy-7-(trifluoromethyl)-1,3-dihydrobenzo[c][1,2]oxaborole-5-carboxamido)pentanoic acid (DS76);

((2S,4S)-1-(5-borono-2-nitrobenzoyl)-4-(1-hydroxy-1,3-dihydrobenzo[c][1,2]oxaborole-6-carboxamido)pyrrolidine-2-carbonyl)glycine (DS77);

((2S,4S)-1-(5-borono-2-(methylsulfonyl)benzoyl)-4-(1-hydroxy-1,3-dihydrobenzo[c][1,2]oxaborole-6-carboxamido)pyrrolidine-2-carbonyl)glycine (DS78);

((2S,4S)-1-(3-borono-2,6-difluorobenzoyl)-4-(1-hydroxy-1,3-dihydrobenzo[c][1,2]oxaborole-6-carboxamido)pyrrolidine-2-carbonyl)glycine (DS79);

(S)-(3-((3-borono-4-fluorobenzyl)(5,6-diamino-6-oxohexyl)carbamoyl)-5-nitrophenyl)boronic acid (DS80);

(S)-(3-((4-borono-3,5-difluorobenzyl)(5,6-diamino-6-oxohexyl)carbamoyl)-5-nitrophenyl)boronic acid (DS81);

(S)-(3-((3-boronobenzyl)(5,6-diamino-6-oxohexyl)carbamoyl)-5-nitrophenyl)boronic acid (DS82);

(S)-(3-((4-borono-2-methoxybenzyl)(5,6-diamino-6-oxohexyl)carbamoyl)-5-nitrophenyl)boronic acid (DS83);

(S)-(3-((4-borono-2-(trifluoromethyl)benzyl)(5,6-diamino-6-oxohexyl)carbamoyl)-5-nitrophenyl)boronic acid (DS84);

(S)-(5-((3-borono-N-(5,6-diamino-6-oxohexyl)-4-fluorobenzamido)methyl)-2-fluorophenyl)boronic acid (DS85);

(S)-(5-((4-borono-3,5-difluorobenzyl)(5,6-diamino-6-oxohexyl)carbamoyl)-2-fluorophenyl)boronic acid (DS86);

(S)-(3-((3-borono-N-(5,6-diamino-6-oxohexyl)-4-fluorobenzamido)methyl) phenyl)boronic acid (DS87);

(S)-(5-((4-borono-2-methoxybenzyl)(5,6-diamino-6-oxohexyl)carbamoyl)-2-fluorophenyl)boronic acid (DS88);

(S)-(5-((4-borono-3-(trifluoromethyl)benzyl)(5,6-diamino-6-oxohexyl)carbamoyl)-2-fluorophenyl)boronic acid (DS89);

(S)-(4-((3-borono-4-fluorobenzyl)(5,6-diamino-6-oxohexyl)carbamoyl)-2-fluorophenyl)boronic acid (DS90);

(S)-(4-((4-borono-3,5-difluorobenzyl)(5,6-diamino-6-oxohexyl)carbamoyl)-2-fluorophenyl)boronic acid (DS91);

(S)-(4-((3-boronobenzyl)(5,6-diamino-6-oxohexyl)carbamoyl)-2-fluorophenyl)boronic acid (DS92);

(S)-(4-((4-borono-2-methoxybenzyl)(5,6-diamino-6-oxohexyl)carbamoyl)-2-fluorophenyl)boronic acid (DS93);

(S)-(4-((4-borono-2-(trifluoromethyl)benzyl)(5,6-diamino-6-oxohexyl)carbamoyl)-2-fluorophenyl)boronic acid (DS94);

(S)-(5-((3-borono-5-bromo-N-(5,6-diamino-6-oxohexyl)benzamido)methyl)-2-fluorophenyl)boronic acid (DS95);

(S)-(3-((4-borono-3,5-difluorobenzyl)(5,6-diamino-6-oxohexyl)carbamoyl)-5-bromophenyl)boronic acid (DS96);

(S)-(3-((3-borono-5-bromo-N-(5,6-diamino-6-oxohexyl)benzamido)methyl) phenyl)boronic acid (DS97);

(S)-(3-((3-borono-5-bromo-N-(5,6-diamino-6-oxohexyl)benzamido)methyl)-5-methoxyphenyl)boronic acid (DS98);

(S)-(3-((4-borono-2-(trifluoromethyl)benzyl)(5,6-diamino-6-oxohexyl)carbamoyl)-5-bromophenyl)boronic acid (DS99);

(S)-(3-((3-borono-4-fluorobenzyl)(5,6-diamino-6-oxohexyl)carbamoyl)-5-fluorophenyl)boronic acid (DS100);

(S)-(3-((4-borono-3-methoxybenzyl)(5,6-diamino-6-oxohexyl)carbamoyl)-5-fluorophenyl)boronic acid (DS101);

(S)-(3-((4-borono-2-(trifluoromethyl)benzyl)(5,6-diamino-6-oxohexyl)carbamoyl)-5-fluorophenyl)boronic acid (DS102);

(S)-(4-((N-(5,6-diamino-6-oxohexyl)-1-hydroxy-1,3-dihydrobenzo[c][1,2]oxaborole-6-carboxamido)methyl)-2-fluorophenyl)boronic acid (DS103);

(S)-(4-((N-(5,6-diamino-6-oxohexyl)-1-hydroxy-1,3-dihydrobenzo[c][1,2]oxaborole-6-carboxamido)methyl)-2,6-difluorophenyl)boronic acid (DS104);

(S)-(3-((N-(5,6-diamino-6-oxohexyl)-1-hydroxy-1,3-dihydrobenzo[c][1,2]oxaborole-6-carboxamido)methyl)phenyl)boronic acid (DS105);

(S)-(4-((N-(5,6-diamino-6-oxohexyl)-1-hydroxy-1,3-dihydrobenzo[c][1,2]oxaborole-6-carboxamido)methyl)-3-methoxyphenyl)boronic acid (DS106);

(S)—N-(5,6-diamino-6-oxohexyl)-1-hydroxy-N-((1-hydroxy-1,3-dihydrobenzo[c][1,2]oxaborol-6-yl)methyl)-1,3-dihydrobenzo[c][1,2]oxaborole-6-carboxamide (DS107);

(S)—N-(4-amino-3-(1-hydroxy-1,3-dihydrobenzo[c][1,2]oxaborole-6-carboxamido)-4-oxobutyl)-1-hydroxy-N-((1-hydroxy-1,3-dihydrobenzo[c][1,2]oxaborol-6-yl)methyl)-1,3-dihydrobenzo[c][1,2]oxaborole-6-carboxamide (DS108);

(S)—N-(6-amino-5-(1-hydroxy-1,3-dihydrobenzo[c][1,2]oxaborole-6-carboxamido)-6-oxohexyl)-1-hydroxy-N-((1-hydroxy-1,3-dihydrobenzo[c][1,2]oxaborol-6-yl)methyl)-1,3-dihydrobenzo[c][1,2]oxaborole-6-carboxamide (DS109);

(2S,4S)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxylic acid (DS110);

(2S,3S)-2-(1-hydroxy-1,3-dihydrobenzo[c][1,2]oxaborole-5-carboxamido)-3-(1-hydroxy-1,3-dihydrobenzo[c][1,2]oxaborole-6-carboxamido)butanoic acid (DS111);

(2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxylic acid (DS112);

N-(1-hydroxy-3,3-dimethyl-1,3-dihydrobenzo[c][1,2]oxa-borole-6-carbonyl)-N-(2-(1-hydroxy-3,3-dimethyl-1,3-dihydrobenzo[c][1,2]oxaborole-6-carboxamido)ethyl) glycine (DS113);

N-(1-hydroxy-3,4-dihydro-1H-benzo[c][1,2]oxaborinine-7-carbonyl)-N-(2-(1-hydroxy-3,4-dihydro-1H-benzo[c][1, 2]oxaborinine-7-carboxamido)ethyl)glycine (DS114);

N-(2-(2-(1-hydroxy-1,3-dihydrobenzo[c][1,2]oxaborol-7-yl)acetamido)ethyl)-N-(2-(1-hydroxy-1,3-dihydrobenzo [c][1,2]oxaborol-7-yl)acetyl)glycine (DS115);

N-(1-hydroxy-3,3-dimethyl-1,3-dihydrobenzo[c][1,2]oxa-borole-7-carbonyl)-N-(2-(1-hydroxy-3,3-dimethyl-1,3-dihydrobenzo[c][1,2]oxaborole-7-carboxamido)ethyl) glycine (DS116);

N-(1-hydroxy-1,3-dihydrobenzo [c][1,2]oxaborole-3-carbo-nyl)-N-(2-(1-hydroxy-1,3-dihydrobenzo[c][1,2]oxa-borole-3-carboxamido)ethyl)glycine (DS117);

3,5-bis((1-hydroxy-3,3-dimethyl-1,3-dihydrobenzo[c][1,2] oxaborole-6-carboxamido)methyl)benzoic acid (DS118);

3,5-bis((1-hydroxy-3,4-dihydro-1H-benzo[c][1,2]oxabori-nine-7-carboxamido)methyl)benzoic acid (DS119);

3,5-bis((2-(1-hydroxy-1,3-dihydrobenzo[c][1,2]oxaborol-7-yl)acetamido)methyl)benzoic acid (DS120);

3,5-bis((1-hydroxy-3,3-dimethyl-1,3-dihydrobenzo[c][1,2] oxaborole-7-carboxamido)methyl) benzoic acid (DS121);

3,5-bis((1-hydroxy-1,3-dihydrobenzo[c][1,2]oxaborole-3-carboxamido)methyl)benzoic acid (DS122);

(S)-3-(2,3-bis(1-hydroxy-3,3-dimethyl-1,3-dihydrobenzo[c] [1,2]oxaborole-6-carboxamido) propanamido)propanoic acid (DS123);

(S)-3-(2,3-bis(1-hydroxy-3,4-dihydro-1H-benzo[c][1,2] oxaborinine-7-carboxamido) propanamido)propanoic acid (DS124);

(S)-3-(2,3-bis(2-(1-hydroxy-1,3-dihydrobenzo[c][1,2]oxa-borol-7-yl)acetamido) propanamido)propanoic acid (DS125);

(S)-3-(2,3-bis(1-hydroxy-3,3-dimethyl-1,3-dihydrobenzo[c] [1,2]oxaborole-7-carboxamido) propanamido)propanoic acid (DS126);

3-((2S)-2,3-bis(1-hydroxy-1,3-dihydrobenzo[c][1,2]oxa-borole-3-carboxamido) propanamido)propanoic acid (DS127);

(3,5-bis((1-hydroxy-3,3-dimethyl-1,3-dihydrobenzo[c][1,2] oxaborole-6-carboxamido) methyl)benzoyl)glutamic acid (DS128);

(3,5-bis((1-hydroxy-3,4-dihydro-1H-benzo[c][1,2]oxabori-nine-7-carboxamido) methyl)benzoyl)glutamic acid (DS129);

(3,5-bis((2-(1-hydroxy-1,3-dihydrobenzo[c][1,2]oxaborol-7-yl)acetamido)methyl)benzoyl) glutamic acid (DS130);

(3,5-bis((1-hydroxy-3,3-dimethyl-1,3-dihydrobenzo[c][1,2] oxaborole-7-carboxamido)methyl) benzoyl)glutamic acid (DS131);

(3,5-bis((1-hydroxy-1,3-dihydrobenzo[c][1,2]oxaborole-3-carboxamido)methyl)benzoyl) glutamic acid (DS132);

4-(3,4-bis(1-hydroxy-3,3-dimethyl-1,3-dihydrobenzo[c][1, 2]oxaborole-6-carboxamido) pyrrolidin-1-yl)-4-oxobu-tanoic acid (DS133);

4-(3,4-bis(1-hydroxy-3,4-dihydro-1H-benzo[c][1,2]oxa-borinine-7-carboxamido)pyrrolidin-1-yl)-4-oxobutanoic acid (DS134);

4-(3,4-bis(2-(1-hydroxy-1,3-dihydrobenzo[c][1,2]oxaborol-7-yl)acetamido)pyrrolidin-1-yl)-4-oxobutanoic acid (DS135);

4-(3,4-bis(1-hydroxy-3,3-dimethyl-1,3-dihydrobenzo[c][1, 2]oxaborole-7-carboxamido)pyrrolidin-1-yl)-4-oxobu-tanoic acid (DS136);

4-(3,4-bis(1-hydroxy-1,3-dihydrobenzo[c][1,2]oxaborole-3-carboxamido)pyrrolidin-1-yl)-4-oxobutanoic acid (DS137);

((S)-2,3-bis(1-hydroxy-3,3-dimethyl-1,3-dihydrobenzo[c] [1,2]oxaborole-6-carboxamido)propanoyl)-L-glutamic acid (DS138);

((S)-2,3-bis(1-hydroxy-3,4-dihydro-1H-benzo[c][1,2]oxa-borinine-7-carboxamido)propanoyl)-L-glutamic acid (DS139);

((S)-2,3-bis(2-(1-hydroxy-1,3-dihydrobenzo[c][1,2]oxa-borol-7-yl)acetamido)propanoyl)-L-glutamic acid (DS140);

((S)-2,3-bis(1-hydroxy-3,3-dimethyl-1,3-dihydrobenzo[c] [1,2]oxaborole-7-carboxamido) propanoyl)-L-glutamic acid (DS141);

((2S)-2,3-bis(1-hydroxy-1,3-dihydrobenzo[c][1,2]oxa-borole-3-carboxamido)propanoyl)-L-glutamic acid (DS142);

(4-(3,4-bis(1-hydroxy-3,3-dimethyl-1,3-dihydrobenzo[c][1, 2]oxaborole-6-carboxamido)pyrrolidin-1-yl)-4-oxobu-tanoyl)-L-glutamic acid (DS143);

(4-(3,4-bis(1-hydroxy-3,4-dihydro-1H-benzo[c][1,2]oxa-borinine-7-carboxamido)pyrrolidin-1-yl)-4-oxobu-tanoyl)-L-glutamic acid (DS144);

(4-(3,4-bis(2-(1-hydroxy-1,3-dihydrobenzo[c][1,2]oxa-borol-7-yl)acetamido)pyrrolidin-1-yl)-4-oxobutanoyl)-L-glutamic acid (DS145);

(4-(3,4-bis(1-hydroxy-3,3-dimethyl-1,3-dihydrobenzo[c][1, 2]oxaborole-7-carboxamido) pyrrolidin-1-yl)-4-oxobu-tanoyl)-L-glutamic acid (DS146);

(4-(3,4-bis(1-hydroxy-1,3-dihydrobenzo[c][1,2]oxaborole-3-carboxamido)pyrrolidin-1-yl)-4-oxobutanoyl)-L-gluta-mic acid (DS147);

(S)-2,3-bis(1-hydroxy-3,4-dihydro-1H-benzo[c][1,2]oxa-borinine-7-carboxamido)propanoic acid (DS149);

(S)-2,3-bis(2-(1-hydroxy-1,3-dihydrobenzo[c][1,2]oxa-borol-7-yl)acetamido)propanoic acid (DS150);

(S)-2,3-bis(1-hydroxy-3,3-dimethyl-1,3-dihydrobenzo[c][1, 2]oxaborole-7-carboxamido)propanoic acid (DS151); and (2S)-2,3-bis(1-hydroxy-1,3-dihydrobenzo[c][1,2]oxa-borole-3-carboxamido)propanoic acid (DS152).

159. The compound of any one of embodiments 101-150 and 156-158, wherein the compound is used as an interme-diate in the manufacture of a drug substance or a therapeutic of a prophylactic compound.

160. A human insulin analog, comprising an A-chain and a B-chain, wherein the sequence of the A-chain comprises:

$X_{aa}X_{bb}X_{cc}X_{dd}X_{ee}X_{ff}X_{gg}$VEQCCX$_{hh}X_{ii}$ICSLYQLE-NYCNX$_{jj}X_{kk}X_{ll}X_{mm}X_{nn}X_{oo}X_{pp}$(SEQ ID NO:24015); and wherein the sequence of the B-chain comprises:

(i)

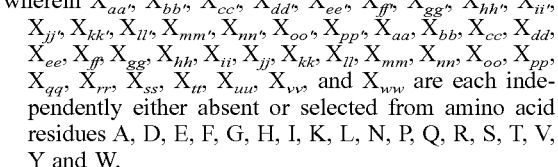

(SEQ ID NO: 24016)

$X_{aa}X_{bb}X_{cc}X_{dd}$KX$_{ee}X_{ff}X_{gg}X_{hh}X_{ii}X_{jj}$KX$_{kk}X_{ll}X_{mm}X_{nn}$QHLCGSHLVEALYLV CX$_{oo}X_{pp}X_{qq}$GFFYTX$_{rr}X_{ss}X_{tt}X_{uu}X_{vv}X_{ww}$, wherein $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each inde-pendently either absent or selected from amino acid residues A, D, E, F, G, H, I, K, L, N, P, Q, R, S, T, V, Y and W, (ii)

(SEQ ID NO: 24017)

$X_{aa'}X_{bb'}X_{cc'}X_{dd'}$KPX$_{ee'}X_{ff'}X_{gg'}X_{hh'}X_{ii'}X_{jj'}X_{kk'}X_{ll'}X_{mm'}X_{nn'}$QHLCGSHLVEALYLV CX$_{oo'}X_{pp'}X_{qq'}$GFFYTX$_{rr'}X_{ss'}X_{tt'}X_{uu'}X_{vv'}X_{ww'}$, wherein $X_{aa'}$, $X_{bb'}$, $X_{cc'}$, $X_{dd'}$, $X_{ee'}$, $X_{ff'}$, $X_{gg'}$, $X_{hh'}$, $X_{ii'}$, $X_{jj'}$, $X_{kk'}$, $X_{ll'}$, $X_{mm'}$, $X_{nn'}$, $X_{oo'}$, $X_{pp'}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, and wherein $X_{ee}$ is selected from amino acid residues A, E, F, H, I, K, L, N, P, Q, R, S, T, V, Y and W, (iii)

(SEQ ID NO: 24018)

$X_{aa'}X_{bb'}X_{cc'}X_{dd'}$KX$_{ee'}X_{ff'}X_{gg'}X_{hh'}X_{ii'}X_{jj'}$KX$_{kk'}X_{ll'}X_{mm'}X_{nn'}$QHLCGSHLVEALYLV CX$_{oo'}X_{pp'}X_{qq'}$GFFYTX$_{rr'}X_{ss'}X_{tt'}X_{uu'}X_{vv'}X_{ww'}$, wherein $X_{aa'}$, $X_{bb'}$, $X_{cc'}$, $X_{dd'}$, $X_{ee'}$, $X_{ff'}$, $X_{gg'}$, $X_{hh'}$, $X_{ii'}$, $X_{jj'}$, $X_{kk'}$, $X_{ll'}$, $X_{mm'}$, $X_{nn'}$, $X_{oo'}$, $X_{pp'}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, and at least one of $X_{ee}$, $X_{ff}$, $X_{gg}$, $X_{hh}$, $X_{ii}$, $X_{jj}$ is present and at least one of $X_{ee}$, $X_{ff}$, $X_{gg}$, $X_{hh}$, $X_{ii}$, $X_{jj}$ is G, (iv)

(SEQ ID NO: 24019)

$X_{aa'}X_{bb'}X_{cc'}X_{dd'}$KX$_{ee'}X_{ff'}X_{gg'}X_{hh'}X_{ii'}X_{jj'}$KX$_{kk'}X_{ll'}X_{mm'}X_{nn'}$QHLCGSHLVEALYLV CX$_{oo'}X_{pp'}X_{qq'}$GFFYTX$_{rr'}X_{ss'}X_{tt'}X_{uu'}X_{vv'}X_{ww'}$, wherein $X_{aa'}$, $X_{bb'}$, $X_{cc'}$, $X_{dd'}$, $X_{ee'}$, $X_{ff'}$, $X_{gg'}$, $X_{hh'}$, $X_{ii'}$, $X_{jj'}$, $X_{kk'}$, $X_{ll'}$, $X_{mm'}$, $X_{nn'}$, $X_{oo'}$, $X_{pp'}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, and at least one of $X_{ee}$, $X_{ff}$, $X_{gg}$, $X_{hh}$, $X_{ii}$, $X_{jj}$ is present and at least one of $X_{ee}$, $X_{ff}$, $X_{gg}$, $X_{hh}$, $X_{ii}$, $X_{jj}$ is S, or (v)

(SEQ ID NO: 24020)

$X_{aa'}X_{bb'}X_{cc'}X_{dd'}$KX$_{ee'}X_{ff'}X_{gg'}X_{hh'}X_{ii'}X_{jj'}$KX$_{kk'}X_{ll'}X_{mm'}X_{nn'}$QHLCGSHLVEALYLV CX$_{oo'}X_{pp'}X_{qq'}$GFFYTX$_{rr'}X_{ss'}X_{tt'}X_{uu'}X_{vv'}X_{ww'}$, wherein $X_{aa'}$, $X_{bb'}$, $X_{cc'}$, $X_{dd'}$, $X_{ee'}$, $X_{ff'}$, $X_{gg'}$, $X_{hh'}$, $X_{ii'}$, $X_{jj'}$, $X_{kk'}$, $X_{ll'}$, $X_{mm'}$, $X_{nn'}$, $X_{oo'}$, $X_{pp'}$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, and $X_{ww}$ are each independently either absent or selected from amino acid residues A, D, E, F, G, H, I, K, L, N, P, Q, R, S, T, V, Y and W, and at least one of $X_{ee}$, $X_{ff}$, $X_{gg}$, $X_{hh}$, $X_{ii}$, $X_{jj}$ are present and at least one of $X_{ee}$, $X_{ff}$, $X_{gg}$, $X_{hh}$, $X_{ii}$, $X_{jj}$ is S, and another is G.

161. The insulin of embodiment 160, wherein the A-chain comprises a sequence selected from SEQ ID NOs 1 and 3 to 33, and is optionally appended at the N-terminus and/or at the C-terminus by at least one selected from KA, KD, KE, KF, KG, KH, KI, KL, KN, KP, KQ, KR, KS, KT, KY, KAA, KAD, KAE, KAF, KAG, KAH, KAI, KAL, KAN, KAQ, KAR, KAS, KAT, KAY, KDA, KDD, KDE, KDF, KDG, KDH, KDI, KDL, KDN, KDQ, KDR, KDS, KDT, KDY, KEA, KED, KEE, KEF, KEG, KEH, KEI, KEL, KEN, KEQ, KER, KES, KET, KEY, KFA, KFD, KFE, KFF, KFG, KFH, KFI, KFL, KFN, KFQ, KFR, KFS, KFT, KFY, KGA, KGD, KGE, KGF, KGG, KGH, KGI, KGL, KGN, KGQ, KGR, KGS, KGT, KGY, KHA, KHD, KHE, KHF, KHG, KHH, KHI, KHL, KHN, KHQ, KHR, KHS, KHT, KHY, KIA, KID, KIE, KIF, KIG, KIH, KII, KIL, KIN, KIQ, KIR, KIS, KIT, KIY, KLA, KLD, KLE, KLF, KLG, KLH, KLI, KLL, KLN, KLQ, KLR, KLS, KLT, KLY, KNA, KND, KNE, KNF, KNG, KNH, KNI, KNL, KNN, KNQ, KNR, KNS, KNT, KNY, KPA, KPD, KPE, KPF, KPG, KPH, KPI, KPL, KPN, KPQ, KPR, KPS, KPT, KPY, KQA, KQD, KQE, KQF, KQG, KQH, KQI, KQL, KQN, KQQ, KQR, KQS, KQT, KQY, KRA, KRD, KRE, KRF, KRG, KRH, KRI, KRL, KRN, KRQ, KRR, KRS, KRT, KRY, KSA, KSD, KSE, KSF, KSG, KSH, KSI, KSL, KSN, KSQ, KSR, KSS, KST, KSY, KTA, KTD, KTE, KTF, KTG, KTH, KTI, KTL, KTN, KTQ, KTR, KTS, KTT, KTY, KYA, KYD, KYE, KYF, KYG, KYH, KYI, KYL, KYN, KYQ, KYR, KYS, KYT, KYY, SEQ ID NOs 75 to 24014, KGSH (SEQ ID NO:24049), GKGSH (SEQ ID NO:24050), GKGSKK (SEQ ID NO:24045), GKKPGKK (SEQ ID NO:24046), GKGPSK (SEQ ID NO:24044), GKPSHKP (SEQ ID NO:24043), and GSHKGSHK (SEQ ID NO:24042); and Wherein the B-chain comprises a sequence selected from SEQ ID NOs 2 and 34 to 74, 24047, and 24048, and is optionally appended at the N-terminus and/or at the C-terminus by at least one selected from KA, KD, KE, KF, KG, KH, KI, KL, KN, KP, KQ, KR, KS, KT, KY, KAA, KAD, KAE, KAF, KAG, KAH, KAI, KAL, KAN, KAQ, KAR, KAS, KAT, KAY, KDA, KDD, KDE, KDF, KDG, KDH, KDI, KDL, KDN, KDQ, KDR, KDS, KDT, KDY, KEA, KED, KEE, KEF, KEG, KEH, KEI, KEL, KEN, KEQ, KER, KES, KET, KEY, KFA, KFD, KFE, KFF, KFG, KFH, KFI, KFL, KFN, KFQ, KFR, KFS, KFT, KFY, KGA, KGD, KGE, KGF, KGG, KGH, KGI, KGL, KGN, KGQ, KGR, KGS, KGT, KGY, KHA, KHD, KHE, KHF, KHG, KHH, KHI, KHL, KHN, KHQ, KHR, KHS, KHT, KHY, KIA, KID, KIE, KIF, KIG, KIH, KII, KIL, KIN, KIQ, KIR, KIS, KIT, KIY, KLA, KLD, KLE, KLF, KLG, KLH, KLI, KLL, KLN, KLQ, KLR, KLS, KLT, KLY, KNA, KND, KNE, KNF, KNG, KNH, KNI, KNL, KNN, KNQ, KNR, KNS, KNT, KNY, KPA, KPD, KPE, KPF, KPG, KPH, KPI, KPL, KPN, KPQ, KPR, KPS, KPT, KPY, KQA, KQD, KQE, KQF, KQG, KQH, KQI, KQL, KQN, KQQ, KQR, KQS, KQT, KQY, KRA, KRD, KRE, KRF, KRG, KRH, KRI, KRL, KRN, KRQ, KRR, KRS, KRT, KRY, KSA, KSD, KSE, KSF, KSG, KSH, KSI, KSL, KSN, KSQ, KSR, KSS, KST, KSY, KTA, KTD, KTE, KTF, KTG, KTH, KTI, KTL, KTN, KTQ, KTR, KTS, KTT, KTY, KYA, KYD, KYE, KYF, KYG, KYH, KYI, KYL, KYN, KYQ, KYR, KYS, KYT, KYY, SEQ ID NOs 75 to 24014, KGSH (SEQ ID NO:24049), GKGSH (SEQ ID NO:24050), GKGSKK (SEQ ID NO:24045), GKKPGKK (SEQ ID NO:24046), GKGPSK (SEQ ID NO:24044), GKPSHKP (SEQ ID NO:24043), and GSHKGSHK (SEQ ID NO:24042).

162. The insulin of embodiment 160, wherein no more than 4 residues are added or deleted from the A-chain and/or the B-chain.

163. The insulin of embodiment 160, wherein a K residue is present at the N-terminus of the A-chain and/or the B-chain, and/or wherein no more than three K residues are present at the N-terminus of the A-chain and/or the B-chain, and/or
    wherein (i) the tyrosine at A14 is replaced with glutamic acid, and/or (ii) the tyrosine at B16 is replaced with histidine, and/or (iii) the phenylalanine at B25 is replaced with a histidine, and/or wherein one to three residues selected from residues B20, B21, and B22-B29 of the B-chain, residues A4 or A8 of the A-chain, and residues of an optionally extended polypeptide, are lysine residues, and/or wherein only one K residue is present within 10 residues of the N-terminus of B-chain.

164. The compound of any one of embodiments 101-150 and 156-159, wherein X1 comprises the insulin of any one of embodiments 160-163.

165. The insulin of any one of embodiments 160-163, wherein an amino group of the side chain(s) of one to four lysine residues is each independently covalently conjugated as described by the formula of embodiment 102.

166. The insulin of any one of embodiments 160-163, wherein the insulin is covalently conjugated as described by the formula of embodiment 102, n'=0 and the C-terminus of Z1a is directly conjugated to the N-terminus of the B-chain of insulin through a peptide bond;

Z1a comprises at least one amino acid selected from K, P, E, G, S, T, A, and R, such that the sequence comprises at least one lysine, at least one proline, and at least one amino acid selected from H, R, A and T; and the amino group of least one lysine side chain in Z1a is covalently conjugated as described by the formula.

167. The insulin of any one of embodiments 160-163, wherein the insulin is covalently conjugated as described by the formula of embodiment 102, Z1a comprises a polypeptide comprising the sequence $(XA1A_2A3X)_m$(SEQ ID NO:24022), wherein:

$A_1$, $A_2$, and $A_3$ are each independently an L- or D-amino acid;

m is an integer in the range of 1 to 4;

each X is K or KP; and the epsilon amine group of at least one lysine side chain in Z1a is covalently conjugated as described by the formula.

168. The insulin of any one of embodiments 160-163, wherein the insulin is covalently conjugated as described by the formula of embodiment 102, Z1a comprises a polypeptide comprising a sequence selected from $(XA1X)_m$(GGGGS)$_n$ (SEQ ID NO:24023), $(XAIA2X)_m$ (GGGGS)n (SEQ ID NO:24024), $(XA1A2A3X)_m$(GGGGS)n (SEQ ID NO:24025), $(XA1X)_m$(GGGGS)n (XA2X)o (SEQ ID NO:24026), and $(XA1A2X)_m$(GGGGS)n (XA3A4X)o (SEQ ID NO:24027), wherein:

$A_1$, $A_2$, $A_3$, and $A_4$ are each independently an L- or D-amino acid;

m is an integer in the range of 1 to 4;

n is an integer in the range of 1 to 4;

is an integer in the range of 1 to 4;

each X is K or KP; and the epsilon amine group of each lysine side chain of at least one lysine side chain in Z1a is further covalently conjugated as described by the formula.

169. The insulin of any one of embodiments 160-163, wherein the insulin is covalently conjugated as described by the formula of embodiment 102, Z1a comprises a polypeptide comprising the sequence $(GX)_m$, wherein:

X is KV;

m is an integer in the range of 1 to 4, and the epsilon amine group of at least one lysine side chain in Z1a is further covalently conjugated as described by the formula.

170. The insulin of any one of embodiments 160-163, wherein the insulin is covalently conjugated as described by the formula of embodiment 102, Z1a comprises a polypeptide comprising a sequence selected from: $(GXA1KGEA2XT)_m$(GGSGSSS)n (GXGXA3GSSSGSSSXT)o (SEQ ID NO:24028), $(GXA1ESA2LYL)_m$ (SEQ ID NO:24029), $(TXEX)_m$ (GPGS)n (SEQ ID NO:24030), $(GXESA1VA)_m$ (KA2K)n (SEQ ID NO:24031), $(GXEA1A2)_m$(GGS)n (TYA3XXT)o (SEQ ID NO:24032), and $(TXAXYT)_m$ (TSSS)n (SEQ ID NO:24033), wherein:

each X is KV or KP;

$A_1$, $A_2$, $A_3$ are each independently an L- or D-amino acid;

m is an integer in the range of 1 to 4;

n is an integer in the range of 1 to 4; and is an integer in the range of 1 to 4; and the epsilon amine group of at least one lysine side chain in Z1a is further covalently conjugated as described by the formula.

171. The insulin of any one of embodiments 160-163, wherein the insulin is covalently conjugated as described by the formula of embodiment 102, Z1a comprises a polypeptide comprising a sequence selected from $(TKPYA1KEVETA2GSGS)_m$ (GGGGS)n (SEQ ID NO:24034), $(YTPLEA1KPYSTSYKPYSEA1L)_m$ (GKPTSLEA2FLVEA2LYTKP)n (SEQ ID NO:24035), and $(GKEALYLTPLESALYKP)_m$(TKPL-EALYLKPEILSLKPESLA)n (GKPGSSSKPDTSSSGTP KTAAGS)o (SEQ ID NO:24036), wherein:

$A_1$ and $A_2$ are each independently an L- or D-amino acid;

m is an integer in the range of 1 to 4;

n is an integer in the range of 1 to 4; and the epsilon amine group of at least one lysine side chain in Z1a is further covalently conjugated as described by the formula.

172. The insulin of embodiment 160, wherein (i) the A- and/or B-chain sequence of the insulin is appended at the N-terminus or C-terminus by KX'K, KX', or X'K wherein X' represents a continuous sequence of 2, 3, 4, or 5 residues selected from within wild-type A-chain (SEQ ID NO:1) and wild-type B-chain (SEQ ID NO:2), or (ii) wherein X' is a polypeptide of up to 30 residues with amino acids independently selected from: K, G, S, E, H, E, N, Q, D, A, P, R and C, and wherein in (i) and (ii) each K residue is optionally and independently covalently conjugated as described by the formula of embodiment 102.

EXAMPLES

The following examples and experimental data are provided for illustrative purposes only, and do not limit the scope of the embodiments of the present disclosure.

The following abbreviations have the definitions set forth below:

| Abbreviation | Full Name |
|---|---|
| Acm | s-Acetamidomethyl group |
| ACN | Acetonitrile |
| ARS | Alizarin Red S |
| Boc | tert-Butyloxycarbonyl |
| DCM | Dichloromethane |
| Dde | 1-(4,4-dimethyl-2,6-dioxocyclohex-1-ylidene)ethyl |
| DIPEA, DIEA | N,N-Diisopropylethylamine |
| DMF | Dimethylformamide |
| DMSO | Dimethyl Sulfoxide |
| DTDP | 2,2,-Dithiopyridine |
| EDC | 3-(Ethyliminomethyleneamino)-N,N-dimethylpropan-1-amine |
| Fmoc | Fluorenylmethyloxycarbonyl Chloride |
| GLP-1 | Glucagon-Like Peptide 1 |
| HATU | Hexafluorophosphate Azabenzotriazole Tetramethyl Uronium |
| HCl | Hydrochloric Acid |
| IGF1 | Insulin-like Growth Factor 1 |
| IPTG | Isopropylthio-β-galactoside |
| IBs | Inclusion Bodies |
| LC-MS | Liquid Chromatography-Mass Spectrometry |
| MeOH | Methanol |
| MIDA | N-methyliminodiacetic acid |
| MODY | Maturity Onset Diabetes of the Young |
| NHS | N-Hydroxysuccinimide |
| Oxyma | Ethyl cyanohydroxyiminoacetate |
| RAM | Rink Amide Matrix |
| PEG | Polyethylene Glycol |
| SDS | Sodium Dodecyl Sulfate |
| tBu | tert-Butyl |
| TFA | Trifluoroacetic Acid |
| TFP | 2,3,5,6-tetrafluorophenol |
| TMB | 3,3',5,5'-tetramethybenzidine |
| Pfp | pentafluorophenol |
| $CaCl_2$ | Calcium Chloride |
| HFIP | 1,1,1,3,3,3-Hexafluoro-2-propanol |
| $SnCl_2$ | Tin Chloride |

A. Preparation of Aromatic Boron-Containing Compounds

The disclosed compounds can be prepared according to the following schemes. The following schemes represent the general methods used in preparing these compounds. However, the synthesis of these compounds is not limited to these representative methods, as they can also be prepared through various other methods by those skilled in the art of synthetic chemistry.

Method A1: Synthesis of Diboronates DS01-DS48:

Chlorotrityl resin (300 mg, 0.45 mmol) was swelled in dry DCM (5 mL) for 30 mins. Solvent was removed with nitrogen and a solution of bromo acetic acid (0.139 g, 1M, 1 mL) in DCM with DIPEA (1M, 0.13 g 1 mL) was added immediately and gently mixed for 1 hr. The mixture was washed with DCM and unreacted sites were capped with a solution of 20% MeOH in a solution of DCM and DIEA (1M) and mixed for 1 hr. The resin was washed with DCM (3×5 mL) then DMF (3×5 mL). A solution of FF-diamine linker propane-1,3-diamine (0.37 g, 1M) in DMF (5 mL) was added to the resin and heated at 50° C. for 10 minutes. The resin was washed with DMF (3×5 mL) and a solution of 3-borono-5-nitrobenzoic acid (0.2M, 0.21 mg, 5 mL) in DMF with N, N'-diisopropylcarbodiimide (DIC) (0.126 g, 1M, 1 mL), Oxyma (0.5 M, 0.142 g, 2 mL) in DMF and heated at 50° C. for 30 min. The resin was washed with DMF (3×5 mL) then DCM (3×5 mL). A solution of trifluoroacetic acid with triisopropyl silane and water (95:2.5:2.5, 5 mL) was added to the resin and mixed for 90 minutes. The solution was collected and dried under vacuum, dissolved in DMSO (100 uL) and fractionated by reverse-phase (RP)

flash chromatography on a C18 column with a gradient of 20% ACN in water with 0.1% TFA to 60% ACN in water with 0.1% TFA over 10 minutes. Pure fractions were isolated, combined, frozen, and lyophilized to yield N-(3-(3-borono-5-nitrobenzamido)propyl)-N-(3-borono-5-nitrobenzoyl)glycine (DS01) as a white powder (7 mg).

Similar procedures are followed for the synthesis of aromatic boron-containing groups DS02-DS48.

Method A2: Synthesis of Symmetric Diboronates with C-Terminus Linker DS49-DS53

Tentagel-S—NH₂ resin (250 mg, 0.05 mmol) was swelled in DMF (5 mL) for 2 hr. The solution was removed under a stream of nitrogen and a solution of Boc-Gly-HMBA (0.2 mmol) was coupled using 1-[Bis(dimethylamino)methylene]-1H-1,2,3-triazolo[4,5-b]pyridinium 3-oxide hexafluorophosphate (HATU, 76 mg, 0.2 mmol), and DIPEA (70 ul) in DMF (2 mL) was added to the resin and mixed at room temperature for 45 minutes. The resin was washed with DMF (3×5 mL) and DCM (3×5 mL). A solution of 50% trifluoroacetic acid in DCM (5 mL) was added to the resin and mixed for 20 minutes to remove the Boc protecting group. This step was repeated twice. The resin was washed with DCM (3×5 mL) and DMF (3×5 mL) and was treated with a solution of 10% DIEA in DMF (5 mL) for 10 minutes, the cycle was repeated twice, and resin was washed with DMF(3×5 mL). A solution of 1-(((9H-fluoren-9-yl)methoxy)carbonyl)-4-((((9H-fluoren-9-yl)methoxy)carbonyl)amino)pyrrolidine-2-carboxylic acid (0.115 g, 0.2 mmol) with 1-[Bis(dimethylamino)methylene]-1H-1,2,3-triazolo[4,5-b]pyridinium 3-oxide hexafluorophosphate (HATU, 0.2 mmol), and DIPEA (70 ul) in DMF (2 mL) was added to the resin and mixed for 45 minutes. The resin was washed with DMF (3×5 mL) and a solution of 20% piperidine in DMF (5 mL×3) was added to resin and mixed for 5 minutes. The resin was washed with DMF (3×5 mL) and a solution of 1-hydroxy-1,3-dihydrobenzo[c][1,2]oxaborole-6-carboxylic acid (0.078 g, 0.4 mmol) with HATU (0.4 mmol) and DIPEA (140 uL) in DMF (2 mL) was added to the resin and mixed for 45 minutes. The resin was washed with DMF (3×5 mL) then DCM (3×5 mL). A solution of 0.1 M NaOH in 1:5 water:THF was added to the resin and mixed for 90 minutes. The solution was filtered and adjusted the pH-2 using 1.0 M HCl and fractionated by reverse-phase (RP) flash chromatography on a C18 column with a gradient of 20% ACN in water with 0.1% TFA to 60% ACN in water with 0.1% TFA over 10 minutes. Pure fractions were isolated, combined, frozen, and lyophilized to yield ((2S,4S)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carbonyl)glycine (DS49) as a white powder (10 mg).

Similar procedures are followed for the synthesis of aromatic boron-containing groups DS50-DS53.

Method A3: Synthesis of Diboronates with Reductive Alkylation on Side Chain Amine DS54-DS63

Rink-amide resin (0.05 mmol, 263 mg) was swelled in DMF (5 mL) for 20 minutes. The solution was removed under a stream of nitrogen and a solution of 20% piperidine in DMF (5 mL) was added to resin and mixed for 5 minutes. The resin was washed with DMF (3×5 mL). A solution of ((S)-2-((((9H-fluoren-9-yl)methoxy)carbonyl)amino)-3-((diphenyl(p-tolyl)methyl)amino) propanoic acid (116 mg, 0.2 mmol) with 1-[Bis(dimethylamino)methylene]-1H-1,2,3-triazolo[4,5-b]pyridinium 3-oxide hexafluorophosphate (HATU, 76 mg, 0.2 mmol), and DIPEA (70 ul) in DMF (2 mL) was added to the resin and mixed at room temperature for 45 minutes. The resin was washed with DMF (3×5 mL)

and DCM (3×5 mL). A solution of 0.2% trifluoroacetic acid in DCM (5 mL) was added to the resin and mixed for 10 minutes to remove Mtt protecting group. This step was repeated twice. The resin was washed with DCM (3×5 mL) and DMF (3×5 mL) and was treated with a solution of 10% DIEA in DMF (5 mL) for 10 minutes, the cycle was repeated twice, and resin was washed with DMF(3×5 mL). A solution of benzaldehyde (0.053 g, 0.5 mol) in trimethyl orthoformate (TMOF) (2 mL) was added to the resin and mixed for 1 hr. The solution was filtered, and resin was washed with DMF (3×5 mL) and 10% acetic acid in methanol (2×5 mL). The solution of NaCNBH₃ (10 equivalents) in 10% acetic acid in methanol was added to the resin and mixed for 1 hr, washed with DMF (3×5 mL). The resin was treated with 20% piperidine in DMF (3×5 mL) to deprotect the Fmoc, washed with DMF (3×5 mL) and coupled with 1-hydroxy-1,3-dihydrobenzo[c][1,2]oxaborole-6-carboxylic acid (0.078 g, 0.4 mmol) using 1-[Bis(dimethylamino)methylene]-1H-1,2,3-triazolo[4,5-b]pyridinium 3-oxide hexafluorophosphate (HATU, 152 mg, 0.4 mmol), and DIPEA (140 ul) in DMF (2 mL) for 45 minutes. After coupling reaction, the resin was washed with DMF (3×5 mL) then with DCM (2×5 mL). A solution of trifluoroacetic acid with triisopropyl silane and water (95:2.5:2.5, 5 mL) was added to the resin and mixed for 90 minutes. The solution was collected and dried under vacuum, dissolved in DMSO (100 uL) and fractionated by reverse-phase (RP) flash chromatography on a C18 column with a gradient of 20% ACN in water with 0.1% TFA to 60% ACN in water with 0.1% TFA over 10 minutes. Pure fractions were isolated, combined, frozen, and lyophilized to yield (S)—N-(3-amino-2-(1-hydroxy-1,3-dihydrobenzo[c][1,2]oxaborole-6-carboxamido)-3-oxopropyl)-N-benzyl-1-hydroxy-1,3-dihydrobenzo[c][1,2]oxaborole-6-carboxamide (DS54) as a white powder (7 mg).

Similar procedures are followed for the synthesis of aromatic boron-containing groups DS55-DS63.

Method A4: Synthesis of Symmetric Diboronates Based on Amino Acids DS64-DS76, DS109-DS111

Rink-amide resin (0.05 mmol, 263 mg) was swelled in DMF (5 mL) for 20 minutes. The solution was removed under a stream of nitrogen and a solution of 20% piperidine in DMF (5 mL) was added to resin and mixed for 5 minutes. The resin was washed with DMF (3×5 mL). A solution of 1-(((9H-fluoren-9-yl)methoxy)carbonyl)-4-((((9H-fluoren-9 yl)methoxy) carbonyl) amino) pyrrolidine-2-carboxylic acid (0.115 g, 0.2 mmol) with 1-[Bis(dimethylamino)methylene]-1H-1,2,3-triazolo[4,5-b]pyridinium 3-oxide hexafluorophosphate (HATU, 0.2 mmol), and DIPEA (70 ul) in DMF (2 mL) was added to the resin and mixed at 50° C. for 20 minutes. The resin was washed with DMF (3×5 mL) and a solution of 20% piperidine in DMF (5 mL) was added to the resin and mixed for 5 minutes. The resin was washed with DMF (3×5 mL) and a solution of 1-hydroxy-1,3-dihydrobenzo[c][1,2]oxaborole-6-carboxylic acid (0.078 g, 0.4 mmol) with HATU (0.4 mmol) and DIPEA (140 uL) in DMF (2 mL) was added to the resin and mixed at 50° C. for 30 minutes. The resin was washed with DMF (3×5 mL) then with DCM (3×5 mL). A solution of trifluoroacetic acid with triisopropyl silane and water (95:2.5:2.5, 5 mL) was added to the resin and mixed for 90 minutes. The solution was collected and dried under vacuum, dissolved in DMSO (100 uL) and fractionated by reverse-phase (RP) flash chromatography on a C18 column with a gradient of 20% ACN in water with 0.1% TFA to 60% ACN in water with 0.1% TFA over 10 minutes. Pure fractions were isolated, combined, frozen, and lyophilized to yield (3-((2S,4S)-4-(5-borono-2-

(methylsulfonyl)benzamido)-2-carbamoylpyrrolidine-1-carbonyl)-4-(methylsulfonyl)phenyl)boronic acid (DS64) as a white powder (10 mg).

Similar procedures are followed for the synthesis of aromatic boron-containing groups DS65-DS76. Similar procedure can be followed for the synthesis of diboronate sensors DS109-DS111 noting that the resin used is 2-chlorotrityl resin and not the Amine Rink-amide resin.

Method A5: Asymmetric Diboronate Synthesis DS77-DS79

Tentagel-S—NH₂ resin (250 mg, 0.05 mmol) was swelled in DMF (5 mL) for 2 hr. The solution was removed under a stream of nitrogen and a solution of Boc-Gly-HMBA (0.2 mmol) was coupled using 1-[Bis(dimethylamino)methylene]-1H-1,2,3-triazolo[4,5-b]pyridinium 3-oxide hexafluorophosphate (HATU, 76 mg, 0.2 mmol), and DIPEA (70 ul) in DMF (2 mL) was added to the resin and mixed at room temperature for 45 minutes. The resin was washed with DMF (3×5 mL) and DCM (3×5 mL). A solution of 50% trifluoroacetic acid in DCM (5 mL) was added to the resin and mixed for 20 minutes. To remove Boc protecting group. This step was repeated twice. The resin was washed with DCM (3×5 mL) and DMF (3×5 mL) and was treated with a solution of 10% DIEA in DMF (5 mL) for 10 minutes, the cycle was repeated twice, and resin was washed with DMF (3×5 mL). A solution of 1-(((9H-fluoren-9-yl)methoxy)carbonyl)-4-((tert-butoxycarbonyl)amino)pyrrolidine-2-carboxylic acid (0.09 g, 0.2 mmol) with 1-[Bis(dimethylamino)methylene]-1H-1,2,3-triazolo[4,5-b]pyridinium 3-oxide hexafluorophosphate (HATU, 0.2 mmol), and DIPEA (70 ul) in DMF (2 mL) was added to the resin and mixed for 45, minutes. The resin was washed with DMF (3×5 mL) and a solution of 20% piperidine in DMF (5 mL×3) was added to resin and mixed for 5 minutes. The resin was washed with DMF (3×5 mL) and a solution of 1-hydroxy-1,3-dihydrobenzo[c][1,2]oxaborole-6-carboxylic acid (0.039 g, 0.2 mmol) with HATU (0.076 g, 0.2 mmol) and DIPEA (140 uL) in DMF (2 mL) was added to the resin and mixed for 45 minutes and DCM (3×5 mL). A solution of 50% trifluoroacetic acid in DCM (5 mL) was added to the resin and mixed for 20 minutes, to remove Boc protecting group. This step was repeated twice. The resin was washed with DCM (3×5 mL) and DMF (3×5 mL) and was treated with a solution of 10% DIEA in DMF (5 mL) for 10 minutes, the cycle was repeated twice, and resin was washed with DMF(3×5 mL). A solution of 5-borono-2-nitrobenzoic acid (0.042 g, 0.2 mmol) with HATU (0.076 g, 0.2 mmol) and DIPEA (140 uL) in DMF (2 mL) was added to the resin and mixed for 45 minutes. The resin was washed with DMF (3×5 mL) then DCM (3×5 mL). A solution of 0.1M NaOH in 1:5 water:THF was added to the resin and mixed for 90 minutes. The solution was filtered and adjusted the pH-2 using 1.0 M HCl and fractionated by reverse-phase (RP) flash chromatography on a C18 column with a gradient of 20% ACN in water with 0.1% TFA to 60% ACN in water with 0.1% TFA over 10 minutes. Pure fractions were isolated, combined, frozen, and lyophilized to yield ((2S,4S)-1-(5-borono-2-nitrobenzoyl)-4-(1-hydroxy-1,3-dihydrobenzo[c][1,2]oxaborole-6-carboxamido)pyrrolidine-2-carbonyl)glycine (DS77) as a white powder (8 mg).

Similar procedures are followed for the synthesis of aromatic boron-containing groups DS78-DS79.

Method A6: Synthesis of Diboronates with Reductive Alkylation on Side Chain DS80-DS109

Amine Rink-amide resin (0.05 mmol, 263 mg) was swelled in DMF (5 mL) for 20 minutes. The solution was removed under a stream of nitrogen and a solution of 20% piperidine in DMF (5 mL) was added to resin and mixed for 5 minutes. The resin was washed with DMF (3×5 mL). A solution of N6-(((9H-fluoren-9-yl)methoxy)carbonyl)-N2-(tert-butoxycarbonyl)lysine (93.6 mg, 0.2 mmol) with 1-[Bis(dimethylamino)methylene]-1H-1,2,3-triazolo[4,5-b]pyridinium 3-oxide hexafluorophosphate (HATU, 76 mg, 0.2 mmol), and DIPEA (70 ul) in DMF (2 mL) was added to the resin and mixed at room temperature for 45 minutes. The resin was washed with DMF (3×5 mL). The Fmoc was removed with 20% piperidine in DMF (2×5 mL) and then washed with additional DMF (3×10 mL) A solution of 4-methyl-3-(4,4,5,5-tetramethyl-1,3,2-dioxaborolan-2-yl)benzaldehyde (123 mg, 0.5 mol) in trimethyl orthoformate (TMOF) (2 mL) was added to the resin and mixed for 1 hr. The solution was filtered, and resin was washed with DMF (3×5 mL) and a solution of NaBH$_4$ (10 equivalents) in 20% methanol in DMF was added to the resin and mixed for 1 hr, washed with DMF (3×5 mL). The reduced amine was then coupled with 3-nitro-5-(4,4,5,5-tetramethyl-1,3,2-dioxaborolan-2-yl)benzoic acid (117 mg, 0.4 mmol) using 1-[Bis(dimethylamino)methylene]-1H-1,2,3-triazolo[4,5-b]pyridinium 3-oxide hexafluorophosphate (HATU, 152 mg, 0.4 mmol), and DIPEA (140 ul) in DMF (2 mL) for 45 minutes. After coupling reaction, the resin was washed with DMF (3×5 mL) then with DCM (2×5 mL). A solution of trifluoroacetic acid with triisopropyl silane and water (95:2.5:2.5, 5 mL) was added to the resin and mixed for 90 minutes. The solution was collected and dried under vacuum, dissolved in DMSO (100 uL) and fractionated by reverse-phase (RP) flash chromatography on a C18 column with a gradient of 20% ACN in water with 0.1% TFA to 60% ACN in water with 0.1% TFA over 10 minutes. Pure fractions were isolated, combined, frozen, and lyophilized to yield diboronate sensor DS80 as a white powder (10 mg). Similar procedure was followed for the synthesis of diboronate sensors DS81-DS109.

Method A7: Synthesis of Diboronated Sensors DS139 and DS139A

On Resin Synthesis of Diboronated Sensor:

2-Chlorotrityl resin 1 (0.30 g, 0.3 mmol) was swelled in dry DCM (5 mL) for 30 mins. Solvent was removed with nitrogen and a solution of (S)-4-((((9H-fluoren-9yl)methoxy)carbonyl)amino)-5-(tert-butoxy)-5-oxopentanoic acid 2 (127 mg, 0.3 mmol) in DCM with DIPEA (0.3 mL, 1.7 mmol) was added immediately and gently mixed for overnight. The mixture was washed with DCM and unreacted sites were capped with a solution of 20% MeOH in a solution of DCM and DIPEA (1M) and mixed for 1 hr to yield 3. The resin was washed with DCM (3×5 mL) then DMF (3×5 mL) and treated with 20% piperidine in DMF for 5 minutes (3×5 mL), washed with DMF (4×5 mL). Solution of (S)-2,3-bis((((9H-fluoren-9-yl)methoxy)carbonyl)amino)propanoic acid 4 (0.219 g, 0.4 mmol), DIPEA (0.14 ml, 0.8 mmol) and HATU (0.152 g, 0.4 mmol) in DMF (5 mL) was added to the resin and heated at 50° C. for 30 min, washed with DMF (4×5 mL) to obtain 5. Resin was treated with 20% piperidine in DMF for 5 minutes (3×5 mL) and washed with DMF (4×5 mL). Solution of 1-hydroxy-3,4-dihydro-1H-benzo[c][1,2]oxaborinine-7-carboxylic acid 6 (0.192 g, 1 mmol), HATU (0.380 g, 1 mmol) and DIPEA (0.35 mL, 2 mmol) were added to the resin and heated at 50° C. for 30 min to get 7. The resin was washed with DMF (4×5 mL) and DCM (3×5 mL).

Cleavage of Diboronated Sensor from Resin

Compound 7 on resin was treated with 20% 1,1,1,3,3,3-Hexafluoro-2-propanol (HFIP) in DCM (7 mL) and gently mixed for 1 hr. The resin was filtered, and filtrate was evaporated under reduced pressure. Residue was further suspended with DCM (2×5 mL) and evaporated to yield diboronated sensor acid DS139-OtBu which was used in the next step without purification. The Boc protecting group of DS139 can be removed under acidic conditions to give DS139.

Figure 11:
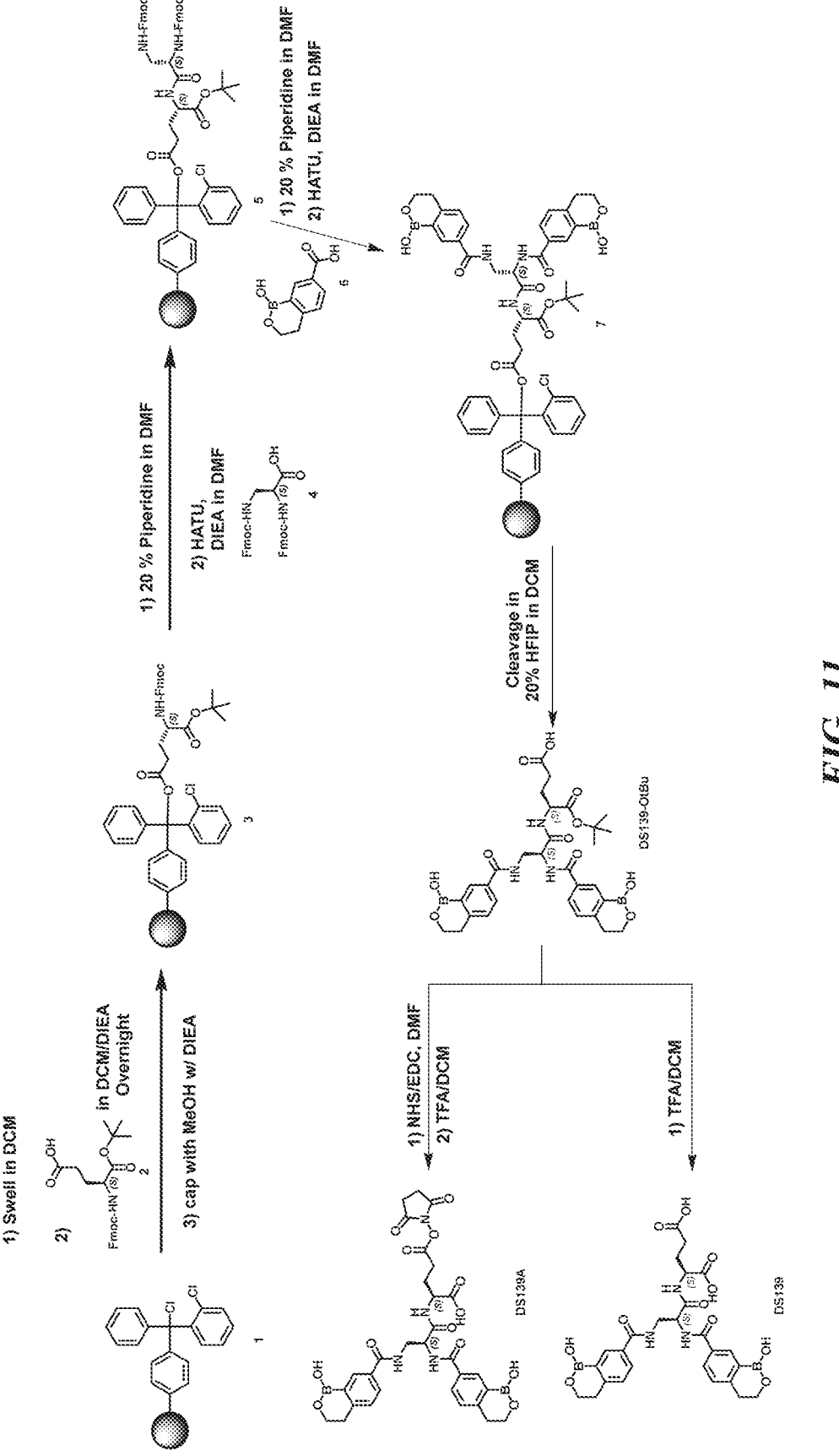

NHS-Activation of Diboronated Sensor:

Crude diboronated sensor acid DS139-OtBu was dissolved in DMF (2 mL) and treated with 3-(3-Dimethylaminopropyl)-1-ethyl-carbodiimide hydrochloride (EDC) (0.096 g, 0.5 mmol), N-hydroxysuccinimide (NHS) (0.115 g, 1 mmol), and gently mixed for overnight. Progress of the reaction was monitored by LCMS. After completion of the reaction, reaction mixture was diluted with ethyl acetate (20 mL) and washed with 100 mmol HCl (10 mL). The organic layer was dried over anhydrous Na$_2$SO$_4$ and evaporated under vacuum. The tert-butyl protecting group was removed with TFA in DCM (50%), allowed to mix for 1 hour, reduced under vacuum then dissolved in DMSO (100 uL) and fractionated by reverse-phase (RP) flash chromatography on a C18 column with a gradient of 20% ACN in water with 0.1% TFA to 60% ACN in water with 0.1% TFA over 10 minutes and analyzed by LCMS. Pure fractions were isolated, combined, frozen, and lyophilized to give DS139A as a white powder. The foregoing synthesis is illustrated in FIG. 11.

Method 8: Synthesis of Diboronated Sensors DS149 and DS149A

2-Chlorotrityl resin 1 (0.30 g, 0.3 mmol) was swelled in dry DCM (5 mL) for 30 mins. Solvent was removed with nitrogen and a solution of (S)-2,3-bis((((9H-fluoren-9-yl)methoxy)carbonyl)amino)propanoic acid 2 (164 mg, 0.3 mmol) in DCM with DIPEA (0.3 mL, 1.7 mmol) was added immediately and gently mixed for overnight. The mixture was washed with DCM and unreacted sites were capped with a solution of 20% MeOH in a solution of DCM and DIPEA (1M) and mixed for 1 hr to yield 3. The resin was washed with DCM (3×5 mL), then DMF (3×5 mL) and treated with 20% piperidine in DMF for 5 minutes (3×5 mL), washed with DMF (4×5 mL). Solution of 1-hydroxy-3,4-dihydro-1H-benzo[c][1,2]oxaborinine-7-carboxylic acid 4 (0.192 g, 1 mmol), HATU (0.380 g, 1 mmol) and DIPEA (0.35 mL, 2 mmol) were added to the resin and heated at 50° C. for 30 min to get 5. The resin was washed with DMF (4×5 mL) and DCM (3×5 mL).

Cleavage of Diboronated Sensor from Resin

Compound 5 on resin was treated with 20% 1,1,1,3,3,3-Hexafluoro-2-propanol (HFIP) in DCM (7 mL) and gently mixed for 1 hr. The resin was filtered, and filtrate was evaporated under reduced pressure. Residue was further suspended with DCM (2×5 mL) and evaporated to yield diboronated sensor acid DS149 which was used in the next step without purification.

NHS-Activation of Diboronated Sensor:

Crude diboronated sensor acid DS149 was dissolved in DMF (2 mL) and treated with 3-(3-Dimethylaminopropyl)-1-ethyl-carbodiimide hydrochloride (EDC) (0.096 g, 0.5 mmol), N-hydroxysuccinimide (NHS) (0.115 g, 1 mmol), and gently mixed for overnight. Progress of the reaction was monitored by LCMS. After completion of the reaction, reaction mixture was diluted with ethyl acetate (20 mL) and washed with 100 mmol HCl (10 mL). The organic layer was dried over anhydrous Na$_2$SO$_4$ and evaporated under vacuum then dissolved in DMSO (100 uL) and fractionated by reverse-phase (RP) flash chromatography on a C18 column with a gradient of 20% ACN in water with 0.1% TFA to 60% ACN in water with 0.1% TFA over 10 minutes and analyzed by LCMS. Pure fractions were isolated, combined, frozen, and lyophilized to give DS149A as a white powder.

Figure 12:
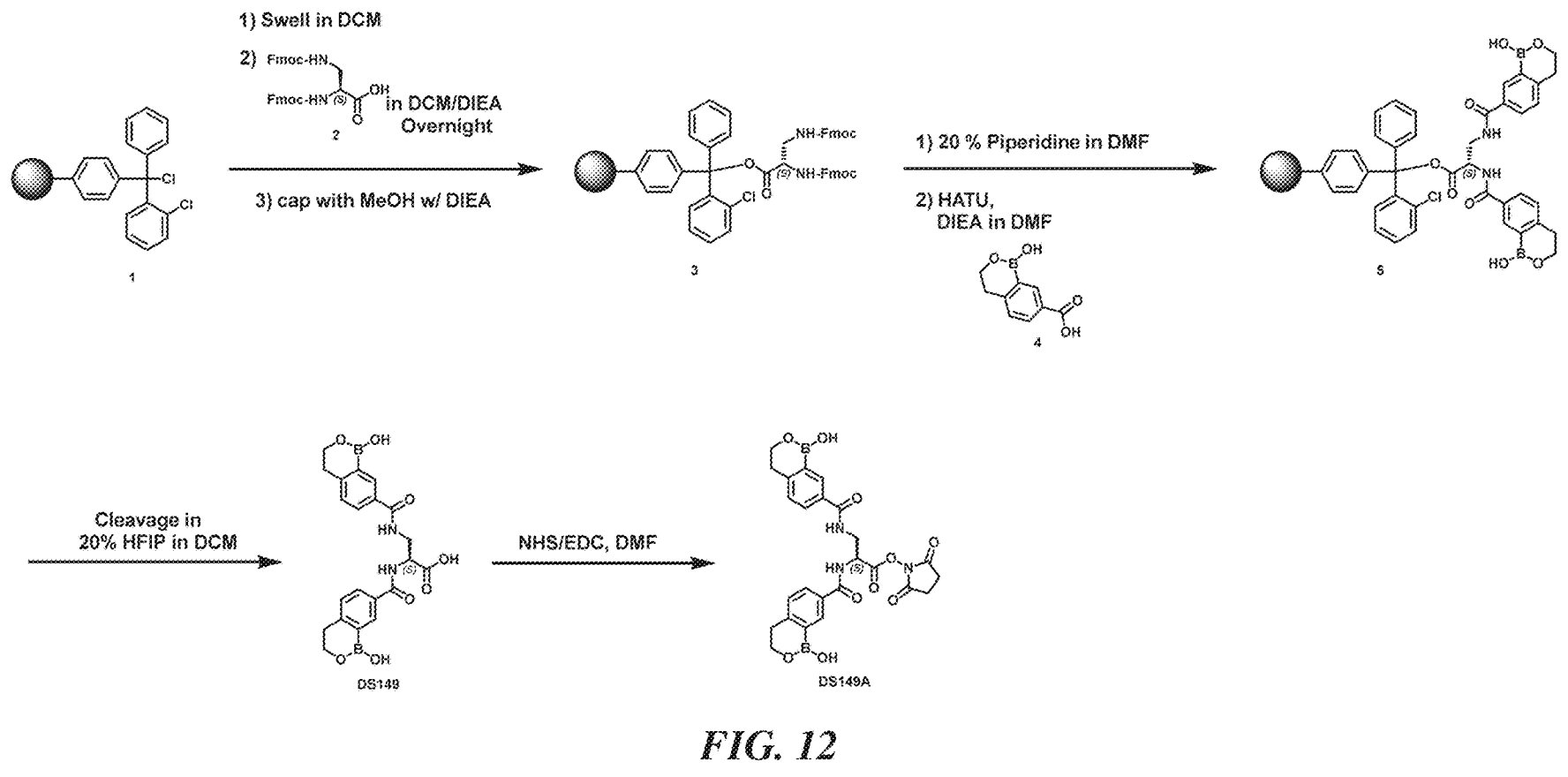

Similar procedures can be followed for the synthesis of aromatic boron-containing groups DS118-DS122 and DS148-DS152. The foregoing synthesis is illustrated in FIG. 12.

The chemical structure and IUPAC name of DS1 to DS109 and DS113 to DS152 are summarized in Table 1 below.

TABLE 1

| Compd # | FF | F | Structure/IUPAC Name |
|---|---|---|---|
| DS01 | FF10 | F1 | N-(3-(3-borono-5-nitrobenzamido)propyl)-N-(3--borono-5-nitrobenzoyl)glycine |
| DS02 | FF217 | F1 | N-(4-((4-(3-borono-5-nitrobenzamido)cyclohexyl)methyl)cyclohexyl)-N-(3-borono-5-nitrobenzoyl)glycine |
| DS03 | FF8 | F1 | N-(4-((3-borono-5-nitrobenzamido)methyl)benzyl)-N-(3-borono-5-nitrobenzoyl)glycine |

TABLE 1-continued

| Compd # | FF | F | Structure/IUPAC Name |
|---------|-----|-----|----------------------|

DS04    FF14    F1

N-(3-((3-borono-5-nitrobenzamido)methyl)benzyl)-N-(3-borono-5-
nitrobenzoyl)glycine

DS05    FF10    F1

N-(4-(3-borono-5-nitrobenzamido)butyl)-N-(3-borono-5-
nitrobenzoyl)glycine

DS06    FF10    F1

N-(3-(3-borono-5-fluorobenzamido)propyl)-N-(3-borono-5-
fluorobenzoyl)glycine

TABLE 1-continued

| Compd # | FF | F | Structure/IUPAC Name |
|---|---|---|---|
| DS07 | FF213 | F1 | <br>N-(3-(3-borono-5-fluorobenzamido)-2,2-dimethylpropyl)-N-(3-borono-5-fluorobenzoyl)glycine |
| DS08 | FF214 | F1 | <br>bis(3-(3-borono-5-fluorobenzamido)propyl)glycine |
| DS09 | FF8 | F1 | <br>N-(4-((3-borono-5-fluorobenzamido)methyl)benzyl)-N-(3-borono-5-fluorobenzoyl)glycine |
| DS10 | FF14 | F | |

TABLE 1-continued

| Compd # | FF | F | Structure/IUPAC Name |
|---------|----|----|----------------------|

N-(3-((3-borono-5-fluorobenzamido)methyl)benzyl)-N-(3-borono-5-fluorobenzoyl)glycine

| DS11 | FF1 | F1 | |

N-(2-(3-borono-5-fluorobenzamido)cyclohexyl)-N-(3-borono-5-fluorobenzoyl)glycine

| DS12 | FF10 | F1 | |

N-(3-(3-borono-4-fluorobenzamido)propyl)-N-(3-borono-4-fluorobenzoyl)glycine

| DS13 | FF217 | F1 | |

N-(4-((4-(3-borono-4-fluorobenzamido)cyclohexyl)methyl)cyclohexyl)-N-(3-borono-4-fluorobenzoyl)glycine TABLE 1-continued

| Compd # | FF | F | Structure/IUPAC Name |
|---|---|---|---|
| DS14 | FF213 | F1 | N-(3-(3-borono-4-fluorobenzamido)-2,2-dimethylpropyl)-N-(3-borono-4-fluorobenzoyl)glycine |
| DS15 | FF8 | F1 | N-(4-((3-borono-4-fluorobenzamido)methyl)benzyl)-N-(3-borono-4-fluorobenzoyl)glycine |
| DS16 | FF14 | F1 | N-(3-((3-borono-4-fluorobenzamido)methyl)benzyl)-N-(3-borono-4-fluorobenzoyl)glycine |
| DS17 | FF1 | F1 | N-((1S,2R)-2-(3-borono-4-fluorobenzamido)cyclohexyl)-N-(3-borono-4-fluorobenzoyl)glycine |

TABLE 1-continued

| Compd # | FF | F | Structure/IUPAC Name |
|---------|-----|-----|---------------------|

DS18　FF1　F1

N-((1S,2S)-2-(3-borono-4-fluorobenzamido)cyclohexyl)-N-(3-
borono-4-fluorobenzoyl)glycine

DS19　FF10　F1

N-(3-(3-borono-5-bromobenzamido)propyl)-N-(3-borono-5-
bromobenzoyl)glycine

DS20　FF217　F1

N-(4-((4-(3-borono-5-
bromobenzamido)cyclohexyl)methyl)cyclohexyl)-N-(3-borono-5-
bromobenzoyl)glycine TABLE 1-continued

| Compd # | FF | F | Structure/IUPAC Name |
|---|---|---|---|

DS21 FF214 F1 bis(3-(3-borono-5-bromobenzamido)propyl)glycine

DS22 FF8 F1

N-(4-((3-borono-5-bromobenzamido)methyl)benzyl)-N-(3-borono-5-bromobenzoyl)glycine

DS23 FF14 F1

N-(3-((3-borono-5-bromobenzamido)methyl)benzyl)-N-(3-borono-5-bromobenzoyl)glycine

DS24 FF1 F1

N-(2-(3-borono-5-bromobenzamido)cyclohexyl)-N-(3-borono-5-bromobenzoyl)glycine

TABLE 1-continued

| Compd # | FF | F | Structure/IUPAC Name |
|---------|-----|-----|----------------------|

DS25 FF10 F1

N-(3-(4-borono-3-fluorobenzamido)propyl)-N-(4-borono-3-
fluorobenzoyl)glycine

DS26 FF217 F1

N-(4-((4-(4-borono-3-
fluorobenzamido)cyclohexyl)methyl)cyclohexyl)-N-(4-borono-3-
fluorobenzoyl)glycine

DS27 FF213 F1

N-(3-(4-borono-3-fluorobenzamido)-2,2-dimethylpropyl)-N-(4-
borono-3-fluorobenzoyl)glycine TABLE 1-continued

| Compd # | FF | F | Structure/IUPAC Name |
|---------|-----|-----|----------------------|

DS28　FF214　F1 bis(3-(4-borono-3-fluorobenzamido)propyl)glycine

DS29　FF8　F1

N-(4-((4-borono-3-fluorobenzamido)methyl)benzyl)-N-(4-borono-
3-fluorobenzoyl)glycine

DS30　FF14　F1

N-(3-((4-borono-3-fluorobenzamido)methyl)benzyl)-N-(4-borono-
3-fluorobenzoyl)glycine

DS31　FF1　F1

N-((1S,2R)-2-(4-borono-3-fluorobenzamido)cyclohexyl)-N-(4-
borono-3-fluorobenzoyl)glycine TABLE 1-continued

| Compd # | FF | F | Structure/IUPAC Name |
|---|---|---|---|
| DS32 | FF10 | F2 | |

N-(1-hydroxxy-1,3-dihydrobenzo[c][1,2]oxaborole-6-carbonyl)-N-
(3-(1-hydroxy-1,3-dihydrobenzo[c][1,2]oxaborole-6-
carboxamido)propyl)glycine

| DS33 | FF10 | F2 | |
|---|---|---|---|

N-(1-hydroxy-1,3-dihydrobenzo[c][1,2]oxaborole-6-carbonyl)-N-
(5-(1-hydroxy-1,3-dihydrobenzo[c][1,2]oxaborole-6-
carboxamido)pentyl)glycine

| DS34 | FF213 | F2 | |
|---|---|---|---|

N-(1-hydroxy-1,3-dihydrobenzo[c][1,2]oxaborole-6-carbonyl)-N-
(3-(1-hydroxy-1,3-dihydrobenzo[c][1,2]oxaborole-6-
carboxamido)-2,2-dimethylpropyl)glycine TABLE 1-continued

| Compd # | FF | F | Structure/IUPAC Name |
|---------|-----|-----|---------------------|
| DS35 | FF214 | F2 | <br>bis(3-(1-hydroxy-1,3-dihydrobenzo[c][1,2]oxaborole-6-carboxamido)propyl)glycine |
| DS36 | FF14 | F2 | <br>N-(1-hydroxy-1,3-dihydrobenzo[c][1,2]oxaborole-6-carbonyl)-N-(3-((1-hydroxy-1,3-dihydrobenzo[c][1,2]oxaborole-6-carboxamido)methyl)benzyl)glycine |
| DS37 | FF1 | F2 | <br>N-(1-hydroxy-1,3-dihydrobenzo[c][1,2]oxaborole-6-carbonyl)-N-((1S,2R)-2-(1-hydroxy-1,3-dihydrobenzo[c][1,2]oxaborole-6-carboxamido)cyclohexyl)glycine |

TABLE 1-continued

| Compd # | FF | F | Structure/IUPAC Name |
|---|---|---|---|
| DS38 | FF10 | F2 | |

N-(1-hydroxy-1,3-dihydrobenzo[c][1,2]oxaborole-6-carbonyl)-N-
(4-(1-hydroxy-1,3-dihydrobenzo[c][1,2]oxaborole-6-
carboxamido)butyl)glycine

| DS39 | FF1 | F2 | |

N-(1-hydroxy-1,3-dihydrobenzo[c][1,2]oxaborole-6-carbonyl)-N-
((1S,2S)-2-(1-hydroxy-1,3-dihydrobenzo[c][1,2]oxaborole-6-
carboxamido)cyclohexyl)glycine

| DS40 | FF15 | F2 | |

(R)-N-(1-hydroxy-1,3-dihydrobenzo[c][1,2]oxaborole-6-carbonyl)-
N-(2-(1-hydroxy-1,3-dihydrobenzo[c][1,2]oxaborole-6-
carboxamido)propyl)glycine TABLE 1-continued

| Compd # | FF | F | Structure/IUPAC Name |
|---------|-----|-----|----------------------|

DS41    FF15    F2

(S)-N-(1-hydroxy-1,3-dihydrobenzo[c][1,2]oxaborole-6-carbonyl)-
N-(2-(1-hydroxy-1,3-dihydrobenzo[c][1,2]oxaborole-6-
carboxamido)propyl)glycine

DS42    FF1    F2

N-(1-hydroxy-1,3-dihydrobenzo[c][1,2]oxaborole-6-carbonyl)-N-
(2-(1-hydroxy-1,3-dihydrobenzo[c][1,2]oxaborole-6-
carboxamido)cyclohexyl)glycine

DS43    FF10    F1

N-(3-(4-borono-3,5-difluorobenzamido)propyl)-N-(4-borono-3,5-
difluorobenzoyl)glycine TABLE 1-continued

| Compd # | FF | F | Structure/IUPAC Name |
|---|---|---|---|
| DS44 | FF10 | F1 |  N-(3-(4-borono-2-fluorobenzamido)propyl)-N-(4-borono-2-fluorobenzoyl)glycine |
| DS45 | FF215 | F2 |  N-(2-(N-ethyl-1-hydroxy-1,3-dihydrobenzo[c][1,2]oxaborole-6-carboxamido)ethyl)-N-(1-hydroxy-1,3-dihydrobenzo[c][1,2]oxaborole-6-carbonyl)glycine |
| DS46 | FF215 | F2 |  N-(1-hydroxy-1,3-dihydrobenzo[c][1,2]oxaborole-6-carbonyl)-N-(2-(1-hydroxy-N-(2-hydroxyethyl)-1,3-dihydrobenzo[c][1,2]oxaborole-6-carboxamido)ethyl)glycine |

TABLE 1-continued

| Compd # | FF | F | Structure/IUPAC Name |
|---|---|---|---|
| DS47 | FF216 | F2 | |

N-(1-hydroxy-1,3-dihydrobenzo[c][1,2]oxaborole-6-carbonyl)-N-
(5-(1-hydroxy-1,3-dihydrobenzo[c][1,2]oxaborole-6-
carboxamido)hexyl)glycine

| DS48 | FF217 | F2 | |
|---|---|---|---|

N-(1-hydroxy-1,3-dihydrobenzo[c][1,2]oxaborole-6-carbonyl)-N-
(4-((4-(1-hydroxy-1,3-dihydrobenzo[c][1,2]oxaborole-6-
carboxamido)cyclohexyl)methyl)cyclohexyl)glycine

| DS49 | FF12 | F2 | |
|---|---|---|---|

((2S,4S)-1-(1-hydroxy-1,3-dihydrobenzo[c][1,2]oxaborole-6-
carbonyl)-4-(1-hydroxy-1,3-dihydrobenzo[c][1,2]oxaborole-6-
carboxamido)pyrrolidine-2-carbonyl)glycine TABLE 1-continued

| Compd # | FF | F | Structure/IUPAC Name |
|---|---|---|---|

DS50 FF12 F1

((2S,4S)-4-(3-borono-4-fluorobenzamido)-1-(3-borono-4-
fluorobenzoyl)pyrrolidine-2-carbonyl)glycine

DS51 FF12 F1

((2S,4S)-4-(3-borono-5-nitrobenzamido)-1-(3-borono-5-
nitrobenzoyl)pyrrolidine-2-carbonyl)glycine

DS52 FF12 F1

((2S,4S)-4-(5-borono-2-fluorobenzamido)-1-(5-borono-2-
fluorobenzoyl)pyrrolidine-2-carbonyl)glycine TABLE 1-continued

| Compd # | FF | F | Structure/IUPAC Name |
|---|---|---|---|
| DS53 | FF9 | F2 |
(S)-(1,4-bis(1-hydroxy-1,3-dihydrobenzo[c][1,2]oxaborole-6-carbonyl)piperazine-2-carbonyl)glycine |
| DS54 | FF208 | F2 |
(S)-N-(3-amino-2-(1-hydroxy-1,3-dihydrobenzo[c][1,2]oxaborole-6-carboxamido)-3-oxopropyl)-N-benzyl-1-hydroxy-1,3-dihydrobenzo[c][1,2]oxaborole-6-carboxamido |
| DS55 | FF208 | F2 |
(S)-N-(3-amino-2-(1-hydroxy-1,3-dihydrobenzo[c][1,2]oxaborole-6-carboxamido)-3-oxopropyl)-1-hydroxy-N-(4-(trifluoromethyl)benzyl)-1,3-dihydrobenzo[c][1,2]oxaborole-6-carboxamide |

TABLE 1-continued

| Compd # | FF | F | Structure/IUPAC Name |
|---|---|---|---|
| DS56 | FF208 | F2 | (S)-N-(3-amino-2-(1-hydroxy-1,3-dihydrobenzo[c][1,2]oxaborole-6-carboxamido)-3-oxopropyl)-N-ethyl-1-hydroxy-1,3-dihydrobenzo[c][1,2]oxaborole-6-carboxamide |
| DS57 | FF208 | F2 | (S)-N-(3-amino-2-(1-hydroxy-1,3-dihydrobenzo[c][1,2]oxaborole-6-carboxamido)-3-oxopropyl)-1-hydroxy-N-propyl-1,3-dihydrobenzo[c][1,2]oxaborole-6-carboxamide |
| DS58 | FF208 | F2 | (S)-N-(3-amino-2-(1-hydroxy-1,3-dihydrobenzo[c][1,2]oxaborole-6-carboxamido)-3-oxopropyl)-1-hydroxy-N-isobutyl-1,3-dihydrobenzo[c][1,2]oxaborole-6-carboxamide |

TABLE 1-continued

| Compd # | FF | F | Structure/IUPAC Name |
|---|---|---|---|
| DS59 | FF208 | F2 | |

(S)-N-(3-amino-2-(1-hydroxy-1,3-dihydrobenzo[c][1,2]oxaborole-
6-carboxamido)-3-oxopropyl)-1-hydroxy-N-((5-(thiophen-2-
yl)pyridin-2-yl)methyl)-1,3-dihydrobenzo[c][1,2]oxaborole-6-
carboxamide

| DS60 | FF208 | F2 | |

(S)-N-(3-amino-2-(1-hydroxy-1,3-dihydrobenzo[c][1,2]oxaborole-
6-carboxamido)-3-oxopropyl)-1-hydroxy-N-isopentyl-1,3-
dihydrobenzo[c][1,2]oxaborole-6-carboxamide

| DS61 | FF208 | F2 | |

TABLE 1-continued

| Compd # | FF | F | Structure/IUPAC Name |
|---------|-----|-----|----------------------|

(S)-N-(3-amino-2-(1-hydroxy-1,3-dihydrobenzo[c][1,2]oxaborole-6-carboxamido)-3-oxopropyl)-1-hydroxy-N-(quinolin-5-ylmethyl)-1,3-dihydrobenzo[c][1,2]oxaborole-6-carboxamide

| DS62 | FF208 | F2 |

(S)-N-(3-amino-2-(1-hydroxy-1,3-dihydrobenzo[c][1,2]oxaborole-6-carboxamido)-3-oxopropyl)-1-hydroxy-N-(2-(trifluoromethoxy)benzyl)-1,3-dihydrobenzo[c][1,2]oxaborole-6-carboxamide

| DS63 | FF208 | F2 |

(S)-N-(3-amino-2-(1-hydroxy-1,3-dihydrobenzo[c][1,2]oxaborole-6-carboxamido)-3-oxopropyl)-1-hydroxy-N-(4-(methylsulfonyl)benzyl)-1,3-dihydrobenzo[c][1,2]oxaborole-6-carboxamide

| DS64 | FF12 | F1 |

TABLE 1-continued

| Compd # | FF | F | Structure/IUPAC Name |
|---|---|---|---|

(3-((2S,4S)-4-(5-borono-2-(methylsulfonyl)benzamido)-2-
carbamoylpyrrolidine-1-carbonyl)-4-
(methylsulfonyl)phenyl)boronic acid

| DS65 | FF12 | F1 | |

(4-(((3S,5S)-1-(4-borono-2,6-difluorobenzoyl)-5-
carbamoylpyrrolidin-3-yl)carbamoyl)-3,5-difluorophenyl)benzoic
acid

| DS66 | FF20 | F2 | |

(R,E)-4,5-bis(1-hydroxy-1,3-dihydrobenzo[c][1,2]oxaborole-6-
carboxamido)pent-2-enoic acid TABLE 1-continued

| Compd # | FF | F | Structure/IUPAC Name |
|---------|-----|-----|---------------------|

DS67   FF12   F2

(2S,4S)-1-(1-hydroxy-4-(trifluoromethyl)-1,3-
dihydrobenzo[c][1,2]oxaborole-6-carbonyl)-4-(1-hydroxy-4-
(trifluoromethyl)-1,3-dihydrobenzo[c][1,2]oxaborole-6-
carboxamido)pyrrolidine-2-carboxamide

DS68   FF116   F2

N,N'-((2S,3S)-1-amino-1-oxobutane-2,3-diyl)bis(1-hydroxy-1,3-
dihydrobenzo[c][1,2]oxaborole-6-carboxamide)

DS69   FF115   F2

TABLE 1-continued

| Compd # | FF | F | Structure/IUPAC Name |
|---------|-----|-----|---------------------|

(R)-3,4-bis(1-hydroxy-1,3-dihydrobenzo[c][1,2]oxaborole-6-carboxamido)butanoic acid

DS70    FF12    F2

3-((2S,4S)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxamido)propanoic acid

DS71    FF115    F2

(S)-3-(1-hydroxy-1,3-dihydrobenzo[c][1,2]oxaborole-5-carboxamido)-4-(1-hydroxy-1,3-dihydrobenzo[c][1,2]oxaborole-6-carboxamido)butanoic acid

DS72    FF14    F2

(R)-4-(1-hydroxy-1,3-dihydrobenzo[c][1,2]oxaborole-5-carboxamido)-5-(1-hydroxy-1,3-dihydrobenzo[c][1,2]oxaborole-6-carboxamido)pentanoic acid TABLE 1-continued

| Compd # | FF | F | Structure/IUPAC Name |
|---|---|---|---|
| DS73 | FF12 | F2 | (2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxylic acid |
| DS74 | FF12 | F2 | (2S,4R)-1-(1-hydroxy-4-(trifluoromethyl)-1,3-dihydrobenzo[c][1,2]oxaborole-6-carbonyl)-4-(1-hydroxy-4-(trifluoromethyl)-1,3-dihydrobenzo[c][1,2]oxaborole-6-carboxamido)pyrrolidine-2-carboxylic acid |
| DS75 | FF16 | F2 | (2S,3S)-3-(1-hydroxy-4-(trifluoromethyl)-1,3-dihydrobenzo[c][1,2]oxaborole-6-carboxamido)-2-(1-hydroxy-7-(trifluoromethyl)-1,3-dihydrobenzo[c][1,2]oxaborole-5-carboxamido)butanoic acid |

TABLE 1-continued

| Compd # | FF | F | Structure/IUPAC Name |
|---------|-----|-----|----------------------|

DS76    FF114    F2

(R)-5-(1-hydroxy-4-(trifluoromethyl)-1,3-
dihydrobenzo[c][1,2]oxaborole-6-carboxamido)-4-(1-hydroxy-7-
(trifluoromethyl)-1,3-dihydrobenzo[c][1,2]oxaborole-5-
carboxamido)pentanoic acid DS77    FF12    F1
and
F2

((2S,4S)-1-(5-borono-2-nitrobenzoyl)-4-(1-hydroxy-1,3-
dihydrobenzo[c][1,2]oxaborole-6-carboxamido)pyrrolidine-2-
carbonyl)glycine DS78    FF12    F1
and
F2

((2S,4S)-1-(5-borono-2-(methylsulfonyl)benzoyl)-4-(1-hydroxy-
1,3-dihydrobenzo[c][1,2]oxaborole-6-carboxamido)pyrrolidine-2-
carbonyl)glycine TABLE 1-continued

| Compd # | FF | F | Structure/IUPAC Name |
|---|---|---|---|
| DS79 | FF12 | F1 and F2 | ((2S,4S)-1-(3-borono-2,6-difluorobenzoyl)-4-(1-hydroxy-1,3-dihydrobenzo[c][1,2]oxaborole-6-carboxamido)pyrrolidine-2-carbonyl)glycine |
| DS80 | FF221 | F1 | (S)-(3-((3-borono-4-fluorobenzyl)(5,6-diamino-6-oxohexyl)carbamoyl)-5-nitrophenyl)boronic acid |
| DS81 | FF221 | F1 | (S)-(3-((4-borono-3,5-difluorobenzyl)(5,6-diamino-6-oxohexyl)carbamoyl)-5-nitrophenyl)boronic acid |
| DS82 | FF221 | F1 | |

TABLE 1-continued

| Compd # | FF | F | Structure/IUPAC Name |
|---------|-----|-----|---------------------|

(S)-(3-((3-boronobenzyl)(5,6-diamino-6-oxohexyl)carbamoyl)-5-nitrophenyl)boronic acid

DS83    FF221    F1

(S)-(3-((4-borono-2-methoxybenzyl)(5,6-diamino-6-oxohexyl)carbamoyl)-5-nitrophenyl)boronic acid

DS84    FF21    F1

(S)-(3-((4-borono-2-(trifluoromethyl)benzyl)(5,6-diamino-6-oxohexyl)carbamoyl)-5-nitrophenyl)boronic acid

DS85    FF221    F1

(S)-(5-((3-borono-N-(5,6-diamino-6-oxohexyl)-4-fluorobenzamido)methyl)-2-fluorophenyl)boronic acid

DS86    FF221    F1

TABLE 1-continued

| Compd # | FF | F | Structure/IUPAC Name |
|---------|-----|-----|----------------------|
| | | | (S)-(5-((4-borono-3,5-difluorobenzyl)(5,6-diamino-6-oxohexyl)carbamoyl)-2-fluorophenyl)boronic acid |
| DS87 | FF221 | F1 | |
| | | | (S)-(3-((3-borono-N-(5,6-diamino-6-oxohexyl)-4-fluorobenzamido)methyl)phenyl)boronic acid |
| DS88 | FF21 | F1 | |
| | | | (S)-(5-((4-borono-2-methoxybenzyl)(5,6-diamino-6-oxohexyl)carbamoyl)-2-fluorophenyl)boronic acid |
| DS89 | FF221 | F1 | |
| | | | (S)-(5-((4-borono-3-(trifluoromethyl)benzyl)(5,6-diamino-6-oxohexyl)carbamoyl)-2-fluorophenyl)boronic acid |
| DS90 | FF221 | F1 | |

TABLE 1-continued

| Compd # | FF | F | Structure/IUPAC Name |
|---|---|---|---|
| | | | (S)-(4-((3-borono-4-fluorobenzyl)(5,6-diamino-6-oxohexyl)carbamoyl)-2-fluorophenyl)boronic acid |
| DS91 | FF221 | F1 | |
| | | | (S)-(4-((4-borono-3,5-difluorobenzyl)(5,6-diamino-6-oxohexyl)carbamoyl)-2-fluorophenyl)boronic acid |
| DS92 | FF221 | F1 | |
| | | | (S)-(4-((3-boronobenzyl)(5,6-diamino-6-oxohexyl)carbamoyl)-2-fluorophenyl)boronic acid |
| DS93 | FF221 | F1 | |
| | | | (S)-(4-((4-borono-2-methoxybenzyl)(5,6-diamino-6-oxohexyl)carbamoyl)-2-fluorophenyl)boronic acid |
| DS94 | FF221 | F1 | |

TABLE 1-continued

| Compd # | FF | F | Structure/IUPAC Name |
|---------|-----|-----|----------------------|
| | | | (S)-(4-((4-borono-2-(trifluoromethyl)benzyl)(5,6-diamino-6-oxohexyl)carbamoyl)-2-fluorophenyl)boronic acid |
| DS95 | FF221 | F1 | |
| | | | (S)-(5-((3-borono-5-bromo-N-(5,6-diamino-6-oxohexyl)benzamido)methyl)-2-fluorophenyl)boronic acid |
| DS96 | FF221 | F1 | |
| | | | (S)-(3-((4-borono-3,5-difluorobenzyl)(5,6-diamino-6-oxohexyl)carbamoyl)-5-bromophenyl)boronic acid |
| DS97 | FF221 | F1 | |
| | | | (S)-(3-((3-borono-5-bromo-N-(5,6-diamino-6-oxohexyl)benzamido)methyl)phenyl)boronic acid |
| DS98 | FF221 | F1 | |

TABLE 1-continued

| Compd # | FF | F | Structure/IUPAC Name |
|---------|-----|-----|-----|

(S)-(3-((3-borono-5-bromo-N-(5,6-diamino-6-oxohexyl)benzamido)methyl)-5-methoxyphenyl)boronic acid

DS99  FF221  F1

(S)-(3-((4-borono-2-(trifluoromethyl)benzyl)(5,6-diamino-6-oxohexyl)carbamoyl)-5-bromophenyl)boronic acid

DS100  FF221  F1

(S)-(3-((3-borono-4-fluorobenzyl)(5,6-diamino-6-oxohexyl)carbamoyl)-5-fluorophenyl)boronic acid

DS101  FF221  F1

(S)-(3-((4-borono-3-methoxybenzyl)(5,6-diamino-6-oxohexyl)carbamoyl)-5-fluorophenyl)boronic acid

DS102  FF221  F1

TABLE 1-continued

| Compd # | FF | F | Structure/IUPAC Name |
|---------|-----|-----|----------------------|

(S)-(3-((4-borono-2-(trifluoromethyl)benzyl)(5,6-diamino-6-
oxohexyl)carbamoyl)-5-fluorophenyl)boronic acid DS103   FF221   F1 and F2

(S)-(4-((N-(5,6-diamino-6-oxohexyl)-1-hydroxy-1,3-
dihydrobenzo[c][1,2]oxaborole-6-carboxamido)methyl)-2-
fluorophenyl)boronic acid DS104   FF221   F1 and F2

(S)-(4-((N-(5,6-diamino-6-oxohexyl)-1-hydroxy-1,3-
dihydrobenzo[c][1,2]oxaborole-6-carboxamido)methyl)-2,6-
difluorophenyl)boronic acid DS105   FF221   F1 and F2

(S)-(3-((N-(5,6-diamino-6-oxohexyl)-1-hydroxy-1,3-
dihydrobenzo[c][1,2]oxaborole-6-
carboxamido)methyl)phenyl)boronic acid TABLE 1-continued

| Compd # | FF | F | Structure/IUPAC Name |
|---|---|---|---|
| DS106 | FF221 | F1 and F2 | <br><br>(S)-(4-((N-(5,6-diamino-6-oxohexyl)-1-hydroxy-1,3-dihydrobenzo[c][1,2]oxaborole-6-carboxamido)methyl)-3-methoxyphenyl)boronic acid |
| DS107 | FF221 | F2 | <br><br>(S)-N-(5,6-diamino-6-oxohexyl)-1-hydroxy-N-((1-hydroxy-1,3-dihydrobenzo[c][1,2]oxaborol-6-yl)methyl)-1,3-dihydrobenzo[c][1,2]oxaborole-6-carboxamide |
| DS108 | FF221 | F2 | <br><br>(S)-N-(4-amino-3-(1-hydroxy-1,3-dihydrobenzo[c][1,2]oxaborole-6-carboxamido)-4-oxobutyl)-1-hydroxy-N-((1-hydroxy-1,3-dihydrobenzo[c][1,2]oxaborol-6-yl)methyl)-1,3-dihydrobenzo[c][1,2]oxaborole-6-carboxamide |

TABLE 1-continued

| Compd # | FF | F | Structure/IUPAC Name |
|---------|-----|-----|----------------------|
| DS109 | FF221 | F2 | <br><br>(S)-N-(6-amino-5-(1-hydroxy-1,3-dihydrobenzo[c][1,2]oxaborole-6-carboxamido)-6-oxohexyl)-1-hydroxy-N-((1-hydroxy-1,3-dihydrobenzo[c][1,2]oxaborol-6-yl)methyl)-1,3-dihydrobenzo[c][1,2]oxaborole-6-carboxamide |
| DS113 | FF225 | F7 | <br><br>N-(1-hydroxy-3,3-dimethyl-1,3-dihydrobenzo[c][1,2]oxaborole-6-carbonyl)-N-(2-(1-hydroxy-3,3-dimethyl-1,3-dihydrobenzo[c][1,2]oxaborole-6-carboxamido)ethyl)glycine |
| DS114 | FF225 | F6 | <br><br>N-(1-hydroxy-3,4-dihydro-1H-benzodihydrobenzo[c][1,2]oxaborinine-7-carbonyl)-N-(2-(1-hydroxy-3,4-dihydro-1H-benzodihydrobenzo[c][1,2]oxaborinine-7-carboxamido)ethyl)glycine |

TABLE 1-continued

| Compd # | FF | F | Structure/IUPAC Name |
|---------|-----|-----|----------------------|

DS115    FF225    F2

N-(2-(2-(1-hydroxy-1,3-dihydrobenzo[c][1,2]oxaborol-7-
yl)acetamido)ethyl)-N-(2-(1-hydroxy-1,3-
dihydrobenzo[c][1,2]oxaborol-7-yl)acetyl)glycine

DS116    FF225    F7

N-(1-hydroxy-3,3-dimethyl-1,3-dihydrobenzo[c][1,2]oxaborole-7-
carbonyl)-N-(2-(1-hydroxy-3,3-dimethyl-1,3-
dihydrobenzo[c][1,2]oxaborole-7-carboxamido)ethyl)glycine

DS117    FF225    F11

N-(1-hydroxy-1,3-dihydrobenzo[c][1,2]oxaborole-3-carbonyl)-N-
(2-(1-hydroxy-1,3-dihydrobenzo[c][1,2]oxaborole-3-
carboxamido)ethyl)glycine TABLE 1-continued

| Compd # | FF | F | Structure/IUPAC Name |
|---|---|---|---|
| DS118 | FF226 | F7 |

3,5-bis((1-hydroxy-3,3-dimethyl-1,3-dihydrobenzo[c][1,2]oxaborole-6-carboxamido)methyl)benzoic acid |
| DS119 | FF226 | F6 |

3,5-bis((1-hydroxy-3,4-dihydro-1H-benzo[c][1,2]oxaborinine-7-carboxamido)methyl)benzoic acid |
| DS120 | FF26 | F2 |

3,5-bis((2-(1-hydroxy-1,3-dihydrobenzo[c][1,2]oxaborol-7-yl)acetamido)methyl)benzoic acid |
| DS121 | FF226 | F7 |

3,5-bis((1-hydroxy-3,3-dimethyl-1,3-dihydrobenzo[c][1,2]oxaborole-7-carboxamido)methyl)benzoic acid |

TABLE 1-continued

| Compd # | FF | F | Structure/IUPAC Name |
|---|---|---|---|
| DS122 | FF226 | F11 | <br>3,5-bis((1-hydroxy-1,3-dihydrobenzo[c][1,2]oxaborole-3-carboxamido)methyl)benzoic acid |
| DS123 | FF227 | F7 | <br>(S)-3-(2,3-bis(1-hydroxy-3,3-dimethyl-1,3-dihydrobenzo[c][1,2]oxaborole-6-carboxamido)propanamido)propanoic acid |
| DS124 | FF227 | F6 | <br>(S)-3-(2,3-bis(1-hydroxy-3,4-dihydro-1H-benzo[c][1,2]oxaborinine-7-carboxamido)propanamido)propanoic acid |

TABLE 1-continued

| Compd # | FF | F | Structure/IUPAC Name |
|---|---|---|---|
| DS125 | FF227 | F2 | |

(S)-3-(2,3-bis(2-(1-hydroxy-1,3-dihydrobenzo[c][1,2]oxaborol-7-yl)acetamido)propanamido)propanoic acid

| DS126 | FF227 | F7 | |

(S)-3-(2,3-bis(1-hydroxy-3,3-dimethyl-1,3-dihydrobenzo[c][1,2]oxaborole-7-carboxamido)propanamido)propanoic acid TABLE 1-continued

| Compd # | FF | F | Structure/IUPAC Name |
|---|---|---|---|
| DS127 | FF227 | F11 |  3-((2S)-2,3-bis(1-hydroxy-1,3-dihydrobenzo[c][1,2]oxaborole-3-carboxamido)propanamido)propanoic acid |
| DS128 | FF229 | F7 |  (3,5-bis((1-hydroxy-3,3-dimethyl-1,3-dihydrobenzo[c][1,2]oxaborole-6-carboxamido)methyl)benzoyl)glutamic acid |
| DS129 | FF229 | F6 |  (3,5-bis((1-hydroxy-3,4-dihydro-1H-benzo[c][1,2]oxaborinine-7-carboxamido)methyl)benzoyl)glutamic acid |

TABLE 1-continued
| Compd # | FF | F | Structure/IUPAC Name |
|---|---|---|---|
DS130   FF229   F2
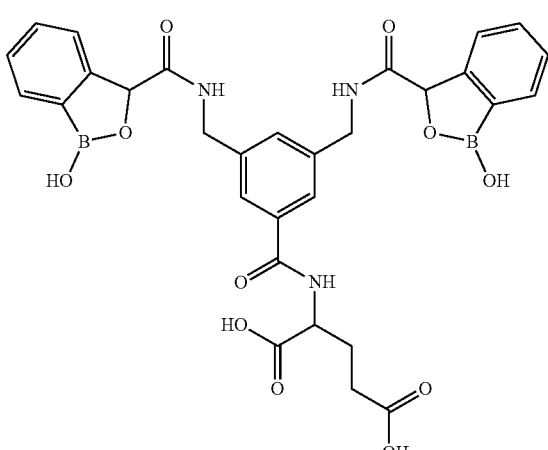
(3,5-bis((2-(1-hydroxy-1,3-dihydrobenzo[c][1,2]oxaborol-7-yl)acetamido)methyl)benzoyl)glutamic acid
DS131   FF229   F7
(3,5-bis((1-hydroxy-3,3-dimethyl-1,3-dihydrobenzo[c][1,2]oxaborole-7-carboxamido)methyl)benzoyl)glutamic acid
DS132   FF229   F11
(3,5-bis((1-hydroxy-1,3-dihydrobenzo[c][1,2]oxaborole-3-carboxamido)methyl)benzoyl)glutamic acid TABLE 1-continued

| Compd # | FF | F | Structure/IUPAC Name |
|---------|-----|-----|----------------------|

DS133 FF228 F7

4-(3,4-bis(1-hydroxy-3,3-dimethyl-1,3-
dihydrobenzo[c][1,2]oxaborole-6-carboxamido)pyrrolidin-1-yl)-4-
oxobutanoic acid

DS134 FF228 F6

4-(3,4-bis(1-hydroxy-3,4-dihydro-1H-benzo[c][1,2]oxaborinine-7-
carboxamido)pyrrolidin-1-yl)-4-oxobutanoic acid

DS135 FF228 F2

4-(3,4-bis(2-(1-hydroxy-1,3-dihydrobenzo[c][1,2]oxaborol-7-
yl)acetamido)pyrrolidin-1-yl)-4-oxobutanoic acid TABLE 1-continued

| Compd # | FF | F | Structure/IUPAC Name |
|---|---|---|---|
| DS136 | FF228 | F7 | <br>4-(3,4-bis(1-hydroxy-3,3-dimethyl-1,3-dihydrobenzo[c][1,2]oxaborole-7-carboxamido)pyrrolidin-1-yl)-4-oxobutanoic acid |
| DS137 | FF228 | F11 | <br>4-(3,4-bis(1-hydroxy-1,3-dihydrobenzo[c][1,2]oxaborole-3-carboxamido)pyrrolidin-1-yl)-4-oxobutanoic acid |
| DS138 | FF230 | F7 | <br>((S)-2,3-bis(1-hydroxy-3,3-dimethyl-1,3-dihydrobenzo[c][1,2]oxaborole-6-carboxamido)propanoyl)-L-glutamic acid |

TABLE 1-continued

| Compd # | FF | F | Structure/IUPAC Name |
|---|---|---|---|

DS139   FF230   F6

((S)-2,3-bis(1-hydroxy-3,4-dihydro-1H-benzo[c][1,2]oxaborinine-
7-carboxamido)propanoyl)-L-glutamic acid

DS140   FF230   F2

((S)-2,3-bis(2-(1-hydroxy-1,3-dihydrobenzo[c][1,2]oxaborol-7-
yl)acetamido)propanoyl)-L-glutamic acid TABLE 1-continued

| Compd # | FF | F | Structure/IUPAC Name |
|---|---|---|---|
| DS141 | FF230 | F7 | ((S)-2,3-bis(1-hydroxy-3,3-dimethyl-1,3-dihydrobenzo[c][1,2]oxaborole-7-carboxamido)propanoyl)-L-glutamic acid |
| DS142 | FF230 | F11 | ((2S)-2,3-bis(1-hydroxy-1,3-dihydrobenzo[c][1,2]oxaborole-3-carboxamido)propanoyl)-L-glutamic acid |
| DS143 | FF231 | F7 | |

TABLE 1-continued

| Compd # | FF | F | Structure/IUPAC Name |
|---|---|---|---|

(4-(3,4-bis(1-hydroxy-3,3-dimethyl-1,3-
dihydrobenzo[c][1,2]oxaborole-6-carboxamido)pyrrolidin-1-yl)-4-
oxobutanoyl)-L-glutamic acid

DS144   FF231   F6

(4-(3,4-bis(1-hydroxy-3,4-dihydro-1H-benzo[c][1,2]oxaborinine-
7-carboxamido)pyrrolidin-1-yl)-4-oxobutanoyl)-L-glutamic acid

DS145   FF231   F2

(4-(3,4-bis(2-(1-hydroxy-1,3-dihydrobenzo[c][1,2]oxaborol-7-
yl)acetamido)pyrrolidin-1-yl)-4-oxobutanoyl)-L-glutamic acid

DS146   FF231   F7

(4-(3,4-bis(1-hydroxy-3,3-dimethyl-1,3-
dihydrobenzo[c][1,2]oxaborole-7-carboxamido)pyrrolidin-1-yl)-4-
oxobutanoyl)-L-glutamic acid TABLE 1-continued

| Compd # | FF | F | Structure/IUPAC Name |
|---|---|---|---|
| DS147 | FF231 | F11 | (4-(3,4-bis(1-hydroxy-1,3-dihydrobenzo[c][1,2]oxaborole-3-carboxamido)pyrrolidin-1-yl)-4-oxobutanoyl)-L-glutamic acid |
| DS148 | FF227 | F7 | (S)-2,3-bis(1-hydroxy-3,3-dimethyl-1,3-dihydrobenzo[c][1,2]oxaborole-6-carboxamido)propanoic acid |
| DS149 | FF227 | F6 | (S)-2,3-bis(1-hydroxy-3,4-dihydro-1H-benzo[c][1,2]oxaborinine-7-carboxamido)propanoic acid |

TABLE 1-continued

| Compd # | FF | F | Structure/IUPAC Name |
|---|---|---|---|
| DS150 | FF227 | F2 | |

(S)-2,3-bis(2-(1-hydroxy-1,3-dihydrobenzo[c][1,2]oxaborol-7-yl)acetamido)propanoic acid

| DS151 | FF27 | F7 | |

(S)-2,3-bis(1-hydroxy-3,3-dimethyl-1,3-dihydrobenzo[c][1,2]oxaborole-7-carboxamido)propanoic acid TABLE 1-continued

| Compd # | FF | F | Structure/IUPAC Name |
|---|---|---|---|
| DS152 | FF227 | F11 | (2S)-2,3-bis(1-hydroxy-1,3-dihydrobenzo[c][1,2]oxaborole-3-carboxamido)propanoic acid |

Synthesis of Compounds of Formula I

Illustrative syntheses protocols are provided that can be used to synthesize any of the examples described.

The lines connecting cysteine residues are disulfide bonds. For the sake of clarity, the H— at the N-terminus of the A- and B-chain of insulin is not histidine, it is the hydrogen of the N-terminus. The —OH shown at the C-terminal end of the A- and B-chain is the C-terminus of the respective chain.

B. Synthesis of Modified Insulins

1. Chain Synthesis:

Cl-MPA resin

Sequence: GIVKQC(Acm)C(Acm)TSIC(Acm)SLYQLE-NYCN (SEQ ID NO:24065)

Synthesis of A-Chain and Modified A-Chain of Example 870 was Accomplished Using Conventional Solid-Phase Peptide Synthesis (SPPS)

MPA resin (0.22 mmol/eq) was swelled in a mixture of DMF:DCM (50:50, v:v). A solution of Potassium Iodide with DIPEA (1 M) in DMF was Added to the Reaction Vessel Along with Fmoc-Asn(Trt)-OH (0.2 M). The reaction vessel was heated to 75° C. Each amino acid coupling step involved i) deprotection with 20% piperidine in DMF at 90° C.; ii) washing with DMF; iii) activation and coupling of Fmoc protected amino acids with 0.5 M N,N'-diisopropyl-carbodiimide (DIC, 1 mL), 0.5 M Oxyma, and 0.2 M Fmoc-amino acid in DMF at 90° C.; iv) washing with DMF. Global Deprotection and Isolation.

Crude peptide was globally deprotected in TFA:TIPS: H₂O (95:2.5:2.5) and gently agitated for 2 h. Crude solution was filtered and peptide was precipitated in cold ether, centrifuged and washed with additional cold ether. Supernatant was decanted and the crude peptide was dried under a gentle stream of nitrogen gas. Crude peptide was dissolved in 20% ACN in water and fractionated by RP-HPLC on a C18 column.

B-chain synthesis:

Sequence: GKFVNQHLC(Acm)GSHLVEALYLVC(DTDP)GERGFFYTPK (SEQ ID NO:24066)

Synthesis of Modified B-Chain Insulins Using Solid-Phase Peptide Synthesis (SPPS)

MPA resin (0.22 mmol/eq) was swelled in a mixture of DMF:DCM (50:50, v:v). A solution of potassium iodide (125 mM) with DIPEA (1 M) in DMF was added to the reaction vessel along with Fmoc-Lys(ivDde)-OH (0.2 M). The reaction vessel was heated to 75° C. Each amino acid coupling step involved i) deprotection with 20% piperidine in DMF at 90° C.; ii) washing with DMF; iii), activation and coupling of Fmoc protected amino acids with 0.5 M N,N'-diisopropylcarbodiimide (DIC), 0.5 M Oxyma, and 0.2 M Fmoc-amino acid in DMF at 90° C.; iv) washing with DMF. Fmoc-Arg(Pbf)-OH was coupled twice using the methods described above.

Deprotection IVdde and Add Diboronates to B Chain.

The ivDde protecting group on the lysine residue was removed with 4% hydrazine in DMF, then washed with DMF. A solution of bromo acetic acid (0.2 M, 2 mL) in DMF with DIC (0.5 M, 2 mL) was added immediately and gently mixed for 4 hr. The resin was washed with DMF (3×5 mL). A solution of 1,3-phenylenedimethanamine (1M) in DMF (5 mL) was added to the resin and heated at 50 C for 10 minutes. The resin was washed with DMF (3×5 mL) and a Cl-MPA resin

SPPS

H—G—K—F—V—N—Q—H—L—C—G—S—H—L—V—E—A—L—Y—L—V—C—G—K—R—G—F—F—Y—T—P—K—T

IVdde ... IVdde 1. 4% Hydrazine/DMF
2. bromo acetic acid/DIEA
3. Diamine
4. Boronation
5. cleavage with DTDP Acm

H—G—K—F—V—N—Q—H—L—C—G—S—H—L—V—E—A—L—Y—L—V—C—G—K—R—G—F—F—Y—T—P—K—T—OH solution of 1-hydroxy-1,3-dihydrobenzo[c][1,2]oxaborole-6-carboxylic acid (0.2 M, 5 mL) in DMF with 1 M N,N'-diisopropylcarbodiimide (DIC, 1M, 1 mL), Oxyma (0.5 M, 2 mL) in DMF and heated at 50 C for 30 min.

Cleavage and Addition of DTDP to B-Chain.

Crude peptide was globally deprotected with 2,2'-Dithio-pyridine (DTDP) in TFA:TIPS:H$_2$O (95:2.5:2.5) and gently agitated. Crude solution was filtered and peptide was precipitated in cold ether, centrifuged, decanted, washed with additional cold ether, and centrifuged again. Supernatant was decanted and the crude peptide was dried under a gentle stream of nitrogen gas. Crude peptide was dissolved in 20% ACN in water and fractionated by RP-HPLC on a C18 column.

Combination of A and B Chains of Insulin and Modified Insulins.

A chain of insulin was combined with B chain in 0.2 M NH$_4$HCO$_3$ with 6M urea and at pH 8. Mixture was gently agitated, diluted with water and fractionated by RP-HPLC on a C18 column.

Deprotection of Acm Protecting Groups and Final Oxidation.

The combined intermediate was dissolved in glacial acetic acid and water and vortexed vigorously. A solution of iodine in glacial acetic acid (20 equiv) was added to the reaction mixture and gently agitated. A solution of ascorbic acid (5 mM) was added directly to the reaction mixture. The mixture was diluted in 20% ACN in water and fractionated by RP-HPLC on a Higgins C18 column to give Example 870.

+

0.2 M NH$_4$HCO$_3$, 6M Urea

-continued

12/AcPOH

Example B70

Similar procedures can be followed for the synthesis of Examples 1 to 869 and 871 to 876.

C. Alternative Synthesis of Modified Insulins

Conjugation of Diboronate Sensor with Proinsulin

Figure 9A:
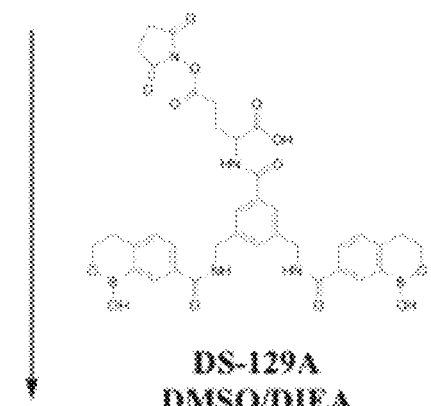
Figure 9B:
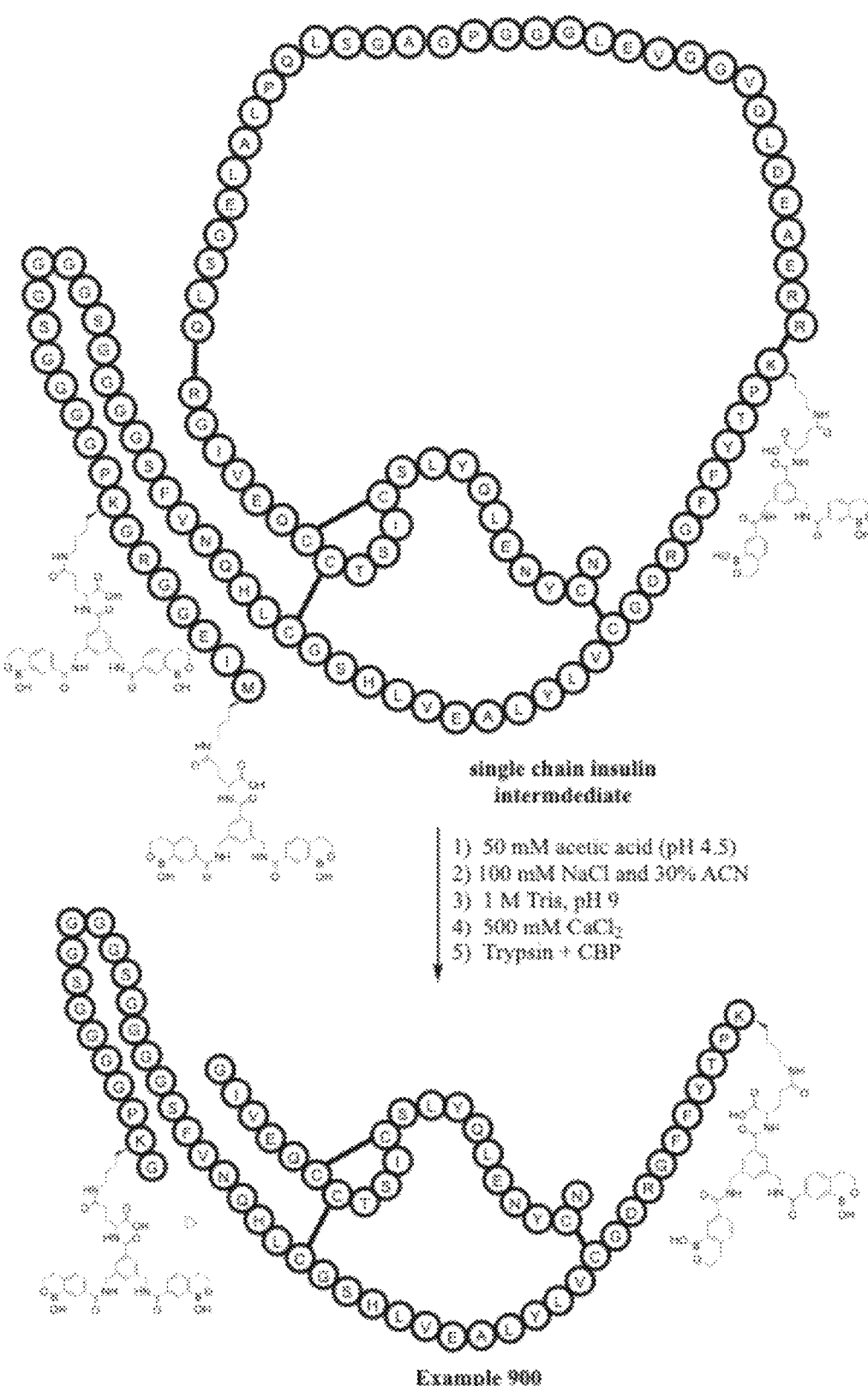

To a solution of single-chain proinsulin (20 mg, the amino acids on the single-chain proinsulin (SEQ ID NO:24067) are depicted in FIG. 9A) in DMSO (200 uL) was added 2-(3, 5-bis((1-hydroxy-3,4-dihydro-1H-benzo[c][1,2]oxabori-nine-7-carboxamido)methyl)benzamido)-5-((2,5-dioxopyr-rolidin-1-yl)oxy)-5-oxopentanoic acid (11, DS-129A 4 mg) in DMSO (50 uL) and diisopropylethylamine (DIPEA, 20 uL). The reaction was stirred at room temperature for 1 hr. Trifluoroacetic acid (TFA, 40 uL) was added to the reaction mixture to precipitate the proinsulin conjugate intermediate (i.e., "single chain insulin intermediate") (SEQ ID NO:24068) (FIG. 9B). The reaction mixture was centrifuged (11000 RPM, 5 min), decanted, and supernatant was resuspended in 100 uL solution of 50 mM acetic acid (pH 4.5), 100 mM NaCl and 30% ACN. Solution was diluted with 500 uL of water then 30 uL of 1M Tris pH 9 (50 mM final concentration), 6 µL of 500 mM CaCl$_2$ (5 mM final concentration) were added. The pH was adjusted with 0.5M NaOH (5-10 uL) to ~9-9.5 and trypsin (1:500 to 1:2000 trypsin mass to insulin mass ~10 uL of 0.2 ug/mL stock solution) and carboxy peptidase (CBP, 1:1000 carboxy peptidase to insulin mass) was added was added. Crude solution was allowed to stir at r.t for 16 hours. The crude conjugated insulin conjugate was precipitated with TFA (~200 uL), centrifuged, decanted. Then crude precipitate was washed with water (2×500 uL) then dissolved in DMSO (100-200 uL), diluted with 20% ACN/Water (5-10 mL), and purified by reverse-phase HPLC. Fractions were collected, frozen, and lyophilized to yield a white powder (5-10 mg) of Example 900 (SEQ ID NO:24069 for the A-chain, SEQ ID NO:24074 for the B-chain) (FIG. 9B).

Similar procedures can be followed for the synthesis of Examples 881 to 915.

D. Testing of Compounds for Activity in Biological Assays

Exemplary compounds DS01-DS152 can be tested using an alizarin red S (ARS) displacement assay. DS01-DS109 were tested using an ARS displacement assay.
Procedure for Determination of the Glucose, Fructose, and Lactate Binding (Kd) Using ARS Displacement Assay The association constant for the binding event between ARS and the exemplary compounds tested was determined using standard methods in the art. Triplicate titrations of 10$^{-5}$ M ARS in 0.1 M phosphate buffer, pH 7.4, were performed in a 96-well plate against serial dilutions of example compounds, ranging in concentration from 0-0.1M at 25° C. The example compound-ARS solution was incubated for 5-45 minutes at 25° C., and fluorescence intensity was measured using excitation wavelength 468 nm and emission wavelength 585 nm. Changes in intensity were plotted against the concentration of the example compound, and the intensity data was fitted to yield an association constant for ARS binding.

The association constant for the binding between a target sugar compound (e.g., glucose) and the tested aromatic boron-containing groups was determined via the displacement of ARS bound to the example compounds. Triplicate wells of 10$^{-5}$ M ARS and 0.1 M example compounds in 0.1 M phosphate buffer, pH 7.4, were titrated in a 96-well plate against serial dilutions of the target sugar compound, ranging in concentration from 0-2.0 M at 25° C. The boron-ARS-carbohydrate solution was incubated for 30-60 minutes at 25° C. and the intensity of each well was measured in a plate reader at excitation wavelength 468 nm and emission wavelength 585 nm.

Changes in intensity were plotted against concentration of the target sugar compound, and the data was fitted to a one-site competition equation:

$$y = \min(y) + (\max(y) - \min(y))/\left(1 + 10^{x - logEC50}\right)$$

to yield an association constant for the boron compound-target sugar compound binding event.

The binding constants of DS compounds, such as DS01-DS152, to glucose, fructose, and/or lactate can be tested and calculated. The binding constants of DS01-DS109 to glucose, fructose, and/or lactate were tested and were calculated, except DS76 was not tested for glucose binding, DS57 and DS75 were not tested for fructose or lactate binding. The tested compounds had Kd values ranging from ~0.8 mM to ~486 mM for glucose, ~0.9 mM to ~52 mM for fructose, and ~24 to ~425 mM for lactate. Some exemplary DS compounds disclosed herein have binding affinity to glucose with a Kd value ranging from about 0.01 mM to about 5 mM. Some exemplary DS compounds disclosed herein have binding affinity to glucose with a Kd value ranging from about 0.5 mM to about 2.5 mM.

In Vitro Demonstration of Activity for Compounds of Formula I

CHO cells constitutively expressing Human Insulin Receptor Isoform B were plated in a 96-well tissue culture microplate at 35,000 cells/well and grown overnight in RPMI media supplemented with Glutamine and 10% Fetal Bovine Serum (growth media). The next morning, growth media was replaced with fresh growth media.

A separate microplate was prepared with a stepwise serial dilution of glucose-responsive insulin in DMEM media, without glucose, without phenol red, with 4% w/v serum albumin; wells of serially diluted compoundsof Formula I were prepared in triplicate with an appropriate "high" and "low" concentration of glucose to determine change in potency of compounds of Formula I at various potential blood glucose levels.

Growth media on cells was then replaced with DMEM media, no glucose, no phenol red for 5 minutes. The media was aspirated and replaced with the contents of the prepared plate (spiking media) for 10 minutes. The spiking media was aspirated and the cells were fixed with 10% neutral buffered formalin for 10 minutes. The neutral buffered formalin was aspirated, and the microplate was stringently washed with PBS, pH 7.4. The microplate was then blocked with PBS, pH 7.4 supplemented with 10% v/v Fetal Bovine Serum and 0.1% Triton X-100 for 30 minutes. The plate was then stained at 4° C. overnight with 5% FBS in PBS+1:680 v:v of Rb α-phospho-Y1150/Y1151 IR antibody (Cell Signaling Technologies #3024). After stringent washes with PBS, pH 7.4, the microplate was incubated at 37° C. in 5% FBS in PBS+1:1000 of 2° Ab, HRP α-Rabbit (Cell Signaling Technologies, #7074) for 100 minutes. The plate was stringently washed with PBS, pH 7.4, and colorimetric readout was developed for 15 minutes at 37° C. using TMB substrate. Color development was stopped with the addition of 0.1 M hydrochloric acid and absorbance measured at 450 nm. Triplicate absorbance values were plotted in GraphPad Prism and analyzed using a four-parameter logistic regression to generate dose-response curves, and the EC50 of the dose-response curves were compared to assess fold activation of the exemplary compounds of Formula I from low to high glucose concentration.

Examples 25A, 28A, 315, 318, 320, 565, 590, 606, 611, and 803-880 had an insulin receptor phosphorylation (IR Phosphorylation) (fold change) ranging from ≥1.2 to 45. Some examples disclosed herein have an insulin receptor phosphorylation (IR Phosphorylation) (fold change) ranging from ≥1.2 to 10. For examples, Examples 25 A and 28A disclosed herein have an insulin receptor phosphorylation (IR Phosphorylation) (fold change) ranging from ≥2 to 8, such as from 2.5 to 6, or 2.8 to 4.

In Vivo Demonstration of Activity for Compounds of Formula I

Diabetes was induced in 12-week-old B6 mice using streptozocin (STZ) treatment. Three weeks after the final STZ treatment, blood glucose of the mice was sampled from lateral tail vein to confirm diabetes. Mice with blood glucose of >200 mg/dl were deemed to be diabetic and fasted for 1-6 hours prior to injection. Human insulin and a compound of Formula I in sterile phosphate buffered saline, pH 7.4 were injected either subcutaneously via neck scruff or intraperitoneally, depending on the experiment. Blood glucose was sampled with a glucometer via lateral tail vein at 15-minute intervals. After one hour of initial stabilization of blood glucose levels post-insulin injection, mice were challenged with an intraperitoneal injection of glucose (e.g., 2 g/kg, 4 g/kg, or 6 g/kg; the actual dose depends on the example and experiment) in sterile phosphate buffered saline. The exemplary compound activated to lower blood glucose upon the introduction of a glucose bolus, while human insulin did not activate in a glucose-dependent manner.

The above experiment showed in vivo preferential activity response of an exemplary compound of the disclosure to glucose.

Streptozotocin-treated mice (55 mg/kg, 5 days) undergo surgical catheterization of a carotid artery and jugular vein for blood sampling and infusions. After a recovery period of 3-4 days, mice are placed in an experimental chamber, connected to sampling/infusion lines, and briefly fasted. Somatostatin (5 mg/kg/min) is continuously infused throughout the study. At time 0 min, biosynthetic human insulin (BHI) or a compound of Formula I are infused at 4 mU/kg/min and glucose is infused at variable rates to achieve steady state ("clamped") at pre-determined glycemic levels. Blood glucose (BG) is clamped in windows of stepwise increasing blood glucose concentration. Steady-state Glucose Infusion Rate (GIR) is measured for each step increase in clamped blood glucose and plotted to assess the increase in GIR as a function of increasing blood glucose. As BG increases, compounds of Formula I require greater GIR to maintain clamped BG than does BHI, demonstrating a glucose-responsive increase in compound glucose-lowering action with increased BG concentrations.

It is also observed in cell-based experiments on compounds containing formulae FF50-FF62, FF116, and FF121-FF134 that sensors with geminal alkyl substituent on the same carbon as the nitrogen conjugated to the boroxole or boronates provided between 5-56% higher glucose responsiveness in the range of 3-20 mM glucose in comparison to variants that do not have the geminal alkyl substituents. For example, when a Z C represented by one of formulae FF50-FF62, FF116, and FF121-134 is conjugated to lysine residues in insulin wherein the boronates (B1,B2) in formulae FF50-FF62, FF116, and FF121-134 are represented by F2, the resulting insulin is observed to be between 11-56% more responsive to changes in glucose levels between 3-20 mM glucose than if instead of one of formulae FF50-FF62, FF116, and FF121-134, one uses 2,3-diaminopropionic acid. This data shows that the presence of the geminal alkyl substituent on the same carbon as the nitrogen conjugated to the boroxole or boronates improves glucose responsiveness of the resulting insulin conjugate, and in tested variations in the 3-20 mM glucose range. Without wishing to be bound by theory, it is believed that this general principle extends to other formulae FF50-FF62, FF116, and FF121-FF134 providing a framework for enhancement of glucose responsiveness by at least 5%, at least 10%, at least 20%, or at least 40% in the 3-20 mM or 2-50 mM glucose ranges. Without wishing to be bound by theory, it is believed based on observations of glucose responsiveness trends, that the presence of the carbonyl group adjacent to- or within less than two carbon centers away from the amine groups in FF formulae (to which aromatic boron-containing groups are conjugated) enhances glucose responsiveness through impacting ability to turn off activity of drug substance through plasma protein interactions such as with albumin and that this is independent of glucose affinity such that glucose affinity is not impacted by the position of this carbonyl group. Without wishing to be bound by theory, it is believed that the pharmacokinetics of the molecules and potential albumin or blood proteins binding is impacted by the position of this carbonyl group, and thereby enhances overall glucose responsiveness whilst the absolute glucose affinity is maintained or nearly identical. Therefore, in certain embodiments of the present invention, the carbonyl group (as part of an acid, amid or linkage to X in FF formulae) is placed within less than three-, or within less than two-carbon center away from one of the two amines to which the boron-containing compounds are conjugated. In certain embodiments, the placement of amines within two carbon centers from each other enables the spatial and geometric constraining of the aromatic boron containing groups to enhance glucose binding and selectively, and furthermore the presence of a carbonyl group (for example, as part of an amide linkage) which is within less than two carbon centers, from one of the two amines (to which aromatic boron containing groups are attached) ensures differential albumin binding in a manner that results in the compound exhibiting glucose responsiveness in the blood and in the body. In some embodiments, the combination of geometrical constraining of the two amines to which the aromatic boron containing groups are conjugated, as well as the presence of the carbonyl within one to two carbon centers from one of the amines provides the necessary requirements for glucose responsiveness in physiological blood and plasma glucose levels. Experiments on cell-based assays of insulins with lysines conjugated with one of formulae FF50-FF62, FF116, and FF121-134 demonstrated that the enhanced glucose responsiveness of the insulins is increased when one or more lysines are modified as described by Formula I using one of formulae FF50-FF62, FF116, and FF121-134, and wherein the lysines are present in insulin (as insertions or mutations) or in a polypeptide that is appended to the N- or C-terminus of the B-chain of insulin or the C-terminus of the A-chain of insulin, and wherein there are additional lysine residues within the insulin sequence that are similarly modified. The results are further corroborated by testing of the compounds of Formula I in STZ diabetic mouse models wherein the activity of the insulin is measured through bolus injections of the compounds of Formula I followed by glucose challenges and measurements of blood glucose, or through glucose clamp assays in which activity of the insulins is measured as a function of blood glucose levels. The results further showed that exemplary compounds of Formula I disclosed herein function in the body and are responsive to physiological changes in blood glucose and provide dynamic insulin action in the body in response to changes in blood glucose levels.

E. Preparation of Aromatic Boron-Containing Compounds

The disclosed compounds can be prepared according to the following schemes. The following schemes represent the general methods used in preparing these compounds. However, the synthesis of these compounds is not limited to these representative methods, as they can also be prepared through various other methods by those skilled in the art of synthetic chemistry.

DSL Synthesis Method 1:

2-Chlorotrityl resin 1 (300 mg, 0.3 mmol) was swelled in dry DCM (5 mL) for 30 mins. Solvent was removed with nitrogen and a solution of 3-((((9H-fluoren-9-yl)methoxy) carbonyl) amino)propanoic acid 2 (94 mg, 0.3 mmol) in DCM with DIEA (0.3 mL, 1.7 mmol) was added immediately and gently mixed for overnight. The mixture was washed with DCM and unreacted sites were capped with a solution of 20% MeOH in a solution of DCM and DIEA (1M) and mixed for 1 hr to yield 3. The resin was washed with DCM (3×5 mL) then DMF (3×5 mL) and treated with 20% piperidine in DMF for 5 minutes (3×5 mL), washed with DMF (4×5 mL). Solution of $N^2$-(((9H-fluoren-9-yl) methoxy)carbonyl)-$N^6$-((allyloxy)carbonyl)-L-lysine 4 (0.181 g, 0.4 mmol), DIEA (0.14 ml, 0.8 mmol) and HATU (0.152 g, 0.4 mmol) in DMF (5 mL) was added to the resin and heated at 50° C. for 30 min, washed with DMF (4×5 mL) to obtain 5 followed by treatment with 20% piperidine in DMF for 5 minutes (3×5 mL) and washed with DMF (4×5 mL). Solution of (2S,4R)-1-(((9H-fluoren-9-yl)methoxy) carbonyl)-4-((((9H-fluoren-9-yl)methoxy)carbonyl)amino) pyrrolidine-2-carboxylic acid, 6 (0.229 g, 0.4 mmol), DIEA (0.14 ml, 0.8 mmol) and HATU (0.152 g, 0.4 mmol) in DMF (5 mL) was added to the resin and heated at 50° C. for 30 min, washed with DMF (4×5 mL) to obtain 7. Resin was treated with 20% piperidine in DMF for 5 minutes (3×5 mL) and washed with DMF (4×5 mL). Solution of 1-hydroxy-3H-2,1-benzoxaborole-6-carboxylic acid 8 (0.178 g, 1 mmol), HATU (0.380 g, 1 mmol) and DIEA (0.35 mL, 2 mmol) were added to the resin and heated at 50° C. for 30 min to get 9. The resin was washed with DMF (4×5 mL) and DCM (3×5 mL) and treated with Tetrakis(triphenylphosphine)palladium (20 mol %, 46 mg) and phenylsilane (493 ul, 4 mmol) in 6 mL DCM was agitated at room temperature for 1 h and washed with DCM (3×5 mL) and DMF (3×5 mL). Solution of hexanoic acid 10 (50 ul, 0.4 mmol), DIEA (0.14 ml, 0.8 mmol) and HATU (0.152 g, 0.4 mmol) in DMF (5 mL) was added to the resin and heated at 50° C. for 30 min, washed with DMF (4×5 mL) to obtain 11.

Cleavage of Diboronated Sensor from Resin

Compound 11 on resin was treated with 20% 1,1,1,3,3,3-Hexafluoro-2-propanol (HFIP) in DCM (7 mL) and gently mixed for 1 hr. The resin was filtered, and filtrate was evaporated under reduced pressure. Residue was further suspended with DCM (2×5 mL) and evaporated to yield diboronated sensor acid DSL-2A which was used in the next step without purification.

Figure 13:
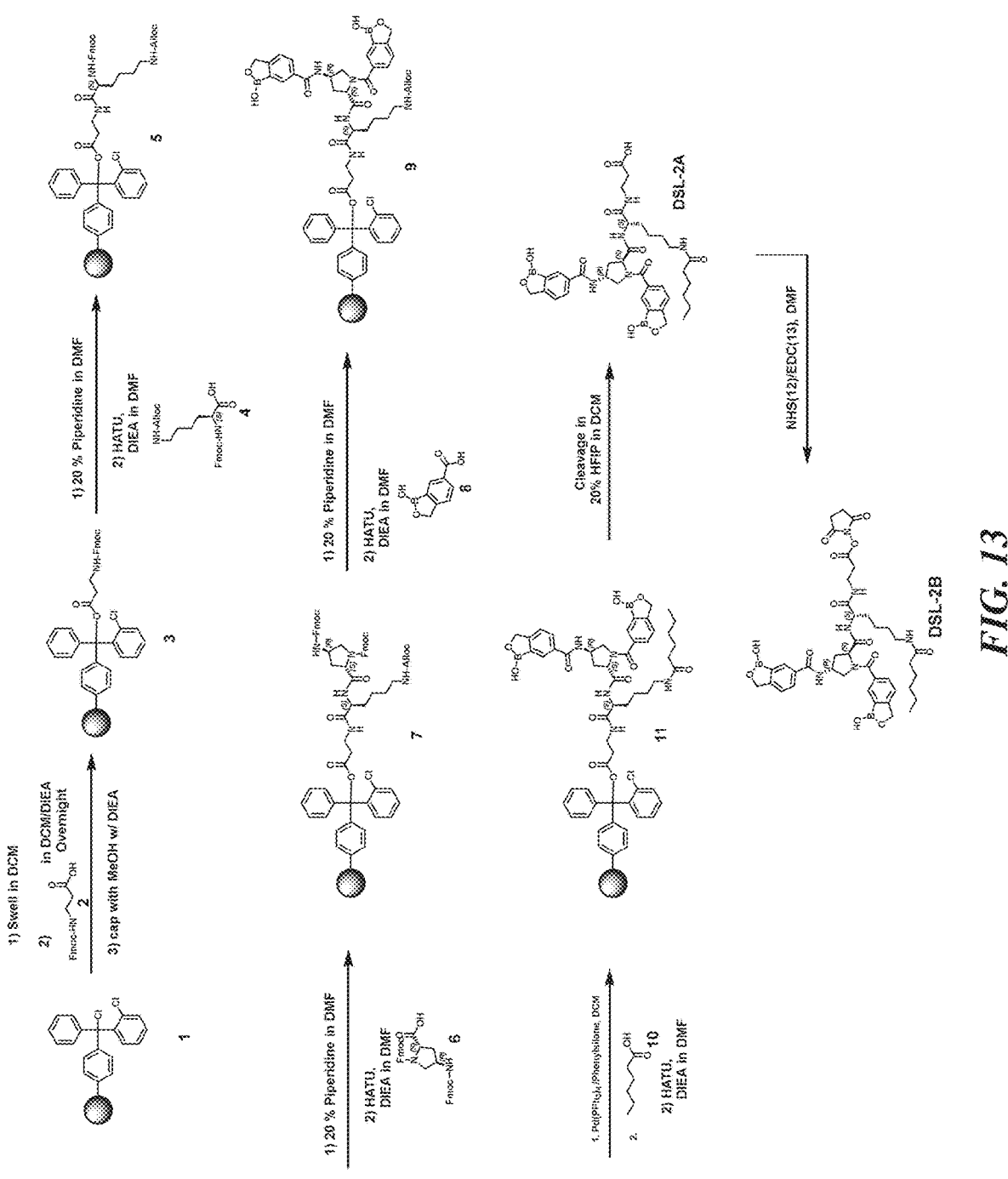

1b: NHS-Activation of Diboronated Sensor:

Crude diboronated sensor acid DSL-2A was dissolved in DMF (2 mL) and treated with 3(3-Dimethylaminopropyl)-1-ethyl-carbodiimide hydrochloride 13 (EDC) (0.096 g, 0.5 mmol), N-hydroxysuccinimide 12 (NHS) (0.115 g, 1 mmol), and stirred for overnight. Progress of the reaction was monitored by LCMS. After completion of the reaction, reaction mixture was diluted with ethyl acetate (20 mL) and washed with 100 mmol HCl (10 mL). The organic layer was dried over anhydrous $Na_2SO_4$ and evaporated under vacuum, dissolved in DMSO (100 uL) and fractionated by reverse-phase (RP) flash chromatography on a C18 column with a gradient of 20% ACN in water with 0.1% TFA to 60% ACN in water with 0.1% TFA over 10 minutes and analyzed by LCMS. Pure fractions were isolated, combined, frozen, and lyophilized to give 2,5-dioxopyrrolidin-1-yl 3-((S)-6-hexanamido-2-((2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxamido)hexanamido)propanoate DSL-2B in ~50% yield (126 mg). Calculated mass (M+H)$^+$=845.37 Da, Observed mass (M+H)$^+$=845.17 Da. The foregoing synthesis is illustrated in FIG. 13.

Examples DSL-4B, DSL-5B, DSL-17B, DSL-18B, DSL-30B-DSL-39B, DSL-41B-DSL-44B, DSL-46B, DSL-55B, DSL-66B, and DSL-115B listed in Table I below were synthesized under similar conditions.

DSL-1B, DSL-6B, DSL-7B, DSL-15B, DSL-16B, DSL-19B-DSL-21B, DSL-29B, DSL-40B, DSL-50B-DSL-54B, DSL-56B- DSL-65B, DSL-67B, DSL-150B, DSL-151B, DSL-153B, DSL-161B, DSL-163B, DSL-171B, and DSL-172B can be synthesized under similar conditions.

TABLE I

| DSL-B Examples | Mass Calculated [M + H]$^{+1}$ | Mass Observed [M + H]$^{+1}$ |
| --- | --- | --- |
| DSL-4B | 901.43 | 901.21 |
| DSL-5B | 929.47 | 929.26 |
| DSL-6B | 957.49 | 957.22 |
| DSL-7B | 985.52 | 985.24 |
| DSL16B | 901.42 | 901.25 |
| DSL-17B | 929.47 | 929.25 |
| DSL-18B | 957.50 | 957.33 |
| DSL-26B | 1015.49 | 1015.55 |
| DSL-30B | 921.40 | 921.42 |
| DSL-31B | 935.42 | 935.42 |
| DSL-32B | 851.32 | 851.20 |
| DSL-33B | 879.36 | 879.08 |
| DSL-34B | 879.35 | 879.25 |
| DSL-35B | 893.37 | 893.25 |
| DSL-36B | 893.36 | 893.36 |
| DSL-37B | 947.34 | 947.17 |
| DSL-38B | 923.37 | 923.37 |
| DSL-39B | 897.35 | 897.33 |
| DSL-40B | 897.34 | 897.33 |
| DSL-41B | 907.38 | 907.38 |
| DSL-42B | 915.34 | 915.08 |
| DSL-43B | 1301.07 | 1301.05 |
| DSL-44B | 1059.29 | 1059.10 |
| DSL-46B | 907.34 | 907.20 |
| DSL-53B | 907.38 | 907.42 |
| DSL-55B | 935.42 | 935.33 |
| DSL-58B | 1003.40 | 1003.47 |
| DSL-60B | 953.40 | 953.46 |
| DSL-63B | 971.39 | 971.47 |
| DSL-66B | 1080.48 | 1080.25 |
| DSL-115B | 907.39 | 907.25 |

DSL Synthesis Method 2:

2-Chlorotrityl resin 1 (300 mg, 0.3 mmol) was swelled in dry DCM (5 mL) for 30 mins. Solvent was removed with nitrogen and a solution of 3-((((9H-fluoren-9-yl)methoxy)carbonyl)amino) propanoic acid 2 (94 mg, 0.3 mmol) in DCM with DIEA (0.3 mL, 1.7 mmol) was added immediately and gently mixed for overnight. The mixture was washed with DCM and unreacted sites were capped with a solution of 20% MeOH in a solution of DCM and DIEA (1M) and mixed for 1 hr to yield 3. The resin was washed with DCM (3×5 mL) then DMF (3×5 mL) and treated with 20% piperidine in DMF for 5 minutes (3×5 ML), washed with DMF (4×5 mL). Solution of N$^2$-(((9H-fluoren-9-yl)methoxy)carbonyl)-N$^6$-((allyloxy)carbonyl)-L-lysine 4 (0.181 g, 0.4 mmol), DIEA (0.14 ml, 0.8 mmol) and HATU (0.152 g, 0.4 mmol) in DMF (5 mL) was added to the resin and heated at 50° C. for 30 min, washed with DMF (4×5 mL) to obtain 5 followed by treatment with 20% piperidine in DMF for 5 minutes (3×5 mL) and washed with DMF (4×5 mL). Solution of (2S,4R)-1-(((9H-fluoren-9-yl)methoxy)carbonyl)-4-((((9H-fluoren-9-yl)methoxy)carbonyl)amino) pyrrolidine-2-carboxylic acid, 6 (0.229 g, 0.4 mmol), DIEA (0.14 ml, 0.8 mmol) and HATU (0.152 g, 0.4 mmol) in DMF (5 mL) was added to the resin and heated at 50° C. for 30 min, washed with DMF (4×5 mL) to obtain 7. Resin was treated with 20% piperidine in DMF for 5 minutes (3×5 mL) and washed with DMF (4×5 mL). Solution of 1-hydroxy-3H-2,1-benzoxaborole-6-carboxylic acid 8 (0.178 g, 1 mmol), HATU (0.380 g, 1 mmol) and DIEA (0.35 mL, 2 mmol) were added to the resin and heated at 50° C. for 30 min to get 9. The resin was washed with DMF (4×5 mL) and DCM (3×5 mL) and treated with Tetrakis(triphenylphosphine)palladium (20 mol %, 46 mg) and phenylsilane (493 ul, 4 mmol) in 6 mL DCM was agitated at room temperature for 1 h and washed with DCM (3×5 mL) and DMF (3×5 mL). Solution of 6-(tert-butoxy)-6-oxohexanoic acid 14 (77 ul, 0.4 mmol), DIEA (0.14 ml, 0.8 mmol) and HATU (0.152 g, 0.4 mmol) in DMF (5 mL) was added to the resin and heated at 50° C. for 30 min, washed with DMF (4×5 mL) to obtain 15.

Cleavage of Diboronated Sensor from Resin

Compound 15 on resin was treated with 20% 1,1,1,3,3,3-Hexafluoro-2-propanol (HFIP) in DCM (7 mL) and gently mixed for 1 hr. The resin was filtered, and filtrate was evaporated under reduced pressure. Residue was further suspended with DCM (2×5 mL) and evaporated to yield diboronated sensor acid DSL-9A which was used in the next step without purification.

Figure 14:
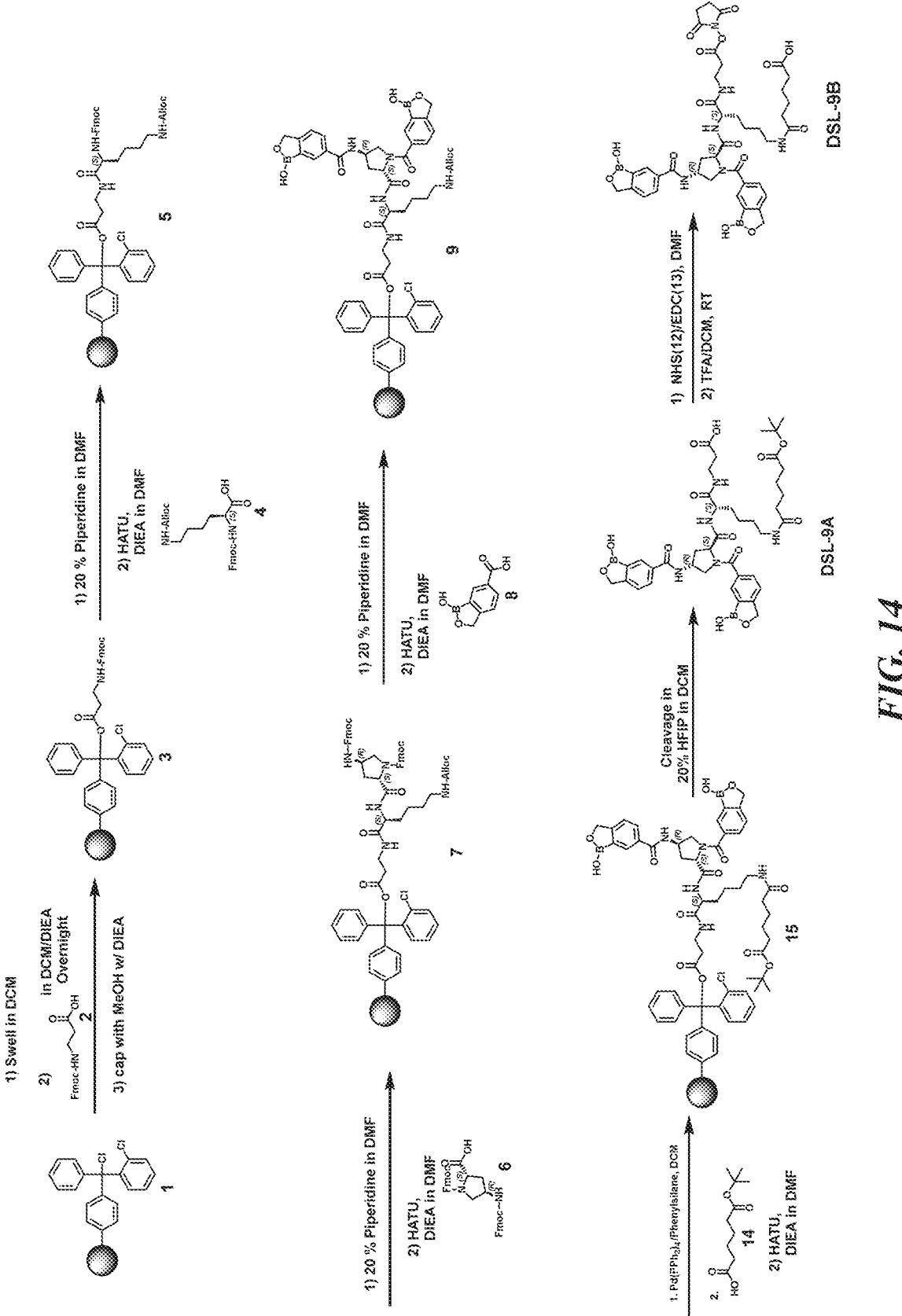

2b: NHS-Activation of Diboronated Sensor:

Crude diboronated sensor acid DSL-9A was dissolved in DMF (2 mL) and treated with 3-(3-Dimethylaminopropyl)-1-ethyl-carbodiimide hydrochloride 13 (EDC) (0.096 g, 0.5 mmol), N-hydroxysuccinimide 12 (NHS) (0.115 g, 1 mmol), and stirred for overnight. Progress of the reaction was monitored by LCMS. After completion of the reaction, reaction mixture was diluted with ethyl acetate (20 mL) and washed with 100 mmol HCl (10 mL). The organic layer was dried over anhydrous Na$_2$SO$_4$ and evaporated under vacuum. The tert-butyl protecting group was removed with TFA in DCM (50%), allowed to mix for 1 hour, solvent was evaporated under vacuum then dissolved in DMSO (100 uL) and fractionated by reverse-phase (RP) flash chromatography on a C18 column with a gradient of 20% ACN in water with 0.1% TFA to 60% ACN in water with 0.1% TFA over 10 minutes and analyzed by LCMS. Pure fractions were isolated, combined, frozen, and lyophilized to give 6-(((S)-6-((3-((2,5-dioxopyrrolidin-1-yl)oxy)-3-oxopropyl)amino)-5-((2S,4R)-1-(1-hydroxy-1,3-dihydrobenzo[c][1,2]oxaborole-6-carbonyl)-4-(1-hydroxy-1,3-dihydrobenzo[c][1,2] oxaborole-6-carboxamido)pyrrolidine-2-carboxamido)-6-oxohexyl)amino)-6-oxohexanoic acid DSL-9B in ~45% yield (118 mg). Calculated mass (M+H)$^+$=875.35 Da, Observed mass (M+H)$^+$=874.88 Da. The foregoing synthesis is illustrated in FIG. 14.

Examples DSL-10B-DSL-14B, DSL-23B-DSL-27B, DSL-45B, DSL-47B, DSL-68B, DSL-69B, DSL-117B, and DSL-136B listed in Table II below were synthesized under similar conditions.

DSL-8B, DSL-22B, DSL-26B-DSL-28B, DSL-48B, DSL-49B, DSL-70B, DSL-138B, DSL-152B, DSL-154B, DSL-162B, DSL-165B, DSL-169B, and DSL-170B can be synthesized using similar conditions.

TABLE II

| DSL-B Examples | Mass Calculated [M + H]$^{+1}$ | Mass Observed [M + H]$^{+1}$ |
|---|---|---|
| DSL-10B | 903.38 | 902.86 |
| DSL-11B | 931.41 | 930.88 |
| DSL-12B | 959.44 | 958.98 |
| DSL-13B | 987.47 | 987.05 |
| DSL-14B | 1015.50 | 1015.03 |
| DSL-23B | 931.41 | 931.00 |
| DSL-24B | 959.44 | 958.92 |
| DSL-25B | 987.47 | 987.00 |
| DSL-45B | 1035.42 | 1035.22 |
| DSL-47B | 979.41 | 961.33 |
| DSL-68B | 951.38 | 951.17 |
| DSL-69B | 979.41 | 979.08 |
| DSL-117B | 951.38 | 951.17 |
| DSL-136B | 951.38 | 951.00 |

DSL Synthesis Method 3:

2-Chlorotrityl resin 1 (300 mg, 0.3 mmol) was swelled in dry DCM (5 mL) for 30 mins. Solvent was removed with nitrogen and a solution of (S)-4-((((9H-fluoren-9-yl)methoxy)carbonyl) amino)-5-(tert-butoxy)-5-oxopentanoic acid 16 (127 mg, 0.3 mmol) in DCM with DIEA (0.3 mL, 1.7 mmol) was added immediately and gently mixed for overnight. The mixture was washed with DCM and unreacted sites were capped with a solution of 20% MeOH in a solution of DCM and DIEA (1M) and mixed for 1 hr to yield 17. The resin was washed with DCM (3×5 mL) then DMF (3×5 mL) and treated with 20% piperidine in DMF for 5 minutes (3×5 mL), washed with DMF (4×5 mL). Solution of N$^2$-(((9H-fluoren-9-yl)methoxy)carbonyl)-N$^6$-((allyloxy)carbonyl)-L-lysine 4 (0.181 g, 0.4 mmol), DIEA (0.14 ml, 0.8 mmol) and HATU (0.152 g, 0.4 mmol) in DMF (5 mL) was added to the resin and heated at 50° C. for 30 min, washed with DMF (4×5 mL) to obtain 18 followed by treatment with 20% piperidine in DMF for 5 minutes (3×5 mL) and washed with DMF (4×5 mL). Solution of (2S,4R)-1-(((9H-fluoren-9-yl)methoxy)carbonyl)-4-((((9H-fluoren-9-yl)methoxy)carbonyl)amino)pyrrolidine-2-carboxylic acid, 6 (0.229 g, 0.4 mmol), DIEA (0.14 ml, 0.8 mmol) and HATU (0.152 g, 0.4 mmol) in DMF (5 mL) was added to the resin and heated at 50° C. for 30 min, washed with DMF (4×5 mL) to obtain 19. Resin was treated with 20% piperidine in DMF for 5 minutes (3×5 mL) and washed with DMF (4×5 mL). Solution of 1-hydroxy-3H-2,1-benzoxaborole-6-carboxylic acid 8 (0.178 g, 1 mmol), HATU (0.380 g, 1 mmol) and DIEA (0.35 mL, 2 mmol) were added to the resin and heated at 50° C. for 30 min to get 20. The resin was washed with DMF (4×5 mL) and DCM (3×5 mL) and treated with Tetrakis(triphenylphosphine)palladium (20 mol %, 46 mg) and phenylsilane (493 ul, 4 mmol) in 6 mL DCM was agitated at room temperature for 1 h and washed with DCM (3×5 mL) and DMF (3×5 mL). Solution of 12-(tert-butoxy)-12-oxododecanoic acid 21 (114 mg, 0.4 mmol), DIEA (0.14 ml, 0.8 mmol) and HATU (0.152 g, 0.4 mmol) in DMF (5 mL) was added to the resin and heated at 50° C. for 30 min, washed with DMF (4×5 mL) to obtain 22.

Cleavage of Diboronated Sensor from Resin

Compound 22 on resin was treated with 20% 1,1,1,3,3,3-Hexafluoro-2-propanol (HFIP) in DCM (7 mL) and gently mixed for 1 hr. The resin was filtered, and filtrate was evaporated under reduced pressure. Residue was further suspended with DCM (2×5 mL) and evaporated to yield diboronated sensor acid DSL-82A which was used in the next step without purification.

Figure 15:
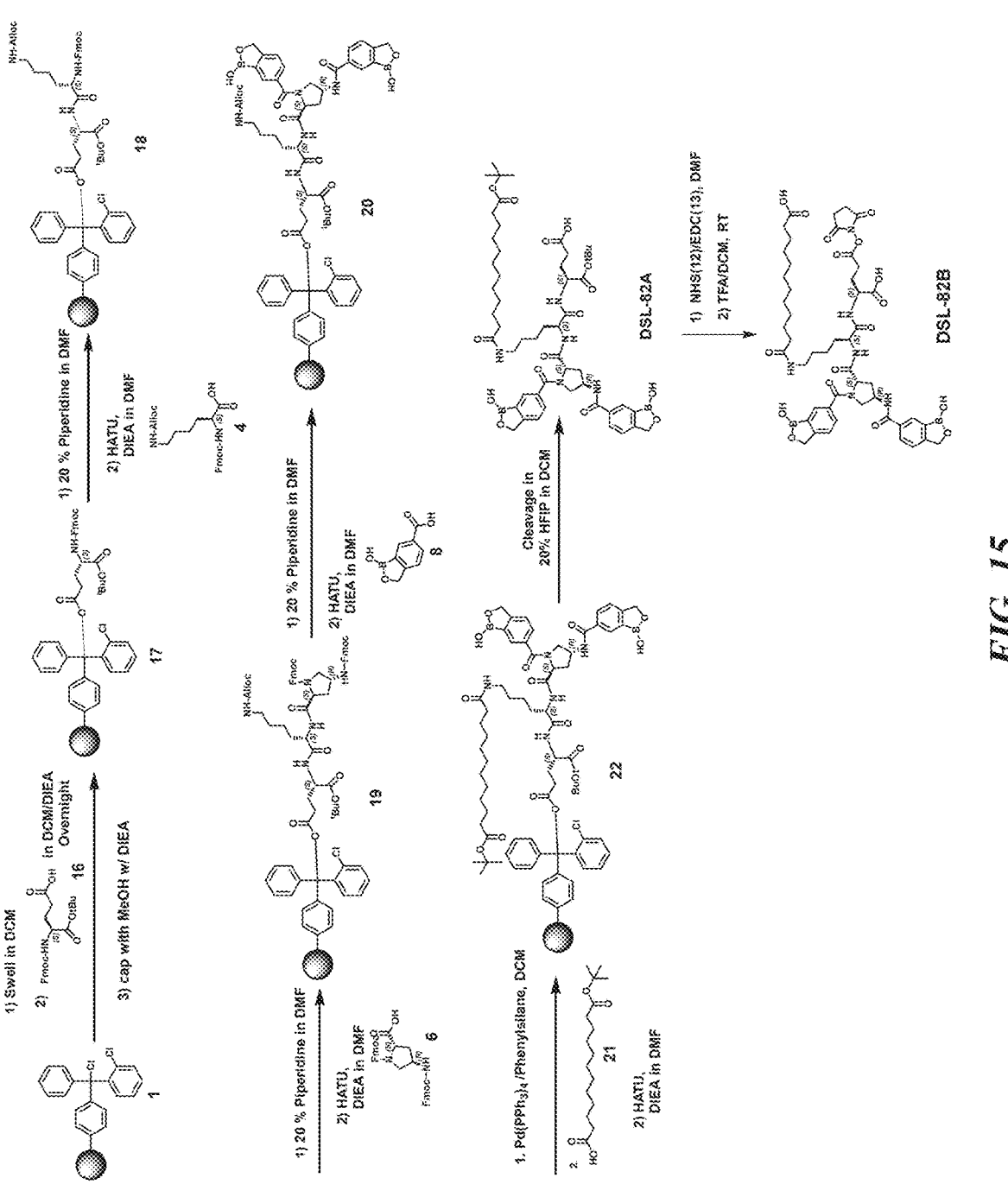

3b: NHS-Activation of Diboronated Sensor:

Crude diboronated sensor acid DSL-82A was dissolved in DMF (2 mL) and treated with 3-(3-Dimethylaminopropyl)-1-ethyl-carbodiimide hydrochloride 13 (EDC) (0.096 g, 0.5 mmol), N-hydroxysuccinimide 12 (NHS) (0.115 g, 1 mmol), and gently mixed for overnight. Progress of the reaction was monitored by LCMS. After completion of the reaction, reaction mixture was diluted with ethyl acetate (20 mL) and washed with 100 mmol HCl (10 mL). The organic layer was dried over anhydrous Na$_2$SO$_4$ and evaporated under vacuum. The tert-butyl protecting group was removed with TFA in DCM (50%), allowed to mix for 1 hour, solvent was evaporated under vacuum then dissolved in DMSO (100 uL) and fractionated by reverse-phase (RP) flash chromatography on a C18 column with a gradient of 20% ACN in water with 0.1% TFA to 60% ACN in water with 0.1% TFA over 10 minutes and analyzed by LCMS. Pure fractions were isolated, combined, frozen, and lyophilized to give 12-(((S)-6-(((S)-1-carboxy-4-((2,5-dioxopyrrolidin-1-yl)oxy)-4-oxobutyl)amino)-5-((2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxamido)-6-oxohexyl)amino)-12-oxododecanoic acid DSL-82B in ~55% yield (167 mg). Calculated mass (M+H)$^+$=1017.45 Da, Observed mass (M+H)$^+$=1017.00 Da. The foregoing synthesis is illustrated in FIG. 15.

Examples DSL-94B and DSL-125B listed in Table III below were synthesized under similar conditions.

DSL-71B-DSL-81B, DSL-83B-DSL-93B, DSL-95B-DSL-114B, DSL-116B, DSL-118B-DSL-124B, DSL-126B-DSL-135B, DSL-137B, DSL-139B, DSL-140B, and DSL-141B can be synthesized under similar conditions.

TABLE III

| DSL-B Examples | Mass Calculated [M + H]$^{+1}$ | Mass Observed [M + H]$^{+1}$ |
|---|---|---|
| DSL-94B | 1017.45 | 1017.00 |
| DSL-125B | 993.42 | 993.17 |
| DSL-141B | 675.26 | 675.17 |
| DSL-142B | 663.26 | 663.17 |

DSL Synthesis Method 4:

2-Chlorotrityl resin 1 (300 mg, 0.3 mmol) was swelled in dry DCM (5 mL) for 30 mins. Solvent was removed with nitrogen and a solution of (S)-3-((((9H-fluoren-9-yl)methoxy)carbonyl)amino)-5-phenylpentanoic acid 23 (124 mg, 0.3 mmol) in DCM with DIEA (0.3 mL, 1.7 mmol) was added immediately and gently mixed for overnight. The mixture was washed with DCM and unreacted sites were capped with a solution of 20% MeOH in a solution of DCM and DIEA (1 M) and mixed for 1 hr to yield 24. The resin was washed with DCM (3×5 mL) then DMF (3×5 mL) and treated with 20% piperidine in DMF for 5 minutes (3×5 mL), washed with DMF (4×5 mL). Solution of (2S,4R)-1-(((9H-fluoren-9-yl)methoxy)carbonyl)-4-((((9H-fluoren-9-yl)methoxy)carbonyl)amino)pyrrolidine-2-carboxylic acid, 6 (0.229 g, 0.4 mmol), DIEA (0.14 ml, 0.8 mmol) and HATU (0.152 g, 0.4 mmol) in DMF (5 mL) was added to the resin and heated at 50° C. for 30 min, washed with DMF (4×5 mL) to obtain 25. Resin was treated with 20% piperidine in DMF for 5 minutes (3×5 mL) and washed with DMF (4×5 mL). Solution of 1-hydroxy-3,3-dimethyl-1,3-dihydrobenzo[c][1,2]oxaborole-6-carboxylic acid 26 (0.206 g, 1 mmol), HATU (0.380 g, 1 mmol) and DIEA (0.35 mL, 2 mmol) were added to the resin and heated at 50° C. for 30 min to get 27. The resin was washed with DMF (4×5 mL) and DCM (3×5 mL).

Cleavage of Diboronated Sensor from Resin

Compound 27 on resin was treated with 20% 1,1,1,3,3, 3-Hexafluoro-2-propanol (HFIP) in DCM (7 mL) and gently mixed for 1 hr. The resin was filtered, and filtrate was evaporated under reduced pressure. Residue was further suspended with DCM (2×5 mL) and evaporated to yield diboronated sensor acid DSL-143A which was used in the next step without purification.

4b: NHS-Activation of Diboronated Sensor:

Crude diboronated sensor acid DSL-143A was dissolved in DMF (2 mL) and treated with 3-(3-Dimethylaminopropyl)-1-ethyl-carbodiimide hydrochloride 13 (EDC) (0.096 g, 0.5 mmol), N-hydroxysuccinimide 12 (NHS) (0.115 g, 1 mmol), and stirred for overnight. Progress of the reaction was monitored by LCMS. After completion of the reaction, reaction mixture was diluted with ethyl acetate (20 mL) and washed with 100 mmol HCl (10 mL). The organic layer was dried over anhydrous $Na_2SO_4$ and evaporated under vacuum, dissolved in DMSO (100 uL) and fractionated by reverse-phase (RP) flash chromatography on a C18 column with a gradient of 20% ACN in water with 0.1% TFA to 60% ACN in water with 0.1% TFA over 10 minutes and analyzed by LCMS. Pure fractions were isolated, combined, frozen, and lyophilized to give 2,5-dioxopyrrolidin-1-yl (S)-3-((2S, 4R)-1-(1-hydroxy-3,3-dimethyl-1,3-dihydrobenzo[c][1,2]oxaborole-6-carbonyl)-4-(1-hydroxy-3,3-dimethyl-1,3-di-hydrobenzo[c][1,2]oxaborole-6-carboxamido)pyrrolidine-2-carboxamido)-5-phenylpentanoate DSL-143B in ~30% yield (23.3 mg). Calculated mass $(M+H)^+=779.33$ Da, Observed mass $(M+H)^+=779.25$ Da.

Figure 16:
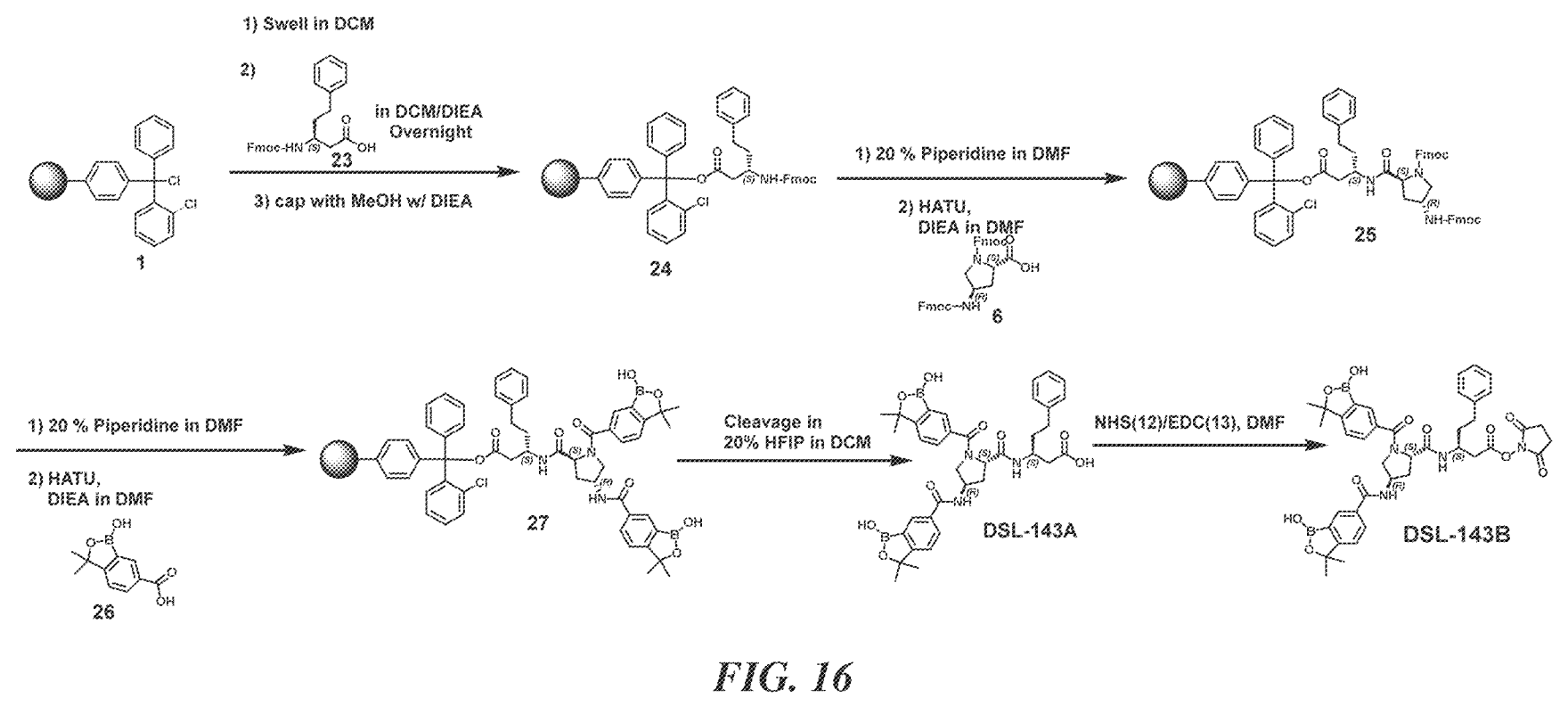

Example DSL-147B can be synthesized under similar conditions. The foregoing synthesis is illustrated in FIG. 16. DSL Synthesis Method 5:

2-Chlorotrityl resin 1 (300 mg, 0.3 mmol) was swelled in dry DCM (5 mL) for 30 mins. Solvent was removed with nitrogen and a solution of 3-((((9H-fluoren-9-yl)methoxy) carbonyl) amino)propanoic acid 2 (94 mg, 0.3 mmol) in DCM with DIEA (0.3 mL, 1.7 mmol) was added immediately and gently mixed for overnight. The mixture was washed with DCM and unreacted sites were capped with a solution of 20% MeOH in a solution of DCM and DIEA (1M) and mixed for 1 hr to yield 3. The resin was washed with DCM (3×5 mL) then DMF (3×5 mL) and treated with 20% piperidine in DMF for 5 minutes (3×5 mL), washed with DMF (4×5 mL). Solution of (2S,4R)-1-(((9H-fluoren-9-yl)methoxy)carbonyl)-4-((((9H-fluoren-9-yl)methoxy) carbonyl)amino)pyrrolidine-2-carboxylic acid, 6 (0.229 g, 0.4 mmol), DIEA (0.14 ml, 0.8 mmol) and HATU (0.152 g, 0.4 mmol) in DMF (5 mL) was added to the resin and heated at 50° C. for 30 min, washed with DMF (4×5 mL) to obtain 28. Resin was treated with 20% piperidine in DMF for 5 minutes (3×5 mL) and washed with DMF (4×5 mL). Solution of 1-hydroxy-1,3-dihydrobenzo[c][1,2]oxaborole-7-carboxylic acid 29 (0.178 g, 1 mmol), HATU (0.380 g, 1 mmol) and DIEA (0.35 mL, 2 mmol) were added to the resin and heated at 50° C. for 30 min to get 30. The resin was washed with DMF (4×5 mL) and DCM (3×5 mL).

Cleavage of Diboronated Sensor from Resin

Compound 30 on resin was treated with 20% 1,1,1,3,3, 3-Hexafluoro-2-propanol (HFIP) in DCM (7 mL) and gently mixed for 1 hr. The resin was filtered; and filtrate was evaporated under reduced pressure. Residue was further suspended with DCM (2×5 mL) and evaporated to yield diboronated sensor acid DSL-155A which was used in the next step without purification.

5b: NHS-Activation of Diboronated Sensor:

Crude diboronated sensor acid DSL-155A was dissolved in DMF (2 mL) and treated with 3-(3-Dimethylaminopropyl)-1-ethyl-carbodiimide hydrochloride 13 (EDC) (0.096 g, 0.5 mmol), N-hydroxysuccinimide 12 (NHS) (0.115 g, 1 mmol), and stirred for overnight. Progress of the reaction was monitored by LCMS. After completion of the reaction, reaction mixture was diluted with ethyl acetate (20 mL) and washed with 100 mmol HCl (10 mL). The organic layer was dried over anhydrous $Na_2SO_4$ and evaporated under vacuum, dissolved in DMSO (100 uL) and fractionated by reverse-phase (RP) flash chromatography on a C18 column with a gradient of 20% ACN in water with 0.1% TFA to 60% ACN in water with 0.1% TFA over 10 minutes and analyzed by LCMS. Pure fractions were isolated, combined, frozen, and lyophilized to give 2,5-dioxopyrrolidin-1-yl 3-((2S,4R)-1-(1-hydroxy-1,3-dihydrobenzo[c][1,2]oxaborole-7-carbonyl)-4-(1-hydroxy-1,3-dihydrobenzo[c][1,2]oxaborole-7-carboxamido)pyrrolidine-2-carboxamido)propanoate DSL-155B in ~20% yield (37 mg). Calculated mass $(M+H)^+$ =619.20 Da, Observed mass $(M+H)^+=619.08$ Da. The foregoing synthesis is illustrated in FIG. 17.

Examples DSL-156B-DSL-162B listed in Table IV below were synthesized under, similar conditions.

DSL-145B-DSL-154B, and DSL-163B-DSL-168B can be synthesized using similar procedure.

TABLE IV

| DSL-B Examples | Mass Calculated $[M + H]^{+1}$ | Mass Observed $[M + H]^{+1}$ |
|---|---|---|
| DSL-156B | 607.20 | 606.92 |
| DSL-157B | 647.24 | 646.75 |
| DSL-158B | 635.24 | 617.08 |
| DSL-159B | 647.24 | 647.17 |
| DSL-160B | 635.24 | 635.08 |
| DSL-161B | 907.39 | 907.17 |
| DSL-162B | 931.41 | 931.17 |

The chemical structure and IUPAC name of DSL-1A to DSL-172A are summarized in Table 1 below.

TABLE 1

| Compound # | FF | F | Z1b | Z1b | A' | A" | Structure/IUPAC |
|---|---|---|---|---|---|---|---|
| DSL-1A | FF12A | F2 | FL3 | FL69A | H | AB-1 | 3-((S)-6-butyramido-2-((2S,4R)-1-(1-hydroxy-1,3-dibydrobenzo[c][1,2]oxaborole-6-carbonyl)-4-(1-hydroxy-1,3-dihydrobenzo[e][1,2]oxaborole-6-carboxamido)pyrrolidine-2-carboxamido)hexanamido)propanoic acid |
| DSL-2A | FF12A | F2 | FL3 | FL69A | H | AB-2 | 3-((S)-6-hexanamido-2-((2S,4R)-1-(1-hydroxy-1,3-dibydrobenzo[c][1,2]oxaborole-6-carbonyl)-4-(1-hydroxy-1,3-dihydrobenzo[c][1,2]oxaborole-6-carboxamido)pyrrolidine-2-carboxamido)hexanamido)propanoic acid |

TABLE 1-continued

| Compound # | FF | F | Z1b | Z1b | A' | A" | Structure/IUPAC |
|---|---|---|---|---|---|---|---|
| DSL-3A | FF116A | F7 | FL3 | | | | ((2S,3S)-2,3-bis(1-hydroxy-3,3-dimethyl-1,3-dibydrobenzo[c][1,2]oxaborole-6-carboxamido)butanoyl)-L-glutamic acid |
| DSL-4A | FF12A | F2 | FL3 | FL69A | H | AB-4 | 3-((S)-6-decanamido-2-((2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxamido)hexanamido)propanoic acid |
| DSL-5A | FF12A | F2 | FL3 | FL69A | H | AB-5 | 3-((S)-6-dodecanamido-2-((2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxamido)hexanamido)propanoic acid |

TABLE 1-continued

| Compound # | FF | F | Z1b | Z1b | A' | A" | Structure/IUPAC |
|---|---|---|---|---|---|---|---|
| DSL-6A | FF12A | F2 | FL3 | FL69A | H | AB-6 | |

3-((S)-2-((2S,4R)-1-(1-hydroxy-1,3-
dihydrobenzo[e][1,2]oxaborole-6-
carbonyl)-4-(1-hydroxy-1,3-
dihydrobenzo[c][1,2]oxaborole-6-
carboxamido)pyrrolidine-2-
carboxamido)-6-
tetradecanamidohexanamido)
propanoic acid

| DSL-7A | FF12A | F2 | FL3 | FL69A | H | AB-7 | |
|---|---|---|---|---|---|---|---|

3-((S)-2-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)-6-
palmitamidohexanamido)propanoic
acid

| DSL-8A | FF12A | F2 | FL3 | FL69A | H | AB-8 | |
|---|---|---|---|---|---|---|---|

4-(((S)-6-((2-carboxyethyl)amino)-5-
((2S,4R)-1-(1-hydroxy-1,3-

TABLE 1-continued

| Compound # | FF | F | Z1b | Z1b | A' | A'' | Structure/IUPAC |
|---|---|---|---|---|---|---|---| dihydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)-6-oxohexyl)amino)-4-
oxobutanoic acid

DSL-9A    FF12A    F2    FL3    FL69A    H    AB-9

6-(((S)-6-((2-carboxyethyl)amino)-5-
((2S,4R)-1-(1-hydroxy-1,3-
dihydrobenzo[e][1,2]oxaborole-6-
carbonyl)-4-(1-hydroxy-1,3-
dihydrobenzo[c][1,2]oxaborole-6-
carboxamido)pyrrolidine-2-
carboxamido)-6-oxohexyl)amino)-6-
oxohexanoic acid

DSL-10A    FF12A    F2    FL3    FL69A    H    AB-10

8-(((S)-6-((2-carboxyethyl)amino)-5-
((2S,4R)-1-(1-hydroxy-1,3-
dihydrobenzo[c][1,2]oxaborole-6-
carbonyl)-4-(1-hydroxy-1,3-

TABLE 1-continued

| Compound # | FF | F | Z1b | Z1b | A' | A'' | Structure/IUPAC |
|---|---|---|---|---|---|---|---| dihydrobenzo[c][1,2]oxaborole-6-
carboxamido)pyrrolidine-2-
carboxamido)-6-oxohexyl)amino)-8-
oxooctanoic acid

| DSL-11A | FF12A | F2 | FL3 | FL69A | H | AB-11 | |

10-(((S)-6-((2-carboxyethyl)amino)-5-
((2S,4R)-1-(1-hydroxy-1,3-
dibydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)-6-oxohexyl)amino)-10-
oxodecanoic acid

| DSL-12A | FF12A | F2 | FL3 | FL69A | H | AB-12 | |

12-(((S)-6-((2-carboxyethyl)amino)-5-
((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)-6-oxohexyl)amino)-12-
oxododecanoic acid

| DSL-13A | FF12A | F2 | FL3 | FL69A | H | AB-13 | |

TABLE 1-continued

| Compound # | FF | F | Z1b | Z1b | A' | A" | Structure/IUPAC |
|---|---|---|---|---|---|---|---|
| | | | | | | | 14-(((S)-6-((2-carboxyethyl)amino)-5-((2S,4R)-1-(1-hydroxy-1,3-dihydrobenzo[e][1,2]oxaborole-6-carbonyl)-4-(1-hydroxy-1,3-dihydrobenzo[c][1,2]oxaborole-6-carboxamido)pyrrolidine-2-carboxamido)-6-oxohexyl)amino)-14-oxotetradecanoic acid |
| DSL-14A | FF12A | F2 | FL3 | FL69A | H | AB-14 | 16-(((S)-6-((2-carboxyethyl)amino)-5-((2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxamido)-6-oxohexyl)amino)-16-oxohexadecanoic acid |
| DSL-15A | FF12A | F7 | FL3 | FL69A | H | AB-1 | 3-((S)-6-butyramido-2-((2S,4R)-1-(1-bydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)hexanamido)propanoic acid |

TABLE 1-continued

| Compound # | FF | F | Z1b | Z1b | A' | A" | Structure/IUPAC |
|---|---|---|---|---|---|---|---|
| DSL-16A | FF12A | F7 | FL3 | FL69A | H | AB-2 | |

3-((S)-6-bexanamido-2-((2S,4R)- 1-(1-bydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)hexanamido)propanoic acid

| DSL-17A | FF12A | F7 | FL3 | FL69A | H | AB-3 | |

3-((S)-2-((2S,4R)-1-(1-hydroxy-3,3-dimethyl-1,3-dihydrobenzo[e][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)-6-octanamidohexanamido)propanoic acid TABLE 1-continued

| Compound # | FF | F | Z1b | Z1b | A' | A" | Structure/IUPAC |
|---|---|---|---|---|---|---|---|
| DSL-18A | FF12A | F7 | FL3 | FL69A | H | AB-4 | |

3-((S)-6-decanamido-2-(2S,4R)-1-(1-
hydroxy-3,3-dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)hexanamido)propanoic
acid

| DSL-19A | FF12A | F7 | FL3 | FL69A | H | AB-5 | |
|---|---|---|---|---|---|---|---|

3-((S)-6-dodecanamido-2-((2S,4R)-1-
(1-hydroxy-3,3-dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)hexanamido)propanoic
acid.

| DSL-20A | FF12A | F7 | FL3 | FL69A | H | AB-6 | |
|---|---|---|---|---|---|---|---|

TABLE 1-continued

| Compound # | FF | F | Z1b | Z1b | A' | A'' | Structure/IUPAC |
|---|---|---|---|---|---|---|---|

3-((S)-2-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)-6-tetradecanamidohexanamido)propanoic acid

| DSL-21A | FF12A | F7 | FL3 | FL69A | H | AB-7 | |

3-((S)-2-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)-6-palmitamidohexanamido)propanoic acid

| DSL-22A | FF12A | F7 | FL3 | FL69A | H | AB-8 | |

4-(((S)-6-((2-carboxyethyl)amino)-5-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)-6-oxohexyl)amino)-4-oxobutanoic acid TABLE 1-continued

| Compound # | FF | F | Z1b | Z1b | A' | A" | Structure/IUPAC |
|---|---|---|---|---|---|---|---|
| DSL-23A | FF12A | F7 | FL3 | FL69A | H | AB-9 | |

6-(((S)-6-((2-carboxyethyl)amino)-5-
((2S,4R)-1-(1-hydroxy-3,3-dimethyl-
1,3-dihydrobenzo[e][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-6-oxohexylamino)-6-
oxohexanoic acid

| Compound # | FF | F | Z1b | Z1b | A' | A" | Structure/IUPAC |
|---|---|---|---|---|---|---|---|
| DSL-24A | FF12A | F7 | FL3 | FL69A | H | AB-10 | |

8-(((S)-6-((2-carboxyethyl)amino)-5-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-6-oxohexyl)amino)-8-
oxooctanoic acid TABLE 1-continued

| Compound # | FF | F | Z1b | Z1b | A' | A" | Structure/IUPAC |
|---|---|---|---|---|---|---|---|
| DSL-25A | FF12A | F7 | FL3 | FL69A | H | AB-11 | 10-(((S)-6-((2-carboxyethyl)amino)-5-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)-6-oxohexyl)amino)-10-oxodecanoic acid |
| DSL-26A | FF12A | F7 | FL3 | FL69A | H | AB-12 | 12-(((S)-6-((2-carboxyethyl)amino)-5-((2S,4R)-1-(1-hydroxy-3,3-dimethyl-1,3-dihydrobenzo[e][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)-6-oxohexyl)amino)-12-oxododecanoic acid |
| DSL-27A | FF12A | F7 | FL3 | FL69A | H | AB-13 | 14-(((S)-6-((2-carboxyethyl)amino)-5-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)-6-oxohexyl)amino)-14-oxotetradecanoic acid |

TABLE 1-continued

| Compound # | FF | F | Z1b | Z1b | A' | A" | Structure/IUPAC |
|---|---|---|---|---|---|---|---|
| DSL-28A | FF12A | F7 | FL3 | FL69A | H | AB-14 | |

16-(((S)-6-((2-carboxyethyl)amino)-5-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-6-oxohexyl)amino)-16-
oxohexadecanoic acid

| DSL-29A | FF12A | F2 | FL3 | FL69A | H | AB-15 | |
|---|---|---|---|---|---|---|---|

3-((2S)-2-((2S,4R)-1-(1-hydroxy-1,3-
dihydrobenzo[c][1,2]oxaborole-6-
carbonyl)-4-(1-hydroxy-1,3-
dibydrobenzo[e][1,2]oxaborole-6-
carboxamido)pyrrolidine-2-
carboxamido)-6-(2-
phenylpropanamido)hexanamido)
propanoic acid

| DSL-30A | FF12A | F2 | FL3 | FL69A | H | AB-16 | |
|---|---|---|---|---|---|---|---|

3-((S)-2-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)-6-(2-(4-
isobutylphenyl)acetamido)
hexanamido)propanoic acid TABLE 1-continued

| Compound # | FF | F | Z1b | Z1b | A' | A" | Structure/IUPAC |
|---|---|---|---|---|---|---|---|
| DSL-31A | FF12A | F2 | FL3 | FL69A | H | AB-17 | |

DSL-31A 3-((2S)-2-((2S,4R)-1-(1-hydroxy-1,3-
dihydrobenzo[c][1,2]oxaborole-6-
carbonyl)-4-(1-hydroxy-1,3-
dihydrobenzo[e][1,2]oxaborole-6-
carboxamido)pyrrolidine-2-
carboxamido)-6-(2-(4-
isobutylphenyl)propanamido)
hexanamido)propanoic acid

| DSL-32A | FF12A | F2 | FL3 | FL69A | H | AB-18 | |
|---|---|---|---|---|---|---|---|

3-((S)-6-benzamido-2-
((2S,4R)-1-(1-hydroxy-1,3-
dihydrobenzo[e][1,2]oxaborole-6-
carbonyl)-4-(1-hydroxy-1,3.
dihydrobenzo[c][1,2]oxaborole-6-
carboxamido)pyrrolidine-2-
carboxamido)hexanamido)propanoic
acid TABLE 1-continued

| Compound # | FF | F | Z1b | Z1b | A' | A" | Structure/IUPAC |
|---|---|---|---|---|---|---|---|
| DSL-33A | FF12A | F2 | FL3 | FL69A | H | AB-19 | |

3-((S)-2-((2S,4R)-1-(1-hydroxy-1,3-
dihydrobenzo[c][1,2]oxaborole-6-
carbonyl)-4-(1-hydroxy-1,3-
dihydrobenzo[c]l1,2]oxaborole-6-
carboxamido)pyrrolidine-2-
carboxamido)-6-(2-(p-
tolyl)acetamido)hexanamido)
propanoic acid

| DSL-34A | FF12A | F2 | FL3 | FL69A | H | AB-20 | |

3-((S)-2-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)-6-(3-
phenylpropanamido)hexanamido)
propanoic acid.

TABLE 1-continued

| Compound # | FF | F | Z1b | Z1b | A' | A" | Structure/IUPAC |
|---|---|---|---|---|---|---|---|
| DSL-35A | FF12A | F2 | FL3 | FL69A | H | AB-21 | |

3-((S)-2-((2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxamido)-6-(4-phenylbutanamido)hexanamido)propanoic acid

| Compound # | FF | F | Z1b | Z1b | A' | A" | Structure/IUPAC |
|---|---|---|---|---|---|---|---|
| DSL-36A | FF12A | F2 | FL3 | FL69A | H | AB-22 | |

3-((S)-6-(3-(4-chlorophenyl)propanamido)-2-((2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carboxamido)hexanamido)propanoic acid TABLE 1-continued

| Compound # | FF | F | Z1b | Z1b | A' | A" | Structure/IUPAC |
|---|---|---|---|---|---|---|---|
| DSL-37A | FF12A | F2 | FL3 | FL69A | H | AB-23 | |

3-((S)-2-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)-6-(3-(4-
(trifluoromethyl)phenyl)propanamido)
hexanamido)propanoic acid

| DSL-38A | FF12A | F2 | FL3 | FL69A | H | AB-24 | |
|---|---|---|---|---|---|---|---|

3-((S)-6-(3-(4-
ethoxyphenyl)propanamido)-2-
((2S,4R)-1-(1-hydroxy-1,3-
dihydrobenzo[e][1,2]oxaborole-6-
carbonyl)-4-(1-hydroxy-1,3-
dihydrobenzo[c][1,2]oxaborole-6-
carboxamido)pyrrolidine-2-
carboxamido)hexanamido)propanoic
acid TABLE 1-continued

| Compound # | FF | F | Z1b | Z1b | A' | A" | Structure/IUPAC |
|---|---|---|---|---|---|---|---|
| DSL-39A | FF12A | F2 | FL3 | FL69A | H | AB-25 | |

3-((S)-6-(3-(4-
fluorophenyl)propanamido)-2-
((2S,4R)-1-(1-hydroxy-1,3-
dihydrobenzo[c][1,2]oxaborole-6-
carbonyl)-4-(1-hydroxy-1,3-
dihydrobenzo[e][1,2]oxaborole-6-
carboxamido)pyrrolidine-2-
carboxamido)hexanamido)propanoic
acid

| DSL-40A | FF12A | F2 | FL3 | FL69A | H | AB-26 | |
|---|---|---|---|---|---|---|---|

3-((S)-6-(3-(3-
fluorophenyl)propanamido)-2-
((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)hexanamido)propanoic
acid TABLE 1-continued

| Compound # | FF | F | Z1b | Z1b | A' | A" | Structure/IUPAC |
|---|---|---|---|---|---|---|---|
| DSL-41A | FF12A | F2 | FL3 | FL69A | H | AB-27 | |

3-((S)-2-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)-6-(5-
phenylpentanamido)hexanamido)
propanoic acid

| Compound # | FF | F | Z1b | Z1b | A' | A" | Structure/IUPAC |
|---|---|---|---|---|---|---|---|
| DSL-42A | FF12A | F2 | FL3 | FL69A | H | AB-28 | |

3-((S)-6-(3-(3,5-
difluorophenyl)propanamido)-2-
((2S,4R)-1-(1-hydroxy-1,3-
dibydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)hexanamido)propanoic
acid TABLE 1-continued

| Compound # | FF | F | Z1b | Z1b | A' | A" | Structure/IUPAC |
|---|---|---|---|---|---|---|---|
| DSL-43A | FF12A | F2 | FL3 | FL69A | H | AB-29 | |

3-((2S)-2-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)-6-(2-(3-hydroxy-2,4,6-
triiodobenzyl)butanamido)
hexanamido)propanoic acid

| DSL-44A | FF12A | F2 | FL3 | FL69A | H | AB-30 | |

3-((S)-6-(4-chloro-2-((furan-2-
ylmethyl)amino)-5-
sulfamoylbenzamido)-2-((2S,4R)-1-
(1-hydroxy-1,3-
dihydrobenzo[c][1,2]oxaborole-6-

TABLE 1-continued

| Compound # | FF | F | Z1b | Z1b | A' | A" | Structure/IUPAC |
|---|---|---|---|---|---|---|---|
| | | | | | | | carbonyl)-4-(1-hydroxy-1,3-dihydrobenzo[c][1,2]oxaborole-6-carboxamido)pyrrolidine-2-carboxamido)hexanamido)propanoic acid |
| DSL-45A | FF12A | F7 | FL3 | FL69A | H | AB-35 | |

6-((4-(((S)-6-((2-carboxyethyl)amino)-5-((2S,4R)-1-(1-hydroxy-3,3-dimethyl-1,3-dibydrobenzo[c][1,2]oxaborole-6-carbonyl)-4-(1-hydroxy-3,3-dimethyl-1,3-dihydrobenzo[e][1,2]oxaborole-6-carboxamido)pyrrolidine-2-carboxamido)-6-oxohexyl)carbamoyl)benzyl)amino)-6-oxohexanoic acid

| DSL-46A | FF12A | F2 | FL3 | FL69A | H | AB-32 | |

3-((S)-2-((2S,4R)-1-(1-hydroxy-1,3-dibydrobenzo[c][1,2]oxaborole-6-carbonyl)-4-(1-hydroxy-1,3-dihydrobenzo[c][1,2]oxaborole-6-carboxamido)pyrrolidine-2-carboxamido)-6-(4-oxo-4-phenylbutanamido)hexanamido)propanoic acid TABLE 1-continued

| Compound # | FF | F | Z1b | Z1b | A' | A" | Structure/IUPAC |
|---|---|---|---|---|---|---|---|
| DSL-47A | FF12A | F7 | FL3 | FL69A | H | AB-36 | |

3-(4-(((S)-6-((2-
carboxyethyl)amino)-5-((2S,4R)-1-(1-
bydroxy-3,3-dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-6-
oxohexyl)carbamoyl)phenyl)
propanoic acid

| DSL-48A | FF12A | F2 | FL3 | FL69A | H | AB-34 | |

5-((2S,4R)-1-(1-hydroxy-1,3-
dihydrobenzo[c][1,2]oxaborole-6-
carbonyl)-4-(1-hydroxy-1,3-
dibydrobenzo[c][1,2]oxaborole-6-
carboxamido)pyrrolidine-2-

TABLE 1-continued

| Compound # | FF | F | Z1b | Z1b | A' | A" | Structure/IUPAC |
|---|---|---|---|---|---|---|---| carboxamido)-6-oxohexyl)amino)-3-oxopropyl)benzoic acid

| DSL-49A | FF12A | F2 | FL3 | FL69A | H | AB-31 | |

2-(3-(((S)-6-((2-carboxyethyl)amino)-5-((2S,4R)-1-(1-hydroxy-1,3-dihydrobenzo[c][1,2]oxaborole-6-carbonyl)-4-(1-hydroxy-1,3-dibydrobenzo[c][1,2]oxaborole-6-carboxamido)pyrrolidine-2-carboxamido)-6-oxohexyl)amino)-3-oxopropyl)benzoic acid

| DSL-50A | FF12A | F2 | FL3 | FL69A | H | AB-15 | |

3-((2S)-2-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)-6-(2-

TABLE 1-continued

| Compound # | FF | F | Z1b | Z1b | A' | A" | Structure/IUPAC |
|---|---|---|---|---|---|---|---| pheny lpropanamido)hexanamido)
propanoic acid

| DSL-51A | FF12A | F7 | FL3 | FL69A | H | AB-16 | |

3-((S)-2-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-6-(2-(4-
isobutylphenyl)acetamido)
hexanamido)propanoic acid

| DSL-52A | FF12A | F7 | FL3 | FL69A | H | AB-17 | |

3-((2S)-2-((2S,4R)-1-(1-hydroxy-3,3-
dimethyl-1,3-
dibydrobenzo[c][1,2]oxaborole-6-
carbonyl)-4-(1-hydroxy-3,3-dimethy]-
1,3-dihydrobenzo[c][1,2]oxaborole-6-

TABLE 1-continued

| Compound # | FF | F | Z1b | Z1b | A' | A'' | Structure/IUPAC |
|---|---|---|---|---|---|---|---|
| | | | | | | | carboxamido)pyrrolidine-2-carboxamido)-6-(2-(4-isobutylphenyl)propanamido)hexanamido)propanoic acid |
| DSL-53A | FF12A | F7 | FL3 | FL69A | H | AB-18 | |

3-((S)-6-benzamido-2-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)hexanamido)propanoic acid

| DSL-54A | FF12A | F7 | FL3 | FL69A | H | AB-19 | |

3-((S)-2-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-

TABLE 1-continued

| Compound # | FF | F | Z1b | Z1b | A' | A" | Structure/IUPAC |
|---|---|---|---|---|---|---|---|
| | | | | | | | carboxamido)pyrrolidine-2-carboxamido)-6-(2-(p-tolyl)acetamido)hexanamido) propanoic acid |
| DSL-55A | FF12A | F7 | FL3 | FL69A | H | AB-20 | |

3-((S)-2-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)-6-(3-phenylpropanamido)hexanamido) propanoic acid

| DSL-56A | FF12A | F7 | FL3 | FL69A | H | AB-21 | |

3-((S)-2-((2S,4R)-1-(1-hydroxy-3,3-dimethyl-1,3-dihydrobenzo[c][1,2]oxaborole-6-carbonyl)-4-(1-hydroxy-3,3-dimethyl- TABLE 1-continued

| Compound # | FF | F | Z1b | Z1b | A' | A" | Structure/IUPAC |
|---|---|---|---|---|---|---|---|
| | | | | | | | 1,3-dihydrobenzo[c][1,2]oxaborole-6-carboxamido)pyrrolidine-2-carboxamido)-6-(4-phenylbutanamido)hexanamido)propanoic acid |
| DSL-57A | FF12A | F7 | FL3 | FL69A | H | AB-22 | |

3-((S)-6-(3-(4-chlorophenyl)propanamido)-2-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)hexanamido)propanoic acid

| DSL-58A | FF12A | F7 | FL3 | FL69A | H | AB-23 | |

3-((S)-2-((2S,4R)-1-(1-hydroxy-3,3-dimethyl-1,3-dihydrobenzo[c][1,2]oxaborole-6-carbonyl)-4-(1-hydroxy-3,3-dimethyl- TABLE 1-continued

| Compound # | FF | F | Z1b | Z1b | A' | A'' | Structure/IUPAC |
|------------|-----|-----|------|-------|-----|------|-----------------|

1,3-dihydrobenzo[c][1,2]oxaborole-6-carboxamido)pyrrolidine-2-carboxamido)-6-(3-(4-(trifluoromethyl)phenyl)propanamido)hexanamido)propanoic acid

| DSL-59A | FF12A | F7 | FL3 | FL69A | H | AB-24 | |

3-((S)-6-(3-(4-ethoxyphenyl)propanamido)-2-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)hexanamido)propanoic acid

| DSL-60A | FF12A | F7 | FL3 | FL69A | H | AB-25 | |

3-((S)-6-(3-(4-fluorophenyl)propanamido)-2-((2S,4R)-1-(1-hydroxy-3,3-dimethyl-1,3-dihydrobenzo[c][1,2]oxaborole-6-

TABLE 1-continued

| Compound # | FF | F | Z1b | Z1b | A' | A" | Structure/IUPAC |
|---|---|---|---|---|---|---|---| carbonyl)-4-(1-hydroxy-3,3-dimethyl-
1,3-dihydrobenzo[c][1,2]oxaborole-6-
carboxamido)pyrrolidine-2-
carboxamido)hexanamido)propanoic
acid

DSL-61A FF12A F7 FL3 FL69A H AB-26

3-((5)-6-(3-(3-
fluorophenyl)propanamido)-2-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)hexanamido)propanoic
acid

DSL-62A FF12A F7 FL3 FL69A H AB-27

3-((S)-2-((2S,4R)-1-(1-hydroxy-3,3-
dimethyl-1,3-
dihydrobenzo[c][1,2]oxaborole-6-

TABLE 1-continued

| Compound # | FF | F | Z1b | Z1b | A' | A" | Structure/IUPAC |
|---|---|---|---|---|---|---|---|
| | | | | | | | carbonyl)-4-(1-hydroxy-3,3-dimethyl-1,3-dihydrobenzo[c][1,2]oxaborole-6-carboxamido)pyrrolidine-2-carboxamido)-6-(5-phenylpentanamido)hexanamido)propanoic acid. |
| DSL-63A | FF12A | F7 | FL3 | FL69A | H | AB-28 | 3-((S)-6-(3-(3,5-difluorophenyl)propanamido)-2-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)hexanamido)propanoic acid |
| DSL-64A | FF12A | F7 | FL3 | FL69A | H | AB-29 | 3-((2S)-6-((2-(3-hydroxy-2,4,6-triiodobenzyl)butanoyl)-λ³-oxidaneyl)-2-((2S,4R)-1-(1-hydroxy- |

| Compound # | FF | F | Z1b | Z1b | A' | A" | Structure/IUPAC |
|---|---|---|---|---|---|---|---|
| | | | | | | | 3,3-dimethyl-1,3-dihydrobenzo[c][1,2]oxaborole-6-carbonyl)-4-(1-hydroxy-3,3-dimethyl-1,3-dihydrobenzo[e][1,2]oxaborole-6-carboxamido)pyrrolidine-2-carboxamido)hexanamido)propanoic acid |
| DSL-65A | FF12A | F7 | FL3 | FL69A | H | AB-30 | |

3-((S)-6-(4-chloro-2-((furan-2-ylmethyl)amino)-5-sulfamoylbenzamido)-2-((2,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)hexanamido)propanoic acid TABLE 1-continued

| Compound # | FF | F | Z1b | Z1b | A' | A" | Structure/IUPAC |
|---|---|---|---|---|---|---|---|
| DSL-66A | FF12A | F7 | FL3 | FL69A | H | AB-37 | |

(S)-18-((2S,4R)-1-(1-hydroxy-3,3-
dimethyl-2,3-dihydro-1H-
benzo[b]borole-6-carbonyl)-4-(1-
hydroxy-3,3-dimethyl-2,3-dihydro-
1H-benzo[b]borole-6-
carboxamido)pyrrolidine-2-
carboxamido)-3,12,19-trioxo-1-
phenyl-7,10-dioxa-4,13,20-
triazatricosan-23-oic acid TABLE 1-continued

| Compound # | FF | F | Z1b | Z1b | A' | A" | Structure/IUPAC |
|---|---|---|---|---|---|---|---|
| DSL-67A | FF12A | F7 | FL3 | FL69A | H | AB-32 | |

3-((S)-2-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-6-(4-oxo-4-
phenylbutanamido)hexanamido)
propanoic acid

| DSL-68A | FF12A | F7 | FL3 | FL69A | H | AB-33 | |

4-(((S)-6-((2-carboxyethyl)amino)-5-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-6-
oxohexyl)carbamoyl)benzoic acid TABLE 1-continued

| Compound # | FF | F | Z1b | Z1b | A' | A" | Structure/IUPAC |
|---|---|---|---|---|---|---|---|
| DSL-69A | FF12A | F7 | FL3 | FL69A | H | AB-34 | |

4-(3-(((S)-6-((2-carboxyethyl)amino)-
5-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-6-oxohexyl)amino)-3-
oxopropyl)benzoic acid

| DSL-70A | FF12A | F7 | FL3 | FL69A | H | AB-31 | |
|---|---|---|---|---|---|---|---|

TABLE 1-continued

| Compound # | FF | F | Z1b | Z1b | A' | A" | Structure/IUPAC |
|---|---|---|---|---|---|---|---|
| | | | | | | | 2-(3-(((S)-6-((2-carboxyethyl)amino)-5-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)-6-oxohexyl)amino)-3-oxopropyl)benzoic acid |
| DSL-71A | FF12A | F2 | FL5B | FL69A | H | AB-1 | N6-butyryl-N2-(2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carbonyl)-L-lysyl-L-glutamic acid |
| DSL-72A | FF12A | F2 | FL5B | FL69A | H | AB-2 | |

TABLE 1-continued

| Compound # | FF | F | Z1b | Z1b | A' | A" | Structure/IUPAC |
|---|---|---|---|---|---|---|---|

N⁶-hexanoyl]-N²-((2S,4R)-1-(1-
hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid

DSL-73A    FF12A    F2    FL5B    FL69A    H    AB-3

N²-(2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
N⁶-octanoyl-E-lysyl-L-glutamic acid

DSL-74A    FF12A    F2    FL5B    FL69A    H    AB-4

N⁶-decanoyl-N²-((2S,4R)-1-(1-
hydroxy-1,3-
dihydrobenzo[e][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid TABLE 1-continued

| Compound # | FF | F | Z1b | Z1b | A' | A" | Structure/IUPAC |
|---|---|---|---|---|---|---|---|
| DSL-75A | FF12A | F2 | FL5B | FL69A | H | AB-5 | |

N⁶-dodecanoyl-N²-((2S,4R)-1-(1-
hydroxy-1,3-
dihydrobenzo[e][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid

| Compound # | FF | F | Z1b | Z1b | A' | A" | Structure/IUPAC |
|---|---|---|---|---|---|---|---|
| DSL-76A | FF12A | F2 | FL5B | FL69A | H | AB-6 | |

N²-((2S,4R)-1-(1-hydroxy-1,3-
dihydrobenzo[e][1,2]oxaborole-6-
carbonyl)-4-(1-hydroxy-1,3-
dihydrobenzo[c][1,2]oxaborole-6-
carboxamido)pyrrolidine-2-carbonyl)-
N⁶-tetradecanoyl-L-lysyl-L-glutamic
acid

| Compound # | FF | F | Z1b | Z1b | A' | A" | Structure/IUPAC |
|---|---|---|---|---|---|---|---|
| DSL-77A | FF12A | F2 | FL5B | FL69A | H | AB-7 | |

N²-(2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
N⁶-palmitoyl-L-lysyl-L-glutamic acid TABLE 1-continued

| Compound # | FF | F | Z1b | Z1b | A' | A" | Structure/IUPAC |
|---|---|---|---|---|---|---|---|
| DSL-78A | FF12A | F2 | FL5B | FL69A | H | AB-8 | |

N⁶-(3-carboxypropanoyl)-N²-
((2S,4R)-1-(1-hydroxy-1,3-
dihydrobenzo[c][1,2]oxaborole-6-
carbonyl)-4-(1-hydroxy-1,3-
dibydrobenzo[c][1,2]oxaborole-6-
carboxamido)pyrrolidine-2-carbonyl)-
L-lysyl-L-glutamic acid

| DSL-79A | FF12A | F2 | FL5B | FL69A | H | AB-9 | |
|---|---|---|---|---|---|---|---|

N⁶-(5-carboxypentanoy)-N²-
((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid TABLE 1-continued

| Compound # | FF | F | Z1b | Z1b | A' | A" | Structure/IUPAC |
|---|---|---|---|---|---|---|---|
| DSL-80A | FF12A | F2 | FL5B | FL69A | H | AB-10 | |

$N^6$-(7-carboxyheptanoyl)-$N^2$-
((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid

| DSL-81A | FF12A | F2 | FL5B | FL69A | H | AB-11 | |
|---|---|---|---|---|---|---|---|

$N^6$-(9-carboxynonanoyl)-$N^2$-((2S,4R)-
1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid

| DSL-82A | FF12A | F2 | FL5B | FL69A | H | AB-12 | |
|---|---|---|---|---|---|---|---|

$N^6$-(11-carboxyundecanoy])-$N^2$-
((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid TABLE 1-continued

| Compound # | FF | F | Z1b | Z1b | A' | A" | Structure/IUPAC |
|---|---|---|---|---|---|---|---|
| DSL-83A | FF12A | F2 | FL5B | FL69A | H | AB-13 | |

N<sup>6</sup>-(13-carboxytridecanoyl)-N<sup>2</sup>-
((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid

| DSL-84A | FF12A | F2 | FL5B | FL69A | H | AB-14 | |

N<sup>6</sup>-(15-carboxypentadecanoyl)-N<sup>2</sup>-
((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid

| DSL-85A | FF12A | F7 | FL5B | FL69A | H | AB-1 | |

N<sup>6</sup>-butyryl-N<sup>2</sup>-((2S,4R)-1-(1-
hydroxy-3,3-dimethyl-1,3-
dihydrobenzo[c][1,2]oxaborole-6-
carbonyl)-4-(1-hydroxy-3,3-dimethyl- TABLE 1-continued

| Compound # | FF | F | Z1b | Z1b | A' | A" | Structure/IUPAC |
|---|---|---|---|---|---|---|---|
| | | | | | | | 1,3-dihydrobenzo[c][1,2]oxaborole-6-carboxamido)pyrrolidine-2-carbonyl)-L-lysyl-L-glutamic acid |
| DSL-86A | FF12A | F7 | FL5B | FL69A | H | AB-2 | |

N$^6$-hexanoyl-N$^2$-((2S,4R)-1-(1-
hydroxy-3,3-dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid

| Compound # | FF | F | Z1b | Z1b | A' | A" | Structure/IUPAC |
|---|---|---|---|---|---|---|---|
| DSL-87A | FF12A | F7 | FL5B | FL69A | H | AB-3 | |

N$^2$-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
N$^6$-octanoyl-L-lysyl-L-glutamic acid TABLE 1-continued

| Compound # | FF | F | Z1b | Z1b | A' | A'' | Structure/IUPAC |
|---|---|---|---|---|---|---|---|
| DSL-88A | FF12A | F7 | FL5B | FL69A | H | AB-4 | N⁶-decanoyl-N²-((2S,4R)-1-(1-hydroxy-3,3-dimethyl-1,3-dihydrobenzo[c][1,2]oxaborole-6-carbonyl)-4-(1-hydroxy-3,3-dimethy]-1,3-dihydrobenzo[c][1,2]oxaborole-6-carboxamido)pyrrolidine-2-carbonyl)-L-lysyl-L-glutamic acid |
| DSL-89A | FF12A | F7 | FL5B | FL69A | H | AB-5 | N⁶-dodecanoyl-N²-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carbonyl)-L-lysyl-L-glutamic acid |
| DSL-90A | FF12A | F7 | FL5B | FL69A | H | AB-6 | N²-((2S,4R)-1-(1-hydroxy-3,3-dimethyl-1,3-dibydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carbonyl)-N⁶-tetradecanoyl-L-Jysyl-L-glutamic acid |

TABLE 1-continued

| Compound # | FF | F | Z1b | Z1b | A' | A" | Structure/IUPAC |
|---|---|---|---|---|---|---|---|
| DSL-91A | FF12A | F7 | FL5B | FL69A | H | AB-7 | |

$N^2$-((2S,4R)-1-(1-hydroxy-3,3-
dimethyl-1,3-
dihydrobenzo[e][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
$N^6$-palmitoyl-L-lysyl-L-glutamic acid

| DSL-92A | FF12A | F7 | FL5B | FL69A | H | AB-8 | |
|---|---|---|---|---|---|---|---|

$N^6$-(3-carboxypropanoyl])-$N^2$-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid TABLE 1-continued

| Compound # | FF | F | Z1b | Z1b | A' | A'' | Structure/IUPAC |
|---|---|---|---|---|---|---|---|
| DSL-93A | FF12A | F7 | FL5B | FL69A | H | AB-9 | |

N⁶-(5-carboxypentanoy])-N²-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid

| | | | | | | | |
|---|---|---|---|---|---|---|---|
| DSL-94A | FF12A | F7 | FLSB | FL69A | H | AB-10 | |

N⁶-(7-carboxyheptanoyl)-N²-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid

| | | | | | | | |
|---|---|---|---|---|---|---|---|
| DSL-95A | FF12A | F7 | FL5B | FL69A | H | AB-11 | |

TABLE 1-continued

| Compound # | FF | F | Z1b | Z1b | A' | A'' | Structure/IUPAC |
|---|---|---|---|---|---|---|---|
| | | | | | | | N⁶-(9-carboxynonanoy])-N²-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carbonyl)-L-lysyl-L-glutamic acid |
| DSL-96A | FF12A | F7 | FL5B | FL69A | H | AB-12 | |

N⁶-(11-carboxyundecanoyl)-N²-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid

| DSL-97A | FF12A | F7 | FL5B | FL69A | H | AB-13 | |

N⁶-(13-carboxytridecanoyl)-N²-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid

| DSL-98A | FF12A | F7 | FL5B | FL69A | H | AB-14 | |

N⁶ (15-carboxypentadecanoyl)-N²-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid TABLE 1-continued

| Compound # | FF | F | Z1b | Z1b | A' | A" | Structure/IUPAC |
|---|---|---|---|---|---|---|---|
| DSL-99A | FF12A | F2 | FLSB | FL69A | H | AB-15 | |

$N^2$-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
$N^6$-(2-phenylpropanoyl)-L-lysyl-L-
glutamic acid

| Compound # | FF | F | Z1b | Z1b | A' | A" | Structure/IUPAC |
|---|---|---|---|---|---|---|---|
| DSL-100A | FF12A | F2 | FL5B | FL69A | H | AB-16 | |

$N^2$-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
$N^6$-(2-(4-isobutylphenyl)acetyl)-L-
lysyl-L-glutamic acid TABLE 1-continued

| Compound # | FF | F | Z1b | Z1b | A' | A'' | Structure/IUPAC |
|---|---|---|---|---|---|---|---|
| DSL-101A | FF12A | F2 | FL5B | FL69A | H | AB-17 | |

N²-((2S,4R)-1-(1-hydroxy-1,3-
dibydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
N⁶-(2-(4-isobutylphenyl)propanoyl)-
L-lysyl-L-glutamic acid

| Compound # | FF | F | Z1b | Z1b | A' | A'' | Structure/IUPAC |
|---|---|---|---|---|---|---|---|
| DSL-102A | FF12A | F2 | FLSB | FL69A | H | AB-18 | |

N⁶-benzoyl-N²-((2S,4R)-1-(1-
hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid TABLE 1-continued

| Compound # | FF | F | Z1b | Z1b | A' | A" | Structure/IUPAC |
|---|---|---|---|---|---|---|---|
| DSL-103A | FF12A | F2 | FLSB | FL69A | H | AB-19 | |

N²-((2S,4R)-1-(1-hydroxy-1,3-
dihydrobenzo[c][1,2]oxaborole-6-
carbonyl)-4-(1-hydroxy-1,3-
dihydrobenzo[e][1,2]oxaborole-6-
carboxamido)pyrrolidine-2-carbonyl)-
N⁶-(2-(p-tolyl)acetyl)-L-lysyl-L-
glutamic acid

| DSL-104A | FF12A | F2 | FL5B | FL69A | H | AB-20 | |

N²-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
N⁶-(3-phenylpropanoyl)-L-lysyl-L-
glutamic acid TABLE 1-continued

| Compound # | FF | F | Z1b | Z1b | A' | A" | Structure/IUPAC |
|---|---|---|---|---|---|---|---|
| DSL-105A | FF12A | F2 | FL5B | FL69A | H | AB-21 | |

N²-((2S,4R)-1-(1-hydroxy-1,3.
dibydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
N⁶-(4-phenylbutanoyl)-L-lysyl-L-
glutamic acid

| DSL-106A | FF12A | F2 | FL5B | FL69A | H | AB-22 | |

N⁶-(3-(4-chlorophenyl)propanoyl])-
N²-((2S,4R)-1-(1-hydroxy-1,3-
dihydrobenzo[e][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid TABLE 1-continued

| Compound # | FF | F | Z1b | Z1b | A' | A" | Structure/IUPAC |
|---|---|---|---|---|---|---|---|
| DSL-107A | FF12A | F2 | FL5B | FL69A | H | AB-23 | |

N²-(2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
N⁶-(3-(4-
(trifluoromethyl)pbenyl)propanoyl)-L-
lysyl-L-glutamic acid

| DSL-108A | FF12A | F2 | FL5B | FL69A | H | AB-24 | |

N⁶-(3-(4-ethoxyphenyl)propanoyl)-
N²((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid TABLE 1-continued

| Compound # | FF | F | Z1b | Z1b | A' | A" | Structure/IUPAC |
|---|---|---|---|---|---|---|---|
| DSL-109A | FF12A | F2 | FL5B | FL69A | H | AB-25 | |

N⁶-(3-(4-fluorophenyl)propanoyl)-
N²-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid

| Compound # | FF | F | Z1b | Z1b | A' | A" | Structure/IUPAC |
|---|---|---|---|---|---|---|---|
| DSL-110A | FF12A | F2 | FL5B | FL69A | H | AB-26 | |

N⁶-(3-(3-fluorophenyl)propanoyl)-
N²-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-carbonyl)-
L-lysyl-L-glutamic acid TABLE 1-continued

| Compound # | FF | F | Z1b | Z1b | A' | A" | Structure/IUPAC |
|---|---|---|---|---|---|---|---|
| DSL-111A | FF12A | F2 | FL5B | FL69A | H | AB-27 | |

N²-((2S,4R)-1-(1-hydroxy-1,3-dibydrobenzo[c][1,2]oxaborole-6-carbonyl)-4-(1-hydroxy-1,3-dihydrobenzo[c][1,2]oxaborole-6-carboxamido)pyrrolidine-2-carbonyl)-N⁶-(5-phenylpentanoyl)-L-lysyl-L-glutamic acid

| Compound # | FF | F | Z1b | Z1b | A' | A" | Structure/IUPAC |
|---|---|---|---|---|---|---|---|
| DSL-112A | FF12A | F2 | FL5B | FL69A | H | AB-28 | |

N⁶-(3-(3,5-difluorophenyl)propanoyl)-N²-((2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carbonyl)-L-lysyl-L-glutamic acid TABLE 1-continued

| Compound # | FF | F | Z1b | Z1b | A' | A" | Structure/IUPAC |
|---|---|---|---|---|---|---|---|
| DSL-113A | FF12A | F2 | FLSB | FL69A | H | AB-29 | |

N²-((2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-carboxamido)pyrrolidine-2-carbonyl)-N⁶-(2-(3-hydroxy-2,4,6-triiodobenzyl)butanoyl)-L-lysyl-L-glutamic acid

| Compound # | FF | F | Z1b | Z1b | A' | A" | Structure/IUPAC |
|---|---|---|---|---|---|---|---|
| DSL-114A | FF12A | F2 | FLSB | FL69A | H | AB-30 | |

N⁶-(4-chloro-2-((furan-2-ylmethyl)amino)-5-sulfamoylbenzoyl)-N²-((2S,4R)-1-(1-hydroxy-1,3-dihydrobenzo[c][1,2]oxaborole-6-

TABLE 1-continued

| Compound # | FF | F | Z1b | Z1b | A' | A'' | Structure/IUPAC |
|---|---|---|---|---|---|---|---|
| | | | | | | | carbonyl)-4-(1-hydroxy-1,3-dihydrobenzo[c][1,2]oxaborole-6-carboxamido)pyrrolidine-2-carbonyl)-L-lysyl-L-glutamic acid |
| DSL-115A | FF12A | F7 | FL3 | FL69A | H | AB-20 | |

3-((S)-2-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)-4-(3-phenylpropanamido)butanamido)propanoic acid.

| Compound # | FF | F | Z1b | Z1b | A' | A'' | Structure/IUPAC |
|---|---|---|---|---|---|---|---|
| DSL-116A | FF12A | F2 | FL5B | FL69A | H | AB-32 | |

N²-((2S,4R)-1-(1-hydroxy-1,3-dihydrobenzo[c][1,2]oxaborole-6-carbonyl)-4-(1-hydroxy-1,3-dihydrobenzo[c][1,2]oxaborole-6-

TABLE 1-continued

| Compound # | FF | F | Z1b | Z1b | A' | A" | Structure/IUPAC |
|---|---|---|---|---|---|---|---|
| | | | | | | | carboxamido)pyrrolidine-2-carbonyl)-N⁶-(4-oxo-4-phenylbutanoyl)-L-lysyl-L-glutamic acid |

DSL-117A FF12A F7 FL3 FL69A H AB-34

4-(3-(((S)-4-((2-carboxyethyl)amino)-
3-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-4-oxobutyl)amino)-3-
oxopropyl)benzoic acid

DSL-118A FF12A F2 FL5B FL69A H AB-34

N⁶-(3-(4-carboxyphenyl)propanoyl)-
N²-((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-

TABLE 1-continued

| Compound # | FF | F | Z1b | Z1b | A' | A" | Structure/IUPAC |
|---|---|---|---|---|---|---|---| carboxamido)pyrrolidine-2-carbonyl)-
L-lysyl-L-glutamic acid

DSL-119A    FF12A    F2    FL5B    FL69A    H    AB-31

N⁶-(3-(2-carboxyphenyl)propanoy])-
N²-((2S,4R)-1-(1-hydroxy-1,3-
dihydrobenzo[c][1,2]oxaborole-6-
carbonyl)-4-(1-hydroxy-1,3-
dibydrobenzo[c][1,2]oxaborole-6-
carboxamido)pyrrolidine-2-carbonyl)-
L-lysyl-L-glutamic acid

DSL-120A    FF12A    F7    FL5B    FL69A    H    AB-15

N²-((2S,4R)1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
N⁶-(2-phenylpropanoyl)-L-lysyl-L-
glutamic acid TABLE 1-continued

| Compound # | FF | F | Z1b | Z1b | A' | A'' | Structure/IUPAC |
|---|---|---|---|---|---|---|---|
| DSL-121A | FF12A | F7 | FL5B | FL69A | H | AB-16 | |

N²-(2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
N⁶-(2-(4-isobutylphenyl)acetyl)-L-
lysyl-L-glutamic acid

| Compound # | FF | F | Z1b | Z1b | A' | A'' | Structure/IUPAC |
|---|---|---|---|---|---|---|---|
| DSL-122A | FF12A | F7 | FL5B | FL69A | H | AB-17 | |

N²-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
N⁶-(2-(4-isobutylphenyl)propanoyl)-
L-lysyl-L-glutamic acid TABLE 1-continued

| Compound # | FF | F | Z1b | Z1b | A' | A" | Structure/IUPAC |
|---|---|---|---|---|---|---|---|
| DSL-123A | FF12A | F7 | FL5B | FL69A | H | AB-18 | |

N⁶-benzoyl-N²-((2S,4R)-1-(1-
bydroxy-3,3-dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid

| Compound # | FF | F | Z1b | Z1b | A' | A" | Structure/IUPAC |
|---|---|---|---|---|---|---|---|
| DSL-124A | FF12A | F7 | FL5B | FL69A | H | AB-19 | |

N²-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
N⁶-(2-(p-tolyl)acetyl)-L-lysyl-L-
glutamic acid TABLE 1-continued

| Compound # | FF | F | Z1b | Z1b | A' | A" | Structure/IUPAC |
|---|---|---|---|---|---|---|---|
| DSL-125A | FF12A | F7 | FL5B | FL69A | H | AB-20 | |

N²-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
N⁶-(3-phenylpropanoy])-L-Jysyl-L-
glutamic acid

| DSL-126A | FF12A | F7 | FL5B | FL69A | H | AB-21 | |
|---|---|---|---|---|---|---|---|

N²-((2S,4R)-1-(1-hydroxy-3,3-
dimethyl-1,3-
dibydrobenzo[c][1,2]oxaborole-6-
carbonyl)-4-(1-hydroxy-3,3-dimethy]-
1,3-dihydrobenzo[c][1,2]oxaborole-6-
carboxamido)pyrrolidine-2-carbonyl)-
N⁶-(4-phenylbutanoyl)-L-lysyl-L-
glutamic acid TABLE 1-continued

| Compound # | FF | F | Z1b | Z1b | A' | A" | Structure/IUPAC |
|---|---|---|---|---|---|---|---|
| DSL-127A | FF12A | F7 | FL5B | FL69A | H | AB-22 | |

N⁶-(3-(4-chlorophenyl)propanoy)-
N²-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid

| DSL-128A | FF12A | F7 | FL5B | FL69A | H | AB-23 | |
|---|---|---|---|---|---|---|---|

N²-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
N⁶-(3-(4-
(trifluoromethyl)phenyl)propanoyl)-L-
lysyl-L-glutamic acid TABLE 1-continued

| Compound # | FF | F | Z1b | Z1b | A' | A" | Structure/IUPAC |
|---|---|---|---|---|---|---|---|
| DSL-129A | FF12A | F7 | FL5B | FL69A | H | AB-24 | |

N⁶-(3-(4-ethoxyphenyl)propanoyl)-
N²-((2S,4R)-1-(1-hydroxy-3,3-
dimethyl-1,3-
dibydrobenzo[c][1,2]oxaborole-6-
carbonyl)-4-(1-hydroxy-3,3-dimethy]-
1,3-dihydrobenzo[c][1,2]oxaborole-6-
carboxamido)pyrrolidine-2-carbonyl)-
L-lysyl-L-glutamic acid

| Compound # | FF | F | Z1b | Z1b | A' | A" | Structure/IUPAC |
|---|---|---|---|---|---|---|---|
| DSL-130A | FF12A | F7 | FLSB | FL69A | H | AB-25 | |

N⁶-(3-(4-fluorophenyl)propanoyl)-
N²-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid TABLE 1-continued

| Compound # | FF | F | Z1b | Z1b | A' | A" | Structure/IUPAC |
|---|---|---|---|---|---|---|---|
| DSL-131A | FF12A | F7 | FL5B | FL69A | H | AB-26 | |

N⁶-(3-(3-fluorophenyl)propanoyl)-
N²-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid

| Compound # | FF | F | Z1b | Z1b | A' | A" | Structure/IUPAC |
|---|---|---|---|---|---|---|---|
| DSL-132A | FF12A | F7 | FL5B | FL69A | H | AB-27 | |

N²-((2S,4R)-1-(1-hydroxy-3,3-
dimethyl-1,3-
dibydrobenzo[c][1,2]oxaborole-6-
carbonyl)-4-(1-hydroxy-3,3-dimethy]-
1,3-dihydrobenzo[c][1,2]oxaborole-6-
carboxamido)pyrrolidine-2-carbonyl)-
N⁶-(5-phenylpentanoyl)-L-lysyl-L-
glutamic acid TABLE 1-continued

| Compound # | FF | F | Z1b | Z1b | A' | A" | Structure/IUPAC |
|---|---|---|---|---|---|---|---|
| DSL-133A | FF12A | F7 | FL5B | FL69A | H | AB-28 | |

N⁶-(3-(3,5-
difluorophenyl)propanoyl)-N²-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid

| DSL-134A | FF12A | F7 | FL5B | FL69A | H | AB-29 | |
|---|---|---|---|---|---|---|---|

N⁶-(2-(3-hydroxy-2,4,6-
triiodobenzyl)butanoyl)-N²-((2S,4R)-
1-(1-hydroxy-3,3-dimethyl-1,3-
dihydrobenzo[e][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid TABLE 1-continued

| Compound # | FF | F | Z1b | Z1b | A' | A" | Structure/IUPAC |
|---|---|---|---|---|---|---|---|
| DSL-135A | FF12A | F7 | FL5B | FL69A | H | AB-30 | |

N[6]-(4-chloro-2-((furan-2-
ylmethyl)amino)-5-
sulfamoylbenzoyl)-N[2]-((2S,4R)-1-(1-
hydroxy-3,3-dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid

| DSL-136A | FF12A | F7 | FL3 | FL69A | H | AB-36 | |
|---|---|---|---|---|---|---|---|

3-(4-(((S)-4-((2-carboxyethyl)amino)-
3-((2S,4R)-1-(1-hydroxy-3,3-
dimethyl-1,3-

TABLE 1-continued

| Compound # | FF | F | Z1b | Z1b | A' | A" | Structure/IUPAC |
|---|---|---|---|---|---|---|---| dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-4-
oxobutyl)carbamoyl)phenyl)propanoic
acid

DSL-137A    FF12A    F7    FL5B    FL69A    H    AB-32

N²-(2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
N⁶-(4-oxo-4-phenylbutanoyl)-L-lysyl-
L-glutamic acid

DSL-138A    FF12A    F7    FL5B    FL69A    H    AB-38

TABLE 1-continued

| Compound # | FF | F | Z1b | Z1b | A' | A" | Structure/IUPAC |
|---|---|---|---|---|---|---|---|

2-(2-(((S)-6-((2-carboxyethyl)amino)-
5-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-6-oxohexyl)amino)-2-
oxoethyl)benzoic acid

DSL-139A    FF12A    F7    FL5B    FL69A    H    AB-34

N⁶-(3-(4-carboxyphenyl)propanoyl)-
N²-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-lysyl-L-glutamic acid

DSL-140A    FF12A    F7    FL5B    FL69A    H    AB-31

TABLE 1-continued

| Compound # | FF | F | Z1b | Z1b | A' | A'' | Structure/IUPAC |
|---|---|---|---|---|---|---|---|
| | | | | | | | N<sup>6</sup>-(3-(2-carboxyphenyl)propanoyl)-N<sup>2</sup>-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carbonyl)-L-lysyl-L-glutamic acid |
| DSL-141A | FF12A | F7 | FL3 | | | | |

$N^6$-(3-(2-carboxyphenyl)propanoyl)-$N^2$-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carbonyl)-L-lysyl-L-glutamic acid 3-((2S,4R)-1-(1-hydroxy-3,3-dimethyl-1,3-dihydrobenzo[c][1,2]oxaborole-6-carbonyl)-4-(1-hydroxy-3,3-dimethyl-1,3-dihydrobenzo[c][1,2]oxaborole-6-carboxamido)pyrrolidine-2-carboxamido)propanoic acid

DSL-142A    FF116A    F7    FL3

3-((2S,3S)-2,3-bis(1-hydroxy-3,3-dimethyl-1,3-dihydrobenzo[c][1,2]oxaborole-6-carboxamido)butanamido)propanoic acid TABLE 1-continued

| Compound # | FF | F | Z1b | Z1b | A' | A" | Structure/IUPAC |
|---|---|---|---|---|---|---|---|
| DSL-143A | FF12A | F7 | FL65 | | | | |

(S)-3-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-5-phenylpentanoic acid

| DSL-144A | FF12A | F7 | FL5B | | | | |

((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-carbonyl)-
L-glutamic acid

| Compound # | FF | F | Z1b | Z1b | A' | A" | Structure/IUPAC |
|---|---|---|---|---|---|---|---|
| DSL-145A | FF12A | F13 | FL3 | | | | |

3-((2S,4R)-1-(1-hydroxy-1,3-
dihydrobenzo[c][1,2]oxaborole-3-
carbonyl)-4-(1-hydroxy-1,3-
dihydrobenzo[e][1,2]oxaborole-3-
carboxamido)pyrrolidine-2-
carboxamido)propanoic acid

| DSL-146A | FF116A | F13 | FL3 | | | | |
|---|---|---|---|---|---|---|---|

3-((2S,3S)-2,3-bis(1-hydroxy-1,3-
dihydrobenzo[c][1,2]oxaborole-3-
carboxamido)butanamido)propanoic
acid TABLE 1-continued

| Compound # | FF | F | Z1b | Z1b | A' | A" | Structure/IUPAC |
|---|---|---|---|---|---|---|---|
| DSL-147A | FF12A | F13 | FL65 | | | | |

(3S)-3-((2S,4R)-1-(1-hydroxy-1,3-
dihydrobenzo[c][1,2]oxaborole-3-
carbonyl)-4-(1-hydroxy-1,3-
dibydrobenzo[c][1,2]oxaborole-3-
carboxamido)pyrrolidine-2-
carboxamido)-5-phenylpentanoic acid

| DSL-148A | FF12A | F13 | FL5B | | | | |

((2S,4R)-1-(1-hydroxy-1,3-
dihydrobenzo[c][1,2]oxaborole-3-
carbonyl)-4-(1-hydroxy-1,3-
dihydrobenzo[c][1,2]oxaborole-3-
carboxamido)pyrrolidine-2-carbonyl)-
L-glutamic acid TABLE 1-continued

| Compound # | FF | F | Z1b | Z1b | A' | A" | Structure/IUPAC |
|---|---|---|---|---|---|---|---|
| DSL-149A | FF12A | F13 | FL3 | FL69A | H | AB-20 | |

3-((2S)-2-((2S,4R)-1-(1-hydroxy-1,3-
dihydrobenzo[c][1,2]oxaborole-3-
carbonyl)-4-(1-hydroxy-1,3-
dihydrobenzo[c][1,2]oxaborole-3-
carboxamido)pyrrolidine-2-
carboxamido)-6-(3-
phenylpropanamido)hexanamido)
propanoic acid

| Compound # | FF | F | Z1b | Z1b | A' | A" | Structure/IUPAC |
|---|---|---|---|---|---|---|---|
| DSL-150A | FF12A | F13 | FL3 | FL69A | H | AB-10 | |

8-(((5S)-6-((2-carboxyethyl)amino)-5-
((2S,4R)-1-(1-hydroxy-1,3-
dihydrobenzo[c][1,2]oxaborole-3-
carbonyl)-4-(1-hydroxy-1,3-
dihydrobenzo[c][1,2]oxaborole-3-
carboxamido)pyrrolidine-2-
carboxamido)-6-oxohexyl)amino)-8-
oxooctanoic acid TABLE 1-continued

| Compound # | FF | F | Z1b | Z1b | A' | A'' | Structure/IUPAC |
|---|---|---|---|---|---|---|---|
| DSL-151A | FF12A | F2 | FL3 | FL69A | H | AB-20 | |

3-((S)-2-((2S,4R)-1-(1-hydroxy-1,3-dihydrobenzo[e][1,2]oxaborole-7-carbonyl)-4-(1-hydroxy-1,3-dihydrobenzo[c][1,2]oxaborole-7-carboxamido)pyrrolidine-2-carboxamido)-6-(3-phenylpropanamido)hexanamido) propanoic acid

| Compound # | FF | F | Z1b | Z1b | A' | A'' | Structure/IUPAC |
|---|---|---|---|---|---|---|---|
| DSL-152A | FF12A | F2 | FL3 | FL69A | H | AB-10 | |

8-(((S)-6-((2-carboxyethyl)amino)-5-((2S,4R)-1-(1-hydroxy-1,3-dihydrobenzo[c][1,2]oxaborole-7-carbonyl)-4-(1-hydroxy-1,3-dihydrobenzo[e][1,2]oxaborole-7-carboxamido)pyrrolidine-2-carboxamido)-6-oxohexyl)amino)-8-oxooctanoic acid TABLE 1-continued

| Compound # | FF | F | Z1b | Z1b | A' | A" | Structure/IUPAC |
|---|---|---|---|---|---|---|---|
| DSL-153A | FF12A | F6 | FL3 | FL69A | H | AB-20 | |

3-((S)-2-((2S,4R)-1-(1-hydroxy-3,4-
dihydro-1H-benzo[c][1,2]oxaborinine-
8-carbonyl)-4-(1-hydroxy-3,4-
dihydro-1H-benzo[c][1,2]oxaborinine-
8-carboxamido)pyrrolidine-2-
carboxamido)-6-(3-
pheny lpropanamido)hexanamido)
propanoic acid

| | | | | | | | |
|---|---|---|---|---|---|---|---|
| DSL-154A | FF12A | F6 | FL3 | FL69A | H | AB-10 | |

8-(((S)-6-((2-carboxyethyl)amino)-5-
((2S,4R)-1-(1-hydroxy-3,4-dihydro-
1H-benzo[c][1,2]oxaborinine-8-
carbonyl)-4-(1-hydroxy-3,4-dihydro-
1H-benzo[c][1,2]oxaborinine-8-
carboxamido)pyrrolidine-2-
carboxamido)-6-oxohexyl)amino)-8-
oxooctanoic acid TABLE 1-continued

| Compound # | FF | F | Z1b | Z1b | A' | A" | Structure/IUPAC |
|---|---|---|---|---|---|---|---|
| DSL-155A | FF12A | F2 | FL3 | | | | |

3-((2S,4R)-1-(1-hydroxy-1,3-dihydrobenzo[c][1,2]oxaborole-7-carbonyl)-4-(1-hydroxy-1,3-dihydrobenzo[c][1,2]oxaborole-7-carboxamido)pyrrolidine-2-carboxamido)propanoic acid

| DSL-156A | FF116A | F2 | FL3 | | | | |
|---|---|---|---|---|---|---|---|

3-((2S,3S)-2,3-bis(1-hydroxy-1,3-dihydrobenzo[c][1,2]oxaborole-7-carboxamido)butanamido)propanoic acid TABLE 1-continued

| Compound # | FF | F | Z1b | Z1b | A' | A" | Structure/IUPAC |
|---|---|---|---|---|---|---|---|
| DSL-157A | FF12A | F6 | FL3 | | | | |
| DSL-158A | FF116A | F6 | FL3 | | | | |

DSL-157A 3-((2S,4R)-1-(1-hydroxy-3,4-dihydro-
1H-benzo[c][1,2]oxaborinine-8-
carbonyl)-4-(1-hydroxy-3,4-dihydro-
1H-benzo[c][1,2]oxaborinine-8-
carboxamido)pyrrolidine-2-
carboxamido)propanoic acid

DSL-158A 3-((2S,3S)-2,3-bis(1-hydroxy-3,4-
dihydro-1H-benzo[c][1,2]oxaborinine-
8-carboxamido)butanamido)propanoic
acid TABLE 1-continued

| Compound # | FF | F | Z1b | Z1b | A' | A" | Structure/IUPAC |
|---|---|---|---|---|---|---|---|
| DSL-159A | FF12A | F6 | FL3 | | | | |
| DSL-160A | FF116A | F6 | FL3 | | | | |

DSL-159A structure:

3-((2S,4R)-1-(1-hydroxy-3,4-dihydro-
1H-benzo[c][1,2]oxaborinine-7-
carbonyl)-4-(1-hydroxy-3,4-dihydro-
1H-benzo[c][1,2]oxaborinine-7-
carboxamido)pyrrolidine-2-
carboxamido)propanoic acid DSL-160A structure:

3-(2S,3S)-2,3-bis(1-hydroxy-3,4-
dihydro-1H-benzo[c][1,2]oxaborinine-
7-carboxamido)butanamido)propanoic
acid TABLE 1-continued

| Compound # | FF | F | Z1b | Z1b | A' | A'' | Structure/IUPAC |
|---|---|---|---|---|---|---|---|
| DSL-161A | FF12A | F2 | FL3 | FL69A | H | AB-20 | |

3-((S)-2-((2S,4R)-4-(2-(1-hydroxy-
1,3-dihydrobenzo[c][1,2]oxaborol-7-
yl)acetamido)-1-(2-(1-hydroxy-1,3-
dihydrobenzo[c][1,2]oxaborol-7-
yl)acetyl)pyrrolidine-2-carboxamido)-
6-(3-
phenylpropanamido)hexanamido)
propanoic acid

| DSL-162A | FF12A | F2 | FL3 | FL69A | H | AB-10 | |

8-(((S)-6-((2-carboxyethyl)amino)-5-
((2S,4R)-4-(2-(1-hydroxy-1,3-
dihydrobenzo[c][1,2]oxaborol-7-
yl)acetamido)-1-(2-(1-hydroxy-1,3-
dihydrobenzo[c][1,2]oxaborol-7-
yl)acetyl)pyrrolidine-2-carboxamido)-
6-oxohexyl)amino)-8-oxooctanoic
acid TABLE 1-continued

| Compound # | FF | F | Z1b | Z1b | A' | A" | Structure/IUPAC |
|---|---|---|---|---|---|---|---|
| DSL-163A | FF12A | F2 | FL3 | FL69A | H | AB-20 | |

3-((S)-2-((2S,4R)-1-(1-hydroxy-1,3-
dihydrobenzo[c][1,2]oxaborole-4-
carbonyl)-4-(1-hydroxy-1,3-
dibydrobenzo[c][1,2]oxaborole-4-
carboxamido)pyrrolidine-2-
carboxamido)-6-(3-
phenylpropanamido)hexanamido)
propanoic acid

| DSL-164A | FF12A | F2 | FL3 | | | | |

3-((2S,4R)-4-(2-(1-hydroxy-1,3-
dihydrobenzo[c][1,2]oxaborol-7-
yl)acetamido)-1-(2-(1-hydroxy-1,3-
dibydrobenzo[c][1,2]oxaboro]-7-
yl)acetyl)pyrrolidine-2-
carboxamido)propanoic acid TABLE 1-continued

| Compound # | FF | F | Z1b | Z1b | A' | A" | Structure/IUPAC |
|---|---|---|---|---|---|---|---|
| DSL-165A | FF12A | F2 | FL3 | FL69A | H | AB-10 | |

8-(((S)-6-((2-carboxyethyl)amino)-5-
((2S,4R)-1-(1-hydroxy-1,3-
dihydrobenzo[c][1,2]oxaborole-4-
carbonyl)-4-(1-hydroxy-1,3-
dihydrobenzo[c][1,2]oxaborole-4-
carboxamido)pyrrolidine-2-
carboxamido)-6-oxohexyl)amino)-8-
oxooctanoic acid

| Compound # | FF | F | Z1b | Z1b | A' | A" | Structure/IUPAC |
|---|---|---|---|---|---|---|---|
| DSL-166A | FF116A | F2 | FL3 | | | | |

3-((2S,3S)-2,3-bis(2-(1-hydroxy-1,3-
dihydrobenzo[c][1,2]oxaborol-7-
yl)acetamido)butanamido)propanoic
acid TABLE 1-continued

| Compound # | FF | F | Z1b | Z1b | A' | A'' | Structure/IUPAC |
|---|---|---|---|---|---|---|---|
| DSL-167A | FF12A | F2 | FL3 | | | | |

3-((2S,4R)-1-(1-hydroxy-1,3-
dibydrobenzo[e][1,2]oxaborole-4-
carbonyl)-4-(1-hydroxy-2,3-dihydro-
1H-benzo[b]borole-4-
carboxamido)pyrrolidine-2-
carboxamido)propanoic acid

| DSL-168A | FF116A | F2 | FL3 | | | | |

3-((2S,3S)-2,3-bis(1-hydroxy-1,3-
dihydrobenzo[c][1,2]oxaborole-4-
carboxamido)butanamido)propanoic
acid TABLE 1-continued

| Compound # | FF | F | Z1b | Z1b | A' | A" | Structure/IUPAC |
|---|---|---|---|---|---|---|---|
| DSL-169A | FF12A | F2 | FL3 | FL69A | H | AB-10 | |

8-(((S)-7-((2-carboxyethyl)amino)-5-
((2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)-7-oxoheptyl)amino)-8-
oxooctanoic acid

| Compound # | FF | F | Z1b | Z1b | A' | A" | Structure/IUPAC |
|---|---|---|---|---|---|---|---|
| DSL-170A | FF12A | F7 | FL3 | FL69A | H | AB-10 | |

8-(((S)-7-((2-carboxyethyl)amino)-5-
((2S,4R)-1-(1-hydroxy-3,3-dimethyl-
1,3-dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-7-oxoheptyl)amino)-8-
oxooctanoic acid TABLE 1-continued

| Compound # | FF | F | Z1b | Z1b | A' | A" | Structure/IUPAC |
|---|---|---|---|---|---|---|---|
| DSL-171A | FF12A | F2 | FL3 | FL69A | H | AB-20 | |

3-((S)-3-(2S,4R)-1-(1-hydroxy-1,3-
dihydrobenzo[c][1,2]oxaborole-6-
carbonyl)-4-(1-hydroxy-1,3-
dihydrobenzo[c][1,2]oxaborole-6-
carboxamido)pyrrolidine-2-
carboxamido)-7-(3-
phenylpropanamido)heptanamido)
propanoic acid

| Compound # | FF | F | Z1b | Z1b | A' | A" | Structure/IUPAC |
|---|---|---|---|---|---|---|---|
| DSL-172A | FF12A | F7 | FL3 | FL69A | H | AB-20 | |

3-((S)-3-((2S,4R)-1-(1-hydroxy-3,3-
dimethyl-1,3-
dihydrobenzo[c][1,2]oxaborole-6-
carbonyl)-4-(1-hydroxy-3,3-dimethyl-
1,3-dihydrobenzo[c][1,2]oxaborole-6-
carboxamido)pyrrolidine-2-
carboxamido)-7-(3-
phenylpropanamido)heptanamido)
propanoic acid TABLE 1-continued

| Compound # | FF | F | Z1b | Z1b | A' | A" | Structure/IUPAC |
|---|---|---|---|---|---|---|---|
| DSL-173A | FF12A | F7 | # | # | # | # | |

(S)-1-(2S,4R)-1-(1-hydroxy-3,3-
dimethyl-1,3-
dihydrobenzo[e][1,2]oxaborole-6-
carbonyl)-4-(1-hydroxy-3,3-dimethyl-
1,3-dihydrobenzo[c][1,2]oxaborole-6-
carboxamido)pyrrolidin-2-yl)-1,10,13-
trioxo-12-(4-(3-
phenylpropanamido)butyl)-5,8-dioxa-
2,11-diazaheptadecan-17-oic acid

| DSL-174A | FF12A | F7 | # | # | # | # | |

(S)-10-(2-(4-((3-
carboxypropanamido)methyl)
phenyl)acetamido)-6-((2S,4R)-1-(1-
hydroxy-3,3-dimethyl-1,3-
dihydrobenzo[c][1,2]oxaborole-6-
carbonyl)-4-(1-hydroxy-3,3-
dimethyl-1,3-
dihydrobenzo[c][1,2]oxaborole-6-
carboxamido)pyrrolidine-2-
carboxamido)-5-oxodecanoic acid

| DSL-175A | FF12A | F7 | # | # | # | # | |

$N^2$-((2S,4R)-1-(1-hydroxy-3,3-
dimethyl-1,3-
dihydrobenzo[c][1,2]oxaborole-6-
carbonyl)-4-(1-hydroxy-3,3-
dimethy 1-1,3-

TABLE 1-continued

| Compound # | FF | F | Z1b | Z1b | A' | A" | Structure/IUPAC |
|---|---|---|---|---|---|---|---|
| | | | | | | | dihydrobenzo[c][1,2]oxaborole-6-carboxamido)pyrrolidine-2-carbonyl)-N$^6$-(3-phenylpropanoyl)-L-lysyl-L-glutamic acid |

F. Synthesis of Compounds of Formula IB

Illustrative synthesis protocols are provided that can be used to synthesize the examples described.

The lines connecting cysteine residues are disulfide bonds. For the sake of clarity, the H- at the N-terminus of the A- and B-chain of insulin is not histidine, it is the hydrogen of the N-terminus. The —OH shown at the C-terminal end of the A- and B-chain is the C-terminus of the respective chain.

Insulin Expression and Conjugation Method 1

1a. Expression of proinsulin

Proinsulin can be expressed using standard IPTG induction of IPTG inducible expression constructs and vectors in E. coli strains such as B21 strain. Briefly, the expression construct consists of the B-chain, C-peptide, A-chain. For example, the c-peptide sequence of EAEDLQVGQVEL-GGGPGAGSLQPLALEGSLQR (SEQ ID NO:24070) can be used for expression of the proinsulin. Proinsulin is expressed in inclusion bodies (IBs), IBs are captured, washed and further purified, for example via an existing his-tag before sensor conjugation. Expression of the desired single-chain proinsulin can be performed via known procedures in the art. See, e.g., U.S. Pat. Nos. 5,457,066, 5,700, 662, 5,514,646, 9,050,371, and 10400021.

1b. Conjugation of Diboronate Sensor DSL-34B with Proinsulin.

Figure 10A:
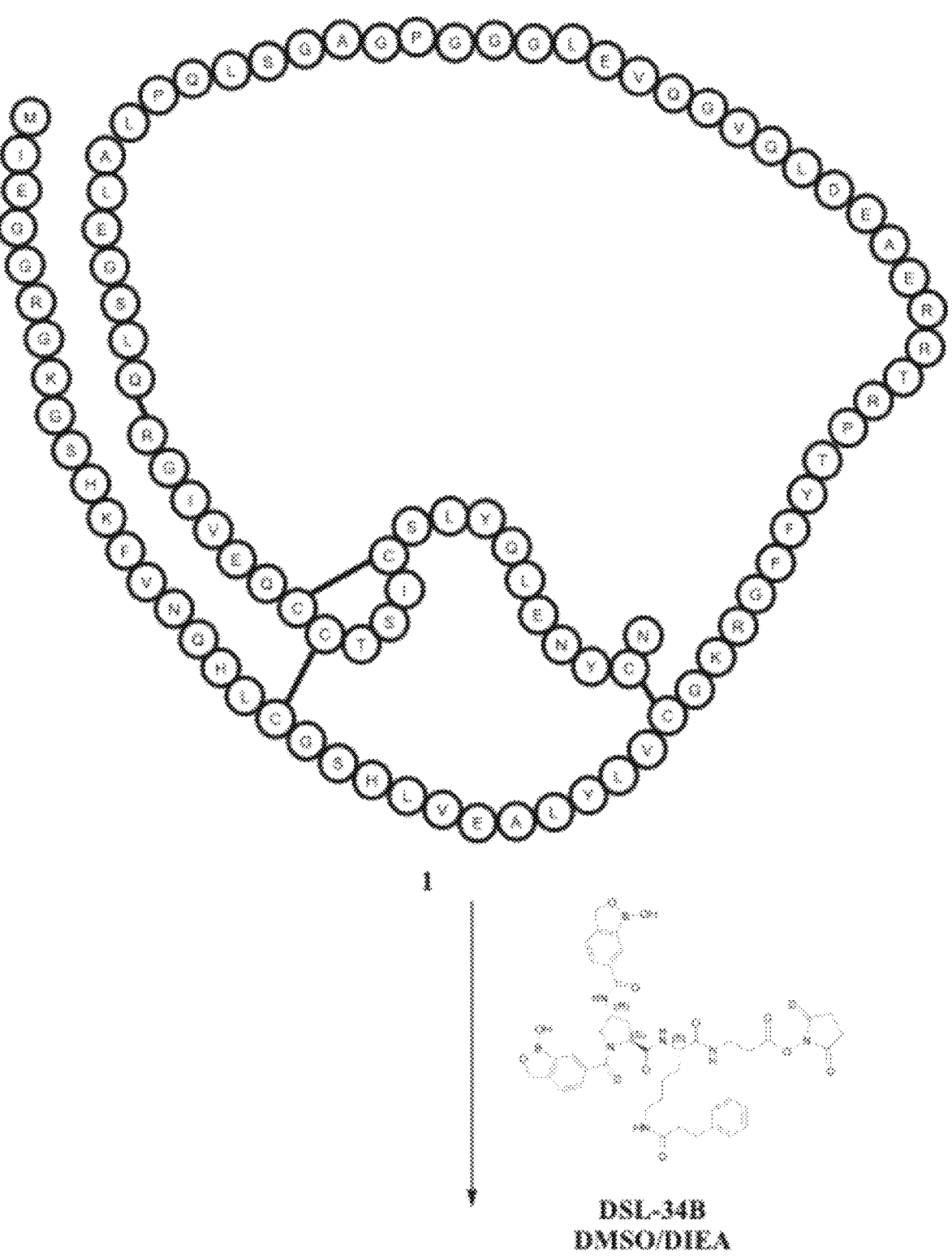
Figure 10B:
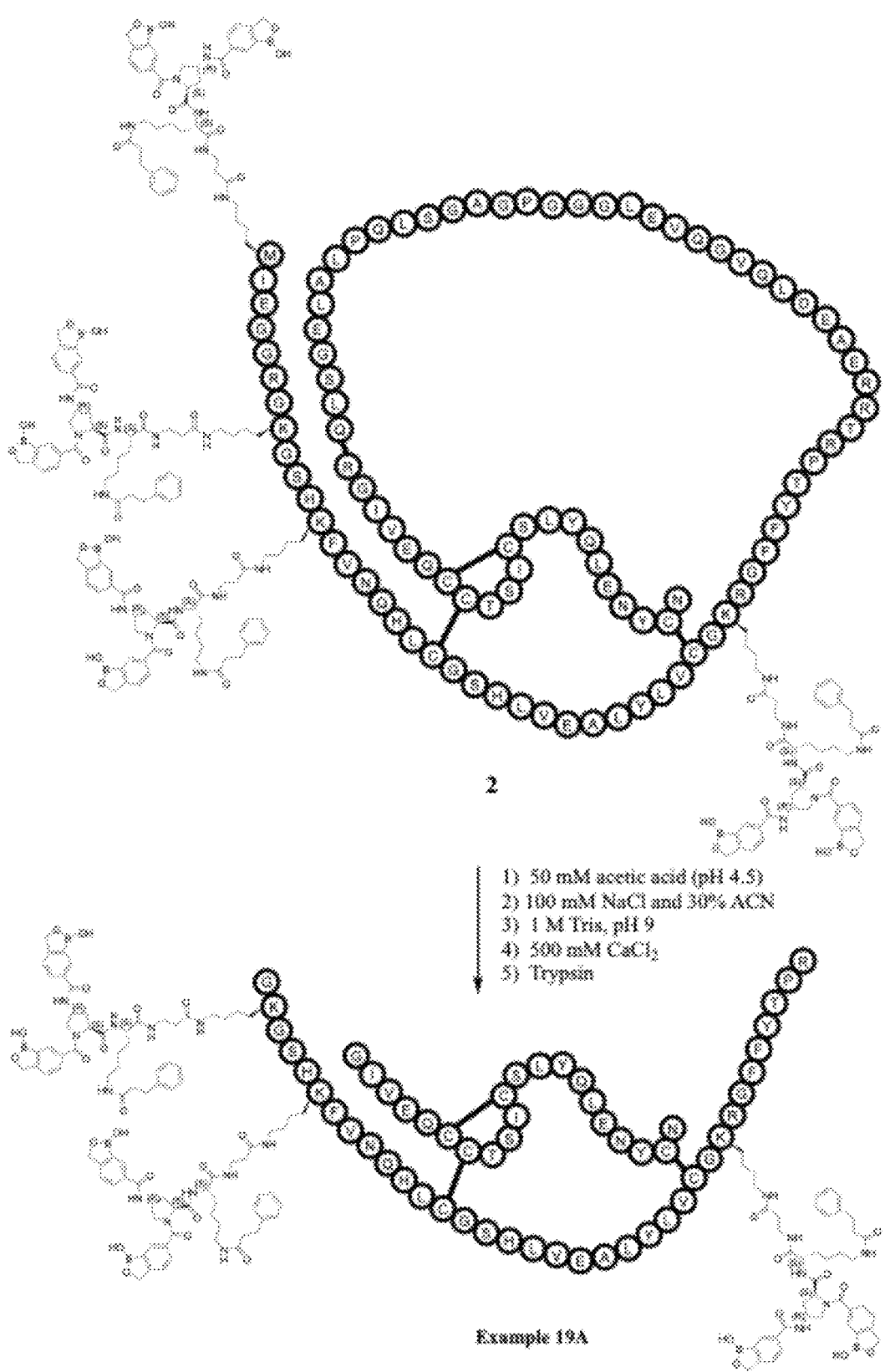

To a solution of single-chain proinsulin 1 (SEQ ID NO:24071) (20 mg) in DMSO (200 uL) was added 2,5-dioxopyrrolidin-1-yl 3-((S)-2-((2S,4R)-1-(1-hydroxy-1,3- dihydrobenzo[c][1,2]oxaborole-6-carbonyl)-4-(1-hydroxy-1,3-dihydrobenzo[c][1,2]oxaborole-6-carboxamido) pyrrolidine-2-carboxamido)-6-(3-phenylpropanamido) hexanamido)propanoate (DSL-34B, 9.2 mg) in DMSO (200 uL) and diisopropylethylamine (DIPEA, 20 uL) (FIG. 10A). The reaction was stirred at room temperature for 1 hr. Trifluoroacetic acid (TFA, 40 uL) was added to the reaction mixture to precipitate the proinsulin conjugate intermediate 2 (SEQ ID NO:24072) (FIG. 10B). Reaction mixture was centrifuged (11000 RPM, 5 min), decanted, and supernatant was resuspended in 100 uL solution of 50 mM acetic acid (pH 4.5), 100 mM NaCl and 30% ACN. Solution was diluted with 500 uL of water then 30 uL of 1M Tris pH 9 (50 mM final concentration), 6 uL of 500 mM CaCl$_2$) (5 mM final concentration) were added. The pH was adjusted with 0.5M NaOH (5-10 uL) to ~9-9.5 and trypsin (1:500 to 1:2000 trypsin mass to insulin mass ~10 uL of 0.2 ug/mL stock solution) was added. Crude solution was allowed to stir at r.t for 16 hours. The crude conjugated insulin conjugate was precipitated with TFA (~200 uL), centrifuged, decanted. Then crude precipitate was washed with water (2×500 uL) then dissolved in DMSO (100-200 uL), diluted with 20% ACN/Water (5-10 mL), and purified by reverse-phase HPLC. Fractions were collected, frozen, and lyophilized to yield a white powder (4-7 mg) of Example 19A (SEQ ID NO:24073 for the A-chain, SEQ ID NO:24075 for the B-chain) (FIG. 10B).

Examples IA, 4A, 6A-10A, 13A, 14A, 18A, 19A, 23, 25A, 26A, 28A, 30A, 32A-36A, 44A, 45A, 47A, 67A, 73A, 76A-82A, 84A, and 85A were synthesized under similar conditions.

| Example | Mass Expected (whole mass) | Mass Calculated [M + 5H − 5H$_2$O]$^{5+}$ | Mass Observed [M + 5H − 5H$_2$O]$^{5+}$ | Mass Calculated [M + 6H − 5H$_2$O]$^{6+}$ | Mass Observed [M + 6H − 5H$_2$O]$^{6+}$ |
|---|---|---|---|---|---|
| Example 1A | 8613.9331 | 1705.7866 | 1705.5606 | 1421.6555 | 1421.4915 |
| Example 4A | 8740.0719 | 1731.0144 | 1730.8393 | 1442.6787 | 1442.5644 |
| Example 6A | 9153.7526 | 1813.7505 | 1813.7420 | 1511.6254 | 1511.5718 |
| Example 7A | 7923.6145 | 1567.7229 | 1567.6899 | 1306.6024 | 1306.4176 |
| Example 8A | 8782.1189 | 1739.4238 | 1739.1836 | 1449.6865 | 1449.4731 |
| Example 9A | 8817.8932 | 1746.5786 | 1746.4686 | 1454.8155 | 1454.6752 |
| Example 10A | 8001.6615 | 1583.3323 | 1583.1050 | 1319.6102 | 1319.4272 |
| Example 13A | 8697.9158 | 1722.5862 | 1722.4869 | 1435.6526 | 1435.5521 |
| Example 14A | 7965.6615 | 1576.1323 | 1576.1914 | 1313.6102 | 1313.6601 |
| Example 18A | 8313.8493 | 1645.7699 | 1645.5378 | 1371.6416 | 1371.2578 |
| Example 19A | 8613.9311 | 1705.7862 | 1705.7672 | 1421.6552 | 1422.1946 |
| Example 23A | 8721.8746 | 1727.3749 | 1727.4543 | 1439.6458 | 1439.5606 |
| Example 25A | 8782.1189 | 1739.4238 | 1739.3922 | 1449.6865 | 1449.5164 |
| Example 26A | 8770.0884 | 1737.0176 | 1737.0506 | 1447.6814 | 1447.5519 |
| Example 28A | 8854.18 | 1753.8360 | 1753.5987 | 1461.6967 | 1461.5313 |
| Example 30A | 8938.2762 | 1770.6552 | 1770.4166 | 1475.7127 | 1475.5168 |
| Example 32A | 8601.9006 | 1703.3801 | 1703.5236 | 1419.6501 | 1419.6037 |
| Example 33A | 8938.2762 | 1770.6552 | 1770.7111 | 1475.7127 | 1475.7613 |
| Example 34A | 8685.9945 | 1720.1989 | 1720.3890 | 1433.6657 | 1433.8151 |
| Example 35A | 9022.3701 | 1787.4740 | 1787.5328 | 1489.7283 | 1489.7827 |
| Example 36A | 8770.0884 | 1737.0176 | 1737.1763 | 1447.6814 | 1447.6647 |
| Example 44A | 8764.2597 | 1735.8519 | 1735.8280 | 1446.7099 | 1446.6923 |
| Example 45A | 8680.1658 | 1719.0331 | 1719.2042 | 1432.6943 | 1432.4948 |
| Example 47A | 8764.2597 | 1735.8519 | 1735.6199 | 1446.7099 | 1446.4966 |

-continued

| Example | Mass Expected (whole mass) | Mass Calculated $[M + 5H - 5H_2O]^{5+}$ | Mass Observed $[M + 5H - 5H_2O]^{5+}$ | Mass Calculated $[M + 6H - 5H_2O]^{6+}$ | Mass Observed $[M + 6H - 5H_2O]^{6+}$ |
|---|---|---|---|---|---|
| Example 49A | 8848.3536 | 1752.6707 | 1752.6371 | 1460.7256 | 1460.6795 |
| Example 67A | 9082.2762 | 1799.4552 | 1799.2259 | 1499.7127 | 1499.5198 |
| Example 73A | 8956 | 1774.20 | 1773.98 | 1475.66 | 1475.48 |
| | | | | $[M + 6H - 6H_2O]^{6+}$ | |
| Example 76A | 8914.0884 | 1765.8177 | 1765.5883 | 1471.6814 | 1471.5017 |
| Example 77A | 8829.9445 | 1748.9889 | 1748.7934 | 1457.6574 | 1457.4832 |
| Example 78A | 8829.9445 | 1748.9889 | 1748.7364 | 1457.6574 | 1457.5006 |
| Example 79A | 9127.1997 | 1808.4399 | 1808.2167 | 1507.1999 | 1507.1909 |
| Example 80A | 8698.0250 | 1722.6050 | 1722.5434 | 1435.6708 | 1435.6550 |
| Example 81A | 9217.3406 | 1826.4621 | 1826.4406 | 1522.2234 | 1522.0216 |
| Example 82A | 8745.9006 | 1732.1801 | 1731.9653 | 1443.6501 | 1443.4628 |
| Example 84A | 9127.1997 | 1294.5999 | 1295.09 | 1510.1999 | 1510.4 |
| | | | $[M + 7H - 4H_2O]^{7+}$ | | $[M + 6H - 4H_2O]^{6+}$ |
| Example 85A | 8956.1353 | 1774.2270 | 1774.2454 | 1478.6892 | 1478.6870 |

G. Testing of Compounds for Activity in Biological Assays

Exemplary compounds (e.g. diboronated sensors) of the present disclosure can be tested using an alizarin red S (ARS) displacement assay.

G.1 Procedure for Determination of the Glucose, Fructose, and Lactate Binding (Kd) Using ARS Displacement Assay The association constant for the binding event between Alizarin Red S (ARS) and the exemplary compounds can be determined using standard methods in the art. Triplicate titrations of $10^{-5}$ M ARS in 0.1 M phosphate buffer, pH 7.4, is performed in a 96-well plate against serial dilutions of example compounds, ranging in concentration from 0-0.1M at 25° C. The example compound-ARS solution is incubated for 5-45 minutes at 25° C., and fluorescence intensity is measured using excitation wavelength 468 nm and emission wavelength 585 nm. Changes in intensity is plotted against the concentration of the example compound, and the intensity data is fitted to yield an association constant for ARS binding.

The association constant for the binding between a target sugar compound (e.g., glucose) and the aromatic boron-containing groups (DSL compounds) is determined via the displacement of ARS bound to the example compounds. Triplicate wells of $10^{-5}$ M ARS and 0.1 M example compounds in 0.1 M phosphate buffer, pH 7.4, is titrated in a 96-well plate against serial dilutions of the target sugar compound, ranging in concentration from 0-2.0 M at 25° C. The boron-ARS-carbohydrate solution is incubated for 30-60 minutes at 25° C. and the intensity of each well is measured in a plate reader at excitation wavelength 468 nm and emission wavelength 585 nm.

Changes in intensity are plotted against concentration of the target sugar compound, and the data is fitted to a one-site competition equation:

$$y = \min(y) + (\max(y) - \min(y))/(1 + 10^{x - logEC50})$$

to yield an association constant for the boron compound-target sugar compound binding event.

The binding constants of DSL compounds, such as DSL-1A to DSL-172A, to glucose, fructose, and/or lactate can be tested and calculated.

G.2 In Vitro Demonstration of Activity for Compounds of Formula IB

Chinese hamster ovary (CHO) cells constitutively expressing Human Insulin Receptor Isoform β were seeded in a 96-well tissue culture microplate at 35,000 cells/well and grown overnight in Roswell Park Memorial Institute (RPMI) 1640 media supplemented with Glutamine and 10% Fetal Bovine Serum (growth media). The next morning, growth media was replaced with fresh growth media.

A separate microplate of spiking media was prepared with a stepwise serial dilution of compounds of Formula IB in Dulbecco's Modified Eagle Medium (DMEM) media (without glucose, without phenol red, with 4% w/v serum albumin). Wells of serially diluted compounds of Formula IB were prepared in triplicate with an appropriate "high" (e.g., 20 mM) and "low" (e.g., 3 mM) concentration of glucose to determine change in potency of compounds of Formula IB at various potential blood glucose levels. Wild type insulin served as a positive control and media without any compounds served as a negative control.

Growth media on cells in the 96-well tissue culture microplate was then replaced with DMEM media (without glucose, without phenol red) and the plate was allowed to sit for 5 minutes at 37° C. The media was aspirated and replaced with the contents of the separate prepared plate (spiking media) for 10 minutes at 37° C. After 10 minutes, the spiking media was aspirated and the cells were fixed with 10% neutral buffered formalin for 10 minutes at room temperature. The neutral buffered formalin was then aspirated, and the microplate was stringently washed with PBS, pH 7.4. The microplate was then permeabilized and blocked with PBS, pH 7.4 supplemented with 10% v/v Fetal Bovine Serum and 0.1% Triton X-100 for 30 minutes. The plate was then stained at 4° C. overnight with 5% FBS in PBS+1:680 ratio (v:v) of Rabbit (Rb) α-phospho-Y1150/Y1151 IR antibody (Cell Signaling Technologies #3024). After overnight incubation followed by stringent washes with PBS, pH 7.4, the microplate was incubated at 37° C. in 5% FBS in PBS+1:1000 ratio (v/v) of HRP α-Rabbit antibody (Cell Signaling Technologies, #7074) for 100 minutes. The plate was stringently washed with PBS, pH 7.4, and colorimetric readout was developed for 15 minutes at 37° C. using TMB substrate. Color development was stopped with the addition of 0.1 M hydrochloric acid and absorbance measured at 450 nm. Triplicate absorbance values were plotted in GraphPad Prism and analyzed using a four-parameter logistic regression to generate dose-response curves. The EC50 of the dose-response curves were compared to assess fold activation of the exemplary compounds of Formula IB from low to high glucose concentration. The ratio of EC50 values for GSI at high and low glucose concentrations were taken to calculate fold-change in insulin activity. The EC50 was calculated using the following equation:

$$Y=\text{Bottom}+(X\hat{}\,\text{Hillslope})*(\text{Top}-\text{Bottom})/$$
$$(X\hat{}\,\text{HillSlope}+\text{EC50}\hat{}\,\text{HillSlope}).$$

Some examples disclosed herein have an insulin receptor phosphorylation (IR Phosphorylation) (fold change) ranging from ≥1.2 to 20. Some examples disclosed herein had an insulin receptor phosphorylation (IR Phosphorylation) (fold change) ranging from ≥1.2 to 14.

G.3 In Vivo Demonstration of Activity for Compounds of Formula I

Male Sprague-Dawley rats underwent surgical cannulation of a carotid artery and jugular vein for blood sampling and infusions and were allowed to recover for one week. Cannulated rats were treated with streptozotocin (STZ, 55 mg/kg, 7 days) to induce a diabetic state (blood glucose concentration >300 mg/dL). Diabetic rats were fasted overnight, then placed in a solo experimental chamber and connected to sampling/infusion lines. Prior to injection of insulin examples, glucose was infused to raise the blood glucose level (BG) or phloridzin is used to lower the BG of each rat to achieve a cohort of rats in a hyperglycemic state (200 mg/dL, N=6-8) or euglycemic state (100 mg/dL, N=6-8). Blood glucose and the glucose infusion rate (GIR) required to maintain clamped BG were measured every 5 minutes and the GIR was adjusted to maintain the desired BG level. Somatostatin (5 ug/kg/min) was continuously infused throughout the study beginning with the administration of phloridzin or glucose. At time 0 min, a bolus dose (1 nmol/kg to 60 nmol/kg) of a compound of Formula IB was infused over a 10 second period, and glucose was continuously infused at variable rates to maintain the hyperglycemia (200 mg/dL) or euglycemia steady state (100 mg/dL) for 300 minutes. The total area-under-the-curve (AUC) value of total glucose infusion post-compound injection until the GIR returned to its pre-compound injection value or 300 minutes was achieved was calculated for both hyperglycemic (200 mg/dL) and euglycemic (100 mg/dL) levels. Area under the curve (AUC) was calculated using the trapezoid rule and with baseline correction applied. Averaged GIR values from 30 minutes prior to injections to the injections were subtracted from each GIR value from time 0 to time 600 min for baseline correction. The trapezoidal calculation is as follows:

$$\int_a^b f(x)dx \approx (b-a)\cdot\frac{1}{2}(f(a)+f(b)).$$

Where a is the first time point (0 min) and b is the last time point (300 min). The area was calculated as a subdivision of small trapezoids as follows:

$$\int_a^b f(x)dx \approx$$
$$\frac{\Delta x}{2}(f(x_0)+2f(x_1)+2f(x_2)+2f(x_3)+2f(x_4)+\cdots+2f(x_{N-1})+x(f_N)).$$

Such that $\Delta x$ is the difference between each time point.

Compounds of Formula IB require greater GIR and total glucose infusion AUC to maintain clamped hyperglycemic BG than euglycemic BG, demonstrating a glucose-responsive increase in compound glucose-lowering action at increased BG. Compounds exhibited AUC values ranging from 250 to-5100 under hyperglycemic conditions and 200-to-4600 under euglycemic levels. The ratio of hyperglycemic AUC to euglycemic AUC ranged from 0.1-to-3.3 in 200 mg/dL to 100 mg/dL.

G.4 Pharmacokinetics for Compounds of Formula I

Pharmacokinetic (PK) properties of examples disclosed herein were also characterized following injection of insulin examples in euglycemic-treated rats as described above. Data was generated using the Meso Scale Discovery (MSD) ruthenium based electrochemiluminescence assay. Blood samples were taken at 0 min, 1 min, 5 min, 10 min, 15 min, 30 min, 60 min, 90 min, 120 min, 150 min, 180 min, 210 min, 240 min, 270 min, and 300 min for euglycemic experiments. Clearance values (CL), terminal half-life (t1/2), and apparent volume of distribution at steady state (Vss) were determined using non-compartmental analysis (NCA). See, e.g., Kittrell H C, et al. Pharmacokinetics of Intravenous, Intramuscular, Oral, and Transdermal Administration of Flunixin Meglumine in Pre-wean Piglets. *Front Vet Sci.* 2020 (using PKanalix (Monolix Suite 2019R2, Lixoft, France)); Nnane et al. Non-Clinical Pharmacokinetics, Prediction of Human Pharmacokinetics and First-in-Human Dose Selection for CNTO 5825, an Anti-Interleukin-13 Monoclonal Antibody, *Basic & Clinical Pharmacology & Toxicology,* 2015, 117, 219-225 (using a non-compartmental analysis module in WinNonlin (version 5.2.1) (Pharsight, Mountain View, CA, USA) to calculate PK parameters).

Generally, NCA will determine the following directly from the data:

Cmax—Maximum observed concentration (units=concentration)

Tmax—The time where the maximum concentration was observed (units=time)

AUC—The area under the curve (units=time×concentration)

AUMC—The area under the first moment curve (units=time$^2$×concentration)

Each sampling interval is a trapezoid and the area of each can be calculated and added up for all of the n samples:

$$AUC = \int_0^{t_f} Cdt \approx \sum_{i=1}^{n-1}\frac{C_i+C_{i+1}}{2}\times(t_{i+1}-t_i)$$

$$AUMC = \int_0^{t_f} t\times Cdt \approx \sum_{i=1}^{n-1}\frac{t_iC_i+t_{i+1}C_{i+1}}{2}\times(t_{i+1}-t_i)$$

The CL, Vss, and terminal half-life can be calculated as follows:

Clearance: CL=Dose/AUC

Mean residence time: MRT=AUMC/AUC

Apparent volume of distribution at steady state: Vss=MRT×CL

Half-life: Terminal slope of the natural log of the data

Properties like AUC and AUMC can also be calculated using extrapolation from the last time point to infinity to account for data beyond the observations at hand.

The subsequent values of clearance, volumes of distribution, etc. can also change with extrapolation.

Some examples disclosed herein exhibited (a) CL values ranging from about 0.13 ml/min/kg to about 2.4 ml/min/kg; (b) terminal half-life ranging from at least about 100 minutes, for example 100 minutes to about 260 minutes; and (c) Vss values ranging from about 18 mL/kg to about 123 mL/kg. The data supports an extended duration of bioavailability for compounds disclosed herein.

It is also observed in cell-based experiments on compounds containing formulae FF116, and FF116A-D that sensors with geminal alkyl substituent on the same carbon as the nitrogen conjugated to the boroxole or boronates provided between 5-56% higher glucose responsiveness in the range of 3-20 mM glucose in comparison to variants that do not have the geminal alkyl substituents. For example, when a Z1C represented by one of formulae FF12, FF12A-D, FF116, FF116A-D is conjugated to lysine residues in insulin wherein the boronates (B1, B2) in formulae FF12, FF12A-D, FF116, and FF116A-D are represented by F2, the resulting insulin is observed to be between 11-56% more responsive to changes in glucose levels between 3-20 mM glucose than if instead of one of the formulae FF12, FF12A-D, FF116, and FF116A-D one uses 2,3-diaminopropionic acid. This data shows that the presence of the geminal alkyl substituent on the same carbon as the nitrogen conjugated to the boroxole or boronates improves glucose responsiveness of the resulting insulin conjugate, and in tested variations in the 3-20 mM glucose range.

In some embodiments, it is believed that this general principle extends to other formulae FF12, FF12A-D, FF114, FF115, FF116, FF116A-D, FF117, FF193, and FF203 providing a framework for enhancement of glucose responsiveness by at least 5%, at least 10%, at least 20%, or at least 40% in the 3-20 mM or 2-50 mM glucose ranges.

In some embodiments, the presence of the carbonyl group adjacent to- or within less than two carbon centers away from the amine groups in FF formulae (to which aromatic boron-containing groups are conjugated) may enhance glucose responsiveness through impacting ability to turn off activity of drug substance through plasma protein interactions such as with albumin and that this is independent of glucose affinity such that glucose affinity is not impacted by the position of this carbonyl group.

In further embodiments, the pharmacokinetics of the molecules and potential albumin or blood proteins binding may be impacted by the position of this carbonyl group, and thereby enhance overall glucose responsiveness whilst the absolute glucose affinity is maintained or nearly identical. Therefore, in certain embodiments of the present disclosure, the carbonyl group (as part of an acid, amid or linkage to X in FF formulae) is placed within less than three, or within less than two-carbon centers away from one of the two amines to which the boron-containing compounds are conjugated. In certain embodiments, the placement of amines within two carbon centers from each other enables the spatial and geometric constraining of the aromatic boron-containing groups to enhance glucose binding and selectively, and furthermore the presence of a carbonyl group (for example, as part of an amide linkage) which is within less than two carbon centers, from one of the two amines (to which aromatic boron-containing groups are attached) ensures differential albumin binding in a manner that results in the compound exhibiting glucose responsiveness in the blood and in the body. In some embodiments, the combination of geometrical constraining of the two amines to which the aromatic boron-containing groups are conjugated, as well as the presence of the carbonyl within one to two carbon centers from one of the amines provides the necessary requirements for glucose responsiveness in physiological blood and plasma glucose levels.

In some embodiments, the interaction of the linker with the Z1c may help further enhance glucose responsiveness. For example, enhanced glucose responsiveness may result in some embodiments where Z1c is selected from FF12, FF12A-D, FF116, FF116A-D, B1 and B2 are represented by F2 or F7, wherein each of the remaining R1 is H, and wherein the linker is selected from a relatively hydrophobic amino acid or contains a relatively hydrophobic molecule (e.g., linker) selected from FL3, FL65A, FL65B, FL69, FL69A, FL69B, FL70, FL70A, and FL70B. For example, enhanced glucose responsiveness may result in some embodiments where Z1c is selected from FF12, FF12A-D, FF116, FF116A-D, B1 and B2 are represented by F2 or F7, wherein one of the remaining R1 is $CF_3$ and the remaining R1 is H, and wherein the linker is selected from a hydrophilic amino acid or contains a hydrophilic molecule (e.g., linker) selected from FL5, FL5A, and FL5B.

In some embodiments, glucose responsiveness at physiological ranges of 3-10 mM, 4-10 mM, 3-20 mM or 4-20 mM glucose is further enhanced either by (i) a combination of a relatively hydrophobic linker (e.g., FL3, FL65A, FL65B, FL69, FL69A, FL69B, FL70, FL70A, and FL70B) and a Z1c in which both B1 and B2 are selected from F2 or F7, wherein all remaining R1 are H, or (ii) a combination of a relatively hydrophilic linker (e.g., FL5, FL5A, FL5B) and a Z1c in which both B1 and B2 are selected from F2 or F7, wherein one of the remaining R1 is CF3.

In some embodiments, glucose responsiveness of an insulin at physiological ranges of 3-10 mM, 4-10 mM, 3-20 mM or 4-20 mM glucose is further enhanced either by (i) a combination of a relatively hydrophobic linker and a Z1c in which both B1 and B2 are selected from F2, wherein all remaining R1 are H, wherein at least three or at least four lysine residues in the insulin are conjugated to a Z1c or (ii) a combination of a relatively hydrophilic linker and a Z1c in which both B1 and B2 are selected from F2, wherein one of the remaining R1 is CF3, and wherein at least two or at least three lysine residues in the insulin are conjugated to a Z1c.

In some embodiments, glucose responsiveness of an insulin at physiological ranges of 3-10 mM, 4-10 mM, 3-20 mM or 4-20 mM glucose is further enhanced either by (i) a combination of a relatively hydrophobic linker and a Z1c in which both B1 and B2 are selected from F7, wherein all remaining R1 are H, wherein at least three or at least four lysine residues in the insulin are conjugated to a Z1c or (ii) a combination of a relatively hydrophilic linker and a Z1c in which both B1 and B2 are selected from F7, wherein one of the remaining R1 is CF3, and wherein at least two or at least three lysine residues in the insulin are conjugated to a Z1c.

In some embodiments, glucose responsiveness is enhanced through selection of combination of the linker and Z1c is selected from (i) a combination of a relatively hydrophobic linker and a Z1c in which both B1 and B2 are selected from F2, wherein all remaining R1 are H, or (ii) a combination of a relatively hydrophilic linker and a Z1c in which both B1 and B2 are selected from F2, wherein one of the remaining R1 is CF3 and the remaining R1 is H.

In some embodiments, glucose responsiveness is enhanced through selection of combination of the linker and Z1c is selected from (i) a combination of a relatively hydrophobic linker and a Z1c in which both B1 and B2 are selected from F2, wherein all remaining R1 are H, or (ii) a combination of a relatively hydrophilic linker and a Z1c in which both B1 and B2 are selected from F2, wherein one of the remaining R1 is CF3 and the remaining R1 is H.

In some embodiments, glucose responsiveness is enhanced through selection of combination of the linker and Z1c is selected from (i) a combination of a relatively hydrophobic linker and a Z1C selected from FF12, FF12A-D, FF116, FF116A-D, in which both B1 and B2 are selected from F2, wherein all remaining $R_1$ are H, or (ii) a combination of a relatively hydrophilic linker and a Z1c selected from FF12, FF12A-D, FF116, FF116A-D, in which both B1 and B2 are selected from F2, wherein one of the remaining $R_1$ is $CF_3$ and the remaining $R_1$ is H.

Experiments on cell-based assays of insulins with lysine residues conjugated with one of formulae FF12, FF12A-D, FF114, FF115, FF116, FF116A-D, FF117, FF193, and FF203, demonstrated that the enhanced glucose responsiveness of the insulins is increased when one or more lysine residues are modified as described by Formula IB using one of formulae FF12, FF12A-D, FF114, FF115, FF116, FF116A-D, FF117, FF193, and FF203, and wherein the lysine residues are present in insulin (as insertions or mutations) or in a polypeptide that is appended to the N- or C-terminus of the B-chain of insulin or the C-terminus of the A-chain of insulin, and wherein there are additional lysine residues within the insulin sequence that are similarly modified. The results are further corroborated by testing of the compounds of Formula IB in STZ diabetic mouse models wherein the activity of the insulin is measured through bolus injections of the compounds of Formula IB followed by glucose challenges and measurements of blood glucose, or through glucose clamp assays in which activity of the insulins is measured as a function of blood glucose levels. The results further showed that exemplary compounds of Formula IB disclosed herein function in the body and are responsive to physiological changes in blood glucose and provide dynamic insulin action in the body in response to changes in blood glucose levels. In certain embodiments one or more lysine residues near the N-terminus of a polypeptide appended to the N-terminus of the B-chain of insulin, as well as at least one additional lysine in the B-chain of insulin are conjugated as described by Formula I.

Sequences

In certain embodiments, a sequence is appended to the N-terminus and/or C-terminus, and/or inserted into the sequence of the A-chain of insulin, wherein the A-chain of insulin comprises one of the following sequences, optionally with up to four additional deletions and/or mutations:

```
                            (SEQ ID NO: 1)
GIVEQCCTSICSLYQLENYCN;

(SEQ ID NO: 3)
GIVKQCCTSICSLYQLENYCN;

(SEQ ID NO: 4)
GIVEQCCHSICSLYQLENYCN;

(SEQ ID NO: 5)
GIVEQCCASICSLYQLENYCN;

(SEQ ID NO: 6)
GIVEQCCTRICSLYQLENYCN;

(SEQ ID NO: 7)
GIVEQCCTKICSLYQLENYCN;

(SEQ ID NO: 8)
GIVEQCCTSICSEYQENYCN;
```

-continued

```
                            (SEQ ID NO: 9)
GIVKQCCTSICSLYQLENYCG;

(SEQ ID NO: 10)
GIVEQCCHSICSLYQLENYCG;

(SEQ ID NO: 11)
GIVEQCCASICSLYQLENYCG;

(SEQ ID NO: 12)
GIVEQCCTRICSLYQLENYCG;

(SEQ ID NO: 13)
GIVEQCCTKICSLYQLENYCG;

(SEQ ID NO: 14)
GIVEQCCTSICSEYQENYCG;

(SEQ ID NO: 15)
GIVEQCCTSICSEYQENYC;

(SEQ ID NO: 16)
GIVEQCCTSICSLYQLENYCNK;

(SEQ ID NO: 17)
KPGIVEQCCTSICSLYQLENYCN;

(SEQ ID NO: 18)
KPIVEQCCTSICSLYQLENYCN;

(SEQ ID NO: 19)
KPVEQCCTSICSLYQLENYCN;

(SEQ ID NO: 20)
KPGVEQCCTSICSLYQLENYCN;

(SEQ ID NO: 21)
GEKPVEQCCTSICSLYQLENYCN;

(SEQ ID NO: 22)
KPGEKPVEQCCTSICSLYQLENYCN;

(SEQ ID NO: 23)
KPVEQCCTSICSLYQLENYCNK;

(SEQ ID NO: 24)
KPVEQCCTSICSLYQLENYCNEKP;

(SEQ ID NO: 25)
GIVEQCCTSICSLYQLENYCGK;

(SEQ ID NO: 26)
KPGIVEQCCTSICSLYQLENYCG;

(SEQ ID NO: 27)
KPIVEQCCTSICSLYQLENYCG;

(SEQ ID NO: 28)
KPVEQCCTSICSLYQLENYCG;

(SEQ ID NO: 29)
KPGVEQCCTSICSLYQLENYCG;

(SEQ ID NO: 30)
GEKPVEQCCTSICSLYQLENYCG;

(SEQ ID NO: 31)
KPGEKPVEQCCTSICSLYQLENYCG;

(SEQ ID NO: 32)
KPVEQCCTSICSLYQLENYCGK;

(SEQ ID NO: 33)
KPVEQCCTSICSLYQLENYCGEKP;
```

-continued

```
                              (SEQ ID NO: 24051)
GIVEQCCTSICSLYQLENYCG;
and (SEQ ID NO: 24052)
GIVEQCCTSICSLEQLENYCG;
``` and/or a sequence is appended to the N-terminus and/or C-terminus, and/or inserted into the sequence of the B-chain of insulin, wherein the B-chain of insulin comprises one of following sequences, and optionally with up to four additional deletions and/or mutations:

```
                              (SEQ  ID NO: 2)
FVNQHLCGSHLVEALYLVCGERGFFYTPKT;

(SEQ  ID NO: 34)
FVNQHLCGSHLVEALYLVCGERGFFYTP;

(SEQ  ID NO: 35)
FVNQHLCGSHLVEALYLVCGKRGFFYTP;

(SEQ  ID NO: 36)
FVNQHLCGSHLVEALYLVCGKRGFFYTPRT;

(SEQ  ID NO: 37)
FVNQHLCGSHLVEALYLVCGKRGFFYT;

(SEQ  ID NO: 38)
VNQHLCGSHLVEALYLVCGERGFFYTPKT;

(SEQ  ID NO: 39)
NQHLCGSHLVEALYLVCGERGFFYTPKT;

(SEQ  ID NO: 40)
QHLCGSHLVEALYLVCGERGFFYTPKT;

(SEQ  ID NO: 41)
PFVNQHLCGSHLVEALYLVCGERGFFYTPKT;

(SEQ  ID NO: 42)
PFVNQHLCGSHLVEALYLVCGKRGFFYTPRT;

(SEQ  ID NO: 43)
PFVNQHLCGSHLVEALYLVCGKEGFFYTPRT;

(SEQ  ID NO: 44)
PFVNQHLCGSHLVEALYLVCGKRGFFYTPR;

(SEQ  ID NO: 45)
PFVNQHLCGSHLVEALYLVCGKRGFFYTRPT;

(SEQ  ID NO: 46)
PFVNQHLCGSHLVEALYLVCGKRGFFYTRP;

(SEQ  ID NO: 47)
PFVNQHLCGSHLVEALYLVCGKNGFFYTPRT;

(SEQ  ID NO: 48)
PFVNQHLCGSHLVEALYLVCGKNGFFYTPRT;

(SEQ  ID NO: 49)
PFVNQHLCGSHLVEALYLVCGKNGFFYTPR;

(SEQ  ID NO: 50)
PFVNQHLCGSHLVEALYLVCGKNGFFYTRPT;

(SEQ  ID NO: 51)
PFVNQHLCGSHLVEALYLVCGKNGFFYTRP;

(SEQ  ID NO: 52)
PFVNQHLCGSHLVEALYLVCGKEGFFYTPRT;

(SEQ  ID NO: 53)
PFVNQHLCGSHLVEALYLVCGKEGFFYTPRT;

(SEQ  ID NO: 54)
PFVNQHLCGSHLVEALYLVCGKEGFFYTPR;

(SEQ  ID NO: 55)
PFVNQHLCGSHLVEALYLVCGKEGFFYTRPT;

(SEQ  ID NO: 56)
PFVNQHLCGSHLVEALYLVCGKEGFFYTRP;
```

-continued (SEQ  ID NO: 57)
PFVNQHLCGSHLVEALYLVCGKRGFFYTPR;

(SEQ  ID NO: 58)
PVNQHLCGSHLVEALYLVCGERGFFYTPKT;

(SEQ  ID NO: 59)
PVNQHLCGSHLVEALYLVCGKRGFFYTPRT;

(SEQ  ID NO: 60)
PVNQHLCGSHLVEALYLVCGKRGFFYTPR;

(SEQ  ID NO: 61)
PNQHLCGSHLVEALYLVCGERGFFYTPKT;

(SEQ  ID NO: 62)
PNQHLCGSHLVEALYLVCGKRGFFYTPRT;

(SEQ  ID NO: 63)
PNQHLCGSHLVEALYLVCGKRGFFYTPR;

(SEQ  ID NO: 64)
PQHLCGSHLVEALYLVCGERGFFYTPKT;

(SEQ  ID NO: 65)
PQHLCGSHLVEALYLVCGKRGFFYTPRT;

(SEQ  ID NO: 66)
PQHLCGSHLVEALYLVCGKRGFFYTPR;

(SEQ  ID NO: 67)
PFVNQHLCGSHLVEALYLVCGERGFFYTKPT;

(SEQ  ID NO: 68)
PFVNQHLCGSHLVEALYLVCGERGFFYTKP;

(SEQ  ID NO: 69)
PVNQHLCGSHLVEALYLVCGERGFFYTKPT;

(SEQ  ID NO: 70)
PVNQHLCGSHLVEALYLVCGERGFFYTKP;

(SEQ  ID NO: 71)
PNQHLCQSHLVEALYLVCGERGFFYTKPT;

(SEQ  ID NO: 72)
PNQHLCGSHLVEALYLVCGERGFFYTKP;

(SEQ  ID NO: 73)
PQHLCGSHLVEALYLVCGERGFFYTKPT;

(SEQ  ID NO: 74)
FVNQHLCGSHLVEALYLVCGERGFFYTPK;

(SEQ  ID NO: 24047)
FVNQHLCGSHLVEALYLVCGKRGFFYTPKT;

(SEQ  ID NO: 24048)
FVNQHLCGSHLVEALYLVCGKRGFFYTPR;

(SEQ  ID NO: 24060)
KFVNQHLCGSHLVEALYLVCGKRGFFYTPKT;

(SEQ  ID NO: 24061)
KGSHFVNQHLCGSHLVEALYLVCGKRGFFYTPR;

(SEQ  ID NO: 24062)
KGSHQHLCGSHLVEALYLVCGKRGFFYTPR;

(SEQ  ID NO: 24063)
KQSHKQHLCGSHLVEALYLVCGKRGFFYTPR;

(SEQ  ID NO: 24064)
GKPGGGGSGGGGSGGGGSFVNQHLCGSHLVEALYLVCGDRGFFYTPK;

(SEQ  ID NO: 25000)
KFVNQHLCGSHLVEALYLVCGKRGFFYTRPT;

(SEQ  ID NO: 25001)
KFVGQHLCGSHLVEALYLVCGKRGFFYTRPT;

-continued

```
                                       (SEQ ID NO: 25002)
KHLCGSHLVEALYLVCGKRGFFYTRPT;

(SEQ ID NO: 25003)
KFVNQHLCGSHLVEALYLVCGKRGFFYTRP;

(SEQ ID NO: 25004)
KFVGQHLCGSHLVEALYLVCGKRGFFYTRP;

(SEQ ID NO: 25005)
KHLCGSHLVEALYLVCGKRGFFYTRP;

(SEQ ID NO: 25006)
KFVSQHLCGSHLVEALYLVCGKRGFFYTPR;

(SEQ ID NO: 25007)
KFVTQHLCGSHLVEALYLVCGKRGFFYTPR;

(SEQ ID NO: 25008)
KFVGQHLCGSHLVEALYLVCGKRGFFYTPR;

(SEQ ID NO: 25009)
KFVNQHLCGSHLVEALYLVCGKRGFFYTPR;

(SEQ ID NO: 25010)
KHLCGSHLVEALYLVCGKRGFFYTPR;

(SEQ ID NO: 25011)
KFVNQHLCGSHLVEALYLVCGERGFFYTKPT;

(SEQ ID NO: 25012)
KFVGQHLCGSHLVEALYLVCGERGFFYTKPT;

(SEQ ID NO: 25013)
KHLCGSHLVEALYLVCGERGFFYTKPT;

(SEQ ID NO: 25014)
KFVNQHLCGSHLVEALYLVCGERGFFYTKP;

(SEQ ID NO: 25015)
KFVGQHLCGSHLVEALYLVCGERGFFYTKP;

(SEQ ID NO: 25016)
KHLCGSHLVEALYLVCGERGFFYTKP;

(SEQ ID NO: 25017)
KFVSQHLCGSHLVEALYLVCGERGFFYTPK;

(SEQ ID NO: 25018)
KFVTQHLCGSHLVEALYLVCGERGFFYTPK;

(SEQ ID NO: 25019)
KFVGQHLCGSHLVEALYLVCGERGFFYTPK;

(SEQ ID NO: 25020)
KFVNQHLCGSHLVEALYLVCGERGFFYTPK;

(SEQ ID NO: 25021)
KHLCGSHLVEALYLVCGERGFFYTPK;

(SEQ ID NO: 25022)
KFVNQHLCGSHLVEALYLVCGDRGFFYTKPT;

(SEQ ID NO: 25023)
KFVGQHLCGSHLVEALYLVCGDRGFFYTKPT;

(SEQ ID NO: 25024)
KHLCGSHLVEALYLVCGDRGFFYTKPT;

(SEQ ID NO: 25025)
KFVNQHLCGSHLVEALYLVCGDRGFFYTKP;

(SEQ ID NO: 25026)
KFVGQHLCGSHLVEALYLVCGDRGFFYTKP;

(SEQ ID NO: 25027)
KHLCGSHLVEALYLVCGDRGFFYTKP;

(SEQ ID NO: 25028)
KFVSQHLCGSHLVEALYLVCGDRGFFYTPK;
```

-continued

KFVTQHLCGSHLVEALYLVCGDRGFFYTPK;

(SEQ ID NO: 25029)

KFVGQHLCGSHLVEALYLVCGDRGFFYTPK;

(SEQ ID NO: 25030)

KFVNQHLCGSHLVEALYLVCGDRGFFYTPK;

(SEQ ID NO: 25031)

KHLCGSHLVEALYLVCGDRGFFYTPK;

(SEQ ID NO: 25032)

KFVNQHLCGSHLVEALHLVCGKRGFFYTRPT;

(SEQ ID NO: 25033)

KFVGQHLCGSHLVEALHLVCGKRGFFYTRPT;

(SEQ ID NO: 25034)

KHLCGSHLVEALHLVCGKRGFFYTRPT;

(SEQ ID NO: 25035)

KFVNQHLCGSHLVEALHLVCGKRGFFYTRP;

(SEQ ID NO: 25036)

KFVGQHLCGSHLVEALHLVCGKRGFFYTRP;

(SEQ ID NO: 25037)

KHLCGSHLVEALHLVCGKRGFFYTRP;

(SEQ ID NO: 25038)

KFVSQHLCGSHLVEALHLVQGKRGFFYTPR;

(SEQ ID NO: 25039)

KFVTQHLCGSHLVEALHLVCGKRGFFYTPR;

(SEQ ID NO: 25040)

KFVGQHLCGSHLVEALHLVCGKRGFFYTPR;

(SEQ ID NO: 25041)

KFVNQHLCGSHLVEALHLVCGKRGFFYTPR;

(SEQ ID NO: 25042)

KHLCGSHLVEALHLVCGKRGFFYTPR;

(SEQ ID NO: 25043)

KFVGQHLCGSHLVEALHLVCGDRGFFYTKPT;

(SEQ ID NO: 25044)

KHLCGSHLVEALHLVCGDRGFFYTKPT;

(SEQ ID NO: 25045)

KFVNQHLCGSHLVEALHLVCGDRGFFYTKP;

(SEQ ID NO: 25046)

KFVGQHLCGSHLVEALHLVCGDRGFFYTKP;

(SEQ ID NO: 25047)

KHLCGSHLVEALHLVCGDRGFFYTKP;

(SEQ ID NO: 25048)

KFVSQHLCGSHLVEALHLVCGDRGFFYTPK;

(SEQ ID NO: 25049)

KFVTQHLCGSHLVEALHLVCGDRGFFYTPK;

(SEQ ID NO: 25050)

KFVGQHLCGSHLVEALHLVCGDRGFFYTPK;

(SEQ ID NO: 25051)

KFVNQHLCGSHLVEALHLVCGDRGFFYTPK;

(SEQ ID NO: 25052)

KHLCGSHLVEALHLVCGDRGFFYTPK;

(SEQ ID NO: 25053)

KFVNQHLCGSHLVEALHLVCGKRGFHYTRPT;

(SEQ ID NO: 25054)

KFVGQHLCGSHLVEALHLVCGKRGFHYTRPT;

(SEQ ID NO: 25055)

-continued

```
                                    (SEQ  ID NO: 25056)
KHLCGSHLVEALHLVCGKRGFHYTRPT;

(SEQ  ID) NO: 25057)
KFVNQHLCGSHLVEALHLVCGKRGFHYTRP;

(SEQ  ID NO: 25058)
KFVGQHLCGSHLVEALHLVCGKRGFHYTRP;

(SEQ  ID NO: 25059)
KHLCGSHLVEALHLVCGKRGFHYTRP;

(SEQ  ID NO: 25060)
KFVSQHLCGSHLVEALHLVCGKRGFHYTPR;

(SEQ  ID NO: 25061)
KFVTQHLCGSHLVEALHLVCGKRGFHYTPR;

(SEQ  ID NO: 25062)
KFVGQHLCGSHLVEALHLVCGKRGFHYTPR;

(SEQ  ID NO: 25063)
KFVNQHLCGSHLVEALHLVCGKRGFHYTPR;

(SEQ  ID NO: 25064)
KHLCGSHLVEALHLVCGKRGFHYTPR;

(SEQ  ID NO: 25065)
KFVNQHLCGSHLVEALHLVCGDRGFHYTKPT;

(SEQ  ID NO: 25066)
KFVGQHLCGSHLVEALHLVCGDRGFHYTKPT;

(SEQ  ID NO: 25067)
KHLCGSHLVEALHLVCGDRGFHYTKPT;

(SEQ  ID NO: 25068)
KFVNQHLCGSHLVEALHLVCGDRGFHYTKP;

(SEQ  ID NO: 25069)
KFVGQHLCGSHLVEALHLVCGDRGFHYTKP;

(SEQ  ID NO: 25070)
KHLCGSHLVEALHLVCGDRGFHYTKP;

(SEQ  ID NO: 25071)
KFVSQHLCGSHLVEALHLVCGDRGFHYTPK;

(SEQ  ID NO: 25072)
KFVTQHLCGSHLVEALHLVCGDRGFHYTPK;

(SEQ  ID NO: 25073)
KFVGQHLCQSHLVEALHLVCGDRGFHYTPK;

(SEQ  ID NO: 25074)
KFVNQHLCGSHLVEALHLVCGDRGFHYTPK;

(SEQ  ID NO: 25075)
KHLCGSHLVEALHLVCGDRGFHYTPK;

(SEQ  ID NO: 25076)
KGSHGGGGSGGGGSGGGGSFVNQHLCGSHLVEALYLVCGKRGFFYTRPT;

(SEQ  ID NO: 25077)
KGSHGGGGSGGGGSGGGGSFVGQHLCGSHLVEALYLVCGKRGFFYTRPT;

(SEQ  ID NO: 25078)
KGSHGGGGSGGGGSGGGGSHLCGSHLVEALYLVCGKRGFFYTRPT;

(SEQ  ID NO: 25079)
KGSHGGGGSGGGGSGGGGSFVNQHLCGSHLVEALYLVCGKRGFFYTRP;

(SEQ  ID NO: 25080)
KGSHGGGGSGGGGSGGGGSFVGQHLCGSHLVEALYLVCGKRGFFYTRP;

(SEQ  ID NO: 25081)
KGSHGGGGSGGGGSGGGGSHLCGSHLVEALYLVQGKRGFFYTRP;

(SEQ  ID NO: 25082)
KGSHGGGGSGGGGSGGGGSFVSQHLCGSHLVEALYLVCGKRGFFYTPR;
```

-continued

```
                                    (SEQ ID NO: 25083)
KGSHGGGGSGGGGSGGGGSFVTQHLCGSHLVEALYLVCGKRGFFYTPR;

(SEQ ID NO: 25084)
KGSHGGGGSGGGGSGGGGSFVGQHLCGSHLVEALYLVCGKRGFFYTPR;

(SEQ ID NO: 25085)
KGSHGGGGSGGGGSGGGGSFVNQHLCGSHLVEALYLVCGKRGFFYTPR;

(SEQ ID NO: 25086)
KGSHGGGGSGGGGSGGGGSHLCGSHLVEALYLVCGKRGFFYTPR;

(SEQ ID NO: 25087)
KGSHGGGGSGGGGSGGGGSFVNQHLCGSHLVEALYLVCGERGFFYTKPT;

(SEQ ID NO: 25088)
KGSHGGGGSGGGGSGGGGSFVGQHLCGSHLVEALYLVCGERGFFYTKPT;

(SEQ ID NO: 25089)
KGSHGGGGSGGGGSGGGGSHLCGSHLVEALYLVCGERGFFYTKPT;

(SEQ ID NO: 25090)
KGSHGGGGSGGGGSGGGGSFVNQHLCGSHLVEALYLVCGERGFFYTKP;

(SEQ ID NO: 25091)
KGSHGGGGSGGGGSGGGGSFVGQHLCGSHLVEALYLVCGERGFFYTKP;

(SEQ ID NO: 25092)
KGSHGGGGSGGGGSGGGGSHLCGSHLVEALYLVCGERGFFYTKP;

(SEQ ID NO: 25093)
KGSHGGGGSGGGGSGGGGSFVSQHLCGSHLVEALYLVCGERGFFYTPK;

(SEQ ID NO: 25094)
KGSHGGGGSGGGGSGGGGSFVTQHLCGSHLVEALYLVCGERGFFYTPK;

(SEQ ID NO: 25095)
KGSHGGGGSGGGGSGGGGSFVGQHLCGSHLVEALYLVCGERGFFYTPK;

(SEQ ID NO: 25096)
KGSHGGGGSGGGGSGGGGSFVNQHLCGSHLVEALYLVCGERGFFYTPK;

(SEQ ID NO: 25097)
KGSHGGGGSGGGGSGGGGSHLCGSHLVEALYLVCGERGFFYTPK;

(SEQ ID NO: 25098)
KGSHGGGGSGGGGSGGGGSFVNQHLCGSHLVEALYLVCGDRGFFYTKPT;

(SEQ ID NO: 25099)
KGSHGGGGSGGGGSGGGGSFVGQHLCGSHLVEALYLVCGDRGFFYTKPT;

(SEQ ID NO: 25100)
KGSHGGGGSGGGGSGGGGSHLCGSHLVEALYLVCGDRGFFYTKPT;

(SEQ ID NO: 25101)
KGSHGGGGSGGGGSGGGGSFVNQHLCGSHLVEALYLVCGDRGFFYTKP;

(SEQ ID NO: 25102)
KGSHGGGGSGGGGSGGGGSFVGQHLCGSHLVEALYLVCGDRGFFYTKP;

(SEQ ID NO: 25103)
KGSHGGGGSGGGGSGGGGSHLCGSHLVEALYLVCGDRGFFYTKP;

(SEQ ID NO: 25104)
KGSHGGGGSGGGGSGGGGSFVSQHLCGSHLVEALYLVQGDRGFFYTPK;

(SEQ ID NO: 25105)
KGSHGGGGSGGGGSGGGGSFVTQHLCGSHLVEALYLVCGDRGFFYTPK;

(SEQ ID NO: 25106)
KGSHGGGGSGGGGSGGGGSFVGQHLCGSHLVEALYLVCGDRGFFYTPK;

(SEQ ID NO: 25107)
KGSHGGGGSGGGGSGGGGSFVNQHLCGSHLVEALYLVCGDRGFFYTPK;

(SEQ ID NO: 25108)
KGSHGGGGSGGGGSGGGGSHLCGSHLVEALYLVCGDRGFFYTPK;

(SEQ ID NO: 25109)
KGSHGGGGSGGGGSGGGGSFVNQHLCGSHLVEALHLVCGKRGFFYTRPT;
```

-continued

```
                                       (SEQ  ID NO: 25110)
KGSHGGGGSGGGGSGGGGSFVGQHLCGSHLVEALHLVCGKRGFFYTRPT;

(SEQ  ID NO: 25111)
KGSHGGGGSGGGGSGGGGSHLCGSHLVEALHLVCGKRGFFYTRPT;

(SEQ  ID NO: 25112)
KGSHGGGGSGGGGSGGGGSFVNQHLCGSHLVEALHLVCGKRGFFYTRP;

(SEQ  ID NO: 25113)
KGSHGGGGSGGGGSGGGGSFVGQHLCGSHLVEALHLVCGKRGFFYTRP;

(SEQ  ID NO: 25114)
KGSHGGGGSGGGGSGGGGSHLCGSHLVEALHLVCGKRGFFYTRP;

(SEQ  ID NO: 25115)
KGSHGGGGSGGGGSGGGGSFVSQHLCGSHLVEALHLVQGKRGFFYTPR;

(SEQ  ID NO: 25116)
KGSHGGGGSGGGGSGGGGSFVTQHLCGSHLVEALHLVCGKRGFFYTPR;

(SEQ  ID NO: 25117)
KGSHGGGGSGGGGSGGGGSFVGQHLCGSHLVEALHLVCGKRGFFYTPR;

(SEQ  ID NO: 25118)
KGSHGGGGSGGGGSGGGGSFVNQHLCGSHLVEALHLVCGKRGFFYTPR;

(SEQ  ID NO: 25119)
KGSHGGGGSGGGGSGGGGSHLCGSHLVEALHLVCGKRGFFYTPR;

(SEQ  ID NO: 25120)
KGSHGGGGSGGGGSGGGGSFVGQHLCGSHLVEALHLVCGDRGFFYTKPT;

(SEQ  ID NO: 25121)
KGSHGGGGSGGGGSGGGGSHLCGSHLVEALHLVCGDRGFFYTKPT;

(SEQ  ID NO: 25122)
KGSHGGGGSGGGGSGGGGSFVNQHLCGSHLVEALHLVCGDRGFFYTKP;

(SEQ  ID NO: 25123)
KGSHGGGGSGGGGSGGGGSFVGQHLCGSHLVEALHLVCGDRGFFYTKP;

(SEQ  ID NO: 25124)
KGSHGGGGSGGGGSGGGGSHLCGSHLVEALHLVCGDRGFFYTKP;

(SEQ  ID NO: 25125)
KGSHGGGGSGGGGSGGGGSFVSQHLCGSHLVEALHLVCGDRGFFYTPK;

(SEQ  ID NO: 25126)
KGSHGGGGSGGGGSGGGGSFVTQHLCGSHLVEALHLVCGDRGFFYTPK;

(SEQ  ID NO: 25127)
KGSHGGGGSGGGGSGGGGSFVGQHLCGSHLVEALHLVCGDRGFFYTPK;

(SEQ  ID NO: 25128)
KGSHGGGGSGGGGSGGGGSFVNQHLCGSHLVEALHLVCGDRGFFYTPK;

(SEQ  ID NO: 25129)
KGSHGGGGSGGGGSGGGGSHLCGSHLVEALHLVCGDRGFFYTPK;

(SEQ  ID NO: 25130)
KGSHGGGGSGGGGSGGGGSFVNQHLCGSHLVEALHLVCGKRGFHYTRPT;

(SEQ  ID NO: 25131)
KGSHGGGGSGGGGSGGGGSFVGQHLCGSHLVEALHLVCGKRGFHYTRPT;

(SEQ  ID NO: 25132)
KGSHGGGGSGGGGSGGGGSHLCGSHLVEALHLVCGKRGFHYTRPT;

(SEQ  ID NO: 25133)
KGSHGGGGSGGGGSGGGGSFVNQHLCGSHLVEALHLVCGKRGFHYTRP;

(SEQ  ID NO: 25134)
KGSHGGGGSGGGGSGGGGSFVGQHLCGSHLVEALHLVCGKRGFHYTRP;

(SEQ  ID NO: 25135)
KGSHGGGGSGGGGSGGGGSHLCGSHLVEALHLVCGKRGFHYTRP;

(SEQ  ID NO: 25136)
KGSHGGGGSGGGGSGGGGSFVSQHLCGSHLVEALHLVCGKRGFHYTPR;
```

-continued

```
                                 (SEQ ID NO: 25137)
KGSHGGGGSGGGGSGGGGSFVTQHLCGSHLVEALHLVCGKRGFHYTPR;

(SEQ ID NO: 25138)
KGSHGGGGSGGGGSGGGGSFVGQHLCGSHLVEALHLVCGKRGFHYTPR;

(SEQ ID NO: 25139)
KGSHGGGGSGGGGSGGGGSFVNQHLCGSHLVEALHLVCGKRGFHYTPR;

(SEQ ID NO: 25140)
KGSHGGGGSGGGGSGGGGSHLCGSHLVEALHLVCGKRGFHYTPR;

(SEQ ID NO: 25141)
KGSHGGGGSGGGGSGGGGSFVNQHLCGSHLVEALHLVCGDRGFHYTKPT;

(SEQ ID NO: 25142)
KGSHGGGGSGGGGSGGGGSFVGQHLCGSHLVEALHLVCGDRGFHYTKPT;

(SEQ ID NO: 25143)
KGSHGGGGSGGGGSGGGGSHLCGSHLVEALHLVCGDRGFHYTKPT;

(SEQ ID NO: 25144)
KGSHGGGGSGGGGSGGGGSFVNQHLCGSHLVEALHLVCGDRGFHYTKP;

(SEQ ID NO: 25145)
KGSHGGGGSGGGGSGGGGSFVGQHLCGSHLVEALHLVCGDRGFHYTKP;

(SEQ ID NO: 25146)
KGSHGGGGSGGGGSGGGGSHLCGSHLVEALHLVCGDRGFHYTKP;

(SEQ ID NO: 25147)
KGSHGGGGSGGGGSGGGGSFVSQHLCGSHLVEALHLVCGDRGFHYTPK;

(SEQ ID NO: 25148)
KGSHGGGGSGGGGSGGGGSFVTQHLCGSHLVEALHLVCGDRGFHYTPK;

(SEQ ID NO: 25149)
KGSHGGGGSGGGGSGGGGSFVGQHLCGSHLVEALHLVCGDRGFHYTPK;

(SEQ ID NO: 25150)
KGSHGGGGSGGGGSGGGGSFVNQHLCGSHLVEALHLVCGDRGFHYTPK;

(SEQ ID NO: 25151)
KGSHGGGGSGGGGSGGGGSHLCGSHLVEALHLVCGDRGFHYTPK;

(SEQ ID NO: 25152)
KGSHGGGGSGGGGSGGGGSGGGGSFVNQHLCGSHLVEALYLVCGKRGFFYTRPT;

(SEQ ID NO: 25153)
KGSHGGGGSGGGGSGGGGSGGGGSFVGQHLCGSHLVEALYLVCGKRGFFYTRPT;

(SEQ ID NO: 25154)
KGSHGGGGSGGGGSGGGGSGGGGSHLCGSHLVEALYLVCGKRGFFYTRPT;

(SEQ ID NO: 25155)
KGSHGGGGSGGGGSGGGGSGGGGSFVNQHLCGSHLVEALYLVCGKRGFFYTRP;

(SEQ ID NO: 25156)
KGSHGGGGSGGGGSGGGGSGGGGSFVGQHLCGSHLVEALYLVCGKRGFFYTRP;

(SEQ ID NO: 25157)
KGSHGGGGSGGGGSGGGGSGGGGSHLCGSHLVEALYLVCGKRGFFYTRP;

(SEQ ID NO: 25158)
KGSHGGGGSGGGGSGGGGSGGGGSFVSQHLCGSHLVEALYLVCGKRGFFYTPR;

(SEQ ID NO: 25159)
KGSHGGGGSGGGGSGGGGSGGGGSFVTQHLCGSHLVEALYLVCGKRGFFYTPR;

(SEQ ID NO: 25160)
KGSHGGGGSGGGGSGGGGSGGGGSFVGQHLCGSHLVEALYLVCGKRGFFYTPR;

(SEQ ID NO: 25161)
KGSHGGGGSGGGGSGGGGSGGGGSFVNQHLCGSHLVEALYLVCGKRGFFYTPR;

(SEQ ID NO: 25162)
KGSHGGGGSGGGGSGGGGSGGGGSHLCGSHLVEALYLVCGKRGFFYTPR;

(SEQ ID NO: 25163)
KGSHGGGGSGGGGSGGGGSGGGGSFVNQHLCGSHLVEALYLVCGERGFFYTKPT;
```

-continued

```
                                        (SEQ  ID NO: 25164)
KGSHGGGGSGGGGSGGGGSGGGGSFVGQHLCGSHLVEALYLVCGERGFFYTKPT;

(SEQ  ID NO: 25165)
KGSHGGGGSGGGGSGGGGSGGGGSHLCGSHLVEALYLVCGERGFFYTKPT;

(SEQ  ID NO: 25166)
KGSHGGGGSGGGGSGGGGSGGGGSFVNQHLCGSHLVEALYLVCGERGFFYTKP;

(SEQ  ID NO: 25167)
KGSHGGGGSGGGGSGGGGSGGGGSFVGQHLCGSHLVEALYLVCGERGFFYTKP;

(SEQ  ID NO: 25168)
KGSHGGGGSGGGGSGGGGSGGGGSHLCGSHLVEALYLVCGERGFFYTKP;

(SEQ  ID NO: 25169)
KGSHGGGGSGGGGSGGGGSGGGGSFVSQHLCGSHLVEALYLVCGERGFFYTPK;

(SEQ  ID NO: 25170)
KGSHGGGGSGGGGSGGGGSGGGGSFVTQHLCGSHLVEALYLVCGERGFFYTPK;

(SEQ  ID NO: 25171)
KGSHGGGGSGGGGSGGGGSGGGGSFVGQHLCGSHLVEALYLVCGERGFFYTPK;

(SEQ  ID NO: 25172)
KGSHGGGGSGGGGSGGGGSGGGGSFVNQHLCGSHLVEALYLVCGERGFFYTPK;

(SEQ  ID NO: 25173)
KGSHGGGGSGGGGSGGGGSGGGGSHLCGSHLVEALYLVCGERGFFYTPK;

(SEQ  ID NO: 25174)
KGSHGGGGSGGGGSGGGGSGGGGSFVNQHLCGSHLVEALYLVCGDRGFFYTKPT;

(SEQ  ID NO: 25175)
KGSHGGGGSGGGGSGGGGSGGGGSFVGQHLCGSHLVEALYLVCGDRGFFYTKPT;

(SEQ  ID NO: 25176)
KGSHGGGGSGGGGSGGGGSGGGGSHLCGSHLVEALYLVCGDRGFFYTKPT;

(SEQ  ID NO: 25177)
KGSHGGGGSGGGGSGGGGSGGGGSFVNQHLCGSHLVEALYLVCGDRGFFYTKP;

(SEQ  ID NO: 25178)
KGSHGGGGSGGGGSGGGGSGGGGSFVGQHLCGSHLVEALYLVCGDRGFFYTKP;

(SEQ  ID NO: 25179)
KGSHGGGGSGGGGSGGGGSGGGGSHLCGSHLVEALYLVCGDRGFFYTKP;

(SEQ  ID NO: 25180)
KGSHGGGGSGGGGSGGGGSGGGGSFVSQHLCGSHLVEALYLVCQDRGFFYTPK;

(SEQ  ID NO: 25181)
KGSHGGGGSGGGGSGGGGSGGGGSFVTQHLCGSHLVEALYLVCGDRGFFYTPK;

(SEQ  ID NO: 25182)
KGSHGGGGSGGGGSGGGGSGGGGSFVGQHLCGSHLVEALYLVCGDRGFFYTPK;

(SEQ  ID NO: 25183)
KGSHGGGGSGGGGSGGGGSGGGGSFVNQHLCGSHLVEALYLVCGDRGFFYTPK;

(SEQ  ID NO: 25184)
KGSHGGGGSGGGGSGGGGSGGGGSHLCGSHLVEALYLVCGDRGFFYTPK;

(SEQ  ID NO: 25185)
KGSHGGGGSGGGGSGGGGSGGGGSFVNQHLCGSHLVEALHLVCGKRGFFYTRPT;

(SEQ  ID NO: 25186)
KGSHGGGGSGGGGSGGGGSGGGGSFVGQHLCGSHLVEALHLVCGKRGFFYTRPT;

(SEQ  ID NO: 25187)
KGSHGGGGSGGGGSGGGGSGGGGSHLCGSHLVEALHLVCGKRGFFYTRPT;

(SEQ  ID NO: 25188)
KGSHGGGGSGGGGSGGGGSGGGGSFVNQHLCGSHLVEALHLVCGKRGFFYTRP;

(SEQ  ID NO: 25189)
KGSHGGGGSGGGGSGGGGSGGGGSFVGQHLCGSHLVEALHLVCGKRGFFYTRP;

(SEQ  ID NO: 25190)
KGSHGGGGSGGGGSGGGGSGGGGSHLCGSHLVEALHLVCGKRGFFYTRP;
```

-continued

```
                                        (SEQ  ID NO: 25191)
KGSHGGGGSGGGGSGGGGSGGGGSFVSQHLCGSHLVEALHLVCGKRGFFYTPR;

(SEQ  ID NO: 25192)
KGSHGGGGSGGGGSGGGGSGGGGSFVTQHLCGSHLVEALHLVCGKRGFFYTPR;

(SEQ  ID NO: 25193)
KGSHGGGGSGGGGSGGGGSGGGGSFVGQHLCGSHLVEALHLVCGKRGFFYTPR;

(SEQ  ID NO: 25194)
KGSHGGGGSGGGGSGGGGSGGGGSFVNQHLCGSHLVEALHLVCGKRGFFYTPR;

(SEQ  ID NO: 25195)
KGSHGGGGSGGGGSGGGGSGGGGSHLCGSHLVEALHLVCGKRGFFYTPR;

(SEQ  ID NO: 25196)
KGSHGGGGSGGGGSGGGGSGGGGSFVGQHLCGSHLVEALHLVCGDRGFFYTKPT;

(SEQ  ID NO: 25197)
KGSHGGGGSGGGGSGGGGSGGGGSHLCGSHLVEALHLVCQDRGFFYTKPT;

(SEQ  ID NO: 25198)
KGSHGGGGSGGGGSGGGGSGGGGSFVNQHLCGSHLVEALHLVCGDRGFFYTKP;

(SEQ  ID NO: 25199)
KGSHGGGGSGGGGSGGGGSGGGGSFVGQHLCGSHLVEALHLVCGDRGFFYTKP;

(SEQ  ID NO: 25200)
KGSHGGGGSGGGGSGGGGSGGGGSHLCGSHLVEALHLVCGDRGFFYTKP;

(SEQ  ID NO: 25201)
KGSHGGGGSGGGGSGGGGSGGGGSFVSQHLCGSHLVEALHLVCGDRGFFYTPK;

(SEQ  ID NO: 25202)
KGSHGGGGSGGGGSGGGGSGGGGSFVTQHLCGSHLVEALHLVCGDRGFFYTPK;

(SEQ  ID NO: 25203)
KGSHGGGGSGGGGSGGGGSGGGGSFVGQHLCGSHLVEALHLVCGDRGFFYTPK;

(SEQ  ID NO: 25204)
KGSHGGGGSGGGGSGGGGSGGGGSFVNQHLCGSHLVEALHLVCGDRGFFYTPK;

(SEQ  ID NO: 25205)
KGSHGGGGSGGGGSGGGGSGGGGSHLCGSHLVEALHLVCGDRGFFYTPK;

(SEQ  ID NO: 25206)
KGSHGGGGSGGGGSGGGGSGGGGSFVNQHLCGSHLVEALHLVCGKRGFHYTRPT;

(SEQ  ID NO: 25207)
KGSHGGGGSGGGGSGGGGSGGGGSFVGQHLCGSHLVEALHLVCGKRGFHYTRPT;

(SEQ  ID NO: 25208)
KGSHGGGGSGGGGSGGGGSGGGGSHLCGSHLVEALHLVCQKRGFHYTRPT;

(SEQ  ID NO: 25209)
KGSHGGGGSGGGGSGGGGSGGGGSFVNQHLCGSHLVEALHLVCGKRGFHYTRP;

(SEQ  ID NO: 25210)
KGSHGGGGSGGGGSGGGGSGGGGSFVGQHLCGSHLVEALHLVCGKRGFHYTRP;

(SEQ  ID NO: 25211)
KGSHGGGGSGGGGSGGGGSGGGGSHLCGSHLVEALHLVCGKRGFHYTRP;

(SEQ  ID NO: 25212)
KGSHGGGGSGGGGSGGGGSGGGGSFVSQHLCGSHLVEALHLVCGKRGFHYTPR;

(SEQ  ID NO: 25213)
KGSHGGGGSGGGGSGGGGSGGGGSFVTQHLCGSHLVEALHLVCGKRGFHYTPR;

(SEQ  ID NO: 25214)
KGSHGGGGSGGGGSGGGGSGGGGSFVGQHLCGSHLVEALHLVCGKRGFHYTPR;

(SEQ  ID NO: 25215)
KGSHGGGGSGGGGSGGGGSGGGGSFVNQHLCGSHLVEALHLVCGKRGFHYTPR;

(SEQ  ID NO: 25216)
KGSHGGGGSGGGGSGGGGSGGGGSHLCGSHLVEALHLVCGKRGFHYTPR;

(SEQ  ID NO: 25217)
KGSHGGGGSGGGGSGGGGSGGGGSFVNQHLCGSHLVEALHLVCGDRGFHYTKPT;
```

-continued

```
                                 (SEQ  ID NO: 25218)
KGSHGGGGSGGGGSGGGGSGGGGSFVGQHLCGSHLVEALHLVCGDRGFHYTKPT;

(SEQ  ID NO: 25219)
KGSHGGGGSGGGGSGGGGSGGGGSHLCGSHLVEALHLVCGDRGFHYTKPT;

(SEQ  ID NO: 25220)
KGSHGGGGSGGGGSGGGGSGGGGSFVNQHLCGSHLVEALHLVCGDRGFHYTKP;

(SEQ  ID NO: 25221)
KGSHGGGGSGGGGSGGGGSGGGGSFVGQHLCGSHLVEALHLVCGDRGFHYTKP;

(SEQ  ID NO: 25222)
KGSHGGGGSGGGGSGGGGSGGGGSHLCGSHLVEALHLVCGDRGFHYTKP;

(SEQ  ID NO: 25223)
KGSHGGGGSGGGGSGGGGSGGGGSFVSQHLCGSHLVEALHLVCGDRGFHYTPK;

(SEQ  ID NO: 25224)
KGSHGGGGSGGGGSGGGGSGGGGSFVTQHLCGSHLVEALHLVCGDRGFHYTPK;

(SEQ  ID NO: 25225)
KGSHGGGGSGGGGSGGGGSGGGGSFVGQHLCGSHLVEALHLVCGDRGFHYTPK;

(SEQ  ID NO: 25226)
KGSHGGGGSGGGGSGGGGSGGGGSFVNQHLCGSHLVEALHLVCGDRGFHYTPK;

(SEQ  ID NO: 25227)
KGSHGGGGSGGGGSGGGGSGGGGSHLCGSHLVEALHLVCGDRGFHYTPK;

(SEQ  ID NO: 25228)
GKGSHKFVNQHLCGSHLVEALYLVCGKRGFFYTPR;

(SEQ  ID NO: 25229)
GKGSHKFVGQHLCGSHLVEALYLVCGKRGFFYTRPT;

(SEQ  ID NO: 25230)
GKGSHKHLCGSHLVEALYLVCGKRGFFYTRPT;

(SEQ  ID NO: 25231)
GKGSHKFVNQHLCGSHLVEALYLVCGKRGFFYTRP;

(SEQ  ID NO: 25232)
GKGSHKFVGQHLCGSHLVEALYLVCGKRGFFYTRP;

(SEQ  ID NO: 25233)
GKGSHKHLCGSHLVEALYLVCGKRGFFYTRP;

(SEQ  ID NO: 25234)
GKGSHKFVSQHLCGSHLVEALYLVCGKRGFFYTPR;

(SEQ  ID NO: 25235)
GKGSHKFVTQHLCGSHLVEALYLVCGKRGFFYTPR;

(SEQ  ID NO: 25236)
GKGSHKFVGQHLCGSHLVEALYLVCGKRGFFYTPR;

(SEQ  ID NO: 25237)
GKGSHKFVNQHLCGSHLVEALYLVCGKRGFFYTPRT;

(SEQ  ID NO: 25238)
GKGSHKHLCGSHLVEALYLVCGKRGFFYTPR;

(SEQ  ID NO: 25239)
GKGSHKFVNQHLCGSHLVEALYLVCGERGFFYTKPT;

(SEQ  ID NO: 25240)
GKGSHKFVGQHLCGSHLVEALYLVCGERGFFYTKPT;

(SEQ  ID NO: 25241)
GKGSHKHLCGSHLVEALYLVCGERGFFYTKPT;

(SEQ  ID NO: 25242)
GKGSHKFVNQHLCGSHLVEALYLVCGERGFFYTKP;

(SEQ  ID NO: 25243)
GKGSHKFVGQHLCGSHLVEALYLVCGERGFFYTKP;

(SEQ  ID NO: 25244)
GKGSHKHLCGSHLVEALYLVCGERGFFYTKP;
```

-continued

```
                                        (SEQ ID NO: 25245)
GKGSHKFVSQHLCGSHLVEALYLVCGERGFFYTPK;

(SEQ ID NO: 25246)
GKGSHKFVTQHLCGSHLVEALYLVCGERGFFYTPK;

(SEQ ID NO: 25247)
GKGSHKFVGQHLCGSHLVEALYLVCGERGFFYTPK;

(SEQ ID NO: 25248)
GKGSHKFVNQHLCGSHLVEALYLVCGERGFFYTPK;

(SEQ ID NO: 25249)
GKGSHKHLCQSHLVEALYLVCGERGFFYTPK;

(SEQ ID NO: 25250)
GKGSHKFVNQHLCGSHLVEALYLVCGDRGFFYTKPT;

(SEQ ID NO: 25251)
GKGSHKFVGQHLCGSHLVEALYLVCGDRGFFYTKPT;

(SEQ ID NO: 25252)
GKGSHKHLCGSHLVEALYLVCGDRGFFYTKPT;

(SEQ ID NO: 25253)
GKGSHKFVNQHLCGSHLVEALYLVCGDRGFFYTKP;

(SEQ ID NO: 25254)
GKGSHKFVGQHLCGSHLVEALYLVCGDRGFFYTKP;

(SEQ ID NO: 25255)
GKGSHKHLCGSHLVEALYLVCGDRGFFYTKP;

(SEQ ID NO: 25256)
GKGSHKFVSQHLCGSHLVEALYLVCGDRGFFYTPK;

(SEQ ID NO: 25257)
GKGSHKFVTQHLCGSHLVEALYLVCGDRGFFYTPK;

(SEQ ID NO: 25258)
GKGSHKFVGQHLCGSHLVEALYLVCGDRGFFYTPK;

(SEQ ID NO: 25259)
GKGSHKFVNQHLCGSHLVEALYLVCGDRGFFYTPK;

(SEQ ID NO: 25260)
GKGSHKHLCGSHLVEALYLVCGDRGFFYTPK;

(SEQ ID NO: 25261)
GKGSHKFVNQHLCGSHLVEALHLVCGKRGFFYTRPT;

(SEQ ID NO: 25262)
GKGSHKFVGQHLCGSHLVEALHLVCGKRGFFYTRPT;

(SEQ ID NO: 25263)
GKGSHKHLCGSHLVEALHLVCGKRGFFYTRPT;

(SEQ ID NO: 25264)
GKGSHKFVNQHLCGSHLVEALHLVCGKRGFFYTRP;

(SEQ ID NO: 25265)
GKGSHKFVGQHLCGSHLVEALHLVCGKRGFFYTRP;

(SEQ ID NO: 25266)
GKGSHKHLCGSHLVEALHLVCGKRGFFYTRP;

(SEQ ID NO: 25267)
GKGSHKFVSQHLCGSHLVEALHLVCGKRGFFYTPR;

(SEQ ID NO: 25268)
GKGSHKFVTQHLCGSHLVEALHLVCGKRGFFYTPR;

(SEQ ID NO: 25269)
GKGSHKFVGQHLCGSHLVEALHLVCGKRGFFYTPR;

(SEQ ID NO: 25270)
GKGSHKFVNQHLCGSHLVEALHLVCGKRGFFYTPR;

(SEQ ID NO: 25271)
GKGSHKHLCGSHLVEALHLVCGKRGFFYTPR;
```

-continued

```
                                    (SEQ  ID NO: 25272)
GKGSHKFVGQHLCGSHLVEALHLVCGDRGFFYTKPT;

(SEQ  ID NO: 25273)
GKGSHKHLCGSHLVEALHLVCGDRGFFYTKPT;

(SEQ  ID NO: 25274)
GKGSHKFVNQHLCGSHLVEALHLVCGDRGFFYTKP;

(SEQ  ID NO: 25275)
GKGSHKFVGQHLCGSHLVEALHLVCGDRGFFYTKP;

(SEQ  ID NO: 25276)
GKGSHKHLCGSHLVEALHLVCGDRGFFYTKP;

(SEQ  ID NO: 25277)
GKGSHKFVSQHLCGSHLVEALHLVCGDRGFFYTPK;

(SEQ  ID NO: 25278)
GKGSHKFVTQHLCGSHLVEALHLVCGDRGFFYTPK;

(SEQ  ID NO: 25279)
GKGSHKFVGQHLCGSHLVEALHLVCGDRGFFYTPK;

(SEQ  ID NO: 25280)
GKGSHKFVNQHLCGSHLVEALHLVCGDRGFFYTPK;

(SEQ  ID NO: 25281)
GKGSHKHLCGSHLVEALHLVCGDRGFFYTPK;

(SEQ  ID NO: 25282)
GKGSHKFVNQHLCGSHLVEALHLVCGKRGFHYTRPT;

(SEQ  ID NO: 25283)
GKGSHKFVGQHLCGSHLVEALHLVCGKRGFHYTRPT;

(SEQ  ID NO: 25284)
GKGSHKHLCGSHLVEALHLVCGKRGFHYTRPT;

(SEQ  ID NO: 25285)
GKGSHKFVNQHLCGSHLVEALHLVCGKRGFHYTRP;

(SEQ  ID NO: 25286)
GKGSHKFVGQHLCGSHLVEALHLVCGKRGFHYTRP;

(SEQ  ID NO: 25287)
GKGSHKHLCGSHLVEALHLVCGKRGFHYTRP;

(SEQ  ID NO: 25288)
GKGSHKFVSQHLCGSHLVEALHLVCGKRGFHYTPR;

(SEQ  ID NO: 25289)
GKGSHKFVTQHLCGSHLVEALHLVCGKRGFHYTPR;

(SEQ  ID NO: 25290)
GKGSHKFVGQHLCGSHLVEALHLVCGKRGFHYTPR;

(SEQ  ID NO: 25291)
GKGSHKFVNQHLCGSHLVEALHLVCGKRGFHYTPR;

(SEQ  ID NO: 25292)
GKGSHKHLCGSHLVEALHLVCGKRGFHYTPR;

(SEQ  ID NO: 25293)
GKGSHKFVNQHLCGSHLVEALHLVCGDRGFHYTKPT;

(SEQ  ID NO: 25294)
GKGSHKFVGQHLCGSHLVEALHLVCGDRGFHYTKPT;

(SEQ  ID NO: 25295)
GKGSHKHLCGSHLVEALHLVCGDRGFHYTKPT;

(SEQ  ID NO: 25296)
GKGSHKFVNQHLCGSHLVEALHLVCGDRGFHYTKP;

(SEQ  ID NO: 25297)
GKGSHKFVGQHLCGSHLVEALHLVCGDRGFHYTKP;

(SEQ  ID NO: 25298)
GKGSHKHLCGSHLVEALHLVCGDRGFHYTKP;
```

-continued

```
                                       (SEQ ID NO: 25299)
GKGSHKFVSQHLCGSHLVEALHLVCGDRGFHYTPK;

(SEQ ID NO: 25300)
GKGSHKFVTQHLCGSHLVEALHLVCGDRGFHYTPK;

(SEQ ID NO: 25301)
GKGSHKFVGQHLCGSHLVEALHLVCGDRGFHYTPK;

(SEQ ID NO: 25302)
GKGSHKFVNQHLCGSHLVEALHLVCGDRGFHYTPK;

(SEQ ID NO: 25303)
GKGSHKHLCGSHLVEALHLVCGDRGFHYTPK;

(SEQ ID NO: 25304)
KGSHKFVNQHLCGSHLVEALYLVCGKRGFFYTRPT;

(SEQ ID NO: 25305)
KGSHKFVGQHLCGSHLVEALYLVCGKRGFFYTRPT;

(SEQ ID NO: 25306)
KGSHKHLCGSHLVEALYLVCGKRGFFYTRPT;

(SEQ ID NO: 25307)
KGSHKFVNQHLCGSHLVEALYLVCGKRGFFYTRP;

(SEQ ID NO: 25308)
KGSHKFVGQHLCGSHLVEALYLVCGKRGFFYTRP;

(SEQ ID NO: 25309)
KGSHKHLCGSHLVEALYLVCGKRGFFYTRP;

(SEQ ID NO: 25310)
KGSHKFVSQHLCGSHLVEALYLVCGKRGFFYTPR;

(SEQ ID NO: 25311)
KGSHKFVTQHLCGSHLVEALYLVCGKRGFFYTPR;

(SEQ ID NO: 25312)
KGSHKFVGQHLCGSHLVEALYLVCGKRGFFYTPR;

(SEQ ID NO: 25313)
KGSHKFVNQHLCGSHLVEALYLVCGKRGFFYTPR;

(SEQ ID NO: 25314)
KGSHKHLCQSHLVEALYLVCGKRGFFYTPR;

(SEQ ID NO: 25315)
KGSHKFVNQHLCGSHLVEALYLVCGERGFFYTKPT;

(SEQ ID NO: 25316)
KGSHKFVGQHLCGSHLVEALYLVCGERGFFYTKPT;

(SEQ ID NO: 25317)
KGSHKHLCGSHLVEALYLVCGERGFFYTKPT;

(SEQ ID NO: 25318)
KGSHKFVNQHLCGSHLVEALYLVCGERGFFYTKP;

(SEQ ID NO: 25319)
KGSHKFVGQHLCGSHLVEALYLVCGERGFFYTKP;

(SEQ ID NO: 25320)
KGSHKHLCGSHLVEALYLVCGERGFFYTKP;

(SEQ ID NO: 25321)
KGSHKFVSQHLCGSHLVEALYLVCGERGFFYTPK;

(SEQ ID NO: 25322)
KGSHKFVTQHLCGSHLVEALYLVCGERGFFYTPK;

(SEQ ID NO: 25323)
KGSHKFVGQHLCGSHLVEALYLVCGERGFFYTPK;

(SEQ ID NO: 25324)
KGSHKFVNQHLCGSHLVEALYLVCGERGFFYTPK;

(SEQ ID NO: 25325)
KGSHKHLCGSHLVEALYLVCGERGFFYTPK;
```

-continued

```
                                         (SEQ  ID NO: 25326)
KGSHKFVNQHLCGSHLVEALYLVCGDRGFFYTKPT;

(SEQ  ID NO: 25327)
KGSHKFVGQHLCGSHLVEALYLVCGDRGFFYTKPT;

(SEQ  ID NO: 25328)
KGSHKHLCGSHLVEALYLVCGDRGFFYTKPT;

(SEQ  ID NO: 25329)
KGSHKFVNQHLCGSHLVEALYLVCGDRGFFYTKP;

(SEQ  ID NO: 25330)
KGSHKFVGQHLCGSHLVEALYLVCGDRGFFYTKP;

(SEQ  ID NO: 25331)
KGSHKHLCGSHLVEALYLVCGDRGFFYTKP;

(SEQ  ID NO: 25332)
KGSHKFVSQHLCGSHLVEALYLVQGDRGFFYTPK;

(SEQ  ID NO: 25333)
KGSHKFVTQHLCGSHLVEALYLVCGDRGFFYTPK;

(SEQ  ID NO: 25334)
KGSHKFVGQHLCGSHLVEALYLVCGDRGFFYTPK;

(SEQ  ID NO: 25335)
KGSHKFVNQHLCGSHLVEALYLVCGDRGFFYTPK;

(SEQ  ID NO: 25336)
KGSHKHLCGSHLVEALYLVCGDRGFFYTPK;

(SEQ  ID NO: 25337)
KGSHKFVNQHLCGSHLVEALHLVCGKRGFFYTRPT;

(SEQ  ID NO: 25338)
KGSHKFVGQHLCGSHLVEALHLVCGKRGFFYTRPT;

(SEQ  ID NO: 25339)
KGSHKHLCGSHLVEALHLVCGKRGFFYTRPT;

(SEQ  ID NO: 25340)
KGSHKFVNQHLCGSHLVEALHLVCGKRGFFYTRP;

(SEQ  ID NO: 25341)
KGSHKFVGQHLCGSHLVEALHLVCGKRGFFYTRP;

(SEQ  ID NO: 25342)
KGSHKHLCGSHLVEALHLVCGKRGFFYTRP;

(SEQ  ID NO: 25343)
KGSHKFVSQHLCGSHLVEALHLVCGKRGFFYTPR;

(SEQ  ID NO: 25344)
KGSHKFVTQHLCGSHLVEALHLVCGKRGFFYTPR;

(SEQ  ID NO: 25345)
KGSHKFVGQHLCGSHLVEALHLVCGKRGFFYTPR;

(SEQ  ID NO: 25346)
KGSHKFVNQHLCGSHLVEALHLVCGKRGFFYTPR;

(SEQ  ID NO: 25347)
KGSHKHLCGSHLVEALHLVCGKRGFFYTPR;

(SEQ  ID NO: 25348)
KGSHKFVGQHLCGSHLVBALHLVCGDRGFFYTKPT;

(SEQ  ID NO: 25349)
KGSHKHLCGSHLVEALHLVCGDRGFFYTKPT;

(SEQ  ID NO: 25350)
KGSHKFVNQHLCGSHLVEALHLVCGDRGFFYTKP;

(SEQ  ID NO: 25351)
KGSHKFVGQHLCGSHLVEALHLVCGDRGFFYTKP;

(SEQ  ID NO: 25352)
KGSHKHLCGSHLVEALHLVCGDRGFFYTKP;
```

-continued

```
                                   (SEQ  ID NO: 25353)
KGSHKFVSQHLCGSHLVEALHLVCGDRGFFYTPK;

(SEQ  ID NO: 25354)
KGSHKFVTQHLCGSHLVEALHLVCGDRGFFYTPK;

(SEQ  ID NO: 25355)
KGSHKFVGQHLCGSHLVEALHLVCGDRGFFYTPK;

(SEQ  ID NO: 25356)
KGSHKFVNQHLCGSHLVEALHLVCGDRGFFYTPK;

(SEQ  ID NO: 25357)
KGSHKHLCGSHLVEALHLVCGDRGFFYTPK;

(SEQ  ID NO: 25358)
KGSHKFVNQHLCGSHLVEALHLVCGKRGFHYTRPT;

(SEQ  ID NO: 25359)
KGSHKFVGQHLCGSHLVEALHLVCGKRGFHYTRPT;

(SEQ  ID NO: 25360)
KGSHKHLCGSHLVEALHLVCGKRGFHYTRPT;

(SEQ  ID NO: 25361)
KGSHKFVNQHLCGSHLVEALHLVCGKRGFHYTRP;

(SEQ  ID NO: 25362)
KGSHKFVGQHLCGSHLVEALHLVCGKRGFHYTRP;

(SEQ  ID NO: 25363)
KGSHKHLCGSHLVEALHLVCGKRGFHYTRP;

(SEQ  ID NO: 25364)
KGSHKFVSQHLCGSHLVEALHLVCGKRGFHYTPR;

(SEQ  ID NO: 25365)
KGSHKFVTQHLCGSHLVEALHLVCGKRGFHYTPR;

(SEQ  ID NO: 25366)
KGSHKFVGQHLCGSHLVBALHLVCGKRGFHYTPR;

(SEQ  ID NO: 25367)
KGSHKFVNQHLCGSHLVEALHLVCGKRGFHYTPR;

(SEQ  ID NO: 25368)
KGSHKHLCGSHLVEALHLVCGKRGFHYTPR;

(SEQ  ID NO: 25369)
KGSHKFVNQHLCGSHLVEALHLVCGDRGFHYTKPT;

(SEQ  ID NO: 25370)
KGSHKFVGQHLCGSHLVEALHLVCGDRGFHYTKPT;

(SEQ  ID NO: 25371)
KGSHKHLCGSHLVEALHLVCGDRGFHYTKPT;

(SEQ  ID NO: 25372)
KGSHKFVNQHLCGSHLVEALHLVCGDRGFHYTKP;

(SEQ  ID NO: 25373)
KGSHKFVGQHLCGSHLVEALHLVCGDRGFHYTKP;

(SEQ  ID NO: 25374)
KGSHKHLCGSHLVEALHLVCGDRGFHYTKP;

(SEQ  ID NO: 25375)
KGSHKFVSQHLCGSHLVEALHLVCGDRGFHYTPK;

(SEQ  ID NO: 25376)
KGSHKFVTQHLCGSHLVEALHLVCGDRGFHYTPK;
```

-continued

```
                                 (SEQ  ID NO: 25377)
KGSHKFVGQHLCGSHLVEALHLVCGDRGFHYTPK;

(SEQ  ID NO: 25378)
KGSHKFVNQHLCGSHLVEALHLVCGDRGFHYTPK;

(SEQ  ID NO: 25379)
KGSHKHLCGSHLVEALHLVCGDRGFHYTPK;

(SEQ  ID NO: 25380)
KGSHKFVGQHLCGSHLVEALYLVCGKRGFFYTPRT;

(SEQ  ID NO: 25381)
GKGSHKFVGQHLCGSHLVEALYLVCGKRGFFYTPRT;

(SEQ  ID NO: 25382)
KGGGGGGGGSGGGGSFVGQHLCGSHLVEALYLVCGERGFFYTPK;

(SEQ  ID NO: 25383)
GKGGGGSGGGGSGGGGSFVGQHLCGSHLVEALYLVCGERGFFYTPK;

(SEQ  ID NO: 25384)
KGGGGSGGGGSGGGGSFVGQHLCGSHLVEALYLVCGERGFFYTPKT;

(SEQ  ID NO: 25385)
GKGGGGSGGGGSGGGGSFVGQHLCGSHLVEALYLVCGERGFFYTPKT;

(SEQ  ID NO: 25386)
KGSHGGGGSGGGGSGGGGSFVGQHLCGSHLVEALYLVCGERGFFYTPKT;

(SEQ  ID NO: 25387)
GKGSHGGGGSGGGGSGGGGSFVGQHLCGSHLVEALYLVCGERGFFYTPK;

(SEQ  ID NO: 25388)
GKGSHGGGGSGGGGSGGGGSFVGQHLCGSHLVEALYLVCGERGFFYTPKT;

(SEQ  ID NO: 25389)
KGGGGSGGGGSGGGGSFVGQHLCGSHLVEALYLVCGKRGFFYTPR;

(SEQ  ID NO: 25390)
GKGGGGSGGGGSGGGGSFVGQHLCGSHLVEALYLVCGKRGFFYTPR;

(SEQ  ID NO: 25391)
KGGGGSGGGGGGGGSFVGQHLCGSHLVEALYLVCGKRGFFYTPRT;

(SEQ  ID NO: 25392)
GKGGGGSGGGGGGGGSFVGQHLCGSHLVEALYLVCGKRGFFYTPRT;

(SEQ  ID NO: 25393)
KGSHKFVDQHLCGSHLVEALYLVCGKRGFFYTPR;

(SEQ  ID NO: 25394)
KFVDQHLCGSHLVEALYLVCGKRGFFYTPKT;

(SEQ  ID NO: 25395)
KGGGGSGGGGSGGGGSFVNQHLCGSHLVEALYLVCGERGFFYTPK;

(SEQ  ID NO: 25396)
GKGSHKFVNQHLCGSHLVEALYLVCGKRGFFYTRPT;
and (SEQ  ID NO: 25397)
GKGGGGSGGGGSGGGGSFVNQHLCGSHLVEALYLVCGERGFFYTPK.
```

SEQUENCE LISTING

The patent contains a lengthy sequence listing. A copy of the sequence listing is available in electronic form from the USPTO web site (https://seqdata.uspto.gov/docdetail?docId=US12655188B2). An electronic copy of the sequence listing will also be available from the USPTO upon request and payment of the fee set forth in 37 CFR 1.19(b)(3).

What is claimed is:

1. A compound selected from:

Example 1A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 2A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH, 3499             3500

Example 3A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 4A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

3501                                                                 3502

Example 5A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 6A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 7A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 8A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH, 3505                                                                           3506

Example 9A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH,

Example 10A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH,

Example 11A

H–G–I–V–E–Q–C–C–T–S–I–C–S–L–Y–Q–L–E–N–Y–C–N–OH

H–G–K–G–S–H–K–F–V–N–Q–H–L–C–G–S–H–L–V–E–A–L–Y–L–V–C–G–K–R–G–F–F–Y–T–P–R–OH,

Example 12A

H–G–I–V–E–Q–C–C–T–S–I–C–S–L–Y–Q–L–E–N–Y–C–N–OH

H–G–K–G–S–H–K–F–V–N–Q–H–L–C–G–S–H–L–V–E–A–L–Y–L–V–C–G–K–R–G–F–F–Y–T–P–R–OH, 3509                                                                3510

Example 13A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 14A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH, 3511 3512

Example 15A

H–G–I–V–E–Q–C–C–T–S–I–C–S–L–Y–Q–L–E–N–Y–C–N–OH

H–G–K–G–S–H–K–F–V–N–Q–H–L–C–G–S–H–L–V–E–A–L–Y–L–V–C–G–K–R–G–F–F–Y–T–P–R–OH,

Example 16A

H–G–I–V–E–Q–C–C–T–S–I–C–S–L–Y–Q–L–E–N–Y–C–N–OH

H–G–K–G–S–H–K–F–V–N–Q–H–L–C–G–S–H–L–V–E–A–L–Y–L–V–C–G–K–R–G–F–F–Y–T–P–R–OH,

Example 17A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 18A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

3515

3516

Example 19A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 20A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 21A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 22A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 23A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH,

Example 24A

H—G—I—V—E—Q—C—C—T—S—I—C—S—L—Y—Q—L—E—N—Y—C—N—OH

H—G—K—G—S—H—K—F—V—N—Q—H—L—C—G—S—H—L—V—E—A—L—Y—L—V—C—G—K—R—G—F—F—Y—T—P—R—OH,

3521 3522

Example 25A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 26A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

3523            3524

Example 27A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 28A

H-G-I-V-E-Q-C-C-T-S-I-C-S-L-Y-Q-L-E-N-Y-C-N-OH

H-G-K-G-S-H-K-F-V-N-Q-H-L-C-G-S-H-L-V-E-A-L-Y-L-V-C-G-K-R-G-F-F-Y-T-P-R-OH,

Example 29A

H‑G‑I‑V‑E‑Q‑C‑C‑T‑S‑I‑C‑S‑L‑Y‑Q‑L‑E‑N‑Y‑C‑N‑OH

H‑G‑K‑G‑S‑H‑K‑F‑V‑N‑Q‑H‑L‑C‑G‑S‑H‑L‑V‑E‑A‑L‑Y‑L‑V‑C‑G‑K‑R‑G‑F‑F‑Y‑T‑P‑R‑OH,

Prophetic

Example 30A

H‑G‑I‑V‑E‑Q‑C‑C‑T‑S‑I‑C‑S‑L‑Y‑Q‑L‑E‑N‑Y‑C‑N‑OH

H‑G‑K‑G‑S‑H‑K‑F‑V‑N‑Q‑H‑L‑C‑G‑S‑H‑L‑V‑E‑A‑L‑Y‑L‑V‑C‑G‑K‑R‑G‑F‑F‑Y‑T‑P‑R‑OH 3527 3528

Example 31A

H-G-I-V-E-Q-C-C-T-S-I—C-S-L-Q-L-E-N-Y-C-N-OH
H-G-K-G-S-H-K-F-V-N-Q—H-L-C-G-S-H-L-V-E-A—L-Y-L-V-C-G-K-R-G-F-F-Y-T-P-R-OH,

Example 32A

H-G-I-V-E-Q-C-C-T-S-I—C-S-L-Q-L-E-N-Y-C-N-OH
H-G-K-G-S-H-K-F-V-N-Q—H-L-C-G-S-H-L-V-E-A—L-Y-L-V-C-G-K-R-G-F-F-Y-T-P-R-OH, 3529                                                                                                    3530

Example 33A

H-G-I-V-E-Q-C-C-T-S-I—C-S-L-Q-L-E-N-Y-C-N-OH
H-G-K-G-S-H-K-F-V-N-Q—H-L-C-G-S-H-L-V-E-A—L-Y-L-V-C-G-K-R-G-F-F-Y-T-P-R-OH,

Example 34A

H-G-I-V-E-Q-C-C-T-S-I—C-S-L-Q-L-E-N-Y-C-N-OH
H-G-K-G-S-H-K-F-V-N-Q—H-L-C-G-S-H-L-V-E-A—L-Y-L-V-C-G-K-R-G-F-F-Y-T-P-R-OH, 3531                                                                                                    3532

Example 35A

H·G·I·V·E·Q·C·C·T·S·I—C·S·L·Q·L·E·N·Y·C·N·OH

H·G·K·G·S·H·K·F·V·N·Q——H·L·C·G·S·H·L·V·E·A——L·Y·L·V·C·G·K·R·G·F·F·Y·T·P·R·OH,

Example 36A

H·G·I·V·E·Q·C·C·T·S·I—C·S·L·Q·L·E·N·Y·C·N·OH

H·G·K·G·S·H·K·F·V·N·Q——H·L·C·G·S·H·L·V·E·A——L·Y·L·V·C·G·K·R·G·F·F·Y·T·P·R·OH, 3533 3534

Example 37A

H·G·I·V·E·Q·C·C·T·S·I—C·S·L·Q·L·E·N·Y·C·N—OH

H·G·K·G·S·H·K·F·V·N·Q—H·L·C·G·S·H·L·V·E·A—L·Y·L·V·C·G·K·R·G·F·F·Y·T·P·R·OH,

Example 38B

H·G·I·V·E·Q·C·C·T·S·I—C·S·L·Q·L·E·N·Y·C·N—OH

H·G·K·G·S·H·K·F·V·N·Q—H·L·C·G·S·H·L·V·E·A—L·Y·L·V·C·G·K·R·G·F·F·Y·T·P·R·OH, 3535                                                                        3536

Example 39A

H-G-I-V-E-Q-C-C-T-S-I—C-S-L-Q-L-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH,

Example 40A

H-G-I-V-E-Q-C-C-T-S-I—C-S-L-Q-L-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH, 3537             3538

Example 41A

H‑G‑I‑V‑E‑Q‑C‑C‑T‑S‑I—C‑S‑L‑Q‑L‑E‑N‑Y‑C‑N‑OH

H‑G‑K‑G‑S‑H‑K‑F‑V‑N‑Q—H‑L‑C‑G‑S‑H‑L‑V‑E‑A—L‑Y‑L‑V‑C‑G‑K‑R‑G‑F‑F‑Y‑T‑P‑R‑OH,

Example 42A

H‑G‑I‑V‑E‑Q‑C‑C‑T‑S‑I—C‑S‑L‑Q‑L‑E‑N‑Y‑C‑N‑OH

H‑G‑K‑G‑S‑H‑K‑F‑V‑N‑Q—H‑L‑C‑G‑S‑H‑L‑V‑E‑A—L‑Y‑L‑V‑C‑G‑K‑R‑G‑F‑F‑Y‑T‑P‑R‑OH,

Example 43A

H-G-I-V-E-Q-C-C-T-S-I-C-S-L-Q-L-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH,

Example 44A

H-G-I-V-E-Q-C-C-T-S-I-C-S-L-Q-L-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH, 3541                                                                                     3542

Example 45A

H-G-I-V-E-Q-C-C-T-S-I—C-S-L-Q-L-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH,

Example 46A

H-G-I-V-E-Q-C-C-T-S-I—C-S-L-Q-L-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH, 3543                                                                 3544

Example 47A

H-G-I-V-E-Q-C-C-T-S-I—C-S-L-Q-L-E-N-Y-C-N-OH

H-G-K-G-S-H-K-F-V-N-Q——H-L-C-G-S-H-L-V-E-A—L-Y-L-V-C-G-K-R-G-F-F-Y-T-P-R-OH,

Example 48A

H-G-I-V-E-Q-C-C-T-S-I—C-S-L-Q-L-E-N-Y-C-N-OH

H-G-K-G-S-H-K-F-V-N-Q——H-L-C-G-S-H-L-V-E-A—L-Y-L-V-C-G-K-R-G-F-F-Y-T-P-R-OH, 3545                                                                              3546

Example 49A

H-G-I-V-E-Q-C-C-T-S-I-C-S-L-Q-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH,

Example 50A

H-G-I-V-E-Q-C-C-T-S-I-C-S-L-Q-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH, 3547                                                                 3548

Example 51a

H—G—I—V—E—Q—C—C—T—S—I——C—S—L—Q—L—E—N—Y—C—N—OH

H—G—K—G—S—H—K—F—V—N—Q——H—L—C—G—S—H—L—V—E—A——L—Y—L—V—C—G—K—R—G—F—F—Y—T—P—R—OH,

Example 52A

H—G—I—V—E—Q—C—C—T—S—I——C—S—L—Q—L—E—N—Y—C—N—OH

H—G—K—G—S—H—K—F—V—N—Q——H—L—C—G—S—H—L—V—E—A——L—Y—L—V—C—G—K—R—G—F—F—Y—T—P—R—OH, 3549                                                                              3550

Example 53A

H-G-I-V-E-Q-C-C-T-S-I—C-S-L-Q-L-E-N-Y-C-N-OH

H-G-K-G-S-H-K-F-V-N-Q——H-L-C-G-S-H-L-V-E-A—L-Y-L-V-C-G-K-R-G-F-F-Y-T-P-R-OH,

Example 54A

H-G-I-V-E-Q-C-C-T-S-I—C-S-L-Q-L-E-N-Y-C-N-OH

H-G-K-G-S-H-K-F-V-N-Q——H-L-C-G-S-H-L-V-E-A—L-Y-L-V-C-G-K-R-G-F-F-Y-T-P-R-OH,

3551                                                              3552

Example 55A

H-G-I-V-E-Q-C-C-T-S-I——C-S-L-Q-L-E-N-Y-C-N-OH

H-G-K-G-S-H-K-F-V-N-Q——H-L-C-G-S-H-L-V-E-A——L-Y-L-V-C-G-K-R-G-F-F-Y-T-P-R-OH,

Example 56A

H-G-I-V-E-Q-C-C-T-S-I——C-S-L-Q-L-E-N-Y-C-N-OH

H-G-K-G-S-H-K-F-V-N-Q——H-L-C-G-S-H-L-V-E-A——L-Y-L-V-C-G-K-R-G-F-F-Y-T-P-R-OH,

3553　　　　　　　　3554

-continued

Example 57A

H-G—I—V—E—Q—C—C—T—S—I——C—S—L—Q—L—E—N—Y—C—N—OH

H-G—K—G—S—H—K—F—V—N—Q——H—L—C—G—S—H—L—V—E—A——L—Y—L—V—C—G—K—R—G—F—F—Y—T—P—R—OH,

3555 3556

Example 58A

H-G-I-V-E-Q-C-C-T-S-I——C-S-L-Q-L-E-N-Y-C-N-OH

H-G-K-G-S-H-K-F-V-N-Q——H-L-C-G-S-H-L-V-E-A——L-Y-L-V-C-G-K-R-G-F-F-Y-T-P-R-OH,

Example 59A

H-G-I-V-E-Q-C-C-T-S-I——C-S-L-Q-L-E-N-Y-C-N-OH

H-G-K-G-S-H-K-F-V-N-Q——H-L-C-G-S-H-L-V-E-A——L-Y-L-V-C-G-K-R-G-F-F-Y-T-P-R-OH,

3557 3558

-continued

Example 60A

H-G-I-V-E-Q-C-C-T-S-I—C-S-L-Q-L-E-N-Y-C-N-OH

H-G-K-G-S-H-K-F-V-N-Q—H-L-C-G-S-H-L-V-E-A—L-Y-L-V-C-G-K-R-G-F-F-Y-T-P-R-OH,

Example 61A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH

-continued

Example 62A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH

Example 63A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

-continued

Example 64A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

Example 65A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

Example 66A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

-continued

Example 67A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

-continued

Example 68A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

Example 69A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

-continued

Example 70A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH

-continued

Example 71A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

-continued

Example 72A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

Example 73A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH

-continued

Example 74A

H—G-I-V-E-Q-C-C-T-S-I-C-S-L-Y-Q-L-E-N-Y-C—N—OH

H-G-K-G-S-H-K-F-V-N-Q-H-L-C-G-S-H-L-V-E-A-L-Y-L-V-C-G-K-R-G-F-F-Y-T-P-R—OH 3581 3582

Example 75A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

Example 76A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

3583                                                                 3584

Example 77A

H—G-I-V-E-Q-C-C-T-S-I-C-S-L-Y-Q-L-E-N-Y-C—N—OH

H-G-K-G-S-H-K-F-V-N-Q-H-L-C-G-S-H-L-V-E-A-L-Y-L-V-C-G-K-R-G-F-F-Y-T-P-R—OH

-continued

Example 78A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH

Example 79A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH

Example 80A

H—G-I-V-E-Q-C-C-T-S-I-C-S-L-Y-Q-L-E-N-Y-C—N—OH

-continued

H—G-K-G-S-H-K-F-V-N-Q-H-L-C-G-S-H-L-V-E-A-L-Y-L-V-C-G-K-R-G-F-F-Y-T-P-R—OH

Example 81A

H—G-I-V-E-Q-C-C-T-S-I-C-S-L-Y-Q-L-E-N-Y-C—N—OH

3591

3592

-continued

H—G-K-G-S-H-K-F-V-N-Q-H-L-C-G-S-H-L-V-E-A-L-Y-L-V-C-G-K-R-G-F-F-Y-T-P-R—OH

Example 82A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH 3593 3594

-continued

Example 83A

H—G-I-V-E-Q-C-C-T-S-I-C-S-L-Y-Q-L-E-N-Y-C—N—OH

3595  3596

-continued

H—G-K-G-S-H-K-F-V-N-Q-H-L-C-G-S-H-L-V-E-A-L-Y-L-V-C-G-K-R-G-F-F-Y-T-P-R—OH

Example 84A

3597  3598

-continued

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH,

Example 85A

H—G-I-V-E-Q-C-C-T-S-I-C-S-L-Y-Q-L-E-N-Y-C—N—OH

H—G-K-G-S-H-K-F-V-N-Q-H-L-C-G-S-H-L-V-E-A-L-Y-L-V-C-G-K-R-G-F-F-Y-T-P-R—OH

-continued or a pharmaceutically acceptable salt thereof, an isotope thereof, and combinations thereof.

2. The compound according to claim 1, wherein the compound is Example 1A or a pharmaceutically acceptable salt thereof.

3. The compound according to claim 1, wherein the compound is Example 2A or a pharmaceutically acceptable salt thereof.

4. The compound according to claim 1, wherein the compound is Example 7A or a pharmaceutically acceptable salt thereof.

5. The compound according to claim 1, wherein the compound is Example 9A or a pharmaceutically acceptable salt thereof.

6. The compound according to claim 1, wherein the compound is Example 14A or a pharmaceutically acceptable salt thereof.

7. The compound according to claim 1, wherein the compound is Example 15A or a pharmaceutically acceptable salt thereof.

8. The compound according to claim 1, wherein the compound is Example 16A or a pharmaceutically acceptable salt thereof.

9. The compound according to claim 1, wherein the compound is Example 18A or a pharmaceutically acceptable salt thereof.

10. The compound according to claim 1, wherein the compound is Example 19A or a pharmaceutically acceptable salt thereof.

11. The compound according to claim 1, wherein the compound is Example 22A or a pharmaceutically acceptable salt thereof.

12. The compound according to claim 1, wherein the compound is Example 25A or a pharmaceutically acceptable salt thereof.

13. The compound according to claim 1, wherein the compound is Example 26A or a pharmaceutically acceptable salt thereof.

14. The compound according to claim 1, wherein the compound is Example 27A or a pharmaceutically acceptable salt thereof.

15. The compound according to claim 1, wherein the compound is Example 28A or a pharmaceutically acceptable salt thereof.

16. The compound according to claim 1, wherein the compound is Example 30A or a pharmaceutically acceptable salt thereof.

17. The compound according to claim 1, wherein the compound is Example 31A or a pharmaceutically acceptable salt thereof.

18. The compound according to claim 1, wherein the compound is Example 46A or a pharmaceutically acceptable salt thereof.

19. The compound according to claim 1, wherein the compound is Example 47A or a pharmaceutically acceptable salt thereof.

20. The compound according to claim 1, wherein the compound is Example 49A or a pharmaceutically acceptable salt thereof.

21. The compound according to claim 1, wherein the compound is Example 51A or a pharmaceutically acceptable salt thereof.

22. The compound according to claim 1, wherein the compound is Example 63A or a pharmaceutically acceptable salt thereof.

23. The compound according to claim 1, wherein the compound is Example 68A or a pharmaceutically acceptable salt thereof.

24. The compound according to claim 1, wherein the compound is Example 71A or a pharmaceutically acceptable salt thereof.

25. The compound according to claim 1, wherein the compound is Example 73A or a pharmaceutically acceptable salt thereof.

26. The compound according to claim 1, wherein the compound is Example 75A or a pharmaceutically acceptable salt thereof.

27. The compound according to claim 1, wherein the compound is Example 77A or a pharmaceutically acceptable salt thereof.

28. The compound according to claim 1, wherein the compound is Example 78A or a pharmaceutically acceptable salt thereof.

29. A pharmaceutical composition comprising at least one compound or a pharmaceutically acceptable salt thereof according to any one of claims 1-28 and a pharmaceutically acceptable carrier.

* * * * *